US012740991B2

(12) United States Patent
Weinstein et al.

(10) Patent No.: US 12,740,991 B2
(45) Date of Patent: Sep. 22, 2026

(54) INHIBITORS AND USES THEREOF

(71) Applicant: Vividion Therapeutics, Inc., San Diego, CA (US)

(72) Inventors: David Weinstein, San Diego, CA (US); Jason Green, Poway, CA (US); Shota Kikuchi, San Diego, CA (US); Donald C Rogness, San Diego, CA (US); Philip Alabi, Escondido, CA (US); Matthew Patricelli, San Diego, CA (US); Nilotpal Roy, San Diego, CA (US); I-Chung Lo, San Diego, CA (US)

(73) Assignee: VIVIDION THERAPEUTICS, INC., San Diego, CA (US)

( * ) Notice: Subject to any disclaimer, the term of this patent is extended or adjusted under 35 U.S.C. 154(b) by 468 days.

(21) Appl. No.: 18/477,240

(22) Filed: Sep. 28, 2023

(65) Prior Publication Data

US 2024/0226114 A1 Jul. 11, 2024

Related U.S. Application Data

(60) Provisional application No. 63/519,541, filed on Aug. 14, 2023, provisional application No. 63/377,589, filed on Sep. 29, 2022.

(51) Int. Cl.

| | |
|---|---|
| ***A61K 31/553*** | (2006.01) |
| ***A61K 31/496*** | (2006.01) |
| ***A61K 31/506*** | (2006.01) |
| ***A61K 31/53*** | (2006.01) |
| ***A61K 31/5377*** | (2006.01) |
| ***A61K 31/5386*** | (2006.01) |
| ***A61K 31/541*** | (2006.01) |
| ***A61P 35/00*** | (2006.01) |
| ***C07D 241/04*** | (2006.01) |
| ***C07D 265/30*** | (2006.01) |
| ***C07D 265/34*** | (2006.01) |
| ***C07D 401/10*** | (2006.01) |
| ***C07D 401/14*** | (2006.01) |
| ***C07D 403/10*** | (2006.01) |
| ***C07D 405/10*** | (2006.01) |
| ***C07D 413/10*** | (2006.01) |
| ***C07D 413/14*** | (2006.01) |
| ***C07D 417/10*** | (2006.01) |
| ***C07D 471/04*** | (2006.01) |
| ***C07D 487/04*** | (2006.01) |
| ***C07D 491/107*** | (2006.01) |
| ***C07D 498/10*** | (2006.01) |

(52) U.S. Cl.

CPC .......... *A61K 31/553* (2013.01); *A61K 31/496* (2013.01); *A61K 31/506* (2013.01); *A61K 31/53* (2013.01); *A61K 31/5377* (2013.01); *A61K 31/5386* (2013.01); *A61K 31/541* (2013.01); *A61P 35/00* (2018.01); *C07D 241/04* (2013.01); *C07D 265/30* (2013.01); *C07D 265/34* (2013.01); *C07D 401/10* (2013.01); *C07D 401/14* (2013.01); *C07D 403/10* (2013.01); *C07D 405/10* (2013.01); *C07D 413/10* (2013.01); *C07D 413/14* (2013.01); *C07D 417/10* (2013.01); *C07D 471/04* (2013.01); *C07D 487/04* (2013.01); *C07D 491/107* (2013.01); *C07D 498/10* (2013.01)

(58) Field of Classification Search

CPC ................ A61K 31/553; A61K 31/496; A61K 31/506; A61K 31/53; A61K 31/5377; A61K 31/5386; A61K 31/541; A61P 35/00; C07D 241/04; C07D 265/30; C07D 265/34; C07D 401/10; C07D 401/14; C07D 403/10; C07D 405/10; C07D 413/10; C07D 413/14; C07D 417/10; C07D 471/04; C07D 487/04; C07D 491/107; C07D 498/10

See application file for complete search history.

(56) References Cited

FOREIGN PATENT DOCUMENTS

| | | | | | |
|---|---|---|---|---|---|
| WO | 2016065236 | A1 | | 4/2016 | |
| WO | 2019122265 | A1 | | 6/2019 | |
| WO | 2020030925 | A1 | | 2/2020 | |
| WO | WO-2023067353 | A1 | * | 4/2023 | ........... C07D 519/00 |
| WO | 2024073587 | A1 | | 4/2024 | |

OTHER PUBLICATIONS

Singh et al. ACS Chemical Biology.2016;11(11):3214-3225 (Year: 2016).*

Kwarcinski, et al., "Discovery of Bivalent Kinase Inhibitors via Enzyme-Templated Fragment Elaboration", ACS Medical Chemistry Letters, 2015, 6, pp. 898-901.

Zhou, et al., "Recent progress in the development of small molecule Nrf2 activators: a patent review (2017-present)", Expert Opinion on Therapeutic Patents, Feb. 6, 2020, vol. 30, No. 3, pp. 209-225.

International Search Report and Written Opinion for PCT/US2023/075401, dated Nov. 29, 2023.

Kwarcinski, et al., "Discovery of Bivalent Kinase Inhibitors via Enzyme-Templated Fragment Elaboration", ACS Medicinal Chemistry Letters, vol. 6, No. 8, Aug. 13, 2015, pp. 898-901.

Kwarcinski, et al., "Supporting Information—Discovery of Bivalent Kinase Inhibitors via Enzyme-Templated Fragment Elaboration", ACS Med. Chem. Lett., Jul. 13, 2015, pp. S1-S53.

(Continued)

*Primary Examiner* — Clinton A Brooks
*Assistant Examiner* — Jerica Katlynn Wilson
(74) *Attorney, Agent, or Firm* — Quarles & Brady LLP

(57) ABSTRACT

Compounds and methods for inhibiting Nrf2 by activating KEAP1.

10 Claims, No Drawings

Specification includes a Sequence Listing.

(56) References Cited

OTHER PUBLICATIONS

Zhou, et al., "Recent progress in the development of small molecule Nrf2 activators: a patent review (2017-present)", Expert Opinion on Therapeutic Patents, vol. 30, No. 3, Feb. 6, 2020, pp. 209-225.
International Search Report and Written Opinion for PCT/US2024/033911, dated Jan. 17, 2025, 10 pages.

* cited by examiner

SEQUENCE LISTING

```
Sequence total quantity: 1
SEQ ID NO: 1           moltype = AA  length = 624
FEATURE                Location/Qualifiers
source                 1..624
                       mol_type = protein
                       organism = synthetic construct
VARIANT                151
                       note = A variant having one of numerous possible chemical
                        residues at cysteine 151 as described by paragraphs
                        [00168] of the present specification.
SEQUENCE: 1
MQPDPRPSGA GACCRFLPLQ SQCPEGAGDA VMYASTECKA EVTPSQHGNR TFSYTLEDHT  60
KQAFGIMNEL RLSQQLCDVT LQVKYQDAPA AQFMAHKVVL ASSSPVFKAM FTNGLREQGM  120
EVVSIEGIHP KVMERLIEFA YTASISMGEK CVLHVMNGAV MYQIDSVVRA CSDFLVQQLD  180
PSNAIGIANF AEQIGCVELH QRAREYIYMH FGEVAKQEEF FNLSHCQLVT LISRDDLNVR  240
CESEVFHACI NWVKYDCEQR RFYVQALLRA VRCHSLTPNF LQMQLQKCEI LQSDSRCKDY  300
LVKIFEELTL HKPTQVMPCR APKVGRLIYT AGGYFRQSLS YLEAYNPSDG TWLRLADLQV  360
PRSGLAGCVV GGLLYAVGGR NNSPDGNTDS SALDCYNPMT NQWSPCAPMS VPRNRIGVGV  420
IDGHIYAVGG SHGCIHHNSV ERYEPERDEW HLVAPMLTRR IGVGVAVLNR LLYAVGGFDG  480
TNRLNSAECY YPERNEWRMI TAMNTIRSGA GVCVLHNCIY AAGGYDGQDQ LNSVERYDVE  540
TETWTFVAPM KHRRSALGIT VHQGRIYVLG GYDGHTFLDS VECYDPDTDT WSEVTRMTSG  600
RSGVGVAVTM EPCRKQIDQQ NCTC                                         624
```

INHIBITORS AND USES THEREOF

CROSS REFERENCE TO RELATED APPLICATIONS

The present application claims the benefit under 35 U.S.C. § 119(e) of the earlier filing dates of U.S. Provisional Patent Application No. 63/377,589, filed Sep. 29, 2022, and U.S. Provisional Patent Application No. 63/519,541, filed Aug. 14, 2023, the entire contents of each of which are incorporated herein by reference in its entirety.

STATEMENT REGARDING SEQUENCE LISTING

A sequence listing having the name "BHC234005US02.xml" was created on Feb. 26, 2024, having a file size of 2.96 kilobytes, and is herein incorporated by reference in its entirety. The sequence listing is being filed herewith.

FIELD OF THE DISCLOSURE

The disclosure relates to compounds and methods for modulating KEAP1, or modulating Nrf2 by mediating the activation of KEAP1.

BACKGROUND OF THE DISCLOSURE

Diseases such as neurodegenerative diseases and cancer are widely abundant. Improved therapeutics are needed for treating these diseases.

SUMMARY

Disclosed herein, in some aspects, are modulators of Kelch-like ECH-associated protein 1 (KEAP1). Some such aspects relate to a KEAP1 agonist. The KEAP1 agonist may include a compound described herein. The KEAP1 agonist may be useful in a method described herein.

Disclosed herein, in some aspects, are compounds that inhibit nuclear factor erythroid-2-related factor 2 (Nrf2). The inhibition of Nrf2 may be indirect. For example, some aspects relate to a KEAP1 agonist that indirectly inhibits Nrf2. Some such aspects may include a Nrf2 inhibitor. The Nrf2 inhibitor may include a compound described herein. The Nrf2 inhibitor may be useful in a method described herein. The inhibition of Nrf2 may include Nrf2degradation. For example, a Nrf2 inhibitor may mediate its degradation.

In one aspect, described herein is a compound that has the structure of Formula (I), or a pharmaceutically acceptable salt or solvate thereof:

Formula (I)

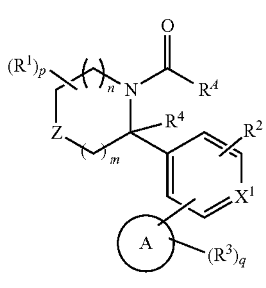

wherein;

$R^A$ is

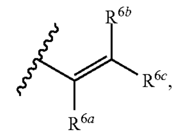

wherein $R^{6a}$ is H, D, halogen, or $C_1$-$C_6$ haloalkyl, and $R^{6b}$ and $R^{6c}$ are each independently H or D;

ring A is aryl, heteroaryl, or heterocyclyl;

Z is O, $S(=O)_2$, $C(R^1)_2$, or $NR^7$;

$R^7$ is $—C(=O)R^{7a}$, $S(=O)R^{7a}$, or $S(=O)_2R^{7a}$, wherein $R^{7a}$ is H, optionally substituted $C_1$-$C_6$ alkyl, or optionally substituted $C_3$-$C_7$ cycloalkyl;

each $R^1$ is independently H, halogen, —OH, optionally substituted $C_1$-$C_6$ alkyl, optionally substituted $C_1$-$C_6$ haloalkyl, optionally substituted $C_1$-$C_6$ hydroxyalkyl, or $—C(=O)N(R^b)_2$, or two $R^1$ are taken together with the atom(s) to which they are attached form an optionally substituted $C_3$-$C_8$ cycloalkyl or an optionally substituted 3 to 8-membered heterocycloalkyl;

$X^1$ is N or $CR^2$;

each $R^2$ is independently H, halogen, CN, OH, optionally substituted $C_1$-$C_6$ alkyl, optionally substituted $C_1$-$C_6$ haloalkyl, or optionally substituted $C_1$-$C_6$ hydroxyalkyl;

$R^4$ is H or optionally substituted $C_1$-$C_6$ alkyl;

or one of $R^2$ and $R^4$ together with the atoms to which they are attached form an optionally substituted 5 to 7-membered heterocycloalkyl;

each $R^3$ is independently H, D, halogen, oxo (=O), thio (=S), —CN, —OH, $—OR^a$, —SH, $—SR^a$, $—S(=O)R^a$, $—NO_2$, $—N(R^b)_2$, $—S(=O)_2R^a$, $—NHS(=O)_2R^a$, $—S(=O)_2N(R^b)_2$, $—C(=O)R^a$, $—C(=O)OR^b$, $—C(=O)NH_2$, $—OC(=O)N(R^b)_2$, $—NR^bC(=O)N(R^b)_2$, $—NR^bC(=O)R^a$, $—NR^bC(=O)OR^b$, optionally substituted $C_1$-$C_6$ alkyl, optionally substituted $C_1$-$C_6$haloalkyl, optionally substituted $C_1$-$C_6$ hydroxyalkyl, optionally substituted $C_3$-$C_8$ cycloalkyl, or optionally substituted 4 to 8-membered heterocycloalkyl;

or two $R^3$ on adjacent atoms combine together with the atom(s) to which they are attached to form an optionally substituted aryl, optionally substituted heteroaryl ring, or optionally substituted heterocycloalkyl;

each $R^a$ is independently $C_1$-$C_6$ alkyl, $C_1$-$C_6$ heteroalkyl, cycloalkyl, heterocycloalkyl, aryl, heteroaryl, $—C_1$-$C_6$ alkyl(aryl), $—C_1$-$C_6$ alkyl(heteroaryl), $—C_1$-$C_6$ alkyl(cycloalkyl), or $—C_1$-$C_6$ alkyl(heterocycloalkyl); wherein each alkyl, heteroalkyl, cycloalkyl, heterocycloalkyl, aryl, and heteroaryl is independently optionally substituted with one, two, or three —OH, $C_1$-$C_6$ alkyl, or $C_1$-$C_6$ haloalkyl; and each $R^b$ is independently H, $C_1$-$C_6$ alkyl, $C_1$-$C_6$ heteroalkyl, cycloalkyl, heterocycloalkyl, aryl, or heteroaryl; wherein the alkyl, heteroalkyl, cycloalkyl, heterocycloalkyl, aryl, and heteroaryl is independently optionally substituted with one, two, or three —OH, $C_1$-$C_6$ alkyl, or $C_1$-$C_6$ haloalkyl;

or two $R^b$ groups on a nitrogen atom are taken together with the nitrogen atom to which they are attached to form a heterocycloalkyl which is optionally substituted with one, two, or three $C_1$-$C_6$ alkyl, or $C_1$-$C_6$ haloalkyl;

m is 0, 1, 2, or 3;

n is 0, 1, 2, or 3;

p is an integer from 1-12; and q is an integer from 1-10.

In some embodiments, the compound of Formula (I) has the structure of Formula (II), or a pharmaceutically acceptable salt or solvate thereof:

Formula (II)

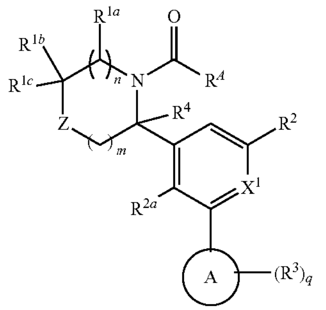

wherein,

Z is O, $S(=O)_2$, $CR^{1d}R^{1e}$, or $NR^7$;

$R^{1a}$, $R^{1b}$, $R^{1c}$, $R^{1d}$, and $R^{1e}$ are ach independently H, halogen, —OH, optionally substituted $C_1$-$C_6$ alkyl, optionally substituted $C_1$-$C_6$ haloalkyl, optionally substituted $C_1$-$C_6$ hydroxyalkyl, or $—C(=O)N(R^b)_2$;

or $R^{1a}$ and $R^{1b}$ together with atoms to which they are attached form an optionally substituted $C_3$-$C_5$ cycloalkyl;

or $R^{1b}$ and $R^{1c}$ together with the carbon atom to which they are attached form an optionally substituted $C_3$-$C_5$ cycloalkyl or an optionally substituted 3 to 8-membered heterocycloalkyl;

or $R^{1d}$ and $R^{1e}$ together with the carbon atom to which they are attached form an optionally substituted $C_3$-$C_8$ cycloalkyl or an optionally substituted 3 to 8-membered heterocycloalkyl;

$R^{2a}$ is H, halogen, CN, OH, optionally substituted $C_1$-$C_6$ alkyl, optionally substituted $C_1$-$C_6$ haloalkyl, or optionally substituted $C_1$-$C_6$ hydroxyalkyl; and $R^4$ is H or optionally substituted $C_1$-$C_6$ alkyl;

or $R^{2a}$ and $R^4$ together with the atoms to which they are attached form an optionally substituted 5 to 7-membered heterocycloalkyl.

In some embodiments, ring A is:

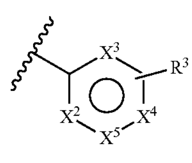

wherein, $X^2$, $X^3$, $X^4$, and $X^5$ are each independently N, $NR^{3a}$, or $CR^3$;

each $R^{3a}$ is independently H or an optionally substituted $C_1$-$C_6$ alkyl;

each $R^3$ is independently H, D, halogen, oxo (=O), —CN, —OH, $—OR^a$, —SH, $—SR^a$, $—S(=O)R^a$, $—NO_2$, $—N(R^b)_2$, $—S(=O)_2R^a$, $—NHS(=O)_2R^a$, $—S(=O)_2N(R^b)_2$, $—C(=O)R^a$, $—C(=O)OR^b$, $—C(=O)NH_2$, $—OC(=O)N(R^b)_2$, $—NR^bC(=O)N(R^b)_2$, $—NR^bC(=O)R^a$, $—NR^bC(=O)OR^b$, optionally substituted $C_1$-$C_6$ alkyl, optionally substituted $C_1$-$C_6$haloalkyl, optionally substituted $C_1$-$C_6$ hydroxyalkyl, optionally substituted $C_3$-$C_8$ cycloalkyl, or optionally substituted 4 to 8-membered heterocycloalkyl;

or two $R^3$ or two $R^{3a}$ or $R^3$ and $R^{3a}$ on adjacent atoms combine together with the atom(s) to which they are attached to form an optionally substituted aryl, optionally substituted heteroaryl ring, or optionally substituted heterocycloalkyl.

In some embodiments, the compound of Formula (I) has the structure of Formula (III), or a pharmaceutically acceptable salt or solvate thereof:

Formula (III)

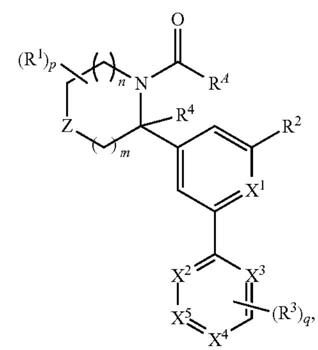

wherein, $X^2$, $X^3$, and $X^4$ are each independently N, $NR^{3a}$, or $CR^3$;

each $R^{3a}$ is independently H or an optionally substituted $C_1$-$C_6$ alkyl;

each $R^3$ is independently H, D, halogen, oxo (=O), —CN, —OH, $—OR^a$, —SH, $—SR^a$, $—S(=O)R^a$, $—NO_2$, $—N(R^b)_2$, $—S(=O)_2R^a$, $—NHS(=O)_2R^a$, $—S(=O)_2N(R^b)_2$, $—C(=O)R^a$, $—C(=O)OR^b$, $—C(=O)NH_2$, $—OC(=O)N(R^b)_2$, $—NR^bC(=O)N(R^b)_2$, $—NR^bC(=O)R^a$, $—NR^bC(=O)OR^b$, optionally substituted $C_1$-$C_6$ alkyl, optionally substituted $C_1$-$C_6$haloalkyl, optionally substituted $C_1$-$C_6$ hydroxyalkyl, optionally substituted $C_3$-$C_8$ cycloalkyl, or optionally substituted 4 to 8-membered heterocycloalkyl;

or two $R^3$ or two $R^{3a}$ or $R^3$ and $R^{3a}$ on adjacent atoms combine together with the atom(s) to which they are attached to form an optionally substituted aryl, optionally substituted heteroaryl ring, or optionally substituted heterocycloalkyl.

In some embodiments, the compound of Formula (I) has the structure of Formula (IIIa), or a pharmaceutically acceptable salt or solvate thereof:

Formula (IIIa)

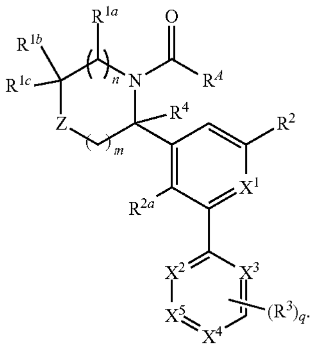

In some embodiments, the compound of Formula (I) has the structure of Formula (IV), or a pharmaceutically acceptable salt or solvate thereof:

Formula (IV)

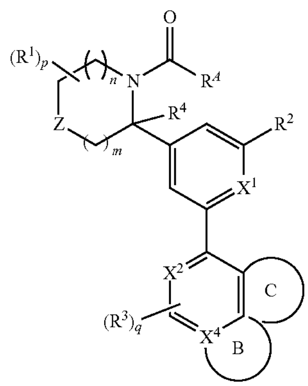

wherein,

- $X^2$ is N or $CR^3$;
- $X^4$ is N or C; and
- ring B is an optionally substituted 5 to 6-membered heteroaryl; or
- ring C is an optionally substituted 5 to 6-membered heteroaryl.

In another aspect, provided herein is a pharmaceutical composition comprising a compound disclosed herein, or a pharmaceutically acceptable salt, or solvate thereof, and at least one pharmaceutically acceptable excipient.

In another aspect, provided herein is a method of inhibiting Nrf2 by mediating the activation of KEAP1, the method comprising administering to a subject in need thereof a therapeutically effective amount of a compound of Formula (I), or a pharmaceutically acceptable salt or solvate thereof.

In another aspect, provided herein is a method of treating a disease mediated by the activation of KEAP1 and the inhibition of Nrf2, the method comprising administering to a subject in need thereof a therapeutically effective amount of a compound of Formula (I), or a pharmaceutically acceptable salt or solvate thereof In some embodiments, the disease is associated with oxidative stress. In some embodiments, the disease is a cancer.

In another aspect, the present disclosure provides the compounds disclosed herein for use as a medicament.

In another aspect, the present disclosure provides the compounds disclosed herein for use in the treatment of a disease mediated by the activation of KEAP1 and the inhibition of Nrf2.

In another aspect, the present disclosure provides for use of the compounds of the present disclosure in the manufacture of a medicament useful for the treatment of a disease mediated by the activation of KEAP1 and the inhibition of Nrf2. Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

DETAILED DESCRIPTION

Nuclear factor erythroid-2-related factor 2 (Nrf2) is a transcription factor that may play a central role in cytoprotection against electrophilic and oxidative stress. Nrf2 may up-regulate expression of a range of cytoprotective enzymes with antioxidant response elements in their promoter regions and thus can protect cells against oxidative damage or affect oxidative cell signaling.

In some cases, Nrf2 is constantly synthesized under normal conditions, but is degraded due to interaction with Kelch-like ECH-associated protein 1 (KEAP1). KEAP1 may be included as a substrate adapter protein in an E3 ubiquitin ligase complex with RBX1 and Cul3. In some cases, the E3 ubiquitin ligase continuously degrades Nrf2. KEAP1 behaves as a fast-acting thiol sensor to electrophiles and oxidants.

In some conditions such as oxidative stress or oxidative signaling, cysteine 151 of KEAP1 (and possibly other KEAP1 cysteines) may be oxidized, and the E3 ubiquitin ligase complex may be destabilized. Nrf2 may accumulate and translocate to the nucleus, bind to an ARE element, and initiate transcription of genes that respond to the oxidative stress. Some compounds that bind cysteine 151 may be useful for modulating this pathway.

Reducing Nrf2 activity (for example, when Nrf2 is upregulated or active without being degraded) may be useful as a therapeutic intervention in a range of chronic neurodegenerative conditions and cancer chemoprevention. One mechanism by which Nrf2 may be negatively regulated involves an interaction with the ubiquitination facilitator protein, Kelch-like ECH-associated protein 1 (KEAP1) that facilitates degradation of Nrf2. Inhibition of this process may underly a mode of action of a broad group of compounds that increase Nrf2 activity. A number of natural products, including the isothiocyanate sulforaphane, up-regulate Nrf2 by interacting with KEAP1 in a covalent manner to stall its activity.

The transcription factor nuclear factor erythroid-2-related factor 2 (Nrf2) up-regulates the expression of a range of cytoprotective enzymes with antioxidant response elements in their promoter regions and thus can protect cells against oxidative damage. Increasing Nrf2 activity may be useful as a therapeutic intervention in a range of chronic neurodegenerative conditions and cancer chemoprevention. One mechanism by which Nrf2 is negatively regulated involves an interaction with the ubiquitination facilitator protein, Kelch-like ECH-associated protein 1 (KEAP1) that facilitates degradation of Nrf2. Inhibition of this process underlies the mode of action of a broad group of compounds that increase Nrf2 activity. A number of natural products, including the isothiocyanate sulforaphane, up-regulate Nrf2 by interacting with KEAP1 in a covalent manner to stall its activity. Agents which decrease levels of Nrf2 in a cell may make the cell more susceptible to oxidative stress. In some embodiments, a compound described herein enhances oxidative stress, such as in a cancer cell or in a damaged cell such as in a neurodegenerative disease. This may lead to the cell being destroyed.

Disclosed herein are compounds and methods for inhibiting Nrf2 by mediating the activation of KEAP1. Some embodiments relate to a compound or method of inhibiting Nrf2. The Nrf2 inhibition may be in vitro or in vivo. The Nrf2 inhibition may include contacting a KEAP1 protein with a compound disclosed herein. The Nrf2 inhibition may increase an antioxidant or improve an antioxidant capacity in a subject or cell. The compound for inhibiting Nrf2 may be formulated for administration to a subject. The Nrf2 inhibition may be performed in a subject.

Details and examples of some Nrf2 proteins may be found at www.uniprot.org under accession number Q16236 (as of the priority date of this application). An Nrf2 protein may include a peptide of about 705 amino acids long, or that includes a mass of about 68 kD.

Some embodiments relate to a compound or method of activating KEAP1. The KEAP1 activation may be in vitro or in vivo. The KEAP1 activation may include contacting the KEAP1 with a compound disclosed herein. The KEAP1 activation may increase an antioxidant or improve an antioxidant capacity in a subject or cell. The compound for activating KEAP1 may be formulated for administration to a subject. The AP1 activation may be performed in a subject. Details and examples of some KEAP1 proteins may be found at www.uniprot.org under accession number Q14145 (as of the priority date of this application). A KEAP1 may include a peptide of about 624 amino acids long, or that includes a mass of about 70 kD.

The compounds disclosed herein may be useful for treatment of diseases where Nrf2 activity may be a concern, such as a neurodegenerative disease or cancer. In some cases, the compounds are useful in diseases where reductive stress is present, or when oxidative signaling is diminished. In some embodiments, the compound is used for treatment of a neurodegenerative disease. In some embodiments, the compound is used for treatment of cancer. The compounds may be useful for treating a disorder associated with oxidative stress, or for reducing oxidative stress or damage.

Compounds of the Disclosure

Disclosed herein, in some embodiments, are modulators of Kelch-like ECH-associated protein 1 (KEAP1). Some such aspects relate to a KEAP1 agonist. In some embodiments, the KEAP1 agonist inhibits nuclear factor erythroid-2-related factor 2 (Nrf2). Some embodiments relate to a Nrf2 modulator such as an inhibitor of Nrf2. The inhibition of Nrf2 may be indirect, such as by activation of KEAP1. The inhibition of Nrf2 may include Nrf2 degradation. A compound comprising an KEAP1 agonist may stabilize an E3 ubiquitin ligase comprising the KEAP1, and increase or result in degradation of Nrf2.

In one embodiment, provided herein is a compound having structure of Formula (I), or a pharmaceutically acceptable salt or solvate thereof:

Formula (I)

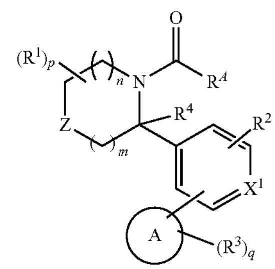

wherein;

$R^A$ is

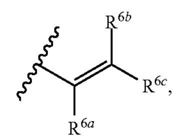

wherein $R^{6a}$ is H, D, halogen, or $C_1$-$C_6$haloalkyl, and $R^{6b}$ and $R^{6c}$ are each independently H or D;

ring A is aryl, heteroaryl, or heterocyclyl;

Z is O, $S(=O)_2$, $C(R^1)_2$, or $NR^7$;

$R^7$ is $—C(=O)R^{7a}$, $S(=O)R^{7a}$, or $S(=O)_2R^{7a}$, wherein $R^{7a}$ is H, optionally substituted $C_1$-$C_6$ alkyl, or optionally substituted $C_3$-$C_7$ cycloalkyl;

each $R^1$ is independently H, halogen, —OH, optionally substituted $C_1$-$C_6$ alkyl, optionally substituted $C_1$-$C_6$ haloalkyl, optionally substituted $C_1$-$C_6$ hydroxyalkyl, or $—C(=O)N(R^b)_2$, or two $R^1$ are taken together with the atom(s) to which they are attached form an optionally substituted $C_3$-$C_8$ cycloalkyl or an optionally substituted 3 to 8-membered heterocycloalkyl;

$X^1$ is N or $CR^2$;

each $R^2$ is independently H, halogen, CN, OH, optionally substituted $C_1$-$C_6$ alkyl, optionally substituted $C_1$-$C_6$ haloalkyl, or optionally substituted $C_1$-$C_6$ hydroxyalkyl;

$R^4$ is H or optionally substituted $C_1$-$C_6$ alkyl;

or one of $R^2$ and $R^4$ together with the atoms to which they are attached form an optionally substituted 5 to 7-membered heterocycloalkyl;

each $R^3$ is independently H, D, halogen, oxo (=O), thio (=S), —CN, —OH, $—OR^a$, —SH, $—SR^a$, $—S(=O)R^a$, $—NO_2$, $—N(R^b)_2$, $—S(=O)_2R^a$, $—NHS(=O)_2R^a$, $—S(=O)_2N(R^b)_2$, $—C(=O)R^a$, $—C(=O)OR^b$, $—C(=O)NH_2$, $—OC(=O)N(R^b)_2$, $—NR^bC(=O)N(R^b)_2$, $—NR^bC(=O)R^a$, $—NR^bC(=O)OR^b$, optionally substituted $C_1$-$C_6$ alkyl, optionally substituted $C_1$-$C_6$haloalkyl, optionally substituted $C_1$-$C_6$ hydroxyalkyl, optionally substituted $C_3$-$C_8$ cycloalkyl, or optionally substituted 4 to 8-membered heterocycloalkyl;

or two $R^3$ on adjacent atoms combine together with the atom(s) to which they are attached to form an optionally substituted aryl, optionally substituted heteroaryl ring, or optionally substituted heterocycloalkyl;

each $R^a$ is independently $C_1$-$C_6$ alkyl, $C_1$-$C_6$ heteroalkyl, cycloalkyl, heterocycloalkyl, aryl, heteroaryl, —$C_1$-$C_6$ alkyl(aryl), —$C_1$-$C_6$ alkyl(heteroaryl), —$C_1$-$C_6$ alkyl(cycloalkyl), or —$C_1$-$C_6$ alkyl(heterocycloalkyl); wherein each alkyl, heteroalkyl, cycloalkyl, heterocycloalkyl, aryl, and heteroaryl is independently optionally substituted with one, two, or three —OH, $C_1$-$C_6$ alkyl, or $C_1$-$C_6$haloalkyl; and each $R^b$ is independently H, $C_1$-$C_6$ alkyl, $C_1$-$C_6$ heteroalkyl, cycloalkyl, heterocycloalkyl, aryl, or heteroaryl; wherein the alkyl, heteroalkyl, cycloalkyl, heterocycloalkyl, aryl, and heteroaryl is independently optionally substituted with one, two, or three —OH, $C_1$-$C_6$ alkyl, or $C_1$-$C_6$ haloalkyl;

or two $R^b$ groups on a nitrogen atom are taken together with the nitrogen atom to which they are attached to form a heterocycloalkyl which is optionally substituted with one, two, or three $C_1$-$C_6$ alkyl, or $C_1$-$C_6$ haloalkyl;

m is 0, 1, 2, or 3;

n is 0, 1, 2, or 3;

p is an integer from 1-12; and q is an integer from 1-10.

In one embodiment, provided herein is a compound having structure of Formula (I), or a pharmaceutically acceptable salt or solvate thereof:

Formula (I)

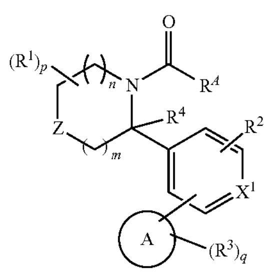

wherein;

$R^A$ is

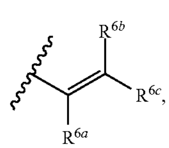

wherein $R^{6a}$ is H, D, or chloro, and $R^{6b}$ and $R^{6c}$ are independently H or D;

ring A is imidazolyl, isoxazolyl, oxazolyl, phenyl, pyridinyl, pyrimidinyl, diydropyrimidinyl, tetrahydropyrimidinyl, pyrazinyl, triazinyl, purinyl, or pyrrolo[3,2-c]pyridinyl;

Z is O, S(=O)$_2$, C($R^1$)$_2$, or $NR^7$; wherein $R^7$ is —C(=O)$R^{7a}$, wherein $R^{7a}$ is $C_1$-$C_3$-alkyl or $C_3$-$C_7$ cycloalkyl;

each $R^1$ is independently H, —OH, fluoro, $C_1$-$C_3$-alkyl, or $C_1$-$C_3$-haloalkyl;

or two $R^1$ are taken together with the atom(s) to which they are attached form a $C_3$-$C_8$ cycloalkyl;

$X^1$ is N or CH;

$R^2$ is chloro;

$R^4$ is H o methyl;

each $R^3$ is independently H, halogen, $C_1$-$C_3$-alkyl, $C_1$-$C_3$-alkoxy, thio (=S), amino, $C_1$-$C_3$-alkylamino, di-$C_1$-$C_3$-alkylamino, —C(=O)$NH_2$ or N,N-di-$C_1$-$C_2$-alkylamino-$C_2$-$C_3$-alkyl;

m is 1;

n is 1 or 2;

p is 6 or 8; and q is 2, 3, 4, or 5.

In some embodiments, the compound of Formula (I) has the structure of Formula (II), or a pharmaceutically acceptable salt or solvate thereof:

Formula (II)

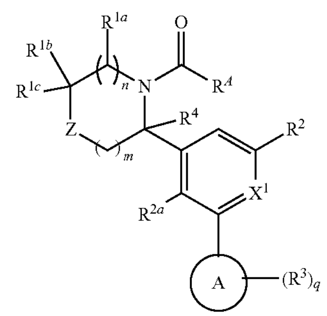

wherein,

Z is O, S(=O)$_2$, $CR^{1d}R^{1e}$, or $NR^7$;

$R^{1a}$, $R^{1b}$, $R^{1c}$, $R^{1d}$, and $R^{1e}$ are ach independently H, halogen, —OH, optionally substituted $C_1$-$C_6$ alkyl, optionally substituted $C_1$-$C_6$ haloalkyl, optionally substituted $C_1$-$C_6$ hydroxyalkyl, or —C(=O)N($R^b$)$_2$;

or $R^{1a}$ and $R^{1b}$ together with atoms to which they are attached form an optionally substituted $C_3$-$C_8$ cycloalkyl;

or $R^{1b}$ and $R^{1c}$ together with the carbon atom to which they are attached form an optionally substituted $C_3$-$C_8$ cycloalkyl or an optionally substituted 3 to 8-membered heterocycloalkyl;

or $R^{1d}$ and $R^{1e}$ together with the carbon atom to which they are attached form an optionally substituted $C_3$-$C_8$ cycloalkyl or an optionally substituted 3 to 8-membered heterocycloalkyl;

$R^{2a}$ is H, halogen, CN, OH, optionally substituted $C_1$-$C_6$ alkyl, optionally substituted $C_1$-$C_6$ haloalkyl, or optionally substituted $C_1$-$C_6$ hydroxyalkyl; and $R^4$ is H or optionally substituted $C_1$-$C_6$ alkyl;

or $R^{2a}$ and $R^4$ together with the atoms to which they are attached form an optionally substituted 5 to 7-membered heterocycloalkyl.

In some embodiments, $R^{1a}$ and $R^{1b}$ together with atoms to which they are attached form an optionally substituted $C_3$-$C_8$ cycloalkyl. In some embodiments, $R^{1a}$ and $R^{1b}$ together with atoms to which they are attached form a cyclopropyl, cyclobutyl, cyclopentyl, or cyclohexyl. In some embodiments, $R^{1a}$ and $R^{1b}$ together with atoms to which they are attached form a cyclopropyl. In some embodiments, $R^{1a}$ and $R^{1b}$ together with atoms to which they are attached form cyclobutyl. In some embodiments, $R^{1a}$ and $R^{1b}$ together with atoms to which they are attached form a cyclopentyl.

In some embodiments, $R^{1b}$ and $R^{1c}$ together with the carbon atom to which they are attached form an optionally substituted $C_3$-$C_8$ cycloalkyl. In some embodiments, $R^{1b}$ and $R^{1c}$ together with the carbon atom to which they are attached form a cyclopropyl, cyclobutyl, or cyclopentyl. In some embodiments, $R^{1b}$ and $R^{1c}$ together with the carbon atom to which they are attached form a cyclopropyl. n some embodiments, $R^{1b}$ and $R^{1c}$ together with the carbon atom to which they are attached form a cyclobutyl. In some embodiments, $R^{1b}$ and $R^{1c}$ together with the carbon atom to which they are attached form a cyclopentyl.

In some embodiments, $R^{1d}$ and $R^{1e}$ together with the carbon atom to which they are attached form an optionally substituted $C_3$-$C_8$ cycloalkyl. In some embodiments, $R^{1d}$ and $R^{1e}$ together with the carbon atom to which they are attached form a cyclopropyl, cyclobutyl, or cyclopentyl. In some embodiments, $R^{1d}$ and $R^{1e}$ together with the carbon atom to which they are attached form a cyclopropyl. n some embodiments, $R^{1d}$ and $R^{1e}$ together with the carbon atom to which they are attached form a cyclobutyl. In some embodiments, $R^{1d}$ and $R^{1e}$ together with the carbon atom to which they are attached form a cyclopentyl.

In some embodiments, $R^{1d}$ and $R^{1e}$ together with the carbon atom to which they are attached form an optionally substituted 3 to 8-membered heterocycloalkyl, comprising 1, 2, or 3 heteroatoms selected from N, O, or S. In some embodiments, $R^{1d}$ and $R^{1e}$ together with the carbon atom to which they are attached form an optionally substituted 5 to 6-membered heterocycloalkyl, comprising 1 or 2 heteroatoms selected from N or O. In some embodiments, $R^{1d}$ and $R^{1e}$ together with the carbon atom to which they are attached form an optionally substituted 4-membered heterocycloalkyl. In some embodiments, $R^{1d}$ and $R^{1e}$ together with the carbon atom to which they are attached form an optionally substituted 5-membered heterocycloalkyl. In some embodiments, $R^{1d}$ and $R^{1e}$ together with the carbon atom to which they are attached form an optionally substituted 6-membered heterocycloalkyl.

In some embodiments, $R^{1a}$ is H; and $R^{1b}$ and $R^{1c}$ are each independently H, halogen, —OH, optionally substituted $C_1$-$C_6$ alkyl, optionally substituted $C_1$-$C_6$ haloalkyl, optionally substituted $C_1$-$C_6$ hydroxyalkyl, or —C(═O)N($R^b$)$_2$. In some embodiments, $R^{1b}$ and $R^{1c}$ are each independently H or an optionally substituted $C_1$-$C_6$ alkyl. In some embodiments, $R^{1b}$ and $R^{1c}$ are each independently methyl or ethyl. In some embodiments, $R^{1b}$ and $R^{1c}$ are each methyl. In some embodiments, $R^{1b}$ and $R^{1c}$ are each H.

In some embodiments, $R^{1a}$ is halogen, —OH, optionally substituted $C_1$-$C_6$ alkyl, optionally substituted $C_1$-$C_6$ haloalkyl, optionally substituted $C_1$-$C_6$ hydroxyalkyl, or —C(═O)N($R^b$)$_2$; and $R^{1b}$ and $R^{1c}$ are each H. In some embodiments, $R^{1a}$ is optionally substituted $C_1$-$C_6$ alkyl, optionally substituted $C_1$-$C_6$ haloalkyl, or optionally substituted $C_1$-$C_6$ hydroxyalkyl. In some embodiments, $R^{1a}$ is optionally substituted $C_1$-$C_6$ alkyl. In some embodiments, $R^{1a}$ is isopropyl, ethyl, or methyl. In some embodiments, $R^{1a}$ is methyl. In some embodiments, $R^{1a}$ is optionally substituted $C_1$-$C_6$ haloalkyl. In some embodiments, $R^{1a}$ is $CHF_2$ of $CF_3$. In some embodiments, $R^{1a}$ is —C(═O)N($R^b$)$_2$. In some embodiments, $R^{1a}$ is —C(═O)N($CH_3$)$_2$, —C(═O)NH$CH_3$, or —C(═O)$NH_2$.

In some embodiments, Z is $CR^{1d}R^{1e}$; and $R^{1d}$ and $R^{1e}$ are each independently H, halogen, —OH, optionally substituted $C_1$-$C_6$ alkyl, optionally substituted $C_1$-$C_6$ haloalkyl, optionally substituted $C_1$-$C_6$ hydroxyalkyl, or —C(═O)N($R^b$)$_2$. In some embodiments, $R^{1d}$ and $R^{1e}$ are each independently H, halogen, —OH, optionally substituted $C_1$-$C_6$ alkyl. In some embodiments, $R^{1d}$ and $R^{1e}$ are each independently halogen. In some embodiments, $R^{1d}$ and $R^{1e}$ are each independently Cl or F. In some embodiments, $R^{1d}$ and $R^{1e}$ are each H.

In some embodiments, $R^{2a}$ and $R^4$ together with the atoms to which they are attached form an optionally substituted 5 to 7-membered heterocycloalkyl, wherein the heteroatom is selected from N or O. In some embodiments, the heteroatom is O. In some embodiments, $R^{2a}$ and $R^4$ together with the atoms to which they are attached form a 5-membered heteroalkyl. In some embodiments, $R^{2a}$ and $R^4$ together with the atoms to which they are attached form a 6-membered heterocycloalkyl. In some embodiments, $R^{2a}$ and $R^4$ together with the atoms to which they are attached form a 7-membered heterocycloalkyl.

In some embodiments, $R^{2a}$ is H, halogen, CN, or OH. In some embodiments, $R^{2a}$ is halogen. In some embodiments, $R^{2a}$ is H.

In some embodiments, ring A and $R^2$ are in a 1,2,5 configuration. In some embodiments, ring A and $R^2$ are in a 1,3,5 configuration. In some embodiments, ring A and $R^2$ are in a 1,4,5 configuration.

In some embodiments, ring A is $C_{6-10}$ aryl, 5 to 10-membered heteroaryl, or 5 to 10-membered heterocycloalkyl.

In some embodiments, ring A is a 6-membered heteroaryl comprising 1, 2, or 3 heteroatoms selected from N. In some embodiments, ring A is phenyl, pyridinyl, pyrazinyl, pyrimidinyl, or pyridazinyl. In some embodiments, ring A is phenyl. In some embodiments, ring A is pyridinyl or pyrazinyl. In some embodiments, ring A is pyridinyl. In some embodiments, ring A is pyrazinyl. In some embodiments, ring A is pyrimidinyl.

In some embodiments, ring A is:

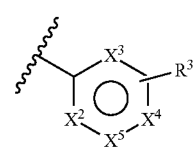

wherein,

- $X^2$, $X^3$, $X^4$, and $X^5$ are each independently N, $NR^{3a}$, or $CR^3$;
- each $R^{3a}$ is independently H or an optionally substituted $C_1$-$C_6$ alkyl;
- each $R^3$ is independently H, D, halogen, oxo (═O), —CN, —OH, —$OR^a$, —SH, —$SR^a$, —S(═O)$R^a$, —$NO_2$, —N($R^b$)$_2$, —S(═O)$_2R^a$, —NHS(═O)$_2R^a$, —S(═O)$_2$N($R^b$)$_2$, —C(═O)$R^a$, —C(═O)$OR^b$, —C(═O)$NH_2$, —OC(═O)N($R^b$)$_2$, —$NR^b$C(═O)N($R^b$)$_2$, —$NR^b$C(═O)$R^a$, —$NR^b$C(═O)$OR^b$, optionally substituted $C_1$-$C_6$ alkyl, optionally substituted $C_1$-$C_6$haloalkyl, optionally substituted $C_1$-$C_6$ hydroxyalkyl, optionally substituted $C_3$-$C_8$ cycloalkyl, or optionally substituted 4 to 8-membered heterocycloalkyl;
- or two $R^3$ or two $R^{3a}$ or $R^3$ and $R^{3a}$ on adjacent atoms combine together with the atom(s) to which they are attached to form an optionally substituted aryl, optionally substituted heteroaryl ring, or optionally substituted heterocycloalkyl.

All other substituents are as defined above.

In some embodiments, the compound is of Formula (III), or a pharmaceutically acceptable salt or solvate thereof:

Formula (III)

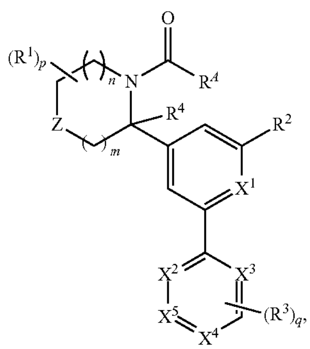

wherein, $X^2$, $X^3$, $X^4$, and $X^5$ are each independently N, $NR^{3a}$, or $CR^3$;

each $R^{3a}$ is independently H or an optionally substituted $C_1$-$C_6$ alkyl;

each $R^3$ is independently H, D, halogen, oxo (═O), —CN, —OH, —$OR^a$, —SH, —$SR^a$, —S(═O)$R^a$, —$NO_2$, —$N(R^b)_2$, —$S(=O)_2R^a$, —NHS(═O)$_2R^a$, —$S(=O)_2N(R^b)_2$, —C(═O)$R^a$, —C(═O)$OR^b$, —C(═O)$NH_2$, —OC(═O)$N(R^b)_2$, —$NR^b$C(═O)N$(R^b)_2$, —$NR^b$C(═O)$R^a$, —$NR^b$C(═O)$OR^b$, optionally substituted $C_1$-$C_6$ alkyl, optionally substituted $C_1$-$C_6$haloalkyl, optionally substituted $C_1$-$C_6$ hydroxyalkyl, optionally substituted $C_3$-$C_8$ cycloalkyl, or optionally substituted 4 to 8-membered heterocycloalkyl;

or two $R^3$ or two $R^{3a}$ or $R^3$ and $R^{3a}$ on adjacent atoms combine together with the atom(s) to which they are attached to form an optionally substituted aryl, optionally substituted heteroaryl ring, or optionally substituted heterocycloalkyl.

All other substituents are as defined above.

In some embodiments, the compound is of Formula (III), or a pharmaceutically acceptable salt or solvate thereof:

Formula (III)

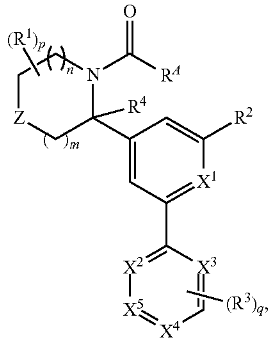

wherein $R^A$ is

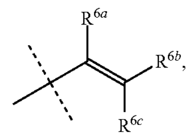

wherein $R^{6a}$ is H, D, halogen, and $R^{6b}$ and $R^{6c}$ are each independently H or D;

Z is O, $S(=O)_2$, $C(R^1)_2$, or $NR^7$; wherein $R^7$ is —C(═O)$R^{7a}$, wherein $R^{7a}$ is optionally substituted $C_3$-$C_5$ cycloalkyl;

each $R^1$ is independently H, —OH, fluorine, $C_1$-$C_3$-alkyl or $C_1$-$C_3$-fluoroalkyl, or two $R^1$ together with the carbon atom(s) to which they are attached form $C_3$-$C_4$-cycloalkyl, $X^1$ is N or CH;

$R^2$ is chloro;

each $R^3$ is independently H, D, chloro, fluoro, —O—$C_1$-$C_4$ alkyl, —$NH_2$, —NH—$C_1$-$C_4$ alkyl, —NH—$C_{2-3}$-alkyl-N$(CH_3)_2$, —C(═O)N$(H)_2$, or optionally substituted $C_1$-$C_4$ alkyl;

or two $R^3$ on adjacent atoms combine together with the atom(s) to which they are attached to form an optionally substituted pyrrolyl or imidazolyl ring;

$R^4$ is H or methyl;

$X^2$, $X^3$, $X^4$ and $X^5$ are each independently N, or $CR^3$;

m is 1;

n is 1 or 2;

p is 6 or 8;

q is an integer from 2-5.

In some embodiments, the compound is of Formula (IIIx), or a pharmaceutically acceptable salt or solvate thereof:

Formula (IIIx)

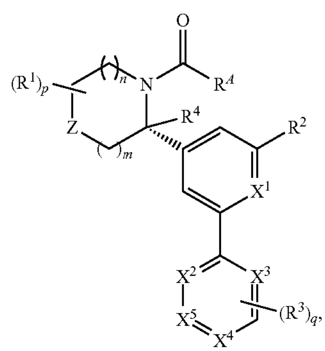

wherein,

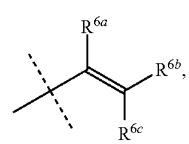

$R^A$ is wherein $R^{6a}$, $R^{6b}$ and $R^{6c}$ are each independently H;

Z is O;

each $R^1$ is independently H or methyl, with the proviso that not more than two $R^1$ are methyl;
$X^1$ is CH;
$R^2$ is chlorine;
each $R^3$ is independently H, D, —O—$CH_3$, —$NH_2$, —NH—$CH_3$ or methyl;
$R^4$ is H;
$X^2$, $X^3$, $X^4$ and $X^5$ are each independently N, or $CR^3$;
wherein at least one but not more than three of $X^2$, $X^3$, $X^4$ and $X^5$ are N;
m is 1;
n is 1;
p is 6;
q is an integer from 2-4.

In some embodiments, the compound is of Formula (IIIa), or a pharmaceutically acceptable salt thereof:

Formula (IIIa)

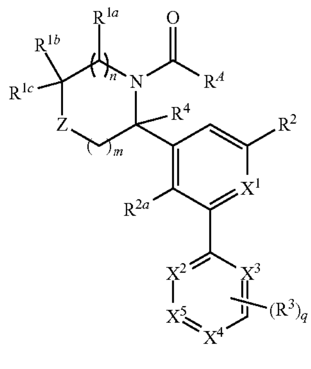

wherein,
$R^A$ is

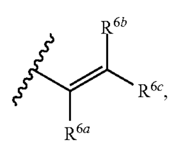

wherein
$R^{6a}$ is H, D, or chloro, and $R^{6b}$ and $R^{6c}$ are independently H or D;
Z is O, S(=O)$_2$, $CR^{1d}R^{1c}$, or $NR^7$; wherein
$R^7$ is —C(=O)$R^{7a}$, wherein $R^{7a}$ is a $C_3$-$C_5$ cycloalkyl;
each $R^{1a}$ is independently H, $C_1$-$C_4$ alkyl, or $C_1$-$C_4$ haloalkyl;
each $R^{1b}$ is independently H or $C_1$-$C_4$ alkyl;
each $R^{1c}$ is independently H or $C_1$-$C_4$ alkyl;
or $R^{1b}$ and $R^{1c}$ taken together with the atom to which they are attached form a $C_3$-$C_5$ cycloalkyl;
each $R^{1d}$ and $R^{1e}$ is independently H, fluoro, hydroxy, or methyl;
$X^1$ is N or CH;
$R^2$ is halogen;
$R^4$ is H or $C_1$-$C_4$ alkyl;
$X^2$, $X^3$, $X^4$, and $X^5$ are each independently N or $CR^3$;
each $R^3$ is independently H, D, halogen, —$OR^a$, —$N(R^b)_2$, —C(=O)$NH_2$, or $C_1$-$C_4$ alkyl;
or two $R^3$ on adjacent atoms combine together with the atom(s) to which they are attached to form an optionally substituted heteroaryl ring;
each $R^a$ is independently $C_1$-$C_4$ alkyl;
each $R^b$ is independently H, $C_1$-$C_4$ alkyl, wherein the alkyl, is independently optionally substituted with one, two, or three —OH, $C_1$-$C_4$ alkyl, $C_1$-$C_4$ haloalkyl, or —$C_1$-$C_4$ alkyl-N(methyl)$_2$;
m is 1 or 2,
n is 1 or 2;
p is 6 or 8; and
q is an integer from 1-10.

In some embodiments, $X^2$ is N. In some embodiments, $X^2$ is $NR^{3a}$. In some embodiments, $X^2$ is $CR^3$. In some embodiments, $X^3$ is N. In some embodiments, $X^3$ is $NR^{3a}$. In some embodiments, $X^3$ is $CR^3$. In some embodiments, $X^4$ is N. In some embodiments, $X^4$ is $NR^3$a. In some embodiments, $X^4$ is $CR^3$. In some embodiments, $X^5$ is N. In some embodiments, $X^5$ is $NR^{3a}$. In some embodiments, $X^5$ is $CR^3$.

In some embodiments, $X^2$ is N; and $X^3$, $X^4$ and $X^5$ are each $CR^3$. In some embodiments, $X^3$ is N; and $X^2$, $X^4$ and $X^5$ are each $CR^3$. In some embodiments, $X^4$ is N; and $X^2$, $X^3$ and $X^5$ are each $CR^3$. In some embodiments, $X^5$ is N; and $X^2$, $X^3$ and $X^5$ are each $CR^3$.

In some embodiments, $X^2$ and $X^3$ are each N; and $X^4$ and $X^5$ are each $CR^3$. In some embodiments, $X^2$ and $X^5$ are N; and $X^3$ and $X^4$ are each $CR^3$. In some embodiments, $X^4$ and $X^5$ are N; and $X^2$ and $X^3$ are each $CR^3$. In some embodiments, $X^3$ and $X^4$ are N; and $X^2$ and $X^5$ are each $CR^3$. In some embodiments, $X^2$, $X^3$ and $X^4$ are each N; and $X^5$ is $CR^3$.

All other substituents are as defined above.

In some embodiments, the compound of Formula (III) has the structure of Formula (IIIb), or a pharmaceutically acceptable salt or solvate thereof:

Formula (IIIb)

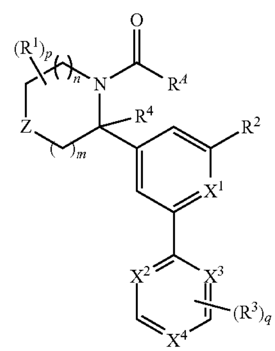

wherein,
$X^2$, $X^3$, and $X^4$ are each independently N, $NR^{3a}$, or $CR^3$;
each $R^{3a}$ is independently H or an optionally substituted $C_1$-$C_6$ alkyl;
each $R^3$ is independently H, D, halogen, oxo (=O), —CN, —OH, —$OR^a$, —SH, —$SR^a$, —S(=O)$R^a$, —$NO_2$, —$N(R^b)_2$, —S(=O)$_2R^a$, —NHS(=O)$_2R^a$, —S(=O)$_2NH_2$, —C(=O)$R^a$, —C(=O)$OR^b$, —C(=O)$NH_2$, —OC(=O)$N(R^b)_2$, —$NR^b$C(=O)$N(R^b)_2$, —$NR^b$C(=O)$R^a$, —$NR^b$C(=O)$OR^b$, optionally substituted $C_1$-$C_6$ alkyl, optionally substituted $C_1$-$C_6$ haloalkyl, optionally substituted $C_1$-$C_6$ hydroxyalkyl, optionally substituted $C_3$-$C_8$ cycloalkyl, or optionally substituted 4 to 8-membered heterocycloalkyl.

In some embodiments, $X^2$ and $X^3$ are each independently N; and $X^4$ is $CR^3$. In some embodiments, $X^2$ and $X^4$ are each independently N; and $X^3$ is $CR^3$. In some embodiments, $X^4$ is N; and $X^2$ and $X^3$ are each $CR^3$. In some embodiments, $X^2$, $X^3$, and $X^4$ are each N.

In some embodiments, ring A is a bicyclic heteroaryl comprising 1, 2, 3, or 4 heteroatoms selected from N, O, and S. In some embodiments, ring A is a bicyclic heteroaryl comprising 1, 2, 3, or 4 heteroatoms selected N.

In some embodiments, ring A is quinoxaline, naphthyridine, imidazopyridine, imidazopyrimidine, pyrrolopyridine, triazolopyridine, or purine. In some embodiments, ring A is quinoxaline or naphthyridine. In some embodiments, ring A is imidazopyridine, imidazopyrimidine, pyrrolopyridine, triazolopyridine, or purine.

All other substituents are as defined above.

In some embodiments, the compound is of Formula (IV), or a pharmaceutically acceptable salt or solvate thereof:

Formula (IV)

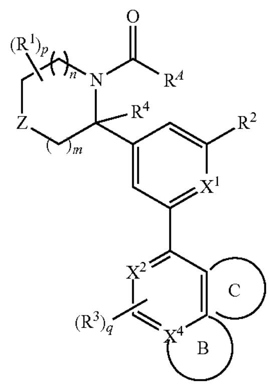

wherein, $X^2$ is N or $CR^3$;

$X^4$ is N or C; and ring B is an optionally substituted 5 to 6-memebered heteroaryl; or ring C is an optionally substituted 5 to 6-membered heteroaryl.

All other substituents are as defined above.

In some embodiments, the compound is of Formula (IVa), or a pharmaceutically acceptable salt or solvate thereof Formula (IVa)

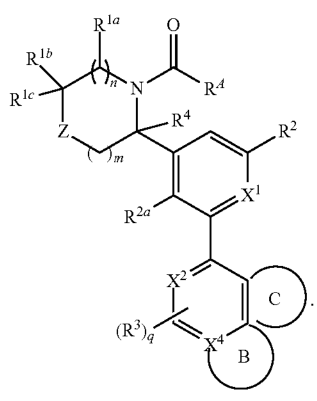

In some embodiments, ring B is an optionally substituted 5 to 6-membered heteroaryl. In some embodiments, ring B is pyridinyl, pyrazinyl, pyrrolyl, furanyl, imidazolyl, pyrazolyl, oxazolyl, or thiophenyl. In some embodiments, ring B is pyridinyl or pyrazinyl. In some embodiments, ring B is pyrrolyl, imidazolyl, or pyrazolyl.

In some embodiments, ring C is an optionally substituted 5 to 6-membered heteroaryl. In some embodiments, ring C is pyridinyl, pyrazinyl, pyrrolyl, furanyl, imidazolyl, pyrazolyl, oxazolyl, or thiophenyl. In some embodiments, ring C is pyridinyl or pyrazinyl. In some embodiments, ring C is pyrrolyl, imidazolyl, or pyrazolyl.

In some embodiments, ring A is a 5-membered heteroaryl comprising 1, 2, 3, or 4 heteroatoms selected from N, O, and S. In some embodiments, ring A is a 5-membered heteroaryl comprising 1, 2, or 3 heteroatoms selected from N or O.

In some embodiments, ring A is triazinyl, pyrrolyl, furanyl, imidazolyl, pyrazolyl, oxazolyl, isoxazolyl, thiophenyl, thiazolyl, isothiazolyl, triazolyl, oxadiazolyl, thiadiazolyl, or tetrazolyl. In some embodiments, ring A is triazinyl, pyrrolyl, imidazolyl, pyrazolyl, or tetrazolyl. In some embodiments, ring A is trizynyl. In some embodiments, ring A is pyrrolyl. In some embodiments, ring A is imidazolyl. In some embodiments, ring A is pyrazolyl.

In some embodiments, ring A is:

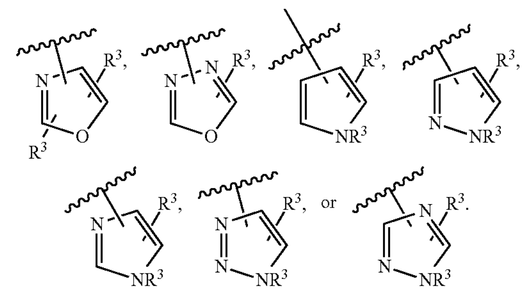

In some embodiments, ring A is:

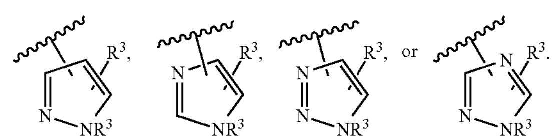

In some embodiments, ring A is:

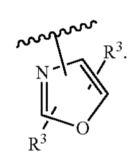

In some embodiments, ring A is:

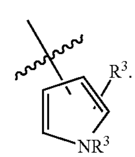

In some embodiments, ring A is:

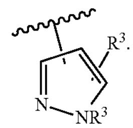

In some embodiments, ring A is:

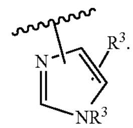

In some embodiments, ring A is

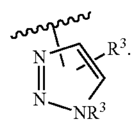

In some embodiments, ring A is

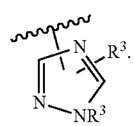

In some embodiments, ring A is a heterocycloalkyl. In some embodiments, the heterocycloalkyl is monocyclic, bicyclic, or polycyclic and can be fully or partially saturated. In some embodiments, the heterocycloalkyl has 1, 2, or 3 heteroatoms selected from N, O, and S.

In some embodiments, the heterocycloalkyl is an optionally substituted piperazine, piperdine, morpholine, tertrahydropyran, pyrrolidine, or tetrahydrofuran.

In some embodiments, ring A is:

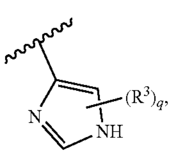
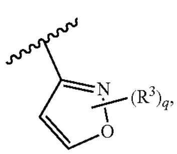
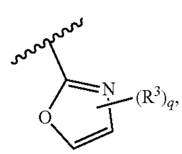
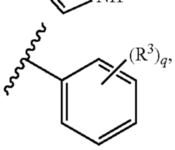
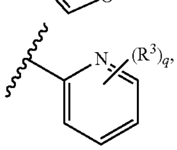
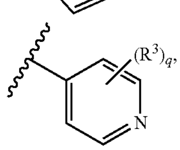
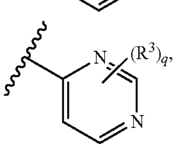
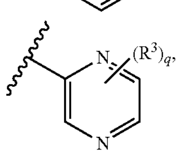
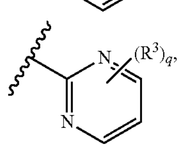

-continued

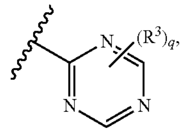
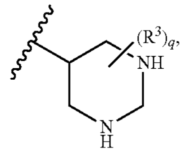
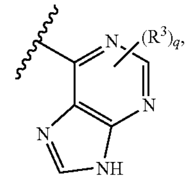
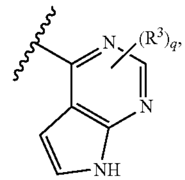
or
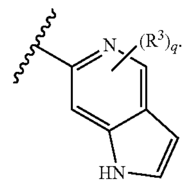

In some embodiments,

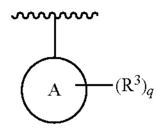
is:

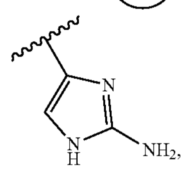
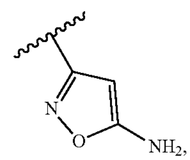
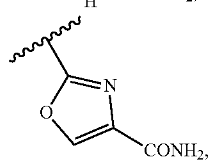
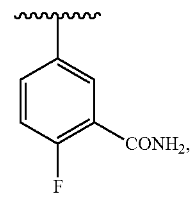
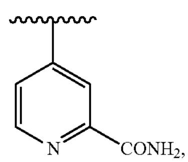
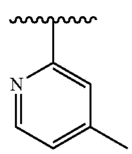
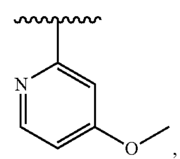
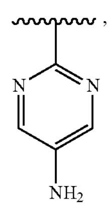
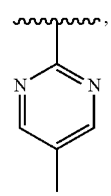
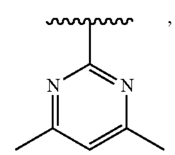
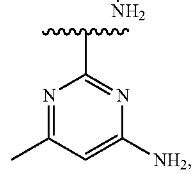
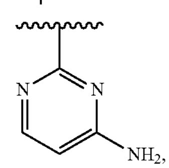
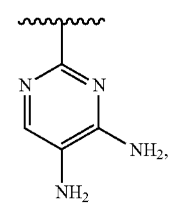
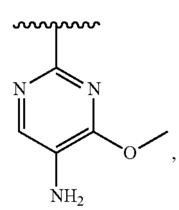
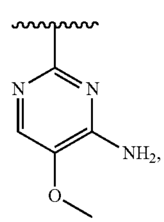
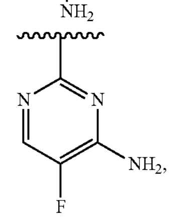

-continued

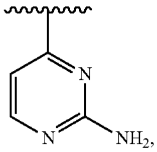 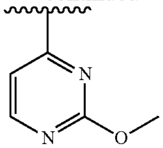, 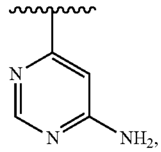

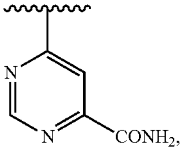 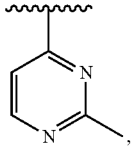, 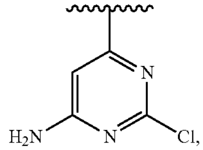

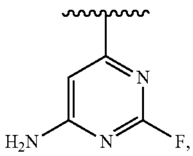 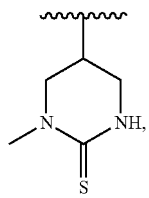 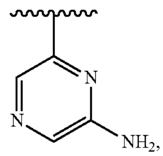

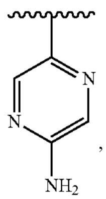, 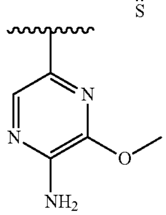, 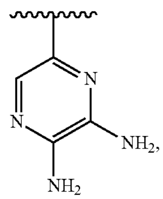

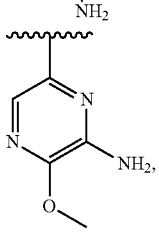 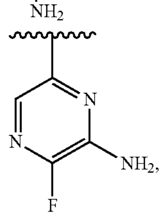 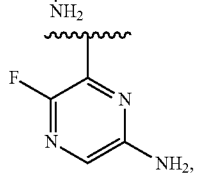

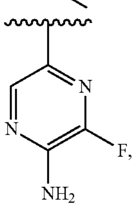 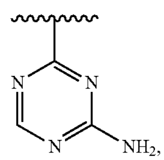 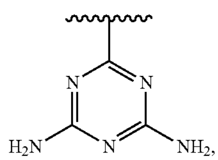

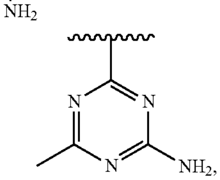 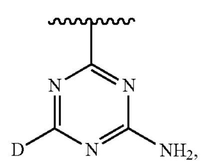

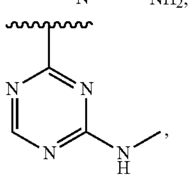, 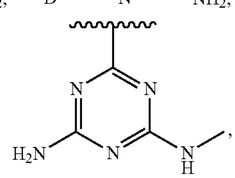,

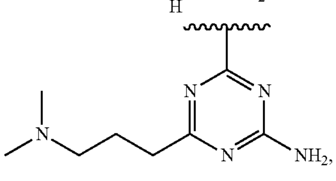 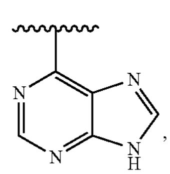,

-continued

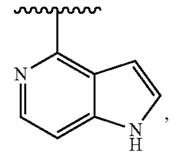, or 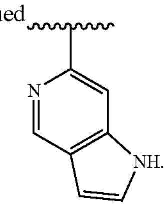

In some embodiments, Z is —O— or —$SO_2$—. In some embodiments, Z is —O—. In some embodiments, Z is —$SO_2$—.

In some embodiments, Z is $C(R^1)_2$. In some embodiments, Z is $CF_2$. In some embodiments, Z is $CH_2$.

In some embodiments, Z is $NR^7$, wherein $R^7$ is —C(═O)$R^{7a}$, S(═O)$R^{7a}$, or S(═O)$_2R^{7a}$. In some embodiments, Z is NC(═O)$R^{7a}$. In some embodiments, Z is NC(═O)$CH_3$. In some embodiments, Z is NC(═O)(cyclopropyl). In some embodiments, Z is NS(═O)$_2R^{7a}$. In some embodiments, Z is NS(═O)$_2CH_3$. In some embodiments, Z is NS(═O)$R^{7a}$.

In some embodiments, $R^{7a}$ is H. In some embodiments, $R^{7a}$ is an optionally substituted $C_1$-$C_6$ alkyl. In some embodiments, $R^{7a}$ is an optionally substituted $C_3$-$C_7$ cycloalkyl. In some embodiments, $R^{7a}$ is cyclopropyl, cyclobutyl, cyclopentyl, or cyclohexyl. In some embodiments, $R^{7a}$ is cyclopropyl, cyclobutyl or cyclopentyl. In some embodiments, $R^{7a}$ is cyclopropyl.

In some embodiments, each $R^1$ is independently H, halogen, —OH, optionally substituted $C_1$-$C_6$ alkyl, optionally substituted $C_1$-$C_6$ haloalkyl, optionally substituted $C_1$-$C_6$ hydroxyalkyl, or —C(═O)N$(R^b)_2$.

In some embodiments, each $R^1$ is independently H, halogen, or —OH, In some embodiments, each $R^1$ is independently an optionally substituted $C_1$-$C_6$ alkyl or optionally substituted $C_1$-$C_6$ haloalkyl. In some embodiments, each $R^1$ is independently H, F, Cl, OH, $CH_3$, $CF_3$, or $CHF_2$. In some embodiments, each $R^1$ is independently H, F, or $CH_3$. In some embodiments, each $R^1$ is independently H or $CH_3$. In some embodiments, each $R^1$ is independently —C(═O)N$(R^b)_2$. In some embodiments, each $R^1$ is independently —C(═O)N$(CH_3)_2$, —C(═O)NHCH$_3$, or —C(═O)NH$_2$.

In some embodiments, two $R^1$ are taken together with the atom(s) to which they are attached form an optionally substituted $C_3$-$C_8$ cycloalkyl or an optionally substituted 3 to 8-membered heterocycloalkyl. In some embodiments, two $R^1$ on the same carbon atom or on adjacent carbon atoms are taken together with the atom(s) to which they are attached form an optionally substituted $C_3$-$C_8$ cycloalkyl. In some embodiments, two $R^1$ are taken together with the atom(s) to which they are attached form a cyclopropyl, cyclobutyl, cyclopentyl, or cyclohexyl. In some embodiments, two $R^1$ are taken together with the atoms to which they are attached to form a cyclopropyl, cyclobutyl, or cyclopentyl. In some embodiments, two $R^1$ are taken together with the atoms to which they are attached to form a cyclopropyl. In some embodiments, two $R^1$ are taken together with the atoms to which they are attached to form a cyclobutyl. In some embodiments, two $R^1$ are taken together with the atoms to which they are attached to form a cyclopentyl.

In some embodiments, two $R^1$ on the same carbon atom or on adjacent carbon atoms are taken together with the atom(s) to which they are attached form an optionally substituted 3 to 8-membered heterocycloalkyl. In some embodiments, two $R^1$ are taken together with the atom(s) to which they are attached to form a 4 to 6-membered heterocyclic ring. In some embodiments, two $R^1$ are taken together with the atom(s) to which they are attached to form an oxetenyl.

In some embodiments, $X^1$ is N. In some embodiments, $X^1$ is $CR^2$.

In some embodiments, $R^2$ is an optionally substituted $C_1$-$C_6$ alkyl, optionally substituted $C_1$-$C_6$ haloalkyl, or optionally substituted $C_1$-$C_6$ hydroxyalkyl. In some embodiments, $R^2$ is halogen or CN. In some embodiments, $R^2$ is halogen. In some embodiments, $R^2$ is Cl or F. In some embodiments, $R^2$ is Cl. In some embodiments, $R^2$ is F. In some embodiments, $R^2$ is CN.

In some embodiments, each $R^3$ is independently H, halogen, oxo (=O), —CN, —OH, —$OR^a$, —SH, —$SR^a$, —S(=O)$R^a$, —$NO_2$, —$N(R^b)_2$, —$S(=O)_2R^a$, —NHS$(=O)_2R^a$, —$S(=O)_2N(R^b)_2$, —C(=O)$R^a$, —C(=O)$OR^b$, —C(=O)$NH_2$, —OC(=O)$N(R^b)_2$, —$NR^b$C(=O)$N(R^b)_2$, —$NR^b$C(=O)$R^a$, —$NR^b$C(=O)$OR^b$, optionally substituted $C_1$-$C_6$ alkyl, optionally substituted $C_1$-$C_6$haloalkyl, optionally substituted $C_1$-$C_6$ hydroxyalkyl, optionally substituted $C_3$-$C_8$ cycloalkyl, or optionally substituted 4 to 8-membered heterocycloalkyl. In some embodiments, each $R^3$ is independently H, halogen, oxo (=O), —CN, —OH, —$OR^a$, —$N(R^b)_2$, —C(=O)$R^a$, —C(=O)$OR^b$, —C(=O)$NH_2$, —OC(=O)$N(R^b)_2$, —$NR^b$C(=O)$N(R^b)_2$, —$NR^b$C(=O)$R^a$, —$NR^b$C(=O)$OR^b$, optionally substituted $C_1$-$C_6$ alkyl, optionally substituted $C_1$-$C_6$ haloalkyl, optionally substituted $C_1$-$C_6$ hydroxyalkyl, or optionally substituted 4 to 8-membered heterocycloalkyl.

In some embodiments, each $R^3$ is independently an optionally substituted $C_1$-$C_6$ alkyl, optionally substituted $C_1$-$C_6$haloalkyl, or optionally substituted $C_1$-$C_6$ hydroxyalkyl. In some embodiments, each $R^3$ is independently $CH_3$, $CF_3$, $CHF_2$, or —$OCH_3$.

In some embodiments, each $R^3$ is independently an optionally substituted $C_3$-$C_8$ cycloalkyl or optionally substituted 4 to 8-membered heterocycloalkyl. In some embodiments, each $R^3$ is independently an optionally substituted 4 to 8-membered heterocycloalkyl.

In some embodiments, each $R^3$ is independently H, halogen, —$N(R^b)_2$, —C(=O)$R^a$, —C(=O)$OR^b$, or —C(=O)$NH_2$. In some embodiments, each $R^3$ is independently H, Cl, F, —$NH_2$, or —C(=O)$NH_2$. In some embodiments, each $R^3$ is independently H, —$NH_2$, or —C(=O)$NH_2$.

In some embodiments, each $R^3$ is independently H.

In some embodiments, each $R^3$ is independently oxo (=O).

In some embodiments, or two $R^3$ or two $R^{3a}$ or an $R^3$ and $R^{3a}$ on adjacent atoms combine together with the atom(s) to which they are attached to form an optionally substituted aryl, optionally substituted heteroaryl ring, or optionally substituted heterocycloalkyl.

In some embodiments, two $R^3$ on adjacent atoms combine together with the atom(s) to which they are attached to form an optionally substituted aryl, optionally substituted heteroaryl ring, or optionally substituted heterocycloalkyl. In some embodiments, two $R^3$ on adjacent atoms combine together with the atom(s) to which they are attached to form an optionally substituted aryl. In some embodiments, two $R^3$ on adjacent atoms combine together with the atom(s) to which they are attached to form an optionally substituted heteroaryl. In some embodiments, two $R^3$ on adjacent atoms combine together with the atom(s) to which they are attached to form an optionally substituted heterocycloalkyl.

In some embodiments, two $R^{3a}$ on adjacent atoms combine together with the atom(s) to which they are attached to form an optionally substituted aryl, optionally substituted heteroaryl ring, or optionally substituted heterocycloalkyl.

In some embodiments, $R^3$ and $R^{3a}$ on adjacent atoms combine together with the atom(s) to which they are attached to form an optionally substituted aryl, optionally substituted heteroaryl ring, or optionally substituted heterocycloalkyl.

In some embodiments, each $R^{3a}$ is independently H or an optionally substituted $C_1$-$C_6$ alkyl. In some embodiments, each $R^{3a}$ is independently an optionally substituted $C_1$-$C_6$ alkyl. In some embodiments, each $R^{3a}$ is independently methyl or ethyl. In some embodiments, each $R^{3a}$ is independently H.

In some embodiments, $R^4$ is optionally substituted $C_1$-$C_6$ alkyl. In some embodiments, $R^4$ is methyl or ethyl. In some embodiments, $R^4$ is methyl. In some embodiments, $R^4$ is H.

In some embodiments, $R^A$ is a reactive group comprising a Michael acceptor. In some embodiments, $R^A$ is a reactive group capable of forming a bond with a sulfur group.

In some embodiments, $R^A$ is:

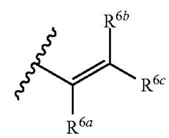

wherein;

$R^{6a}$ is H, D, halogen, or $C_1$-$C_6$haloalkyl, and $R^{6b}$ and $R^{6c}$ are each independently H or D;

or $R^{6b}$ and $R^{6d}$ together with the carbon atom to which they are attached form a cyclopropyl ring.

In some embodiments, $R^{6a}$ is H or D. In some embodiments, $R^{6a}$ is H. In some embodiments, $R^{6a}$ is D. In some embodiments, $R^{6a}$ is halogen. In some embodiments, $R^{6a}$ is Br, Cl, or F. In some embodiments, $R^{6a}$ is Br. In some embodiments, $R^{6a}$ is Cl. In some embodiments. $R^{6a}$ is F. In some embodiments, $R^{6a}$ is $C_1$-$C_6$haloalkyl. In some embodiments, $R^{6a}$ is $CF_3$ or $CHF_2$.

In some embodiments, $R^{6b}$ and $R^{6c}$ are each independently H. In some embodiments, $R^{6b}$ and $R^{6c}$ are each independently D. In embodiments, $R^{6b}$ is H and $R^{6c}$ is D. In some embodiments, $R^{6b}$ is D and $R^{6c}$ is H.

In some embodiments, $R^{6b}$ and $R^{6d}$ together with the carbon atom to which they are attached form a cyclopropyl ring.

In some embodiments, $R^A$ is

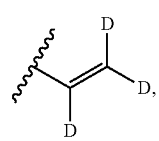 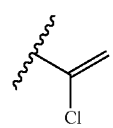, 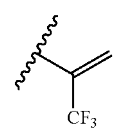, 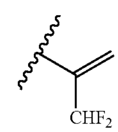,

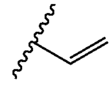, or 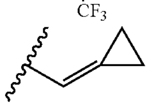.

In some embodiments, $R^A$ is

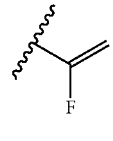, 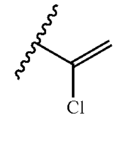, 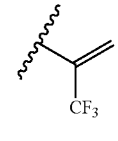, 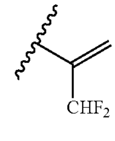, or

-continued

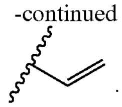

In some embodiments, $R^A$ is

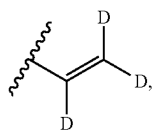 , 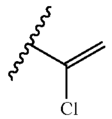 , or 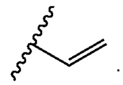

In some embodiments, $R^A$ is

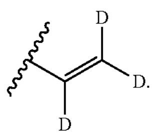

In some embodiments, $R^A$is

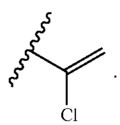 [SMILES: *C(=C)Cl ; "."]

In some embodiments, $R^A$ is

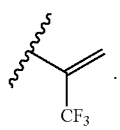 [SMILES: *C(=C)C(F)(F)F ; "."]

In some embodiments, $R^A$ is

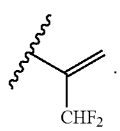

In some embodiments, $R^A$ is

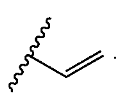 [SMILES: *C=C ; "."]

In some embodiments, m is 1, 2, or 3. In some embodiments, m is 1, or 2. In some embodiments, m is 2. In some embodiments, m is 1.

In some embodiments, n is 0, 1, 2, or 3. In some embodiments, n is 1 or 2. In some embodiments, n is 2. In some embodiments, n is 1.

In some embodiments, p is an integer from 1, 2, 3, 4, 5, 6, 7, 8, 9, 10, 11, or 12. In some embodiments, p is an integer from 1, 2, 3, 4, 5, 6, 7, 8, 9, or 10. In some embodiments, p is an integer from 1, 2, 3, 4, 5, 6, 7, or 8. In some embodiments, p is an integer from 1, 2, 3, 4, 5, or 6. In some embodiments, p is 1, 2, 3, or 4. In some embodiments, p is 1 or 2. In some embodiments, p is 3. In some embodiments, p is 2. In some embodiments, p is 1.

In some embodiments, q is an integer from 1, 2, 3, 4, 5, 6, 7, 8, 9, or 10. In some embodiments, q is 1, 2, 3, 4, or 5. In some embodiments, q is 1, 2, or 3. In some embodiments, q is 1 or 2. In some embodiments, q is 3. In some embodiments, q is 2. In some embodiments, q is 1.

In some embodiments, each $R^a$ is independently $C_1$-$C_6$ alkyl, $C_1$-$C_6$ heteroalkyl, cycloalkyl, heterocycloalkyl, aryl, heteroaryl, —$C_1$-$C_6$ alkyl(aryl), —$C_1$-$C_6$ alkyl(heteroaryl), —$C_1$-$C_6$ alkyl(cycloalkyl), or —$C_1$-$C_6$ alkyl(heterocycloalkyl); wherein each alkyl, heteroalkyl, cycloalkyl, heterocycloalkyl, aryl, and heteroaryl is independently optionally substituted with one, two, or three —OH, $C_1$-$C_6$ alkyl, or $C_1$-$C_6$ haloalkyl. In some embodiments, each $R^a$ is independently $C_1$-$C_6$ alkyl, $C_1$-$C_6$ heteroalkyl, cycloalkyl, heterocycloalkyl, aryl, or heteroaryl; wherein the alkyl, heteroalkyl, cycloalkyl, heterocycloalkyl, aryl, and heteroaryl is independently optionally substituted with one, two, or three —OH, $C_1$-$C_6$ alkyl, or $C_1$-$C_6$ haloalkyl. In some embodiments each $R^a$ is independently $C_1$-$C_6$ alkyl or $C_1$-$C_6$ heteroalkyl; wherein the alkyl or heteroalkyl is independently optionally substituted with one, two, or three —OH, $C_1$-$C_6$ alkyl, or $C_1$-$C_6$ haloalkyl.

In some embodiments, each $R^b$ is independently hydrogen, $C_1$-$C_6$ alkyl, $C_1$-$C_6$ heteroalkyl, cycloalkyl, heterocycloalkyl, aryl, or heteroaryl; wherein the alkyl, heteroalkyl, cycloalkyl, heterocycloalkyl, aryl, and heteroaryl is independently optionally substituted with one, two, or three —OH, $C_1$-$C_6$ alkyl, or $C_1$-$C_6$ haloalkyl. In some embodiments, each $R^b$ is independently hydrogen, $C_1$-$C_6$ alkyl, $C_1$-$C_6$ heteroalkyl, cycloalkyl, heterocycloalkyl, aryl, or heteroaryl; wherein the alkyl, heteroalkyl, cycloalkyl, heterocycloalkyl, aryl, and heteroaryl is independently optionally substituted with one, two, or three —OH, $C_1$-$C_6$ alkyl, or $C_1$-$C_6$ haloalkyl. In some embodiments, each $R^b$ is independently hydrogen, $C_1$-$C_6$ alkyl or $C_1$-$C_6$ heteroalkyl; wherein the alkyl or heteroalkyl is independently optionally substituted with one, two, or three —OH, $C_1$-$C_6$ alkyl, or $C_1$-$C_6$ haloalkyl. In some embodiments, each $R^b$ is hydrogen.

In some embodiments, two $R^b$ groups on a nitrogen atom are taken together with the nitrogen atom to which they are attached to form a heterocycloalkyl which is optionally substituted with one, two, or three $C_1$-$C_6$ alkyl, or $C_1$-$C_6$ haloalkyl. In some embodiments, two $R^b$ groups on a nitrogen atom are taken together with the nitrogen atom to which they are attached to form a 3- to 7-membered heterocycloalkyl which is optionally substituted with one, two, or three $C_1$-$C_6$ alkyl, or $C_1$-$C_6$ haloalkyl. In some embodiments, two $R^b$ groups on a nitrogen atom are taken together with the nitrogen atom to which they are attached to form a 5- or 6-membered heterocycloalkyl which is optionally substituted with one, two, or three $C_1$-$C_6$ alkyl, or $C_1$-$C_6$ haloalkyl. In some embodiments, two $R^b$ groups on a nitrogen atom are taken together with the nitrogen atom to which they are attached to form pyrrolidine, piperidine, or morpholine which is optionally substituted with one, two, or three $C_1$-$C_6$ alkyl, or $C_1$-$C_6$ haloalkyl. In some embodiments, two $R^b$ groups on a nitrogen atom are taken together with the nitrogen atom to which they are attached to form pyrrolidine, piperidine, or morpholine.

Any combination of the groups described above for the various variables is contemplated herein. Throughout the specification, groups and substituents thereof are chosen by one skilled in the field to provide stable moieties and compounds.

The compounds of Formula (I), (II), (III), (IIIa), (IIIb), (IV), or (IVa) can be present in chiral or achiral form. The form may either be racemic or R or S configuration.

Compounds of the disclosure include, but are not limited to:

TABLE 1

Compounds of the Disclosure.

| Structure | No. | Name | Stereochemistry | NMR |
|---|---|---|---|---|
| 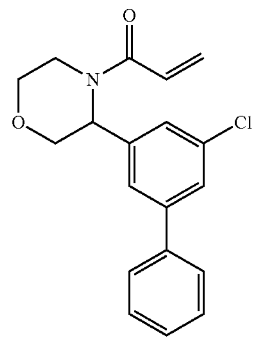 [SMILES: C=CC(=O)N1CCOCC1c1cc(Cl)cc(-c2ccccc2)c1] | 1 | 1-(3-(5-chloro-[1,1'-biphenyl]-3-yl)morpholino)prop-2-en-1-one | racemic | 1H NMR (400 MHz, CHLOROFORM-d) δ ppm 7.33-7.65 (m, 8 H) 6.51-6.64 (m, 1 H) 6.36-6.48 (m, 1 H) 5.79 (dd, J = 10.42, 1.88 Hz, 2 H) 4.50 (d, J = 12.30 Hz, 1 H) 3.80-4.03 (m, 2 H) 3.10-3.72 (m, 3 H) |
| 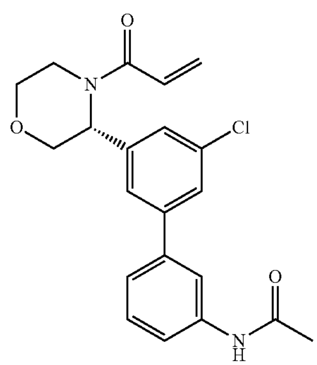 [SMILES: C=CC(=O)N1CCOC[C@H]1c1cc(Cl)cc(-c2cccc(NC(C)=O)c2)c1] | 2 | (R)-N-(3'-(4-acryloylmorpholin-3-yl)-5'-chloro-[1,1'-biphenyl]-3-yl)acetamide | Single enantiomer of known absolute configuration | 1H NMR (399 MHz, CHOROFORM-d) δ ppm 7.47-7.67 (m, 4 H) 7.40 (t, J = 7.89 Hz, 1 H) 7.29 (td d, J = 7.89 Hz, 1 H) 6.53-6.62 (m, 1 H) 6.36-6.45 (m, 1 H) 5.47-5.89 (m, 2 H) 4.49 (d, J = 12.28 Hz, 1 H) 3.17-4.04 (m, 5 H) 2.22 (s, 3 H) |
| 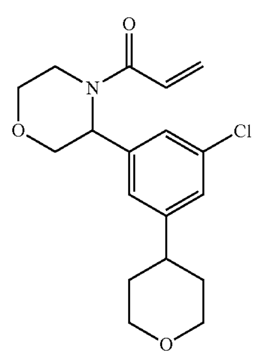 [SMILES: C=CC(=O)N1CCOCC1c1cc(Cl)cc(C2CCOCC2)c1] | 5 | 1-(3-(3-chloro-5-(tetrahydro-2H-pyran-4-yl)phenyl)morpholino)prop-2-en-1-one | Single enantiomer of unknown absolute configuration | 1H NMR (400 MHz, CHLOROFORM-d) δ ppm 7.36 (br s, 1 H) 7.01-7.23 (m, 2 H) 6.49-6.62 (m, 1 H) 6.34-6.46 (m, 1 H) 5.78 (dd, J = 10.42, 1.88 Hz, 1 H) 4.31-4.49 (m, 1 H) 3.81-4.14 (m, 2 H) 3.72-4.00 (m, 3 H) 3.33-3.64 (m, 5 H) 2.75 (tt, J = 10.51, 5.36 Hz, 1 H) 1.71-1.81 (m, 4 H |
| 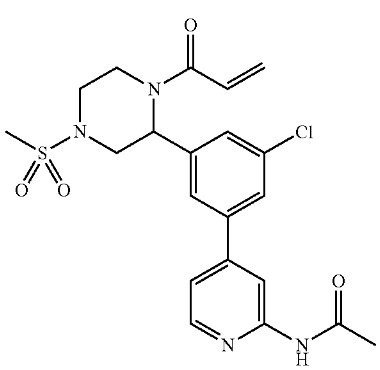 [SMILES: C=CC(=O)N1CCN(S(C)(=O)=O)CC1c1cc(Cl)cc(-c2ccnc(NC(C)=O)c2)c1] | 6 | N-(4-(3-(1-acryloyl-4-(methylsulfonyl)piperazin-2-yl)-5-chlorophenyl)pyridin-2-yl)acetamide | Single enantiomer of unknown absolute configuration | 1H NMR (399 MHz, CHLOROFORM-d) δ = 8.43 (br s, 1H), 8.34-8.26 (m, 2H), 7.72-7.57 (m, 2H), 7.42 (br s, 1H), 7.30-7.27 (m, 1H), 6.68-6.58 (m, 1H), 6.50-6.44 (m, 1H), 6.05 (br s, 1H), 5.89-5.84 (m, 1H), 4.47 (br d, J = 12.7 Hz, 1H), 3.89-3.69 (m, 1H), 3.30-3.10 (m, 2H), 3.02-2.71 (m, 4H), 2.27-2.21 (m, 3H) |

TABLE 1-continued

| Compounds of the Disclosure. | | | | |
|---|---|---|---|---|
| Structure | No. | Name | Stereochemistry | NMR |
| 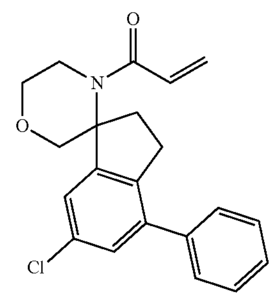 [SMILES: C=CC(=O)N1CCOCC12CCc1c(-c3ccccc3)cc(Cl)cc12] | 7 | 1-(5-chloro-7-phenyl-2H-spiro[benzofuran-3',3'-morpholin'-4'-yl)prop-2-en-1-one | racemic | 1H NMR (400 MHz, CHLOROFORM-d) ppm 3.30-3.40 (m, 1 H) 3.30-3.40 (m, 1 H) 3.57-3.63 (m, 1 H) 3.68-3.74 (m, 1 H) 3.79-4.00 (m, 3 H) 4.58-4.71 (m, 2 H) 5.56 (dd, J = 10.42, 1.63 Hz, 1 H) 6.12-6.21 (m, 1 H) 6.27-6.39 (m, 1 H) 6.95 (d, J = 2.13 Hz, 1 H) 7.23-7.30 (m, 2 H) 7.33-7.40 (m, 2 H) 7.58-7.65 (m, 2 H) |
| 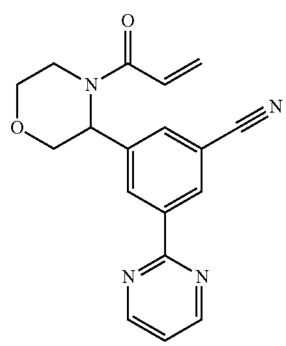 [SMILES: C=CC(=O)N1CCOCC1c1cc(C#N)cc(-c2ncccn2)c1] | 8 | 3-(4-acryloylmorpholin-3-yl)-5-(pyrimidin-2-yl)benzonitrile | Single enantiomer of unknown absolute configuration | 1H NMR (400 MHz, CHLOROFORM-d) δ ppm 8.04-8.21 (m, 2 H) 7.50-7.63 (m, 1 H) 7.27 (s, 1 H) 6.52-6.64 (m, 1 H) 6.35-6.50 (m, 1 H) 5.80 (dd, J = 10.42, 1.88 Hz, 2 H) 4.48-4.58 (m, 1 H) 4.51 (d, J = 12.17 Hz, 1 H) 4.41 (s, 3 H) 3.85-4.06 (m, 2 H) |
| 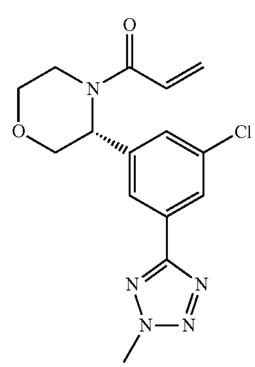 [SMILES: C=CC(=O)N1CCOC[C@H]1c1cc(Cl)cc(-c2nnn(C)n2)c1] | 9 | (R)-1-(3-(3-chloro-5-(2-methyl-2H-tetrazol-5-yl)phenyl)morpholino)prop-2-en-1-one | Single enantiomer of known absolute configuration | 1H NMR (400 MHz, CHLOROFORM-d) δ ppm 8.04-8.21 (m, 2 H) 7.50-7.63 (m, 1 H) 7.27 (s, 1 H) 6.52-6.64 (m, 1 H) 6.35-6.50 (m, 1 H) 5.80 (dd, J = 10.42, 1.88 Hz, 2 H) 4.48-4.58 (m, 1 H) 4.51 (d, J = 12.17 Hz, 1 H) 4.41 (s, 3 H) 3.85-4.06 (m, 2 H) |
| 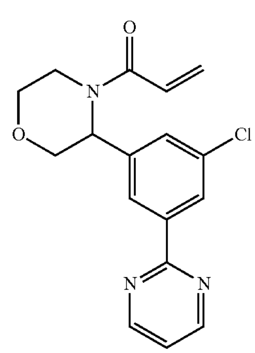 [SMILES: C=CC(=O)N1CCOCC1c1cc(Cl)cc(-c2ncccn2)c1] | 10 | (R)-1-(3-(3-chloro-5-(pyrimidin-2-yl)phenyl)morpholino)prop-2-en-1-one | Single enantiomer of known absolute configuration | 1H NMR (400 MHz, CHLOROFORM-d) δ ppm 2.97-3.92 (m, 3 H) 3.92-4.03 (m, 2 H) 4.56 (d, J = 12.06 Hz, 1 H) 5.79 (d, J = 10.30 Hz, 2 H) 6.35-6.50 (m, 1 H) 6.53-6.70 (m, 1 H) 7.24 (t, J = 4.71 Hz, 1 H) 7.47-7.67 (m, 1 H) 8.29-8.60 (m, 2 H) 8.82 (d, J = 4.82 Hz, 2 H) |

TABLE 1-continued

Compounds of the Disclosure.

| Structure | No. | Name | Stereochemistry | NMR |
|---|---|---|---|---|
| 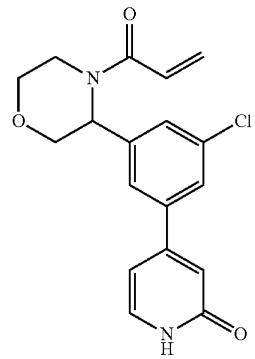 | 11 | 4-(3-(4-acryloylmorpholin-3-yl)-5-chlorophenyl)pyridin-2(1H)-one | Single enantiomer of unknown absolute configuration | 1H NMR (400 MHz, CHLOROFORM-d) δ = 7.60 (br s, 2H), 7.52-7.47 (m, 2H), 6.76 (s, 1H), 6.63-6.49 (m, 2H), 6.46-6.36 (m, 1H), 5.79 (dd, J = 1.6, 10.4 Hz, 2H), 4.45 (d, J = 12.2 Hz, 1H), 4.03-3.85 (m, 2H), 3.83-2.91 (m, 3H) |
| 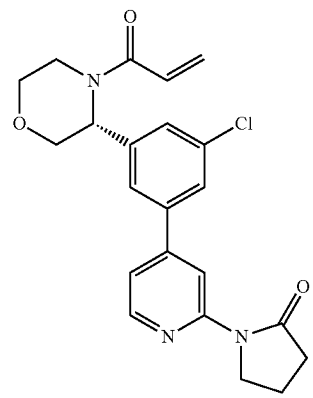 [SMILES: C=CC(=O)N1CCOC[C@H]1c1cc(Cl)cc(-c2ccnc(N3CCCC3=O)c2)c1] | 12 | (R)-1-(4-(3-(4-acryloylmorpholin-3-yl)-5-chlorophenyl)pyridin-2-yl)pyrrolidin-2-one | Single enantiomer of known absolute configuration | 1H NMR (400 MHz, CHLOROFORM-d) δ ppm 1.15-1.30 (m, 1 H) 2.15 (quin, J = 7.59 Hz, 2 H) 2.68 (t, J = 8.03 Hz, 2H) 2.74-3.73 (m, 1 H) 3.48-3.71 (m, 1 H) 3.80-4.02 (m, 2 H) 4.05-4.20 (m, 2 H) 4.47 (d, J = 12.30 Hz, 1 H) 5.77 (dd, J = 10.42, 1.38 Hz, 2 H) 6.27-6.46 (m, 1 H) 6.49-6.64 (m, 1 H) 7.19 (br d, J = 4.64 Hz, 1 H) 7.51-7.71 (m 3 H) 8.38 (d, J = 5.27 Hz, 1 H) 8.61 (s, 1 H) |
| 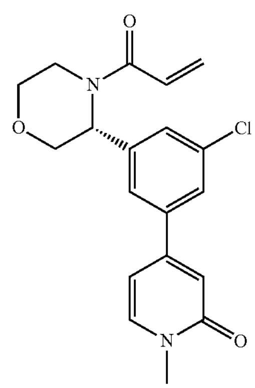 [SMILES: C=CC(=O)N1CCOC[C@H]1c1cc(Cl)cc(-c2ccn(C)c(=O)c2)c1] | 13 | (R)-4-(3-(4-acryloylmorpholin-3-yl)-5-chlorophenyl)-1-methylpyridin-2(1H)-one | Single enantiomer of known absolute configuration | 1H NMR (400 MHz, CHLOROFORM-d) δ ppm 7.42-7.68 (m, 3 H) 7.36 (d, J = 7.03 Hz, 1 H) 6.76 (d, J = 1.63 Hz, 1 H) 6.50-6.64 (m, 1 H) 6.33-6.47 (m, 2 H) 5.80 (dd, J = 10.35, 1.82 Hz, 1 H) 5.16-6.07 (m, 1 H) 4.45 (d, J = 12.42 Hz, 1 H) 3.95-4.02 (m, 1 H) 3.99 (dd, J = 11.2,3 3.20 Hz, 1 H) 3.90 (dd, J = 12.30, 3.64 Hz, 1 H) 2.51-3.83 (m, 6 H) |
| 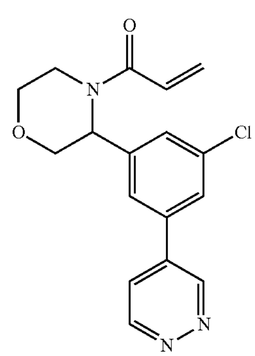 | 14 | 1-(3-(3-chloro-5-(pyridazin-4-yl)phenyl)morpholino)prop-2-en-1-one | Single enantiomer of unknown absolute configuration | 1H NMR (400 MHz, CHLOROFORM-d) δ ppm 3.19-3.83 (m, 3 H) 3.88-4.06 (m, 2 H) 4.48 (d, J = 12.42 Hz, 1 H) 5.82 (dd, J = 10.35, 1.82 Hz, 2 H) 6.34-6.49 (m, 1 H) 6.51-6.65 (m, 1 H) 7.50-7.86 (m, 4 H) 9.27 (d, J = 5.27 Hz, 1 H) 9.43 (d, J = 1.25 Hz, 1 H) |

TABLE 1-continued

| Compounds of the Disclosure. | | | | |
|---|---|---|---|---|
| Structure | No. | Name | Stereochemistry | NMR |
| 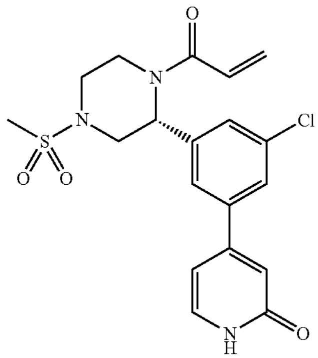 [SMILES: C=CC(=O)N1CCN(S(C)(=O)=O)C[C@H]1c1cc(Cl)cc(-c2cc[nH]c(=O)c2)c1] | 15 | (R)-4-(3-(1-acryloyl-4-(methylsulfonyl)piperazin-2-yl)-5-chlorophenyl)pyridin-2(1H)-one | Single enantiomer of known absolute configuration | 1H NMR (400 MHz, CHLOROFORM-d) δ ppm 7.63 (br s, 1 H) 7.53 (s, 1 H) 7.45 (br d, J = 6.65 Hz, 2 H) 6.77 (s, 1 H) 6.59-6.67 (m, 1 H) 6.56 (br d, J = 6.90 Hz, 1H) 6.42-6.52 (m, 1 H) 6.42-6.52 (m, 1 H) 5.88 (d, J = 10.79 Hz, 1 H) 4.46 (br d, J = 12.67 Hz, 1 H) 3.49-4.11 (m, 2 H) 3.16 (br d, J = 9.41 Hz, 2 H) 2.84-2.95 (m, 1 H) 2.83 (s, 3 H) |
| 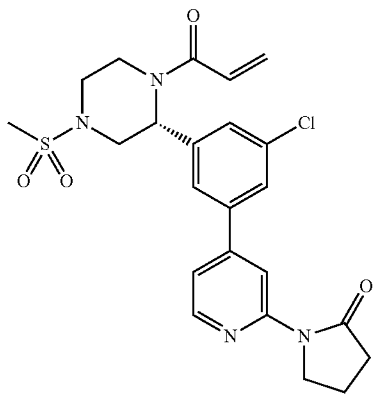 [SMILES: C=CC(=O)N1CCN(S(C)(=O)=O)C[C@H]1c1cc(Cl)cc(-c2ccnc(N3CCCC3=O)c2)c1] | 16 | (R)-1-(4-(3-(1-acryloyl-4-(methylsulfonyl)piperazin-2-yl)-5-chlorophenyl)pyridin-2-yl)pyrrolidin-2-one | Single enantiomer of known absolute configuration | 1H NMR (400 MHz, CHLOROFORM-d) δ ppm 8.63 (s, 1 H) 8.42 (d, J = 5.13 Hz, 1 H) 7.60-7.69 (m, 2 H) 7.41 (br s, 1 H) 7.28 (br s, 1 H) 6.57-6.69 (m, 1 H) 6.41-6.53 (m, 1 H) 5.63-6.23 (m, 1 H) 5.86 (dd, J = 10.45, 1.41 Hz, 1 H) 4.47 (br d, J = 12.59 Hz, 1 H) 4.15 (t, J = 7.09 Hz, 3 H) 3.75 (br d, J = 11.13 Hz, 1 H) 3.03-3.38 (m, 2 H) 2.78-2.93 (m 4 H) 2.69 (t, J = 8.07 Hz, 2 H) 2.17 (quin, J = 7.58 Hz, 2 H) |
| 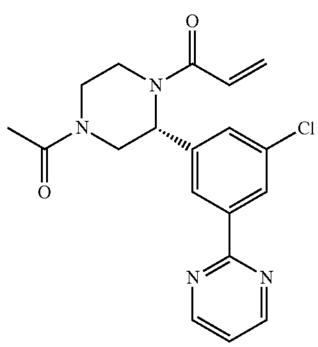 [SMILES: C=CC(=O)N1CCN(C(C)=O)C[C@H]1c1cc(Cl)cc(-c2ncccn2)c1] | 17 | (R)-1-(4-acetyl-2-(3-chloro-5-(pyrimidin-2-yl)phenyl)piperazin-1-yl)prop-2-en-1-one | Single enantiomer of known absolute configuration | 1H NMR (400 MHz, CHLOROFORM-d) δ ppm 8.81 (d, J = 4.85 Hz, 2 H) 8.27-8.46 (m, 2 H) 7.30-7.44 (m, 1 H) 7.21-7.27 (m, 1 H) 6.20-6.79 (m, 2 H) 5.10-6.08 (m, 2 H) 4.14-4.98 (m, 2 H) 3.57-4.09 (m, 2 H) 2.96-3.55 (m, 2 H) 2.04-2.18 (m, 3 H) |
| 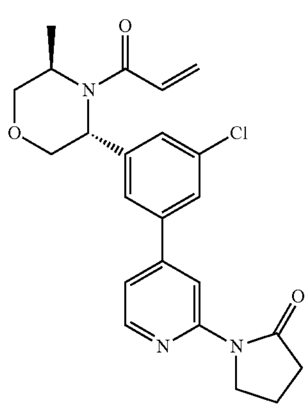 [SMILES: C=CC(=O)N1[C@H](C)COC[C@H]1c1cc(Cl)cc(-c2ccnc(N3CCCC3=O)c2)c1] | 18 | 1-(4-(3-((3R,5R)-4-acryloyl-5-methylmorpholin-3-yl)-5-chlorophenyl)pyridin-2-yl)pyrrolidin-2-one | Single enantiomer of known absolute configuration | 1H NMR (400 MHz, CHLOROFORM-d) δ ppm 1.44 (d, J = 6.78 Hz, 3 H) 2.17 (quin, J = 7.62 Hz, 2 H) 2.70 (t, J = 8.09 Hz, 2H) 3.57-3.76 (m, 1 H) 3.81 (br d, J = 11.67 Hz, 1 H) 3.99 (dd, J = 11.67, 3.14 Hz, 1 H) 4.16 (t, J = 7.09 Hz, 3 H) 4.23-4.35 (m, 1 H) 4.82-4.92 (m, 1 H) 5.61-5.74 (m, 1 H) 6.29-6.37 (m, 1 H) 6.40-6.68 (m, 1 H) 7.20 (dd, J = 5.21, 1.57 Hz, 1 H) 7.31 (s, 1 H) 7.44 (s, 1 H) 7.52 (s, 1 H) 8.40 (d, J = 5.27 Hz, 1 H) 8.63 (d, J = 0.88 Hz, 1 H) |

TABLE 1-continued

| Compounds of the Disclosure. | | | | |
|---|---|---|---|---|
| Structure | No. | Name | Stereochemistry | NMR |
| 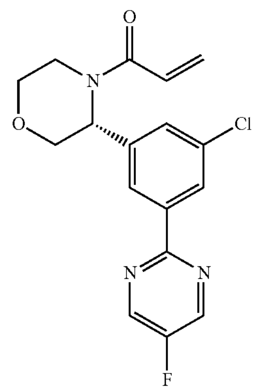 [SMILES: C=CC(=O)N1CCOC[C@H]1c1cc(Cl)cc(-c2ncc(F)cn2)c1] | 19 | (R)-1-(3-(3-chloro-5-(5-fluoropyrimidin-2-yl)phenyl)morpholino)prop-2-en-1-one | Single enantiomer of known absolute configuration | 1H NMR (400 MHz, CHLOROFORM-d) δ ppm 8.65-8.68 (m, 2 H) 8.30-8.50 (m, 2 H) 7.44-7.68 (m, 1 H) 6.59 (dd, J = 16.81, 10.42 Hz, 1 H) 6.43 (dd, J = 16.69, 1.88 Hz, 1 H) 5.79 (dd, J = 10.48, 1.94 Hz, 1 H) 4.54 (d, J = 12.30 Hz, 2 H) 3.90-4.01 (m, 2 H) 3.64 (td, J = 11.76, 2.82 Hz, 2 H) 2.81-3.52 (m, 1 H) |
| 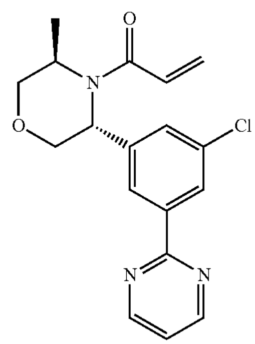 [SMILES: C=CC(=O)N1[C@H](C)COC[C@H]1c1cc(Cl)cc(-c2ncccn2)c1] | 20 | 1-((3R,5R)-3-(3-chloro-5-(pyrimidin-2-yl)phenyl)-5-methylmorpholino) prop-2-en-1-one | Single enantiomer of known absolute configuration | 1H NMR (400 MHz, CHLOROFORM-d) δ = 8.80 (d, J = 4.9 Hz, 2H), 8.30 (s, 2H), 7.37 (s, 1H), 7.22 (t, J = 4.8 Hz, 1H), 6.65-6.19 (m, 2H), 5.63 (br s, 1H), 4.98-4.86 (m, 1H), 4.41-3.99 (m, 3H), 3.80 (br d, J = 11.7 Hz, 2H), 1.46 (br d, J = 6.8 Hz, 3H) |
| 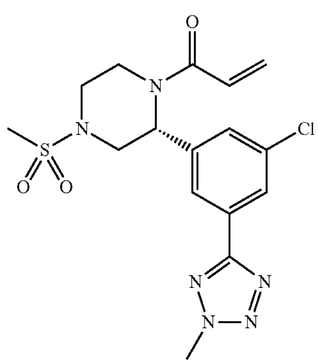 [SMILES: C=CC(=O)N1CCN(S(C)(=O)=O)C[C@H]1c1cc(Cl)cc(-c2nnn(C)n2)c1] | 21 | (R)-1-(2-(3-chloro-5-(2-methyl-2H-tetrazol-5-yl)phenyl)-4-(methylsulfonyl)piperazin-1-yl)prop-2-en-1-one | Single enantiomer of known absolute configuration | 1H NMR (400 MHz, DMSO-d6) δ = 8.02-7.86 (m, 2H), 7.55 (br s, 1H), 7.01-6.86 (m, 1H), 6.28 (dd, J = 2.0, 16.7 Hz, 1H), 6.07-5.79 (m, 2H), 4.43 (s, 3H), 4.39-3.87 (m, 2H), 3.48 (br d, J = 9.4 Hz, 1H), 3.32-3.19 (m, 2H), 2.93 (s, 4H) |
| 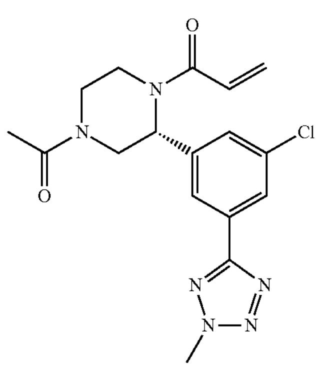 [SMILES: C=CC(=O)N1CCN(C(C)=O)C[C@H]1c1cc(Cl)cc(-c2nnn(C)n2)c1] | 22 | (R)-1-(4-acetyl-2-(3-chloro-5-(2-methyl-2H-tetrazol-5-yl)phenyl)piperazin-1-yl)prop-2-en-1-one | Single enantiomer of known absolute configuration | 1H NMR (400 MHz, DMSO-d6) δ = 7.84 (s, 1H), 8.01-7.81 (m, 1H), 7.64-7.46 (m, 1H), 7.11-6.61 (m, 1H), 6.29-6.13 (m, 1H), 5.86-5.51 (m, 2H), 4.98-4.49 (m, 1H), 4.43 (d, J = 1.5 Hz, 3H), 4.14 (br dd, J = 4.9, 14.4 Hz, 1H), 3.96-3.50 (m, 2H), 3.48-3.35 (m, 1H), 3.30-3.13 (m, 1H), 2.01-1.88 (m, 3H) |

TABLE 1-continued

| Compounds of the Disclosure. | | | | |
|---|---|---|---|---|
| Structure | No. | Name | Stereochemistry | NMR |
| 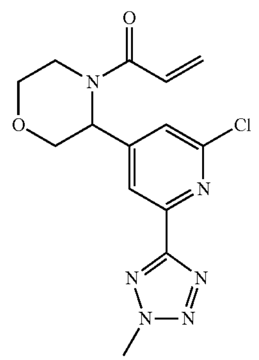 [SMILES: C=CC(=O)N1CCOCC1c1cc(Cl)nc(-c2nnn(C)n2)c1] | 23 | 1-(3-(2-chloro-6-(2-methyl-2H-tetrazol-5-yl)pyridin-4-yl)morpholino)prop-2-en-1-one | Single enantiomer of unknown absolute configuration | 1H NMR (400 MHz, CHLOROFORM-d) δ ppm 3.39 (br s, 1 H) 3.64 (td, J = 11.79, 2.81 Hz, 1 H) 3.78 (br s, 1H) 3.92 (dd, J = 12.51, 3.50 Hz, 1 H) 4.00 (dd, J = 11.38, 3.38 Hz, 1 H) 4.46 (s, 3 H) 4.51 (d, J = 12.38 Hz, 1H) 5.85 (dd, J = 10.38, 1.75 Hz, 2H) 6.41-6.50 (m, 1 H) 6.53-6.69 (m, 1 H) 7.52 (br s, 1 H) 8.26 (br s, 1 H) |
| 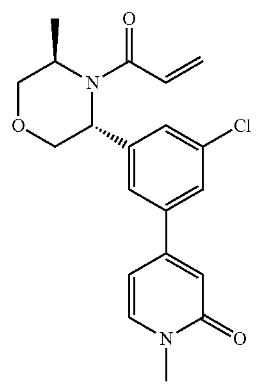 [SMILES: C=CC(=O)N1[C@H](C)COC[C@H]1c1cc(Cl)cc(-c2ccn(C)c(=O)c2)c1] | 24 | 4-(3-((3R,5R)-4-acryloyl-5-methylmorpholin-3-yl)-5-chlorophenyl)-1-methylpyridin-2(1H)-one | Single enantiomer of known absolute configuration | 1H NMR (400 MHz, CHLOROFORM-d) δ ppm 7.41 (br s, 2 H) 7.31-7.38 (m, 2 H) 6.49-6.79 (m, 2 H) 6.33 (br d, J = 15.69 Hz, 2 H) 5.69 (br s, 1 H) 4.77-4.92 (m, 1 H) 4.27 (br s, 1 H) 4.11 (br s, 1 H) 3.77-4.00 (m, 2 H) 3.63 (br s, 4 H) 1.43 (br d, J = 6.02 Hz, 3 H) |
| 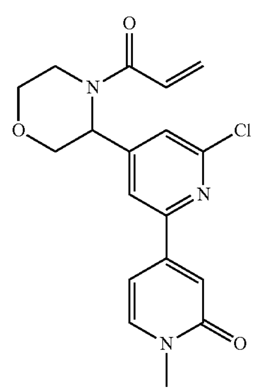 [SMILES: C=CC(=O)N1CCOCC1c1cc(Cl)nc(-c2ccn(C)c(=O)c2)c1] | 25 | 4-(4-acryloylmorpholin-3-yl)-6-chloro-1'-methyl-(2,4'-bipyridin)-2'(1'H)-one | Single enantiomer of unknown absolute configuration | 1H NMR (400 MHz, CHLOROFORM-d) δ = 8.05-7.83 (m, 1H), 7.66 (br s, 1H) 7.55 (br d, J = 7.0 Hz, 1H), 7.27 (s, 1H), 7.07 (br d, J = 6.3 Hz, 1H), 6.81-6.67 (m, 1H), 6.66-6.54 (m, 1H), 6.12-5.82 (m, 2H), 4.61 (br d, J = 12.4 Hz, 1H), 4.24-4.11 (m, 1H), 4.07 (br dd, J = 2.9, 12.3 Hz, 1H), 3.99-3.68 (m, 5H), 3.64-3.31(m, 1H) |
| 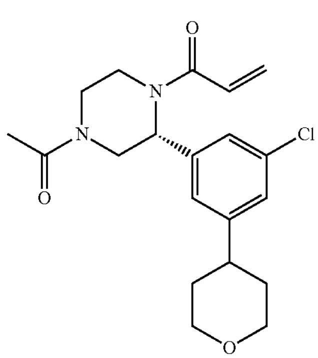 [SMILES: C=CC(=O)N1CCN(C(C)=O)C[C@H]1c1cc(Cl)cc(C2CCOCC2)c1] | 26 | (R)-1-(4-acetyl-2-(3-chloro-5-(tetrahydro-2H-pyran-4-yl)phenyl)piperazin-1-yl)prop-2-en-1-one | Single enantiomer of known absolute configuration | 1H NMR (400 MHz, DMSO-d6) δ = 7.43-7.01 (m, 3H), 6.98-6.34 (m, 1H), 6.26-6.10 (m, 1H), 5.87-5.31 (m, 2H), 4.66 (br s, 1H), 4.14 (br dd, J = 3.8, 14.1 Hz, 1H), 3.93 (br d, J = 10.3 Hz, 2H), 3.85-3.58 (m, 2H), 3.43-3.34 (m, 3H), 3.21-3.04 (m, 1H), 2.86-2.69 (m, 1H), 2.00-1.82 (m, 3H), 1.77-1.51 (m, 4H) |

TABLE 1-continued

Compounds of the Disclosure.

| Structure | No. | Name | Stereochemistry | NMR |
|---|---|---|---|---|
| 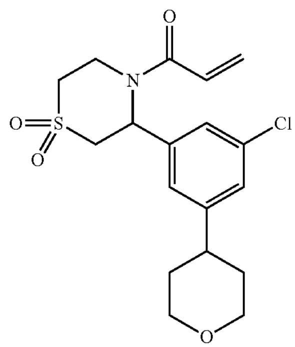 [SMILES: C=CC(=O)N1CCS(=O)(=O)CC1c1cc(Cl)cc(C2CCOCC2)c1] | 28 | 1-(3-(3-chloro-5-(tetrahydro-2H-pyran-4-yl)phenyl)-1,1-dioxidothiomorpholino)prop-2-en-1-one | racemic | 1H NMR (400 MHz, CHLOROFORM-d) δ ppm 1.71-1.87 (m, 4 H) 2.77 (br d, J = 4.63 Hz, 1 H) 3.10 (br d, J = 14.26 Hz, 1 H) 3.17-3.30 (m, 1 H) 3.39-3.57 (m, 3 H) 3.63 (br t, J = 13.32 Hz, 1 H) 3.84 (br d, J = 14.88 Hz, 1 H) 4.09 (br d, J = 11.26 Hz, 2 H) 4.64 (br s, 1 H) 5.90 (br d, J = 9.88 Hz, 1 H) 6.10 (br s, 1 H) 6.41-6.65 (m, 2 H) 7.10 (s, 1 H) 7.14 (s, 1 H) 7.20 (s, 1 H) |
| 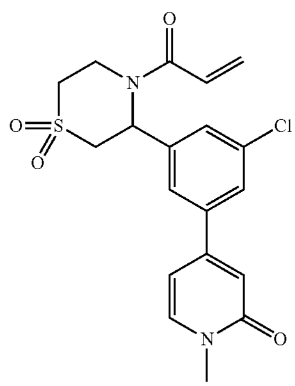 [SMILES: C=CC(=O)N1CCS(=O)(=O)CC1c1cc(Cl)cc(-c2ccn(C)c(=O)c2)c1] | 29 | 4-(3-(4-acryloyl-1,1-dioxidothiomorpholin-3-yl)-5-chlorophenyl)-1-methylpyridin-2(1H)-one | racemic | 1H NMR (400 MHz, DMSO-d6) δ = 7.80 (d, J = 7.2 Hz, 1H), 7.71 (s, 1H), 7.63 (s, 1H), 7.39 (s, 1H), 6.90 (br s, 1H), 6.77 (d, J = 1.9 Hz, 1H), 6.61 (dd, J = 2.1, 7.1 Hz, 1H), 6.23 (dd, J = 2.1, 16.7 Hz, 1H), 6.09 (br s, 1H), 5.80 (br d, J = 10.7 Hz, 1H), 4.65 (br s, 1H), 4.39-4.27 (m, 1H), 3.76 (br dd, J = 6.0, 15.0 Hz, 1H), 3.54 (br s, 1H), 3.46 (s, 3H), 3.39 (br d, J = 10.9 Hz, 1H), 3.43-3.34 (m, 1H), 3.15 (br dd, J = 2.6, 13.5 Hz, 1H) |
| 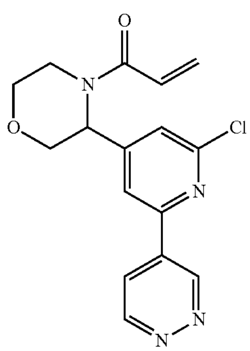 | 30 | 1-(3-(2-chloro-6-(pyridazin-4-yl)pyridin-4-yl)morpholino)prop-2-en-1-one | Single enantiomer of unknown absolute configuration | 1H NMR (400 MHz, CHLOROFORM-d) δ ppm 9.78 (br s, 1 H) 9.33 (br s, 1 H) 7.59-8.15 (m, 3 H) 6.40-6.65 (m, 2 H) 5.85 (br s, 2 H) 4.47 (br s, 1 H) 3.90-4.05 (m, 2 H) 3.66 (br s, 2 H) 3.32 (br s, 1 H) |
| 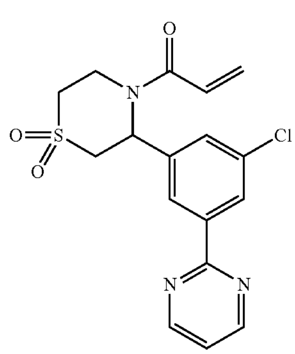 [SMILES: C=CC(=O)N1CCS(=O)(=O)CC1c1cc(Cl)cc(-c2ncccn2)c1] | 31 | 1-(3-(3-chloro-5-(pyrimidin-2-yl)phenyl)-1,1-dioxidothiomorpholino)prop-2-en-1-one | Single enantiomer of unknown absolute configuration | 1H NMR (400 MHz, CHLOROFORM-d) δ ppm 8.83 (d, J = 4.89 Hz, 2 H) 8.36-8.51 (m, 2 H) 7.39 (d, J = 0.75 Hz, 1 H) 7.28 (br s, 0.5 H) 7.26 (s, 0.5 H) 6.54-6.66 (m, 1 H) 6.51 (d, J = 1.88 Hz, 1 H) 6.15 (br s, 1 H) 5.89 (dd, J = 10.29, 1.76 Hz, 1 H) 4.73 (br s, 1 H) 3.96 (dt, J = 14.96, 3.31 Hz, 1 H) 3.89-4.04 (m, 1 H) 3.74 (br t, J = 13.05 Hz, 1 H) 3.51 (dd, J = 15.06, 6.02 Hz, 1 H) 3.28 (td, J = 13.11, 4.14 Hz, 1 H) 3.13 (dd, J = 13.80, 2.76 Hz, 1 H) |

TABLE 1-continued

| Compounds of the Disclosure. | | | | |
|---|---|---|---|---|
| Structure | No. | Name | Stereochemistry | NMR |
| 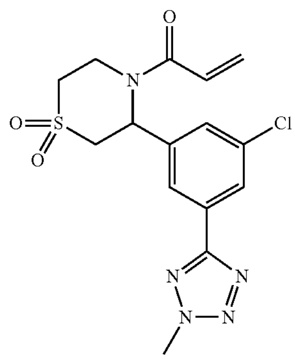 [SMILES: C=CC(=O)N1CCS(=O)(=O)CC1c1cc(Cl)cc(-c2nnn(C)n2)c1] | 32 | 1-(3-(3-chloro-5-(2-methyl-2H-tetrazol-5-yl)phenyl)-1,1-dioxidothiomorpholino)prop-2-en-1-one | Single enantiomer of unknown absolute configuration | 1H NMR (40 0MHz, CHLOROFORM-d) δ ppm 8.13 (s, 1 H) 8.03 (s, 1 H) 7.39 (d, J = 0.88 Hz, 1 H) 6.55-6.67 (m, 1 H) 6.45-6.53 (m, 1 H) 6.19 (br s, 1 H) 5.91 (dd, J = 10.23, 1.69 Hz, 1 H) 4.57-4.85 (m, 1 H) 4.42 (s, 3 H) 3.91 (dt, J = 14.96, 3.37 Hz, 1 H) 3.73 (br t, J = 13.11 Hz, 1 H) 3.50 (dd, J = 15.12, 5.96 Hz, 1 H) 3.26 (td, J = 13.05, 3.89 Hz, 1 H) 3.11 (dd, J = 13.87, 2.82 Hz, 1 H) |
| 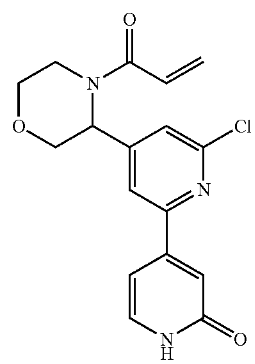 [SMILES: C=CC(=O)N1CCOCC1c1cc(Cl)nc(-c2cc[nH]c(=O)c2)c1] | 33 | 4-(4-acryloylmorpholin-3-yl)-6-chloro-[2,4'-bipyridin]-2'(1'H)-one | Single enantiomer of unknown absolute configuration | 1H NMR (400 MHz, CHLOROFORM-d) δ ppm 3.18-3.46 (m, 1 H) 3.53-3.84 (m, 2 H) 3.87-4.06 (m, 2 H) 4.46 (d, J = 12.51 Hz, 1 H) 5.66-5.97 (m, 2 H) 6.39-6.67 (m, 2 H) 6.99 (dd, J = 6.82, 1.19 Hz, 1 H) 7.12 (s, 1 H) 7.43 (d, J = 6.88 Hz, 1 H) 7.48-7.63 (m, 1 H) 7.70-7.90 (m, 1 H) |
| 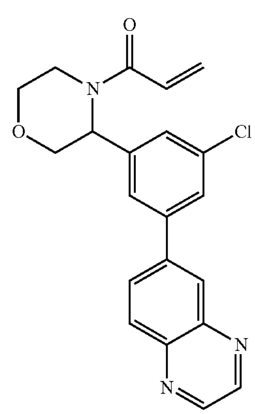 [SMILES: C=CC(=O)N1CCOCC1c1cc(Cl)cc(-c2ccc3nccnc3c2)c1] | 34 | 1-(3-(3-chloro-5-(quinoxalin-6-yl)phenyl)morpholino)prop-2-en-1-one | Single enantiomer of unknown absolute configuration | 1H NMR (400 MHz, DMSO-d6) δ = 9.00 (dd, J = 1.7, 12.4 Hz, 3H), 8.38 (s, 1H), 8.21 (s, 3H), 7.91 (s, 1H), 7.83-7.75 (m, 1H), 7.45 (br s, 1H), 6.90 (dd, J = 10.5, 16.6 Hz, 1H), 6.24 (dd, J = 1.9, 16.6 Hz, 1H), 5.77 (dd, J = 2.2, 10.4 Hz, 2H), 4.56 (d, J = 12.5 Hz, 1H), 3.95-3.78 (m, 3H), 3.59-3.48 (m, 1H) |
| 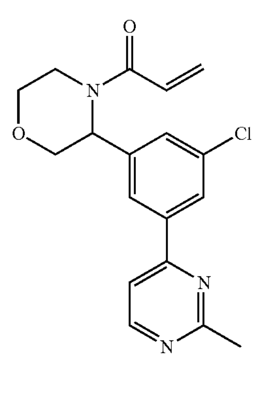 | 35 | 1-(3-(3-chloro-5-(2-methylpyrimidin-4-yl)phenyl)morpholino)prop-2-en-1-one | Single enantiomer of unknown absolute configuration | 1H NMR (400 MHz, CHLOROFORM-d) ppm 2.81 (s, 3 H) 3.12-3.75 (m, 3 H) 3.76-4.10 (m, 3 H) 4.51 (d, J = 12.26 Hz, 1 H) 5.80 (dd, J = 10.38, 1.88 Hz, 1 H) 6.39-6.45 (m, 1 H) 6.53-6.63 (m, 1 H) 7.48-7.70 (m, 2 H) 8.04 (s, 2 H) 8.70 (br d, J = 5.13 Hz, 1 H) |

TABLE 1-continued

| Compounds of the Disclosure. | | | | |
|---|---|---|---|---|
| Structure | No. | Name | Stereochemistry | NMR |
| 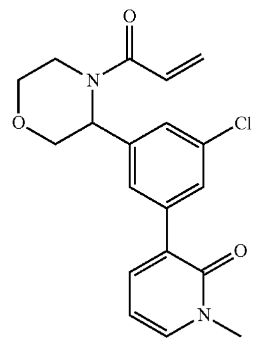 [SMILES: C=CC(=O)N1CCOCC1c1cc(Cl)cc(-c2cccn(C)c2=O)c1] | 36 | 3-(3-(4-acryloylmorpholin-3-yl)-5-chlorophenyl)-1-methylpyridin-2(1H)-one | Single enantiomer of unknown absolute configuration | 1H NMR (400 MHz, CHLOROFORM-d) δ ppm 7.67 (br d, J = 7.75 Hz, 2 H) 7.48 (dd, J = 7.00, 2.00 Hz, 2 H) 7.34 (dd, J = 6.69, 1.81 Hz, 1 H) 6.49-6.63 (m, 1 H) 6.32-6.44 (m, 1 H) 6.26 (t, J = 6.82 Hz, 1 H) 5.76 (dd, J = 10.38, 1.88 Hz, 2 H) 4.48 (d, J = 12.26 Hz, 1 H) 3.97 (dd, J = 11.13, 3.00 Hz, 1 H) 3.88 (dd, J = 12.19, 3.56 Hz, 1 H) 3.63-3.77 (m, 1 H) 3.62 (s, 3 H) 3.05-3.60 (m, 2 H) |
| 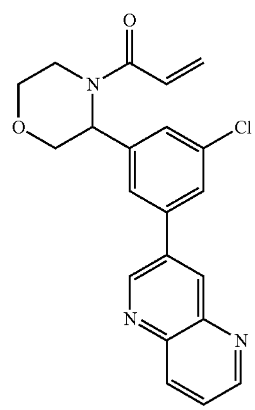 [SMILES: C=CC(=O)N1CCOCC1c1cc(Cl)cc(-c2cnc3cccnc3c2)c1] | 37 | 1-(3-(3-chloro-5-(1,5-naphthyridin-3-yl)phenyl)morpholino)prop-2-en-1-one | Single enantiomer of unknown absolute configuration | 1H NMR (400 MHz, CHLOROFORM-d) δ ppm 9.20 (d, J = 2.13 Hz, 1 H) 9.05 (dd, J= 4.13, 1.38 Hz, 1 H) 8.41-8.64 (m, 2 H) 7.50-7.90 (m, 4 H) 6.54-6.69 (m, 1 H) 6.35-6.50 (m, 1 H) 5.81 (dd, J = 10.38, 1.75 Hz, 1 H) 4.52 (d, J = 12.38 Hz, 1 H) 3.80-4.37 (m, 3 H) 2.79-3.79 (m, 3 H) |
| 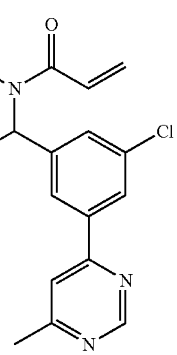 | 38 | 1-(3-(3-chloro-5-(6-methylpyrimidin-4-yl)phenyl)morpholino)prop-2-en-1-one | Single enantiomer of unknown absolute configuration | 1H NMR (400 MHz, CHLOROFORM-d) ppm 1.22-1.31 (m, 2 H) 1.60 (br s, 3 H) 2.62 (s, 3 H) 2.75-3.86 (m, 3 H) 3.93 (dd, J = 12.36, 3.58 Hz, 1 H) 4.01 (dd, J = 11.29, 3.14 Hz, 1 H) 4.52 (d, J = 12.42 Hz, 1 H) 5.81 (dd, J = 10.42, 1.88 Hz, 2 H) 6.39-6.46 (m, 1 H) 6.53-6.62 (m, 1 H) 7.56 (s, 2 H) 7.99-8.10 (m, 2 H) 9.15 (s, 1 H) |
| 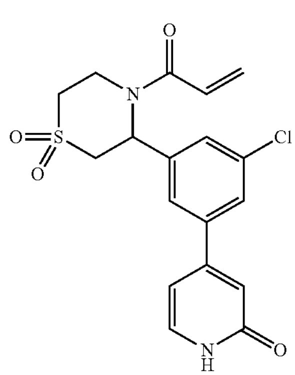 [SMILES: C=CC(=O)N1CCS(=O)(=O)CC1c1cc(Cl)cc(-c2cc[nH]c(=O)c2)c1] | 39 | 4-(3-(4-acryloyl-1,1-dioxidothiomorpholin-3-yl)-5-chlorophenyl)pyridin-2(1H)-one | Single enantiomer of unknown absolute configuration | 1H NMR (400 MHz, DMSO-d6) δ = 11.68 (br s, 1H), 7.68 (s, 1H), 7.60 (s, 1H), 7.47 (d, J = 6.8 Hz, 1H), 7.40 (s, 1H), 6.92 (br d, J = 19.7 Hz, 1H), 6.67 (s, 1H), 6.53 (br d, J = 6.4 Hz, 1H), 6.23 (dd, J = 1.8, 16.7 Hz, 1H), 6.09 (br s, 1H), 5.80 (br d, J = 11.1 Hz, 1H), 4.64 (br s, 1H), 4.33 (br d, J = 14.7 Hz, 1H), 3.76 (br dd, J = 5.5, 14.9 Hz, 1H), 3.53 (br s, 1H), 3.37 (br s, 1H), 3.15 (br d, J = 11.4 Hz, 1H) |

TABLE 1-continued

Compounds of the Disclosure.

| Structure | No. | Name | Stereochemistry | NMR |
| --- | --- | --- | --- | --- |
| 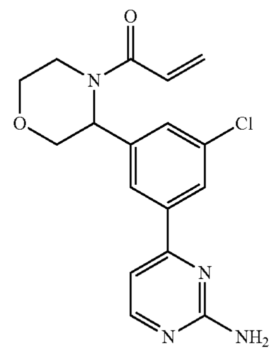 [SMILES: C=CC(=O)N1CCOCC1c1cc(Cl)cc(-c2ccnc(N)n2)c1] | 40 | 1-(3-(3-(2-aminopyrimidin-4-yl)-5-chlorophenyl)morpholino)prop-2-en-1-one | Single enantiomer of unknown absolute configuration | 1H NMR (400 MHz, CHLOROFORM-d) δ ppm 3.01-3.91 (m, 3 H) 3.91-4.10 (m, 2 H) 4.50 (d, J = 12.28 Hz, 1 H) 5.27 (br s, 2 H) 5.79 (dd, J = 10.41, 1.64 Hz, 2 H) 6.35-6.48 (m, 1 H) 6.54-6.64 (m, 1 H) 7.01 (d, J = 5.26 Hz, 1 H) 7.63 (br s, 1 H) 7.94 (s, 1 H) 7.99 (br s, 1 H) 8.36 (d, J = 5.26 Hz, 1 H) |
| 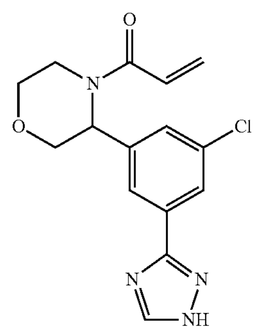 [SMILES: C=CC(=O)N1CCOCC1c1cc(Cl)cc(-c2nc[nH]n2)c1] | 41 | 1-(3-(3-chloro-5-(1H-1,2,4-triazol-3-yl)phenyl)morpholino)prop-2-en-1-one | Single enantiomer of unknown absolute configuration | 1H NMR (400 MHz, CHLOROFORM-d) δ ppm 3.64 (td, J = 11.80, 2.76 Hz, 3 H) 3.92 (dd, J = 12.36, 3.58 Hz, 1 H) 4.00 (br d, J = 8.66 Hz, 1 H) 4.51 (d, J = 12.30 Hz, 1 H) 4.45-4.56 (m, 1 H) 5.80 (dd, J = 10.42, 1.63 Hz, 2 H) 6.37-6.48 (m, 1 H) 6.51-6.64 (m, 1 H) 7.55 (br d, J = 15.56 Hz, 1 H) 8.07 (s, 2 H) 8.29 (s, 1 H) |
| 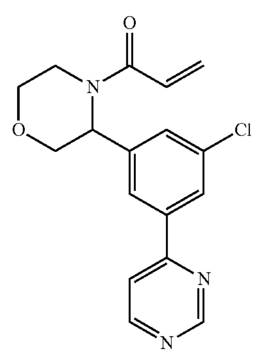 [SMILES: C=CC(=O)N1CCOCC1c1cc(Cl)cc(-c2ccncn2)c1] | 42 | 1-(3-(3-chloro-5-(pyrimidin-4-yl)phenyl)morpholino)prop-2-en-1-one | Single enantiomer of unknown absolute configuration | 1H NMR (400 MHz, CHLOROFORM-d) δ = 9.28 (s, 1H), 8.80 (br d, J = 5.0 Hz, 1H), 8.21-7.99 (m, 2H), 7.70 (br d, J = 5.0 Hz, 2H), 6.65-6.51 (m, 1H), 6.49-6.33 (m, 1H), 5.80 (dd, J = 1.8, 10.3 Hz, 1H), 4.51 (d, J = 12.2 Hz, 1H), 4.00 (dd, J = 3.0, 11.3 Hz, 1H), 3.93 (dd, J = 3.5, 12.4 Hz, 1H), 3.64 (dt, J = 2.6, 11.8 Hz, 1H), 3.58-3.06 (m, 1H) |
| 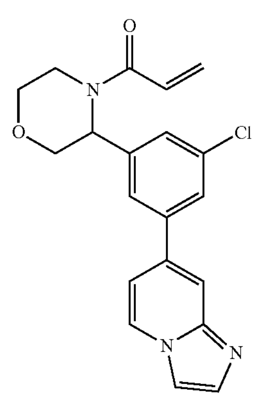 [SMILES: C=CC(=O)N1CCOCC1c1cc(Cl)cc(-c2ccn3ccnc3c2)c1] | 43 | 1-(3-(3-chloro-5-(imidazo[1,2-a]pyridin-7-yl)phenyl)morpholino)prop-2-en-1-one | Single enantiomer of unknown absolute configuration | 1H NMR (400 MHz, CHLOROFORM-d) δ = 8.22 (d, J = 7.0 Hz, 1H), 7.90 (br s, 1H), 7.78-7.47 (m, 6H), 7.15-7.04 (m, 1H), 6.66-6.52 (m, 1H), 6.50-6.34 (m, 1H), 5.81 (br d, J = 10.3 Hz, 2H), 4.49 (br d, J = 12.3 Hz, 1H), 4.08-3.97 (m, 1H), 3.93 (br dd, J = 1.0, 11.5 Hz, 1H), 3.84-3.58 (m, 2H), 3.55-3.18 (m, 1H) |

TABLE 1-continued

| Compounds of the Disclosure. | | | | |
|---|---|---|---|---|
| Structure | No. | Name | Stereochemistry | NMR |
| 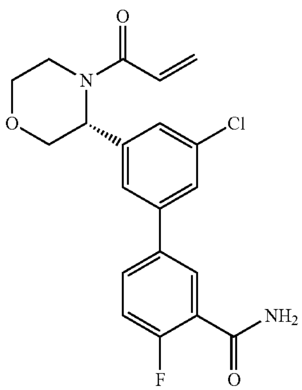 [SMILES: C=CC(=O)N1CCOC[C@H]1c1cc(Cl)cc(-c2ccc(F)c(C(N)=O)c2)c1] | 44 | (R)-3'-(4-acryloylmorpholin-3-yl)-5'-chloro-4-fluoro-[1,1'-biphenyl]-3-carboxamide | Single enantiomer of known absolute configuration | 1H NMR (400 MHz, CHLOROFORM-d) δ = 8.31 (dd, J = 2.5, 7.4 Hz, 1H), 7.78-7.63 (m, 1H), 7.52 (s, 3H), 7.23 (dd, J = 8.6, 11.4 Hz, 1H), 6.82-6.66 (m, 1H), 6.64-6.51 (m, 1H), 6.47-6.36 (m, 1H), 5.79 (dd, J = 1.7, 10.5 Hz, 2H), 4.49 (d, J = 12.2 Hz, 1H), 3.99 (dd, J = 3.1, 11.0 Hz, 1H), 3.91 (dd, J = 3.5, 12.2 Hz, 1H), 3.63 (dt, J = 2.4, 11.9 Hz, 3H) |
| 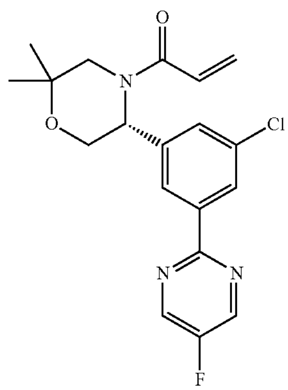 [SMILES: C=CC(=O)N1CC(C)(C)OC[C@H]1c1cc(Cl)cc(-c2ncc(F)cn2)c1] | 45 | (R)-1-(5-(3-chloro-5-(5-fluoropyrimidin-2-yl)phenyl)-2,2-dimethylmorpholino)prop-2-en-1-one | Single enantiomer of known absolute configuration | 1H NMR (400 MHz, DMSO-d6) δ = 9.03 (s, 2H), 8.28 (br s, 1H), 8.23 (s, 1H), 7.59 (s, 1H), 6.94-6.69 (m, 1H), 6.25 (dd, J = 1.5, 16.5 Hz, 1H), 5.77 (br d, J = 8.6 Hz, 1H), 5.61-5.31 (m, 1H), 4.35-4.08 (m, 1H), 4.05-3.78 (m, 2H), 3.11-2.74 (m, 1H), 1.17 (s, 3H), 1.13 (s, 3H) |
| 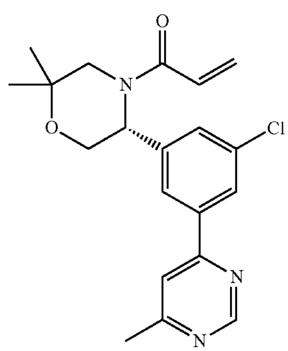 [SMILES: C=CC(=O)N1CC(C)(C)OC[C@H]1c1cc(Cl)cc(-c2cc(C)ncn2)c1] | 46 | (R)-1-(5-(3-chloro-5-(6-methylpyrimidin-4-yl)phenyl)-2,2-dimethylmorpholino)prop-2-en-1-one | Single enantiomer of known absolute configuration | 1H NMR (400 MHz, DMSO-d6) δ = 9.12 (d, J = 0.9 Hz, 1H), 8.14 (br d, J = 6.4 Hz, 2H), 8.08 (s, 1H), 7.55 (s, 1H), 7.00-6.63 (m, 1H), 6.24 (dd, J = 2.0, 16.5 Hz, 1H), 5.85-5.71 (m, 1H), 5.55-5.15 (m, 1H), 4.36-4.08 (m, 1H), 4.06-3.83 (m, 2H), 3.15-2.79 (m, 1H), 2.54 (s, 3H), 1.17 (s, 3H), 1.13 (s, 3H) |
| 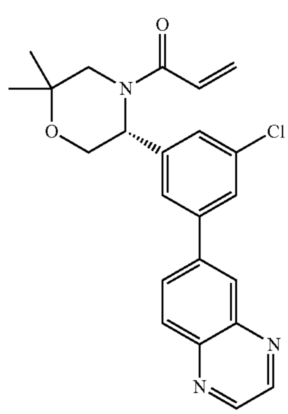 [SMILES: C=CC(=O)N1CC(C)(C)OC[C@H]1c1cc(Cl)cc(-c2ccc3nccnc3c2)c1] | 47 | (R)-1-(5-(3-chloro-5-(quinoxalin-6-yl)phenyl)-2,2-dimethylmorpholino)prop-2-en-1-one | Single enantiomer of knwon absolute configuration | 1H NMR (400 MHz, CHLOROFORM-d) δ ppm 1.26 (s, 2 H) 1.31 (s, 2 H) 1.58 (br s, 1 H) 4.19 (br s, 1 H) 5.63-5.88 (m, 1 H) 6.31-6.72 (m, 1 H) 7.68 (s, 1 H) 8.00 (br d, J = 8.55 Hz, 1 H) 8.20 (d, J = 8.77 Hz, 1 H) 8.28 (s, 1 H) 8.89 (d, J = 8.33 Hz, 1 H) |

TABLE 1-continued

| Structure | No. | Name | Stereochemistry | NMR |
|---|---|---|---|---|
| Compounds of the Disclosure. | | | | |
| 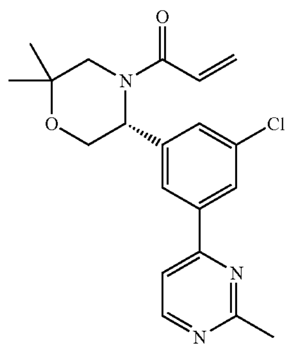 | 48 | (R)-1-(5-(3-chloro-5-(2-methylpyrimidin-4-yl)phenyl)-2,2-dimethylmorpholino)prop-2-en-1-one | Single enantiomer of known absolute configuration | 1H NMR (400 MHz, CHLOROFORM-d) δ ppm 8.70 (br d, 1 H) 8.04 (br s, 2 H) 7.41-7.76 (m, 2 H) 6.37-6.65 (m, 2 H) 5.79 (br dd, 2 H) 4.07-4.35 (m, 2 H) 3.00-3.59 (m, 2 H) 2.80 (s, 3 H) 1.18-1.32 (m, 6 H) |
| 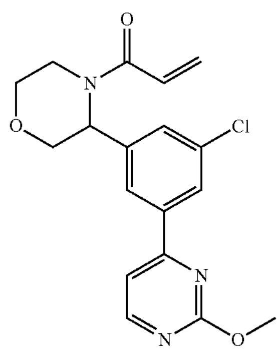 [SMILES: C=CC(=O)N1CCOCC1c1cc(Cl)cc(-c2ccnc(OC)n2)c1] | 49 | 1-(3-(3-chloro-5-(2-methoxypyrimidin-4-yl)phenyl)morpholino)prop-2-en-1-one | Single enantiomer of unknown absolute configuration | 1H NMR (400 MHz, CHLOROFORM-d) δ ppm 3.34 (br s, 1 H) 3.51-3.85 (m, 2 H) 3.86-4.02 (m, 2 H) 4.09 (s, 3 H) 4.50 (d, J = 12.38 Hz, 1 H) 5.79 (dd, J = 10.38, 1.63 Hz, 2 H) 6.34-6.49 (m, 1 H) 6.51-6.64 (m, 1 H) 7.33 (d, J = 5.13 Hz, 1 H) 7.65 (br s, 1 H) 8.06 (br s, 2 H) 8.58 (d, J = 5.13 Hz, 1 H) |
| 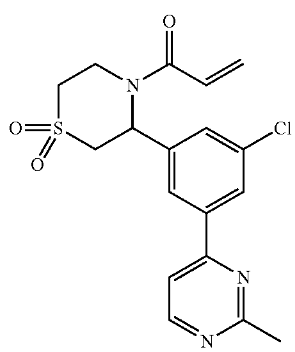 [SMILES: C=CC(=O)N1CCS(=O)(=O)CC1c1cc(Cl)cc(-c2ccnc(C)n2)c1] | 50 | 1-(3-(3-chloro-5-(6-methylpyridin-2-yl)phenyl)-1,1-dioxidothiomorpholino)prop-2-en-1-one | Single enantiomer of unknown absolute configuration | 1H NMR (400 MHz, CHLOROFORM-d) δ ppm 3.04-3.30 (m, 2 H) 3.53 (dd, J = 15.13, 6.00 Hz, 1 H) 3.59-3.73 (m, 1 H) 3.96 (br d, J = 15.13 Hz, 1 H) 4.58 (br s, 1 H) 5.89-6.03 (m, 1 H) 6.34 (br s, 1 H) 6.49-6.70 (m, 2 H) 7.24 (d, J = 6.25 Hz, 1 H) 7.52-7.60 (m, 1 H) 8.06 (br d, J = 18.89 Hz, 2 H) 8.22 (d, J = 6.25 Hz, 1 H) |
| 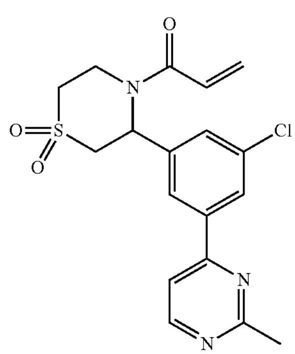 [SMILES: C=CC(=O)N1CCS(=O)(=O)CC1c1cc(Cl)cc(-c2ccnc(C)n2)c1] | 51 | 1-(3-(3-chloro-5-(6-methylpyridin-2-yl)phenyl)-1,1-dioxidothiomorpholino)prop-2-en-1-one | Single enantiomer of unknown absolute configuration | 1H NMR (400 MHz, CHLOROFORM-d) δ ppm 3.03-3.28 (m, 2 H) 3.40-3.73 (m, 2 H) 3.96 (br d, J = 13.88 Hz, 1 H) 4.56 (br s, 1 H) 5.96 (br d, J = 9.63 Hz, 1 H) 6.33 (br s, 1 H) 6.50-6.69 (m, 2 H) 7.22 (br s, 1 H) 7.55 (br s, 1 H) 8.05 (br d, J = 15.26 Hz, 2 H) 8.20 (br s, 1 H) |

TABLE 1-continued

| Structure | No. | Name | Stereochemistry | NMR |
|---|---|---|---|---|
| Compounds of the Disclosure. | | | | |
| 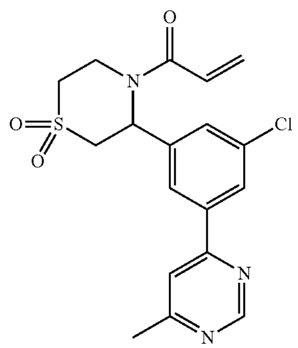 [SMILES: C=CC(=O)N1CCS(=O)(=O)CC1c1cc(Cl)cc(-c2cc(C)ncn2)c1] | 52 | 1-(3-(3-chloro-5-(6-methylpyrimidin-4-yl)phenyl)-1,1-dioxidothiomorpholino)prop-2-en-1-one | Single enantiomer of unknown absolute configuration | 1H NMR (400 MHz, CHLOROFORM-d) δ ppm 2.72 (s, 3 H) 3.07-3.33 (m, 2 H) 3.53 (dd, J = 15.13, 6.00 Hz, 1 H) 3.70 (br t, J = 13.70 Hz, 1 H) 3.95 (dt, J = 15.13, 3.00 Hz, 1 H) 4.2 (br s, 1 H) 5.94 (dd, J = 10.32, 1.56 Hz, 1 H) 6.28 (br s, 1 H) 6.45-6.70 (m, 2 H) 7.48 (s, 1 H) 7.68 (s, 1 H) 8.06 (s, 2 H) 9.24 (s, 1 H) |
| 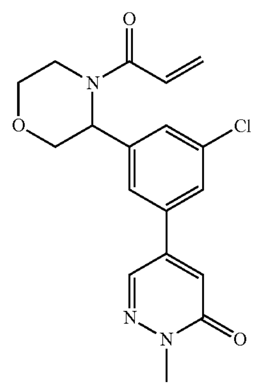 [SMILES: C=CC(=O)N1CCOCC1c1cc(Cl)cc(-c2cnn(C)c(=O)c2)c1] | 53 | 5-(3-(4-acryloylmorpholin-3-yl)-5-chlorophenyl)-2-methylpyridazin-3(2H)-one | Single enantiomer of unknown absolute configuration | 1H NMR (400 MHz, CHLOROFORM-d) δ ppm 3.34 (br s, 1 H) 3.64 (br t, J = 10.88 Hz, 1 H) 3.84 (s, 3 H) 3.87-4.14 (m, 3 H) 4.45 (br d, J = 12.26 Hz, 1 H) 5.81 (br d, J = 10.01 Hz, 2 H) 6.36-6.65 (m, 2 H) 7.04 (s, 1 H) 7.36-7.80 (m, 3 H) 7.97 (s, 1 H) |
| 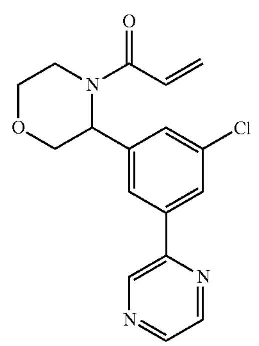 [SMILES: C=CC(=O)N1CCOCC1c1cc(Cl)cc(-c2cnccn2)c1] | 54 | 1-(3-(3-chloro-5-(pyrazin-2-yl)phenyl)morpholino)prop-2-en-1-one | Single enantiomer of unknown absolute configuration | 1H NMR (400 MHz, CHLOROFORM-d) δ ppm 3.10-3.68 (m, 2 H) 3.70-4.05 (m, 3 H) 4.52 (d, J = 12.17 Hz, 1 H) 5.80 (dd, J = 10.42, 1.76 Hz, 2 H) 6.35-6.48 (m, 1 H) 6.52-6.64 (m, 1 H) 7.62 (br s, 1 H) 7.90-8.13 (m, 2 H) 8.56 (s, 1 H) 8.65 (s, 1 H) 9.01 (s, 1 H) |
| 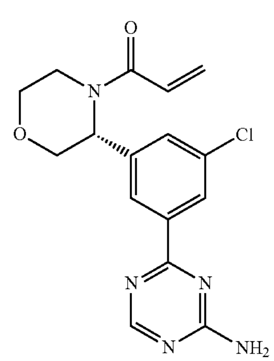 [SMILES: C=CC(=O)N1CCOC[C@H]1c1cc(Cl)cc(-c2ncnc(N)n2)c1] | 55 | (R)-1-(3-(3-(4-amino-1,3,5-triazin-2-yl)-5-chlorophenyl)morpholino)prop-2-en-1-one | Single enantiomer of known absolute configuration | 1H NMR (400 MHz, CHLOROFORM-d) δ ppm 3.12-3.87 (m, 3 H) 3.91-4.04 (m, 2 H) 4.53 (d, J = 12.26 Hz, 1 H) 5.60 (br s, 2 H) 5.80 (dd, J = 10.38, 1.88 Hz, 2 H) 6.40-6.46 (m, 1 H) 6.54-6.64 (m, 1 H) 7.52-7.75 (m, 1 H) 8.35 (s, 1 H) 8.41 (br s, 1 H) 8.68 (s, 1 H) |

TABLE 1-continued

| Compounds of the Disclosure. | | | | |
|---|---|---|---|---|
| Structure | No. | Name | Stereochemistry | NMR |
| 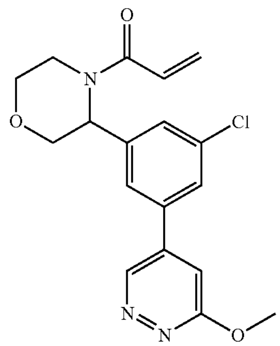 [SMILES: C=CC(=O)N1CCOCC1c1cc(Cl)cc(-c2cnnc(OC)c2)c1] | 56 | 1-(3-(3-chloro-5-(6-methoxypyridazin-4-yl)phenyl)morpholino)prop-2-en-1-one | Single enantiomer of unknown absolute configuration | 1H NMR (400 MHz, CHLOROFORM-d) δ ppm 3.35 (br s, 1 H) 3.64 (td, J = 11.76, 2.57 Hz, 2 H) 3.81-4.05 (m, 2 H) 4.20 (s, 3 H) 4.47 (br d, J = 12.30 Hz, 1 H) 5.81 (dd, J = 10.29, 1.63 Hz, 2 H) 6.34-6.72 (m, 2 H) 7.09 (s, 1H) 7.47-7.85 (m, 3 H) 9.06 (s, 1 H) |
| 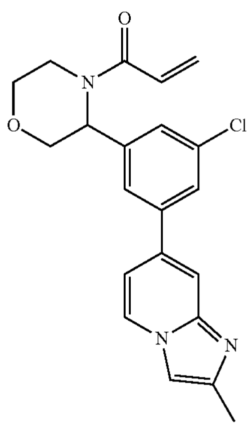 [SMILES: C=CC(=O)N1CCOCC1c1cc(Cl)cc(-c2ccn3cc(C)nc3c2)c1] | 57 | 1-(3-(3-chloro-5-(2-methylimidazo[1,2-a]pyridin-7-yl)phenyl)morpholino)prop-2-en-1-one | Single enantiomer of unknown absolute configuration | 1H NMR (400 MHz, CHLOROFORM-d) δ ppm 2.48 (s, 3 H) 3.24-3.67 (m, 2 H) 3.67-4.06 (m, 3 H) 4.48 (d, J = 12.17 Hz, 1 H) 5.79 (dd, J = 10.42, 1.88 Hz, 2 H) 6.37-6.48 (m, 1 H) 6.54-6.63 (m, 1 H) 6.96 (dd, J = 7.03, 1.51 Hz, 1 H) 7.36 (s, 1 H) 7.54 (s, 2 H) 7.60-7.73 (m, 2 H) 8.08 (d, J = 7.03 Hz, 1 H) |
| 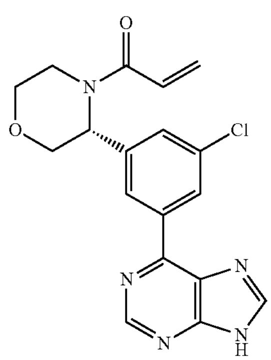 [SMILES: C=CC(=O)N1CCOC[C@H]1c1cc(Cl)cc(-c2ncnc3[nH]cnc23)c1] | 58 | (R)-1-(3-(3-chloro-5-(9H-purin-6-yl)phenyl)morpholino)prop-2-en-1-one | Single enantiomer of known absolute configuration | 1H NMR (400 MHz, CHLOROFORM-d) δ ppm 3.16-3.91 (m, 3 H) 3.93-4.08 (m, 2 H) 4.60 (d, J = 12.17 Hz, 1 H) 5.82 (dd, J = 10.54, 1.63 Hz, 2 H) 6.40-6.51 (m, 1 H) 6.64 (dd, J = 16.81, 10.54 Hz, 1 H) 7.47-7.82 (m, 1 H) 8.35 (s, 1 H) 8.74 (br s, 1 H) 8.86 (s, 1 H) 9.02 (s, 1 H) |
| 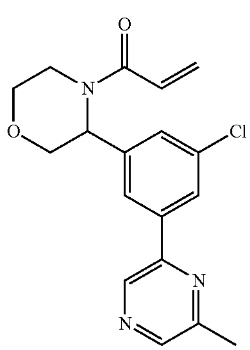 [SMILES: C=CC(=O)N1CCOCC1c1cc(Cl)cc(-c2cncc(C)n2)c1] | 59 | 1-(3-(3-chloro-5-(6-methylpyrazin-2-yl)phenyl)morpholino)prop-2-en-1-one | Single enantiomer of unknown absolute configuration | 1H NMR (400 MHz, CHLOROFORM-d) δ = 8.79 (br s, 1H), 8.44 (br s, 1H) 8.06-7.88 (m, 2H), 7.61 (br s, 1H), 6.65-6.51 (m, 1H), 6.50-6.26 (m, 1H), 5.80 (dd, J = 1.8, 10.4 Hz, 2H), 4.53 (d, J = 12.3 Hz, 1H), 4.05-3.79 (m, 2H), 3.78-2.92 (m, 3H), 2.64 (s, 3H) |

TABLE 1-continued

Compounds of the Disclosure.

| Structure | No. | Name | Stereochemistry | NMR |
|---|---|---|---|---|
| 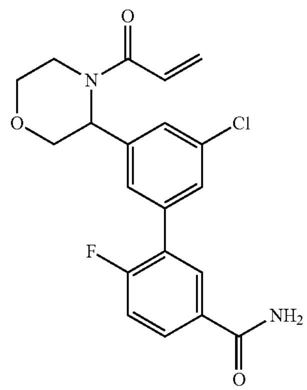 [SMILES: C=CC(=O)N1CCOCC1c1cc(Cl)cc(-c2cc(C(N)=O)ccc2F)c1] | 60 | 3'-(4-acryloylmorpholin-3-yl)-5'-chloro-6-fluoro-[1,1'-biphenyl]-3-carboxamide | Single enantiomer of unknown absolute configuration | 1H NMR (400 MHz, DMSO-d6) δ = 8.14-8.07 (m, 1H), 8.07-8.01 (m, 1H), 7.99-7.91 (m, 1H), 7.68-7.58 (m, 1H), 7.57-7.33 (m, 4H), 6.95-6.76 (m, 1H), 6.28-6.14 (m, 1H), 5.82-5.70 (m, 1H), 5.67-5.27 (m, 1H), 4.52-4.40 (m, 1H), 4.31-3.93 (m, 1H), 3.92-3.85 (m, 1H), 3.84-3.73 (m, 1H), 3.56-3.46 (m, 1H), 3.30-2.86 (m, 1H) |
| 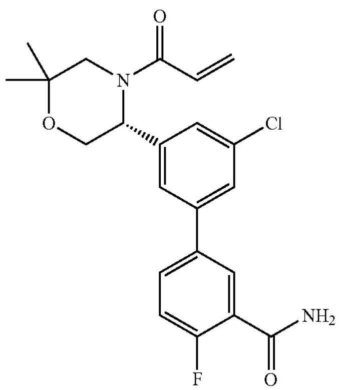 [SMILES: C=CC(=O)N1CC(C)(C)OC[C@H]1c1cc(Cl)cc(-c2ccc(F)c(C(N)=O)c2)c1] | 61 | (R)-3'-(4-acryloyl-6,6-dimethylmorpholin-3-yl)-5'-chloro-4-fluoro-[1,1'-biphenyl]-3-carboxamide | Single enantiomer of known absolute configuration | 1H NMR (400 MHz, DMSO-d6) δ ppm 1.15 (br d, J = 9.06 Hz, 5 H) 1.12-1.12 (m, 1 H) 2.83-3.17 (m, 1 H) 3.76-4.32 (m, 3 H) 5.19-5.57 (m, 1 H) 5.74 (d, J = J = 9.89 Hz, 1H) 6.22 (dd, J = 16.57, 2.15 Hz, 1 H) 6.66-6.96 (m, 1 H) 7.34-7.44 (m, 2 H) 7.58 (br s, 1 H) 7.70 (br s, 2 H) 7.85 (br s, 2 H) 7.88 (dd, J = 6.74, 2.21 Hz, 1 H) |
| 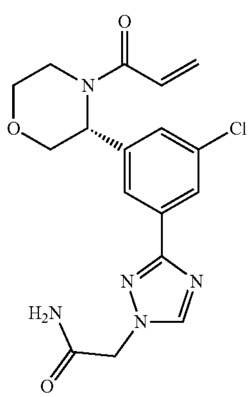 [SMILES: C=CC(=O)N1CCOC[C@H]1c1cc(Cl)cc(-c2ncn(CC(N)=O)n2)c1] | 62 | (R)-2-(3-(3-(4-acryloylmorpholin-3-yl)-5-chlorophenyl)-1H-1,2,4-triazol-1-yl)acetamide | Single enantiomer of known absolute configuration | 1H NMR (400 MHz, CHLOROFORM-d) δ ppm 3.09-3.79 (m, 2 H) 3.86-4.05 (m, 2 H) 4.51 (d, J = 12.28 Hz, 1 H) 4.85-4.97 (m, 2 H) 5.71-5.84 (m, 2 H) 6.33-6.49 (m, 2 H) 6.52-6.66 (m, 1 H) 7.39-7.61 (m, 1 H) 7.99-8.13 (m, 2 H) 8.22 (s, 1 H) |
| 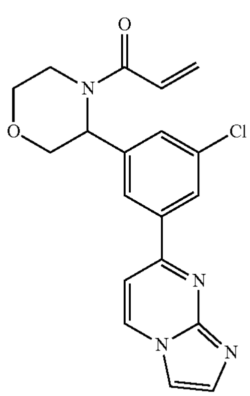 [SMILES: C=CC(=O)N1CCOCC1c1cc(Cl)cc(-c2ccn3ccnc3n2)c1] | 63 | 1-(3-(3-chloro-5-(imidazo[1,2-a]pyrimidin-7-yl)phenyl)morpholino)prop-2-en-1-one | Single enantiomer of unknown absolute configuration | 1H NMR (400 MHz, CHLOROFORM-d) δ ppm 3.23-3.77 (m, 3 H) 3.79-4.06 (m, 2 H) 4.52 (d, J = 12.26 Hz, 1 H) 5.81 (br d, J = 10.51 Hz, 2 H) 6.37-6.48 (m, 1 H) 6.53-6.67 (m, 1 H) 7.39 (br d, J = 6.75 Hz, 1 H) 7.64 (s, 2 H) 7.87 (s, 1 H) 8.15 (br s, 2 H) 8.57 (br d, J = 6.88 Hz, 1 H) |

TABLE 1-continued

| Compounds of the Disclosure. | | | | |
|---|---|---|---|---|
| Structure | No. | Name | Stereochemistry | NMR |
| 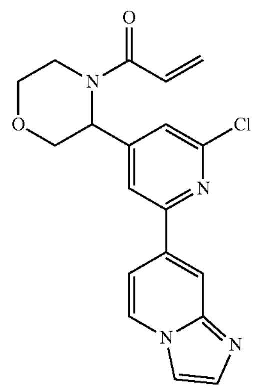 [SMILES: C=CC(=O)N1CCOCC1c1cc(Cl)nc(-c2ccn3ccnc3c2)c1] | 64 | 1-(3-(2-chloro-6-(imidazo[1,2-a]pyridin-7-yl)pyridin-4-yl)morpholino)prop-2-en-1-one | Single enantiomer of unknown absolute configuration | 1H NMR (400 MHz, CHLOROFORM-d) δ = 8.46 (br s, 1H), 8.29 (br d, J = 6.9 Hz, 1H), 7.93 (br s, 1H), 7.85 (br d, J = 6.0 Hz, 1H), 7.80 (s, 1H), 7.70 (s, 1H), 7.54-7.42 (m, 1 H), 6.66-6.56 (m, 1H), 6.52-6.40 (m, 1H), 5.86 (br d, J = 10.3 Hz, 2H), 4.49 (br d, J = 12.3 Hz, 1H), 4.02 (br d, J = 11.5 Hz, 1H), 3.94 (br d, J = 12.3 Hz, 1H), 3.69-3.64 (m, 2H), 3.41 (br s, 1H) |
| 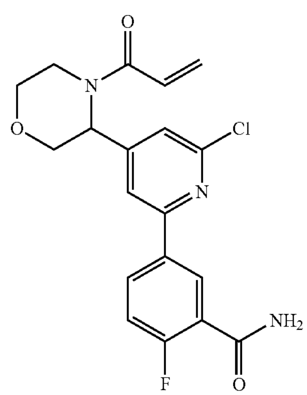 [SMILES: C=CC(=O)N1CCOCC1c1cc(Cl)nc(-c2ccc(F)c(C(N)=O)c2)c1] | 65 | 5-(4-(4-acryloylmorpholin-3-yl)-6-chloropyridin-2-yl)-2-fluorobenzamide | Single enantiomer of unknown absolute configuration | 1H NMR (400 MHz, CHLOROFORM-d) δ = 8.65 (dd, J = 2.4, 7.3 Hz, 1H), 8.24 (br d, J = 2.8 Hz, 1H), 7.77 (br s, 1H), 7.41 (br s, 1H), 7.24 (s, 1H), 6.69 (br s, 1H), 6.63-6.54 (m, 1H), 6.49-6.42 (m, 1H), 5.84 (br d, J = 11.7 Hz, 3H), 4.49 (d, J = 12.3 Hz, 1H), 4.04-3.68 (m, 3H), 3.67-3.60 (m, 1H), 3.36 (br s, 1H) |
| 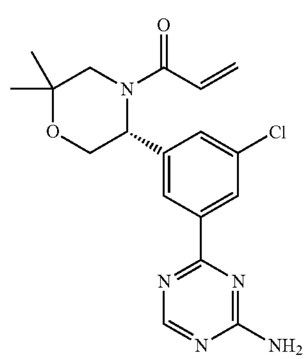 [SMILES: C=CC(=O)N1CC(C)(C)OC[C@H]1c1cc(Cl)cc(-c2ncnc(N)n2)c1] | 66 | (R)-1-(5-(3-(4-amino-1,3,5-triazin-2-yl)-5-chlorophenyl)-2,2-dimethylmorpholino) prop-2-en-1-one | Single enantiomer of known absolute configuration | 1H NMR (400 MHz, CHLOROFORM-d) δ ppm 1.24 (s, 3 H) 1.30 (s, 3 H) 2.85-3.60 (m, 2 H) 4.00-5.25 (m, 3 H) 5.62 (br s, 2 H) 5.78 (br d, J = 10.04 Hz, 2 H) 6.40-6.60 (m, 2 H) 7.43-7.75 (m, 1 H) 8.34 (s, 2 H) 8.68 (s, 1 H) |
| 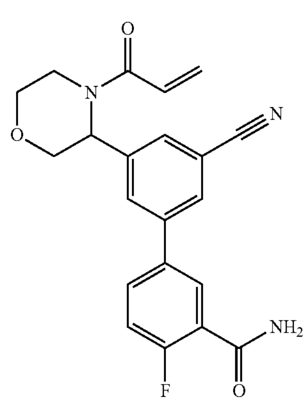 [SMILES: C=CC(=O)N1CCOCC1c1cc(C#N)cc(-c2ccc(F)c(C(N)=O)c2)c1] | 67 | 3'-(4-acryloylmorpholin-3-yl)-5'-cyano-4-fluoro-[1,1'-biphenyl]-3-carboxamide | Single enantiomer of unknown absolute configuration | 1H NMR (400 MHz, CHLOROFORM-d) δ ppm 3.13-3.86 (m, 3 H) 3.88-4.29 (m, 2 H) 4.49 (d, J = 12.30 Hz, 1 H) 5.82 (dd, J = 10.42, 1.38 Hz, 2 H) 5.98 (br s, 1 H) 6.37-6.48 (m, 1 H) 6.51-6.63 (m, 1 H) 6.73 (br d, J = 11.42 Hz, 1 H) 7.27 (s, 1 H) 7.63-7.72 (m, 1 H) 7.78-7.99 (m, 3 H) 8.31 (dd, J = 7.28, 2.38 Hz, 1 H) |

TABLE 1-continued

| Compounds of the Disclosure. | | | | |
|---|---|---|---|---|
| Structure | No. | Name | Stereochemistry | NMR |
| 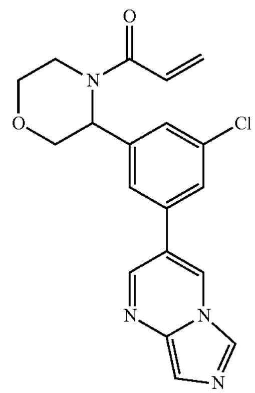 [SMILES: C=CC(=O)N1CCOCC1c1cc(Cl)cc(-c2cnc3cncn3c2)c1] | 68 | 1-(3-(3-chloro-5-(imidazo[1,5-a]pyrimidin-3-yl)phenyl)morpholino)prop-2-en-1-one | Single enantiomer of unknown absolute configuration | 1H NMR (400 MHz, CHLOROFORM-d) δ ppm 8.40-8.67 (m, 3 H) 7.47-7.90 (m, 4 H) 6.52-6.65 (m, 1 H) 6.33-6.47 (m, 1 H) 5.82 (br dd, 2 H) 4.49 (br d, 1 H) 3.93-4.07 (m, 2 H) 3.25-3.86 (m, 3 H) |
| 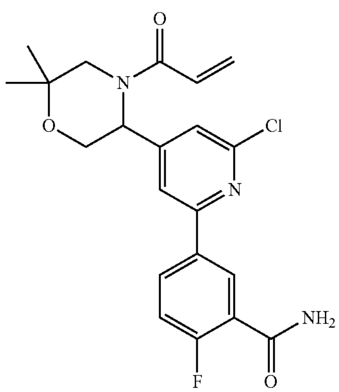 [SMILES: C=CC(=O)N1CC(C)(C)OCC1c1cc(Cl)nc(-c2ccc(F)c(C(N)=O)c2)c1] | 69 | 5-(4-(4-acryloyl-6,6-dimethylmorpholin-3-yl)-6-chloropyridin-2-yl)-2-fluorobenzamide | Single enantiomer of unknown absolute configuration | 1H NMR (400 MHz, CHLOROFORM-d) δ ppm 8.65 (dd, 1 H) 8.17-8.32 (m, 1 H) 7.32-7.90 (m, 2 H) 7.22-7.26 (m, 1 H) 6.69-6.78 (m, 1 H) 6.41-6.60 (m, 2 H) 5.71-5.95 (m, 3 H) 4.10-4.32 (m, 2 H) 2.92-3.65 (m, 2 H) 1.23-1.32 (m, 6 H) |
| 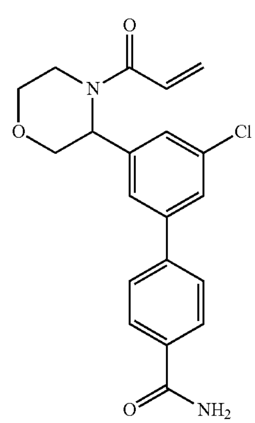 [SMILES: C=CC(=O)N1CCOCC1c1cc(Cl)cc(-c2ccc(C(N)=O)cc2)c1] | 70 | 3'-(4-acryloylmorpholin-3-yl)-5'-chloro-[1,1'-biphenyl]-4-carboxamide | Single enantiomer of unknown absolute configuration | 1H NMR (CHLOROFORM-d, 400 MHz): δ = 7.90 (d, J = 8.1 Hz, 2H), 7.48-7.72 (m, 5H), 6.35-6.66 (m, 2H), 6.17 (br s, 1H), 5.80 (br dd, J = 10.4, 1.6 Hz, 2H), 4.50 (d, J = 12.3 Hz, 1H), 3.63-4.47 (m, 4H), 2.83-3.63 ppm (m, 2H) |

TABLE 1-continued

| Compounds of the Disclosure. | | | | |
|---|---|---|---|---|
| Structure | No. | Name | Stereochemistry | NMR |
| 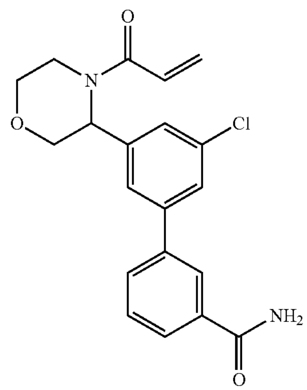 [SMILES: C=CC(=O)N1CCOCC1c1cc(Cl)cc(-c2cccc(C(N)=O)c2)c1] | 71 | 3'-(4-acryloylmorpholin-3-yl)-5'-chloro-[1,1'-biphenyl]-3-carboxamide | Single enantiomer of unknown absolute configuration | 1H NMR (400 MHz, CHLOROFORM-d) δ = 8.06-7.97 (m, 1H), 7.86-7.77 (m, 1H), 7.74-7.67 (m, 1H), 7.65-7.44 (m, 4H), 6.65-6.49 (m, 1H), 6.48-6.34 (m, 1H), 6.32-5.25 (m, 3H), 4.55-4.44 (m, 1H), 4.18-2.99 (m, 5H) |
| 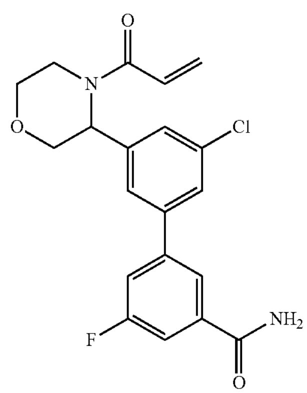 [SMILES: C=CC(=O)N1CCOCC1c1cc(Cl)cc(-c2cc(F)cc(C(N)=O)c2)c1] | 72 | 3'-(4-acryloylmorpholin-3-yl)-5'-chloro-5-fluoro-[1,1'-biphenyl]-3-carboxamide | Single enantiomer of unknown absolute configuration | 1H NMR (400 MHz, CHLOROFORM-d) δ ppm 3.07-4.02 (m, 1 H), 3.64 (td, J = 11.77, 2.63 Hz, 1 H) 3.86-4.06 (m, 2 H) 4.49 (d, J = 12.35 Hz, 1 H) 5.55-5.81 (m, 1 H) 5.80 (dd, J = 10.39, 1.83 Hz, 1 H) 6.16 (br s, 1 H) 6.33-6.46 (m, 1 H) 6.52-6.65 (m, 1 H) 7.40 (br d, J = 9.05 Hz, 1 H) 7.48-7.69 (m, 4 H) 7.76 (d, J = 1.34 Hz, 1 H) |
| 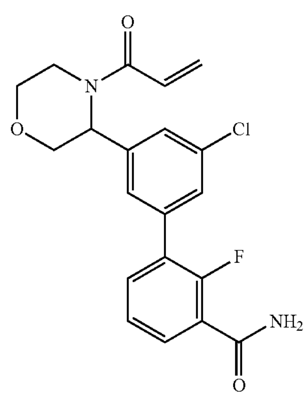 [SMILES: C=CC(=O)N1CCOCC1c1cc(Cl)cc(-c2cccc(C(N)=O)c2F)c1] | 73 | 3'-(4-acryloylmorpholin-3-yl)-5'-chloro-2-fluoro-[1,1'-biphenyl]-3-carboxamide | Single enantiomer of unknown absolute configuration | 1 H NMR (400 MHz, CHLOROFORM-d) δ ppm 3.41 (br s, 1 H) 3.44-4.05 (m, 1 H) 3.92 (dd, J = 12.29, 3.61 Hz, 1 H) 3.98-4.05 (m, 1 H) 4.48 (d, J = 12.10 Hz, 1 H) 5.67-6.00 (m, 2 H) 6.34-6.45 (m, 1 H) 6.50-6.62 (m, 1 H) 6.68 (br s, 1 H) 7.35 (t, J = 7.70 Hz, 1 H) 7.43-7.66 (m, 4 H) 8.05-8.19 (m, 1 H) |
| 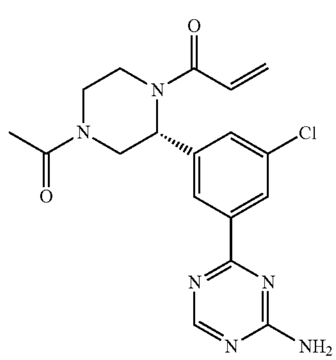 [SMILES: C=CC(=O)N1CCN(C(C)=O)C[C@H]1c1cc(Cl)cc(-c2ncnc(N)n2)c1] | 74 | (R)-1-(4-acetyl-2-(3-(4-amino-1,3,5-triazin-2-yl)-5-chlorophenyl)piperazin-1-yl)prop-2-en-1-one | Single enantiomer of known absolute configuration | 1H NMR (400 MHz, DMSO-d6) δ ppm 1.90-2.00 (m, 3 H) 3.35 (br s, 1 H) 3.48-3.92 (m, 2 H) 4.03-4.69 (m, 2 H) 5.50-5.82 (m, 2 H) 6.12-6.28 (m, 1 H) 6.37-6.74 (m, 1 H) 6.75-7.08 (m, 1 H) 7.49-7.65 (m, 1 H) 7.73 (br s, 2 H) 8.05-8.27 (m, 2 H) 8.61 (d, J = 4.50 Hz, 1 H) |

TABLE 1-continued

Compounds of the Disclosure.

| Structure | No. | Name | Stereochemistry | NMR |
|---|---|---|---|---|
| 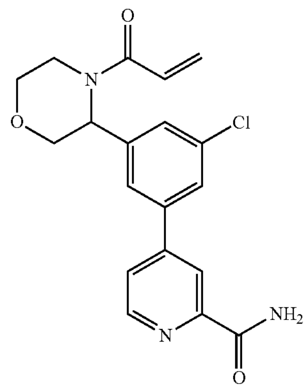 [SMILES: C=CC(=O)N1CCOCC1c1cc(Cl)cc(-c2ccnc(C(N)=O)c2)c1] | 75 | 4-(3-(4-acryloylmorpholin-3-yl)-5-chlorophenyl)picolinamide | Single enantiomer of unknown absolute configuration | 1H NMR (400 MHz, CHLOROFORM-d) δ = 8.64 (d, J = 4.9 Hz, 1H), 8.42 (s, 1H), 7.93 (br s, 1H), 7.64 (br s, 4H), 6.63-6.53 (m, 1H), 6.48-6.38 (m, 1H), 5.81 (br d, J = 10.4 Hz, 2H), 5.63 (br s, 1H), 4.49 (d, J = 12.4 Hz, 1H), 4.03-3.89 (m, 2H), 3.64 (br t, J = 11.5 Hz, 1H), 3.35 (br s, 1H) |
| 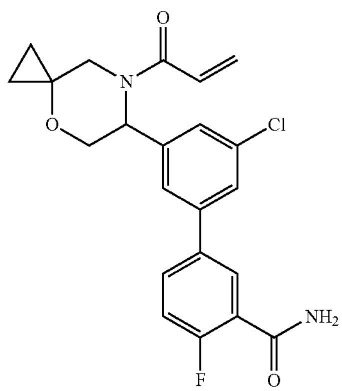 [SMILES: C=CC(=O)N1CC2(CC2)OCC1c1cc(Cl)cc(-c2ccc(F)c(C(N)=O)c2)c1] | 76 | 3'-(7-acryloyl-4-oxa-7-azaspiro[2.5]octan-6-yl)-5'-chloro-4-fluoro-[1,1'-biphenyl]-3-carboxamide | Single enantiomer of unknown absolute configuration | 1H NMR (400 MHz, CHLOROFORM-d) δ = 8.31 (br d, J = 6.8 Hz, 1H), 7.67 (br s, 1H), 7.53 (br s, 2H), 7.26-7.18 (m, 1H), 6.74 (br s, 1H), 6.61-6.31 (m, 2H), 5.86 (br s, 1H), 5.78 (br d, J = 10.0 Hz, 1H), 4.43 (br d, J = 11.6 Hz, 1H), 4.09 (br d, J = 12.3 Hz, 1H), 3.84 (br s, 1H), 3.09 (br s, 1H), 1.33-0.93 (m, 2H), 0.80-0.63 (m, 2H) |
| 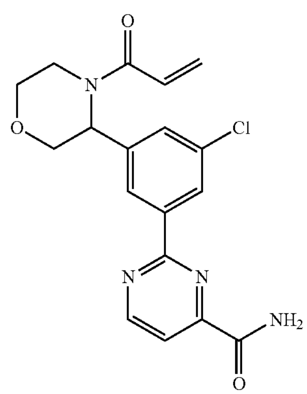 [SMILES: C=CC(=O)N1CCOCC1c1cc(Cl)cc(-c2nccc(C(N)=O)n2)c1] | 77 | 2-(3-(4-acryloylmorpholin-3-yl)-5-chlorophenyl)pyrimidine-4-carboxamide | Single enantiomer of unknown absolute configuration | 1H NMR (400 MHz, DMSO-d6) δ = 9.15 (d, J = 4.9 Hz, 1H), 8.78-8.68 (m, 2H), 8.47 (br s, 1H), 8.05 (br s, 1H), 7.95 (d, J = 4.9 Hz, 1H), 7.54 (br s, 1H), 6.89 (br dd, J = 10.6, 16.4 Hz, 1H), 6.24 (dd, J = 2.3, 16.5 Hz, 1H), 5.78 (br d, J = 10.4 Hz, 1H), 5.60 (br s, 1H), 4.52 (d, J = 12.1 Hz, 1H), 4.16-3.95 (m, 1H), 3.92-3.76 (m, 2H), 3.59-3.47 (m, 1H), 3.31-3.09 (m, 1H) |
| 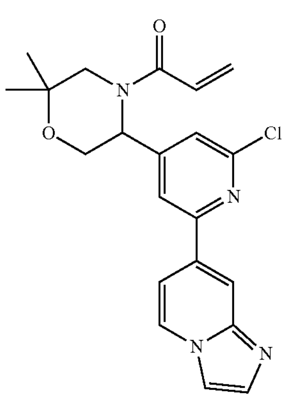 [SMILES: C=CC(=O)N1CC(C)(C)OCC1c1cc(Cl)nc(-c2ccn3ccnc3c2)c1] | 78 | 1-(5-(2-chloro-6-(imidazo[1,2-a]pyridin-7-yl)pyridin-4-yl)-2,2-dimethylmorpholino)prop-2-en-1-one | Single enantiomer of unknown absolute configuration | 1H NMR (400 MHz, CHLOROFORM-d) δ ppm 9.03 (br s, 1 H) 8.40 (d, 1 H) 8.16-8.28 (m, 1 H) 7.90-8.02 (m, 2 H) 7.77 (s, 1 H) 7.42-7.58 (m, 1 H) 6.57-6.78 (m, 1 H) 6.37-6.53 (m, 1 H) 5.66-5.95 (m, 2 H) 4.20 (br s, 2 H) 3.51-3.78 (m, 1 H) 3.10-3.46 (m, 1 H) 1.32 (s, 3 H) 1.27 (s, 3 H) |

TABLE 1-continued

| Structure | No. | Name | Stereochemistry | NMR |
|---|---|---|---|---|
| Compounds of the Disclosure. | | | | |
| 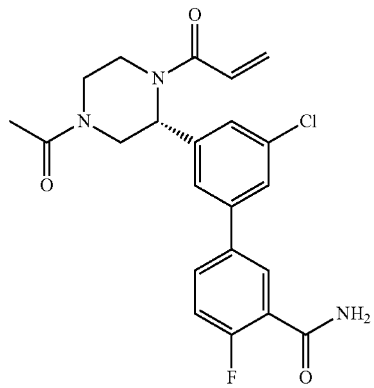 [SMILES: C=CC(=O)N1CCN(C(C)=O)C[C@H]1c1cc(Cl)cc(-c2ccc(F)c(C(N)=O)c2)c1] | 79 | (R)-3'-(4-acetyl-1-acryloylpiperazin-2-yl)-5'-chloro-4-fluoro-[1,1'-biphenyl]-3-carboxamide | Single enantiomer of known absolute configuration | 1H NMR (400 MHz, CHLOROFORM-d) δ ppm 8.22-8.36 (m, 1 H) 7.78 (s, 1 H) 7.45-7.55 (m, 2 H) 7.28-7.38 (m, 1 H) 7.20-7.27 (m, 2 H) 6.76-6.95 (m, 1 H) 6.36-6.65 (m, 2 H) 6.13-6.27 (m, 1 H) 5.71-5.90 (m, 1 H) 4.53-5.42 (m, 2 H) 4.07-4.37 (m, 1 H) 3.70-3.88 (m, 1 H) 3.50-3.67 (m, 1 H) 3.15-3.47 (m, 2 H) 1.97-2.17 (m, 3 H) |
| 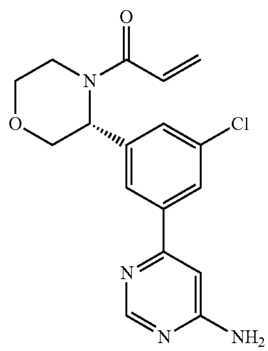 | 80 | (R)-1-(3-(3-(6-aminopyrimidin-4-yl)-5-chlorophenyl)morpholino)prop-2-en-1-one | Single enantiomer of known absolute configuration | 1H NMR (400 MHz, CHLOROFORM-d) δ ppm 3.11-3.50 (m, 1 H) 3.63 (td, J = 11.76, 2.25 Hz, 1 H) 3.85-4.09 (m, 2 H) 4.50 (d, J = 12.26 Hz, 1 H) 5.07 (br s, 2 H) 5.79 (dd, J = 10.38, 1.63 Hz, 2 H) 6.34-6.65 (m, 2 H) 6.79 (s, 1 H) 7.27 (s, 1 H) 7.63 (br d, J = 3.00 Hz, 1 H) 7.95 (br s, 2 H) 8.65 (s, 1 H) |
| 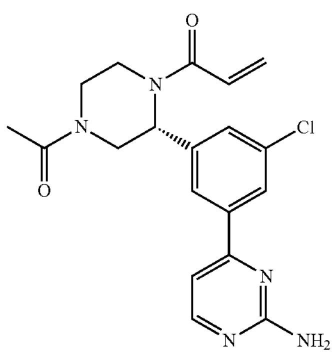 [SMILES: C=CC(=O)N1CCN(C(C)=O)C[C@H]1c1cc(Cl)cc(-c2ccnc(N)n2)c1] | 81 | (R)-1-(4-acetyl-2-(3-(2-aminopyrimidin-4-yl)-5-chlorophenyl)piperazin-1-yl)prop-2-en-1-one | Single enantiomer of known absolute configuration | 1H NMR (CHLOROFORM-d, 400 MHz): δ = 8.38 (d, J = 5.3 Hz, 1H), 7.85-8.07 (m, 2H), 7.36 (s, 1H), 6.94-7.18 (m, 1H), 6.35-6.83 (m, 2H), 5.81 (br s, 1H), 5.17-5.37 (m, 2H), 4.15-4.71 (m, 1H), 2.99-3.92 (m, 4H), 2.06-2.12 ppm (m, 3H) |
| 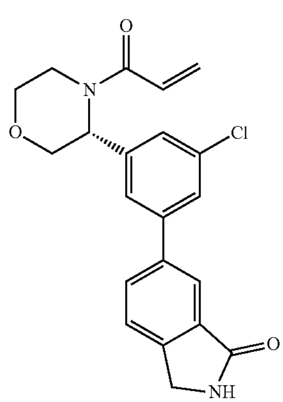 [SMILES: C=CC(=O)N1CCOC[C@H]1c1cc(Cl)cc(-c2ccc3c(c2)C(=O)NC3)c1] | 82 | (R)-6-(3-(4-acryloylmorpholin-3-yl)-5-chlorophenyl)isoindolin-1-one | Single enantiomer of known absolute configuration | 1H NMR (CHLOROFORM-d, 400 MHz): δ = 8.06 (d, J = 1.1 Hz, 1H), 7.76 (dd, J = 7.9, 1.5 Hz, 1H), 7.42-7.70 (m, 4H), 6.70-6.82 (m, 1H), 6.35-6.66 (m, 2H), 5.80 (dd, J = 10.4, 1.9 Hz, 2H), 4.48-4.57 (m, 3H), 3.87-4.09 (m, 2H), 3.63 (td, J = 11.7, 2.5 Hz, 2H), 3.41 (br s, 1H) |

TABLE 1-continued

| Structure | No. | Name | Stereochemistry | NMR |
|---|---|---|---|---|
| Compounds of the Disclosure. | | | | |
| 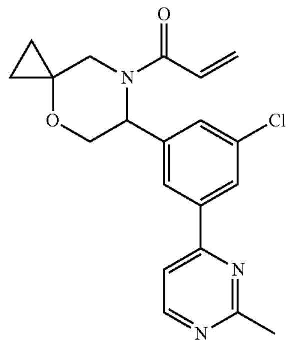 [SMILES: C=CC(=O)N1CC2(CC2)OCC1c1cc(Cl)cc(-c2ccnc(C)n2)c1] | 83 | 1-(6-(3-chloro-5-(2-methylpyrimidin-4-yl)phenyl)-4-oxa-7-azaspiro[2.5]octan-7-yl)prop-2-en-1-one | Single enantiomer of unknown absolute configuration | 1H NMR (400 MHz, CHLOROFORM-d) δ = 8.77-8.60 (m, 1H), 8.13-7.95 (m, 2H), 7.81-7.57 (m, 1H), 7.56-7.42 (m, 1H), 6.61-6.35 (m, 2H), 6.11-5.62 (m, 2H), 4.51-4.41 (m, 1H), 4.16-3.68 (m, 2H), 3.35-2.88 (m, 1H), 2.87-2.72 (m, 3H), 1.10-0.96 (m, 1H), 0.85-0.75 (m, 1H), 0.73-0.66 (m, 1H), 0.64-0.48 (m, 1H) |
| 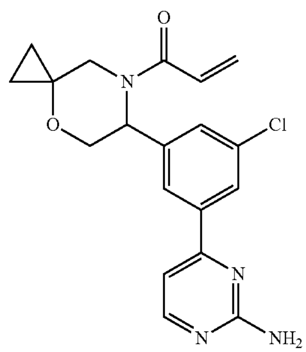 [SMILES: C=CC(=O)N1CC2(CC2)OCC1c1cc(Cl)cc(-c2ccnc(N)n2)c1] | 84 | 1-(6-(3-(2-aminopyrimidin-4-yl)-5-chlorophenyl)-4-oxa-7-azaspiro[2.5]octan-7-yl)prop-2-en-1-one | Single enantiomer of unknown absolute configuration | 1H NMR (400 MHz, CHLOROFORM-d) δ ppm 0.48-0.65 (m, 1 H) 0.66-0.74 (m, 1 H) 0.75-0.84 (m, 1 H) 0.95-1.11 (m, 1 H) 2.99-3.22 (m, 1 H) 3.70-4.20 (m, 2 H) 4.37-4.52 (m, 1 H) 5.29-5.62 (m, 2 H) 5.68-6.07 (m, 2 H) 6.34-6.61 (m, 2 H) 6.99-7.13 (m, 1 H) 7.59-7.81 (m, 1 H) 7.92-8.13 (m, 2 H) 8.29-8.40 (m, 1 H) |
| 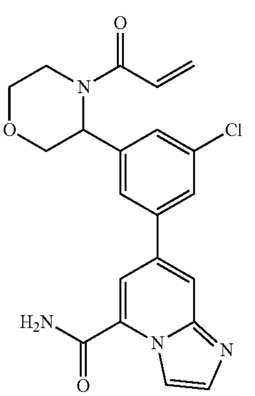 [SMILES: C=CC(=O)N1CCOCC1c1cc(Cl)cc(-c2cc(C(N)=O)n3ccnc3c2)c1] | 85 | 7-(3-(4-acryloylmorpholin-3-yl)-5-chlorophenyl)imidazo[1,2-a]pyridine-5-carboxamide | Single enantiomer of unknown absolute configuration | 1H NMR (DMSO-d6) δ: 8.49-8.69 (m, 2H), 8.16 (s, 1H), 7.93-8.03 (m, 2H), 7.86 (d, J = 1.5 Hz, 1H), 7.82 (br s, 1H), 7.75 (d, J = 0.8 Hz, 1H), 7.35 (br s, 1H), 6.89 (br dd, J = 15.8, 10.9 Hz, 1H), 6.23 (dd, J = 16.6, 2.3 Hz, 1H), 5.72-5.83 (m, 1H), 5.20-5.70 (m, 1H), 4.58 (d, J = 12.3 Hz, 1H), 3.72-4.40 (m, 3H), 3.46-3.60 (m, 1H), 2.78-3.29 (m, 1H) |
| 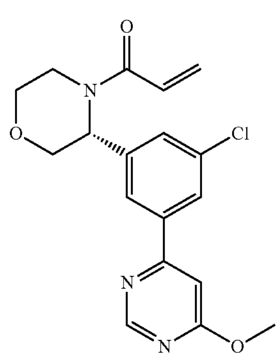 | 86 | (R)-1-(3-(3-chloro-5-(6-methoxypyrimidin-4-yl)phenyl)morpholino)prop-2-en-1-one | Single enantiomer of known absolute configuration | 1H NMR (CHLOROFORM-d) δ: 8.84 (s, 1H), 7.89-8.10 (m, 2H), 7.62 (br s, 1H), 7.08 (s, 1H), 6.52-6.65 (m, 1H), 6.36-6.49 (m, 1H), 5.80 (dd, J = 10.4, 1.7 Hz, 1H), 4.51 (d, J = 12.3 Hz, 1H), 3.92 (dd, J = 12.3, 3.4 Hz, 1H), 3.87-4.14 (m, 5H), 3.63 (td, J = 11.7, 2.3 Hz, 1H), 3.52-3.86 (m, 1H), 3.15-3.51 (m, 1H), 1.67 (br s, 1H) |

TABLE 1-continued

Compounds of the Disclosure.

| Structure | No. | Name | Stereochemistry | NMR |
|---|---|---|---|---|
| 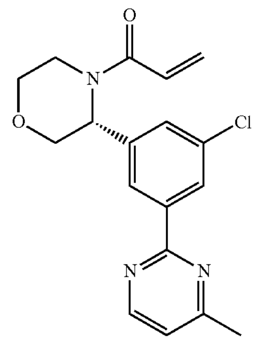 [SMILES: C=CC(=O)N1CCOC[C@H]1c1cc(Cl)cc(-c2nccc(C)n2)c1] | 87 | (R)-1-(3-(3-chloro-5-(4-methylpyrimidin-2-yl)phenyl)morpholino)prop-2-en-1-one | Single enantiomer of known absolute configuration | 1H NMR (400 MHz, CHLOROFORM-d) δ = 8.65 (br d, J = 4.8 Hz, 1H), 8.52-8.35 (m, 2H), 7.54 (br d, J = 7.6 Hz, 1H), 7.10 (d, J = 4.5 Hz, 1H), 6.66-6.54 (m, 1H), 6.47-6.37 (m, 1H), 5.79 (dd, J = 1.5, 10.4 Hz, 2H), 4.57 (d, J = 12.1 Hz, 1H), 3.99 (br dd, J = 3.0, 11.3 Hz, 1H), 4.04-3.96 (m, 1H), 3.92 (dd, J = 3.5, 12.3 Hz, 1H), 3.64 (dt, J = 2.4, 11.7 Hz, 1H), 3.37 (br s, 1H), 3.85-3.01 (m, 1H), 2.60 (s, 3H), 1.27-1.22 (m, 1H) |
| 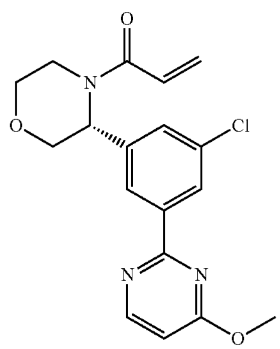 [SMILES: C=CC(=O)N1CCOC[C@H]1c1cc(Cl)cc(-c2nccc(OC)n2)c1] | 88 | (R)-1-(3-(3-chloro-5-(4-methoxypyrimidin-2-yl)phenyl)morpholino)prop-2-en-1-one | Single enantiomer of known absolute configuration | 1H NMR (400 MHz, CHLOROFORM-d) δ = 8.50 (d, J = 5.8 Hz, 1H), 8.45 (br s, 1H), 8.36 (s, 1H), 7.56 (br s, 1H), 6.67 (d, J = 5.6 Hz, 1H), 6.60 (d, J = 6.3 Hz, 1H), 6.42 (dd, J = 1.1, 16.6 Hz, 1H), 5.79 (dd, J = 1.8, 10.4 Hz, 1H), 4.55 (d, J = 12.1 Hz, 1H), 4.08 (s, 3H), 4.02-3.88 (m, 3H), 3.69-3.51 (m, 2H), 3.43-3.24 (m, 1H) |
| 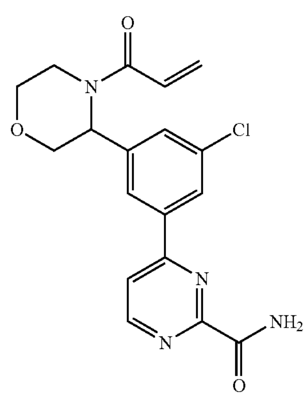 [SMILES: C=CC(=O)N1CCOCC1c1cc(Cl)cc(-c2ccnc(C(N)=O)n2)c1] | 89 | 4-(3-(4-acryloylmorpholin-3-yl)-5-chlorophenyl)pyrimidine-2-carboxamide | Single enantiomer of unknown absolute configuration | 1H NMR (400 MHz, CHLOROFORM-d) δ ppm 3.07-3.48 (m, 1 H) 3.66 (td, J = 11.82, 2.38 Hz, 2 H) 3.90-4.09 (m, 2 H) 4.51 (d, J = 12.26 Hz, 1 H) 5.81 (dd, J = 10.44, 1.56 Hz, 2 H) 5.94 (br s, 1H) 6.33-6.49 (m, 1 H) 6.51-6.68 (m, 1 H) 7.60-7.99 (m, 3 H) 8.11 (br s, 2 H) 8.78-9.26 (m, 1 H) |
| 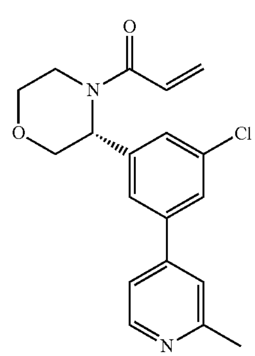 [SMILES: C=CC(=O)N1CCOC[C@H]1c1cc(Cl)cc(-c2ccnc(C)c2)c1] | 90 | (R)-1-(3-(3-chloro-5-(2-methylpyridin-4-yl)phenyl)morpholino)prop-2-en-1-one | Single enantiomer of known absolute configuration | 1H NMR (400 MHz, CHLOROFORM-d) δ ppm 2.92 (s, 3 H) 3.42 (br d, J = 8.76 Hz, 1 H) 3.58-3.82 (m, 2 H) 3.97 (dd, J = 12.51, 3.63 Hz, 1 H) 4.06 (br d, J = 11.01 Hz, 1 H) 4.50 (br d, J = 12.38 Hz, 1 H) 5.76-5.98 (m, 2 H) 6.33-6.48 (m, 1 H) 6.50-6.65 (m, 1 H) 7.66 (s, 1 H) 7.70-7.99 (m, 4 H) 8.81 (br d, J = 6.00 Hz, 1 H) |

TABLE 1-continued

| Compounds of the Disclosure. | | | | |
|---|---|---|---|---|
| Structure | No. | Name | Stereochemistry | NMR |
| 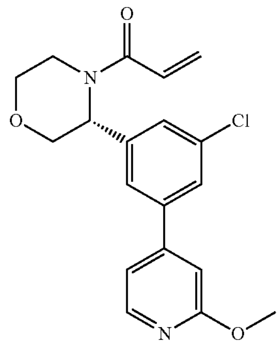 [SMILES: C=CC(=O)N1CCOC[C@H]1c1cc(Cl)cc(-c2ccnc(OC)c2)c1] | 91 | (R)-1-(3-(3-chloro-5-(2-methoxypyridin-4-yl)phenyl)morpholino)prop-2-en-1-one | Single enantiomer of known absolute configuration | 1H NMR (400 MHz, CHLOROFORM-d) δ ppm 3.06-3.45 (m, 1 H) 3.46-3.87 (m, 2 H) 3.91 (dd, J = 12.32, 3.56 Hz, 1 H) 3.99 (s, 4 H) 4.48 (d, J = 12.26 Hz, 1 H) 5.80 (dd, J = 10.38, 1.88 Hz, 2H) 6.35-6.48 (m, 1 H) 6.50-6.65 (m, 1 H) 6.91 (s, 1 H) 6.99-7.15 (m, 1 H) 7.40-7.79 (m, 3 H) 8.23 (d, J = 5.38 Hz, 1 H) |
| 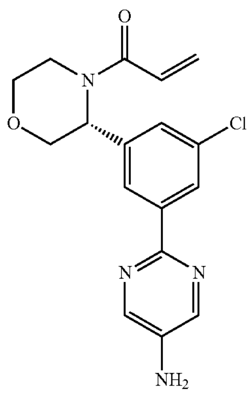 [SMILES: C=CC(=O)N1CCOC[C@H]1c1cc(Cl)cc(-c2ncc(N)cn2)c1] | 92 | (R)-1-(3-(3-chloro-5-(5-methylpyrimidin-2-yl)phenyl)morpholino)prop-2-en-1-one | Single enantiomer of known absolute configuration | 1H NMR (CHLOROFORM-d) δ: 8.31 (s, 3H), 8.25 (s, 1H), 7.34-7.63 (m, 1H), 6.52-6.67 (m, 1H), 6.35-6.50 (m, 1H), 5.78 (br dd, J = 10.4, 1.7 Hz, 1H), 4.56 (d, J = 12.1 Hz, 1 H), 3.99 (br dd, J = 11.3, 3.1 Hz, 1 H), 3.87-3.95 (m, 1H), 3.56-3.80 (m, 2H), 2.99-3.55 (m, 2H) |
| 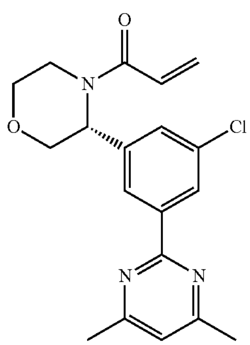 [SMILES: C=CC(=O)N1CCOC[C@H]1c1cc(Cl)cc(-c2nc(C)cc(C)n2)c1] | 93 | (R)-1-(3-(3-chloro-5-(4,6-dimethylpyrimidin-2-yl)phenyl)morpholino)prop-2-en-1-one | Single enantiomer of known abolsute configuration | 1H NMR (400 MHz, CHLOROFORM-d) δ ppm 2.54 (s, 6 H) 3.38 (br d, J = 6.80 Hz, 1 H) 3.61 (s, 1 H) 3.63-3.68 (m, 1 H) 3.87-4.02 (m, 3 H) 4.57 (d, J = 12.28 Hz, 1 H) 5.79 (dd, J = 10.52, 1.75 Hz, 1 H) 6.39-6.45 (m, 1 H) 6.56-6.64 (m, 1 H) 6.96 (s, 1 H) 7.53 (br s, 1 H) 8.38 (s, 1 H) 8.42 (br s, 1 H) |
| 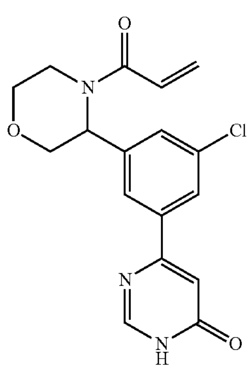 [SMILES: C=CC(=O)N1CCOCC1c1cc(Cl)cc(-c2cc(=O)[nH]cn2)c1] | 94 | 6-(3-(4-acryloylmorpholin-3-yl)-5-chlorophenyl)pyrimidin-4(3H)-one | Single enantiomer of unknown absolute configuration | 1H NMR (400 MHz, DMSO-d6) δ ppm 3.41-3.44 (m, 2 H) 3.47-3.56 (m, 2 H) 3.78 (br d, J = 10.01 Hz, 1 H) 3.88 (br d, J = 10.13 Hz, 1 H) 4.47 (br d, J = 12.26 Hz, 1 H) 5.57 (br s, 1 H) 5.77 (br d, J = 10.38 Hz, 1 H) 6.22 (dd, J = 16.57, 2.06 Hz, 1 H) 6.71-7.04 (m, 2 H) 7.48 (br s, 1 H) 7.91-8.05 (m, 2 H) 8.30 (s, 1 H) |

TABLE 1-continued

| Structure | No. | Name | Stereochemistry | NMR |
|---|---|---|---|---|
| 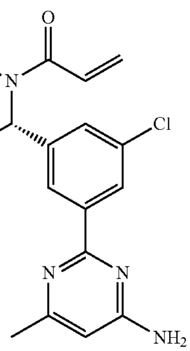 | 95 | (R)-1-(3-(3-(4-amino-6-methylpyrimidin-2-yl)-5-chlorophenyl)morpholino)prop-2-en-1-one | Single enantiomer of known absolute configuration | 1H NMR (400 MHz, DMSO-d6) δ ppm 2.28 (s, 3 H) 3.29 (br s, 1 H) 3.46-3.56 (m, 1 H) 3.80 (br d, J = 11.63 Hz, 1 H) 3.89 (br d, J = 8.63 Hz, 1 H) 4.17 (br d, J = 10.51 Hz, 1 H) 4.41 (br d, J = 12.13 Hz, 1 H) 5.53 (br d, J = 17.64 Hz, 1 H) 5.77 (dd, J = 10.44, 2.19 Hz, 1 H) 6.16-6.33 (m, 2 H) 6.76-6.94 (m, 3 H) 7.46 (br s, 1 H) 8.12-8.31 (m, 2 H) |
| 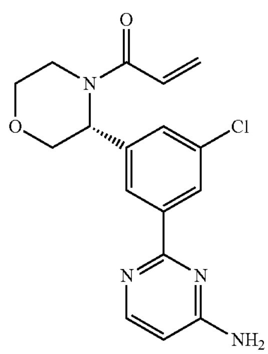 [SMILES: C=CC(=O)N1CCOC[C@H]1c1cc(Cl)cc(-c2nccc(N)n2)c1] | 96 | (R)-1-(3-(3-(4-aminopyrimidin-2-yl)-5-chlorophenyl)morpholino)prop-2-en-1-one | Single enantiomer of known absolute configuration | 1H NMR (400 MHz, CHLOROFORM-d) δ = 8.46-8.18 (m, 3H), 7.53 (br s, 1H), 6.63-6.55 (m, 1H), 6.45-6.37 (m, 3H), 5.78 (dd, J = 1.9, 10.4 Hz, 1H), 5.10 (br s, 2H), 4.54 (d, J = 12.1 Hz, 2H), 3.99 (dd, J = 3.3, 11.3 Hz, 1H), 3.91 (dd, J = 3.6, 12.3 Hz, 1H), 3.63 (dt, J = 2.8, 11.8 Hz, 2 H), 3.35 (br s, 1H) |
| 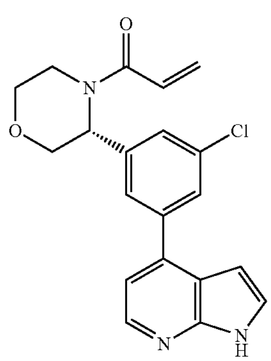 [SMILES: C=CC(=O)N1CCOC[C@H]1c1cc(Cl)cc(-c2ccnc3[nH]ccc23)c1] | 97 | (R)-1-(3-(3-chloro-5-(1H-pyrrolo[2,3-b]pyridin-4-yl)phenyl)morpholino)prop-2-en-1-one | Single enantiomer of known absolute configuration | 1H NMR (400 MHz, CHLOROFORM-d) δ ppm 3.43 (br s, 1 H) 3.65 (td, J = 11.79, 2.44 Hz, 2 H) 3.87-4.08 (m, 2 H) 4.52 (d, J = 12.26 Hz, 1 H) 5.80 (dd, J = 10.44, 1.81 Hz, 1 H) 6.35-6.50 (m, 1 H) 6.52-6.74 (m, 2 H) 7.17 (d, J = 5.00 Hz, 1 H) 7.34-7.93 (m, 2 H) 7.42 (d, J = 3.38 Hz, 1 H) 8.39 (d, J = 5.00 Hz, 1 H) 9.69 (br s, 1 H) |
| 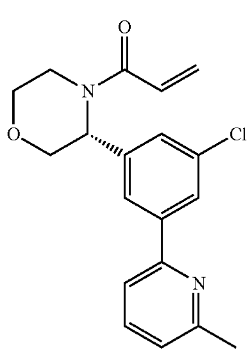 [SMILES: C=CC(=O)N1CCOC[C@H]1c1cc(Cl)cc(-c2cccc(C)n2)c1] | 98 | (R)-1-(3-(3-chloro-5-(6-methylpyridin-2-yl)phenyl)morpholino)prop-2-en-1-one | Single enantiomer of known absolute configuration | 1H NMR (400 MHz, CHLOROFORM-d) δ = 7.99 (t, J = 7.7 Hz, 1H), 7.91 (br s, 1H), 7.79 (s, 1H), 7.63 (br d, J = 7.8 Hz, 2H), 7.40 (d, J = 7.8 Hz, 1H), 6.68-6.53 (m, 1H), 6.40 (br d, J = 16.4 Hz, 1H), 5.80 (br d, J = 10.4 Hz, 2H), 4.51 (br d, J = 12.3 Hz, 1H), 4.07-3.84 (m, 2H), 3.81-3.04 (m, 3H), 2.81 (s, 3H) |

TABLE 1-continued

| Compounds of the Disclosure. | | | | |
|---|---|---|---|---|
| Structure | No. | Name | Stereochemistry | NMR |
| 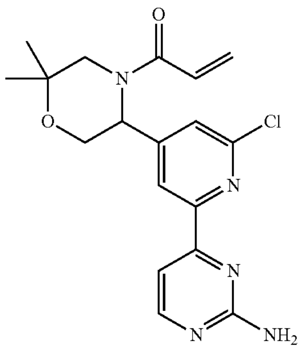 [SMILES: C=CC(=O)N1CC(C)(C)OCC1c1cc(Cl)nc(-c2ccnc(N)n2)c1] | 99 | 1-(5-(2-(2-aminopyrimidin-4-yl)-6-chloropyridin-4-yl)-2,2-dimethylmorpholino)prop-2-en-1-one | Single enantiomer of unknown absolute configuration | 1H NMR (400 MHz, CHLOROFORM-d) δ = 8.44 (br d, J = 5.2 Hz, 1H), 8.42-8.33 (m, 1H), 7.68 (d, J = 5.1 Hz, 1H), 7.53 (br s, 1H), 6.68-6.41 (m, 2H), 6.06-5.62 (m, 2H), 5.40-5.18 (m, 2H), 4.31-4.12 (m, 2H), 3.75-3.31 (m, 1H), 3.21-2.83 (m, 1H), 1.30 (s, 1H), 1.23 (s, 1H) |
| 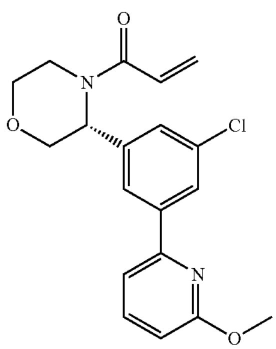 [SMILES: C=CC(=O)N1CCOC[C@H]1c1cc(Cl)cc(-c2cccc(OC)n2)c1] | 100 | (R)-1-(3-(3-chloro-5-(6-methoxypyridin-2-yl)phenyl)morpholino)prop-2-en-1-one | Single enantiomer of known absolute configuration | 1H NMR (400 MHz, CHLOROFORM-d) δ = 7.98 (s, 2H), 7.64 (t, J = 7.8 Hz, 2H), 7.31 (d, J = 7.3 Hz, 1H), 6.73 (d, J = 8.2 Hz, 1H), 6.57 (br d, J = 10.3 Hz, 1H), 6.47-6.37 (m, 1H), 5.76-5.75 (m, 1H), 5.79 (dd, J = 1.9, 10.4 Hz, 1H), 4.52 (d, J = 12.3 Hz, 1H), 4.03 (s, 3H), 4.01-3.96 (m, 1H), 3.92 (dd, J = 3.6, 12.2 Hz, 1H), 3.64 (dt, J = 2.6, 11.7 Hz, 3H) |
| 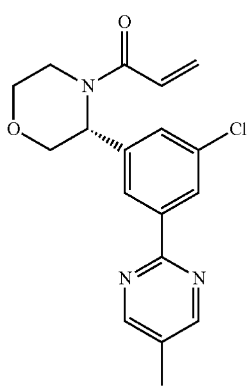 [SMILES: C=CC(=O)N1CCOC[C@H]1c1cc(Cl)cc(-c2ncc(C)cn2)c1] | 101 | (R)-1-(3-(3-chloro-5-(5-methylpyrimidin-2-yl)phenyl)morpholino)prop-2-en-1-one | Single enantiomer of known absolute configuration | H NMR (400 MHz, CHLOROFORM-d) δ = 8.64 (s, 2H), 8.42 (br d, J = 1.3 Hz, 1H), 8.36 (s, 1H), 7.53 (br d, J = 1.0 Hz, 1H), 6.63-6.56 (m, 1H), 6.45-6.40 (m, 1H), 5.80-5.77 (m, 1H), 4.56 (d, J = 12.3 Hz, 1H), 4.02-3.90 (m, 3H), 3.63 (dt, J = 2.5, 11.8 Hz, 2H), 3.44-3.26 (m, 1H), 2.36 (s, 3H) |
| 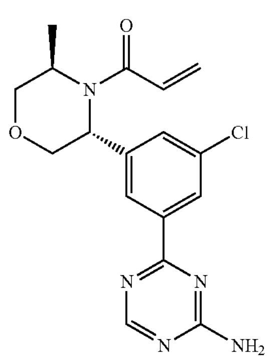 [SMILES: C=CC(=O)N1[C@H](C)COC[C@H]1c1cc(Cl)cc(-c2ncnc(N)n2)c1] | 102 | 1-((3R,5R)-3-(3-(4-amino-1,3,5-triazin-2-yl)-5-chlorophenyl)-5-methylmorpholino)prop-2-en-1-one | Single enantiomer of known absolute configuration | 1H NMR (400 MHz, CHLOROFORM-d) δ ppm 1.45 (br d, J = 6.56 Hz, 3 H) 3.61-3.86 (m, 2 H) 4.00 (dd, J = 11.56, 3.10 Hz, 1 H) 4.06-4.42 (m, 2 H) 4.91 (br d, J = 4.41 Hz, 1 H) 5.39-5.75 (m, 3 H) 6.32 (br d, J = 15.50 Hz, 1 H) 7.42 (s, 1 H) 8.20-8.33 (m, 2 H) 8.67 (s, 1 H) |

TABLE 1-continued

| Compounds of the Disclosure. | | | | |
|---|---|---|---|---|
| Structure | No. | Name | Stereochemistry | NMR |
| 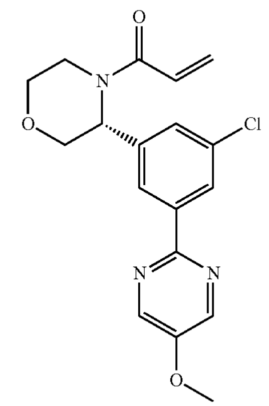 [SMILES: C=CC(=O)N1CCOC[C@H]1c1cc(Cl)cc(-c2ncc(OC)cn2)c1] | 103 | (R)-1-(3-(3-chloro-5-(5-methoxypyrimidin-2-yl)phenyl)morpholino)prop-2-en-1-one | Single enantiomer of known absolute configuration | 1H NMR (400 MHz, CHLOROFORM-d) δ = 8.47 (s, 2H), 8.43-8.27 (m, 2H), 7.51 (br d, J = 11.1 Hz, 1H), 6.65-6.54 (m, 1H), 6.48-6.38 (m, 1H), 5.79 (dd, J = 1.9, 10.5 Hz, 2H), 4.55 (d, J = 12.1 Hz, 1H), 4.06-3.95 (m, 5H), 3.92 (dd, J = 3.6, 12.2 Hz, 1H), 3.63 (dt, J = 2.7, 11.7 Hz, 1H), 3.35 (br s, 1H) |
| 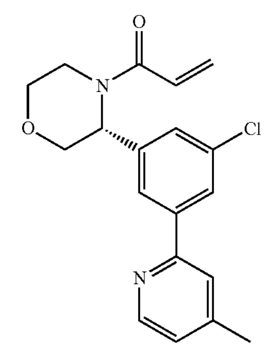 [SMILES: C=CC(=O)N1CCOC[C@H]1c1cc(Cl)cc(-c2cc(C)ccn2)c1] | 104 | (R)-1-(3-(3-chloro-5-(4-methylpyridin-2-yl)phenyl)morpholino)prop-2-en-1-one | Single enantiomer of known absolute configuration | 1H NMR (CHLOROFORM-d, 400 MHz): δ = 8.51-8.66 (m, 1H), 7.89-8.10 (m, 2H), 7.56 (br s, 2H), 7.20 (br s, 1H), 6.35-6.73 (m, 2H), 5.55-6.01 (m, 2H), 4.55 (br d, J = 12.0 Hz, 1H), 3.70-4.17 (m, 3H), 3.64 (br t, J = 11.9 Hz, 1H), 3.49 (s, 1H), 2.48 ppm (br s, 3H) |
| 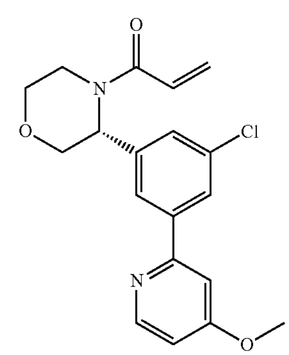 [SMILES: C=CC(=O)N1CCOC[C@H]1c1cc(Cl)cc(-c2cc(OC)ccn2)c1] | 105 | (R)-1-(3-(3-chloro-5-(4-methoxypyridin-2-yl)phenyl)morpholino)prop-2-en-1-one | Single enantiomer of known absolute configuration | 1H NMR (CHLOROFORM-d, 400 MHz): δ = 8.58 (br s, 1H), 7.83-8.05 (m, 2H), 7.46-7.72 (m, 1H), 7.22 (s, 1H), 6.90 (br s, 1H), 6.32-6.68 (m, 2H), 5.66-5.99 (m, 2H), 4.55 (br d, J = 11.9 Hz, 1H), 3.86-4.05 (m, 6H), 3.63 ppm (br t, J = 11.6 Hz, 2H) |
| 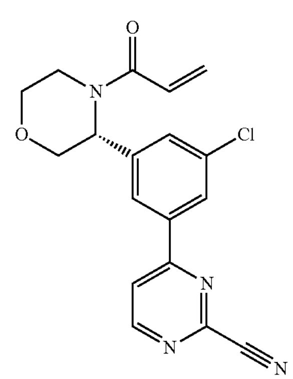 [SMILES: C=CC(=O)N1CCOC[C@H]1c1cc(Cl)cc(-c2ccnc(C#N)n2)c1] | 106 | (R)-4-(3-(4-acryloylmorpholin-3-yl)-5-chlorophenyl)pyrimidine-2-carbonitrile | Single enantiomer of known absolute configuration | 1H NMR (CHLOROFORM-d, 400 MHz): δ = 8.88 (d, J = 5.4 Hz, 1H), 8.09 (br s, 2H), 7.69-7.94 (m, 2H), 6.346.75 (m, 2H), 5.57-5.97 (m, 2H), 4.50 (d, J = 12.3 Hz, 1H), 3.89-4.14 (m, 2H), 3.55-3.88 (m, 2H), 3.07-3.53 ppm (m, 1H) |

TABLE 1-continued

Compounds of the Disclosure.

| Structure | No. | Name | Stereochemistry | NMR |
|---|---|---|---|---|
| 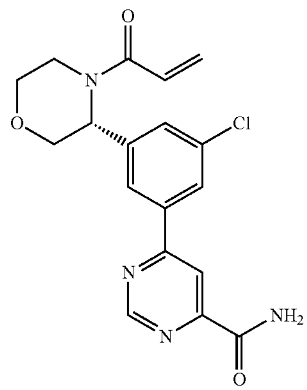 [SMILES: C=CC(=O)N1CCOC[C@H]1c1cc(Cl)cc(-c2cc(C(N)=O)ncn2)c1] | 107 | 6-(3-(4-acryloylmorpholin-3-yl)-5-chlorophenyl)pyrimidine-4-carboxamide | Single enantiomer of unknown absolute configuration | 1H NMR (400 MHz, CHLOROFORM-d) δ ppm 9.22 (d, J = 1.25 Hz, 1 H) 8.43 (d, J = 1.25 Hz, 1 H) 8.14 (br s, 1 H) 8.00-8.06 (m, 1 H) 7.77 (br s, 1 H) 7.59 (br s, 1 H) 6.44-6.59 (m, 1 H) 6.29-6.42 (m, 1 H) 5.64-5.79 (m, 2 H) 4.45 (d, J = 12.30 Hz, 1 H) 2.91-4.01 (m, 5 H) |
| 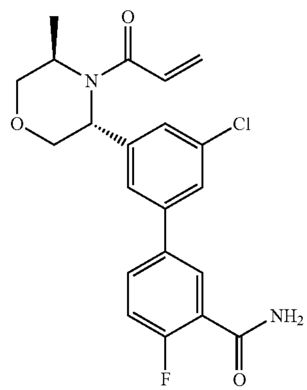 [SMILES: C=CC(=O)N1[C@H](C)COC[C@H]1c1cc(Cl)cc(-c2ccc(F)c(C(N)=O)c2)c1] | 108 | 3'-((3R,5R)-4-acryloyl-5-methylmorpholin-3-yl)-5'-chloro-4-fluoro-[1,1'-biphenyl]-3-carboxamide | Single enantiomer of known absolute configuration | 1H NMR (400 MHz, CHLOROFORM-d) δ = 8.19 (t, J = 8.3 Hz, 1H), 7.48-7.45 (m, 2H), 7.38-7.30 (m, 3H), 6.85 (br d, J = 11.5 Hz, 1H), 6.52-6.48 (m, 1H), 6.35 (dd, J = 1.4, 16.6 Hz, 1H), 5.75-5.70 (m, 1H), 4.87 (br d, J = 6.5 Hz, 1H), 4.32-4.23 (m, 1H), 4.13 (ddd, J = 3.2, 5.1, 8.2 Hz, 1H), 3.98 (dd, J = 2.8, 11.6 Hz, 1H), 3.83 (br d, J = 11.3 Hz, 1H), 3.72-3.54 (m, 1H), 1.45 (d, J = 6.8 Hz, 3H) |
| 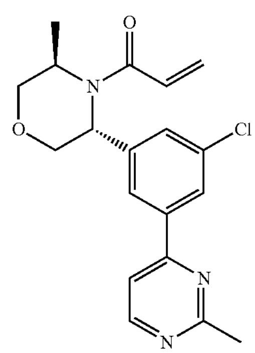 [SMILES: C=CC(=O)N1[C@H](C)COC[C@H]1c1cc(Cl)cc(-c2ccnc(C)n2)c1] | 109 | 1-((3R,5R)-3-(3-chloro-5-(2-methylpyrimidin-4-yl)phenyl)-5-methylmorpholino)prop-2-en-1-one | Single enantiomer of known absolute configuration | 1H NMR (400 MHz, CHLOROFORM-d) δ = 8.69 (d, J = 5.3 Hz, 1H), 7.94 (s, 1H), 7.89 (s, 1H), 7.47 (d, J = 5.3 Hz, 1H), 7.38 (s, 1H), 6.55 (br s, 1H), 6.33 (dd, J = 1.6, 16.6 Hz, 1H), 5.68 (br d, J = 8.5 Hz, 1H), 4.90 (br dd, J = 4.5, 7.6 Hz, 1H), 4.38-4.07 (m, 2H), 3.98 (dd, J = 3.1, 11.6 Hz, 1H), 3.81 (br d, J = 11.5 Hz, 1H), 3.70 (br s, 1H), 2.80 (s, 3H), 1.45 (d, J = 6.8 Hz, 3H) |
| 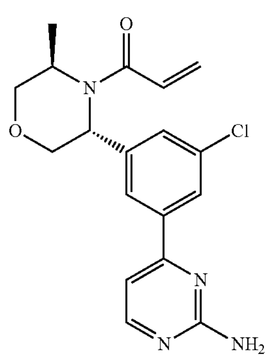 [SMILES: C=CC(=O)N1[C@H](C)COC[C@H]1c1cc(Cl)cc(-c2ccnc(N)n2)c1] | 110 | 1-((3R,5R)-3-(3-(2-aminopyrimidin-4-yl)-5-chlorophenyl)-5-methylmorpholino)prop-2-en-1-one | Single enantiomer of known absolute configuration | 1H NMR (400 MHz, CHLOROFORM-d) δ ppm 1.44 (d, J = 6.84 Hz, 3 H) 3.57-3.86 (m, 2 H) 3.98 (dd, J = 11.47, 2.65 Hz, 1 H) 4.12 (br s, 1 H) 4.29 (br s, 1 H) 4.89 (br s, 1 H) 5.15 (br s, 2 H) 5.67 (br s, 1 H) 6.33 (br d, J = 16.76 Hz, 1 H) 6.55 (br s, 1 H) 7.00 (d, J = 5.29 Hz, 1 H) 7.36 (s, 1 H) 7.82 (s, 1 H) 7.86 (s, 1 H) 8.36 (d, J = 5.29 Hz, 1 H) |

TABLE 1-continued

| Compounds of the Disclosure. | | | | |
|---|---|---|---|---|
| Structure | No. | Name | Stereochemistry | NMR |
| 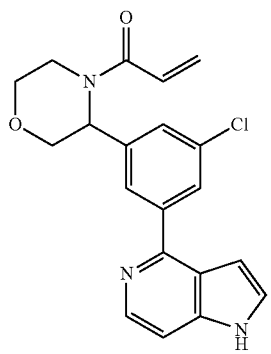 [SMILES: C=CC(=O)N1CCOCC1c1cc(Cl)cc(-c2nccc3[nH]ccc23)c1] | 111 | 1-(3-(3-chloro-5-(1H-pyrrolo[3,2-c]pyridin-4-yl)phenyl)morpholino)prop-2-en-1-one | Single enantiomer of unknown absolute configuration | 1H NMR (400 MHz, CHLOROFORM-d) δ ppm 9.15-9.75 (m, 1 H) 8.24-8.41 (m, 1 H) 7.86-8.17 (m, 2 H) 7.48-7.74 (m, 1 H) 7.31-7.40 (m, 2 H) 6.80 (d, 1 H) 6.53-6.67 (m, 1 H) 6.48 (s, 1 H) 5.63-6.00 (m, 2 H) 4.55 (d, 1 H) 3.82-4.10 (m, 2 H) 3.15-3.81 (m, 3 H) |
| 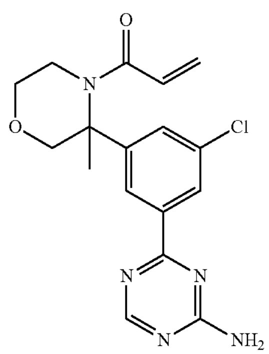 [SMILES: C=CC(=O)N1CCOCC1(C)c1cc(Cl)cc(-c2ncnc(N)n2)c1] | 112 | 1-(3-(3-(4-amino-1,3,5-triazin-2-yl)-5-chlorophenyl)-3-methylmorpholino) prop-2-en-1-one | Single enantiomer of unknown absolute configuration | 1H NMR (400 MHz, CHLOROFORM-d) δ ppm 1.91 (s, 3 H) 3.56 (d, J = 12.01 Hz, 1 H) 3.64-3.75 (m, 2 H) 3.87-3.99 (m, 2 H) 4.01-4.21 (m, 1 H) 5.51 (br s, 3 H) 6.06-6.51 (m, 2 H) 7.56 (s, 1 H) 8.20-8.44 (m, 2 H) 8.69 (s, 1 H) |
| 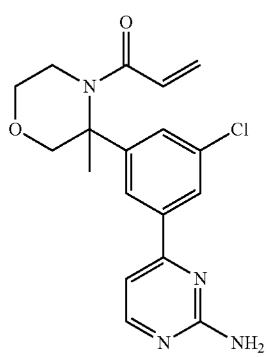 [SMILES: C=CC(=O)N1CCOCC1(C)c1cc(Cl)cc(-c2ccnc(N)n2)c1] | 113 | 1-(3-(3-(2-aminopyrimidin-4-yl)-5-chlorophenyl)-3-methylmorpholino) prop-2-en-1-one | Single enantiomer of unknown absolute configuration | 1H NMR (400 MHz, CHLOROFORM-d) δ ppm 1.90 (s, 3 H) 3.56 (d, J = 12.13 Hz, 1H) 3.66-3.77 (m, 2 H) 3.87-3.98 (m, 2 H) 4.04-4.14 (m, 1 H) 5.59 (br d, J = 10.01 Hz, 1 H) 5.98 (br s, 2 H) 6.19 (br d, J = 15.63 Hz, 1 H) 6.39 (br s, 1 H) 7.09 (d, J = 5.63 Hz, 1 H) 7.56 (s, 1 H) 7.87 (s, 1 H) 8.02 (s, 1 H) 8.33 (d, J = 5.25 Hz, 1 H |
| 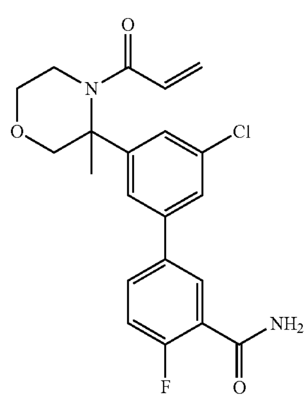 [SMILES: C=CC(=O)N1CCOCC1(C)c1cc(Cl)cc(-c2ccc(F)c(C(N)=O)c2)c1] | 114 | 3'-(4-acryloyl-3-methylmorpholin-3-yl)-5'-chloro-4-fluoro-[1,1'-biphenyl]-3-carboxamide | Single enantiomer of unknown absolute configuration | 1H NMR (400 MHz, CHLOROFORM-d) δ ppm 1.89 (s, 3 H) 3.56 (d, J = 12.01 Hz, 1 H) 3.63-3.77 (m, 2 H) 3.90 (br d, J = 9.76 Hz, 2 H) 4.03-4.16 (m, 1 H) 5.57 (br s, 1 H) 5.83 (br s, 1 H) 6.11-6.46 (m, 2 H) 6.73 (br s, 1 H) 7.17-7.26 (m, 1 H) 7.34-7.49 (m, 3 H) 7.67 (br s, 1 H) 8.31 (br d, J = 6.13 Hz, 1 H) |

TABLE 1-continued

| Structure | No. | Name | Stereochemistry | NMR |
|---|---|---|---|---|
| Compounds of the Disclosure. | | | | |
| 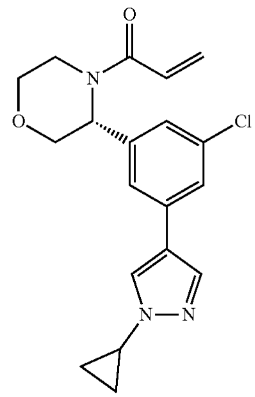 [SMILES: C=CC(=O)N1CCOC[C@H]1c1cc(Cl)cc(-c2cnn(C3CC3)c2)c1] | 115 | (R)-1-(3-(3-chloro-5-(1-cyclopropyl-1H-pyrazol-4-yl)phenyl)morpholino)prop-2-en-1-one | Single enantiomer of known absolute configuration | 1H NMR (400 MHz, CHLOROFORM-d) δ = 7.72 (d, J = 5.4 Hz, 2H), 7.39 (s, 3H), 6.65-6.52 (m, 1 H), 6.48-6.34 (m, 1 H), 5.79 (dd, J = 1.9, 10.4 Hz, 1H), 4.46 (d, J = 12.3 Hz, 1H), 3.98 (br d, J = 8.2 Hz, 1H), 3.89 (dd, J = 3.5, 12.2 Hz, 1H), 3.74-3.02 (m, 4H), 1.20-1.15 (m, 2H), 1.10-1.04 (m, 2H) |
| 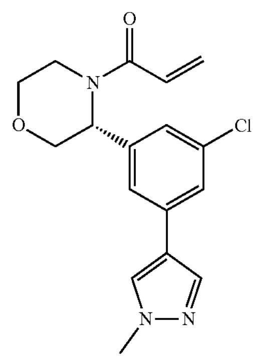 [SMILES: C=CC(=O)N1CCOC[C@H]1c1cc(Cl)cc(-c2cnn(C)c2)c1] | 116 | (R)-1-(3-(3-chloro-5-(1-methyl-1H-pyrazol-4-yl)phenyl)morpholino)prop-2-en-1-one | Single enantiomer of known absolute configuration | 1H NMR (400 MHz, CHLOROFORM-d) δ ppm 3.20-3.67 (m, 3 H) 3.89 (dd, J = 12.23, 3.58 Hz, 1 H) 3.95 (s, 3 H) 3.98 (dd, J = 11.42, 3.26 Hz, 1 H) 4.46 (d, J = 12.17 Hz, 1 H) 5.79 (dd, J = 10.42, 1.88 Hz, 2 H) 6.36-6.46 (m, 1 H) 6.52-6.62 (m, 1 H) 7.39 (s, 3 H) 7.62 (s, 1 H) 7.73 (s, 1 H) |
| 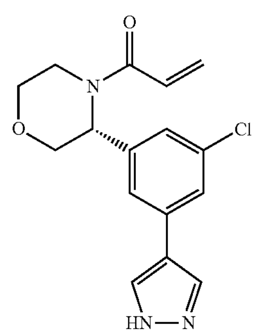 [SMILES: C=CC(=O)N1CCOC[C@H]1c1cc(Cl)cc(-c2cn[nH]c2)c1] | 117 | (R)-1-(3-(3-chloro-5-(1H-pyrazol-4-yl)phenyl)morpholino)prop-2-en-1-one | Single enantiomer of known absolute configuration | 1H NMR (400 MHz, CHLOROFORM-d) δ ppm 3.05-3.71 (m, 3 H) 3.86-4.03 (m, 2 H) 4.36-4.66 (m, 1 H) 5.55-5.89 (m, 2 H) 6.33-6.49 (m, 1 H) 6.51-6.66 (m, 1 H) 7.32-7.62 (m, 4 H) 7.85 (br s, 2 H) |
| 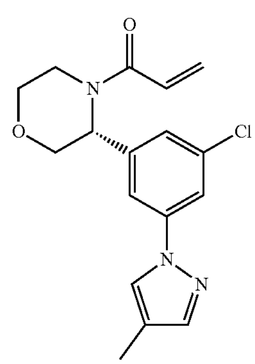 [SMILES: C=CC(=O)N1CCOC[C@H]1c1cc(Cl)cc(-n2cc(C)cn2)c1] | 118 | (R)-1-(3-(3-chloro-5-(4-methyl-1H-pyrazol-1-yl)phenyl)morpholino)prop-2-en-1-one | Single enantiomer of known absolute configuration | 1H NMR (400 MHz, CHLOROFORM-d) δ ppm 2.08-2.19 (m, 3 H) 3.35 (br s, 1 H) 3.62 (td, J = 11.74, 2.69 Hz, 1 H) 3.90 (dd, J = 12.29, 3.61 Hz, 1 H) 3.99 (dd, J = 11.31, 3.36 Hz, 1 H) 4.48 (d, J = 12.23 Hz, 1 H) 5.80 (dd, J = 10.39, 1.96 Hz, 2 H) 6.38-6.46 (m, 1 H) 6.51-6.61 (m, 1 H) 7.39 (br s, 1 H) 7.52-7.56 (m, 1 H) 7.54 (s, 1 H) 7.59-7.78 (m, 3 H) |

TABLE 1-continued

Compounds of the Disclosure.

| Structure | No. | Name | Stereochemistry | NMR |
|---|---|---|---|---|
| 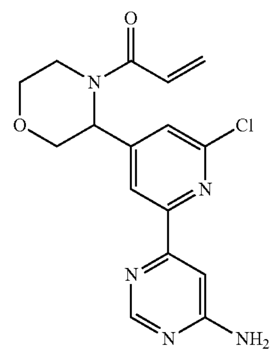 [SMILES: C=CC(=O)N1CCOCC1c1cc(Cl)nc(-c2cc(N)ncn2)c1] | 119 | 1-(3-(2-(6-aminopyrimidin-4-yl)-6-chloropyridin-4-yl)morpholino)prop-2-en-1-one | Single enantiomer of unknown absolute configuration | 1H NMR (400 MHz, CHLOROFORM-d) δ ppm 8.64 (d, J = 1.00 Hz, 1 H) 8.42 (br s, 1 H) 7.48 (d, J = 1.00 Hz, 2 H) 6.52-6.69 (m, 1 H) 6.37-6.51 (m, 1H) 5.64-5.93 (m, 2 H) 5.14 (br s, 2 H) 4.53 (d, J = 12.30 Hz, 1 H) 3.87-4.05 (m, 2 H) 3.02-3.86 (m, 3 H) |
| 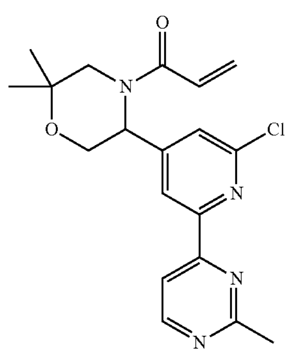 | 120 | 1-(5-(2-chloro-6-(2-methylpyrimidin-4-yl)pyridin-4-yl)-2,2-dimethylmorpholino) prop-2-en-1-one | Single enantiomer of unknown absolute configuration | 1H NMR (400 MHz, CHLOROFORM-d) δ = 8.78 (d, J = 5.3 Hz, 1H), 8.59-8.35 (m, 1H), 8.13 (d, J = 5.3 Hz, 1H), 7.58-7.38 (m, 1H), 6.65-6.51 (m, 1H), 6.51-6.43 (m, 1H), 5.92-5.69 (m, 2H), 4.35-4.12 (m, 2H), 3.81-2.86 (m, 1H), 2.85-2.76 (m, 3H), 1.34-1.28 (m, 1H), 1.24 (s, 1H) |
| 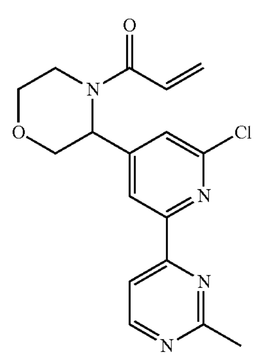 [SMILES: C=CC(=O)N1CCOCC1c1cc(Cl)nc(-c2ccnc(C)n2)c1] | 121 | 1-(3-(2-chloro-6-(2-methylpyrimidin-4-yl)pyridin-4-yl)morpholino)prop-2-en-1-one | Single enantiomer of unknown absolute configuration | 1H NMR (400 MHz, CHLOROFORM-d) δ = 8.79 (d, J = 5.3 Hz, 1H), 8.52 (br s, 1H), 8.14 (d, J = 5.1 Hz, 1H), 7.59-7.42 (m, 1H), 6.68-6.54 (m, 1H), 6.53-6.41 (m, 1H), 5.92-5.66 (m, 2H), 4.56 (d, J = 12.3 Hz, 1H), 4.06-3.87 (m, 2H), 3.86-3.54 (m, 2H), 3.53-3.18 (m, 1H), 2.82 (s, 1H) |
| 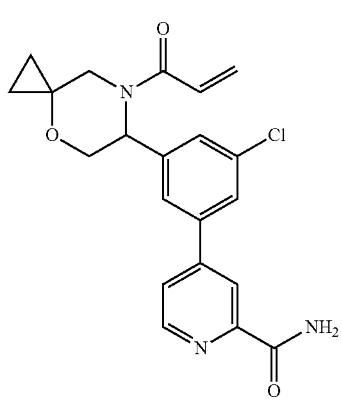 [SMILES: C=CC(=O)N1CC2(CC2)OCC1c1cc(Cl)cc(-c2ccnc(C(N)=O)c2)c1] | 122 | 4-(3-(7-acryloyl-4-oxa-7-azaspiro[2.5]octan-6-yl)-5-chlorophenyl)picolinamide | Single enantiomer of unknown absolute configuration | 1H NMR (400 MHz, CHLOROFORM-d) δ = 8.73-8.56 (m, 1H), 8.52-8.29 (m, 1H), 8.01-7.81 (m, 1H), 7.78-7.39 (m, 4H), 6.86-6.30 (m, 2H), 6.07-5.50 (m, 3H), 4.54-4.32 (m, 1H), 4.22-2.82 (m, 3H), 1.10-0.95 (m, 1H), 0.87-0.75 (m, 1H), 0.74-0.66 (m, 1H), 0.64-0.46 (m, 1H) |

TABLE 1-continued

| Compounds of the Disclosure. | | | | |
|---|---|---|---|---|
| Structure | No. | Name | Stereochemistry | NMR |
| 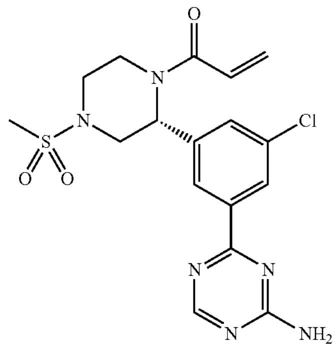 [SMILES: C=CC(=O)N1CCN(S(C)(=O)=O)C[C@H]1c1cc(Cl)cc(-c2ncnc(N)n2)c1] | 123 | (R)-1-(2-(3-(4-amino-1,3,5-triazin-2-yl)-5-chlorophenyl)-4-(methylsulfonyl)piperazin-1-yl)prop-2-en-1-one | Single enantiomer of known absolute configuration | 1H NMR (400 MHz, CHLOROFORM-d) δ = 8.68 (s, 1H), 8.52-8.29 (m, 2H), 7.56 (br s, 1H), 6.60 (br d, J = 10.4 Hz, 1H), 6.51-6.41 (m, 1H), 5.85 (br d, J = 10.3 Hz, 2H), 5.54 (br s, 2H), 4.44 (br d, J = 12.3 Hz, 1H), 3.74 (br d, J = 10.3 Hz, 1H), 3.21 (br d, J = 10.1 Hz, 2H), 2.83 (s, 5H) |
| 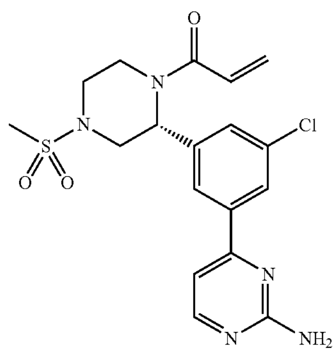 [SMILES: C=CC(=O)N1CCN(S(C)(=O)=O)C[C@H]1c1cc(Cl)cc(-c2ccnc(N)n2)c1] | 124 | (R)-1-(2-(3-(2-aminopyrimidin-4-yl)-5-chlorophenyl)-4-(methylsulfonyl)piperazin-1-yl)prop-2-en-1-one | Single enanitomer of known absolute configuration | 1H NMR (400 MHz, CHLOROFORM-d) δ = 8.38 (br d, J = 5.0 Hz, 1H), 8.04 (s, 2H), 7.47 (br s, 1H), 7.12 (br d, J = 5.0 Hz, 1H), 6.62 (br d, J = 10.3 Hz, 1H), 6.53-6.39 (m, 1H), 5.87 (br d, J = 10.8 Hz, 2H), 5.19 (br s, 2H), 4.49 (br d, J = 12.5 Hz, 1H), 3.76 (br d, J = 10.3 Hz, 2H), 3.18 (br d, J = 12.6 Hz, 2H), 2.84 (s, 4H) |
| 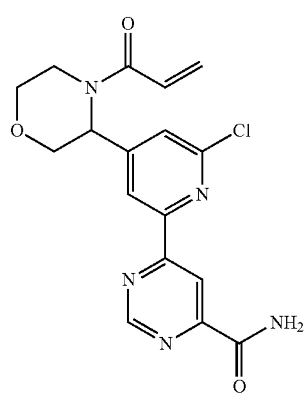 [SMILES: C=CC(=O)N1CCOCC1c1cc(Cl)nc(-c2cc(C(N)=O)ncn2)c1] | 125 | 6-(4-(4-acryloylmorpholin-3-yl)-6-chloropyridin-2-yl)pyrimidine-4-carboxamide | Single enantiomer of unknown absolute configuration | 1H NMR (400 MHz, CHLOROFORM-d) δ ppm 9.30 (d, J = 1.26 Hz, 1 H) 9.13 (s, 1 H) 8.55 (br s, 1 H) 7.83 (br s, 1 H) 7.47-7.64 (m, 1 H) 6.53-6.67 (m, 1 H) 6.40-6.52 (m, 1 H) 5.85 (dd, J = 10.29, 1.76 Hz, 1 H) 5.77 (br s, 1 H) 4.54 (d, J = 12.55 Hz, 1 H) 4.00 (dd, J = 11.48, 3.20 Hz, 1 H) 3.94 (dd, J = 12.30, 3.39 Hz, 1 H) 3.50-3.88 (m, 2 H) 3.07-3.50 (m, 1 H) |
| 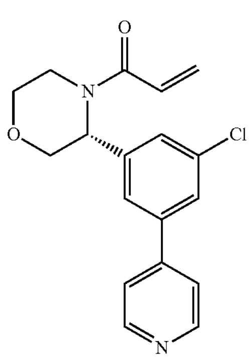 [SMILES: C=CC(=O)N1CCOC[C@H]1c1cc(Cl)cc(-c2ccncc2)c1] | 126 | (R)-1-(3-(3-chloro-5-(pyridin-4-yl)phenyl)morpholino)prop-2-en-1-one | Single enantiomer of known absolute configuration | 1H NMR (400 MHz, CHLOROFORM-d) δ ppm 3.64 (br d, J = 2.76 Hz, 2 H) 3.87-4.08 (m, 2 H) 4.49 (d, J = 12.30 Hz, 1 H) 5.81 (dd, J = 10.42, 1.88 Hz, 1 H) 5.63-5.76 (m, 1 H) 6.36-6.49 (m, 1 H) 6.52-6.65 (m, 1 H) 7.45-7.76 (m, 5 H) 8.62-8.75 (m, 2 H) |

TABLE 1-continued

| Compounds of the Disclosure. | | | | |
|---|---|---|---|---|
| Structure | No. | Name | Stereochemistry | NMR |
| 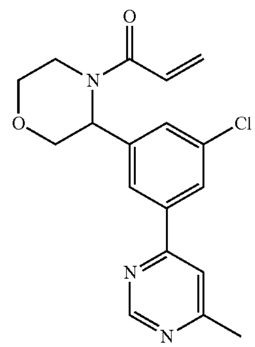 [SMILES: C=CC(=O)N1CCOCC1c1cc(Cl)cc(-c2cc(C)ncn2)c1] | 127 | 1-(3-(2-(6-aminopyrimidin-4-yl)-6-chloropyridin-4-yl)morpholino)prop-2-en-1-one | Single enantiomer of unknown absolute configuration | 1H NMR (400 MHz, CHLOROFORM-d) δ = 9.24-9.07 (m, 1H), 8.62-8.43 (m, 1H), 8.29-8.15 (m, 1H), 7.62-7.39 (m, 1H), 6.69-6.37 (m, 2H), 5.97-5.59 (m, 2H), 4.60-4.47 (m, 1H), 4.07-3.88 (m, 2H), 3.84-3.24 (m, 3H), 2.70-2.57 (m, 3H) |
| 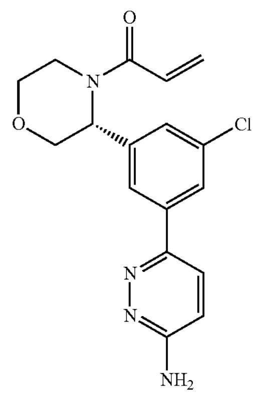 [SMILES: C=CC(=O)N1CCOC[C@H]1c1cc(Cl)cc(-c2ccc(N)nn2)c1] | 128 | (R)-1-(3-(3-(6-aminopyridazin-3-yl)-5-chlorophenyl)morpholino)prop-2-en-1-one | Single enantiomer of known absolute configuration | 1H NMR (400 MHz, CHLOROFORM-d) δ = 7.93 (br s, 2H), 7.60 (d, J = 9.1 Hz, 2H), 6.83 (d, J = 9.1 Hz, 1H), 6.65-6.51 (m, 1H), 6.47-6.35 (m, 1H), 6.00-5.55 (m, 2H), 4.87 (br s, 2H), 4.51 (br d, J = 12.1 Hz, 1H), 3.99 (br dd, J = 2.3, 11.0 Hz, 1H), 3.91 (dd, J = 3.5, 12.3 Hz, 1H), 3.80-2.62 (m, 3H) |
| 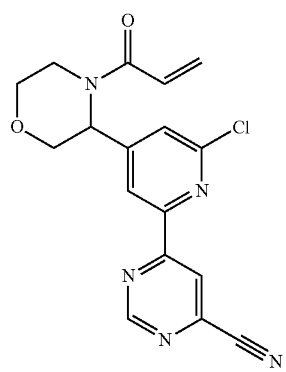 [SMILES: C=CC(=O)N1CCOCC1c1cc(Cl)nc(-c2cc(C#N)ncn2)c1] | 129 | 6-(4-(4-acryloylmorpholin-3-yl)-6-chloropyridin-2-yl)pyrimidine-4-carbonitrile | Single enantiomer of unknown absolute configuration | 1H NMR (400 MHz, CHLOROFORM-d) δ ppm 9.31 (d, J = 1.38 Hz, 1 H) 8.63 (d, J = 1.25 Hz, 1 H) 8.50 (br s, 1 H) 7.54 (br s, 1 H) 6.46-6.58 (m, 1 H) 6.35-6.44 (m, 1 H) 5.61-5.90 (m, 2 H) 4.44 (d, J = 12.51 Hz, 1 H) 3.93 (dd, J = 11.38, 3.25 Hz, 1 H) 3.87 (dd, J = 12.51, 3.50 Hz, 1 H) 3.47-3.81 (m, 2 H) 3.02-3.43 (m, 1 H) |
| 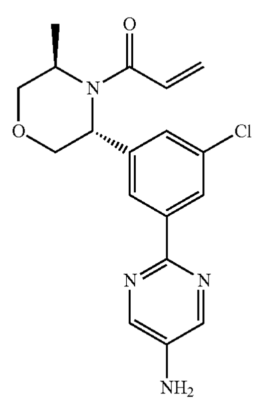 [SMILES: C=CC(=O)N1[C@H](C)COC[C@H]1c1cc(Cl)cc(-c2ncc(N)cn2)c1] | 130 | 1-((3R,5R)-3-(3-(5-aminopyrimidin-2-yl)-5-chlorophenyl)-5-methylmorpholino)prop-2-en-1-one | Single enantiomer of known absolute configuration | 1H NMR (400 MHz, CHLOROFORM-d) δ ppm 1.46 (br d, J = 6.68 Hz, 3 H) 3.72-3.88 (m, 4 H) 4.02 (dd, J = 11.62, 2.80 Hz, 1 H) 4.08-4.45 (m, 2 H) 4.91 (br s, 1 H) 5.63 (br s, 1 H) 6.31 (br d, J = 16.21 Hz, 1 H) 6.47 (br s, 1 H) 8.13 (s, 1 H) 8.17-8.27 (m, 3 H) |

TABLE 1-continued

Compounds of the Disclosure.

| Structure | No. | Name | Stereochemistry | NMR |
|---|---|---|---|---|
| 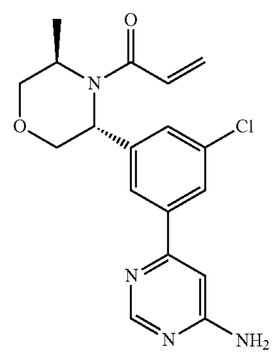 [SMILES: C=CC(=O)N1[C@H](C)COC[C@H]1c1cc(Cl)cc(-c2cc(N)ncn2)c1] | 131 | 1-((3R,5R)-3-(3-(6-aminopyrimidin-4-yl)-5-chlorophenyl)-5-methylmorpholino)prop-2-en-1-one | Single enantiomer of known absolute configuration | 1H NMR (400 MHz, CHLOROFORM-d) δ = 8.76-8.57 (m, 1H), 7.88-7.71 (m, 2H), 7.35 (s, 1H), 6.84-6.68 (m, 1H), 6.64-6.40 (m, 1H), 6.32 (br d, J = 16.5 Hz, 1H), 5.73-5.59 (m, 1H), 5.10 (br s, 2H), 4.89 (br s, 1H), 4.34-4.10 (m, 2H), 3.99 (dd, J = 2.8, 11.6 Hz, 1H), 3.83-3.67 (m, 2H), 1.44 (br d, J = 6.6 Hz, 3H) |
| 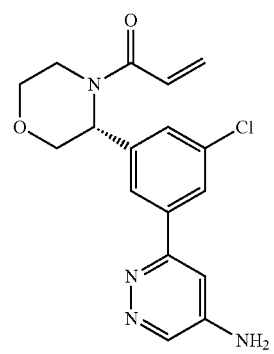 [SMILES: C=CC(=O)N1CCOC[C@H]1c1cc(Cl)cc(-c2cc(N)cnn2)c1] | 132 | (R)-1-(3-(3-(5-aminopyridazin-3-yl)-5-chlorophenyl)morpholino)prop-2-en-1-one | Single enantiomer of known absolute configuration | 1H NMR (400 MHz, CHLOROFORM-d) δ ppm 3.35 (br s, 1 H) 3.58-3.69 (m, 1 H) 3.88-4.02 (m, 2 H) 4.40 (br s, 1 H) 4.55-4.59 (m, 1 H) 5.79 (dd, J = 10.44, 1.81 Hz, 2 H) 6.31-6.48 (m, 1 H) 6.51-6.64 (m, 1 H) 6.96 (d, J = 2.63 Hz, 1 H) 7.45-7.73 (m, 1 H) 7.86-8.06 (m, 2 H) 8.66 (d, J = 2.63 Hz, 1 H) |
| 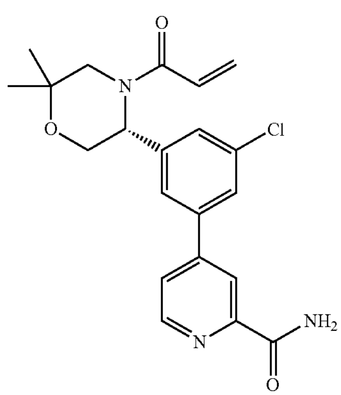 [SMILES: C=CC(=O)N1CC(C)(C)OC[C@H]1c1cc(Cl)cc(-c2ccnc(C(N)=O)c2)c1] | 133 | (R)-4-(3-(4-acryloyl-6,6-dimethylmorpholin-3-yl)-5-chlorophenyl)picolinamide | Single enantiomer of known absolute configuration | 1H NMR (400 MHz, CHLOROFORM-d) δ ppm 1.25 (s, 3 H) 1.30 (s, 3 H) 2.86-3.70 (m, 1 H) 4.17 (br s, 2 H) 5.63 (br s, 1 H) 5.79 (br d, J = 10.13 Hz, 2 H) 6.40-6.58 (m, 2 H) 7.64 (s, 1 H) 7.62-7.65 (m, 1 H) 7.65-7.67 (m, 1 H) 7.97 (br s, 1 H) 8.42 (s, 1 H) 8.65 (d, J = 5.13 Hz, 1 H) |
| 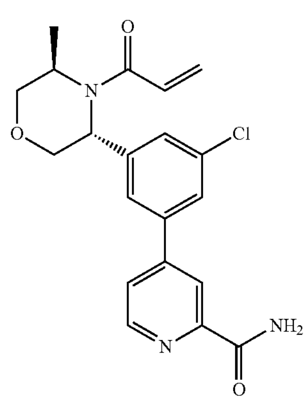 [SMILES: C=CC(=O)N1[C@H](C)COC[C@H]1c1cc(Cl)cc(-c2ccnc(C(N)=O)c2)c1] | 134 | 4-(3-((3R,5R)-4-acryloyl-5-methylmorpholin-3-yl)-5-chlorophenyl)picolinamide | Single enantiomer of known absolute configuration | 1H NMR (400 MHz, CHLOROFORM-d) δ = 8.63 (d, J = 5.1 Hz, 1H), 8.40 (s, 1H), 7.91 (br s, 1H), 7.66-7.59 (m, 1H), 7.58-7.53 (m, 1 H), 7.50-7.45 (m, 1H), 7.37-7.33 (m, 1H), 6.75-6.47 (m, 1H), 6.40-6.25 (m, 1H), 5.75-5.61 (m, 2H), 4.89-4.80 (m, 1H), 4.33-4.19 (m, 1H), 4.17-4.06 (m, 1H), 4.03-3.96 (m, 1H), 3.87-3.80 (m, 1H), 3.73 (br s, 1H), 1.47-1.40 (m, 3H) |

TABLE 1-continued

| Compounds of the Disclosure. | | | | |
|---|---|---|---|---|
| Structure | No. | Name | Stereochemistry | NMR |
| 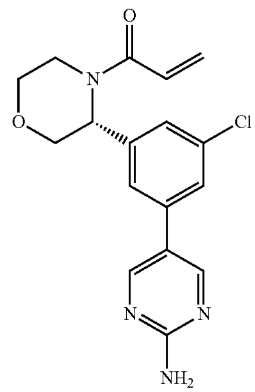 [SMILES: C=CC(=O)N1CCOC[C@H]1c1cc(Cl)cc(-c2cnc(N)nc2)c1] | 135 | (R)-1-(3-(3-(5-aminopyrimidin-2-yl)-5-chlorophenyl)morpholino)prop-2-en-1-one | Single enantiomer of known absolute configuration | 1H NMR (400 MHz, CHLOROFORM-d) δ = 8.49 (s, 2H), 7.40 (s, 3H), 6.65-6.51 (m, 1H), 6.50-6.38 (m, 1H), 5.84-5.80 (dd, J = 1.6, 10.4 Hz, 2H), 5.29 (br s, 2H), 4.47 (d, J = 12.3 Hz, 1H), 4.06-3.95 (m, 1H), 3.92-3.91 (m, 1H), 3.63 (dt, J = 2.1, 11.8 Hz, 3H) |
| 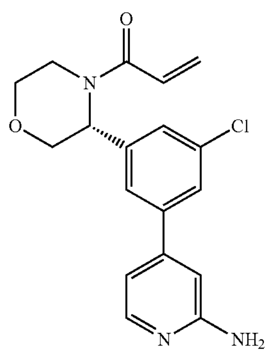 [SMILES: C=CC(=O)N1CCOC[C@H]1c1cc(Cl)cc(-c2ccnc(N)c2)c1] | 136 | (R)-1-(3-(3-(2-aminopyridin-4-yl)-5-chlorophenyl)morpholino)prop-2-en-1-one | Single enantiomer of known absolute configuration | 1H NMR (CHLOROFORM-d, 400 MHz): δ = 8.12 (d, J = 5.4 Hz, 1H), 7.45-7.72 (m, 3H), 6.83 (br d, J = 5.1 Hz, 1H), 6.67 (s, 1H), 6.37-6.62 (m, 2H), 5.80 (dd, J = 10.4, 1.5 Hz, 2H), 4.70 (br s, 2H), 4.48 (d, J = 12.1 Hz, 1H), 3.83-4.05 (m, 2H), 3.57-3.82 (m, 2H), 3.36 ppm (br s, 1H) |
| 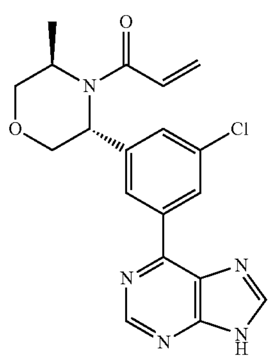 [SMILES: C=CC(=O)N1[C@H](C)COC[C@H]1c1cc(Cl)cc(-c2ncnc3[nH]cnc23)c1] | 137 | 1-((3R,5R)-3-(3-chloro-5-(9H-purin-6-yl)phenyl)-5-methylmorpholino)prop-2-en-1-one | Single enantiomer of known absolute configuration | 1H NMR (400 MHz, CHLOROFORM-d) δ = 8.92 (br s, 1H), 8.74 (s, 1H), 8.53 (br s, 1H), 8.17-7.92 (m, 1H), 7.41 (s, 1H), 6.79 (s, 1H), 6.40 (br d, J = 16.4 Hz, 1H), 5.80 (br s, 1H), 5.09-4.96 (m, 1H), 4.40 (br s, 1H), 4.18 (br s, 1H), 4.11 (br d, J = 11.4 Hz, 1H), 3.86 (br d, J = 11.4 Hz, 1H), 3.79-3.62 (m, 1H), 1.51 (d, J = 6.8 Hz, 3H), 1.34-1.21 (m, 1H) |
| 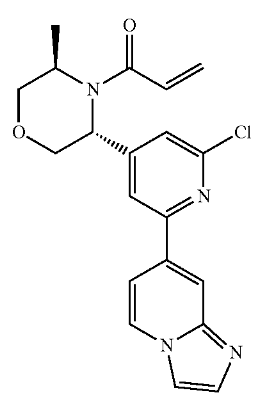 [SMILES: C=CC(=O)N1[C@H](C)COC[C@H]1c1cc(Cl)nc(-c2ccn3ccnc3c2)c1] | 138 | 1-((3R,5R)-3-(2-chloro-6-(imidazo[1,2-a]pyridin-7-yl)pyridin-4-yl)-5-methylmorpholino)prop-2-en-1-one | Single enantiomer of known absolute configuration | 1H NMR (400 MHz, CHLOROFORM-d) δ = 8.44-8.40 (m, 1H), 8.33-8.26 (m, 1H), 8.16-8.12 (m, 1H), 8.03-7.96 (m, 1H), 7.38-7.79 (m, 1H), 7.83-7.75 (m, 1H), 7.74-7.66 (m, 2H), 7.65-7.60 (m, 1H), 6.7-6.61 (m, 1H), 6.40-6.29 (m, 1H), 5.82-5.73 (m, 1H), 4.83-4.74 (m, 1H), 4.32-4.23 (m, 1H), 4.15-4.05 (m, 1H), 4.04-3.93 (m, 1H), 3.92-3.84 (m, 1H), 3.60-3.44 (m, 1H), 1.43 (d, J = 6.7 Hz, 3H) |

TABLE 1-continued

| Compounds of the Disclosure. | | | | |
|---|---|---|---|---|
| Structure | No. | Name | Stereochemistry | NMR |
| 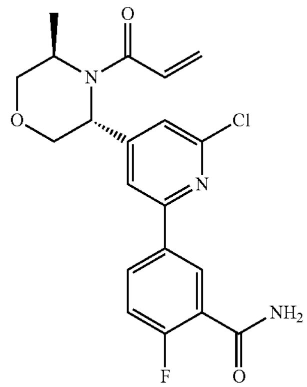 [SMILES: C=CC(=O)N1[C@H](C)COC[C@H]1c1cc(Cl)nc(-c2ccc(F)c(C(N)=O)c2)c1] | 139 | 5-(4-((3R,5R)-4-acryloyl-5-methylmorpholin-3-yl)-6-chloropyridin-2-yl)-2-fluorobenzamide | Single enantiomer of known absolute configuration | 1H NMR (400 MHz, CHLOROFORM-d) δ ppm 1.44 (d, J = 6.85 Hz, 3 H) 3.42-3.67 (m, 1 H) 3.80-3.93 (m, 1 H) 3.95-4.02 (m, 1 H) 4.09 (br d, J = 7.46 Hz, 1 H) 4.26 (br s, 1 H) 4.77 (br dd, J = 9.11, 4.58 Hz, 1 H) 5.70-5.94 (m, 2 H) 6.35 (dd, J = 16.69, 1.65 Hz, 1 H) 6.49-6.85 (m, 2 H) 7.19 (s, 1 H) 7.22-7.27 (m, 1 H) 7.60 (d, J = 0.73 Hz, 1 H) 8.33 (ddd, J = 8.65, 5.10, 2.51 Hz, 1 H) 8.61 (dd, J = 7.34, 2.57 Hz, 1 H) |
| 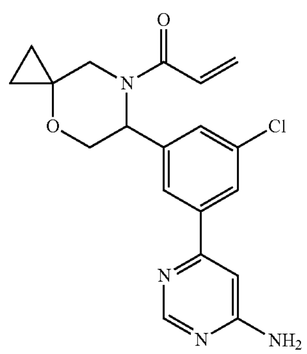 [SMILES: C=CC(=O)N1CC2(CC2)OCC1c1cc(Cl)cc(-c2cc(N)ncn2)c1] | 140 | 1-(6-(3-(6-aminopyrimidin-4-yl)-5-chlorophenyl)-4-oxa-7-azaspiro[2.5]octan-7-yl)prop-2-en-1-one | Single enantiomer of unknown absolute configuration | 1H NM (400 MHz, CHLOROFORM-d) δ ppm 0.54-0.73 (m, 2 H) 0.75-1.04 (m, 2 H) 2.91-3.30 (m, 1 H) 3.77-4.15 (m, 2 H) 4.45 (d, J = 12.05 Hz, 1 H) 5.08 (br s, 2 H) 5.75-6.00 (m, 2 H) 6.37-6.57 (m, 2 H) 6.80 (s, 1H ) 7.69 (br d, J = 6.15 Hz, 1 H) 7.96 (br s, 2 H) 8.66 (d, J = 0.75 Hz, 1 H) |
| 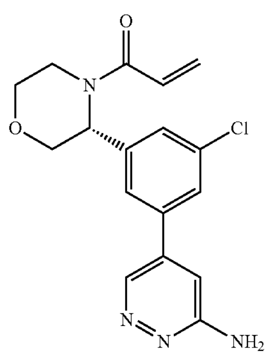 [SMILES: C=CC(=O)N1CCOC[C@H]1c1cc(Cl)cc(-c2cnnc(N)c2)c1] | 141 | (R)-1-(3-(3-(6-aminopyridazin-4-yl)-5-chlorophenyl)morpholino)prop-2-en-1-one | Single enantiomer of known absolute configuration | 1H NMR (400 MHz, CHLOROFORM-d) δ = 8.67 (d, J = 2.5 Hz, 1 H), 7.91 (br d, J = 7.6 Hz, 2H), 7.71-7.56 (m, 1 H), 7.08-7.03 (m, 1H), 6.64-6.55 (m, 1H), 6.43-6.35 (m, 1H), 5.87-5.72 (m, 2H), 5.65-5.43 (m, 1H), 4.56-4.48 (m, 1H), 4.03-3.96 (m, 1H), 3.94-3.87 (m, 1H), 3.67-3.57 (m, 1H), 3.51-3.30 (m, 1H) |
| 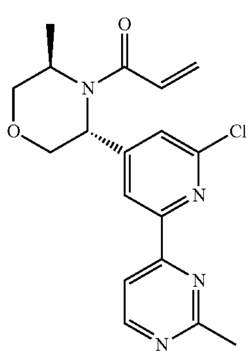 [SMILES: C=CC(=O)N1[C@H](C)COC[C@H]1c1cc(Cl)nc(-c2ccnc(C)n2)c1] | 142 | 1-((3R,5R)-3-(2-chloro-6-(2-methylpyrimidin-4-50yridinedin-4-yl)-5-methylmorpholino)prop-2-en-1-one | Single enantiomer of known absolute configuration | 1H NMR (400 MHz, CHLOROFORM-d) δ = 8.76 (d, J = 5.3 Hz, 1H), 8.34 (s, 1H), 8.12 (d, J = 5.3 Hz, 1H), 7.29 (s, 1H), 6.71-6.53 (m, 1H), 6.34 (dd, J = 1.6, 16.7 Hz, 1H), 5.75 (br d, J = 10.5 Hz, 1H), 4.84 (br dd, J = 4.1, 8.8 Hz, 1H), 4.26 (br s, 1H), 4.12 (br d, J = 8.4 Hz, 1H), 4.01-3.93 (m, 1H), 3.92-3.81 (m, 1H), 3.58 (br d, J = 1.0 Hz, 1H), 2.80 (s, 3H), 1.43 (d, J = 6.8 Hz, 3H) |

TABLE 1-continued

| Compounds of the Disclosure. | | | | |
|---|---|---|---|---|
| Structure | No. | Name | Stereochemistry | NMR |
| 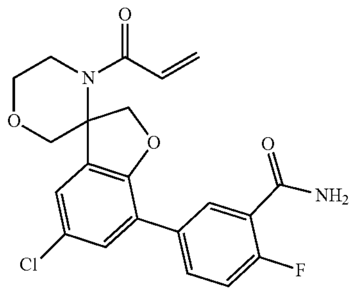 [SMILES: C=CC(=O)N1CCOCC12COc1c(-c3ccc(F)c(C(N)=O)c3)cc(Cl)cc12] | 143 | 5-(4'-acryloyl-5-chloro-2H-spiro[benzofuran-3,3'-morpholin]-7-yl)-2-fluorobenzamide | Single enantiomer of unknown absolute configuration | 1H NMR (400 MHz, CHLOROFORM-d) δ ppm 8.43 (dd, J = 7.57, 2.44 Hz, 1 H) 7.91 (ddd, J = 8.54, 4.97, 2.50 Hz, 1 H) 7.37 (d, J = 2.13 Hz, 1 H) 7.20 (dd, J = 11.57, 8.69 Hz, 1 H) 7.05 (d, J = 2.13 Hz, 1 H) 6.59-6.77 (m, 1 H) 6.37-6.50 (m, 1 H) 6.19-6.31 (m, 1 H) 5.88 (br s, 1 H) 5.67 (dd, J = 10.38, 1.50 Hz, 1 H) 4.73-4.81 (m, 1 H) 4.64-4.73 (m, 1 H) 4.00-4.10 (m, 1 H) 3.87-4.00 (m, 2 H) 3.74-3.84 (m, 1 H) 3.61-3.73 (m, 1 H) 3.36-3.50 (m, 1 H) |
| 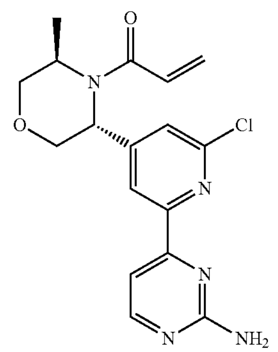 [SMILES: C=CC(=O)N1[C@H](C)COC[C@H]1c1cc(Cl)nc(-c2ccnc(N)n2)c1] | 144 | 1-((3R,5R)-3-(2-(2-aminopyrimidin-4-yl)-6-chloropyridin-4-yl)-5-methylmorpholino)prop-2-en-1-one | Single enantiomer of known absolute configuration | 1H NMR (400 MHz, CHLOROFORM-d) δ = 8.43 (d, J = 5.3 Hz, 1H), 8.21 (s, 1H), 7.67 (d, J = 5.3 Hz, 1H), 7.28 (br s, 1H), 6.70-6.54 (m, 1H), 6.35 (dd, J = 1.6, 16.7 Hz, 1H), 5.75 (br d, J = 10.0 Hz, 1H), 5.24 (br s, 2H), 4.82 (br dd, J = 4.5, 8.9 Hz, 1H), 4.26 (br s, 1H), 4.10 (br d, J = 7.6 Hz, 1H), 3.99-3.94 (m, 1H), 3.88-3.82 (m, 1H), 3.66-3.51 (m, 1H), 1.43 (d, J = 6.8 Hz, 3H) |
| 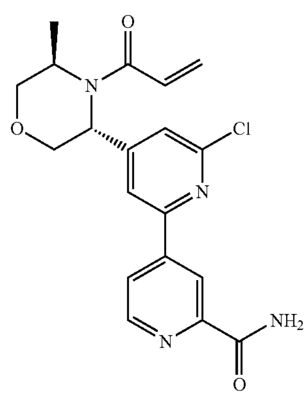 [SMILES: C=CC(=O)N1[C@H](C)COC[C@H]1c1cc(Cl)nc(-c2ccnc(C(N)=O)c2)c1] | 145 | 4-((3R,5R)-4-acryloyl-5-methylmorpholin-3-yl)-6-chloro-[2,4'-bipyridine]-2'-carboxamide | Single enantiomer of known absolute configuration | 1H NMR (400 MHz, CHLOROFORM-d) δ = 8.43 (d, J = 5.3 Hz, 1H), 8.21 (s, 1H), 7.67 (d, J = 5.3 Hz, 1H), 7.28 (br s, 1H), 6.70-6.54 (m, 1H), 6.35 (dd, J = 1.6, 16.7 Hz, 1H), 5.75 (br d, J = 10.0 Hz, 1H), 5.24 (br s, 2H), 4.82 (br dd, J = 4.5, 8.9 Hz, 1H), 4.26 (br s, 1H), 4.10 (br d, J = 7.6 Hz, 1H), 3.99-3.94 (m, 1H), 3.88-3.82 (m, 1H), 3.66-3.51 (m, 1H), 1.43 (d, J = 6.8 Hz, 3H) |
| 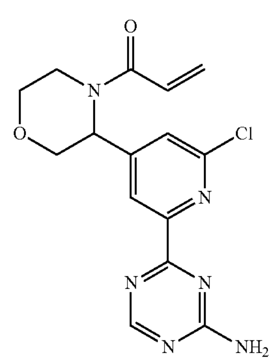 [SMILES: C=CC(=O)N1CCOCC1c1cc(Cl)nc(-c2ncnc(N)n2)c1] | 146 | 1-(3-(2-(4-amino-1,3,5-triazin-2-yl)-6-chloropyridin-4-yl)morpholino)prop-2-en-1-one | Single enantiomer of unknown absolute configuration | 1H NMR (400 MHz, CHLOROFORM-d) δ ppm 3.36 (br d, J = 9.78 Hz, 1H) 3.58-3.85 (m, 2 H) 3.87-4.09 (m, 2 H) 4.53 (d, J = 12.47 Hz, 1 H) 5.54-6.14 (m, 3 H) 6.43-6.68 (m, 3 H) 7.50-7.69 (m, 1 H) 8.53 (br s, 1 H) 8.76 (s, 1 H) |

TABLE 1-continued

| Compounds of the Disclosure. | | | | |
|---|---|---|---|---|
| Structure | No. | Name | Stereochemistry | NMR |
| 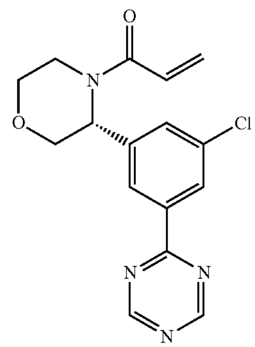 [SMILES: C=CC(=O)N1CCOC[C@H]1c1cc(Cl)cc(-c2ncncn2)c1] | 147 | (R)-1-(3-(3-chloro-5-(1,3,5-triazin-2-yl)phenyl)morpholino)prop-2-en-1-one | Single enantiomer of known absolute configuration | 1H NMR (CHLOROFORM-d, 400 MHz): δ = 9.24 (s, 2H), 8.38-8.68 (m, 2H), 7.70 (br s, 1H), 6.39-6.66 (m, 2H), 5.81 (dd, J = 10.4, 1.8 Hz, 2H), 4.54 (d, J = 12.3 Hz, 1H), 3.91-4.03 (m, 2H), 3.54-3.87 (m, 2H), 3.19-3.53 ppm (m, 1H) |
| 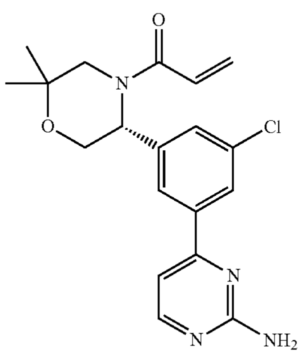 [SMILES: C=CC(=O)N1CC(C)(C)OC[C@H]1c1cc(Cl)cc(-c2ccnc(N)n2)c1] | 148 | (R)-1-(5-(3-(2-aminopyrimidin-4-yl)-5-chlorophenyl)-2,2-dimethylmorpholino)prop-2-en-1-one | Single enantiomer of known absolute configuration | 1H NMR (400 MHz, CHLOROFORM-d) δ ppm 1.25 (s, 3 H) 1.30 (s, 3 H) 2.85-3.56 (m, 2 H) 4.11-4.29 (m, 2 H) 5.80 (br d, J = 10.13 Hz, 2 H) 6.09 (br s, 1 H) 6.35-6.59 (m, 2 H) 7.11 (br s, 1 H) 7.70 (br s, 1 H) 7.90-8.16 (m, 2 H) 8.27-8.36 (m, 1 H) |
| 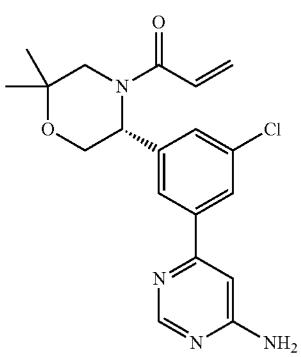 [SMILES: C=CC(=O)N1CC(C)(C)OC[C@H]1c1cc(Cl)cc(-c2cc(N)ncn2)c1] | 149 | (R)-1-(5-(3-(6-aminopyrimidin-4-yl)-5-chlorophenyl)-2,2-dimethymorpholino)prop-2-en-1-one | Single enantiomer of known absolute configuration | 1H NMR (400 MHz, CHLOROFORM-d) δ ppm 1.25 (s, 3 H) 1.30 (s, 3 H) 3.04-3.68 (m, 2 H) 4.11-4.29 (m, 2 H) 5.80 (br d, J = 10.51 Hz, 2 H) 6.27-6.72 (m, 3 H) 6.98 (br s, 1 H) 7.68 (br s, 1 H) 7.83-8.00 (m, 2 H) 8.62 (br s, 1 H) |
| 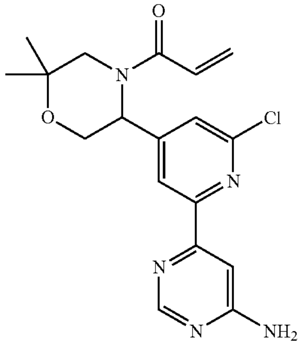 [SMILES: C=CC(=O)N1CC(C)(C)OCC1c1cc(Cl)nc(-c2cc(N)ncn2)c1] | 150 | 1-(5-(2-(6-aminopyrimidin-4-yl)-6-chloropyridin-4-yl)-2,2-dimethylmorpholino)prop-2-en-1-one | Single enantiomer of unknown absolute configuration | 1H NMR (400 MHz, CHLOROFORM-d) δ ppm 1.23 (s, 3 H) 1.30 (s, 3 H) 3.13 (br s, 1 H) 3.54 (br s, 1 H) 3.98-4.67 (m, 2 H) 5.00 (br s, 2 H) 5.82 (br d, J = 9.91 Hz, 2 H) 6.37-6.71 (m, 2 H) 7.36-7.56 (m, 2 H) 8.41 (br s, 1 H) 8.65 (s, 1 H) |

TABLE 1-continued

Compounds of the Disclosure.

| Structure | No. | Name | Stereochemistry | NMR |
|---|---|---|---|---|
| 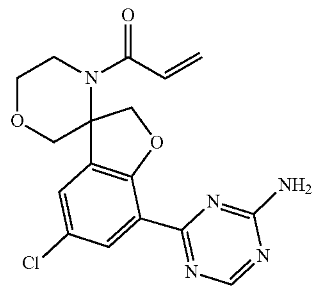 | 151 | 1-(7-(4-amino-1,3,5-triazin-2-yl)-5-chloro-2H-spiro[benzofuran-3,3'-morpholin]-4'-yl)prop-2-en-1-one | Single enantiomer of unknown absolute configuration | 1H NMR (400 MHz, CHLOROFORM-d) δ ppm 8.72 (s, 1 H) 8.12 (d, J = 2.25 Hz, 1 H) 7.18 (d, J = 2.25 Hz, 1 H) 6.38-6.52 (m, 1 H) 6.22-6.33 (m, 1 H) 5.75-6.16 (m, 2 H) 5.69 (dd, J = 10.32, 1.44 Hz, 1 H) 4.86-4.94 (m, 1 H) 4.80 (d, J = 9.13 Hz, 1 H) 4.01-4.09 (m, 1 H) 3.87-4.00 (m, 2 H) 3.82 (d, J = 12.01 Hz, 1 H) 3.58-3.70 (m, 1 H) 3.35-3.49 (m, 1 H) |
| 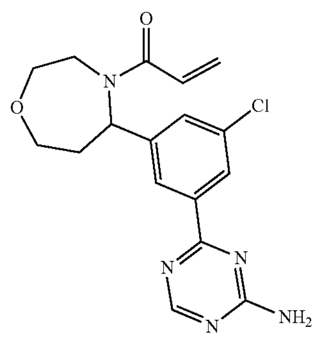 [SMILES: C=CC(=O)N1CCOCCC1c1cc(Cl)cc(-c2ncnc(N)n2)c1] | 152 | 1-(5-(3-(4-amino-1,3,5-triazin-2-yl)-5-chlorophenyl)-1,4-oxazepan-4-yl)prop-2-en-1-one | Racemic | 1H NMR (400 MHz, DMSO-d6) δ ppm 2.10-2.23 (m, 1 H) 2.10-2.23 (m, 1 H) 2.52 (br s, 1 H) 3.31-3.63 (m, 3 H) 3.78-4.07 (m, 1 H) 4.14 (s, 1 H) 5.27-5.85 (m, 2 H) 6.13 (br d, J = 16.75 Hz, 1 H) 6.72 (s, 1 H) 7.31-7.52 (m, 3 H) 8.17 (br d, J = 8.68 Hz, 2 H) 8.60 (s, 1 H) |
| 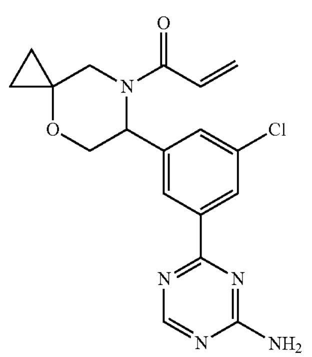 | 153 | 1-(6-(3-(4-amino-1,3,5-triazin-2-yl)-5-chlorophenyl)-4-oxa-7-azaspiro[2.5]octan-7-yl)prop-2-en-1-one | Single enantiomer of unknown absolute configuration | 1H NMR (400 MHz, CHLOROFORM-d) δ ppm 0.49-0.73 (m, 2 H) 0.75-1.09 (m, 2 H) 3.14 (br s, 1 H) 3.62-4.21 (m, 2 H) 4.47 (d, J = 11.86 Hz, 1 H) 5.59 (br s, 2 H) 5.64-6.13 (m, 2 H) 6.39-6.67 (m, 2 H) 7.51-7.79 (m, 1 H) 8.32-8.54 (m, 2 H) 8.68 (s, 1 H) |
| 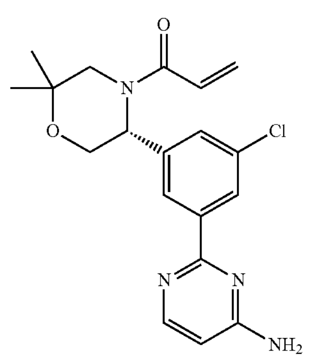 [SMILES: C=CC(=O)N1CC(C)(C)OC[C@H]1c1cc(Cl)cc(-c2nccc(N)n2)c1] | 155 | (R)-1-(5-(3-(4-aminopyrimidin-2-yl)-5-chlorophenyl)-2,2-dimethylmorpholino)prop-2-en-1-one | Single enantiomer of known absolute configuration | 1H NMR (40 0MHz, CHLOROFORM-d) δ ppm 8.04-8.44 (m, 3 H) 7.35-7.76 (m, 1 H) 6.26-6.72 (m, 3 H) 5.76 (br d, J = 9.76 Hz, 2 H) 4.89-5.35 (m, 2 H) 4.05-4.60 (m, 2 H) 2.76-3.76 (m, 2 H) 1.16-1.35 (m, 6 H) |

TABLE 1-continued

Compounds of the Disclosure.

| Structure | No. | Name | Stereochemistry | NMR |
|---|---|---|---|---|
| 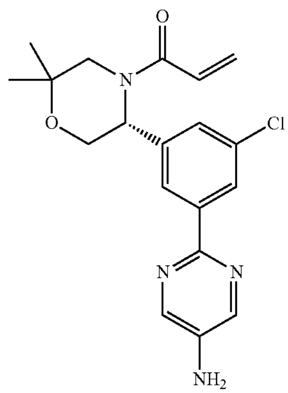 [SMILES: C=CC(=O)N1CC(C)(C)OC[C@H]1c1cc(Cl)cc(-c2ncc(N)cn2)c1] | 156 | (R)-1-(5-(3-(5-aminopyrimidin-2-yl)-5-chlorophenyl)-2,2-dimethylmorpholino)prop-2-en-1-one | Single enantiomer of known absolute configuration | 1H NMR (400 MHz, METHANOL-d4) δ ppm 7.97-8.50 (m, 4 H) 7.32-7.52 (m, 1 H) 6.69-6.92 (m, 1 H) 6.33 (dd, J = 16.63, 1.88 Hz, 1 H) 5.73-5.90 (m, 1 H) 5.26 (br s, 1 H) 3.79 (br s, 3 H) 2.88-3.28 (m, 1 H) 1.16-1.32 (m, 6 H) |
| 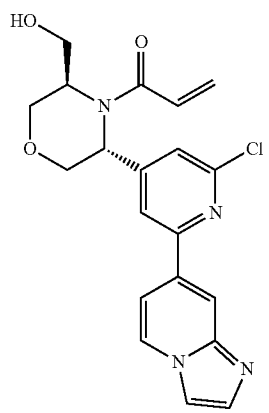 [SMILES: C=CC(=O)N1[C@H](CO)COC[C@H]1c1cc(Cl)nc(-c2ccn3ccnc3c2)c1] | 157 | 1-((3R,5R)-3-(2-chloro-6-(imidazo[1,2-a]pyridin-7-yl)pyridin-4-yl)-5-(hydroxymethyl)morpholino)prop-2-en-1-one | Single enantiomer of known absolute configuration | 1H NMR (400 MHz, ACETONITRILE-d3) δ = 8.39 (d, J = 7.1 Hz, 1H), 8.16 (s, 1H), 7.81 (s, 2H), 7.64 (s, 1H), 7.53 (dd, J = 1.5, 7.3 Hz, 1H), 7.33-7.18 (m, 1H), 6.85-6.67 (m, 1H), 6.13 (br d, J = 16.4 Hz, 1H), 5.71-5.59 (m, 1H), 4.79-4.67 (m, 1H), 4.15-3.99 (m, 3H), 3.88 (dd, J = 3.1, 11.9 Hz, 1H), 3.78 (dd, J = 7.9, 10.9 Hz, 1H), 3.70-3.61 (m, 1H), 3.53-3.40 (m, 1H) |
| 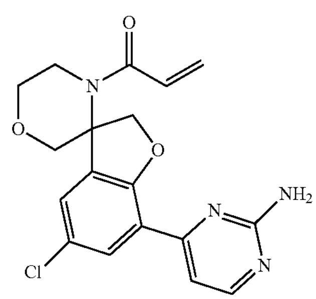 [SMILES: C=CC(=O)N1CCOCC12COc1c(-c3ccnc(N)n3)cc(Cl)cc12] | 158 | 1-(7-(2-aminopyrimidin-4-yl)-5-chloro-2H-spiro[benzofuran-3,3'-morpholin]-4'-yl)prop-2-en-1-one | Single enantiomer of unknown absolute configuration | 1H NMR (400 MHz, CHLOROFORM-d) δ ppm 8.21-8.30 (m, 1 H) 8.07 (d, J = 2.25 Hz, 1 H) 7.45 (d, J = 5.25 Hz, 1 H) 7.05 (d, J = 2.25 Hz, 1 H) 6.29-6.40 (m, 1 H) 6.10-6.21 (m, 1 H) 5.53-5.63 (m, 1 H) 4.96 (br s, 2 H) 4.63-4.76 (m, 2 H) 3.93-4.04 (m, 1 H) 3.82-3.92 (m, 2 H) 3.66-3.73 (m, 1 H) 3.56-3.62 (m, 1 H) 3.29-3.41 (m, 1 H) |
| 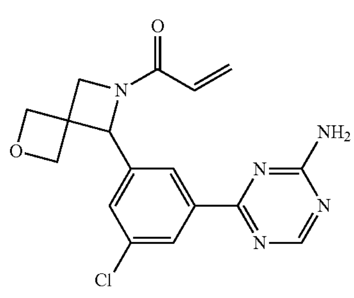 [SMILES: C=CC(=O)N1CC2(COC2)C1c1cc(Cl)cc(-c2ncnc(N)n2)c1] | 159 | 1-(5-(3-(4-amino-1,3,5-triazin-2-yl)-5-chlorophenyl)-2-oxa-6-azaspiro[3.3]heptan-6-yl)prop-2-en-1-one | Single enantiomer of unknown absolute configuration | 1H NMR (400 MHz, CHLOROFORM-d) δ = 8.75-8.65 (m, 1H), 8.52-8.35 (m, 1H), 8.31-8.18 (m, 1H), 7.51-7.35 (m, 1H), 6.47-6.28 (m, 1H), 5.94-5.74 (m, 1H), 5.63-5.47 (m, 3H), 5.46-5.43 (m, 1H), 4.98-4.79 (m, 2H), 4.59-4.40 (m, 2H), 4.38-4.06 (m, 2H) |

TABLE 1-continued

| Compounds of the Disclosure. | | | | |
|---|---|---|---|---|
| Structure | No. | Name | Stereochemistry | NMR |
| 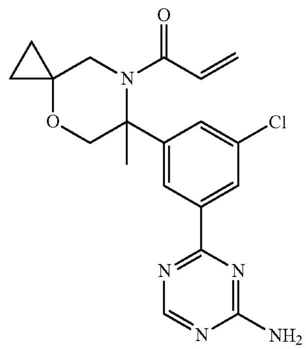 [SMILES: C=CC(=O)N1CC2(CC2)OCC1(C)c1cc(Cl)cc(-c2ncnc(N)n2)c1] | 160 | 1-(6-(3-(4-amino-1,3,5-triazin-2-yl)-5-chlorophenyl)-6-methyl-4-oxa-7-azaspiro[2.5]octan-7-yl)prop-2-en-1-one | Single enantiomer of unknown absolute configuration | 1H NMR (400 MHz, CHLOROFORM-d) δ ppm 8.68 (s, 1 H) 8.37-8.42 (m, 1 H) 8.32 (s, 1 H) 7.60 (t, J = 1.69 Hz, 1 H) 6.09-6.40 (m, 2 H) 5.34-5.75 (m, 3 H) 3.74-3.98 (m, 2 H) 3.48-3.72 (m, 2 H) 1.95 (s, 3 H) 0.98-1.06 (m, 1 H) 0.87-0.96 (m, 1 H) 0.71-0.83 (m, 2 H) |
| 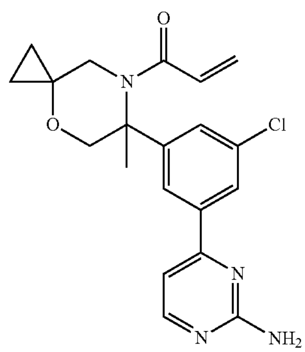 [SMILES: C=CC(=O)N1CC2(CC2)OCC1(C)c1cc(Cl)cc(-c2ccnc(N)n2)c1] | 161 | 1-(6-(3-(2-aminopyrimidin-4-yl)-5-chlorophenyl)-6-methyl-4-oxa-7-azaspiro[2.5]octan-7-yl)prop-2-en-1-one | Single enantiomer of unknown absolute configuration | 1H NMR (400 MHz, CHLOROFORM-d) δ ppm 8.37 (d, J = 5.13 Hz, 1 H) 7.94-8.00 (m, 1 H) 7.88 (s, 1 H) 7.53 (t, J = 1.75 Hz, 1 H) 7.00 (d, J = 5.25 Hz, 1 H) 6.08-6.44 (m, 2 H) 5.51 (br s, 1 H) 5.15 (br s, 2 H) 3.83 (br t, J = 11.94 Hz, 2 H), 3.48-3.71 (m, 2 H) 1.94 (s, 3 H) 0.96-1.08 (m, 1 H) 0.86-0.95 (m, 1 H) 0.71-0.82 (m, 2 H) |
| 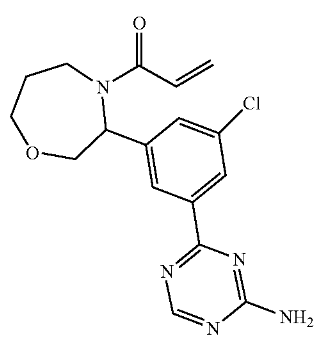 [SMILES: C=CC(=O)N1CCCOCC1c1cc(Cl)cc(-c2ncnc(N)n2)c1] | 162 | 1-(3-(3-(4-amino-1,3,5-triazin-2-yl)-5-chlorophenyl)-1,4-oxazepan-4-yl)prop-2-en-1-one | Racemic | 1H NMR (400 MHz, DMSO-d6) δ ppm 1.70-1.86 (m, 2 H) 3.46-3.97 (m, 3 H) 4.11-4.60 (m, 1 H) 4.17 (dd, J = 13.59, 5.48 Hz, 1 H) 5.42 (dd, J = 9.65, 5.48 Hz, 1 H) 5.53 (dd, J = 10.30, 5.70 Hz, 1 H) 5.61 (dd, J = 10.41, 2.30 Hz, 1 H) 5.73 (dd, J = 10.41, 2.30 Hz, 1 H) 6.05-6.19 (m, 1 H) 6.39-6.96 (m, 1 H) 7.55-7.62 (m, 1 H) 7.74 (br d, J = 3.51 Hz, 2 H) 8.13 (s, 1 H) 8.18 (d, J = 13.37 Hz, 1 H) 8.61 (d, J = 1.53 Hz, 1 H) |
| 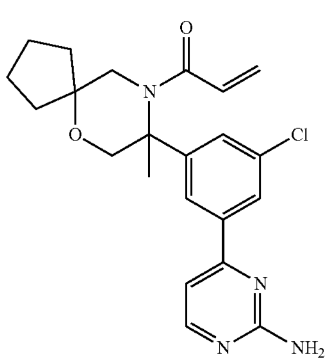 [SMILES: C=CC(=O)N1CC2(CCCC2)OCC1(C)c1cc(Cl)cc(-c2ccnc(N)n2)c1] | 163 | 1-(8-(3-(2-aminopyrimidin-4-yl)-5-chlorophenyl)-8-methyl-6-oxa-9-azaspiro[4.5]decan-9-yl)prop-2-en-1-one | Single enantiomer of unknown absolute configuration | 1H NMR (400 MHz, CHLOROFORM-d) δ ppm 1.68 (br s, 2 H) 1.69-1.76 (m, 2 H) 1.82 (br s, 2 H) 1.89 (br s, 2 H) 1.90 (s, 3 H) 3.56 (d, J = 12.38 Hz, 1 H) 3.65-4.07 (m, 3 H) 5.15 (br s, 2 H) 5.41-5.69 (m, 1 H) 6.07-6.58 (m, 2 H) 6.99 (d, J = 5.13 Hz, 1 H) 7.45 (t, J = 1.63 Hz, 1 H) 7.86-7.93 (m, 2 H) 8.36 (d, J = 5.25 Hz, 1 H) |

TABLE 1-continued

| Compounds of the Disclosure. | | | | |
|---|---|---|---|---|
| Structure | No. | Name | Stereochemistry | NMR |
| 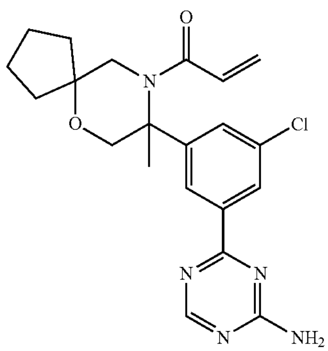 | 164 | 1-(8-(3-(4-amino-1,3,5-triazin-2-yl)-5-chlorophenyl)-8-methyl-6-oxa-9-azaspiro[4.5]decan-9-yl)prop-2-en-1-one | Single enantiomer of unknown absolute configuration | 1H NMR (400 MHz, CHLOROFORM-d) δ ppm 1.59 (br s, 3 H) 1.64 (br d, J = 13.55 Hz, 2 H) 1.68-1.78 (m, 2 H) 1.78-1.83 (m, 2 H) 1.84-1.91 (m, 2 H) 3.55 (d, J = 12.42 Hz, 1 H) 3.65-4.08 (m, 3 H) 5.47 (br s, 3 H) 6.24 (br d, J = 15.69 Hz, 1 H) 7.49-7.55 (m, 1 H) 8.27-8.35 (m, 2 H) 8.68 (s, 1 H) |
| 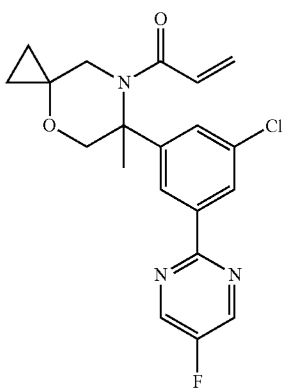 [SMILES: C=CC(=O)N1CC2(CC2)OCC1(C)c1cc(Cl)cc(-c2ncc(F)cn2)c1] | 165 | 1-(6-(3-chloro-5-(5-fluoropyrimidin-2-yl)phenyl)-6-methyl-4-oxa-7-azaspiro[2.5]octan-7-yl)prop-2-en-1-one | Single enantiomer of unknown absolute configuration | 1H NMR (400 MHz, CHLOROFORM-d) δ ppm 8.66 (s, 2 H) 8.39 (s, 2 H) 7.54 (s, 1 H) 6.01-6.43 (m, 2 H) 5.49 (br s, 1 H) 3.86 (s, 2 H) 3.58 (s, 2 H) 1.96 (s, 3H) 1.02 (br dd, J = 10.63, 5.13 Hz, 1 H) 0.85-0.95 (m, 1 H) 0.78 (s, 2 H) |
| 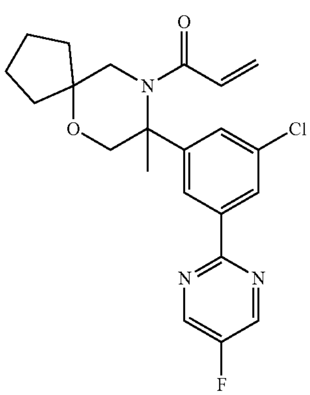 [SMILES: C=CC(=O)N1CC2(CCCC2)OCC1(C)c1cc(Cl)cc(-c2ncc(F)cn2)c1] | 166 | 1-(8-(3-chloro-5-(5-fluoropyrimidin-2-yl)phenyl)-8-methyl-6-oxa-9-azaspiro[4.5]decan-9-yl)prop-2-en-1-one | Single enantiomer of unknown absolute configuration | 1H NMR (400 MHz, CHLOROFORM-d) δ ppm 1.61-1.69 (m, 2 H) 1.78 (br d, J = 6.0 0Hz, 2 H) 1.80-1.84 (m, 2 H) 1.85-1.92 (m, 2 H) 1.94 (s, 3H) 3.56 (d, J = 12.38 Hz, 1 H) 3.64-4.18 (m, 3 H) 5.38-5.66 (m, 1 H) 5.88-6.64 (m, 2 H) 7.46 (t, J = 1.88 Hz, 1 H) 8.25-8.36 (m, 2 H) 8.66 (s, 2 H) |
| 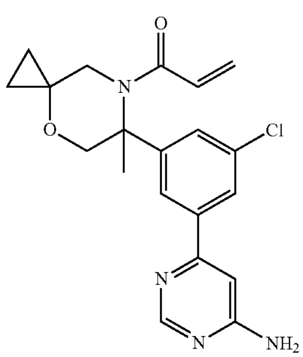 [SMILES: C=CC(=O)N1CC2(CC2)OCC1(C)c1cc(Cl)cc(-c2cc(N)ncn2)c1] | 167 | 1-(6-(3-(6-aminopyrimidin-4-yl)-5-chlorophenyl)-6-methyl-4-oxa-7-azaspiro[2.5]octan-7-yl)prop-2-en-1-one | Single enantiomer of unknown absolute configuration | 1H NMR (400 MHz, CHLOROFORM-d) δ ppm 8.67 (s, 1 H) 7.96 (t, J = 1.50 Hz, 1 H) 7.85 (s, 1 H) 7.53 (t, J = 1.69 Hz, 1 H) 6.78 (d, J = 1.00 Hz, 1 H) 5.93-6.52 (m, 2 H) 5.51 (br d, J = 2.25 Hz, 1 H) 4.99 (br s, 2 H) 3.74-3.97 (m, 2H) 3.44-3.70 (m, 2 H) 1.95 (s, 3 H) 0.97-1.07 (m, 1 H) 0.85-0.96 (m, 1 H) 0.70-0.82 (m, 2 H) |

TABLE 1-continued

| Compounds of the Disclosure. | | | | |
|---|---|---|---|---|
| Structure | No. | Name | Stereochemistry | NMR |
| 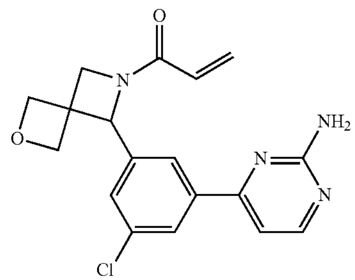 [SMILES: C=CC(=O)N1CC2(COC2)C1c1cc(Cl)cc(-c2ccnc(N)n2)c1] | 168 | 1-(5-(3-(2-aminopyrimidin-4-yl)-5-chlorophenyl)-2-oxa-6-azaspiro[3.3]heptan-6-yl)prop-2-en-1-one | Single enantiomer of known absolute configuration | 1H NMR (400 MHz, CHLOROFORM-d) δ ppm 4.13 (br d, J = 6.00 Hz, 1 H) 4.31 (br d, J = 10.51 Hz, 1 H) 4.42-4.51 (m, 2 H) 4.88 (b rs, 2 H) 5.18 (br s, 2 H) 5.45 (s, 1 H) 5.51-5.95 (m, 2 H) 6.38 (br d, J= 15.01 Hz, 1 H) 7.03 (d, J = 5.25 Hz, 1 H) 7.32-7.45 (m, 1 H) 7.86 (br s, 1 H) 8.00 (br s, 1 H) 8.38-8.43 (m, 1 H) |
| 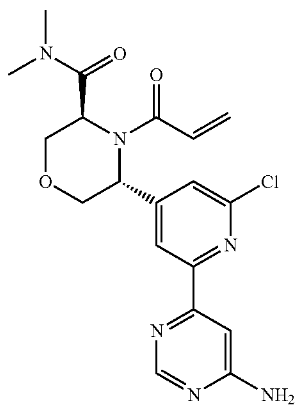 [SMILES: C=CC(=O)N1[C@H](C(=O)N(C)C)COC[C@H]1c1cc(Cl)nc(-c2cc(N)ncn2)c1] | 169 | (3S,5R)-4-acryloyl-5-(2-(6-aminopyrimidin-4-yl)-6-chloropyridin-4-yl)-N,N-dimethylmorpholine-3-carboxamide | Single enantiomer of known absolute configuration | 1H NMR (400 MHz, CHLOROFORM-d) δ ppm 3.00-3.26 (m, 6 H) 3.85-4.49 (m, 4 H) 4.88-5.41 (m, 4 H) 5.58 (br d, J = 8.63 Hz, 1 H) 6.16-6.35 (m, 2 H) 7.31 (br s, 1 H) 7.51 (s, 1 H) 8.30 (br s, 1 H) 8.64 (s, 1 H) |
| 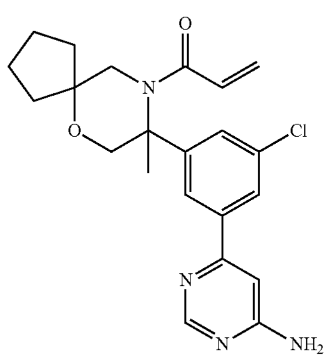 [SMILES: C=CC(=O)N1CC2(CCCC2)OCC1(C)c1cc(Cl)cc(-c2cc(N)ncn2)c1] | 170 | 1-(8-(3-(6-aminopyrimidin-4-yl)-5-chlorophenyl)-8-methyl-6-oxa-9-azaspiro[4.5]decan-9-yl)prop-2-en-1-one | Single enantiomer of unknown absolute configuration | 1H NMR (400 MHz, CHLOROFORM-d) δ ppm 1.71 (br d, J = 4.38 Hz, 2 H) 1.73-1.80 (m, 2 H) 1.80-1.85 (m, 2 H) 1.86-1.91 (m, 2 H) 1.92 (s, 3 H) 3.55 (d, J = 12.38 Hz, 1 H) 3.61-4.19 (m, 3 H) 5.02 (br s, 2 H) 5.41-5.68 (m, 1 H) 5.88-6.57 (m, 2 H) 6.76 (d, J = 0.88 Hz, 1 H) 7.38-7.50 (m, 1 H) 7.78-7.94 (m, 2 H) 8.65 (s, 1 H) |
| 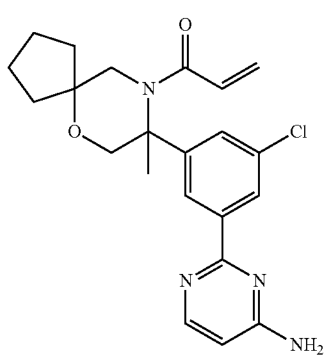 [SMILES: C=CC(=O)N1CC2(CCCC2)OCC1(C)c1cc(Cl)cc(-c2nccc(N)n2)c1] | 171 | 1-(8-(3-(4-aminopyrimidin-2-yl)-5-chlorophenyl)-8-methyl-6-oxa-9-azaspiro[4.5]decan-9-yl)prop-2-en-1-one | Single enantiomer of unknown absolute configuration | 1H NMR (400 MHz, CHLOROFORM-d) δ ppm 1.64-1.67 (m, 2 H) 1.68-1.78 (m, 2 H) 1.80 (br d, J = 5.13 Hz, 2 H) 1.85-1.92 (m, 2 H) 1.94 (s, 3 H) 3.53 (d, J = 12.38 Hz, 1 H) 3.70-4.24 (m, 3 H) 4.90-5.14 (m, 2 H) 5.34-5.59 (m, 1 H) 6.24 (br d, J = 15.51 Hz, 2 H) 6.36 (d, J = 5.75 Hz, 1 H) 7.42 (t, J = 1.88 Hz, 1 H) 8.28 (br d, J = 1.50 Hz, 2 H) 8.33 (d, J = 5.75 Hz, 1 H) |

TABLE 1-continued

| Compounds of the Disclosure. | | | | |
|---|---|---|---|---|
| Structure | No. | Name | Stereochemistry | NMR |
| 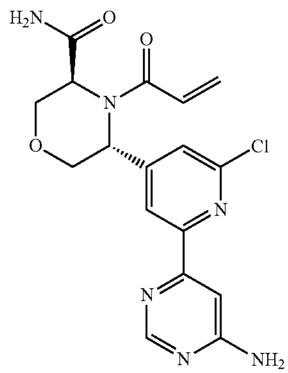 [SMILES: C=CC(=O)N1[C@H](C(N)=O)COC[C@H]1c1cc(Cl)nc(-c2cc(N)ncn2)c1] | 172 | (3S,5R)-4-acryloyl-5-(2-(6-aminopyrimidin-4-yl)-6-chloropyridin-4-yl)morpholine-3-carboxamide | Single enantiomer of known absolute configuration | 1H NMR (400 MHz, METHANOL-d4) δ ppm 3.44-3.63 (m, 1 H) 3.89-4.55 (m, 4 H) 5.02-5.16 (m, 1 H) 5.38-5.76 (m, 1 H) 6.07-6.25 (m, 1 H) 6.42-6.69 (m, 1 H) 7.39-7.46 (m, 1 H) 7.59-7.66 (m, 1 H) 8.12-8.16 (m, 1 H) 8.57-8.61 (m, 1 H) |
| 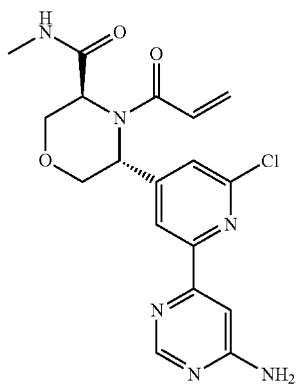 [SMILES: C=CC(=O)N1[C@H](C(=O)NC)COC[C@H]1c1cc(Cl)nc(-c2cc(N)ncn2)c1] | 173 | (3S,5R)-4-acryloyl-5-(2-(6-aminopyrimidin-4-yl)-6-chloropyridin-4-yl)-N-methylmorpholine-3-carboxamide | Single enantiomer of known absolute configuration | 1H NMR (400 MHz, DMSO-d6) δ ppm 2.64 (d, J = 4.38 Hz, 3 H) 3.83-4.10 (m, 3 H) 4.15-4.30 (m, 1 H) 4.66-4.84 (m, 1 H) 4.98 (br d, J = 4.38 Hz, 1 H) 5.43-5.61 (m, 1 H) 5.63-5.71 (m, 1 H) 5.96-6.06 (m, 1 H) 6.35-6.62 (m, 1 H) 7.37 (s, 1 H) 7.63 (s, 1 H) 7.81-7.96 (m, 1 H) 8.08 (br d, J = 3.75 Hz, 1 H) 8.13-8.23 (m, 1 H) 8.56 (s, 1 H) |
| 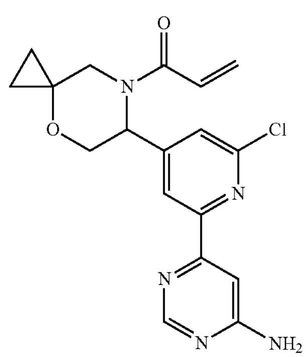 [SMILES: C=CC(=O)N1CC2(CC2)OCC1c1cc(Cl)nc(-c2cc(N)ncn2)c1] | 174 | 1-(6-(2-(6-aminopyrimidin-4-yl)-6-chloropyridin-4-yl)-4-oxa-7-azaspiro[2.5]octan-7-yl)prop-2-en-1-one ENT1 | Single enantiomer of unknown absolute configuration | 1H NMR (400 MHz, CHLOROFORM-d) δ ppm 8.64 (s, 1 H) 8.43 (br s, 1 H) 7.35-7.58 (m, 2 H) 6.38-6.65 (m, 2 H) 5.82 (dd, J = 10.07, 1.56 Hz, 2 H) 5.07 (br s, 2 H) 4.48 (d, J = 12.13 Hz, 1 H) 4.10 (br d, J = 10.63 Hz, 1 H) 3.02-3.92 (m, 2 H) 1.01 (br s, 1 H) 0.75-0.88 (m, 1 H) 0.65-0.74 (m, 1 H) 0.45-0.63 (m, 1 H) |
| 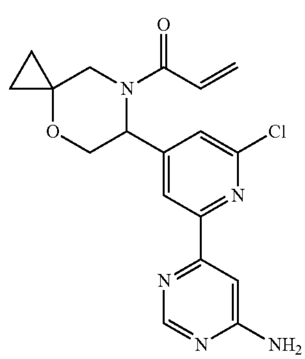 [SMILES: C=CC(=O)N1CC2(CC2)OCC1c1cc(Cl)nc(-c2cc(N)ncn2)c1] | 175 | 1-(6-(2-(6-aminopyrimidin-4-yl)-6-chloropyridin-4-yl)-4-oxa-7-azaspiro[2.5]octan-7-yl)prop-2-en-1-one ENT2 | Single enantiomer of unknown absolute configuration | 1H NMR (400 MHz, CHLOROFORM-d) δ ppm 8.57 (d, J = 0.75 Hz, 1 H) 8.36 (br s, 1 H) 7.32-7.54 (m, 2 H) 6.26-6.56 (m, 2 H) 5.74 (dd, J = 10.01, 2.13 Hz, 2 H) 4.97 (br s, 2 H) 4.40 (d, J = 12.13 Hz, 1 H) 4.02 (brd, J = 10.76 Hz, 1 H) 2.74-3.92 (m, 2 H) 0.93 (br s, 1 H) 0.69-0.82 (m, 1 H) 0.57-0.67 (m, 1 H) 0.38-0.56 (m, 1 H) |

TABLE 1-continued

| Compounds of the Disclosure. | | | | |
|---|---|---|---|---|
| Structure | No. | Name | Stereochemistry | NMR |
| 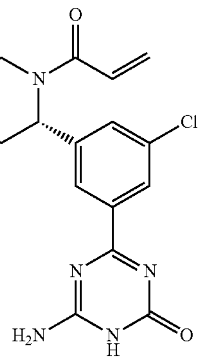 | 177 | (R)-4-(3-(4-acryloylmorpholin-3-yl)-5-chlorophenyl)-6-amino-1,3,5-triazin-2(1H)-one | Single enantiomer of known absolute configuration | 1H NMR (400 MHz, METHANOL-d4) δ ppm 3.50-3.66 (m, 1 H) 3.78-3.97 (m, 3 H) 4.42-4.60 (m, 2 H) 5.79 (dd, J = 10.61, 1.79 Hz, 2 H) 6.28 (dd, J = 16.69, 1.31 Hz, 1 H) 6.77 (dd, J = 16.69, 10.61 Hz, 1 H) 7.63 (br s, 1 H) 8.01-8.58 (m, 2 H) |
| 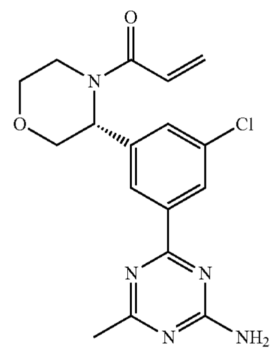 [SMILES: C=CC(=O)N1CCOC[C@H]1c1cc(Cl)cc(-c2nc(C)nc(N)n2)c1] | 178 | (R)-1-(3-(3-(4-amino-6-methyl-1,3,5-triazin-2-yl)-5-chlorophenyl)morpholino)prop-2-en-1-one | Single enantiomer of known absolute configuration | 1H NMR (400 MHz, CHLOROFORM-d) δ ppm 2.53-2.56 (m, 3 H) 3.19-3.47 (m, 1 H) 3.58-3.72 (m, 1 H) 3.86-4.07 (m, 1 H) 3.87-4.03 (m, 1 H) 4.49-4.60 (m, 1 H) 5.37-5.58 (m, 2 H) 5.74-5.85 (m, 1 H) 6.38-6.48 (m, 1 H) 6.51-6.63 (m, 1 H) 7.55-7.73 (m, 1 H) 8.31 (s, 1 H) |
| 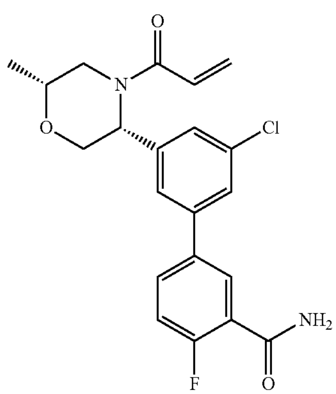 [SMILES: C=CC(=O)N1C[C@@H](C)OC[C@H]1c1cc(Cl)cc(-c2ccc(F)c(C(N)=O)c2)c1] | 179 | 3'-((3R,6R)-4-acryloyl-6-methylmorpholin-3-yl)-5'-chloro-4-fluoro-[1,1'-biphenyl]-3-carboxamide | Single diastereomer of unknown absolute configuration | 1H NMR (400 MHz, METHANOL-d4) δ = 8.02 (br d, J = 5.9 Hz, 1 H), 7.82-7.74 (m, 1H), 7.69-7.56 (m, 2 H), 7.56-7.47 (m, 1H), 7.43-7.28 (m, 1H), 6.91-6.77 (m, 1 H), 6.39-6.25 (m, 1H), 5.87-5.78 (m, 1H), 5.74-5.66 (m, 1H), 5.30-5.22 (m, 1H), 4.61-4.51 (m, 1H), 4.46-4.36 (m, 1H), 4.05-3.88 (m, 2H), 3.74-3.62 (m, 1H), 2.99-2.90 (m, 1H), 2.68-2.57 (m, 1H), 1.24-1.15 (m, 3H) |
| 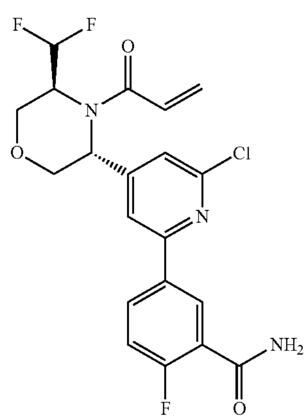 [SMILES: C=CC(=O)N1[C@H](c2cc(Cl)nc(-c3ccc(F)c(C(N)=O)c3)c2)COC[C@H]1C(F)F] | 180 | 5-(4-((3R,5S)-4-acryloyl-5-(difluoromethyl)morpholin-3-yl)-6-chloropyridin-2-yl)-2-fluorobenzamide | Single enantiomer of known absolute configuration | 1H NMR (400 MHz, CHLOROFORM-d) δ ppm 3.38-3.74 (m, 1 H) 3.92-4.15 (m, 2 H) 4.30 (br d, J = 12.13 Hz, 2 H) 4.76 (br s, 1 H) 5.76 (br d, J = 9.13 Hz, 1 H) 5.98 (br s, 1 H) 6.03-6.24 (m, 1 H) 6.27-6.35 (m, 1 H) 6.39-6.58 (m, 1 H) 6.75 (br d, J = 9.88 Hz, 1 H) 7.16 (s, 1 H) 7.21-7.27 (m, 1 H) 7.58 (s, 1 H) 8.31 (ddd, J = 8.60, 5.03, 2.50 Hz, 1 H) 8.59 (dd, J = 7.19, 2.19 Hz, 1 H) |

TABLE 1-continued

| Compounds of the Disclosure. | | | | |
|---|---|---|---|---|
| Structure | No. | Name | Stereochemistry | NMR |
| 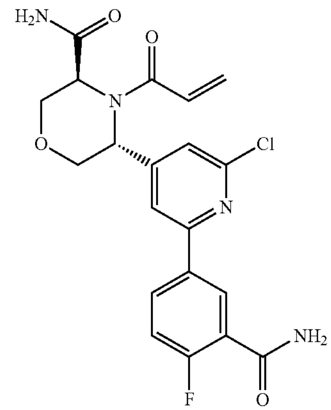 [SMILES: C=CC(=O)N1[C@H](C(N)=O)COC[C@H]1c1cc(Cl)nc(-c2ccc(F)c(C(N)=O)c2)c1] | 181 | (3S,5R)-4-acryloyl-5-(2-(3-carbamoyl-4-fluorophenyl)-6-chloropyridin-4-yl)morpholine-3-carboxamide | Single enantiomer of known absolute configuration | 1H NMR (400 MHz, CHLOROFORM-d) δ ppm 3.46-3.65 (m, 1 H) 3.85-4.01 (m, 1 H) 4.15-4.28 (m, 2 H) 4.68-4.94 (m, 1 H) 4.99-5.14 (m, 1 H) 5.61-5.79 (m, 2 H) 5.97 (br s, 1 H) 6.31-6.46 (m, 2 H) 6.72-6.80 (m, 1 H) 7.18-7.20 (m, 1 H) 7.59-7.65 (m, 1 H) 8.30-8.35 (m, 1 H) 8.57-8.63 (m, 1 H) |
| 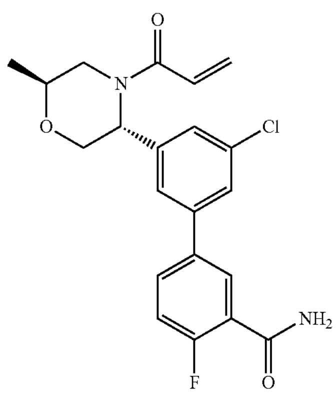 [SMILES: C=CC(=O)N1C[C@H](C)OC[C@H]1c1cc(Cl)cc(-c2ccc(F)c(C(N)=O)c2)c1] | 182 | 3'-((3R,6S)-4-acryloyl-6-methylmorpholin-3-yl)-5'-chloro-4-fluoro-[1,1'-biphenyl]-3-carboxamide | Single entntiomer of unknown absolute configuration | 1H NMR (400 MHz, METHANOL-d4) δ = 8.02 (dd, J = 2.4, 6.9 Hz, 1H), 7.79 (ddd, J = 2.6, 4.7, 8.6 Hz, 1H), 7.62-7.56 (m, 2H), 7.43 (s, 1 H),7.32 (dd, J = 8.7, 10.7 Hz, 1H), 6.75 (dd, J = 10.5, 16.6 Hz, 1H), 6.31 (dd, J = 1.9, 16.7 Hz, 1H), 5.79 (dd, J = 1.9, 10.5 Hz, 1H), 5.46-5.40 (m, 1H), 4.25-4.13 (m, 2H), 4.11-4.04 (m, 1H), 3.92-3.81 (m, 1H), 3.69-3.61 (m, 1H), 1.28 (d, J = 6.5 Hz, 3H) |
| 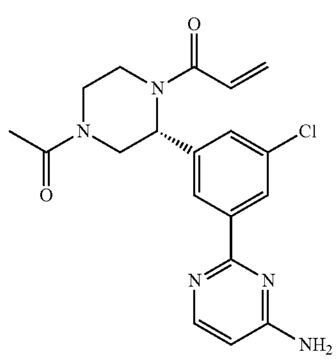 [SMILES: C=CC(=O)N1CCN(C(C)=O)C[C@H]1c1cc(Cl)cc(-c2nccc(N)n2)c1] | 183 | (R)-1-(4-acetyl-2-(3-(4-aminopyrimidin-2-yl)-5-chlorophenyl)piperazin-1-yl)prop-2-en-1-one | Single enantiomer of known absolute configuration | 1H NMR (400 MHz, CHLOROFORM-d) δ ppm 2.05-2.15 (m, 3 H) 3.14-3.57 (m, 2 H) 3.66-4.10 (m, 2 H) 4.17-4.63 (m, 2 H) 4.89-5.44 (m, 3 H) 5.75 (br s, 1 H) 6.33-6.39 (m, 1 H) 6.44 (br d, J = 7.25 Hz, 2 H) 7.28-7.39 (m, 1 H) 8.18-8.28 (m, 1 H) 8.28-8.35 (m, 2 H) |
| 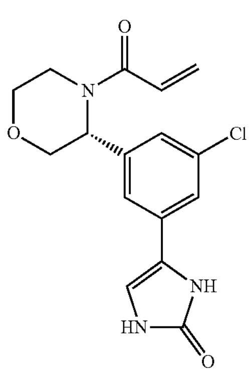 [SMILES: C=CC(=O)N1CCOC[C@H]1c1cc(Cl)cc(-c2c[nH]c(=O)[nH]2)c1] | 184 | (R)-4-(3-(4-acryloylmorpholin-3-yl)-5-chlorophenyl)-1,3-dihydro-2H-imidazol-2-one | Single enantiomer of known absolute configuration | H NMR (400 MHz, CHLOROFORM-d) δ ppm 8.96-9.43 (m, 1 H) 7.50 (br s, 1 H) 7.34 (br s, 1 H) 6.47-6.66 (m, 2 H) 6.32-6.44 (m, 1 H) 5.76 (br d, J = 9.51 Hz, 1 H) 4.36-4.67 (m, 1 H), 3.73-4.19 (m, 3 H) 3.60-3.73 (m, 1 H) 2.98-3.59 (m, 2 H) |

TABLE 1-continued

| Compounds of the Disclosure. | | | | |
|---|---|---|---|---|
| Structure | No. | Name | Stereochemistry | NMR |
| 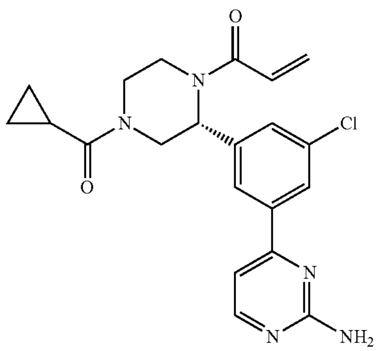 [SMILES: C=CC(=O)N1CCN(C(=O)C2CC2)C[C@H]1c1cc(Cl)cc(-c2ccnc(N)n2)c1] | 185 | (R)-1-(2-(3-(2-aminopyrimidin-4-yl)-5-chlorophenyl)-4-(cyclopropanecarbonyl)piperazin-1-yl)prop-2-en-1-one | Single enantiomer of known absolute configuration | 1H NMR (400 MHz, CHLOROFORM-d) δ ppm 8.35-8.40 (m, 1 H) 7.91-8.07 (m, 1 H) 7.82-7.90 (m, 1 H) 7.35-7.50 (m, 1 H) 6.94-7.15 (m, 1 H) 6.37-6.60 (m, 2 H) 5.71-5.90 (m, 1 H) 5.03-5.35 (m, 3 H) 4.46-4.73 (m, 1 H) 3.76-4.13 (m, 2 H) 3.45-3.71 (m, 1 H) 3.05-3.45 (m, 2 H) 1.61-1.68 (m, 1 H) 1.03-1.11 (m, 1 H) 0.94 (br d, J = 2.25 Hz, 1 H) 0.80 (br dd, J = 14.51, 6.25 Hz, 2 H) |
| 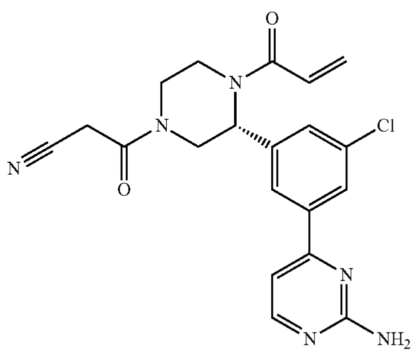 [SMILES: C=CC(=O)N1CCN(C(=O)CC#N)C[C@H]1c1cc(Cl)cc(-c2ccnc(N)n2)c1] | 186 | (R)-3-(4-acryloyl-3-(3-(2-aminopyrimidin-4-yl)-5-chlorophenyl)piperazin-1-yl)-3-oxopropanenitrile | Single enantiomer of known absolute configuration | 1H NMR (400 MHz, CHLOROFORM-d) δ ppm 8.30-8.49 (m, 1 H) 7.93-8.04 (m, 1 H) 7.80-7.93 (m, 1 H) 7.32-7.39 (m, 1 H) 6.96-7.12 (m, 1 H) 6.20-6.72 (m, 2 H) 5.74-5.92 (m, 1 H) 4.96-5.46 (m, 3 H) 4.40-4.96 (m, 1 H) 4.02-4.40 (m, 1 H) 3.60-3.94 (m, 2 H) 3.53-3.60 (m, 1 H) 3.37-3.51 (m, 2 H) 3.10-3.35 (m, 1 H) |
| 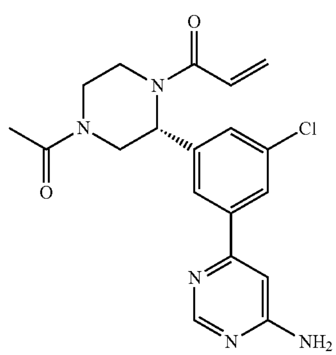 [SMILES: C=CC(=O)N1CCN(C(C)=O)C[C@H]1c1cc(Cl)cc(-c2cc(N)ncn2)c1] | 187 | (R)-1-(4-acetyl-2-(3-(6-aminopyrimidin-4-yl)-5-chlorophenyl)piperazin-1-yl)prop-2-en-1-one | Single enantiomer of known absolute configuration | 1H NMR (400 MHz, CHLOROFORM-d) δ ppm 2.05-2.15 (m, 3 H) 3.14-3.57 (m, 2 H) 3.66-4.10 (m, 2 H) 4.17-4.63 (m, 2 H) 4.89-5.44 (m, 3 H) 5.75 (br s, 1 H) 6.33-6.39 (m, 1 H) 6.44 (br d, J = 7.25 Hz, 2 H) 7.28-7.39 (m, 1 H) 8.18-8.28 (m, 1 H) 8.28-8.35 (m, 2 H) |
| 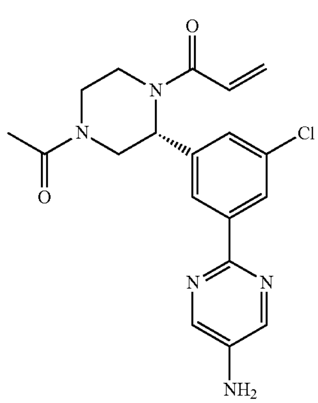 [SMILES: C=CC(=O)N1CCN(C(C)=O)C[C@H]1c1cc(Cl)cc(-c2ncc(N)cn2)c1] | 188 | (R)-1-(4-acetyl-2-(3-(5-aminopyrimidin-2-yl)-5-chlorophenyl)piperazin-1-yl)prop-2-en-1-one | Single enantiomer of known absolute configuration | 1H NMR (400 MHz, CHLOROFORM-d) δ ppm 1.98-2.19 (m, 3 H) 2.99-3.58 (m, 2 H) 3.62-3.76 (m, 1 H) 3.79-3.92 (m, 2 H) 4.16-4.43 (m, 1 H) 5.64-5.86 (m, 1 H) 6.19-6.65 (m, 2 H) 7.21-7.26 (m, 1 H) 7.28-7.32 (m, 1 H) 8.16-8.22 (m, 1 H) 8.23-8.29 (m, 3 H) |

TABLE 1-continued

Compounds of the Disclosure.

| Structure | No. | Name | Stereochemistry | NMR |
|---|---|---|---|---|
| 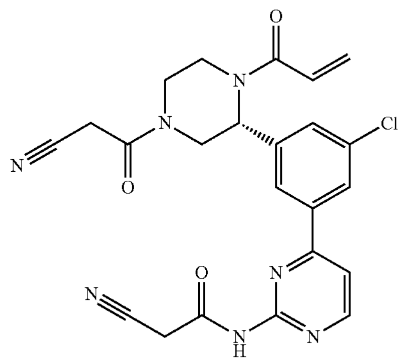 [SMILES: C=CC(=O)N1CCN(C(=O)CC#N)C[C@H]1c1cc(Cl)cc(-c2ccnc(NC(=O)CC#N)n2)c1] | 189 | (R)-N-(4-(3-(1-acrylol-4-(2-cyanoacetyl)piperazin-2-yl)-5-chlorophenyl)pyrimidin-2-yl)-2-cyanoacetamide | Single enantiomer of known absolute configuration | 1H NMR (400 MHz, CHLOROFORM-d) δ ppm 8.62-8.85 (m, 2 H) 7.97-8.21 (m, 1 H) 7.83-7.96 (m, 1 H) 7.44-7.53 (m, 1 H) 7.41 (s, 1 H) 6.37-6.76 (m, 2 H) 5.51-6.23 (m, 2 H) 4.49-5.47 (m, 1 H) 3.94-4.37 (m, 3 H) 3.72 (br d, J = 12.13 Hz, 1 H) 3.20-3.58 (m, 5 H) |
| 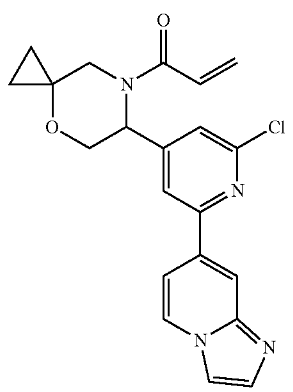 [SMILES: C=CC(=O)N1CC2(CC2)OCC1c1cc(Cl)nc(-c2ccn3ccnc3c2)c1] | 190 | 1-(6-(2-chloro-6-(imidazo[1,2-a]pyridin-7-yl)pyridin-4-yl)-4-oxa-7-azaspiro[2.5]octan-7-yl)prop-2-en-1-one | Single enantiomer of unknown absolute configuration | 1H NMR (400 MHz, CHLOROFORM-d) δ ppm 0.50-0.64 (m, 1 H) 0.66-0.76 (m, 1 H) 0.78-0.91 (m, 1 H) 0.97-1.13 (m, 1 H) 3.06-3.26 (m, 1 H) 3.77-3.89 (m, 1 H) 4.10 (br d, J = 11.37 Hz, 1 H) 4.42 (br d, J = 12.35 Hz, 1 H) 5.77-5.92 (m, 2 H) 6.40-6.56 (m, 2 H) 7.42-7.52 (m, 1 H) 7.59-7.68 (m, 2 H) 7.74 (s, 1 H) 7.86-7.96 (m, 1 H) 8.18-8.26 (m, 2 H) |
| 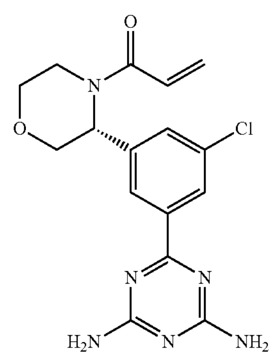 [SMILES: C=CC(=O)N1CCOC[C@H]1c1cc(Cl)cc(-c2nc(N)nc(N)n2)c1] | 191 | (R)-1-(3-(3-chloro-5-(4,6-diamino-1,3,5-triazin-2-yl)phenyl)morpholino)prop-2-en-1-one | Single enantiomer of known absolute configuration | 1H NMR (400 MHz, DMSO-d6) δ = 8.18 (s, 2H), 7.53 (br s, 1H), 6.98-6.70 (m, 5H), 6.27-6.20 (m, 1H), 5.77 (dd, J = 2.3, 10.4 Hz, 1H), 5.67-5.23 (m, 1H), 4.40 (d, J = 12.3 Hz, 1H), 4.26-3.68 (m, 3H), 3.51 (br d, J = 2.5 Hz, 1H), 3.27-2.92 (m, 1H) |
| 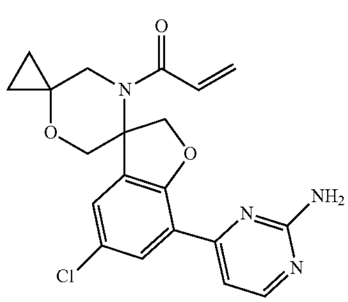 [SMILES: C=CC(=O)N1CC2(CC2)OCC12COc1c(-c3ccnc(N)n3)cc(Cl)cc12] | 192 | 1-(7-(2-aminopyrimidin-4-yl)-5-chloro-2H-dispiro[benzofuran-3,5'-morpholine-2',1''-cyclopropan]-4'-yl)prop-2-en-1-one | Single enantiomer of unknown absolute configuration | 1H NMR (400 MHz, CHLOROFORM-d) δ ppm 8.35 (br s, 1 H) 8.15 (d, J = 2.20 Hz, 1H) 7.54 (d, J = 5.01 Hz, 1 H) 7.19 (d, J = 2.20 Hz, 1 H) 6.29-6.40 (m, 1 H) 6.19-6.27 (m, 1 H) 5.59-5.69 (m, 1 H) 5.13 (br s, 2H) 4.75-4.92 (m, 2 H) 3.69-3.89 (m, 2 H) 3.63 (s, 2 H) 0.94-1.13 (m, 2 H) 0.67-0.86 (m, 2 H) |

TABLE 1-continued

Compounds of the Disclosure.

| Structure | No. | Name | Stereochemistry | NMR |
|---|---|---|---|---|
| 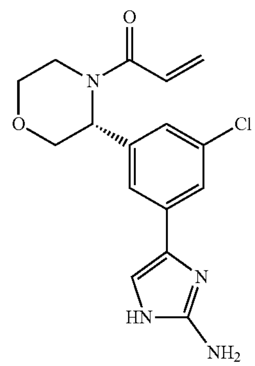 [SMILES: C=CC(=O)N1CCOC[C@H]1c1cc(Cl)cc(-c2c[nH]c(N)n2)c1] | 193 | (R)-1-(3-(3-(2-amino-1H-imidazol-4-yl)-5-chlorophenyl)morpholino)prop-2-en-1-one | Single enantiomer of known absolute configuration | 1H NMR (400 MHz, CHLOROFORM-d) δ ppm 3.44-3.83 (m, 2 H) 3.84-3.93 (m, 1 H) 3.95-4.03 (m, 1 H) 4.34-4.57 (m, 1 H) 5.47-5.92 (m, 2 H) 6.36 (br d, J = 16.63 Hz, 1 H) 6.55-6.89 (m, 2 H) 6.98-7.26 (m, 1 H) 7.29-7.36 (m, 1 H) 7.37-7.59 (m, 2 H) 12.00-13.56 (m, 2 H) |
| 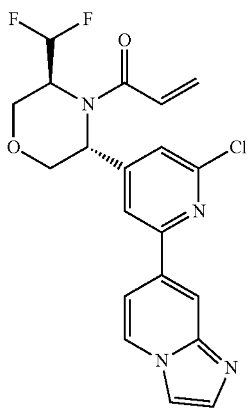 [SMILES: C=CC(=O)N1[C@H](c2cc(Cl)nc(-c3ccn4ccnc4c3)c2)COC[C@H]1C(F)F] | 194 | 1-((3R,5S)-3-(2-chloro-6-(imidazo[1,2-a]pyridin-7-yl)pyridin-4-yl)-5-(difluoromethyl)morpholino)prop-2-en-1-one | Single enantiomer of known absolute configuration | 1H NMR (400 MHz, CHLOROFORM-d) δ ppm 9.26 (s, 1 H) 8.19-8.57 (m, 2 H) 7.93-8.11 (m, 1 H) 7.87 (s, 1 H) 7.74 (s, 1 H) 7.34 (s, 1 H) 6.46-6.95 (m, 1 H) 5.96-6.42 (m, 2 H) 5.62-5.89 (m, 1 H) 4.86 (br s, 1 H) 3.87-4.60 (m, 4 H) 3.23-3.79 (m, 1 H) |
| 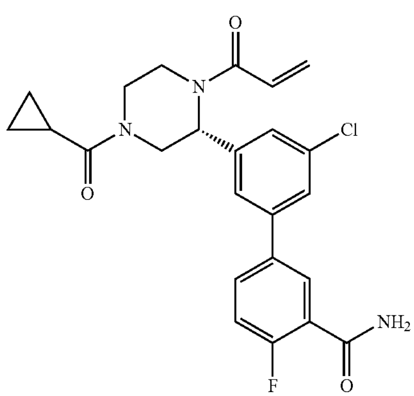 [SMILES: C=CC(=O)N1CCN(C(=O)C2CC2)C[C@H]1c1cc(Cl)cc(-c2ccc(F)c(C(N)=O)c2)c1] | 195 | (R)-3'-(1-acryloyl-4-(cyclopropanecarbonyl)piperazin-2-yl)-5'-chloro-4-fluoro-[1,1'-biphenyl]-3-carboxamide | Single enantiomer of known absolute configuration | 1H NMR (400 MHz, CHLOROFORM-d) δ ppm 8.29 (dd, J = 7.32, 2.31 Hz, 1 H) 7.68 (br s, 1 H) 7.43-7.57 (m, 2 H) 7.29-7.41 (m, 1 H) 7.19-7.25 (m, 1 H) 6.76 (br s, 1 H) 6.36-6.67 (m, 2 H) 5.92 (br s, 1 H) 5.81 (br d, J = 8.00 Hz, 1 H) 4.82-5.51 (m, 1 H) 3.92-4.80 (m, 3 H) 2.98-3.82 (m, 3 H) 1.67 (br s, 1 H) 0.90-1.16 (m, 2 H) 0.79 (br s, 2 H) |
| 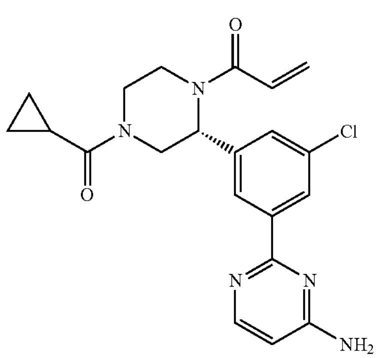 [SMILES: C=CC(=O)N1CCN(C(=O)C2CC2)C[C@H]1c1cc(Cl)cc(-c2nccc(N)n2)c1] | 196 | (R)-1-(2-(3-(4-aminopyrimidin-2-yl)-5-chlorophenyl)-4-(cyclopropanecarbonyl)piperazin-1-yl)prop-2-en-1-one | Single enantiomer of known absolute configuration | 1H NMR (400 MHz, CHLOROFORM-d) δ ppm 8.23-8.36 (m, 3 H) 8.20 (br s, 1 H) 7.35 (s, 1 H) 6.30-6.47 (m, 3 H) 5.61-5.88 (m, 1 H) 5.00-5.26 (m, 3 H) 4.34-4.77 (m, 1 H) 3.84-4.23 (m, 2 H) 3.11-3.78 (m, 2 H) 1.69-1.82 (m, 1 H) 0.91-1.14 (m, 2 H) 0.75-0.83 (m, 2 H) |

TABLE 1-continued

| Compounds of the Disclosure. | | | | |
|---|---|---|---|---|
| Structure | No. | Name | Stereochemistry | NMR |
| 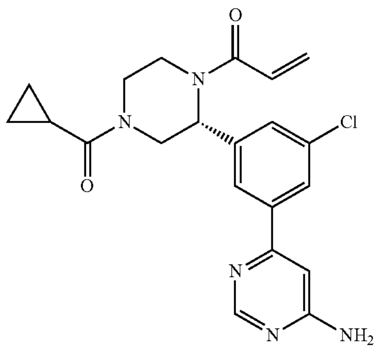 | 197 | (R)-1-(2-(3-(6-aminopyrimidin-4-yl)-5-chlorophenyl)-4-(cyclopropanecarbonyl)piperazin-1-yl)prop-2-en-1-one | Single enantiomer of known absolute configuration | 1H NMR (400 MHz, CHLOROFORM-d) δ ppm 0.74-0.95 (m, 3 H) 0.99-1.14 (m, 1 H) 3.03-3.55 (m, 2 H) 3.64-4.34 (m, 2 H) 4.39-4.73 (m, 1 H) 5.04 (br s, 2 H) 5.69-5.90 (m, 1 H) 6.38-6.70 (m, 2 H) 6.73-7.02 (m, 1 H) 7.29 (br s, 1 H) 7.34 (br s, 1 H) 7.53 (s, 1 H) 7.82-8.10 (m, 1 H) 8.06 (br s, 1 H) 8.65 (s, 1 H) |
| 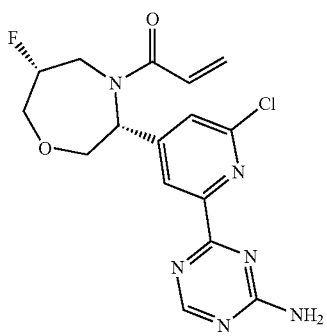 [SMILES: C=CC(=O)N1C[C@@H](F)COC[C@H]1c1cc(Cl)nc(-c2ncnc(N)n2)c1] | 198 | 1-((3R,6R)-3-(2-(6-aminopyrimidin-4-yl)-6-chloropyridin-4-yl)-6-fluoro-1,4-oxazepan-4-yl)prop-2-en-1-one | Single enantiomer of known absolute configuration | 1H NMR (400 MHz, CHLOROFORM-d) δ ppm 3.48-3.77 (m, 1 H) 3.84-4.13 (m, 3 H) 4.22 (dd, J = 13.63, 4.75 Hz, 1 H) 4.35-4.49 (m, 1 H) 4.69-4.97 (m, 1 H) 5.03 (br s, 2 H) 5.75-5.85 (m, 1 H) 5.89-6.03 (m, 1 H) 6.42 (br d, J = 16.51 Hz, 1 H) 6.81 (dd, J = 16.76, 10.51 Hz, 1 H) 7.33 (s, 1 H) 7.49 (s, 1 H) 8.26 (s, 1 H) 8.65 (s, 1 H) |
| 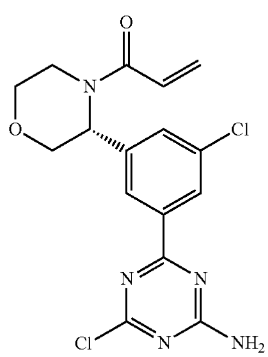 [SMILES: C=CC(=O)N1CCOC[C@H]1c1cc(Cl)cc(-c2nc(N)nc(Cl)n2)c1] | 199 | (R)-1-(3-(3-(4-amino-6-chloro-1,3,5-triazin-2-yl)-5-chlorophenyl)morpholino)prop-2-en-1-one | Single enantiomer of known absolute configuration | 1H NMR (400 MHz, CHLOROFORM-d) δ ppm 8.21-8.50 (m, 2 H) 7.54-7.79 (m, 1 H) 6.51-6.66 (m, 1 H) 6.34-6.51 (m, 1 H) 5.37-6.19 (m, 4 H) 4.52 (d, J = 12.26 Hz, 1 H) 4.00 (br dd, J = 11.26, 3.00 Hz, 1 H) 3.92 (dd, J = 12.32, 3.56 Hz, 1 H) 3.64 (td, J = 11.76, 2.63 Hz, 2 H) 3.14-3.42 (m, 1 H) |
| 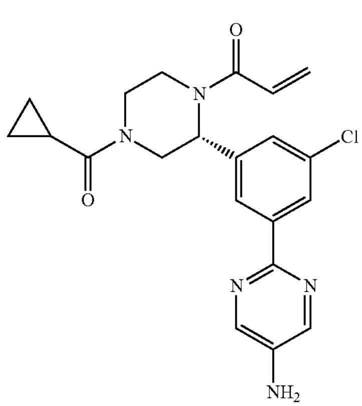 [SMILES: C=CC(=O)N1CCN(C(=O)C2CC2)C[C@H]1c1cc(Cl)cc(-c2ncc(N)cn2)c1] | 200 | (R)-1-(2-(3-(5-aminopyrimidin-2-yl)-5-chlorophenyl)-4-(cyclopropanecarbonyl)piperazin-1-yl)prop-2-en-1-one | Single enantiomer of known absolute configuration | 1H NMR (400 MHz, CHLOROFORM-d) δ ppm 8.26 (s, 2 H) 8.22 (br s, 1 H) 8.14-8.21 (m, 1 H) 7.29 (br d, J = 1.63 Hz, 1 H) 6.42 (br d, J = 14.88 Hz, 1 H) 5.66-6.83 (m, 1 H) 4.87-5.55 (m, 1 H) 4.51-4.82 (m, 1 H) 4.16-4.44 (m, 1 H) 3.88-4.01 (m, 1 H) 3.85 (br s, 2 H) 3.56-3.81 (m, 1 H) 3.41-3.54 (m, 1 H) 2.55-3.30 (m, 1 H) 1.63-1.81 (m, 1 H) 1.01 (br s, 2 H) 0.78 (br d, J = 5.25 Hz, 2 H) |

TABLE 1-continued

| Compounds of the Disclosure. | | | | |
|---|---|---|---|---|
| Structure | No. | Name | Stereochemistry | NMR |
| 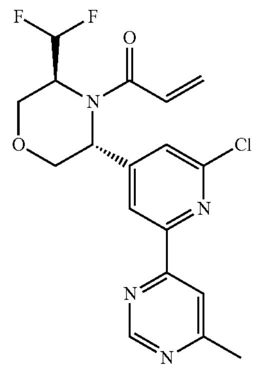 [SMILES: C=CC(=O)N1[C@H](c2cc(Cl)nc(-c3cc(C)ncn3)c2)COC[C@H]1C(F)F] | 201 | 1-((3R,5S)-3-(2-chloro-6-(6-methylpyrimidin-4-yl)pyridin-4-yl)-5-(difluoromethyl)morpholino)prop-2-en-1-one | Single enantiomer of known absolute configuration | 1H NMR (400 MHz, CHLOROFORM-d) δ ppm 9.13 (s, 1 H) 8.30 (s, 1 H) 8.21 (s, 1 H) 7.30 (br d, J = 0.88 Hz, 2 H) 5.97-6.61 (m, 3 H) 5.14-5.89 (m, 1 H) 4.57-5.05 (m, 1 H) 3.99-4.36 (m, 4 H) 2.64 (s, 3 H) |
| 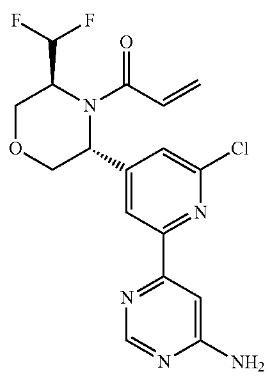 [SMILES: C=CC(=O)N1[C@H](c2cc(Cl)nc(-c3cc(N)ncn3)c2)COC[C@H]1C(F)F] | 202 | 1-((3R,5S)-3-(2-(6-aminopyrimidin-4-yl)-6-chloropyridin-4-yl)-5-(difluoromethyl)morpholino)prop-2-en-1-one | Single enantiomer of known absolute configuration | 1H NMR (400 MHz, CHLOROFORM-d) δ = 8.64 (d, J = 1.0 Hz, 1 H) 8.22 (s, 1 H), 7.50 (d, J = 1.0 Hz, 1 H), 6.54-6.02 (m, 3H), 5.75 (br d, J = 12.0 Hz, 1H), 5.01 (br s, 2H), 4.79 (br s, 1H), 4.29 (br d, J = 10.9 Hz, 1H), 4.16-3.99 (m, 2H), 3.80-3.41 (m, 1H) |
| 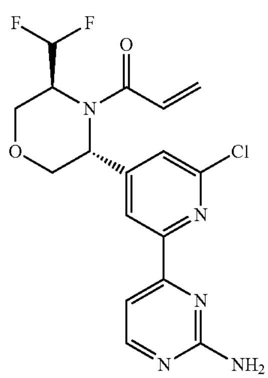 [SMILES: C=CC(=O)N1[C@H](c2cc(Cl)nc(-c3ccnc(N)n3)c2)COC[C@H]1C(F)F] | 203 | 1-((3R,5S)-3-(2-(2-aminopyrimidin-4-yl)-6-chloropyridin-4-yl)-5-(difluoromethyl)morpholino)prop-2-en-1-one | Single enantiomer of known absolute configuration | 1H NMR (400 MHz, DMSO-d6) δ = 8.42 (d, J = 5.0 Hz, 1H), 8.12 (br s, 1H), 7.53 (br s, 1H), 7.33 (d, J = 5.0 Hz, 1H), 6.80 (s, 3H), 6.59-6.27 (m, 1H), 6.07 (br d, J = 16.3 Hz, 1H), 5.72 (br d, J = 10.1 Hz, 1H), 4.78 (br d, J = 78.9 Hz, 2H), 4.11 (s, 1H), 4.18-3.95 (m, 1H), 3.43 (br s, 1H) |
| 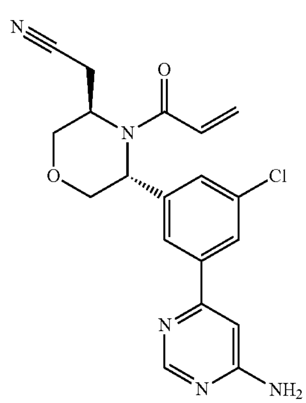 [SMILES: C=CC(=O)N1[C@H](CC#N)COC[C@H]1c1cc(Cl)cc(-c2cc(N)ncn2)c1] | 204 | 2-((3R,5R)-4-acryloyl-5-(3-(6-aminopyrimidin-4-yl)-5-chlorophenyl)morpholin-3-yl)acetonitrile | Single enantiomer of known absolute configuration | 1H NMR (400 MHz, CHLOROFORM-d) δ ppm 8.66 (d, J = 0.88 Hz, 1 H) 7.76-7.93 (m, 2 H) 7.32 (br d, J = 1.50 Hz, 2 H) 6.78 (d, J = 1.00 Hz, 1 H) 6.33 (br d, J = 4.75 Hz, 2 H) 5.60-5.78 (m, 1 H) 5.05 (br s, 2 H) 4.48-4.97 (m, 2 H) 3.92-4.22 (m, 3 H) 3.11 (d, J = 16.51, 9.38 Hz, 1 H) 2.72-2.93 (m, 1 H) |

TABLE 1-continued

| Compounds of the Disclosure. | | | | |
|---|---|---|---|---|
| Structure | No. | Name | Stereochemistry | NMR |
| 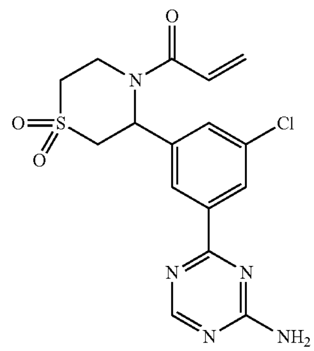 [SMILES: C=CC(=O)N1CCS(=O)(=O)CC1c1cc(Cl)cc(-c2ncnc(N)n2)c1] | 205 | 1-(3-(3-(4-amino-1,3,5-triazin-2-yl)-5-chlorophenyl)-1,1-dioxidothiomorpholino)prop-2-en-1-one Enantiomer 1 | Single enantiomer of unknown absolute configuration | 1H NMR (400 MHz, DMSO-d6) δ ppm 8.61 (s, 1 H) 8.21 (s, 1 H) 8.09 (s, 1 H) 7.73 (br d, J = 4.50 Hz, 3 H) 6.79-7.03 (m, 1 H) 6.25 (dd, J = 16.63, 2.00 Hz, 1 H) 6.15 (br s, 1 H) 5.82 (br d, J = 10.76 Hz, 1 H) 4.52-4.86 (m, 1 H) 4.17 (dt, J = 14.88, 3.50 Hz, 1 H) 3.78 (br dd, J = 14.88, 5.50 Hz, 1 H) 3.34-3.43 (m, 1 H) 3.14 (br dd, J = 13.26, 2.13 Hz, 1 H) |
| 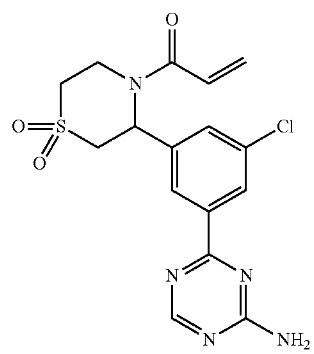 [SMILES: C=CC(=O)N1CCS(=O)(=O)CC1c1cc(Cl)cc(-c2ncnc(N)n2)c1] | 206 | 1-(3-(3-(4-amino-1,3,5-triazin-2-yl)-5-chlorophenyl)-1,1-dioxidothiomorpholino)prop-2-en-1-one Enantiomer 2 | Single enantiomer of unknown absolute configuration | 1H NMR (400 MHz, DMSO-d6) δ ppm 8.61 (s, 1 H) 8.21 (s, 1 H) 8.09 (s, 1 H) 7.73 (br d, J = 4.50 Hz, 3 H) 6.77-7.01 (m, 1 H) 6.25 (dd, J = 16.63, 2.00 Hz, 1 H) 6.16 (br s, 1 H) 5.82 (br d, J = 10.88 Hz, 1 H) 4.53-4.87 (m, 1 H) 4.18 (dt, J = 14.70, 3.53 Hz, 1 H) 3.78 (br dd, J = 15.20, 5.57 Hz, 1 H) 3.35-3.45 (m, 1 H) 3.15 (br dd, J = 13.45, 2.31 Hz, 1 H) |
| 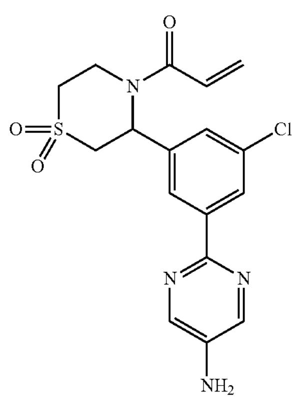 [SMILES: C=CC(=O)N1CCS(=O)(=O)CC1c1cc(Cl)cc(-c2ncc(N)cn2)c1] | 207 | 1-(3-(3-(5-aminopyrimidin-2-yl)-5-chlorophenyl)-1,1-dioxidothiomorpholino)prop-2-en-1-one | Single enantiomer of unknown absolute configuration | 1H NMR (400 MHz, DMSO-d6) δ = 8.22 (s, 2H), 8.09 (s, 1H), 7.99 (s, 1H), 7.47 (s, 1H), 6.99-6.81 (m, 1H), 6.25 (dd, J = 2.0, 16.6 Hz, 1H), 6.18-6.04 (m, 1H), 5.89-5.74 (m, 3H), 4.83-4.62 (m, 1H), 4.16 (td, J = 3.5, 15.0 Hz, 1H), 3.77 (br dd, J = 5.6, 14.8 Hz, 1H), 3.64-3.35 (m, 2H), 3.15 (br dd, J = 2.4, 13.4 Hz, 1H) |
| 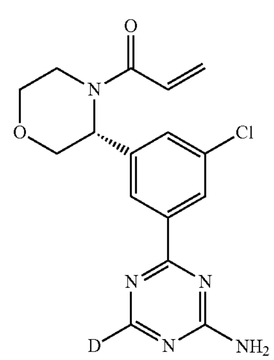 [SMILES: [2H]c1nc(N)nc(-c2cc(Cl)cc([C@@H]3COCCN3C(=O)C=C)c2)n1] | 208 | (R)-1-(3-(3-(4-amino-1,3,5-triazin-2-yl)-6-d)-5-chlorophenyl)morpholino)prop-2-en-1-one | Single enantiomer of known absolute configuration | 1H NMR (400 MHz, CHLOROFORM-d) δ ppm 8.17-8.49 (m, 2 H) 7.45-7.75 (m, 1 H) 6.47-6.62 (m, 1 H) 6.29-6.44 (m, 1 H) 5.75 (br d, J = 10.15 Hz, 2H) 5.54 (br s, 2 H) 4.48 (br d, J = 12.35 Hz, 1 H) 3.94 (br d, J = 10.64 Hz, 1 H) 3.86 (br dd, J = 12.04, 3.36 Hz, 1 H) 3.05-3.73 (m, 3 H) |

TABLE 1-continued

Compounds of the Disclosure.

| Structure | No. | Name | Stereochemistry | NMR |
|---|---|---|---|---|
| 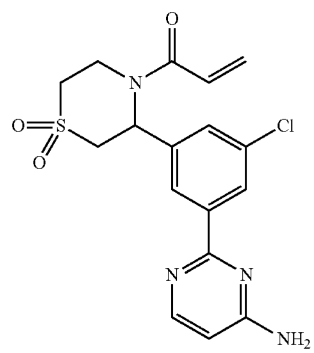 [SMILES: C=CC(=O)N1CCS(=O)(=O)CC1c1cc(Cl)cc(-c2nccc(N)n2)c1] | 209 | 1-(3-(3-(4-aminopyrimidin-2-yl)-5-chlorophenyl)-1,1-dioxidothiomorpholino)prop-2-en-1-one | Single enantiomer of unknown absolute configuration | 1H NMR (400 MHz, DMSO-d6) δ = 8.24-8.12 (m, 2H), 8.05 (s, 1H), 7.58 (s, 1H), 7.12-6.80 (m, 3H), 6.40 (d, J = 5.7 Hz, 1H), 6.25 (dd, J = 2.0, 16.7 Hz, 1H), 6.18-6.07 (m, 1H), 5.73 (s, 1H), 4.81-4.57 (m, 1H), 4.25-4.07 (m, 1 H), 3.84-3.70 (m, 1H), 3.59-3.46 (m, 1H), 3.38 (br d, J = 5.7 Hz, 1H), 3.19-3.10 (m, 1H) |
| 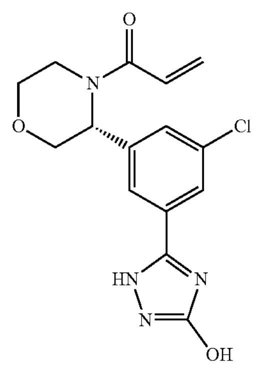 [SMILES: C=CC(=O)N1CCOC[C@H]1c1cc(Cl)cc(-c2nc(O)n[nH]2)c1] | 210 | (R)-1-(3-(3-chloro-5-(3-hydroxy-1H-1,2,4-triazol-5-yl)phenyl)morpholino)prop-2-en-1-one | Single enantiomer of known absolute configuration | 1H NMR (400 MHz, CHLOROFORM-d) δ = 12.11 (br s, 1H), 10.54 (br s, 1H), 7.93 (s, 1H), 7.86 (br s, 1H), 7.72 (br s, 1H), 7.78-7.64 (m, 1H), 6.61-6.41 (m, 2H), 5.82 (br d, J = 11.3 Hz, 2H), 4.53 (br d, J = 13.8 Hz, 1H), 4.08-3.84 (m, 2H), 3.66 (br t, J = 12.3 Hz, 2H), 3.43 (br s, 1H) |
| 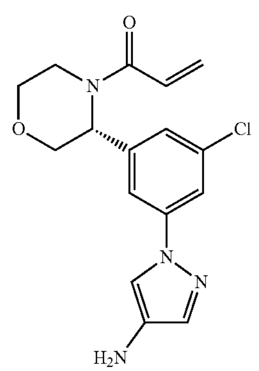 [SMILES: C=CC(=O)N1CCOC[C@H]1c1cc(Cl)cc(-n2cc(N)cn2)c1] | 211 | (R)-1-(3-(3-(4-amino-1H-pyrazol-1-yl)-5-chlorophenyl)morpholino)prop-2-en-1-one | Single enantiomer of known absolute configuration | 1H NMR (400 MHz, CHLOROFORM-d) δ ppm 7.61 (br s, 2 H) 7.49 (s, 1 H) 7.40 (s, 2H) 6.51-6.64 (m, 1 H) 6.35-6.47 (m, 1 H) 5.79 (dd, J = 10.51, 1.75 Hz, 2 H) 4.47 (d, J = 12.26 Hz, 1 H) 3.99 (dd, J = 11.01, 2.88 Hz, 1 H) 3.89 (dd, J = 12.38, 3.50 Hz, 1 H) 3.62 (td, J = 11.79, 2.44 Hz, 2 H) 2.98-3.21 (m, 1 H) |
| 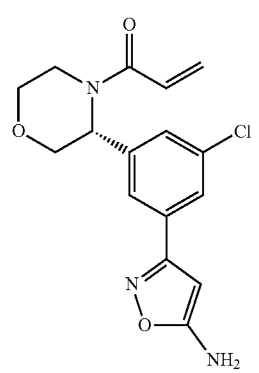 [SMILES: C=CC(=O)N1CCOC[C@H]1c1cc(Cl)cc(-c2cc(N)on2)c1] | 212 | (R)-1-(3-(3-(5-aminoisoxazol-3-yl)-5-chlorophenyl)morpholino)prop-2-en-1-one | Single enantiomer of known absolute configuration | 1H NMR (400 MHz, DMSO-d6) δ ppm 7.60-7.73 (m, 2 H) 7.44 (br s, 1 H) 6.77-6.95 (m, 3 H) 6.22 (dd, J = 16.57, 2.19 Hz, 1 H) 5.76 (dd, J = 10.38, 2.00 Hz, 1 H) 5.44 (s, 2 H) 4.44 (d, J = 12.26 Hz, 1 H) 4.18 (br s, 3 H) 3.50 (td, J = 11.66, 2.56 Hz, 1 H) 2.73-3.27 (m, 1 H) |

TABLE 1-continued

| Structure | No. | Name | Stereochemistry | NMR |
|---|---|---|---|---|
| Compounds of the Disclosure. | | | | |
| 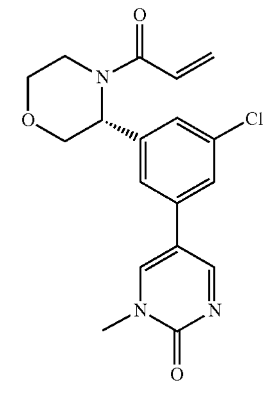 [SMILES: C=CC(=O)N1CCOC[C@H]1c1cc(Cl)cc(-c2cnc(=O)n(C)c2)c1] | 213 | (R)-5-(3-(4-acryloylmorpholin-3-yl)-5-chlorophenyl)-1-methylpyrimidin-2(1H)-one | Single enantiomer of known absolute configuration | 1H NMR (400 MHz, CHLOROFORM-d) δ ppm 8.84 (d, J = 3.38 Hz, 1 H) 7.83 (d, J = 3.38 Hz, 1 H) 7.60 (br d, J = 2.63 Hz, 1 H) 7.40-7.49 (m, 1 H) 7.35 (s, 1 H) 6.33-6.67 (m, 2 H) 5.81 (dd, J = 10.32, 1.81 Hz, 2 H) 4.46 (d, J = 12.26 Hz, 1 H) 3.89-4.03 (m, 2 H) 3.60-3.79 (m, 5 H) 3.20-3.47 (m, 1 H) |
| 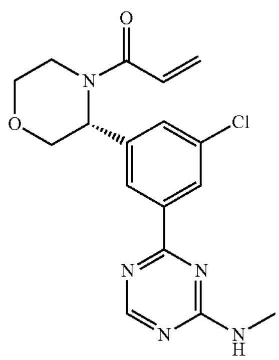 [SMILES: C=CC(=O)N1CCOC[C@H]1c1cc(Cl)cc(-c2ncnc(NC)n2)c1] | 214 | (R)-1-(3-(3-chloro-5-(4-(methylamino)-1,3,5-triazin-2-yl)phenyl)morpholino)prop-2-en-1-one | Single enantiomer of unknown absolute configuration | 1H NMR (400 MHz, CHLOROFORM-d) δ ppm 3.11 (dd, J = 18.09, 4.93 Hz, 3 H) 3.16-3.55 (m, 1 H) 3.58-4.02 (m, 4 H) 4.46-4.59 (m, 1 H) 5.47-5.57 (m, 1 H) 5.77-5.82 (m, 1 H) 6.38-6.47 (m, 1 H) 6.53-6.68 (m, 1 H) 7.50-7.70 (m, 1 H) 8.27-8.38 (m, 1 H) 8.38-8.54 (m, 1 H) 8.55-8.75 (m, 1 H) |
| 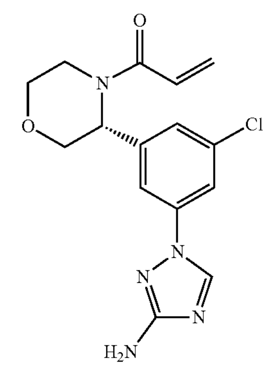 [SMILES: C=CC(=O)N1CCOC[C@H]1c1cc(Cl)cc(-n2cnc(N)n2)c1] | 215 | (R)-1-(3-(3-(3-amino-1H-1,2,4-triazol-1-yl)-5-chlorophenyl)morpholino)prop-2-en-1-one | Single enantiomer of known absolute configuration | 1H NMR (400 MHz, CHLOROFORM-d) δ ppm 8.21 (s, 1 H) 7.64 (br s, 1 H) 7.56 (s, 1 H) 7.47 (br s, 1 H) 6.50-6.64 (m, 1 H) 6.34-6.48 (m, 1 H) 5.81 (dd, J = 10.32, 1.94 Hz, 2 H) 4.46 (d, J = 12.26 Hz, 1 H) 4.34 (br s, 2 H) 3.99 (br dd, J = 11.26, 3.13 Hz, 1 H) 3.90 (dd, J = 12.32, 3.56 Hz, 1 H) 3.63 (td, J = 11.79, 2.69 Hz, 2 H) 3.19-3.44 (m, 1 H) |
| 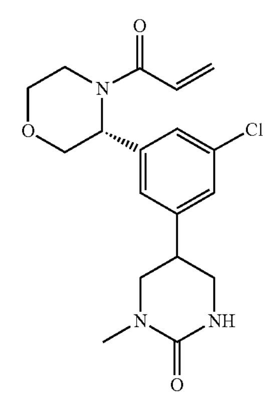 | 216 | 5-(3-((R)-4-acryloylmorpholin-3-yl)-5-chlorophenyl)-1-methyltetrahydropyrimidin-2(1H)-one Diasteromer 1 | Single stereoisomer with unknown absolute configuration at tetrahydropyrimidinone | 1H NMR (400 MHz, CHLOROFORM-d) δ ppm 7.40-7.53 (m, 1 H) 7.21-7.27 (m, 1 H) 7.16 (s, 1 H) 6.39-6.60 (m, 2 H) 5.80 (dd, J = 10.38, 1.88 Hz, 1 H) 4.72 (br s, 1 H) 4.42 (d, J = 12.26 Hz, 1 H) 3.82-4.02 (m, 2 H) 3.56-3.78 (m, 2 H) 3.24-3.52 (m, 6 H) 2.98 (s, 3 H) |

TABLE 1-continued

Compounds of the Disclosure.

| Structure | No. | Name | Stereochemistry | NMR |
|---|---|---|---|---|
| 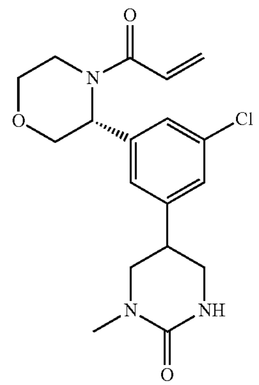 | 217 | 5-(3-((R)-4-acryloylmorpholin-3-yl)-5-chlorophenyl)-1-methyltetrahydropy-rimidin-2(1H)-one Diasteromer 2 | Single stereoisomer with unknown absolute configuration at tetrahydropyrimi-dinone | 1H NMR (400 MHz, CHLOROFORM-d) δ ppm 7.37-7.56 (m, 1 H) 7.20-7.27 (m, 1 H) 7.16 (s, 1 H) 6.35-6.65 (m, 2 H) 5.80 (dd, J = 10.38, 1.88 Hz, 1 H) 4.73 (br s, 1 H) 4.41 (d, J = 12.26 Hz, 1 H) 3.83-4.05 (m, 2 H) 3.62 (td, J = 11.76, 2.75 Hz, 2 H) 3.20-3.51 (m, 6 H) 2.98 (s, 3 H) |
| 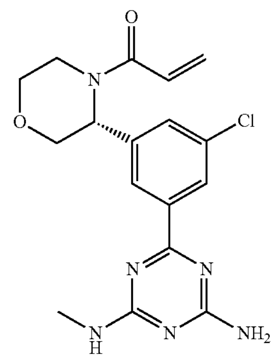 [SMILES: C=CC(=O)N1CCOC[C@H]1c1cc(Cl)cc(-c2nc(N)nc(NC)n2)c1] | 218 | (R)-1-(3-(3-(4-amino-6-(methylamino)-1,3,5-triazin-2-yl)-5-chlorophenyl)morpho-lino)prop-2-en-1-one | Single enantiomer of known absolute configuration | 1H NMR (400 MHz, CHLOROFORM-d) δ = 8.48-8.17 (m, 2H), 7.58 (br s, 1H), 6.64-6.52 (m, 1H), 6.47-6.38 (m, 1H), 5.78 (dd, J = 1.9, 10.4 Hz, 1H), 5.44-4.94 (m, 4H), 4.53 (d, J = 12.1 Hz, 1H), 4.02-3.86 (m, 2H), 3.62 (dt, J = 2.3, 11.7 Hz, 1H), 3.41-3.15 (m, 1H), 3.12-2.95 (m, 3H) |
| 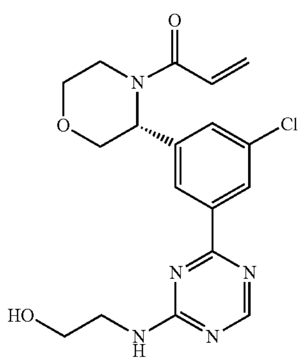 [SMILES: C=CC(=O)N1CCOC[C@H]1c1cc(Cl)cc(-c2ncnc(NCCO)n2)c1] | 219 | (R)-1-(3-(3-chloro-5-(4-((2-hydroxyethyl)amino)-1,3,5-triazin-2-yl)phenyl)morpholi-no)prop-2-en-1-one | Single enantiomer of known absolute configuration | 1H NMR (400 MHz, Dimethyl sulfoxide-d6) δ 8.63 (d, J = 34.6 Hz, 1H), 8.40-8.07 (m, 3H), 7.64 (d, J = 11.1 Hz, 1H), 6.87 (dt, J = 19.4, 9.8 Hz, 1H), 6.24 (dt, J = 16.6, 1.8 Hz, 1H), 5.77 (dd, J = 10.4, 2.4 Hz, 1H), 5.52 (d, J = 71.4 Hz, 1H), 4.44 (t, J = 11.6 Hz, 1H), 3.83 (dd, J = 33.1, 11.8 Hz, 3H), 3.50 (ddt, J = 43.6, 20.6, 6.0 Hz, 5H), 2.90 (s, 1H). |
| 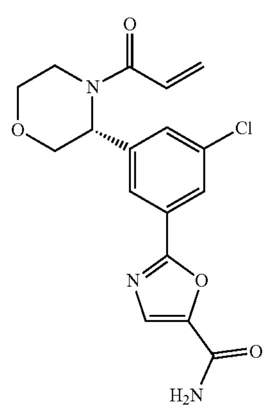 [SMILES: C=CC(=O)N1CCOC[C@H]1c1cc(Cl)cc(-c2ncc(C(N)=O)o2)c1] | 220 | (R)-2-(3-(4-acryloylmorpholin-3-yl)-5-chlorophenyl)oxazole-5-carboxamide | Single enantiomer of known absolute configuration | 1H NMR (400 MHz, CHLOROFORM-d) δ ppm 3.14-3.51 (m, 1 H) 3.52-3.81 (m, 2 H) 3.89-4.07 (m, 2 H) 4.49 (d, J = 12.26 Hz, 1H) 5.56-5.96 (m, 2 H) 6.03-6.35 (m, 1 H) 6.38-6.48 (m, 1 H) 6.39-6.48 (m, 1 H) 6.52-6.65 (m, 1 H) 7.54-7.76 (m, 1 H) 7.86 (s, 1 H) 8.02 (s, 1 H) 8.12 (br s, 1 H) |

TABLE 1-continued

| Compounds of the Disclosure. | | | | |
|---|---|---|---|---|
| Structure | No. | Name | Stereochemistry | NMR |
| 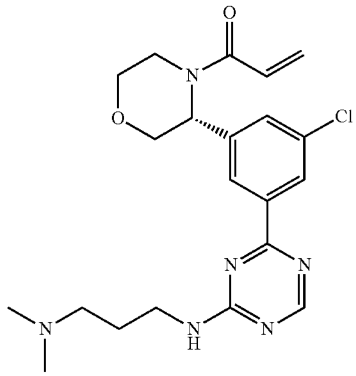 [SMILES: C=CC(=O)N1CCOC[C@H]1c1cc(Cl)cc(-c2ncnc(NCCCN(C)C)n2)c1] | 221 | (R)-1-(3-(3-chloro-5-(4-((3-(dimethylamino)propyl)amino)-1,3,5-triazin-2-yl)phenyl)morpholino)prop-2-en-1-one | Single enantiomer of known absolute configuration | 1H NMR (400 MHz, DMSO-d6) δ ppm 1.86-1.97 (m, 2 H) 2.76 (br s, 6 H) 3.10 (br d, J = 4.75 Hz, 2 H) 3.53 (br s, 4 H) 3.74-3.92 (m, 3 H) 4.43 (br dd, J = 19.26, 12.26 Hz, 1 H) 5.41-5.64 (m, 1 H) 5.67-5.81 (m, 1 H) 6.22 (dt, J = 16.57, 2.85 Hz, 1 H) 6.76-6.92 (m, 1 H) 7.58-7.69 (m, 1 H) 8.18-8.24 (m, 1 H) 8.27-8.35 (m, 1 H) 8.55-8.73 (m, 1 H) 9.50 (br dd, J = 6.57, 3.06 Hz, 1 H) |
| 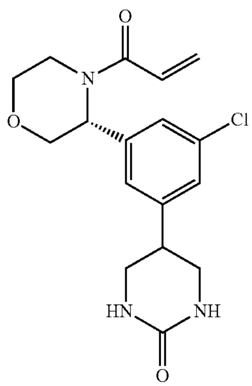 [SMILES: C=CC(=O)N1CCOC[C@H]1c1cc(Cl)cc(C2CNC(=O)NC2)c1] | 222 | (R)-5-(3-(4-acryloylmorpholin-3-yl)-5-chlorophenyl)tetrahydropyrimidin-2(1H)-one | Single enantiomer of known absolute configuration | 1H NMR (400 MHz, CHLOROFORM-d) δ ppm 7.41-7.56 (m, 1 H) 7.07-7.23 (m, 2 H) 6.32-6.62 (m, 2 H) 5.80 (dd, J = 10.38, 1.75 Hz, 2 H) 4.99 (br s, 2 H) 4.41 (d, J = 12.13 Hz, 1H) 3.98 (br dd, J = 11.38, 2.75 Hz, 1 H) 3.88 (br dd, J = 12.19, 3.44 Hz, 1 H) 3.57-3.71 (m, 2 H) 3.39-3.53 (m, 4 H) 3.14-3.39 (m, 2 H) |
| 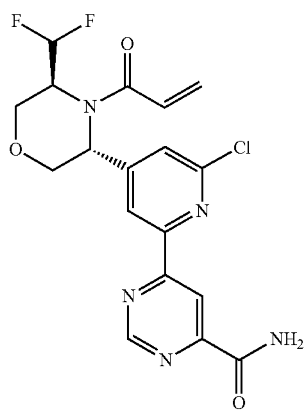 [SMILES: C=CC(=O)N1[C@H](c2cc(Cl)nc(-c3cc(C(N)=O)ncn3)c2)COC[C@H]1C(F)F] | 223 | 6-(4-((3R,5S)-4-acryloyl-5-(difluoromethyl)morpholin-3-yl)-6-chloropyridin-2-yl)pyrimidine-4-carboxamide | Single enantiomer of known absolute configuration | 1H NMR (400 MHz, CHLOROFORM-d) δ = 9.28 (d, J = 1.0 Hz, 1H), 9.16-9.09 (m, 1H), 8.33 (s, 1H), 7.82 (br s, 1H), 7.33 (s, 1H), 6.57-6.03 (m, 3H), 5.75 (br s, 2H), 4.82 (br s, 1H), 4.40-3.95 (m, 4H) |
| 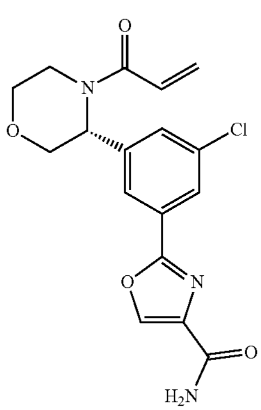 [SMILES: C=CC(=O)N1CCOC[C@H]1c1cc(Cl)cc(-c2nc(C(N)=O)co2)c1] | 224 | (R)-2-(3-(4-acryloylmorpholin-3-yl)-5-chlorophenyl)oxazole-4-carboxamide | Single enantiomer of known absolute configuration | 1H NMR (400 MHz, CHLOROFORM-d) δ ppm 3.20-3.45 (m, 1 H) 3.64 (td, J = 11.79, 2.69 Hz, 2 H) 3.89-4.05 (m, 2 H) 4.50 (d, J = 12.26 Hz, 1 H) 5.58-5.66 (m, 1 H) 5.66-5.93 (m, 2 H) 6.37-6.49 (m, 1 H) 6.53-6.65 (m, 1 H) 6.92 (br s, 1 H) 7.65 (br d, J = 4.63 Hz, 1 H) 7.94-8.17 (m, 2 H) 8.29 (s, 1 H) |

TABLE 1-continued

| Compounds of the Disclosure. | | | | |
|---|---|---|---|---|
| Structure | No. | Name | Stereochemistry | NMR |
| 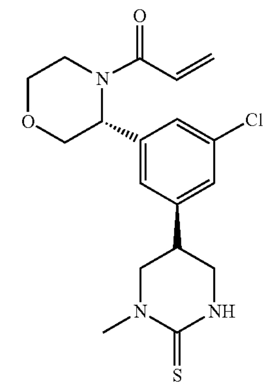 | 226 | 1-((3R)-3-(3-chloro-5-(1-methyl-2-thioxohexahydropyrimidin-5-yl)phenyl)morpholino)prop-2-en-1-one Diastereomer 1 | Single stereoisomer with unknown absolute configuration at tetrahydropyrimidine-thione | 1H NMR (400 MHz, CHLOROFORM-d) δ ppm 7.37-7.59 (m, 1 H) 7.05-7.25 (m, 2 H) 6.51-6.65 (m, 1 H) 6.32-6.50 (m, 2 H) 5.54-5.86 (m, 2 H) 4.32-4.47 (m, 1 H) 3.83-4.04 (m, 3 H) 3.57-3.66 (m, 1 H) 3.46-3.56 (m, 3 H) 3.43-3.45 (m, 3 H) 3.24-3.51 (m, 3 H) |
| 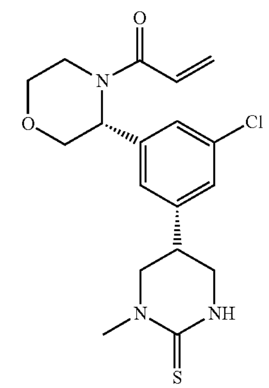 | 227 | 1-((3R)-3-(3-chloro-5-(1-methyl-2-thioxohexahydropyrimidin-5-yl)phenyl)morpholino)prop-2-en-1-one Diastereomer 2 | Single stereoisomer with unknown absolute configuration at tetrahydropyrimidine-thione | 1H NMR (400 MHz, CHLOROFORM-d) δ ppm 7.44-7.62 (m, 1 H) 7.17-7.25 (m, 1 H) 7.11 (s, 1 H) 6.51-6.68 (m, 1 H) 6.41 (br d, J = 15.88 Hz, 2 H) 5.81 (dd, J = 10.44, 1.81 Hz, 2 H) 4.41 (d, J = 12.26 Hz, 1 H) 3.68-4.05 (m, 3 H) 3.46-3.67 (m, 4 H) 3.44 (s, 3 H) 3.19-3.41 (m, 3 H) |
| 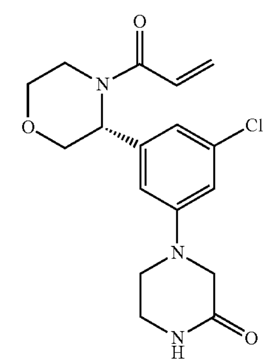 [SMILES: C=CC(=O)N1CCOC[C@H]1c1cc(Cl)cc(N2CCNC(=O)C2)c1] | 228 | (R)-4-(3-(4-acryloylmorpholin-3-yl)-5-chlorophenyl)piperazin-2-one | Single enantiomer of known absolute configuration | 1H NMR (400 MHz, CHLOROFORM-d) δ ppm 6.81-7.23 (m, 2 H) 6.77 (d, J = 1.71 Hz, 1 H) 6.52-6.62 (m, 1 H) 6.33-6.52 (m, 2 H) 5.79 (d, J = 1.83 Hz, 1 H), 5.76 (d, J = 1.83 Hz, 1 H) 4.40 (d, J = 12.10 Hz, 1 H) 3.92-4.01 (m, 1 H) 3.88 (s, 2 H) 3.78-3.88 (m, 1 H) 3.58-3.72 (m, 1 H) 3.47-3.58 (m, 3 H) 3.36-3.47 (m, 2 H) 3.15-3.36 (m, 1 H) |
| 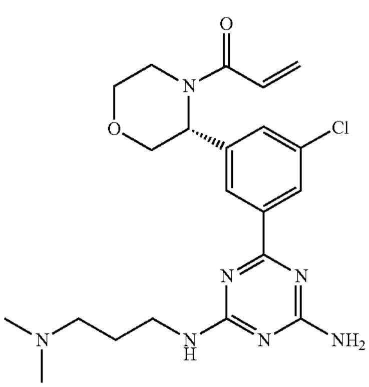 [SMILES: C=CC(=O)N1CCOC[C@H]1c1cc(Cl)cc(-c2nc(N)nc(NCCCN(C)C)n2)c1] | 229 | (R)-1-(3-(3-(4-amino-6-((3-(dimethylamino)propyl)amino)-1,3,5-triazin-2-yl)-5-chlorophenyl)morpholino)prop-2-en-1-one | Single enantiomer of known absolute configuration | 1H NMR (400 MHz, METHANOl-d4) δ ppm 2.40-2.56 (m, 2 H) 3.31 (s, 6H) 3.57-3.69 (m, 2 H) 3.71-3.88 (m, 1 H) 3.90-4.10 (m, 3 H) 4.12-4.51 (m, 3 H) 4.93 (br d, J = 12.42 Hz, 1 H) 5.60-6.36 (m, 2 H) 6.71 (br d, J = 16.81 Hz, 1 H) 7.20 (br dd, J = 16.75, 10.60 Hz, 1 H) 8.11 (br d, J = 0.75 Hz, 1 H) 8.50-8.82 (m, 2 H) |

TABLE 1-continued

| Compounds of the Disclosure. | | | | |
|---|---|---|---|---|
| Structure | No. | Name | Stereochemistry | NMR |
| 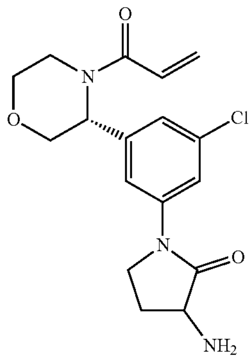 [SMILES: C=CC(=O)N1CCOC[C@H]1c1cc(Cl)cc(N2CCC(N)C2=O)c1] | 230 | 1-(3-((R)-4-acryloylmorpholin-3-yl)-5-chlorophenyl)-3-aminopyrrolidin-2-one | Single enantiomer of known absolute configuration on the morpholine and unknown configuration on the pyrrolidinone | 1H NMR (400 MHz, DEUTERIUM OXIDE) δ ppm 7.55 (s, 1 H) 7.48 (br s, 1 H) 7.31 (br s, 1 H) 6.56-6.85 (m, 1 H) 6.23 (br d, J = 17.01 Hz, 1 H) 5.73-6.01 (m, 1 H) 5.18-5.69 (m, 2 H) 4.49 (br d, J = 12.51 Hz, 1 H) 4.15-4.41 (m, 2 H) 3.81-4.14 (m, 5 H) 3.66 (br d, J = 9.88 Hz, 1 H) 3.01-3.50 (m, 1 H) 2.71 (dt, J = 12.85, 6.52 Hz, 1 H) 2.13-2.36 (m, 1 H) |
| 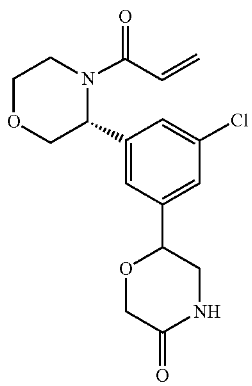 [SMILES: C=CC(=O)N1CCOC[C@H]1c1cc(Cl)cc(C2CNC(=O)CO2)c1] | 231 | 6-(3-((R)-4-acryloylmorpholin-3-yl)-5-chlorophenyl)morpholin-3-one Diastereomer 1 | Single stereoisomer with unknown absolute configuration at the morpholinone | 1H NMR (400 MHz, CHLOROFORM-d) δ = 7.63-7.30 (m, 3H), 6.60-6.36 (m, 2H), 6.04-5.95 (m, 1H), 583-5.74 (m, 1H), 4.80-4.69 (m, 1H), 4.49-4.28 (m, 3H), 3.99-3.83 (m, 2H), 3.74-3.10 (m, 5H) |
| 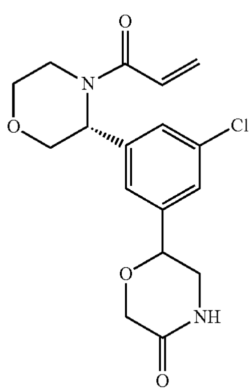 [SMILES: C=CC(=O)N1CCOC[C@H]1c1cc(Cl)cc(C2CNC(=O)CO2)c1] | 232 | 6-(3-((R)-4-acryloylmorpholin-3-yl)-5-chlorophenyl)morpholin-3-one Diastereomer 2 | Single stereoisomer with unknown absolute configuration at the morpholinone | 1H NMR (400 MHz, CHLOROFORM-d) δ = 7.56-7.32 (m, 3H), 6.61-6.51 (m, 1H), 6.45-6.35 (m, 1H), 6.04-5.97 (m, 1H), 5.80 (dd, J = 2.0, 10.4 Hz, 1H), 4.79-4.70 (m, 1H), 4.50-4.30 (m, 3H), 4.02-3.84 (m, 2H), 3.74-3.14 (m, 5H) |
| 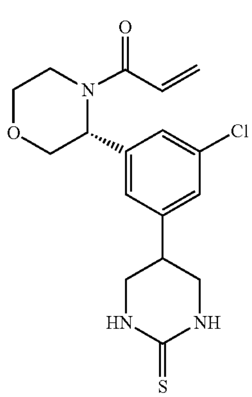 [SMILES: C=CC(=O)N1CCOC[C@H]1c1cc(Cl)cc(C2CNC(=S)NC2)c1] | 233 | (R)-1-(3-(3-chloro-5-(2-thioxohexahydropyrimidin-5-yl)phenyl)morpholino)prop-2-en-1-one | Single enantiomer of nown absolute configuration | 1H NMR (400 MHz, CHLOROFORM-d) δ ppm 7.39-7.61 (m, 1 H) 7.05-7.25 (m, 2 H) 6.35-6.65 (m, 3 H) 5.31-5.97 (m, 2 H) 4.41 (br d, J = 12.38 Hz, 1 H) 3.82-4.05 (m, 2 H) 3.49-3.81 (m, 4 H) 3.13-3.48 (m, 4 H) |

TABLE 1-continued

| Compounds of the Disclosure. | | | | |
|---|---|---|---|---|
| Structure | No. | Name | Stereochemistry | NMR |
| 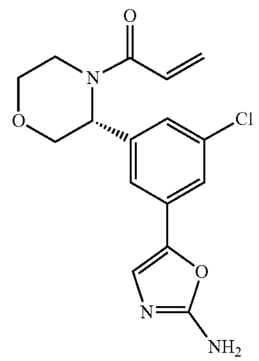 [SMILES: C=CC(=O)N1CCOC[C@H]1c1cc(Cl)cc(-c2cnc(N)o2)c1] | 234 | (R)-1-(3-(3-(2-aminooxazol-5-yl)-5-chlorophenyl)morpholino)prop-2-en-1-one | Single enantiomer of known absolute configuration | 1H NMR (400 MHz, CHLOROFORM-d) δ ppm 8.33-8.55 (m, 1 H) 7.49-7.73 (m, 2 H) 7.39-7.43 (m, 1 H) 7.10-7.17 (m, 1 H) 6.52-6.61 (m, 1 H) 6.38-6.46 (m, 1 H) 5.69-5.88 (m, 2 H) 4.39-4.50 (m, 1 H) 3.97-4.06 (m, 1 H) 3.87-3.96 (m, 1 H) 3.26-3.80 (m, 3 H) |
| 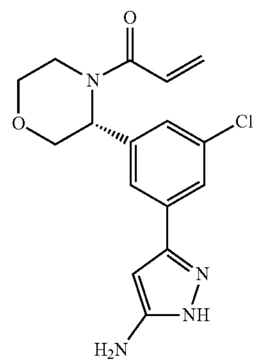 [SMILES: C=CC(=O)N1CCOC[C@H]1c1cc(Cl)cc(-c2cc(N)[nH]n2)c1] | 235 | (R)-1-(3-(3-(5-amino-1H-pyrazol-3-yl)-5-chlorophenyl)morpholino)prop-2-en-1-one | Single enantiomer of known absolute configuration | 1H NMR (400 MHz, DMSO-d6) δ = 7.63-7.55 (m, 2H), 7.27-7.22 (m, 1H), 6.94-6.77 (m, 1H), 6.23 (dd, J = 2.3, 16.6 Hz, 1H), 5.84-5.43 (m, 3H), 5.19-5.00 (m, 1H), 4.44 (br d, J = 12.4 Hz, 1H), 3.95-3.72 (m, 3H), 3.49 (dt, J = 2.3, 11.6 Hz, 1H) |
| 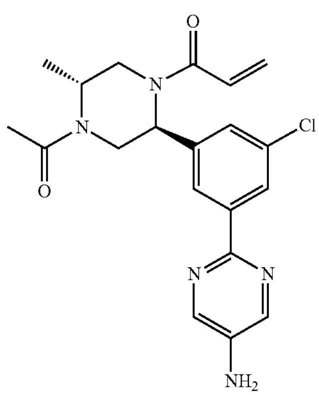 [SMILES: C=CC(=O)N1C[C@@H](C)N(C(C)=O)C[C@@H]1c1cc(Cl)cc(-c2ncc(N)cn2)c1] | 236 | 1-((2S,5R)-4-acetyl-2-(3-(5-aminopyrimidin-2-yl)-5-chlorophenyl)-5-methylpiperazin-1-yl)prop-2-en-1-one | Single enantiomer of unknown absolute configuration | 1H NMR (400 MHz, CHLOROFORM-d) δ ppm 8.21-8.31 (m, 3 H) 8.13-8.21 (m, 1 H) 7.29-7.20 (m, 1 H) 6.56-6.71 (m, 1 H) 6.35-6.54 (m, 1 H) 5.90-6.14 (m, 1 H) 5.64-5.87 (m, 1 H) 5.01-5.26 (m, 1 H) 4.38-4.83 (m, 1 H) 3.84-4.31 (m, 2 H) 3.46-3.81 (m, 2 H) 3.12-3.44 (m, 1 H) 1.90-2.25 (m, 3 H) 1.18-1.36 (m, 3 H) |
| 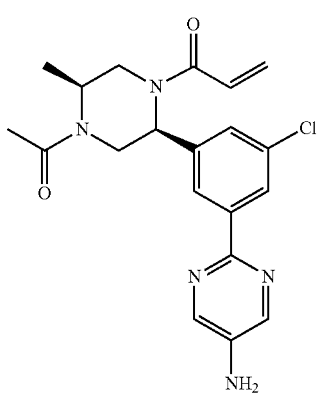 [SMILES: C=CC(=O)N1C[C@H](C)N(C(C)=O)C[C@@H]1c1cc(Cl)cc(-c2ncc(N)cn2)c1] | 237 | 1-((2S,5S)-4-acetyl-2-(3-(5-aminopyrimidin-2-yl)-5-chlorophenyl)-5-methylpiperazin-1-yl)prop-2-en-1-one | Single enantiomer of unknown absolute configuration | 1H NMR (400 MHz, CHLOROFORM-d) δ ppm 8.31 (br s, 3 H) 8.06-8.21 (m, 1 H) 7.30 (s, 1 H) 6.36-6.48 (m, 1 H) 6.11-6.35 (m, 1 H) 5.56-5.83 (m, 1 H) 4.85-5.25 (m, 2 H) 4.11-4.61 (m, 1 H) 3.80-4.08 (m, 2 H) 2.80-3.60 (m, 2 H) 2.09-2.33 (m, 3 H) 1.17-1.36 (m, 3 H) |

TABLE 1-continued

Compounds of the Disclosure.

| Structure | No. | Name | Stereochemistry | NMR |
|---|---|---|---|---|
| 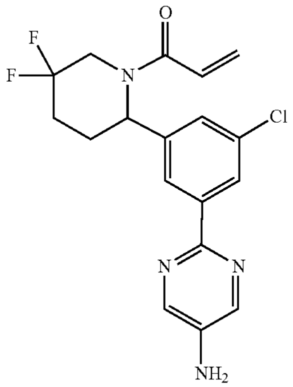 [SMILES: C=CC(=O)N1CC(F)(F)CCC1c1cc(Cl)cc(-c2ncc(N)cn2)c1] | 238 | 1-(2-(3-(5-aminopyrimidin-2-yl)-5-chlorophenyl)-5,5-difluoropiperidin-1-yl)prop-2-en-1-one | Single enantiomer of unknown absolute configuration | 1H NMR (400 MHz, CHLOROFORM-d) δ ppm 8.24-8.34 (m, 3 H) 8.13 (s, 1 H) 7.18-7.24 (m, 1 H) 6.50-6.76 (m, 1 H) 6.38-6.48 (m, 1 H) 5.82 (br d, J = 8.25 Hz, 2 H) 4.51-5.57 (m, 1 H) 3.60-4.31 (m, 2 H) 3.06-3.37 (m, 1 H) 2.52-2.61 (m, 1 H) 2.16-2.33 (m, 2 H) 1.92-2.09 (m, 1 H) |
| 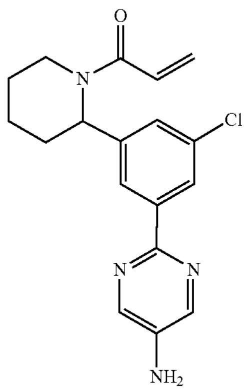 [SMILES: C=CC(=O)N1CCCCC1c1cc(Cl)cc(-c2ncc(N)cn2)c1] | 239 | 1-(2-(3-(5-aminopyrimidin-2-yl)-5-chlorophenyl)piperidin-1-yl)prop-2-en-1-one | Single enantiomer of unknown absolute configuration | 1H NMR (400 MHz, CHLOROFORM-d) δ ppm 8.27 (s, 2 H) 8.21 (br s, 1 H) 8.12 (d, J = 0.88 Hz, 1 H) 7.22 (s, 1 H) 6.51-6.86 (m, 1 H) 6.36 (br d, J = 16.63 Hz, 1 H) 5.59-6.22 (m, 2 H) 4.50-5.50 (m, 1 H) 3.45-4.29 (m, 3 H) 2.70-3.19 (m, 1 H) 2.49 (br d, J = 14.13 Hz, 1 H) 1.96 (br s, 1 H) 1.68 (br d, J = 9.13 Hz, 3 H) |
| 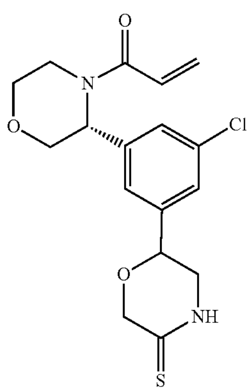 [SMILES: C=CC(=O)N1CCOC[C@H]1c1cc(Cl)cc(C2CNC(=S)CO2)c1] | 240 | 1-((R)-3-(3-chloro-5-((S)-5-thioxomorpholin-2-yl)phenyl)morpholino)prop-2-en-1-one Diastereomer 1 | Single stereoisomer with unknown absolute configuration at the thiomorpholinone | 1H NMR (400 MHz, CHLOROFORM-d) δ = 8.12-8.04 (m, 1H), 7.53-7.32 (m, 3H), 6.58-6.49 (m, 1H), 6.46-6.32 (m, 1H), 5.69-5.67 (m, 1H), 5.80 (dd, J = 1.9, 10.3 Hz, 1H), 4.96-4.84 (m, 1H), 4.78-4.72 (m, 1H), 4.69-4.57 (m, 1H), 4.48-4.36 (m, 1H), 3.97 (dd, J = 3.2, 11.3 Hz, 1H), 3.90 (br s, 1H), 3.67-3.36 (m, 4H) |
| 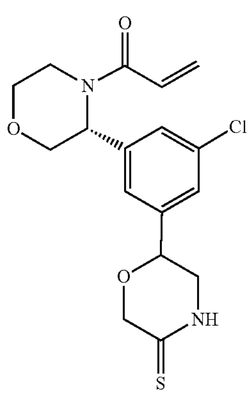 [SMILES: C=CC(=O)N1CCOC[C@H]1c1cc(Cl)cc(C2CNC(=S)CO2)c1] | 241 | 1-((R)-3-(3-chloro-5-((R)-5-thioxomorpholin-2-yl)phenyl)morpholino)prop-2-en-1-one Diastereomer 2 | Single stereoisomer with unknown absolute configuration at the thiomorpholinone | 1H NMR (400 MHz, CHLOROFORM-d) δ = 8.15-7.97 (m, 1H), 7.52-7.32 (m, 3H), 6.60-6.49 (m, 1H), 6.36 (s, 1H), 5.82-5.33 (m, 2H), 4.96-4.83 (m, 1H), 4.78-4.72 (m, 1H), 4.69-4.60 (m, 1H), 4.51-4.33 (m, 1H), 4.02-3.94 (m, 1H), 3.93-3.82 (m, 1H), 3.66-3.19 (m, 4H) |

TABLE 1-continued

| Compounds of the Disclosure. | | | | |
|---|---|---|---|---|
| Structure | No. | Name | Stereochemistry | NMR |
| 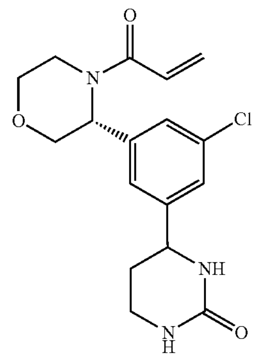 | 242 | 4-(3-((R)-4-acryloylmorpholin-3-yl)-5-chlorophenyl)tetrahydropyrimidin-2(1H)-one | Single enantiomer of known absolute configuration | 1H NMR (400 MHz, METHANOL-d4) δ ppm 7.21-7.48 (m, 3 H) 6.79 (dd, J = 16.70, 10.57 H, 1H) 6.24-6.39 (m, 1 H) 5.76-5.92 (m, 1H) 4.62 (dd, J = 6.38, 4.75 Hz, 1 H) 4.45 (br d, J = 12.26 Hz, 1H) 3.83-3.99 (m, 2 H) 3.54-3.70 (m, 1 H) 3.06-3.28 (m, 3 H) 2.09-2.21 (m, 1 H) 1.86 (dtd, J = 13.45, 6.85, 6.85, 4.13 Hz, 1 H) |
| 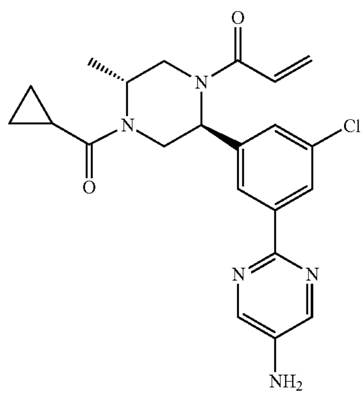 [SMILES: C=CC(=O)N1C[C@@H](C)N(C(=O)C2CC2)C[C@@H]1c1cc(Cl)cc(-c2ncc(N)cn2)c1] | 243 | 1-((2S,5R)-2-(3-(5-aminopyrimidin-2-yl)-5-chlorophenyl)-4-(cyclopropanecarbonyl)-5-methylpiperazin-1-yl)prop-2-en-1-one | Single enantiomer of unknown absolute configuration, known relative trans-configuration | 1H NMR (400 MHz, CHLOROFORM-d) δ ppm 8.28 (br s, 1 H) 8.21-8.26 (m, 1 H) 8.12-8.20 (m, 1 H) 7.28-7.37 (m, 1 H) 6.55-6.72 (m, 1 H) 6.36-6.52 (m, 1 H) 5.83-6.11 (m, 1 H) 5.64-5.83 (m, 1 H) 4.75-5.32 (m, 1 H) 4.33-4.73 (m, 1 H) 3.77-4.21 (m, 1 H) 3.56-3.74 (m, 1 H) 3.29-3.55 (m, 1 H) 1.55-1.90 (m, 1 H) 1.19-1.43 (m, 3 H) 0.87-1.18 (m, 2 H) 0.49-0.86 (m, 2 H) |
| 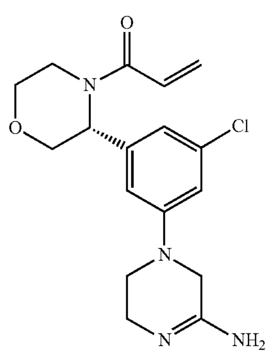 [SMILES: C=CC(=O)N1CCOC[C@H]1c1cc(Cl)cc(N2CCN=C(N)C2)c1] | 244 | (R)-1-(3-(3-(5-amino-3,6-dihydropyrazin-1(2H)-yl)-5-chlorophenyl)morpholino)prop-2-en-1-one | Single enantiomer of known absolute configuration | 1H NMR (400 MHz, CHLOROFORM-d) δ ppm 11.82 (br s, 1 H) 10.43 (br s, 1 H) 7.78 (br dd, J = 7.32, 2.94 Hz, 1 H) 6.87-7.21 (m, 1 H) 6.81 (s, 1 H) 6.50-6.66 (m, 1 H) 6.27-6.46 (m, 1 H) 5.80 (dd, J = 10.51, 1.50 Hz, 1 H) 5.45-5.73 (m, 1 H) 4.40 (br d, J = 12.26 Hz, 1 H) 4.12 (s, 2 H) 3.75-4.06 (m, 3 H) 3.51-3.73 (m, 4 H) 3.25-3.51 (m, 2 H) |
| 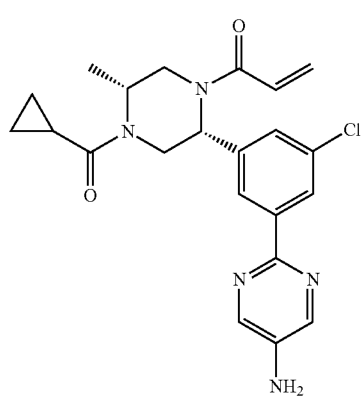 [SMILES: C=CC(=O)N1C[C@@H](C)N(C(=O)C2CC2)C[C@H]1c1cc(Cl)cc(-c2ncc(N)cn2)c1] | 245 | 1-((2R,5R)-4-acetyl-2-(3-(5-aminopyrimidin-2-yl)-5-chlorophenyl)-5-methylpiperazin-1-yl)prop-2-en-1-one | Single enantiomer of unknown absolute configuration known relative cis-configuration | 1H NMR (400 MHz, CHLOROFORM-d) δ ppm 8.27 (s, 3 H) 8.13 (s, 1 H) 7.24 (s, 1 H) 6.35 (s, 1 H) 6.22 (br d, J = 6.63 Hz, 1 H) 5.63 (br s, 1 H) 5.04-5.11 (m, 1 H) 4.89-5.00 (m, 1 H) 4.42 (br s, 1 H) 3.81-3.95 (m, 1 H) 3.06 (br d, J = 1.25 Hz, 1 H) 2.93 (br d, J = 10.76 Hz, 1 H) 1.71 (br s, 3 H) 1.33 (br s, 3 H) 1.05 (br s, 2 H) 0.82-0.88 (m, 2 H) |

TABLE 1-continued

| Compounds of the Disclosure. | | | | |
|---|---|---|---|---|
| Structure | No. | Name | Stereochemistry | NMR |
| 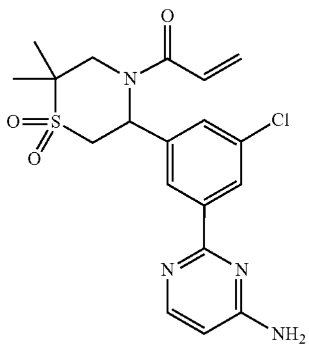 [SMILES: C=CC(=O)N1CC(C)(C)S(=O)(=O)CC1c1cc(Cl)cc(-c2nccc(N)n2)c1] | 246 | 1-(5-(3-(4-aminopyrimidin-2-yl)-5-chlorophenyl)-2,2-dimethyl-1,1-dioxidothiomorpholino)prop-2-en-1-one | Single enantiomer of unknown absolute configuration | 1H NMR (400 MHz, METHANOL-d4) δ = 8.22 (s, 1H), 8.18-8.11 (m, 2H), 7.47 (s, 1H), 7.01-6.84 (m, 1H), 6.51-6.19 (m, 3H), 5.89 (br d, J = 10.5 hz, 1H), 4.61-4.27 (m, 1H), 4.07 (br d, J = 15.4 Hz, 1H), 3.82 (br dd, J = 5.3, 15.5 Hz, 1H), 3.60-3.49 (m, 1H), 1.48 (s, 3H), 1.26 (s, 3H) |
| 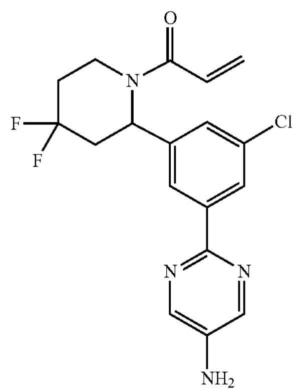 [SMILES: C=CC(=O)N1CCC(F)(F)CC1c1cc(Cl)cc(-c2ncc(N)cn2)c1] | 247 | 1-(2-(3-(5-aminopyrimidin-2-yl)-5-chlorophenyl)-4,4-difluoropiperidin-1-yl)prop-2-en-1-one | Single enantiomer of unknown absolute configuration | 1H NMR (400 MHz, CHLOROFORM-d) δ ppm 8.26 (s, 2 H) 8.24 (s, 1 H) 8.15 (s, 1 H) 7.21 (d, J = 0.63 Hz, 1 H) 6.50-6.69 (m, 1 H) 6.36-6.47 (m, 1 H) 5.78 (br d, J = 11.26 Hz, 2 H) 4.26-4.72 (m, 1 H) 3.86 (br d, J = 2.13 Hz, 2 H) 3.26 (br t, J = 11.82 Hz, 1 H) 2.89-3.04 (m, 1 H) 2.27-2.47 (m, 1 H) 1.91-2.19 (m, 2 H) |
| 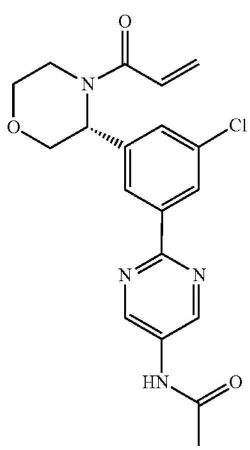 [SMILES: C=CC(=O)N1CCOC[C@H]1c1cc(Cl)cc(-c2ncc(NC(C)=O)cn2)c1] | 248 | (R)-N-(2-(3-(4-acryloylmorpholin-3-yl)-5-chlorophenyl)pyrimidin-5-yl)acetamide | Single enantiomer of known absolute configuration | 1H NMR (400 MHz, METHANOL-d4) δ ppm 9.06 (s, 2 H) 8.39 (br s, 1 H) 8.27 (s, 1 H) 7.54 (br s, 1 H) 6.82 (dd, J = 16.76, 10.63 Hz, 1 H) 6.33 (dd, J = 16.76, 1.25 Hz, 1 H) 5.83 (dd, J = 10.57, 1.94 Hz, 2 H) 4.53 (d, J = 12.38 Hz, 1 H) 3.75-4.09 (m, 3 H) 3.63 (td, J = 11.79, 2.81 Hz, 2 H) 2.20 (s, 3 H) |
| 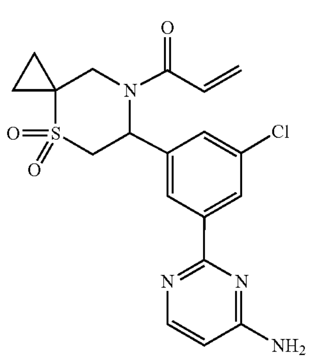 [SMILES: C=CC(=O)N1CC2(CC2)S(=O)(=O)CC1c1cc(Cl)cc(-c2nccc(N)n2)c1] | 249 | (R)-1-(6-(3-(5-aminopyrimidin-2-yl)-5-chlorophenyl)-4,4-dioxido-4-thia-7-azaspiro[2.5]octan-7-yl)prop-2-en-1-one | Single enantiomer of unknown absolute configuraiton | 1H NMR (400 MHz, METHANOL-d4) δ ppm 1.05-1.14 (m, 1 H) 1.18-1.26 (m, 1 H) 1.31-1.39 (m, 1 H) 1.39-1.49 (m, 1 H) 3.71 (br dd, J = 14.95, 5.44 Hz, 1 H) 4.01-4.30 (m, 3 H) 5.87 (br d, J = 10.76 Hz, 1 H) 6.38 (br d, J = 16.88 Hz, 2 H) 6.46 (d, J = 6.00 Hz, 1 H) 6.88 (br dd, J = 16.07, 11.19 Hz, 1 H) 7.52 (s, 1 H) 8.11-8.26 (m, 3 H) |

TABLE 1-continued

| Compounds of the Disclosure. | | | | |
|---|---|---|---|---|
| Structure | No. | Name | Stereochemistry | NMR |
| 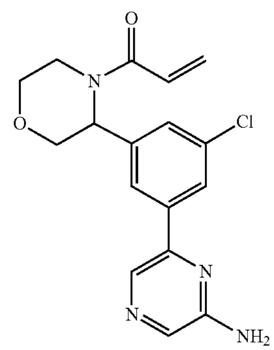 [SMILES: C=CC(=O)N1CCOCC1c1cc(Cl)cc(-c2cncc(N)n2)c1] | 250 | (R)-1-(3-(3-(6-aminopyrazin-2-yl)-5-chlorophenyl)morpholino)prop-2-en-1-one | Single enantiomer of known absolute configuration | 1H NMR (400 MHz, CHLOROFORM-d) δ ppm 8.31 (s, 1 H) 7.90-7.99 (m, 2 H) 7.86 (s, 1 H) 7.46-7.67 (m, 1 H) 6.53-6.63 (m, 1 H) 6.37-6.46 (m, 1 H) 5.52-6.03 (m, 2 H) 4.66-5.13 (m, 2 H) 4.51 (d, J = 12.13 Hz, 1 H) 3.99 (dd, J = 11.26, 3.13 Hz, 1 H) 3.91 (dd, J = 12.26, 3.50 Hz, 1 H) 3.03-3.83 (m, 3 H) |
| 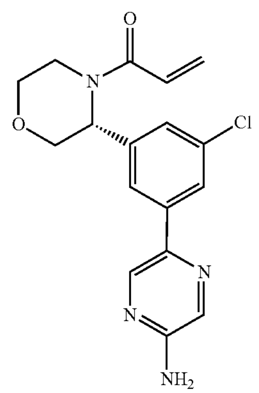 | 251 | (R)-1-(3-(3-(5-aminopyrazin-2-yl)-5-chlorophenyl)morpholino)prop-2-en-1-one | Single enantiomer of known absolute configuration | 1H NMR (400 MHz, CHLOROFORM-d) δ ppm 8.42 (d, J = 1.25 Hz, 1 H) 8.05 (d, J = 1.25 Hz, 1 H) 7.75-7.97 (m, 2 H) 7.48 (br d, J = 2.25 Hz, 1 H) 6.52-6.66 (m, 1 H) 6.32-6.50 (m, 1 H) 5.79 (dd, J = 10.38, 1.88 Hz, 2 H) 4.72 (br s, 2 H) 4.51 (d, J = 12.13 Hz, 1 H) 3.99 (br dd, J = 11.9, 3.19 Hz, 1 H) 3.91 (dd, J = 12.26, 3.63 Hz, 1 H) 3.63 (td, J = 11.79, 2.69 Hz, 2 H) 3.12-3.54 (m, 1 H) |
| 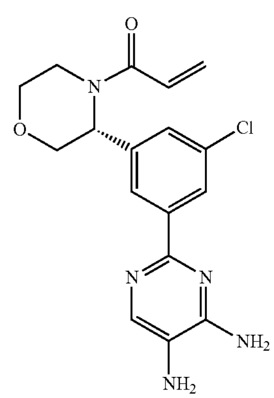 [SMILES: C=CC(=O)N1CCOC[C@H]1c1cc(Cl)cc(-c2ncc(N)c(N)n2)c1] | 253 | (R)-1-(3-(3-chloro-5-(4,5-diaminopyrimidin-2-yl)phenyl)morpholino)prop-2-en-1-one | Single enantiomer of known absolute configuration | 1H NMR (400 MHz, CHLOROFORM-d) δ ppm 8.21 (br d, J = 10.76 Hz, 2 H) 7.94 (s, 1 H) 7.39-7.63 (m, 1 H) 6.51-6.65 (m, 1 H) 6.36-6.46 (m, 1 H) 5.78 (dd, J = 10.44, 1.69 Hz, 1 H) 5.01-5.46 (m, 2 H) 4.53 (d, J = 12.13 Hz, 1 H) 4.00 (br dd, J = 11.26, 2.88 Hz, 1 H) 3.90 (dd, J = 12.19, 3.56 Hz, 1 H) 3.63 (td, J = 11.66, 2.56 Hz, 2 H) 3.17-3.51 (m, 2 H) 1.46-1.87 (m, 2 H) |
| 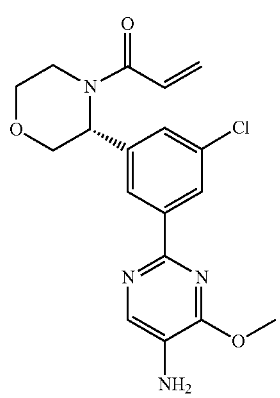 [SMILES: C=CC(=O)N1CCOC[C@H]1c1cc(Cl)cc(-c2ncc(N)c(OC)n2)c1] | 254 | (R)-1-(3-(3-(5-amino-4-methoxypyrimidin-2-yl)-5-chlorophenyl)morpholino)prop-2-en-1-one | Single enantiomer of known absolute configuration | 1H NMR (400 MHz, CHLOROFORM-d) δ ppm 8.24 (s, 2 H) 7.99 (s, 1 H) 7.45 (br s, 1 H) 6.60 (dd, J = 16.70, 10.44 Hz, 1 H) 6.31-6.49 (m, 1 H) 5.77 (dd, J = 10.44, 1.94 Hz, 2 H) 4.54 (d, J = 12.13 Hz, 1 H) 4.13 (s, 3 H) 3.96-4.01 (m, 1 H) 3.91 (dd, J = 12.13, 3.50 Hz, 1 H) 3.82 (br s, 2 H) 3.60-3.67 (m, 1 H) 3.20-3.50 (m, 1 H) 1.63 (br s, 1 H) |

TABLE 1-continued

| Compounds of the Disclosure. | | | | |
|---|---|---|---|---|
| Structure | No. | Name | Stereochemistry | NMR |
| 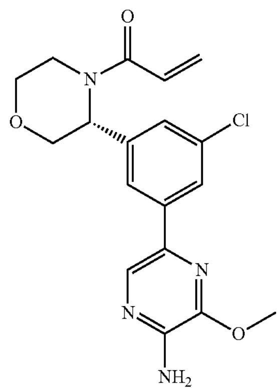 [SMILES: C=CC(=O)N1CCOC[C@H]1c1cc(Cl)cc(-c2cnc(N)c(OC)n2)c1] | 255 | (R)-1-(3-(3-(5-amino-6-methoxypyrazin-2-yl)-5-chlorophenyl)morpholino)prop-2-en-1-one | Single enantiomer of known absolute configuration | 1H NMR (400 MHz, CHLOROFORM-d) δ ppm 8.01 (s, 1 H) 7.83 (s, 2 H) 7.43 (br s, 1 H) 6.53-6.65 (m, 1 H) 6.37-6.46 (m, 1 H) 5.78 (dd, J = 10.37, 1.91 Hz, 1 H) 4.92 (br s, 2 H) 4.50 (d, J = 12.16 Hz, 1 H) 4.08 (s, 3 H) 3.98 (dd, J = 11.27, 3.04 Hz, 1 H) 3.91 (dd, J = 12.22, 3.52 Hz, 1 H) 3.63 (td, J = 11.80, 2.62 Hz, 1 H) 3.19-3.49 (m, 1 H) |
| 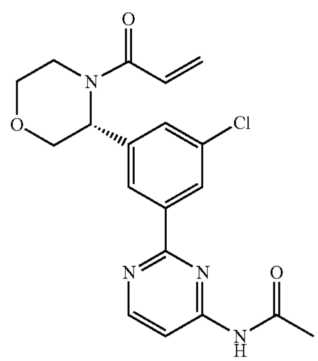 [SMILES: C=CC(=O)N1CCOC[C@H]1c1cc(Cl)cc(-c2nccc(NC(C)=O)n2)c1] | 256 | (R)-N-(2-(3-(4-acryloylmorpholin-3-yl)-5-chlorophenyl)pyrimidin-4-yl)acetamide | Single enantiomer of known absolute configuration | 1H NMR (400 MHz, CHLOROFORM-d) δ ppm 8.68 (d, J = 5.63 Hz, 1 H) 8.27-8.45 (m, 2 H) 8.20 (br s, 1 H) 8.06 (d, J = 5.63 Hz, 1 H) 7.45-7.78 (m, 1 H) 6.53-6.75 (m, 1 H) 6.35-6.49 (m, 1 H) 5.51-6.02 (m, 2 H) 4.53 (d, J = 12.26 Hz, 1 H) 3.88-4.11 (m, 2 H) 3.64 (td, J = 11.73, 2.69 Hz, 2 H) 3.39 (br s, 1 H) 2.30 (s, 3 H) |
| 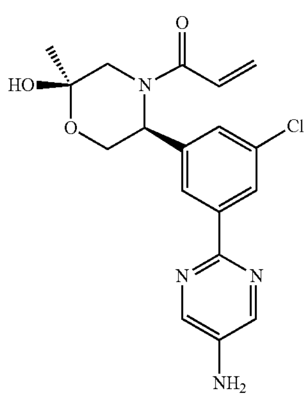 [SMILES: C=CC(=O)N1C[C@](C)(O)OC[C@@H]1c1cc(Cl)cc(-c2ncc(N)cn2)c1] | 257 | 1-((2R,5R)-2-(3-(5-aminopyrimidin-2-yl)-5-chlorophenyl)-5-hydroxy-5-methylpiperidin-1-yl)prop-2-en-1-one | Single enantiomer of unknown absolute configuration, known relative configuration | 1H NMR (400 MHz, CHLOROFORM-d) δ ppm 8.24 (s, 2 H) 8.20 (s, 1 H) 8.10 (s, 1 H) 7.21 (s, 1 H) 6.57-6.71 (m, 1 H) 6.40 (br d, J = 15.97 Hz, 1 H) 5.76 (br d, J = 10.49 Hz, 2 H) 3.31-4.50 (m, 3 H) 2.81-2.94 (m, 1 H) 2.40-2.53 (m, 1 H) 2.00-2.11 (m, 1 H) 1.73 (br d, J = 4.05 Hz, 2 H) 1.71 (br s, 1 H) 1.32 (s, 3 H) |
| 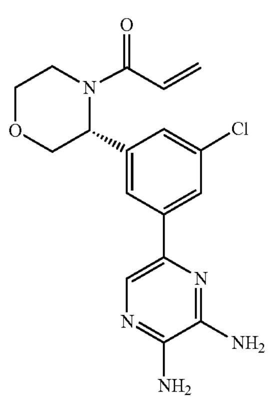 [SMILES: C=CC(=O)N1CCOC[C@H]1c1cc(Cl)cc(-c2cnc(N)c(N)n2)c1] | 258 | (R)-1-(3-(3-chloro-4-(5,6-diaminopyrazin-2-yl)phenyl)morpholino)prop-2-en-1-one | Single enantiomer of known absolute configuration | 1H NMR (400 MHz, CHLOROFORM-d) δ ppm 3.16-3.86 (m, 3 H) 3.91 (dd, J = 12.29, 3.61 Hz, 1 H) 3.95-4.06 (m, 1 H) 4.50 (br d, J = 11.98 Hz, 1 H) 4.58-4.95 (m, 2 H) 4.96-5.60 (m, 2 H) 5.80 (dd, J = 10.45, 1.77 Hz, 2 H) 6.36-6.46 (m, 1 H) 6.52-6.64 (m, 1 H) 7.35-7.66 (m, 1 H) 7.73 (br d, J = 10.88 Hz, 2 H) 7.86 (s, 1 H) |

TABLE 1-continued

| Compounds of the Disclosure. | | | | |
|---|---|---|---|---|
| Structure | No. | Name | Stereochemistry | NMR |
| 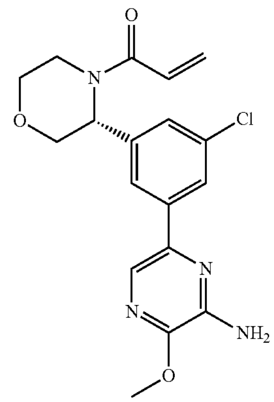 [SMILES: C=CC(=O)N1CCOC[C@H]1c1cc(Cl)cc(-c2cnc(OC)c(N)n2)c1] | 259 | (R)-1-(3-(3-(6-amino-5-methoxypyrazin-2-yl)-5-chlorophenyl)morpholino)prop-2-en-1-one | Single enantiomer of known absolute configuration | 1H NMR (400 MHz, CHLOROFORM-d) δ ppm 7.82 (s, 2 H) 7.78 (s, 1 H) 7.46 (br dd, J = 7.19, 3.06 Hz, 1 H) 6.52-6.65 (m, 1 H) 6.35-6.47 (m, 1 H) 5.78 (dd, J = 10.38, 1.88 Hz, 2 H) 4.90 (br s, 2 H) 4.50 (d, J = 12.13 Hz, 1 H) 4.03 (s, 3 H) 3.88-4.01 (m, 2 H) 3.62 (td, J = 11.79, 2.56 Hz, 2 H) 3.16-3.49 (m, 1 H) |
| 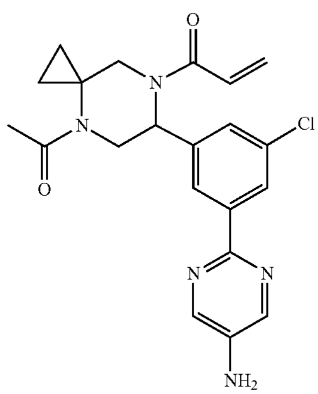 [SMILES: C=CC(=O)N1CC2(CC2)N(C(C)=O)CC1c1cc(Cl)cc(-c2ncc(N)cn2)c1] | 260 | 1-(6-(3-(5-aminopyrimidin-2-yl)-5-chlorophenyl)-4-(cyclopropanecarbonyl)-4,7-diazaspiro[2.5]octan-7-yl)prop-2-en-1-one | Single enantiomer of unknown absolute configuration | 1H NMR (400 MHz, CHLOROFORM-d) δ ppm 0.71 (br d, J = 4.03 Hz, 2 H) 1.21-1.27 (m, 2 H) 2.02 (s, 3H) 3.41-3.60 (m, 2 H) 3.92-4.34 (m, 2 H) 5.29 (br d, J = 13.33 Hz, 1 H) 5.75 (br d, J = 10.03 Hz, 1 H) 6.39 (br d, J = 16.75 Hz, 2 H) 6.46-6.58 (m, 1 H) 7.32 (br s, 1 H) 8.21 (br s, 1 H) 8.23 (br s, 1 H) 8.26 (s, 3 H) |
| 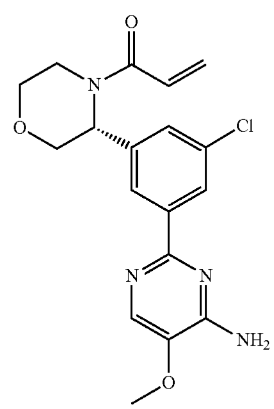 [SMILES: C=CC(=O)N1CCOC[C@H]1c1cc(Cl)cc(-c2ncc(OC)c(N)n2)c1] | 261 | (R)-1-(3-(3-(4-amino-5-methoxypyrimidin-2-yl)-5-chlorophenyl)morpholino)prop-2-en-1-one | Single enantiomer of known absolute configuration | 1H NMR (400 MHz, METHANOL-d4) δ ppm 3.32-3.47 (m, 1 H) 3.56-3.74 (m, 1 H) 3.80-4.13 (m, 6 H) 4.43-4.60 (m, 1 H) 5.54-6.00 (m, 2 H) 6.24-6.42 (m, 1 H) 6.73-6.90 (m, 1 H) 7.66-7.92 (m, 2 H) 8.03-8.23 (m, 2 H) |
| 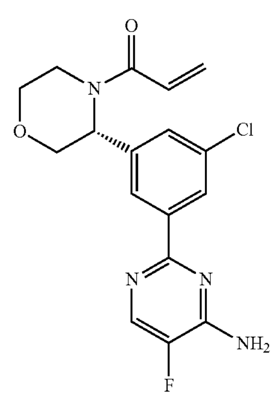 [SMILES: C=CC(=O)N1CCOC[C@H]1c1cc(Cl)cc(-c2ncc(F)c(N)n2)c1] | 263 | (R)-1-(3-(3-(4-amino-5-fluoropyrimidin-2-yl)-5-chlorophenyl)morpholino)prop-2-en-1-one | Single enantiomer of known absolute configuration | 1H NMR (400 MHz, CHLOROFORM-d) δ ppm 8.16-8.42 (m, 3 H) 7.33-7.62 (m, 1 H) 7.27-7.30 (m, 1 H) 6.34-6.67 (m, 2 H) 5.67-5.88 (m, 1 H) 5.10-5.35 (m, 2 H) 4.49-4.66 (m, 1 H) 3.83-4.05 (m, 2 H) 3.52-3.80 (m, 2 H) 2.97-3.47 (m, 1 H) |

TABLE 1-continued

| Structure | No. | Name | Stereochemistry | NMR |
|---|---|---|---|---|
| Compounds of the Disclosure. | | | | |
| 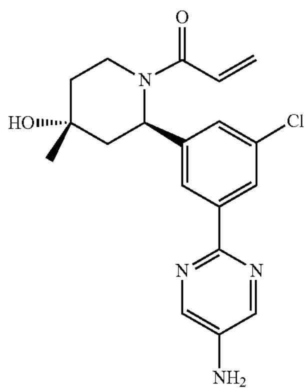 [SMILES: C=CC(=O)N1CC[C@@](C)(O)C[C@@H]1c1cc(Cl)cc(-c2ncc(N)cn2)c1] | 264 | 1-((2R,4R)-2-(3-(5-aminopyrimidin-2-yl)-5-chlorophenyl)-4-hydroxy-4-methylpiperidin-1-yl)prop-2-en-1-one | Single enantiomer of unknown absolute configuration, known relative configuration | 1H NMR (400 MHz, CHLOROFORM-d) δ ppm 8.27 (s, 2 H) 8.21 (s, 1 H) 8.11 (s, 1 H) 7.19 (s, 1 H) 6.39-6.58 (m, 1 H) 6.28-6.37 (m, 1 H) 5.66 (br d, J = 11.13 Hz, 1 H) 5.44-5.58 (m, 1 H) 4.40-4.65 (m, 1 H) 3.85 (s, 2 H) 3.22 (br s, 1 H) 2.30 (br d, J = 6.00 Hz, 1 H) 2.16-2.23 (m, 1 H) 1.79 (s, 2 H) 1.51 (s, 1 H) 1.11 (s, 3 H) |
| 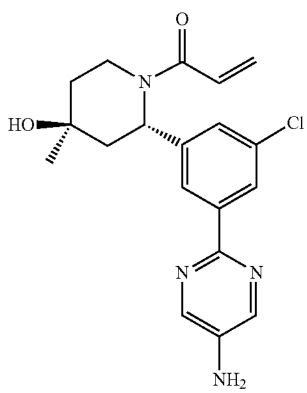 [SMILES: C=CC(=O)N1CC[C@](C)(O)C[C@H]1c1cc(Cl)cc(-c2ncc(N)cn2)c1] | 265 | 1-((2S,4S)-2-(3-(5-aminopyrimidin-2-yl)-5-chlorophenyl)-4-hydroxy-4-methylpiperidin-1-yl)prop-2-en-1-one | Single enantiomer of unknown absolute configuration | 1H NMR (400 MHz, CHLOROFORM-d) δ ppm 8.27 (s, 2 H) 8.21 (s, 1 H) 8.11 (d, J = 0.75 Hz, 1 H) 7.19 (s, 1 H) 6.40-6.55 (m, 1 H) 6.30-6.36 (m, 1 H) 5.66 (br d, J = 11.13 Hz, 1 H) 5.53 (br d, J = 6.13 Hz, 1 H) 4.54 (br d, J = 2.50 Hz, 1 H) 3.85 (s, 2 H) 3.21 (br s, 1 H) 2.30 (br d, J = 5.88 Hz, 1 H) 2.22 (d, J = 6.50 Hz, 1 H) 1.79 (s, 2 H) 1.52 (s, 1 H) 1.11 (s, 3 H) |
| 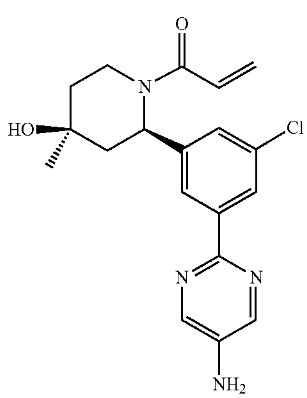 [SMILES: C=CC(=O)N1CC[C@](C)(O)C[C@@H]1c1cc(Cl)cc(-c2ncc(N)cn2)c1] | 266 | 1-((2R,4S)-2-(3-(5-aminopyrimidin-2-yl)-5-chlorophenyl)-4-hydroxy-4-methylpiperidin-1-yl)prop-2-en-1-one | Single enantiomer of unknown absolute configuration | 1H NMR (400 MHz, CHLOROFORM-d) δ ppm 8.25 (s, 2 H) 8.18 (s, 1 H) 8.13 (d, J = 1.00 Hz, 1 H) 7.23 (br s, 1 H) 6.45-6.84 (m, 1 H) 6.37 (br s, 1 H) 5.50-6.24 (m, 2 H) 4.31-5.45 (m, 1 H) 3.85 (s, 2 H) 3.09-3.66 (m, 1 H) 2.56 (br d, J = 14.63 Hz, 1 H) 2.07 (dd, J = 14.63, 6.75 Hz, 1 H) 1.64 (br s, 3 H) 1.29 (s, 3 H) |
| 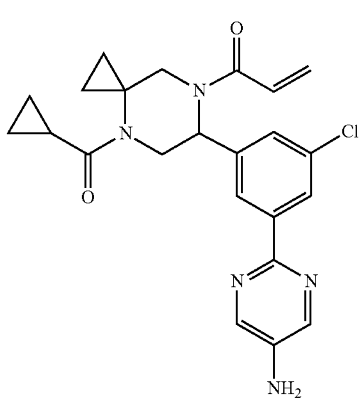 [SMILES: C=CC(=O)N1CC2(CC2)N(C(=O)C2CC2)CC1c1cc(Cl)cc(-c2ncc(N)cn2)c1] | 267 | 1-(4-acetyl-6-(3-(5-aminopyrimidin-2-yl)-5-chlorophenyl)-4,7-diazaspiro[2.5]octan-7-yl)prop-2-en-1-one | Single enantiomer of unknown absolute configuration | 1H NMR (400 MHz, CHLOROFORM-d) δ ppm 0.53 (br s, 2 H) 0.65 (br s, 2 H) 0.69-0.93 (m, 3 H) 1.35-1.90 (m, 2 H) 3.27-4.77 (m, 4 H) 5.13 (br dd, J = 8.86, 3.85 Hz, 1 H) 5.67 (br d, J = 9.78 Hz, 1 H) 6.32 (br d, J = 16.63 Hz, 1 H) 6.39-6.54 (m, 1 H) 7.24 (br s, 1 H) 8.09 (s, 1 H) 8.15 (br s, 1 H) 8.17 (s, 2 H) |

TABLE 1-continued

Compounds of the Disclosure.

| Structure | No. | Name | Stereochemistry | NMR |
|---|---|---|---|---|
| 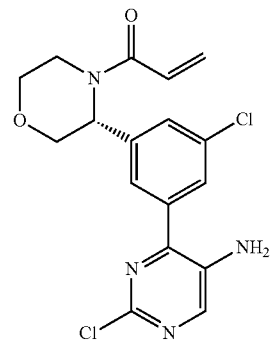 [SMILES: C=CC(=O)N1CCOC[C@H]1c1cc(Cl)cc(-c2nc(Cl)ncc2N)c1] | 268 | (R)-1-(3-(3-(5-amino-2-chloropyrimidin-4-yl)-5-chlorophenyl)morpholino)prop-2-en-1-one | Single enantiomer of known absolute configuration | 1H NMR (400 MHz, CHLOROFORM-d) δ ppm 8.17 (s, 1 H) 7.59-7.83 (m, 3 H) 6.51-6.61 (m, 1 H) 6.40 (br d, J = 15.77 Hz, 1 H) 5.56-5.88 (m, 2 H) 4.47 (d, J = 11.86 Hz, 1 H) 3.85-4.07 (m, 5 H) 3.57-3.79 (m, 2 H) |
| 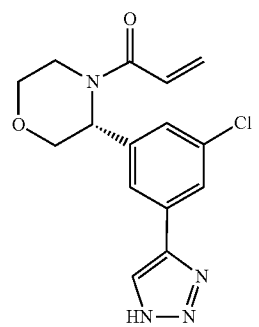 | 269 | (R)-1-(3-(3-chloro-5-(1H-1,2,3-triazol-4-yl)phenyl)morpholino)prop-2-en-1-one | Single enantiomer of known absolute configuration | 1H NMR (400 MHz, CHLOROFORM-d) δ ppm 7.99 (s, 1 H) 7.77 (s, 2 H) 7.34-7.68 (m, 1 H) 6.53-6.65 (m, 1 H) 6.39-6.51 (m, 1 H) 5.67-5.94 (m, 2 H) 4.51 (d, J = 12.23 Hz, 1 H) 3.89-4.06 (m, 2 H) 3.58-3.82 (m, 2 H) 3.30-3.53 (m, 1 H) |
| 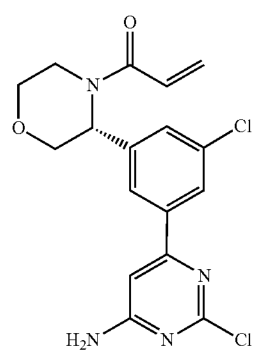 [SMILES: C=CC(=O)N1CCOC[C@H]1c1cc(Cl)cc(-c2cc(N)nc(Cl)n2)c1] | 271 | (R)-1-(3-(3-(6-amino-2-chloropyrimidin-4-yl)-5-chlorophenyl)morpholino)prop-2-en-1-one | Single enantiomer of known absolute configuration | 1H NMR (400 MHz, CHLOROFORM-d) δ ppm 7.96-8.12 (m, 1 H) 7.59-7.95 (m, 2 H) 6.69-6.83 (m, 1 H) 6.51-6.65 (m, 1 H) 6.29-6.48 (m, 1 H) 5.54-5.99 (m, 2 H) 5.29-5.50 (m, 2 H) 4.43-4.59 (m, 1 H) 3.86-4.12 (m, 2 H) 3.51-3.84 (m, 2 H) 3.08-3.48 (m, 1 H) |
| 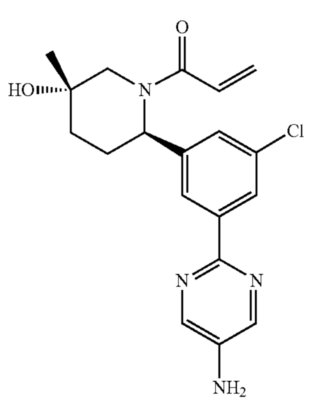 [SMILES: C=CC(=O)N1C[C@@](C)(O)CC[C@@H]1c1cc(Cl)cc(-c2ncc(N)cn2)c1] | 273 | 1-((2R,5S)-2-(3-(5-aminopyrimidin-2-yl)-5-chlorophenyl)-5-hydroxy-5-methylpiperidin-1-yl)prop-2-en-1-one | Single enantiomer of unknown absolute configuration, known relative configuration | 1H NMR (400 MHz, METHANOL-d4) δ ppm 8.32 (d, J = 2.75 Hz, 2 H) 8.11 (s, 1 H) 8.05 (s, 1 H) 7.31 (br s, 1 H) 6.70-7.01 (m, 1 H) 6.30 (br d, J = 16.26 Hz, 1 H) 5.69-6.01 (m, 2 H) 3.81 (br d, J = 13.13 Hz, 1 H) 2.88-3.0 (m, 1 H) 2.40-2.73 (m, 1 H) 2.21-2.38 (m, 2 H) 1.66 (br s, 2 H) 1.19-1.60 (m, 2 H) 1.15 (s, 3 H) |

TABLE 1-continued

| Compounds of the Disclosure. | | | | |
|---|---|---|---|---|
| Structure | No. | Name | Stereochemistry | NMR |
| 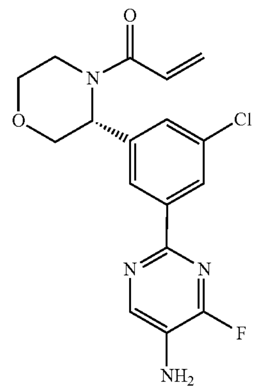 | 278 | (R)-1-(3-(3-(5-amino-4-fluoropyrimidin-2-yl)-5-chlorophenyl)morpholino)prop-2-en-1-one | Single enantiomer of known absolute configuration | 1H NMR (400 MHz, CHLOROFORM-d) δ ppm 8.21-8.33 (m, 3 H) 7.47 (br s, 1 H) 6.54-6.65 (m, 1 H) 6.36-6.48 (m, 1 H) 5.79 (br d, J = 10.38 Hz, 2 H) 4.54 (d, J = 12.13 Hz, 1 H) 3.96-4.02 (m, 1H) 3.88-3.94 (m, 2 H) 3.63 (td, J = 11.66, 2.31 Hz, 1 H) 3.18-3.51 (m, 1 H) |
| 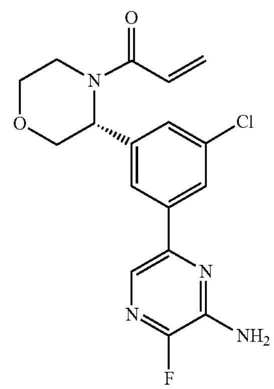 [SMILES: C=CC(=O)N1CCOC[C@H]1c1cc(Cl)cc(-c2cnc(F)c(N)n2)c1] | 279 | (R)-1-(3-(3-(6-amino-5-fluoropyrazin-2-yl)-5-chlorophenyl)morpholino)prop-2-en-1-one | Single enantiomer of known absolute configuration | 1H NMR (400 MHz, CHLOROFORM-d) δ ppm 7.81-7.95 (m, 3 H) 7.56 (br dd, J = 9.48, 2.68 Hz, 1 H) 6.55-6.65 (m, 1 H) 6.39-6.50 (m, 1 H) 5.81 (dd, J = 10.43, 1.85 Hz, 1 H) 4.97 (br s, 2 H) 4.52 (d, J = 12.28 Hz, 1 H) 3.88-4.06 (m, 2 H) 3.65 (td, J = 11.74, 2.62 Hz, 1 H) 3.15-3.49 (m, 1 H) |
| 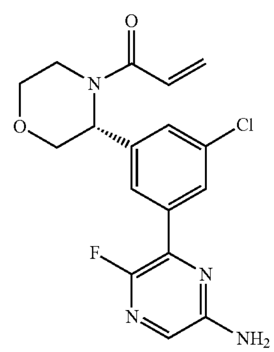 [SMILES: C=CC(=O)N1CCOC[C@H]1c1cc(Cl)cc(-c2nc(N)cnc2F)c1] | 280 | (R)-1-(3-(3-(6-amino-3-fluoropyrazin-2-yl)-5-chlorophenyl)morpholino)prop-2-en-1-one | Single enantiomer of known absolute configuration | 1H NMR (400 MHz, CHLOROFORM-d) δ ppm 7.92-8.08 (m, 2 H) 7.49-7.64 (m, 2 H) 6.53-6.64 (m, 1 H) 6.36-6.47 (m, 1 H) 5.57-5.90 (m, 2 H) 4.61 (br s, 2 H) 4.50 (d, J = 12.16 Hz, 1 H) 3.88-4.01 (m, 2 H) 3.63 (td, J = 11.80, 2.74 Hz, 1 H) 3.17-3.51 (m, 1 H) |
| 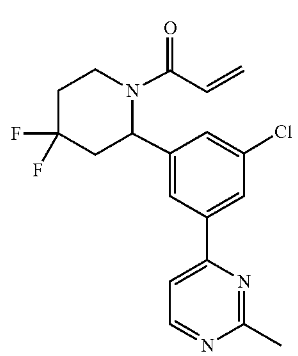 [SMILES: C=CC(=O)N1CCC(F)(F)CC1c1cc(Cl)cc(-c2ccnc(C)n2)c1] | 281 | 1-(2-(3-chloro-5-(2-methylpyrimidin-4-yl)phenyl)-4,4-difluoropiperidin-1-yl)prop-2-en-1-one | Single enantiomer of unknown absolute configuration | 1H NMR (400 MHz, CHLOROFORM-d) δ 8.71 (d, J = 5.3 Hz, 1H), 7.99 (s, 1H), 7.87 (s, 1H), 7.47 (d, J = 5.3 Hz, 1H), 7.36 (s, 1H), 6.70-6.56 (m, 1H), 6.49-6.41 (m, 1H), 6.04-5.88 (m, 1H), 5.84 (br d, J = 10.9 Hz, 2H), 4.41 (br s, 1H), 3.28-3.15 (m, 1H), 3.03-2.90 (m, 1H), 2.81 (s, 3H), 2.48-2.29 (m, 1H), 2.19-1.94 (m, 2H) |

TABLE 1-continued

Compounds of the Disclosure.

| Structure | No. | Name | Stereochemistry | NMR |
|---|---|---|---|---|
| 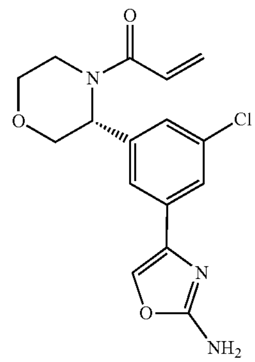 | 282 | 1-(3-(3-(2-aminooxazol-4-yl)-5-chlorophenyl)morpholino)prop-2-en-1-one | Single enantiomer of unknown absolute configuration | 1H NMR (400 MHz, METHANOL-d4) δ ppm 7.69-7.72 (m, 1 H) 7.61-7.68 (m, 1 H) 7.57-7.60 (m, 1 H) 7.29-7.39 (m, 1 H) 6.77-6.85 (m, 1 H) 6.26-6.36 (m, 1 H) 5.78-5.87 (m, 1 H) 5.45-5.74 (m, 1 H) 4.46-4.53 (m, 1 H) 3.82-4.00 (m, 3 H) 3.56-3.66 (m, 1 H) 3.33-3.36 (m, 1 H) |
| 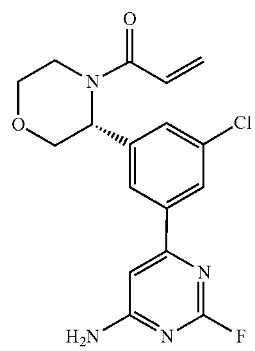 | 283 | (R)-1-(3-(3-(6-amino-2-fluoropyrimidin-4-yl)-5-chlorophenyl)morpholino)prop-2-en-1-one | Single enantiomer of known absolute configuration | 1H NMR (400 MHz, CHLOROFORM-d) δ ppm 7.90-8.00 (m, 2 H) 7.58-7.77 (m, 1 H) 6.71 (d, J = 3.75 Hz, 1 H) 6.52-6.62 (m, 1 H) 6.37-6.46 (m, 1 H) 5.80 (dd, J = 10.38, 1.75 Hz, 1 H) 5.20 (br s, 2 H) 4.50 (d, J = 12.26 Hz, 1 H) 3.83-4.07 (m, 3 H) 3.64 (td, J = 11.82, 2.50 Hz, 2 H) 3.17-3.48 (m, 1 H) |
| 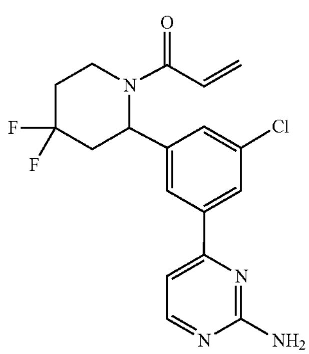 [SMILES: C=CC(=O)N1CCC(F)(F)CC1c1cc(Cl)cc(-c2ccnc(N)n2)c1] | 284 | 1-(2-(3-(2-aminopyrimidin-4-yl)-5-chlorophenyl)-4,4-difluoropiperidin-1-yl)prop-2-en-1-one | Single enantiomer of unknown absolute configuration | 1H NMR (400 MHz, CHLOROFORM-d) δ ppm 8.38 (d, J = 5.13 Hz, 1 H) 7.75-7.97 (m, 2 H) 7.33 (s, 1 H) 7.00 (d, J = 5.13 Hz, 1 H) 6.34-6.72 (m, 2 H) 5.83 (br d, J = 10.76 Hz, 2 H) 5.12 (br s, 2 H) 4.24-4.62 (m, 1 H), 3.21 (br t, J = 11.82 Hz, 1 H) 2.85-3.04 (m, 1 H) 2.26-2.58 (m, 1 H) 1.87-2.22 (m, 2 H) |
| 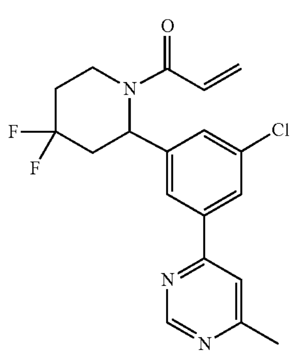 [SMILES: C=CC(=O)N1CCC(F)(F)CC1c1cc(Cl)cc(-c2cc(C)ncn2)c1] | 285 | 1-(2-(3-chloro-5-(6-methylpyrimidin-4-yl)phenyl)-4,4-difluoropiperidin-1-yl)prop-2-en-1-one | Single enantiomer of unknown absolute configuration | 1H NMR (CHLOROFORM-d, 400 MHz): (ppm) 9.01-9.38 (m, 1H), 7.97 (s, 1H), 7.90 (s, 1H), 7.48-7.66 (m, 1H), 7.37 (s, 1H), 6.56-6.69 (m, 1H), 6.40-6.49 (m, 1H), 5.76-6.11 (m, 2H), 4.19-4.67 (m, 1H), 3.15-3.33 (m, 1H), 2.88-3.02 (m, 1H), 2.54-2.71 (m, 3H), 2.27-2.46 (m, 1H), 1.89-2.20 (m, 2H) |

TABLE 1-continued

| Structure | No. | Name | Stereochemistry | NMR |
|---|---|---|---|---|
| 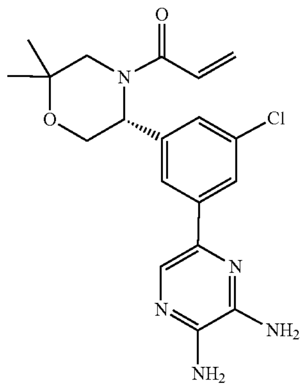 [SMILES: C=CC(=O)N1CC(C)(C)OC[C@H]1c1cc(Cl)cc(-c2cnc(N)c(N)n2)c1] | 286 | (R)-1-(5-(3-chloro-5-(5,6-diaminopyrazin-2-yl)phenyl)-2,2-dimethylmorpholino)prop-2-en-1-one | Single enantiomer of known absolute configuration | 1H NMR (400 MHz, CHLOROFORM-d) δ ppm 7.89 (s, 1 H) 7.74 (br s, 2 H) 7.39-7.61 (m, 1 H) 6.54 (dd, J = 16.75, 10.31 Hz, 1 H) 6.42 (br d, J = 16.57 Hz, 1 H) 5.29-5.86 (m, 2 H) 4.98-5.25 (m, 1 H) 4.31-4.96 (m, 3 H) 4.06-4.24 (m, 2 H) 3.11-3.58 (m, 1 H) 1.30 (s, 3 H) 1.25 (s, 3 H) |
| 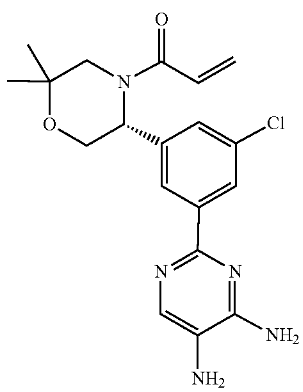 [SMILES: C=CC(=O)N1CC(C)(C)OC[C@H]1c1cc(Cl)cc(-c2ncc(N)c(N)n2)c1] | 287 | (R)-1-(5-(3-chloro-5-(4,5-diaminopyrimidin-2-yl)phenyl)-2,2-dimethylmorpholino)prop-2-en-1-one | Single enantiomer of known absolute configuration | 1H NMR (400 MHz, CHLOROFORM-d) δ ppm 8.10-8.29 (m, 2 H) 7.94 (s, 1 H) 7.32-7.60 (m, 1 H) 6.46-6.60 (m, 1 H) 6.37-6.46 (m, 1 H) 5.53-5.93 (m, 2 H) 4.85-5.39 (m, 2 H) 4.01-4.63 (m, 2 H) 2.88-3.64 (m, 3 H) 1.29 (s, 3 H) 1.24 (s, 3 H) |
| 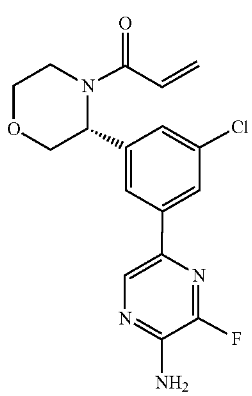 [SMILES: C=CC(=O)N1CCOC[C@H]1c1cc(Cl)cc(-c2cnc(N)c(F)n2)c1] | 289 | (R)-1-(3-(3-(5-amino-6-fluoropyrazin-2-yl)-5-chlorophenyl)morpholino)prop-2-en-1-one | Single enantiomer of known absolute configuration | 1H NMR (400 MHz, CHLOROFORM-d) δ ppm 8.32 (d, J = 4.41 Hz, 1 H) 7.73-7.90 (m, 2 H) 7.38-7.56 (m, 1 H) 6.51-6.64 (m, 1 H) 6.37-6.45 (m, 1 H) 5.80 (dd, J = 10.37, 1.91 Hz, 2 H) 4.94 (br s, 2 H) 4.50 (d, J = 12.28 Hz, 1 H) 3.86-4.01 (m, 2 H) 3.12-3.79 (m, 3 H) |
| 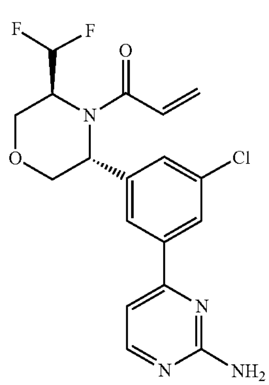 [SMILES: C=CC(=O)N1[C@H](c2cc(Cl)cc(-c3ccnc(N)n3)c2)COC[C@H]1C(F)F] | 290 | 1-((3R,5S)-3-(3-(2-aminopyrimidin-4-yl)-5-chlorophenyl)-5-(difluoromethyl)morpholino)prop-2-en-1-one | Single enantiomer of known absolute configuration | 1H NMR (400 MHz, CHLOROFORM-d) δ ppm 8.37 (d, J = 5.13 Hz, 1 H) 7.89 (s, 1 H) 7.81 (s, 1 H) 7.33 (s, 1 H) 6.99 (d, J = 5.25 Hz, 1 H) 6.40 (br d, J = 1.63 Hz, 1 H) 6.11-6.32 (m, 2 H) 5.65 (br s, 1 H) 5.15 (br s, 2 H) 4.88 (br s, 1 H) 4.28 (br d, J = 2.00 Hz, 2 H) 4.08-4.17 (m, 1 H) 4.02 (br d, J = 12.38 Hz, 1 H) 3.73 (br d, J = 3.38 Hz, 1 H) |

TABLE 1-continued

| Compounds of the Disclosure. | | | | |
|---|---|---|---|---|
| Structure | No. | Name | Stereochemistry | NMR |
| 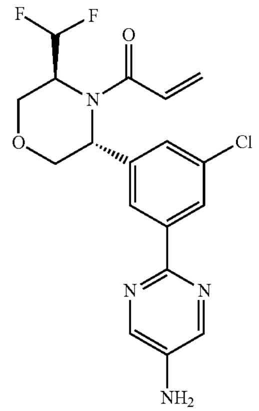 [SMILES: C=CC(=O)N1[C@H](c2cc(Cl)cc(-c3ncc(N)cn3)c2)COC[C@H]1C(F)F] | 291 | 1-((3R,5S)-3-(3-(5-aminopyrimidin-2-yl)-5-chlorophenyl)-5-(difluoromethyl)morpholino)prop-2-en-1-one | Single enantiomer of known absolute configuration | 1H NMR (400 MHz, CHLOROFORM-d) δ ppm 8.26 (s, 3 H) 8.12 (s, 1 H) 7.22-7.26 (m, 1 H) 6.09-6.45 (m, 3 H) 5.59 (br d, J = 6.25 Hz, 1 H) 4.91 (br s, 1 H) 4.38-4.71 (m, 1 H) 4.30 (dd, J = 12.32, 1.69 Hz, 1 H) 4.03-4.18 (m, 2 H) 3.72-3.93 (m, 3 H) |
| 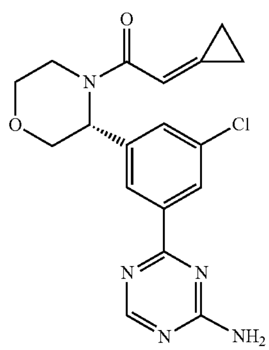 [SMILES: Nc1ncnc(-c2cc(Cl)cc([C@@H]3COCCN3C(=O)C=C3CC3)c2)n1] | 293 | (R)-1-(3-(3-(4-amino-1,3,5-triazin-2-yl)-5-chlorophenyl)morpholino)-2-cyclopropylideneethan-1-one | Single enantiomer of known absolute configuration | 1H NMR (400 MHz, CHLOROFORM-d) δ ppm 8.68 (s, 1 H) 8.43 (br s, 1 H) 8.35 (s, 1 H) 7.66 (br d, J = 0.88 Hz, 1 H) 6.59 (s, 1 H) 5.52 (br s, 2 H) 4.55 (d, J = 12.26 Hz, 1 H) 3.96 (ddd, J = 19.82, 11.82, 3.25 Hz, 2 H) 3.64 (td, J = 11.63, 2.38 Hz, 1 H) 3.06-3.52 (m, 1 H) 1.44-1.51 (m, 2 H) 1.17-1.28 (m, 2 H) |
| 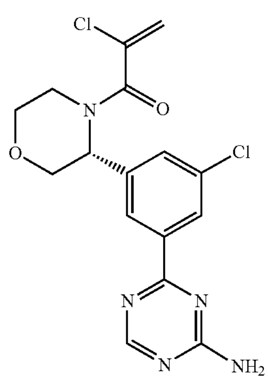 [SMILES: C=C(Cl)C(=O)N1CCOC[C@H]1c1cc(Cl)cc(-c2ncnc(N)n2)c1] | 294 | (R)-1-(3-(3-(4-amino-1,3,5-triazin-2-yl)-5-chlorophenyl)morpholino)-2-chloroprop-2-en-1-one | Single enantiomer of known absolute configuration | 1H NMR (400 MHz, CHLOROFORM-d) δ = 8.81-8.56 (m, 1H), 8.51-8.27 (m, 2H), 7.81-7.52 (m, 1H), 5.77-5.68 (m, 2H), 5.63-5.24 (m, 3H), 4.59-4.52 (m, 1H), 4.03-3.87 (m, 2H), 3.84-3.55 (m, 2H), 3.43-3.14 (m, 1H) |
| 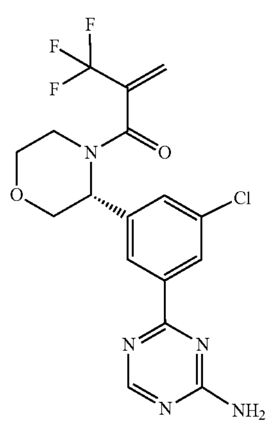 [SMILES: C=C(C(=O)N1CCOC[C@H]1c1cc(Cl)cc(-c2ncnc(N)n2)c1)C(F)(F)F] | 295 | (R)-1-(3-(3-(4-amino-1,3,5-triazin-2-yl)-5-chlorophenyl)morpholino)-2-(trifluoromethyl)prop-2-en-1-one | Single enantiomer of known absolute configuration | 1H NMR (400 MHz, CHLOROFORM-d) δ ppm 8.69 (s, 1 H) 8.36-8.47 (m, 2 H) 7.49-7.70 (m, 1 H) 6.11 (br s, 1 H) 5.73 (s, 1 H) 5.48 (br s, 2 H) 4.57 (br d, J = 12.35 Hz, 1 H) 3.88-4.01 (m, 3 H) 3.53-3.66 (m, 2 H) 3.28-3.40 (m, 1 H) |

TABLE 1-continued

| Structure | No. | Name | Stereochemistry | NMR |
|---|---|---|---|---|
| Compounds of the Disclosure. | | | | |
| 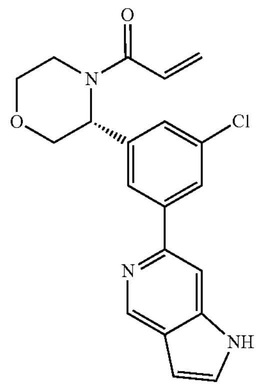 [SMILES: C=CC(=O)N1CCOC[C@H]1c1cc(Cl)cc(-c2cc3[nH]ccc3cn2)c1] | 296 | (R)-1-(3-(3-chloro-5-(1H-pyrrolo[3,2-c]pyridin-6-yl)phenyl)morpholino)prop-2-en-1-one | Single enantiomer of known absolute configuration | 1H NMR (400 MHz, CHLOROFORM-d) δ 9.00 (s, 1H), 8.53 (s, 1H, 7.98 (d, J = 14.5 Hz, 2H), 7.81-7.61 (m, 1H), 7.68-7.40 (m, 2H), 7.32-7.29 (m, 1H), 6.76-6.65 (m, 1H), 6.58 (dd, J = 16.7, 10.3 Hz, 1H), 6.41 (d, J = 16.6 Hz, 1H), 5.77 (dd, J = 10.4, 2.0 Hz, 1H), 4.66-4.26 (m, 2H), 3.95 (ddd, J = 30.8, 11.7, 3.6 Hz, 3H), 3.63 (td, J = 11.5, 2.7 Hz, 2H). |
| 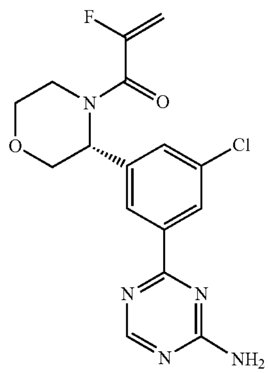 | 297 | (R)-1-(3-(3-(4-amino-1,3,5-triazin-2-yl)-5-chlorophenyl)morpholino)-2-fluoroprop-2-en-1-one | Single enantiomer of known absolute configuration | 1H NMR (400 MHz, DMSO-d6) δ ppm 8.62 (s, 1 H) 8.30 (s, 1 H) 8.24 (d, J = 1.50 Hz, 1 H) 7.76 (s, 2 H) 7.66 (s, 1 H) 5.23-5.46 (m, 3 H) 4.46 (d, J = 12.51 Hz, 1 H) 3.78-3.92 (m, 4 H) 3.53 (br d, J = 2.63 Hz, 1 H) 3.19 (br s, 1 H) |
| 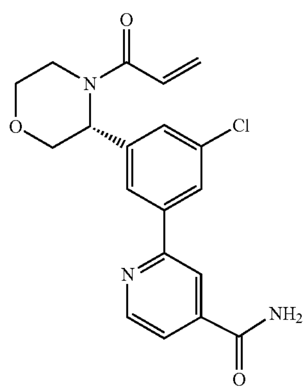 [SMILES: C=CC(=O)N1CCOC[C@H]1c1cc(Cl)cc(-c2cc(C(N)=O)ccn2)c1] | 298 | (R)-2-(3-(4-acryloylmorpholin-3-yl)-5-chlorophenyl)isonicotinamide | Single enantiomer of known absolute configuration | 1H NMR (400 MHz, METHANOL-d4) δ ppm 3.32-3.49 (m, 1 H) 3.64 (td, J = 11.76, 2.63 Hz, 1 H) 3.85-4.07 (m, 3 H) 4.56 (d, J = 12.38 Hz, 1 H) 5.41-6.01 (m, 2 H) 6.32 (br d, J = 16.76 Hz, 1 H) 6.83 (dd, J = 16.76, 10.51 Hz, 1 H) 7.57 (br d, J = 2.00 Hz, 1 H) 7.77 (dd, J = 5.00, 1.13 Hz, 1 H) 7.99-8.17 (m, 2 H) 8.25 (s, 1 H) 8.78 (d, J = 5.00 Hz, 1 H) |

According to further embodiments, compounds of the disclosure are selected from: 1-(3-(3-(2-aminopyrimidin-4-yl)-5-chlorophenyl)morpholino)prop-2-en-1-one;

(R)-3'-(4-acryloylmorpholin-3-yl)-5'-chloro-4-fluoro-[1,1'-biphenyl]-3-carboxamide;

1-(3-(3-chloro-5-(2-methoxypyrimidin-4-yl)phenyl)morpholino)prop-2-en-1-one;

(R)-1-(3-(3-(4-amino-1,3,5-triazin-2-yl)-5-chlorophenyl)morpholino)prop-2-en-1-one;

1-(3-(3-chloro-5-(9H-purin-6-yl)phenyl)morpholino)prop-2-en-1-one;

(R)-1-(5-(3-(4-amino-1,3,5-triazin-2-yl)-5-chlorophenyl)-2,2-dimethylmorpholino)prop-2-en-1-one;

4-(3-(4-acryloylmorpholin-3-yl)-5-chlorophenyl)picolinamide;

3'-(7-acryloyl-4-oxa-7-azaspiro[2.5]octan-6-yl)-5'-chloro-4-fluoro-[1,1'-biphenyl]-3-carboxamide;

(R)-1-(3-(3-(6-aminopyrimidin-4-yl)-5-chlorophenyl)morpholino)prop-2-en-1-one;

1-(6-(3-(2-aminopyrimidin-4-yl)-5-chlorophenyl)-4-oxa-7-azaspiro[2.5]octan-7-yl)prop-2-en-1-one;

(R)-1-(3-(3-chloro-5-(5-methylpyrimidin-2-yl)phenyl)morpholino)prop-2-en-1-one;

(R)-1-(3-(3-chloro-5-(4,6-dimethylpyrimidin-2-yl)phenyl)morpholino)prop-2-en-1-one;

(R)-1-(3-(3-(4-amino-6-methylpyrimidin-2-yl)-5-chlorophenyl)morpholino)prop-2-en-1-one;

(R)-1-(3-(3-(4-aminopyrimidin-2-yl)-5-chlorophenyl)morpholino)prop-2-en-1-one;

1-((3R,5R)-3-(3-(4-amino-1,3,5-triazin-2-yl)-5-chlorophenyl)-5-methylmorpholino)prop-2-en-1-one;

(R)-1-(3-(3-chloro-5-(4-methylpyridin-2-yl)phenyl)morpholino)prop-2-en-1-one;
(R)-1-(3-(3-chloro-5-(4-methoxypyridin-2-yl)phenyl)morpholino)prop-2-en-1-one;
6-(3-(4-acryloylmorpholin-3-yl)-5-chlorophenyl)pyrimidine-4-carboxamide;
1-((3R,5R)-3-(3-chloro-5-(2-methylpyrimidin-4-yl)phenyl)-5-methylmorpholino)prop-2-en-1-one, compounds
1-((3R,5R)-3-(3-(2-aminopyrimidin-4-yl)-5-chlorophenyl)-5-methylmorpholino)prop-2-en-1-one;
1-(3-(3-chloro-5-(1H-pyrrolo[3,2-c]pyridin-4-yl)phenyl)morpholino)prop-2-en-1-one;
1-(3-(3-(4-amino-1,3,5-triazin-2-yl)-5-chlorophenyl)-3-methylmorpholino)prop-2-en-1-one;
1-(3-(3-(2-aminopyrimidin-4-yl)-5-chlorophenyl)-3-methylmorpholino)prop-2-en-1-one;
1-(3-(2-(6-aminopyrimidin-4-yl)-6-chloropyridin-4-yl)morpholino)prop-2-en-1-one;
6-(4-(4-acryloylmorpholin-3-yl)-6-chloropyridin-2-yl)pyrimidine-4-carboxamide;
1-(3-(2-(6-aminopyrimidin-4-yl)-6-chloropyridin-4-yl)morpholino)prop-2-en-1-one;
1-((3R,5R)-3-(3-(6-aminopyrimidin-4-yl)-5-chlorophenyl)-5-methylmorpholino)prop-2-en-1-one;
1-((3R,5R)-3-(3-chloro-5-(9H-purin-6-yl)phenyl)-5-methylmorpholino)prop-2-en-1-one;
5-(4-((3R,5R)-4-acryloyl-5-methylmorpholin-3-yl)-6-chloropyridin-2-yl)-2-fluorobenzamide;
4-((3R,5R)-4-acryloyl-5-methylmorpholin-3-yl)-6-chloro-[2,4'-bipyridine]-2'-carboxamide;
(R)-1-(5-(3-(2-aminopyrimidin-4-yl)-5-chlorophenyl)-2,2-dimethylmorpholino)prop-2-en-1-one;
(R)-1-(5-(3-(6-aminopyrimidin-4-yl)-5-chlorophenyl)-2,2-dimethylmorpholino)prop-2-en-1-one;
1-(5-(2-(6-aminopyrimidin-4-yl)-6-chloropyridin-4-yl)-2,2-dimethylmorpholino)prop-2-en-1-one;
1-(6-(3-(4-amino-1,3,5-triazin-2-yl)-5-chlorophenyl)-4-oxa-7-azaspiro[2.5]octan-7-yl)prop-2-en-1-one;
(R)-1-(5-(3-(4-aminopyrimidin-2-yl)-5-chlorophenyl)-2,2-dimethylmorpholino)prop-2-en-1-one;
(R)-1-(5-(3-(5-aminopyrimidin-2-yl)-5-chlorophenyl)-2,2-dimethylmorpholino)prop-2-en-1-one;
1-(6-(3-(4-amino-1,3,5-triazin-2-yl)-5-chlorophenyl)-6-methyl-4-oxa-7-azaspiro[2.5]octan-7-yl)prop-2-en-1-one;
1-(6-(2-(6-aminopyrimidin-4-yl)-6-chloropyridin-4-yl)-4-oxa-7-azaspiro[2.5]octan-7-yl)prop-2-en-1-one;
(R)-1-(3-(3-(4-amino-6-methyl-1,3,5-triazin-2-yl)-5-chlorophenyl)morpholino)prop-2-en-1-one;
3'-((3R,6R)-4-acryloyl-6-methylmorpholin-3-yl)-5'-chloro-4-fluoro-[1,1'-biphenyl]-3-carboxamide;
5-(4-((3R,5S)-4-acryloyl-5-(difluoromethyl)morpholin-3-yl)-6-chloropyridin-2-yl)-2-fluorobenzamide;
(R)-1-(2-(3-(2-aminopyrimidin-4-yl)-5-chlorophenyl)-4-(cyclopropanecarbonyl)piperazin-1-yl)prop-2-en-1-one;
(R)-1-(3-(3-chloro-5-(4,6-diamino-1,3,5-triazin-2-yl)phenyl)morpholino)prop-2-en-1-one; 191
(R)-1-(3-(3-(2-amino-1H-imidazol-4-yl)-5-chlorophenyl)morpholino)prop-2-en-1-one; 193
(R)-3'-(1-acryloyl-4-(cyclopropanecarbonyl)piperazin-2-yl)-5'-chloro-4-fluoro-[1,1'-biphenyl]-3-carboxamide;
(R)-1-(2-(3-(4-aminopyrimidin-2-yl)-5-chlorophenyl)-4-(cyclopropanecarbonyl)piperazin-1-yl)prop-2-en-1-one;
1-((3R,6R)-3-(2-(6-aminopyrimidin-4-yl)-6-chloropyridin-4-yl)-6-fluoro-1,4-oxazepan-4-yl)prop-2-en-1-one;
(R)-1-(3-(3-(4-amino-6-chloro-1,3,5-triazin-2-yl)-5-chlorophenyl)morpholino)prop-2-en-1-one;
(R)-1-(2-(3-(5-aminopyrimidin-2-yl)-5-chlorophenyl)-4-(cyclopropanecarbonyl)piperazin-1-yl)prop-2-en-1-one;
1-((3R,5S)-3-(2-chloro-6-(6-methylpyrimidin-4-yl)pyridin-4-yl)-5-(difluoromethyl)morpholino)prop-2-en-1-one;
1-((3R,5S)-3-(2-(6-aminopyrimidin-4-yl)-6-chloropyridin-4-yl)-5-(difluoromethyl)morpholino)prop-2-en-1-one;
1-(3-(3-(4-amino-1,3,5-triazin-2-yl)-5-chlorophenyl)-1,1-dioxidothiomorpholino)prop-2-en-1-one;
1-(3-(3-(4-amino-1,3,5-triazin-2-yl)-5-chlorophenyl)-1,1-dioxidothiomorpholino)prop-2-en-1-one;
1-(3-(3-(5-aminopyrimidin-2-yl)-5-chlorophenyl)-1,1-dioxidothiomorpholino)prop-2-en-1-one;
(R)-1-(3-(3-(4-amino-1,3,5-triazin-2-yl-6-d)-5-chlorophenyl)morpholino)prop-2-en-1-one;
1-(3-(3-(4-aminopyrimidin-2-yl)-5-chlorophenyl)-1,1-dioxidothiomorpholino)prop-2-en-1-one;
(R)-1-(3-(3-(5-aminoisoxazol-3-yl)-5-chlorophenyl)morpholino)prop-2-en-1-one;
(R)-1-(3-(3-chloro-5-(4-(methylamino)-1,3,5-triazin-2-yl)phenyl)morpholino)prop-2-en-1-one
(R)-1-(3-(3-(4-amino-6-(methylamino)-1,3,5-triazin-2-yl)-5-chlorophenyl)morpholino)prop-2-en-1-one;
6-(4-((3R,5S)-4-acryloyl-5-(difluoromethyl)morpholin-3-yl)-6-chloropyridin-2-yl)pyrimidine-4-carboxamide;
(R)-2-(3-(4-acryloylmorpholin-3-yl)-5-chlorophenyl)oxazole-4-carboxamide;
1-((3R)-3-(3-chloro-5-(1-methyl-2-thioxohexahydropyrimidin-5-yl)phenyl)morpholino)prop-2-en-1-one;
(R)-1-(3-(3-(4-amino-6-((3-(dimethylamino)propyl)amino)-1,3,5-triazin-2-yl)-5-chlorophenyl)morpholino)prop-2-en-1-one;
1-(5-(3-(4-aminopyrimidin-2-yl)-5-chlorophenyl)-2,2-dimethyl-1,1-dioxidothiomorpholino)prop-2-en-1-one;
1-(2-(3-(5-aminopyrimidin-2-yl)-5-chlorophenyl)-4,4-difluoropiperidin-1-yl)prop-2-en-1-one;
(R)-1-(3-(3-(6-aminopyrazin-2-yl)-5-chlorophenyl)morpholino)prop-2-en-1-one;
(R)-1-(3-(3-(5-aminopyrazin-2-yl)-5-chlorophenyl)morpholino)prop-2-en-1-one;
(R)-1-(3-(3-chloro-5-(4,5-diaminopyrimidin-2-yl)phenyl)morpholino)prop-2-en-1-one;
(R)-1-(3-(3-(5-amino-4-methoxypyrimidin-2-yl)-5-chlorophenyl)morpholino)prop-2-en-1-one;
(R)-1-(3-(3-(5-amino-6-methoxypyrazin-2-yl)-5-chlorophenyl)morpholino)prop-2-en-1-one;
(R)-1-(3-(3-chloro-5-(5,6-diaminopyrazin-2-yl)phenyl)morpholino)prop-2-en-1-one;
(R)-1-(3-(3-(6-amino-5-methoxypyrazin-2-yl)-5-chlorophenyl)morpholino)prop-2-en-1-one;
(R)-1-(3-(3-(4-amino-5-methoxypyrimidin-2-yl)-5-chlorophenyl)morpholino)prop-2-en-1-one;
(R)-1-(3-(3-(4-amino-5-fluoropyrimidin-2-yl)-5-chlorophenyl)morpholino)prop-2-en-1-one;
1-((2R,4S)-2-(3-(5-aminopyrimidin-2-yl)-5-chlorophenyl)-4-hydroxy-4-methylpiperidin-1-yl)prop-2-en-1-one;
1-(4-acetyl-6-(3-(5-aminopyrimidin-2-yl)-5-chlorophenyl)-4,7-diazaspiro[2.5]octan-7-yl)prop-2-en-1-one;
(R)-1-(3-(3-(6-amino-2-chloropyrimidin-4-yl)-5-chlorophenyl)morpholino)prop-2-en-1-one;
(R)-1-(3-(3-(6-amino-5-fluoropyrazin-2-yl)-5-chlorophenyl)morpholino)prop-2-en-1-one;
(R)-1-(3-(3-(6-amino-3-fluoropyrazin-2-yl)-5-chlorophenyl)morpholino)prop-2-en-1-one;
(R)-1-(3-(3-(6-amino-2-fluoropyrimidin-4-yl)-5-chlorophenyl)morpholino)prop-2-en-1-one;
1-(2-(3-(2-aminopyrimidin-4-yl)-5-chlorophenyl)-4,4-difluoropiperidin-1-yl)prop-2-en-1-one;

(R)-1-(5-(3-chloro-5-(5,6-diaminopyrazin-2-yl)phenyl)-2,2-dimethylmorpholino)prop-2-en-1-one;

(R)-1-(5-(3-chloro-5-(4,5-diaminopyrimidin-2-yl)phenyl)-2,2-dimethylmorpholino)prop-2-en-1-one;

(R)-1-(3-(3-(5-amino-6-fluoropyrazin-2-yl)-5-chlorophenyl)morpholino)prop-2-en-1-one;

1-((3R,5S)-3-(3-(2-aminopyrimidin-4-yl)-5-chlorophenyl)-5-(difluoromethyl)morpholino)prop-2-en-1-one;

1-((3R,5S)-3-(3-(5-aminopyrimidin-2-yl)-5-chlorophenyl)-5-(difluoromethyl)morpholino)prop-2-en-1-one;

(R)-1-(3-(3-(4-amino-1,3,5-triazin-2-yl)-5-chlorophenyl)morpholino)-2-chloroprop-2-en-1-one;

(R)-1-(3-(3-chloro-5-(1H-pyrrolo[3,2-c]pyridin-6-yl)phenyl)morpholino)prop-2-en-1-one; or (R)-2-(3-(4-acryloylmorpholin-3-yl)-5-chlorophenyl)isonicotinamide; or a pharmaceutically acceptable salt thereof.

According to further embodiments, compounds of the disclosure are selected from:

(R)-1-(3-(3-(4-amino-1,3,5-triazin-2-yl)-5-chlorophenyl)morpholino)prop-2-en-1-one;

(R)-1-(5-(3-(4-amino-1,3,5-triazin-2-yl)-5-chlorophenyl)-2,2-dimethylmorpholino)prop-2-en-1-one;

(R)-1-(3-(3-(6-aminopyrimidin-4-yl)-5-chlorophenyl)morpholino)prop-2-en-1-one;

(R)-1-(3-(3-chloro-5-(5-methylpyrimidin-2-yl)phenyl)morpholino)prop-2-en-1-one;

(R)-1-(3-(3-chloro-5-(4,6-dimethylpyrimidin-2-yl)phenyl)morpholino)prop-2-en-1-one;

(R)-1-(3-(3-(4-amino-6-methylpyrimidin-2-yl)-5-chlorophenyl)morpholino)prop-2-en-1-one;

(R)-1-(3-(3-(4-aminopyrimidin-2-yl)-5-chlorophenyl)morpholino)prop-2-en-1-one;

1-((3R,5R)-3-(3-(4-amino-1,3,5-triazin-2-yl)-5-chlorophenyl)-5-methylmorpholino)prop-2-en-1-one;

(R)-1-(3-(3-chloro-5-(4-methylpyridin-2-yl)phenyl)morpholino)prop-2-en-1-one;

(R)-1-(3-(3-chloro-5-(4-methoxypyridin-2-yl)phenyl)morpholino)prop-2-en-1-one;

1-((3R,5R)-3-(3-chloro-5-(2-methylpyrimidin-4-yl)phenyl)-5-methylmorpholino)prop-2-en-1-one;

1-((3R,5R)-3-(3-(2-aminopyrimidin-4-yl)-5-chlorophenyl)-5-methylmorpholino)prop-2-en-1-one;

1-((3R,5R)-3-(3-(6-aminopyrimidin-4-yl)-5-chlorophenyl)-5-methylmorpholino)prop-2-en-1-one;

(R)-1-(5-(3-(2-aminopyrimidin-4-yl)-5-chlorophenyl)-2,2-dimethylmorpholino)prop-2-en-1-one;

(R)-1-(5-(3-(6-aminopyrimidin-4-yl)-5-chlorophenyl)-2,2-dimethylmorpholino)prop-2-en-1-one;

(R)-1-(5-(3-(4-aminopyrimidin-2-yl)-5-chlorophenyl)-2,2-dimethylmorpholino)prop-2-en-1-one;

(R)-1-(5-(3-(5-aminopyrimidin-2-yl)-5-chlorophenyl)-2,2-dimethylmorpholino)prop-2-en-1-one;

(R)-1-(3-(3-chloro-5-(4,6-diamino-1,3,5-triazin-2-yl)phenyl)morpholino)prop-2-en-1-one;

(R)-1-(3-(3-(4-amino-1,3,5-triazin-2-yl-6-d)-5-chlorophenyl)morpholino)prop-2-en-1-one;

(R)-1-(3-(3-chloro-5-(4-(methylamino)-1,3,5-triazin-2-yl)phenyl)morpholino)prop-2-en-1-one;

(R)-1-(3-(3-(4-amino-6-(methylamino)-1,3,5-triazin-2-yl)-5-chlorophenyl)morpholino)prop-2-en-1-one;

(R)-1-(3-(3-(6-aminopyrazin-2-yl)-5-chlorophenyl)morpholino)prop-2-en-1-one;

(R)-1-(3-(3-(5-aminopyrazin-2-yl)-5-chlorophenyl)morpholino)prop-2-en-1-one;

(R)-1-(3-(3-chloro-5-(4,5-diaminopyrimidin-2-yl)phenyl)morpholino)prop-2-en-1-one;

(R)-1-(3-(3-(5-amino-4-methoxypyrimidin-2-yl)-5-chlorophenyl)morpholino)prop-2-en-1-one;

(R)-1-(3-(3-(5-amino-6-methoxypyrazin-2-yl)-5-chlorophenyl)morpholino)prop-2-en-1-one;

(R)-1-(3-(3-chloro-5-(5,6-diaminopyrazin-2-yl)phenyl)morpholino)prop-2-en-1-one;

(R)-1-(3-(3-(6-amino-5-methoxypyrazin-2-yl)-5-chlorophenyl)morpholino)prop-2-en-1-one;

(R)-1-(3-(3-(4-amino-5-methoxypyrimidin-2-yl)-5-chlorophenyl)morpholino)prop-2-en-1-one;

(R)-1-(5-(3-chloro-5-(5,6-diaminopyrazin-2-yl)phenyl)-2,2-dimethylmorpholino)prop-2-en-1-one;

(R)-1-(5-(3-chloro-5-(4,5-diaminopyrimidin-2-yl)phenyl)-2,2-dimethylmorpholino)prop-2-en-1-one; or (R)-2-(3-(4-acryloylmorpholin-3-yl)-5-chlorophenyl)isonicotinamide; or a pharmaceutically acceptable salt thereof.

Any combination of the groups described above for the various variables is contemplated herein. Throughout the specification, groups and substituents thereof are chosen by one skilled in the field to provide stable moieties and compounds.

Further Forms of Compounds

In some aspects, a compound disclosed herein possesses one or more stereocenters and each stereocenter exists independently in either the R or S configuration. The compounds presented herein include all diastereomeric, enantiomeric, and epimeric forms as well as the appropriate mixtures thereof. The compounds and methods provided herein include all cis, trans, syn, anti, entgegen (E), and zusammen (Z) isomers as well as the appropriate mixtures thereof. In certain embodiments, compounds described herein are prepared as their individual stereoisomers by reacting a racemic mixture of the compound with an optically active resolving agent to form a pair of diastereoisomeric compounds/salts, separating the diastereomers and recovering the optically pure enantiomers. In some embodiments, resolution of enantiomers is carried out using covalent diastereomeric derivatives of the compounds described herein. In another embodiment, diastereomers are separated by separation/resolution techniques based upon differences in solubility. In other embodiments, separation of stereoisomers is performed by chromatography or by the forming diastereomeric salts and separation by recrystallization, or chromatography, or any combination thereof. Jacques, J., et al., "Enantiomers, Racemates and Resolutions", John Wiley And Sons, Inc., 1981. In one aspect, stereoisomers are obtained by stereoselective synthesis.

In some embodiments, compounds described herein are prepared as prodrugs. A "prodrug" refers to an agent that is converted into the parent drug in vivo. Prodrugs are often useful because, in some situations, they may be easier to administer than the parent drug. They may, for instance, be bioavailable by oral administration whereas the parent is not. The prodrug may also have improved solubility in pharmaceutical compositions over the parent drug. In some embodiments, the design of a prodrug increases the effective water solubility. An example, without limitation, of a prodrug is a compound described herein, which is administered as an ester (the "prodrug") to facilitate transmittal across a cell membrane where water solubility is detrimental to mobility but which then is metabolically hydrolyzed to the carboxylic acid, the active entity, once inside the cell where watersolubility is beneficial. A further example of a prodrug might be a short peptide (polyaminoacid) bonded to an acid group where the peptide is metabolized to reveal the active moiety. In certain embodiments, upon in vivo administration, a prodrug is chemically converted to the biologically, pharmaceutically or therapeutically active form of the compound. In certain embodiments, a prodrug is enzymatically metabolized by one or more steps or processes to the biologically, pharmaceutically or therapeutically active form of the compound.

In one aspect, prodrugs are designed to alter the metabolic stability or the transport characteristics of a drug, to mask side effects or toxicity, to improve the flavor of a drug or to alter other characteristics or properties of a drug. By virtue of knowledge of pharmacokinetic, pharmacodynamic processes and drug metabolism in vivo, once a pharmaceutically active compound is known, the design of prodrugs of the compound is possible. (see, for example, Nogrady (1985) *Medicinal Chemistry A Biochemical Approach, Oxford University Press*, New York, pages 388-392; Silverman (1992), *The Organic Chemistry of Drug Design and Drug Action*, Academic Press, Inc., San Diego, pages 352-401, Rooseboom et al., *Pharmacological Reviews,* 56:53-102, 2004; Aesop Cho, "Recent Advances in Oral Prodrug Discovery", *Annual Reports in Medicinal Chemistry*, Vol. 41, 395-407, 2006; T. Higuchi and V. Stella, *Pro-drugs as Novel Delivery Systems*, Vol. 14 of the *A.C.S. Symposium Series*).

In some embodiments, some of the herein-described compounds may be a prodrug for another derivative or active compound.

In some embodiments, sites on the aromatic ring portion of compounds described herein are susceptible to various metabolic reactions Therefore incorporation of appropriate substituents on the aromatic ring structures will reduce, minimize or eliminate this metabolic pathway. In specific embodiments, the appropriate substituent to decrease or eliminate the susceptibility of the aromatic ring to metabolic reactions is, by way of example only, a halogen, or an alkyl group.

In another embodiment, the compounds described herein are labeled isotopically (e.g., with a radioisotope) or by another other means, including, but not limited to, the use of chromophores or fluorescent moieties, bioluminescent labels, or chemiluminescent labels.

Compounds described herein include isotopically-labeled compounds, which are identical to those recited in the various formulae and structures presented herein, but for the fact that one or more atoms are replaced by an atom having an atomic mass or mass number different from the atomic mass or mass number usually found in nature. Examples of isotopes that can be incorporated into the present compounds include isotopes of hydrogen, carbon, nitrogen, oxygen, sulfur, fluorine, chlorine, and iodine such as, for example, $^{2}H$, $^{3}H$, $^{13}C$, $^{14}C$, $^{15}N$, $^{18}O$, $^{17}O$, $^{35}S$, $^{18}F$, $^{36}Cl$, and $^{125}I$. In one aspect, isotopically-labeled compounds described herein, for example those into which radioactive isotopes such as $^{3}H$ and $^{14}C$ are incorporated, are useful in drug and/or substrate tissue distribution assays. In one aspect, substitution with isotopes such as deuterium affords certain therapeutic advantages resulting from greater metabolic stability, such as, for example, increased in vivo half-life or reduced dosage requirements.

In additional or further embodiments, the compounds described herein are metabolized upon administration to an organism in need to produce a metabolite that is then used to produce a desired effect, including a desired therapeutic effect.

"Pharmaceutically acceptable" as used herein, refers a material, such as a carrier or diluent, which does not abrogate the biological activity or properties of the compound, and is relatively nontoxic, i.e., the material may be administered to an individual without causing undesirable biological effects or interacting in a deleterious manner with any of the components of the composition in which it is contained.

The term "pharmaceutically acceptable salt" refers to a formulation of a compound that does not cause significant irritation to an organism to which it is administered and does not abrogate the biological activity and properties of the compound. In some embodiments, pharmaceutically acceptable salts are obtained by reacting a compound disclosed herein with acids. Pharmaceutically acceptable salts are also obtained by reacting a compound disclosed herein with a base to form a salt.

Compounds described herein may be formed as, and/or used as, pharmaceutically acceptable salts. The type of pharmaceutical acceptable salts, include, but are not limited to: (1) acid addition salts, formed by reacting the free base form of the compound with a pharmaceutically acceptable: inorganic acid, such as, for example, hydrochloric acid, hydrobromic acid, sulfuric acid, phosphoric acid, metaphosphoric acid, and the like; or with an organic acid, such as, for example, acetic acid, propionic acid, hexanoic acid, cyclopentanepropionic acid, glycolic acid, pyruvic acid, lactic acid, malonic acid, succinic acid, malic acid, maleic acid, fumaric acid, trifluoroacetic acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, toluenesulfonic acid, 2-naphthalenesulfonic acid, 4-methylbicyclo-[2.2.2]oct-2-ene-1-carboxylic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, butyric acid, phenylacetic acid, phenylbutyric acid, valproic acid, and the like; (2) salts formed when an acidic proton present in the parent compound is replaced by a metal ion, e.g., an alkali metal ion (e.g., lithium, sodium, potassium), an alkaline earth ion (e.g., magnesium, or calcium), or an aluminum ion. In some cases, compounds described herein may coordinate with an organic base, such as, but not limited to, ethanolamine, diethanolamine, triethanolamine, tromethamine, N-methylglucamine, dicyclohexylamine, tris(hydroxymethyl)methylamine. In other cases, compounds described herein may form salts with amino acids such as, but not limited to, arginine, lysine, and the like. Acceptable inorganic bases used to form salts with compounds that include an acidic proton, include, but are not limited to, aluminum hydroxide, calcium hydroxide, potassium hydroxide, sodium carbonate, sodium hydroxide, and the like.

It should be understood that a reference to a pharmaceutically acceptable salt includes the solvent addition forms, particularly solvates. Solvates contain either stoichiometric or non-stoichiometric amounts of a solvent, and may be formed during the process of crystallization with pharmaceutically acceptable solvents such as water, ethanol, and the like. Hydrates are formed when the solvent is water, or alcoholates are formed when the solvent is alcohol. Solvates of compounds described herein can be conveniently prepared or formed during the processes described herein. In addition, the compounds provided herein can exist in unsolvated as well as solvated forms. In general, the solvated forms are considered equivalent to the unsolvated forms for the purposes of the compounds and methods provided herein.

Methods of Treatment

In another aspect, provided herein is a compound of Formula (I), (II), (III), (IIIx), (IIIa), (IIIb), (IV), or (IVa), or a pharmaceutically acceptable salt thereof, for use in a method of inhibiting Nrf2 by mediating the activation of KEAP1. In some embodiments, provided herein is a method of inhibiting Nrf2 by mediating the activation of KEAP1, the method comprising administering to a subject in need thereof a therapeutically effective amount of a compound of Formula (I), (II), (III), (IIIx), (IIIa), (IIIb), (IV), or (IVa), or a pharmaceutically acceptable salt thereof.

In another aspect, the present disclosure provides the compounds of Formula (I), (II), (III), (IIIx), (IIIa), (IIIb), (IV), or (IVa), or a pharmaceutically acceptable salt thereof, disclosed herein for use as a medicament.

In another aspect, the present disclosure provides the compounds of Formula (I), (II), (III), (IIIx), (IIIa), (IIIb), (IV), or (IVa), or a pharmaceutically acceptable salt thereof, disclosed herein for use in the treatment of a disease mediated by the activation of KEAP1 and the inhibition of Nrf2.

In another aspect, the present disclosure provides for use of the compounds of Formula (I), (II), (III), (IIIx), (IIIa), (IIIb), (IV), or (IVa), or a pharmaceutically acceptable salt thereof, disclosed hereinin the manufacture of a medicament useful for the treatment of a disease mediated by the activation of KEAP1 and the inhibition of Nrf2.

In another aspect, provided herein is a compound of Formula (I), (II), (III), (IIIx), (IIIa), (IIIb), (IV), or (IVa), or a pharmaceutically acceptable salt thereof, for use in a method of treating a disease. In some embodiments, provided herein is a method of treating a disease, the method comprising administering to a subject in need thereof a therapeutically effective amount of a compound of Formula (I), (II), (III), (IIIx), (IIIa), (IIIb), (IV), or (IVa), or a pharmaceutically acceptable salt or solvate thereof. In some embodiments, the disease is mediated by the activation of KEAP1 and the inhibition of Nrf2.

In another embodiment, provided herein is a method of treating a disease mediated by the activation of KEAP1 and the inhibition of Nrf2, the method comprising administering to a subject in need thereof a therapeutically effective amount of a compound of Formula (I), (II), (III), (IIIx), (IIIa), (IIIb), (IV), or (IVa), or a pharmaceutically acceptable salt or solvate thereof.

In some embodiments, the disease is associated with oxidative stress. In some embodiments, a compound described herein (e.g., a compound of Formula (I), or a pharmaceutically acceptable salt thereof) enhances oxidative stress, such as in a cancer cell or in a damaged cell such as in a neurodegenerative disease.

In some embodiments, the disease is diabetes, fibrosis, neurotoxicity, or cancer.

In some embodiments, the disease is selected from the group consisting abdominal aortic aneurysm, acute kidney injury, adult brain glioblastoma, advanced solid tumors lymphoid malignancies, aging, alcohol sensitivity, allergic, Alport syndrome, Alzheimer's disease, asthma, atopic asthmatics, autism spectrum disorder, autosomal dominant polycystic kidney, Barrett esophagus, low-grade dysplasia, brain ischemia, breast cancer or breast neoplasm, cardiovascular risk, cataract surgery, cholelithiasis, cholestasis, chronic hepatitis c, chronic kidney disease, chronic lymphocytic leukemia, chronic renal insufficiency, chronic schizophrenia, chronic subclinical inflammation, CKD associated with type 1 diabetes, cognition, colon cancer, COPD, corneal endothelial cell loss, crohn's disease, cutaneous t cell lymphoma, diabetes mellitus, diabetic nephropathy, diarrhea, endometriosis, environmental carcinogenesis, focal segmental glomerulosclerosis, Friedreich's ataxia, *Helicobacter pylori* infection, hepatic impairment, Huntington disease, IgA nephropathy, inflammation and pain following ocular surgery, insulin resistance, liver disease, lung cancer, non-small cell lung cancer, squamous non-small cell lung cancer, lung adenocarcinoma, esophageal cancer, squamous cell esophageal carcinoma, esophageal adenocarcinoma, head and neck cancer, squamous cell head and neck carcinoma, bladder cancer, squamous cell bladder carcinoma, uterine corpus endometrial carcinoma, cervical cancer, cervical squamous cell carcinoma, major depression, melanoma, metabolic syndrome x, mild cognitive impairment, mitochondrial myopathy, multiple sclerosis, neoplasms, nonalcoholic fatty liver or nonalcoholic steatohepatitis, non-insulin-dependent, nonischemic cardiomyopathy, obstructive sleep apnea, ocular inflammation, ocular pain, polymorphism, prediabetes, primary biliary cirrhosis, primary focal segmental glomerulosclerosis (FSGS), prostate cancer, psoriasis, psychosis, pulmonary arterial hypertension (PAH), pulmonary hypertension, redox status, rheumatoid arthritis, rhinitis, schistosomiasis, schizophrenia, small lymphocytic lymphoma, subarachnoid hemorrhage, and type 2 (type 2 diabetes).

In some embodiments, the disease is selected from the group consisting of adult brain glioblastoma, solid tumors, lymphoid malignancies, breast cancer or breast neoplasm, chronic lymphocytic leukemia, colorectal cancer, cutaneous t cell lymphoma, environmental carcinogenesis, lung cancer, non-small cell lung cancer, squamous non-small cell lung cancer, lung adenocarcinoma, esophageal cancer, squamous cell esophageal carcinoma, esophageal adenocarcinoma, head and neck cancer, squamous cell head and neck carcinoma, bladder cancer, squamous cell bladder carcinoma, uterine corpus endometrial carcinoma, cervical cancer, cervical squamous cell carcinoma, major depression, melanoma, metabolic syndrome x, mild cognitive impairment, mitochondrial myopathy, multiple sclerosis, neoplasms, nonalcoholic fatty liver or nonalcoholic steatohepatitis, non-insulin-dependent, nonischemic cardiomyopathy, obstructive sleep apnea, ocular inflammation, ocular pain, polymorphism, prediabetes, prostate cancer, and small lymphocytic lymphoma.

In some embodiments, the disease is selected from the group consisting of major depression, metabolic syndrome x, mild cognitive impairment, mitochondrial myopathy, multiple sclerosis, neoplasms, nonalcoholic fatty liver or nonalcoholic steatohepatitis, noninsulin-dependent, nonischemic cardiomyopathy, obstructive sleep apnea, ocular inflammation, ocular pain, polymorphism, and prediabetes.

In some embodiments, the disease is cancer.

In some embodiments, the disease is selected from the group consisting of bladder cancer, uterine cancer, head and neck cancer, esophageal cancer, ovarian cancer, liver cancer, cervical cancer, cholangiocarcinoma, gastric cancer, kidney cancer, and pancreatic cancer.

In another aspect, provided herein is a method of degrading Nrf2 in a cell or subject, comprising administering to the cell or subject an effective amount of a compound of any of Formula (I), (II), (III), (IIIx), (IIIa), (IIIb), (IV), or (IVa), or a pharmaceutically acceptable salt thereof. In some embodiments, the compound activates KEAP1, thereby resulting in Nrf2 degradation.

Dosing and Treatment Regimens

In one aspect, the compounds disclosed herein are used in the preparation of medicaments for the treatment of diseases or conditions described herein. In addition, a method for treating any of the diseases or conditions described herein in a subject in need of such treatment, involves administration of pharmaceutical compositions that include at least one compound disclosed herein or a pharmaceutically acceptable salt, active metabolite, prodrug, or solvate thereof, in therapeutically effective amounts to said subject.

In certain embodiments, the compositions containing the compound disclosed herein are administered for prophylactic and/or therapeutic treatments. In certain therapeutic applications, the compositions are administered to a patient already suffering from a disease or condition, in an amount sufficient to cure or at least partially arrest at least one of the symptoms of the disease or condition. Amounts effective for this use depend on the severity and course of the disease or condition, previous therapy, the patient's health status, weight, and response to the drugs, and the judgment of the treating physician. Therapeutically effective amounts are optionally determined by methods including, but not limited to, a dose escalation clinical trial.

In prophylactic applications, compositions containing the compounds disclosed herein are administered to a patient susceptible to or otherwise at risk of a particular disease, disorder or condition.

In certain embodiments, the dose of drug being administered may be temporarily reduced or temporarily suspended for a certain length of time (i.e., a "drug holiday").

Doses employed for adult human treatment are typically in the range of 0.01 mg-5000 mg per day or from about 1 mg to about 1000 mg per day. In one embodiment, the desired dose is conveniently presented in a single dose or in divided doses.

Pharmaceutical Compositions

In another aspect, provided herein is a compound of Formula (I), (II), (III), (IIIx), (IIIa), (IIIb), (IV), or (IVa), or a pharmaceutically acceptable salt or solvate thereof for use in the manufacture of a medicament.

In one aspect, the compounds described herein (e.g., compound of Formula (I), (II), (III), (IIIx), (IIIa), (IIIb), (IV), or (IVa), or pharmaceutically acceptable salts thereof) are formulated into pharmaceutical compositions. Pharmaceutical compositions are formulated in a conventional manner using one or more pharmaceutically acceptable inactive ingredients that facilitate processing of the active compounds into preparations that can be used pharmaceutically. Proper formulation is dependent upon the route of administration chosen. A summary of pharmaceutical compositions described herein can be found, for example, in Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pennsylvania 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999), herein incorporated by reference for such disclosure.

A pharmaceutical composition, as used herein, refers to a mixture of a compound disclosed herein with other chemical components (i.e., pharmaceutically acceptable inactive ingredients), such as carriers, excipients, binders, filling agents, suspending agents, flavoring agents, sweetening agents, disintegrating agents, dispersing agents, surfactants, lubricants, colorants, diluents, solubilizers, moistening agents, plasticizers, stabilizers, penetration enhancers, wetting agents, anti-foaming agents, antioxidants, preservatives, or one or more combination thereof. The pharmaceutical composition facilitates administration of the compound to an organism.

Pharmaceutical formulations described herein are administrable to a subject in a variety of ways by multiple administration routes, including but not limited to, oral, parenteral (e.g., intravenous, subcutaneous, intramuscular, intramedullary injections, intrathecal, direct intraventricular, intraperitoneal, intralymphatic, intranasal injections), intranasal, buccal, topical or transdermal administration routes. The pharmaceutical formulations described herein include, but are not limited to, aqueous liquid dispersions, self-emulsifying dispersions, solid solutions, liposomal dispersions, aerosols, solid dosage forms, powders, immediate release formulations, controlled release formulations, fast melt formulations, tablets, capsules, pills, delayed release formulations, extended release formulations, pulsatile release formulations, multiparticulate formulations, and mixed immediate and controlled release formulations.

In some embodiments, the compounds disclosed herein are administered orally.

In some embodiments, the compounds disclosed herein are administered topically. In such embodiments, the compound disclosed herein is formulated into a variety of topically administrable compositions, such as solutions, suspensions, lotions, gels, pastes, shampoos, scrubs, rubs, smears, medicated sticks, medicated bandages, balms, creams or ointments. In one aspect, the compounds disclosed herein are administered topically to the skin.

In another aspect, the compounds disclosed herein are administered by inhalation.

In another aspect, the compounds disclosed herein are formulated for intranasal administration. Such formulations include nasal sprays, nasal mists, and the like.

In another aspect, the compounds disclosed herein are formulated as eye drops.

In any of the aforementioned aspects are further embodiments in which the effective amount of the compound disclosed herein is: (a) systemically administered to the mammal; and/or (b) administered orally to the mammal; and/or (c) intravenously administered to the mammal; and/or (d) administered by inhalation to the mammal; and/or (e) administered by nasal administration to the mammal; or and/or (f) administered by injection to the mammal; and/or (g) administered topically to the mammal; and/or (h) administered by ophthalmic administration; and/or (i) administered rectally to the mammal; and/or (j) administered non-systemically or locally to the mammal.

In any of the aforementioned aspects are further embodiments comprising single administrations of the effective amount of the compound disclosed herein, including further embodiments in which (i) the compound is administered once; (ii) the compound is administered to the mammal multiple times over the span of one day; (iii) the compound is administered continually; or (iv) the compound is administered continuously.

In any of the aforementioned aspects are further embodiments comprising multiple administrations of the effective amount of the compound disclosed herein, including further embodiments in which (i) the compound is administered continuously or intermittently: as in a single dose; (ii) the time between multiple administrations is every 6 hours; (iii) the compound is administered to the mammal every 8 hours; (iv) the compound is administered to the mammal every 12 hours; (v) the compound is administered to the mammal every 24 hours. In further or alternative embodiments, the method comprises a drug holiday, wherein the administration of the compound disclosed herein is temporarily suspended or the dose of the compound being administered is temporarily reduced; at the end of the drug holiday, dosing of the compound is resumed. In one embodiment, the length of the drug holiday varies from 2 days to 1 year.

In certain embodiments, the compound disclosed herein is administered in a local rather than systemic manner.

In some embodiments, the compound disclosed herein is administered topically. In some embodiments, the compound disclosed herein is administered systemically.

In some embodiments, the pharmaceutical formulation is in the form of a tablet. In other embodiments, pharmaceutical formulations of the compounds disclosed herein are in the form of a capsule.

In one aspect, liquid formulation dosage forms for oral administration are in the form of aqueous suspensions or solutions selected from the group including, but not limited to, aqueous oral dispersions, emulsions, solutions, elixirs, gels, and syrups.

For administration by inhalation, a compound disclosed herein is formulated for use as an aerosol, a mist or a powder.

For buccal or sublingual administration, the compositions may take the form of tablets, lozenges, or gels formulated in a conventional manner.

In some embodiments, compounds disclosed herein are prepared as transdermal dosage forms.

In one aspect, a compound disclosed herein is formulated into a pharmaceutical composition suitable for intramuscular, subcutaneous, or intravenous injection.

In some embodiments, the compound disclosed herein is be administered topically and can be formulated into a variety of topically administrable compositions, such as solutions, suspensions, lotions, gels, pastes, medicated sticks, balms, creams or ointments.

In some embodiments, the compounds disclosed herein are formulated in rectal compositions such as enemas, rectal gels, rectal foams, rectal aerosols, suppositories, jelly suppositories, or retention enemas.

Combination Treatments

In certain instances, it is appropriate to administer at least one compound disclosed herein in combination with another therapeutic agent.

In one specific embodiment, a compound disclosed herein is co-administered with a second therapeutic agent, wherein the compound disclosed herein and the second therapeutic agent modulate different aspects of the disease, disorder or condition being treated, thereby providing a greater overall benefit than administration of either therapeutic agent alone.

For combination therapies described herein, dosages of the co-administered compounds vary depending on the type of co-drug(s) employed, on the specific drug(s) employed, on the disease or condition being treated and so forth. In additional embodiments, when co-administered with one or more other therapeutic agents, the compound provided herein is administered either simultaneously with the one or more other therapeutic agents, or sequentially.

If administration is simultaneous, the multiple therapeutic agents are, by way of example only, provided in a single, unified form, or in multiple forms.

Modified Protein

In another aspect, provided herein is a modified KEAP1 protein comprising a non-naturally occurring small molecule fragment having a covalent bond to cysteine 151 of the KEAP1 protein, wherein the modified KEAP1 protein comprises SEQ ID NO:1 or a variant thereof; and has the structure of Formula (X):

Formula (X)

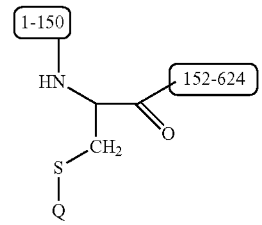

wherein:

S is the sulfur atom of Cysteine 151 in SEQ ID NO: 1 or a variant thereof;

1-150 and 152-624 represent amino acids at positions 1-150 and 152-624 respectively of SEQ ID NO: 1 or the variant thereof; and Q is the small molecule fragment of Formula (X*):

Formula (X*)

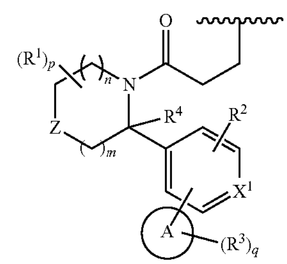

wherein,

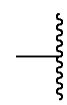

indicates the point of attachment;

ring A is aryl, heteroaryl, or heterocyclyl;

Z is O, $S(=O)_2$, $C(R^1)_2$, or $NR^7$;

$R^7$ is $—C(=O)R^a$, $S(=O)R^a$, or $S(=O)_2R^a$, wherein $R^{7a}$ is H, optionally substituted $C_1$-$C_6$ alkyl, or optionally substituted $C_3$-$C_7$ cycloalkyl;

each $R^1$ is independently H, halogen, —OH, optionally substituted $C_1$-$C_6$ alkyl, optionally substituted $C_1$-$C_6$ haloalkyl, optionally substituted $C_1$-$C_6$ hydroxyalkyl, or $—C(=O)N(R^b)_2$, or two $R^1$ are taken together with the atom(s) to which they are attached form an optionally substituted $C_3$-$C_8$ cycloalkyl or an optionally substituted 3 to 8-membered heterocycloalkyl;

$X^1$ is N or $CR^2$;

each $R^2$ is independently H, halogen, CN, OH, optionally substituted $C_1$-$C_6$ alkyl, optionally substituted $C_1$-$C_6$ haloalkyl, or optionally substituted $C_1$-$C_6$ hydroxyalkyl;

$R^4$ is H or optionally substituted $C_1$-$C_6$ alkyl;

or one of $R^2$ and $R^4$ together with the atoms to which they are attached form an optionally substituted 5 to 7-membered heterocycloalkyl;

each $R^3$ is independently H, D, halogen, oxo (=O), —CN, —OH, $—OR^a$, —SH, $—SR^a$, $—S(=O)R^a$, $—NO_2$, $—N(R^b)_2$, $—S(=O)_2R^a$, —NHS(=O)$_2$R$^a$, —S(=O)$_2$N(R$^b$)$_2$, —C(=O)R$^a$, —C(=O)OR$^b$, —C(=O)NH$_2$, —OC(=O)N(R$^b$)$_2$, —NR$^b$C(=O)N(R$^b$)$_2$, —NR$^b$C(=O)R$^a$, —NR$^b$C(=O)OR$^b$, optionally substituted $C_1$-$C_6$ alkyl, optionally substituted $C_1$-$C_6$haloalkyl, optionally substituted $C_1$-$C_6$ hydroxyalkyl, optionally substituted $C_3$-$C_8$ cycloalkyl, or optionally substituted 4 to 8-membered heterocycloalkyl;

or two $R^3$ on adjacent atoms combine together with the atom(s) to which they are attached to form an optionally substituted aryl, optionally substituted heteroaryl ring, or optionally substituted heterocycloalkyl;

each $R^a$ is independently $C_1$-$C_6$ alkyl, $C_1$-$C_6$ heteroalkyl, cycloalkyl, heterocycloalkyl, aryl, heteroaryl, —$C_1$-$C_6$ alkyl(aryl), —$C_1$-$C_6$ alkyl(heteroaryl), —$C_1$-$C_6$ alkyl(cycloalkyl), or —$C_1$-$C_6$ alkyl(heterocycloalkyl); wherein each alkyl, heteroalkyl, cycloalkyl, heterocycloalkyl, aryl, and heteroaryl is independently optionally substituted with one, two, or three —OH, $C_1$-$C_6$ alkyl, or $C_1$-$C_6$ haloalkyl; and each $R^b$ is independently H, $C_1$-$C_6$ alkyl, $C_1$-$C_6$ heteroalkyl, cycloalkyl, heterocycloalkyl, aryl, or heteroaryl; wherein the alkyl, heteroalkyl, cycloalkyl, heterocycloalkyl, aryl, and heteroaryl is independently optionally substituted with one, two, or three —OH, $C_1$-$C_6$ alkyl, or $C_1$-$C_6$ haloalkyl;

or two $R^b$ groups on a nitrogen atom are taken together with the nitrogen atom to which they are attached to form a heterocycloalkyl which is optionally substituted with one, two, or three $C_1$-$C_6$ alkyl, or $C_1$-$C_6$ haloalkyl;

m is 0, 1, 2, or 3;

n is 0, 1, 2, or 3;

p is an integer from 1-12; and q is an integer from 1-10.

SEQ ID NO:1 relates to the sequence of human KEAP1, also referred to by Uniprot identifier Q14145 (see Uniprot version downloaded 2023-08-23), namely:

```
MQPDPRPSGAGACCRFLPLQSQCPEGAGDAVMYASTECKAEVTPSQHGN

RTFSYTLEDHTKQAFGIMNELRLSQQLCDVTLQVKYQDAPAAQFMAHKV

VLASSSPVFKAMFTNGLREQGMEVVSIEGIHPKVMERLIEFAYTASISM

GEKCVLHVMNGAVMYQIDSVVRACSDFLVQQLDPSNAIGIANFAEQIGC

VELHQRAREYIYMHFGEVAKQEEFFNLSHCQLVTLISRDDLNVRCESEV

FHACINWVKYDCEQRRFYVQALLRAVRCHSLTPNFLQMQLQKCEILQSD

SRCKDYLVKIFEELTLHKPTQVMPCRAPKVGRLIYTAGGYFRQSLSYLE

AYNPSDGTWLRLADLQVPRSGLAGCVVGGLLYAVGGRNNSPDGNTDSSA

LDCYNPMTNQWSPCAPMSVPRNRIGVGVIDGHIYAVGGSHGCIHHNSVE

RYEPERDEWHLVAPMLTRRIGVGVAVLNRLLYAVGGFDGTNRLNSAECY

YPERNEWRMITAMNTIRSGAGVCVLHNCIYAAGGYDGQDQLNSVERYDV

ETETWTFVAPMKHRRSALGITVHQGRIYVLGGYDGHTFLDSVECYDPDT

DTWSEVTRMTSGRSGVGVAVTMEPCRKQIDQQNCTC,
```

wherein the sequence has been modified with any of the compounds listed according to Table 1. According to a highly preferred embodiment cysteine 151 of SEQ ID NO: 1 carries the aforementioned modification according to Table 1, i.e., the respective compound according to the Table in [00100] is covalently bound to the protein encoded by SEQ ID No: 1 via the side chain of C151.

In some embodiments, the KEAP1 protein comprises an amino acid sequence at least 75%, at least 80%, at least 85%, or at least 90% identical to the sequence of SEQ ID NO: 1. In some embodiments, the KEAP1 protein comprises an amino acid sequence at least 91%, at least 92%, at least 93%, at least 94%, at least 95%, at least 96%, at least 97%, at least 98%, or at least 99 identical to the sequence of SEQ ID NO: 1. In some embodiments, the KEAP1 protein comprises an amino acid sequence at least 99.1%, at least 99.2%, at least 99.3%, at least 99.4%, at least 99.5%, at least 99.6%, at least 99.7%, at least 99.8%, or at least 99.9 identical to the sequence of SEQ ID NO: 1. "Sequence identity" or "percent identity" is a number that describes how similar a query sequence is to a target sequence, more precisely how many characters in each sequence are identical after alignment. The most popular tool to calculate sequence identity is BLAST (basic local alignment search tool, https:/iblast.ncbi.nlm.nih.gov/), which performs comparisons between pairs of sequences, searching for regions of local similarity. Suitable alignment methods are known in the art, e.g., Needleman-Wunsch algorithm for global-global alignment, using BLOSUM62 matrix, with gap opening penalty of 11 and a gap extension penalty of 1. Afterwards, the pairs of aligned identical residues can be counted and then divided by the total length of the alignment (including gaps, internal as well as external) to arrive at the percent identity value. The KEAP protein may include a functional fragment of any of these sequences, such as a functional fragment of at least 300 amino acids in length, at least 350 amino acids in length, at least 400 amino acids in length, at least 450 amino acids in length, at least 500 amino acids in length, at least 550 amino acids in length, or at least 600 amino acids in length. According to the current invention a protein fragment is considered functional if the fragment may at least partially exert the biological functions of its parent protein, i.e., in the case of KEAP1 a fragment of the parent protein is called functional e.g., if it has activity in the Nrf2 antagonism assay according to Example 108.

In some embodiments, the compounds described herein form an adduct with the KEAP1 protein at cysteine 151. The cysteine 151 may be a cysteine at amino acid residue position 151 of a polypeptide chain of a KEAP1 protein, as numbered from N to C. The cysteine 151 may be with regard to SEQ ID NO: 1. In embodiments where the KEAP1 amino acid sequence is not 100% identical to SEQ ID NO: 1, the cysteine 151 may be an equivalent cysteine to the cysteine 151 with regard to SEQ ID NO: 1.

In some embodiments, the adduct is a compound fragment that results from the reaction of a compound described herein with the protein thiol group. In some embodiments, the compound prior to reaction with the protein is a compound of any of Formulas (I), (II), (III), (IIIx), (IIIa), (IIIb), (IV), or (IVa), or a pharmaceutically acceptable salt thereof.

Definitions

As used in this specification and the appended claims, the singular forms "a," "an," and "the" include plural referents unless the content clearly dictates otherwise. It should also be noted that the term "or" is generally employed in its sense including "and/or" unless the content clearly dictates otherwise. Further, headings provided herein are for convenience only and do not interpret the scope or meaning of the claimed invention.

The terms below, as used herein, have the following meanings, unless indicated otherwise:

"Oxo" refers to the =O substituent.

"Alkyl" refers to a straight or branched hydrocarbon chain radical, having from one to twenty carbon atoms, and which is attached to the rest of the molecule by a single bond. An alkyl comprising up to 10 carbon atoms is referred to as a $C_1$-$C_{10}$ alkyl, likewise, for example, an alkyl comprising up to 6 carbon atoms is a $C_1$-$C_6$ alkyl. Alkyls (and other moieties defined herein) comprising other numbers of carbon atoms are represented similarly. Alkyl groups include, but are not limited to, $C_1$-$C_{10}$ alkyl, $C_1$-$C_9$ alkyl, $C_1$-$C_8$ alkyl, $C_1$-$C_7$ alkyl, $C_1$-$C_6$ alkyl, $C_1$-$C_5$ alkyl, $C_1$-$C_4$ alkyl, $C_1$-$C_3$ alkyl, $C_1$-$C_2$ alkyl, $C_2$-$C_8$ alkyl, $C_3$-$C_8$ alkyl and $C_4$-$C_8$ alkyl. Representative alkyl groups include, but are not limited to, methyl, ethyl, npropyl, 1methylethyl (ipropyl), nbutyl, i-butyl, s-butyl, npentyl, 1,1dimethylethyl (tbutyl), 3methylhexyl, 2methylhexyl, 1-ethyl-propyl, and the like. In some embodiments, the alkyl is methyl or ethyl. Unless stated otherwise specifically in the specification, an alkyl group may be optionally substituted as described below.

"Alkylene" refers to a straight or branched divalent hydrocarbon chain linking the rest of the molecule to a radical group. In some embodiments, the alkylene is $—CH_2—$, $—CH_2CH_2—$, or $—CH_2CH_2CH_2—$. In some embodiments, the alkylene is $—CH_2—$. In some embodiments, the alkylene is $—CH_2CH_2—$. In some embodiments, the alkylene is $—CH_2CH_2CH_2—$.

"Alkoxy" refers to a radical of the formula OR where R is an alkyl radical as defined. Unless stated otherwise specifically in the specification, an alkoxy group may be optionally substituted as described below. Representative alkoxy groups include, but are not limited to, methoxy, ethoxy, propoxy, butoxy, pentoxy. In some embodiments, the alkoxy is methoxy. In some embodiments, the alkoxy is ethoxy.

"Heteroalkyl" refers to an alkyl radical as described above where one or more carbon atoms of the alkyl is replaced with a 0, N (i.e., NH, N-alkyl) or S atom. "Heteroalkylene" refers to a straight or branched divalent heteroalkyl chain linking the rest of the molecule to a radical group. Unless stated otherwise specifically in the specification, the heteroalkyl or heteroalkylene group may be optionally substituted as described below. Representative heteroalkyl groups include, but are not limited to $—OCH_2OMe$, $—OCH_2CH_2OMe$, or $—OCH_2CH_2OCH_2CH_2NH_2$. Representative heteroalkylene groups include, but are not limited to $—OCH_2CH_2O—$, $—OCH_2CH_2OCH_2CH_2O—$, or $—OCH_2CH_2OCH_2CH_2OCH_2CH_2O—$.

"Alkylamino" refers to a radical of the formula —NHR or —NRR where each R is, independently, an alkyl radical as defined above. Unless stated otherwise specifically in the specification, an alkylamino group may be optionally substituted as described below.

The term "aromatic" refers to a planar ring having a delocalized π-electron system containing 4n+2 π electrons, where n is an integer. Aromatics can be optionally substituted. The term "aromatic" includes both aryl groups (e.g., phenyl, naphthalenyl) and heteroaryl groups (e.g., pyridinyl, quinolinyl).

"Aryl" refers to an aromatic ring wherein each of the atoms forming the ring is a carbon atom. Aryl groups can be optionally substituted. Examples of aryl groups include, but are not limited to phenyl, and naphthyl. In some embodiments, the aryl is phenyl. Depending on the structure, an aryl group can be a monoradical or a diradical (i.e., an arylene group). Unless stated otherwise specifically in the specification, the term "aryl" or the prefix "ar-" (such as in "aralkyl") is meant to include aryl radicals that are optionally substituted.

"Carboxy" refers to $—CO_2H$. In some embodiments, carboxy moieties may be replaced with a "carboxylic acid bioisostere", which refers to a functional group or moiety that exhibits similar physical and/or chemical properties as a carboxylic acid moiety. A carboxylic acid bioisostere has similar biological properties to that of a carboxylic acid group. A compound with a carboxylic acid moiety can have the carboxylic acid moiety exchanged with a carboxylic acid bioisostere and have similar physical and/or biological properties when compared to the carboxylic acid-containing compound. For example, in one embodiment, a carboxylic acid bioisostere would ionize at physiological pH to roughly the same extent as a carboxylic acid group. Examples of bioisosteres of a carboxylic acid include, but are not limited to:

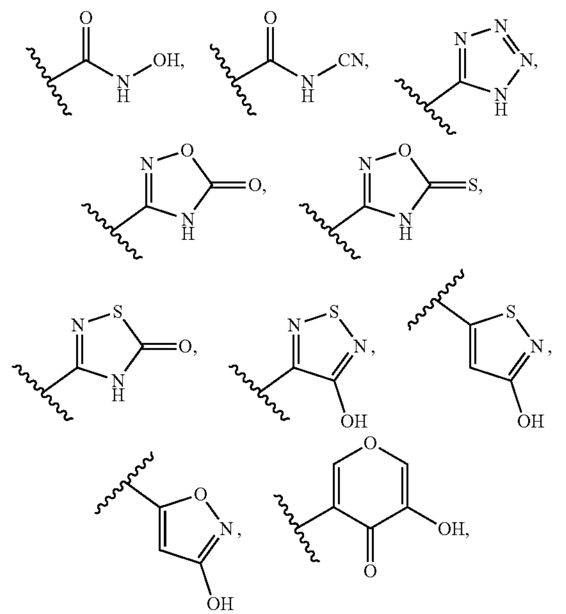

and the like.

"Cycloalkyl" refers to a monocyclic or polycyclic non-aromatic radical, wherein each of the atoms forming the ring (i.e., skeletal atoms) is a carbon atom. Cycloalkyls may be saturated, or partially unsaturated. Cycloalkyls may be fused with an aromatic ring (in which case the cycloalkyl is bonded through a non-aromatic ring carbon atom). Cycloalkyl groups include groups having from 3 to 10 ring atoms. Representative cycloalkyls include, but are not limited to, cycloalkyls having from three to ten carbon atoms, from three to eight carbon atoms, from three to six carbon atoms, or from three to five carbon atoms. In some embodiments, a cycloalkyl is a $C_3$-$C_6$cycloalkyl. In some embodiments, the cycloalkyl is monocyclic, bicyclic or polycyclic. In some embodiments, cycloalkyl groups are selected from among cyclopropyl, cyclobutyl, cyclopentyl, cyclopentenyl, cyclohexyl, cyclohexenyl, cycloheptyl, cyclooctyl, spiro[2.2]pentyl, bicyclo[1.1.1]pentyl, bicyclo[3.3.0]octane, bicyclo[4.3.0]nonane, bicyclo[2.1.1]hexane, bicyclo[2.2.1]heptane, bicyclo[2.2.2]octane, bicyclo[3.2.2]nonane, bicyclo[3.3.2]decane, norbornyl, decalinyl and adamantyl. In some embodiments, the cycloalkyl is monocyclic. Monocyclic cyclcoalkyl radicals include, for example, cyclopropyl, cyclobutyl, cyclopentyl, cyclohexyl, cycloheptyl, and cyclooctyl. In some embodiments, the monocyclic cyclcoalkyl is cyclopropyl, cyclobutyl, cyclopentyl or cyclohexyl. In some embodiments, the cycloalkyl is bicyclic. Bicyclic cycloalkyl groups include fused bicyclic cycloalkyl groups, spiro bicyclic cycloalkyl groups, and bridged bicyclic cycloalkyl groups. In some embodiments, cycloalkyl groups are selected from among spiro[2.2]pentyl, bicyclo[1.1.1]pentyl, bicyclo[3.3.0]octane, bicyclo[4.3.0]nonane, bicyclo[2.1.1]hexane, bicyclo[2.2.1]heptane, bicyclo[2.2.2]octane, bicyclo[3.2.2]nonane, bicyclo[3.3.2]decane, norbornyl, 3,4-dihydronaphthalen-1(2H)-one and decalinyl. In some embodiments, the cycloalkyl is polycyclic. Polycyclic radicals include, for example, adamantyl, and. In some embodiments, the polycyclic cycloalkyl is adamantyl. Unless otherwise stated specifically in the specification, a cycloalkyl group may be optionally substituted.

"Fused" refers to any ring structure described herein which is fused to an existing ring structure. When the fused ring is a heterocyclyl ring or a heteroaryl ring, any carbon atom on the existing ring structure which becomes part of the fused heterocyclyl ring or the fused heteroaryl ring may be replaced with a nitrogen atom.

"Halo" or "halogen" refers to bromo, chloro, fluoro or iodo.

"Haloalkyl" refers to an alkyl radical, as defined above, that is substituted by one or more halo radicals, as defined above, e.g., trifluoromethyl, difluoromethyl, fluoromethyl, trichloromethyl, 2,2,2trifluoroethyl, 1,2difluoroethyl, 3bromo2fluoropropyl, 1,2dibromoethyl, and the like. Unless stated otherwise specifically in the specification, a haloalkyl group may be optionally substituted.

"Haloalkoxy" refers to an alkoxy radical, as defined above, that is substituted by one or more halo radicals, as defined above, e.g., trifluoromethoxy, difluoromethoxy, fluoromethoxy, trichloromethoxy, 2,2,2trifluoroethoxy, 1,2difluoroethoxy, 3bromo2fluoropropoxy, 1,2dibromoethoxy, and the like. Unless stated otherwise specifically in the specification, a haloalkoxy group may be optionally substituted.

"Heterocycloalkyl" or "heterocyclyl" or "heterocyclic ring" refers to a stable 3 to 14membered nonaromatic ring radical comprising 2 to 10 carbon atoms and from one to 4 heteroatoms selected from the group consisting of nitrogen, oxygen, and sulfur. Unless stated otherwise specifically in the specification, the heterocycloalkyl radical may be a monocyclic, bicyclic ring (which may include a fused bicyclic heterocycloalkyl (when fused with an aryl or a heteroaryl ring, the heterocycloalkyl is bonded through a non-aromatic ring atom), bridged heterocycloalkyl or spiro heterocycloalkyl), or polycyclic. In some embodiments, the heterocycloalkyl is monocyclic or bicyclic. In some embodiments, the heterocycloalkyl is monocyclic. In some embodiments, the heterocycloalkyl is bicyclic. The nitrogen, carbon or sulfur atoms in the heterocyclyl radical may be optionally oxidized. The nitrogen atom may be optionally quaternized. The heterocycloalkyl radical is partially or fully saturated. Examples of such heterocycloalkyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2oxopiperazinyl, 2oxopiperidinyl, 2oxopyrrolidinyl, oxazolidinyl, piperidinyl, piperazinyl, 4piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1oxothiomorpholinyl, 1,1dioxothiomorpholinyl. The term heterocycloalkyl also includes all ring forms of carbohydrates, including but not limited to monosaccharides, disaccharides and oligosaccharides. Unless otherwise noted, heterocycloalkyls have from 2 to 10 carbons in the ring. In some embodiments, heterocycloalkyls have from 2 to 8 carbons in the ring. In some embodiments, heterocycloalkyls have from 2 to 8 carbons in the ring and 1 or 2 N atoms. In some embodiments, heterocycloalkyls have from 2 to 10 carbons, 0-2 N atoms, 0-2 O atoms, and 0-1 S atoms in the ring. In some embodiments, heterocycloalkyls have from 2 to 10 carbons, 1-2 N atoms, 0-1 O atoms, and 0-1 S atoms in the ring. It is understood that when referring to the number of carbon atoms in a heterocycloalkyl, the number of carbon atoms in the heterocycloalkyl is not the same as the total number of atoms (including the heteroatoms) that make up the heterocycloalkyl (i.e., skeletal atoms of the heterocycloalkyl ring). Unless stated otherwise specifically in the specification, a heterocycloalkyl group may be optionally substituted.

"Heteroaryl" refers to an aryl group that includes one or more ring heteroatoms selected from nitrogen, oxygen and sulfur. The heteroaryl is monocyclic or bicyclic. Illustrative examples of monocyclic heteroaryls include pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, pyridazinyl, triazinyl, oxadiazolyl, thiadiazolyl, furazanyl, indolizine, indole, benzofuran, benzothiophene, indazole, benzimidazole, purine, quinolizine, quinoline, isoquinoline, cinnoline, phthalazine, quinazoline, quinoxaline, 1,8-naphthyridine, and pteridine. Illustrative examples of monocyclic heteroaryls include pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, pyridazinyl, triazinyl, oxadiazolyl, thiadiazolyl, and furazanyl. Illustrative examples of bicyclic heteroaryls include indolizine, indole, benzofuran, benzothiophene, indazole, benzimidazole, purine, quinolizine, quinoline, isoquinoline, cinnoline, phthalazine, quinazoline, quinoxaline, 1,8-naphthyridine, and pteridine. In some embodiments, heteroaryl is pyridinyl, pyrazinyl, pyrimidinyl, thiazolyl, thienyl, thiadiazolyl or furyl. In some embodiments, a heteroaryl contains 0-4 N atoms in the ring. In some embodiments, a heteroaryl contains 1-4 N atoms in the ring. In some embodiments, a heteroaryl contains 0-4 N atoms, 0-1 O atoms, and 0-1 S atoms in the ring. In some embodiments, a heteroaryl contains 1-4 N atoms, 0-1 O atoms, and 0-1 S atoms in the ring. In some embodiments, heteroaryl is a $C_1$-$C_9$heteroaryl. In some embodiments, monocyclic heteroaryl is a $C_1$-$C_5$heteroaryl. In some embodiments, monocyclic heteroaryl is a 5-membered or 6-membered heteroaryl. In some embodiments, a bicyclic heteroaryl is a $C_6$-$C_9$heteroaryl.

The term "optionally substituted" or "substituted" means that the referenced group may be substituted with one or more additional group(s) individually and independently selected from alkyl, haloalkyl, cycloalkyl, aryl, heteroaryl, heterocycloalkyl, —OH, alkoxy, aryloxy, alkylthio, arylthio, alkylsulfoxide, arylsulfoxide, alkylsulfone, arylsulfone, —CN, alkyne, $C_1$-$C_6$alkylalkyne, halogen, acyl, acyloxy, —$CO_2H$, —$CO_2$alkyl, nitro, and amino, including mono and disubstituted amino groups (e.g., —$NH_2$, —NHR, —$NR_2$), and the protected derivatives thereof. In some embodiments, optional substituents are independently selected from alkyl, alkoxy, haloalkyl, cycloalkyl, halogen, —CN, —$NH_2$, —$NH(CH_3)$, —$N(CH_3)_2$, —OH, —$CO_2H$, and —$CO_2$alkyl. In some embodiments, optional substituents are independently selected from fluoro, chloro, bromo, iodo, —$CH_3$, —$CH_2CH_3$, —$CF_3$, —$OCH_3$, and —$OCF_3$. In some embodiments, substituted groups are substituted with one or two of the preceding groups. In some embodiments, an optional substituent on an aliphatic carbon atom (acyclic or cyclic) includes oxo (═O).

A "tautomer" refers to a proton shift from one atom of a molecule to another atom of the same molecule. The compounds presented herein may exist as tautomers. Tautomers are compounds that are interconvertible by migration of a hydrogen atom, accompanied by a switch of a single bond and adjacent double bond. In bonding arrangements where tautomerization is possible, a chemical equilibrium of the tautomers will exist. All tautomeric forms of the compounds disclosed herein are contemplated. The exact ratio of the tautomers depends on several factors, including temperature, solvent, and pH. Some examples of tautomeric interconversions include:

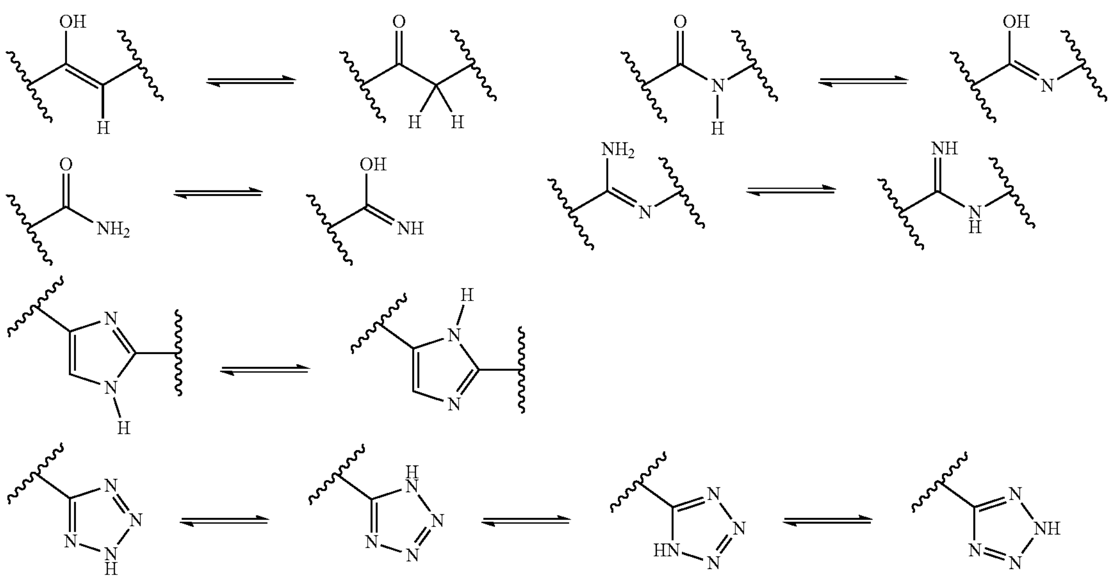

The terms "co-administration" or the like, as used herein, are meant to encompass administration of the selected therapeutic agents to a single patient, and are intended to include treatment regimens in which the agents are administered by the same or different route of administration or at the same or different time.

The terms "effective amount" or "therapeutically effective amount," as used herein, refer to a sufficient amount of an agent or a compound being administered which will relieve to some extent one or more of the symptoms of the disease or condition being treated. The result can be reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in disease symptoms. An appropriate "effective" amount in any individual case may be determined using techniques, such as a dose escalation study. An "effective amount" is an amount sufficient for a compound to accomplish a stated purpose relative to the absence of the compound (e.g., achieve the effect for which it is administered, treat a disease, reduce enzyme activity, increase enzyme activity, reduce a signaling pathway, or reduce one or more symptoms of a disease or condition). An example of an "effective amount" is an amount sufficient to contribute to the treatment, prevention, or reduction of a symptom or symptoms of a disease, which could also be referred to as a "therapeutically effective amount." A "reduction" of a symptom or symptoms (and grammatical equivalents of this phrase) means decreasing of the severity or frequency of the symptom(s), or elimination of the symptom(s). A "prophylactically effective amount" of a drug is an amount of a drug that, when administered to a subject, will have the intended prophylactic effect, e.g., preventing or delaying the onset (or reoccurrence) of an injury, disease, pathology or condition, or reducing the likelihood of the onset (or reoccurrence) of an injury, disease, pathology, or condition, or their symptoms. The full prophylactic effect does not necessarily occur by administration of one dose, and may occur only after administration of a series of doses. Thus, a prophylactically effective amount may be administered in one or more administrations. An "activity decreasing amount," as used herein, refers to an amount of antagonist required to decrease the activity of an enzyme relative to the absence of the antagonist. A "function disrupting amount," as used herein, refers to the amount of antagonist required to disrupt the function of an enzyme or protein relative to the absence of the antagonist. The exact amounts will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy*, 20th Edition, 2003, Gennaro, Ed., Lippincott, Williams & Wilkins).

The term "pharmaceutical combination" as used herein, means a product that results from the mixing or combining of more than one active ingredient and includes both fixed and non-fixed combinations of the active ingredients. The term "fixed combination" means that the active ingredients, e.g., a compound of Formula (I) and a co-agent, are both administered to a patient simultaneously in the form of a single entity or dosage. The term "non-fixed combination"

means that the active ingredients, e.g., a compound of Formula (I) and a co-agent, are administered to a patient as separate entities either simultaneously, concurrently or sequentially with no specific intervening time limits, wherein such administration provides effective levels of the two compounds in the body of the patient. The latter also applies to cocktail therapy, e.g., the administration of three or more active ingredients.

The term "subject" or "patient" encompasses mammals. Examples of mammals include, but are not limited to, humans. In one embodiment, the mammal is a human.

The terms "treat," "treating" or "treatment," as used herein, include alleviating, abating or ameliorating at least one symptom of a disease or condition, preventing additional symptoms, inhibiting the disease or condition, e.g., arresting the development of the disease or condition, relieving the disease or condition, causing regression of the disease or condition, relieving a condition caused by the disease or condition, or stopping the symptoms of the disease or condition either prophylactically and/or therapeutically.

EXAMPLES

The following examples are offered to illustrate, but not to limit the claimed invention. The following examples further illustrate the invention but, of course, should not be construed as in any way limiting its scope.

The following synthetic schemes are provided for purposes of illustration, not limitation. The following examples illustrate the various methods of making compounds described herein. It is understood that one skilled in the art may be able to make these compounds by similar methods or by combining other methods known to one skilled in the art. It is also understood that one skilled in the art would be able to make, in a similar manner as described below by using the appropriate starting materials and modifying the synthetic route as needed. In general, starting materials and reagents can be obtained from commercial vendors or synthesized according to sources known to those skilled in the art or prepared as described herein.

In further embodiments, the compounds described herein, and other related compounds having different substituents are synthesized using techniques and materials described herein as well as those that are recognized in the field, such as described, for example, in Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991), Larock's Comprehensive Organic Transformations (VCH Publishers Inc., 1989), March, Advanced Organic Chemistry 4th Ed., (Wiley 1992); Carey and Sundberg, Advanced Organic Chemistry 4th Ed., Vols. A and B (Plenum 2000, 2001), and Green and Wuts, *Protective Groups in Organic Synthesis* 3rd Ed., (Wiley 1999) (all of which are incorporated by reference for such disclosure). General methods for the preparation of compounds as disclosed herein may be derived from reactions and the reactions may be modified by the use of appropriate reagents and conditions, for the introduction of the various moieties found in the formulae as provided herein. As a guide the following synthetic methods may be utilized.

Abbreviations

DCM: Dichloromethane
DIEA: Diisopropylethylamine
DMAP 4-(Dimethylamino)pyridine
DMF: Dimethyl formamide
DMSO: Dimethyl sulfoxide
EA or EtOAc: Ethyl acetate
ESI: Electrospray ionization
HPLC: High performance liquid chromatography
HRMS: High resolution mass spectrometry
h or hr(s): Hour(s)
MeOH: Methanol
Ms: Mesyl, or methanesulfonyl
min(s): Minutes
m/z: Mass-to-charge ratio
$^{1}$H NMR: Proton nuclear magnetic resonance
$^{13}$C NMR: Carbon nuclear magnetic resonance
PE: Petroleum ether
rt: Room temperature
TLC Thin layer chromatography
TFA: Trifluoroacetic acid

Example 1. Procedure A and Synthesis of 1-(3-(5-chloro-[1,1'-biphenyl]-3-yl)morpholino)prop-2-en-1-one (Compound 1)

Procedure A

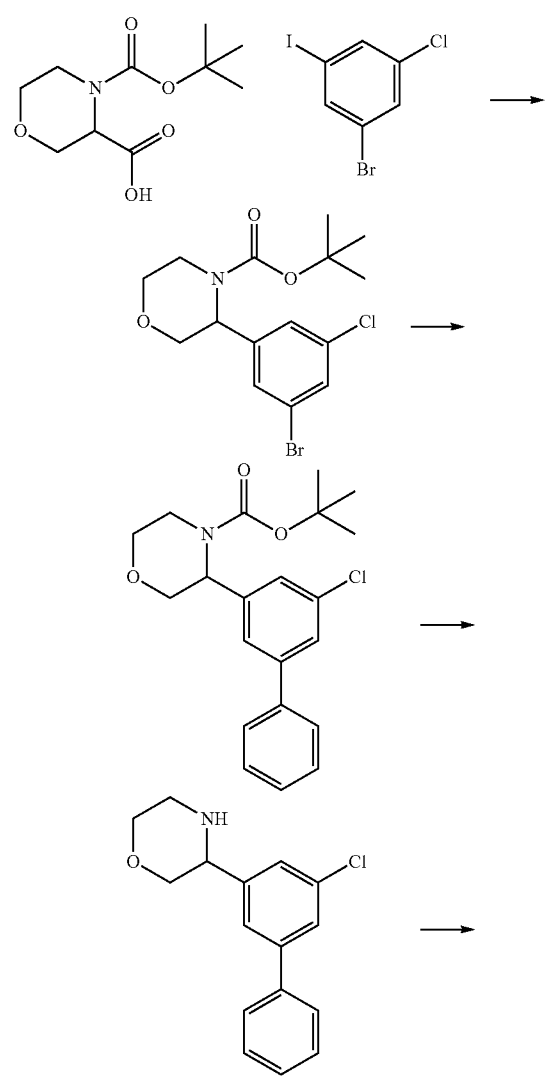

-continued

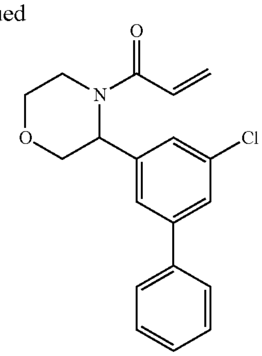

To a mixture of 4-(tert-butoxycarbonyl)morpholine-3-carboxylic acid (200 mg, 0.86 mmol) and 1-bromo-3-chloro-5-iodo-benzene (315 mg, 0.99 mmol) in DMF (6 mL, 0.14 M) was added $[IR(DF(CF_3)PPY)_2(DTBPY)]PF_6$ (9.7 mg, 0.0086 mmol), nickel(II) chloride (19 mg, 0.086 mmol), dtbbpy (34 mg, 0.12 mmol), and $Cs_2CO_3$ (845 mg, 2.59 mmol) at 20° C. under $N_2$ in the glovebox. The mixture was stirred and irradiated using 34 W blue LED lamps for 12 hours at 25° C. The mixture was poured into ice water (100 mL), extracted with EtOAc (50 mL, 2 eq), washed with brine, dried over $Na_2SO_4$, filtered, and concentrated under vacuum. The crude product was chromatographed on silica gel (PE/EtOAc 100:1→0:1) to give the tert-butyl 3-(3-bromo-5-chlorophenyl)morpholine-4-carboxylate (300 mg, 92% yield) as a white solid.

To a mixture of tert-butyl 3-(3-bromo-5-chloro-phenyl) morpholine-4-carboxylate (100 mg, 0.26 mmol) and phenylboronic acid (37 mg, 0.31 mmol) in 1,4-dioxane (2 mL), MeCN (2 mL), and water (1 mL) was added $K_2CO_3$ (2 eq, 75 mg) and $Pd(PPh_3)_4$(30 mg) at 20° C. under $N_2$. The mixture was stirred for 3 hours at 90° C. The reaction solution was poured into ice water (30 mL), extracted with EtOAc (20 mL*2), washed with brine, dried over $Na_2SO_4$, filtered, and concentrated under vacuum. The residue was purified by prep-TLC ($SiO_2$, PE:EtOAc=5:1) to afford tert-butyl 3-(5-chloro-[1,1'-biphenyl]-3-yl)morpholine-4-carboxylate (170 mg) as a yellow oil.

To tert-butyl 3-(3-chloro-5-phenyl-phenyl)morpholine-4-carboxylate (170 mg, 0.45 mmol) in ethyl acetate (5 mL, 0.09 M) was added HCl in EtOAc (10 mL) at 20° C. and stirred for 3 hours. The mixture was concentrated under vacuum to afford 3-(5-chloro-[1,1'-biphenyl]-3-yl)morpholine HCl (170 mg) as a white solid.

To a mixture of 3-(5-chloro-[1,1'-biphenyl]-3-yl)morpholine HCl (170 mg, 0.62 mmol) in DCM (5 mL, 0.12 M) was added triethylamine (94 mg, 0.93 mmol) and acryloyl chloride (56 mg, 0.62 mmol) at 0° C. The mixture was allowed to warm to 25° C. and stirred for 20 minutes. The mixture was poured into ice water (3 mL), extracted with DCM (2 mL*2), washed with brine, dried over $Na_2SO_4$, filtered, and concentrated under vacuum. The residue was purified by prep-TLC and concentrated under vacuum to afford 1-(3-(5-chloro-[1,1'-biphenyl]-3-yl)morpholino)prop-2-en-1-one (48 mg, 22% yield) as a colorless oil. LC-MS m/z: 328.1 [M+1].

Stereochemistry: racemic.

Example 2. Synthesis of 1-(3-(3-chloro-5-(tetrahydro-2H-pyran-4-yl)phenyl)morpholino)prop-2-en-1-one (Compound 5)

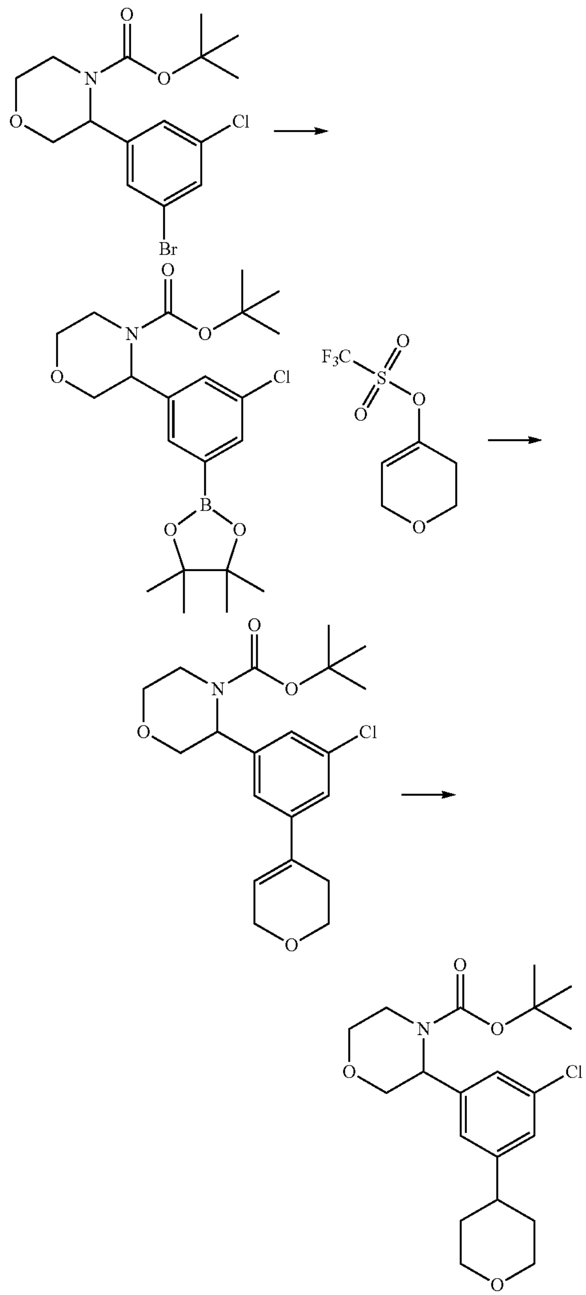

tert-butyl 3-(3-bromo-5-chloro-phenyl)morpholine-4-carboxylate was obtained from Procedure A To a mixture of tert-butyl 3-(3-bromo-5-chloro-phenyl) morpholine-4-carboxylate (660 mg, 1.75 mmol) and bis (pinacolato)diboron (1334 mg, 5.25 mmol) in 1,4-dioxane (10 mL, 0.17 M) was added AcOK (2 eq, 345 mg) and $Pd(dppf)Cl_2{\cdot}CH_2Cl_2$ (0.1 eq, 100 mg) at 25° C. The reaction was stirred for 3 hours at 120° C. under $N_2$. The mixture was poured into ice water (30 mL), extracted with EtOAc (20 mL*2), washed with brine, dried over $Na_2SO_4$, filtered, and concentrated under vacuum. The crude product was chromatographed on silica gel (PE/EtOAc 1:0→0:1) to give tert-butyl 3-(3-chloro-5-(4,4,5,5-tetramethyl-1,3,2-dioxaborolan-2-yl)phenyl)morpholine-4-carboxylate (700 mg, 94% yield) as a white solid.

To a mixture of 3,6-dihydro-2H-pyran-4-yl trifluoromethanesulfonate (263 mg, 1.13 mmol) and tert-butyl 3-(3-chloro-5-(4,4,5,5-tetramethyl-1,3,2-dioxaborolan-2-yl)phenyl)morpholine-4-carboxylate (400 mg, 0.94 mmol) in ethanol (2 mL, 0.14 M), toluene (4 mL, 0.14 M), and water (0.5 mL, 0.14 M) was added $NaHCO_3$ (3 eq, 290 mg) and $Pd(PPh_3)_2Cl_2$ (40 mg) at 25° C. The reaction was stirred for 3 hours at 130° C. under $N_2$. The mixture was poured into ice water (20 mL), extracted with EtOAc (20 mL*2), washed with brine, dried over $Na_2SO_4$, filtered, and concentrated under vacuum. The residue was purified by prep-TLC ($SiO_2$, PE:EtOAc=2:1) and concentrated under vacuum to give tert-butyl 3-(3-chloro-5-(3,6-dihydro-2H-pyran-4-yl)phenyl)morpholine-4-carboxylate (130 mg, 36% yield) as a colorless oil.

To a mixture of tert-butyl 3-(3-chloro-5-(3,6-dihydro-2H-pyran-4-yl)phenyl)morpholine-4-carboxylate (20 mg, 0.052 mmol) in ethyl acetate (5 mL, 0.01 M) was added $PtO_2$ (20 mg) at 25° C. and stirred for 3 hours at 25° C. under H2 (15 psi). The mixture was concentrated under vacuum to give crude tert-butyl 3-(3-chloro-5-(tetrahydro-2H-pyran-4-yl)phenyl)morpholine-4-carboxylate (20 mg) as a colorless oil. The crude material was used for the next step.

Using tert-butyl 3-(3-chloro-5-(tetrahydro-2H-pyran-4-yl)phenyl)morpholine-4-carboxylate at Step 3 of Procedure A, the title compound was obtained. LC-MS m/z: 336.1 [M+1].

Enantiomeric Separation Conditions: Column: REGIS (s,s) WHELK-01 (250 mm*30 mm, 10 um); Mobile Phase: $CO_2$ and MeOH. Retention time 2.03.

Stereochemistry: single enantiomer of unknown absolute configuration.

Example 3. Procedure B and Synthesis of (R)-1-(3-(3-(2-aminopyridin-4-yl)-5-chlorophenyl)morpholino)prop-2-en-1-one (Compound 136)

Procedure B

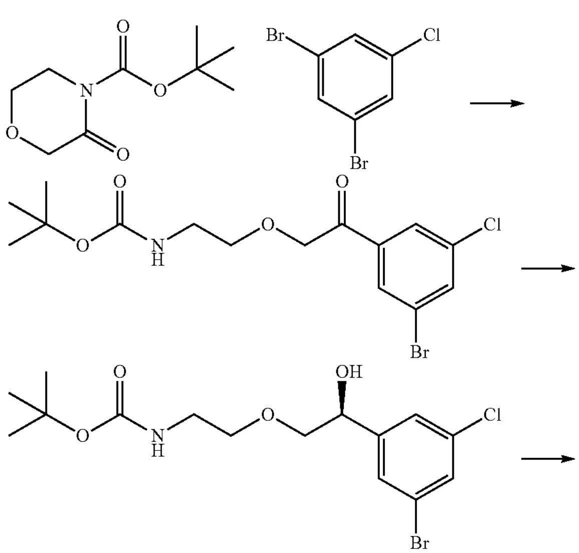

-continued

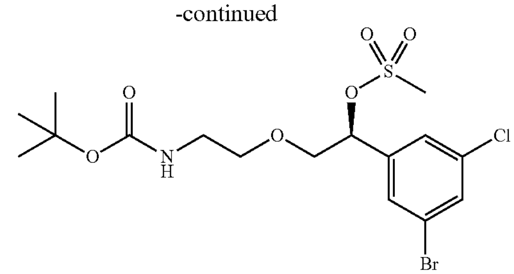

n-Butyllithium (2.5 M, 29.59 mL, 73.97 mmol, 1 equiv) was added dropwise to a solution of 1,3-dibromo-5-chlorobenzene (20 g, 73.97 mmol, 1 equiv) in isopropyl ether (200 mL) at −65° C. under $N_2$ and then stirred for 1 hour. tert-Butyl 3-oxomorpholine-4-carboxylate (14.88 g, 73.97 mmol, 1 equiv) in isopropyl ether (100 mL) was added dropwise and stirred for 1 hour at −65° C.

The mixture was quenched with saturated aqueous $NH_4Cl$ (100 mL). The solution was extracted with EtOAc (100 mL) and the combined organic phase was washed with brine (100 mL), dried by $Na_2SO_4$, filtered, and concentrated under vacuum. The residue was purified by column chromatography ($SiO_2$, petroleum ether:ethyl acetate=1:0 to 4:1) to afford tert-butyl N-[2-[2-(3-bromo-5-chloro-phenyl)-2-oxo-ethoxy]ethyl]carbamate (6.0 g, 15.28 mmol, 21% yield) as yellow oil.

$BH_3$-THF (5.88 mL, 5.88 mmol, 1.1 equiv) was added to (S)-2-methyl-CBS-oxazaborolidine (1.02 g, 1.06 mmol) in THF (10 mL) at 0° C. under $N_2$. The mixture was allowed to warm to 25° C. and stirred for 1 hour. A solution of tert-butyl N-[2-[2-(3-bromo-5-chloro-phenyl)-2-oxo-ethoxy]ethyl]carbamate (2.1 g, 5.34 mmol, 1 equiv) in THF (15 mL) was added at 0° C. The mixture was allowed to warm to 25° C. and stirred for 1 hour. The reaction was quenched with MeOH (15 mL) at 0° C., stirred for 2 hours at 25° C., and then concentrated under vacuum. The crude residue was purified by column chromatography ($SiO_2$, 6-15% EtOAc in pet ether) to afford (S)-(2-(2-(3-bromo-5-chlorophenyl)-2-hydroxyethoxy)ethyl)carbamate (1.80 g, 4.56 mmol, 85% yield) as white oil. Stereochemistry assigned according to Angew. Chem. Int. Ed. 1998, 37, 1986-2012.

To a solution of tert-butyl (S)-(2-(2-(3-bromo-5-chlorophenyl)-2-hydroxyethoxy)ethyl)carbamate (1.80 g, 4.56 mmol, 1 equiv) in DCM (15 mL) was added 4-(dimethylamino)pyridine (27 mg, 0.23 mmol, 0.05 equiv) and triethylamine (1.38 g, 13 mmol) at 0° C. A solution of methylsulfonyl methanesulfonate (1.191 g, 6.84 mmol, 1.5 equiv) in DCM (5 mL) was added slowly at 0° C. and then allowed to warm to room temperature and stirred for 16 hours. The reaction mixture was poured into water (15 mL) and extracted with DCM (20 mL*3). The combined organic layers were washed with brine (15 mL*2), dried over $Na_2SO_4$, filtered, and concentrated under reduced pressure. The residue was purified by column chromatography (petroleum ether:ethyl acetate=3:1 to 0:1) to afford (S)-1-(3-bromo-5-chlorophenyl)-2-(2-((tert-butoxycarbonyl)amino)ethoxy)ethyl methanesulfonate (2.00 g, 4.23 mmol, 93% yield) as white solid.

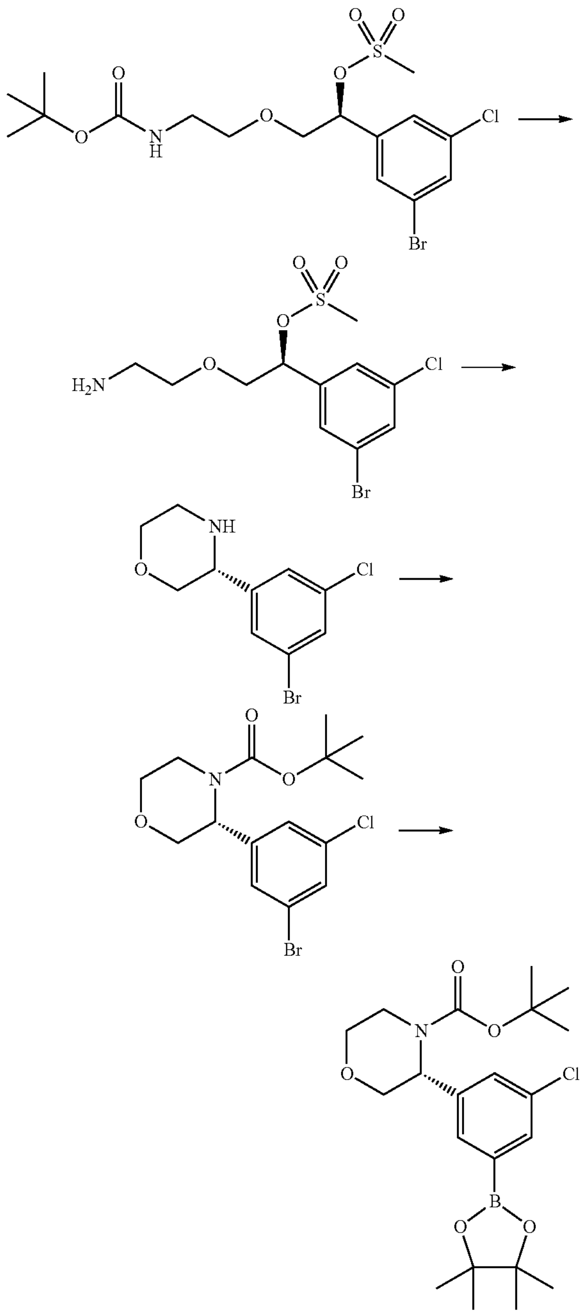

To a solution of (S)-1-(3-bromo-5-chlorophenyl)-2-(2-((tert-butoxycarbonyl)amino)ethoxy)ethyl methanesulfonate (100 g, 211 mmol, 1 equiv) in 1,4-dioxane (200 mL, 1.06 M) was added HCl in dioxane (4 M, 1000 mL) at 0° C. The mixture was allowed to warm to 25° C. and stirred for 3 hours. The mixture was concentrated under vacuum to afford (S)-2-(2-aminoethoxy)-1-(3-bromo-5-chlorophenyl) ethyl methanesulfonate HCl as colorless oil and used in the next step without purification.

To a solution of (S)-2-(2-aminoethoxy)-1-(3-bromo-5-chlorophenyl)ethyl methanesulfonate HCl (16.5 g, 44 mmol) in DCM (200 mL, 0.22 M) was added N,N-diethylethanamine (26.8 g, 265 mmol) at 0° C. under $N_2$. The reaction was stirred at 25° C. for 16 hours. The solution was diluted with $H_2O$ (40 mL), extracted with EtOAc (40 mL*3), washed with brine (100 mL), dried over $Na_2SO_4$, filtered, and concentrated under vacuum. The crude product was purified by silica gel column chromatography (petroleum ether:ethyl acetate=100:0 to 88:12) to afford (R)-3-(3-bromo-5-chlorophenyl)morpholine (3.90 g, 14.1 mmol, 32% yield) as yellow solid.

To a solution of (R)-3-(3-bromo-5-chlorophenyl)morpholine (5 g, 18.07 mmol) in DCE (60 mL, 0.30 M) was added triethylamine (3658 mg, 36 mmol), 4-(dimethylamino)pyridine (2208 mg, 18 mmol), and di-tert-butyl dicarbonate (7891 mg, 36 mmol) at 0° C. The mixture was stirred at 70° C. for 16 hours under $N_2$. The reaction mixture was poured into water (80 mL) and extracted with DCM (80 mL*3). The combined organic layers were washed with brine (50 mL*2), dried over $Na_2SO_4$, filtered, and concentrated under reduced pressure. The residue was purified by flash silica gel chromatography (ISCO®; 80 g SEPAFLASH® Silica Flash column, eluent of 0-30% ethyl acetate/petroleum ether gradient @ 75 mL/min) to afford tert-butyl (R)-3-(3-bromo-5-chlorophenyl)morpholine-4-carboxylate (4.90 g, 13.0 mmol, 72% yield) as a yellow solid.

$Pd(dppf)Cl_2$ (578 mg, 0.1 equiv) was added to a solution tert-butyl (R)-3-(3-bromo-5-chlorophenyl)morpholine-4-carboxylate (3 g, 7.96 mmol, 1 equiv), bis(pinacolato) diboron (2427 mg, 9.55 mmol, 1.2 equiv), and potassium acetate (1954 mg, 19.91 mmol, 2.5 equiv) in 1,4-dioxane (30 mL, 0.26 M) at 25° C. under $N_2$. The reaction was stirred at 80° C. for 3 hours. The mixture was poured into water (10 mL), extracted with ethyl acetate (10 mL*2), washed with brine, dried over $Na_2SO_4$, filtered, and concentrated under vacuum. The crude product was chromatographed on silica gel (pet ether/ethyl acetate) to afford tert-butyl (R)-3-(3-chloro-5-(4,4,5,5-tetramethyl-1,3,2-dioxaborolan-2-yl)phenyl)morpholine-4-carboxylate (2700 mg, 6.37 mmol, 80% yield) as yellow oil.

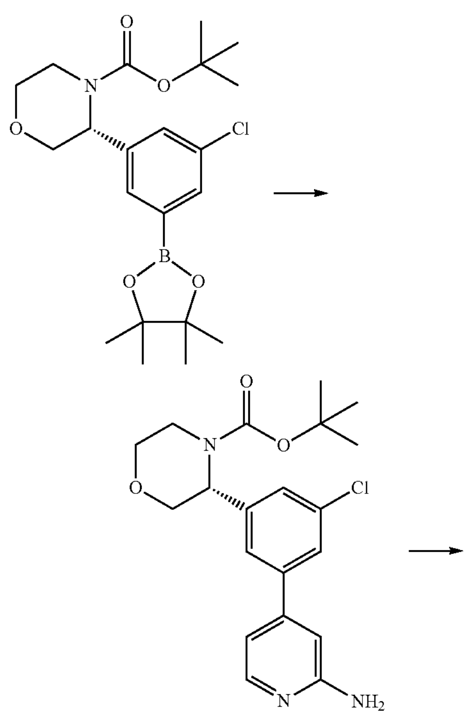

-continued

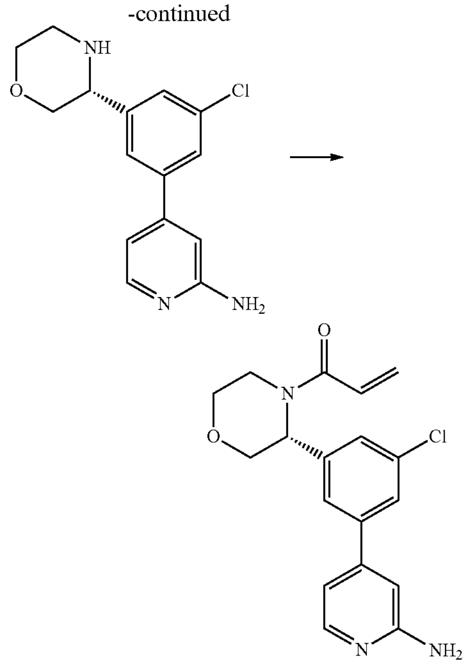

Pd(dppf)$Cl_2$ (20 mg, 0.028 mmol, 0.1 equiv) was added to a solution of tert-butyl (R)-3-(3-chloro-5-(4,4,5,5-tetramethyl-1,3,2-dioxaborolan-2-yl)phenyl)morpholine-4-carboxylate (120 mg, 0.28 mmol, 1 equiv), 2-amino-4-bromopyridine (58 mg, 0.33 mmol, 1.2 equiv), and potassium carbonate (97 mg, 0.70 mmol, 2.5 equiv) in 1,4-dioxane (2 mL) and water (0.4 mL) at 25° C. under $N_2$. The reaction was stirred at 80° C. for 3 hours under $N_2$. The mixture was poured into water (4 mL), extracted with ethyl acetate (4 mL*2), washed with brine, dried over $Na_2SO_4$, filtered, and concentrated under vacuum. The residue was purified by prep-TLC ($SiO_2$, PE:EtOAc=1:5) to afford tert-butyl (R)-3-(3-(2-aminopyridin-4-yl)-5-chlorophenyl)morpholine-4-carboxylate (90 mg, 0.23 mmol, 82% yield) as a yellow oil.

4M HCl in EtOAc (1 mL) was added to a solution tert-butyl (R)-3-(3-(2-aminopyridin-4-yl)-5-chlorophenyl) morpholine-4-carboxylate (100 mg, 0.25 mmol, 1 equiv) in EtOAc (1 mL) at 0° C. The mixture was stirred at 25° C. for 3 hours and then concentrated to afford crude (R)-4-(3-chloro-5-(morpholin-3-yl)phenyl)pyridin-2-amine HCl (100 mg, 0.24 mmol, 94% yield).

Triethylamine (55 mg, 0.55 mmol, 2 equiv) was added to a solution of (R)-4-(3-chloro-5-(morpholin-3-yl)phenyl) pyridin-2-amine HCl (80 mg, 0.27 mmol, 1 equiv) in DCM (1 mL) at 0° C. Acryloyl chloride (14 mg, 0.16 mmol, 0.6 equiv) in DCM (1 mL) was added at 0° C. The mixture was stirred at 25° C. for 1 hour. The reaction mixture was poured into water (3 mL), extracted with DCM (3 mL*3), washed with brine (3 mL*2), dried over $Na_2SO_4$, filtered, and concentrated under reduced pressure. The residue was purified by prep-TLC ($SiO_2$, MeOH:EtOAc=1:10) to afford (R)-1-(3-(3-(2-aminopyridin-4-yl)-5-chlorophenyl)morpholino)prop-2-en-1-one (24 mg, 0.066 mmol, 24% yield) as pale yellow solid. LC-MS m/z: 344.1 [M+1].

Stereochemistry: single enantiomer of known absolute configuration.

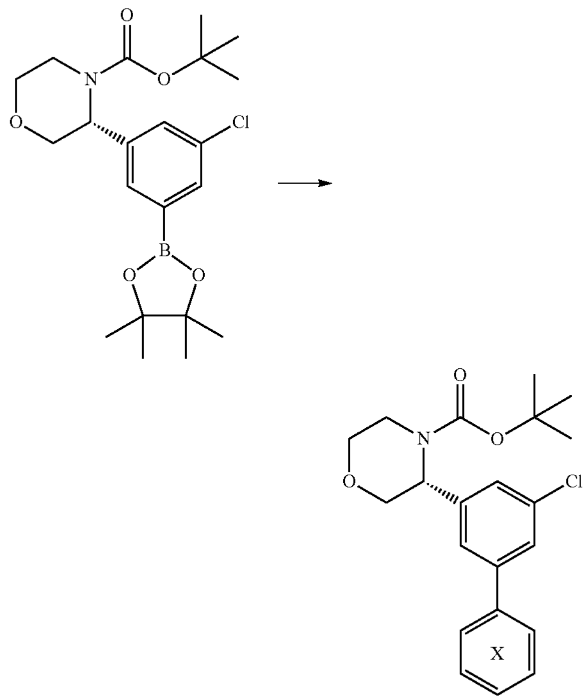

Using the appropriate coupling partner in Procedure B, the title compounds can be obtained. All compounds are single enantiomers of known absolute configuration.

| Cmp | Name | Coupling Partner in Step 8 | LC-MS m/z [M + 1] |
|---|---|---|---|
| 136 | (R)-1-(3-(3-(2-aminopyridin-4-yl)-5-chlorophenyl)morpholino)prop-2-en-1-one | 2-amino-4-bromopyridine | 344.1 |
| 10 | (R)-1-(3-(3-chloro-5-(pyrimidin-2-yl)phenyl)morpholino)prop-2-en-1-one | 2-bromopyridine | 330.1 |
| 12 | (R)-1-(4-(3-(4-acryloylmorpholin-3-yl)-5-chlorophenyl)pyridin-2-yl)pyrrolidin-2-one | 1-(4-bromopyridin-2-yl)pyrrolidin-2-one | 412.1 |
| 13 | (R)-4-(3-(4-acryloylmorpholin-3-yl)-5-chlorophenyl)-1-methylpyridin-2(1H)-one | 4-bromo-1-methylpyridin-2(1H)-one | 359.0 |
| 19 | (R)-1-(3-(3-chloro-5-(5-fluoropyrimidin-2-yl)phenyl)morpholino)prop-2-en-1-one | 2-bromo-5-fluoropyrimidine | 348.0 |
| 62 | (R)-2-(3-(3-(4-acryloylmorpholin-3-yl)-5-chlorophenyl)-1H-1,2,4-triazol-1-yl)acetamide | 2-(3-bromo-1H-1,2,4-triazol-1-yl)acetamide | 376.1 |

-continued

Using the appropriate coupling partner in Procedure B, the title compounds can be obtained. All compounds are single enantiomers of known absolute configuration.

| Cmp | Name | Coupling Partner in Step 8 | LC-MS m/z [M + 1] |
|---|---|---|---|
| 213 | (R)-5-(3-(4-acryloylmorpholin-3-yl)-5-chlorophenyl)-1-methylpyrimidin-2(1H)-one | 5-bromo-1-methylpyrimidin-2(1H)-one | 360.1 |
| 214 | (R)-1-(3-(3-chloro-5-(4-(methylamino)-1,3,5-triazin-2-yl)phenyl)morpholino)prop-2-en-1-one | 4-chloro-N-methyl-1,3,5-triazin-2-amine | 360.1 |
| 298 | (R)-2-(3-(4-acryloylmorpholin-3-yl)-5-chlorophenyl)isonicotinamide | 2-bromoisonicotinamide | 372.1 |

Example 4. Procedure C and Synthesis of (R)-3'-(4-acryloylmorpholin-3-yl)-5'-chloro-4-fluoro-[1,1'-biphenyl]-3-carboxamide (Compound 44)

Procedure C

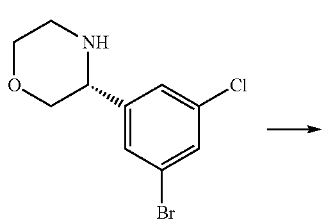

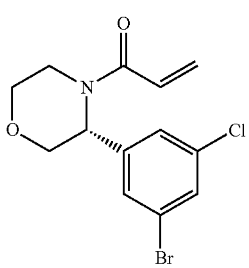

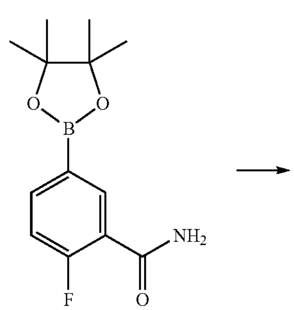

-continued

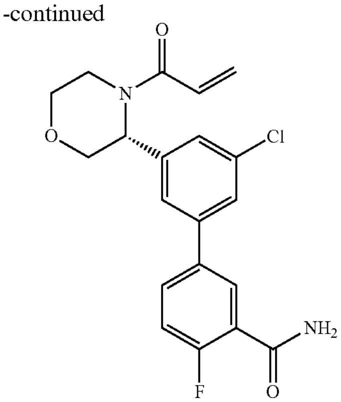

(R)-3-(3-bromo-5-chlorophenyl)morpholine was obtained from Step 5 of Procedure B.

To a solution of (R)-3-(3-bromo-5-chlorophenyl)morpholine (5 g, 18.07 mmol, 1 equiv) in DCM (60 mL, 0.30 M) was added triethylamine (2.74 g, 27 mmol, 1.5 equiv) and acryloyl chloride (1.8 g, 19.88 mmol, 1.1 equiv) dropwise at 0° C. under $N_2$. The mixture was stirred for 2 hours at 25° C. and then poured into $H_2O$ (40 mL). The aqueous phase was extracted with DCM (30 mL*3). The combined organic phase was washed with brine (20 mL*2), dried over $Na_2SO_4$, filtered, and concentrated under vacuum. The residue was purified by flash silica gel chromatography (PE/EA=77/23 to 3/1) to afford (R)-1-(3-(3-bromo-5-chlorophenyl)morpholino)prop-2-en-1-one (5.17 g, 15.6 mmol, 86% yield) as a yellow oil.

To a solution of (R)-1-(3-(3-bromo-5-chlorophenyl)morpholino)prop-2-en-1-one (310 mg, 0.93 mmol) in 1,4-dioxane (8 mL, 0.09 M) and water (1.6 mL, 0.097 M) was added 2-fluoro-5-(4,4,5,5-tetramethyl-1,3,2-dioxaborolan-2-yl)benzamide (298 mg, 1.12 mmol, 1.2 equiv) and potassium carbonate (324 mg, 2.34 mmol, 2.5 equiv). Pd(dppf)$Cl_2$ (68 mg, 0.093 mmol) was added, and the resulting mixture was stirred at 80° C. for 16 hours under $N_2$. The reaction mixture was quenched by saturated aqueous $NH_4Cl$ (15 mL) and extracted with EtOAc (20 mL*3). The organic layers were washed 20 mL saturated brine solution. The organic layer was then separated, dried over $Na_2SO_4$, filtered, and concentrated. The crude residue was purified by column chromatography ($SiO_2$, petroleum ether/ethyl acetate=0.5/1 to 0/1) to afford the title compound (96.8 mg, 0.36 mmol, 38% yield) as white solid. LC-MS m/z: 389.1 [M+1].

Stereochemistry: single enantiomer of known absolute configuration.

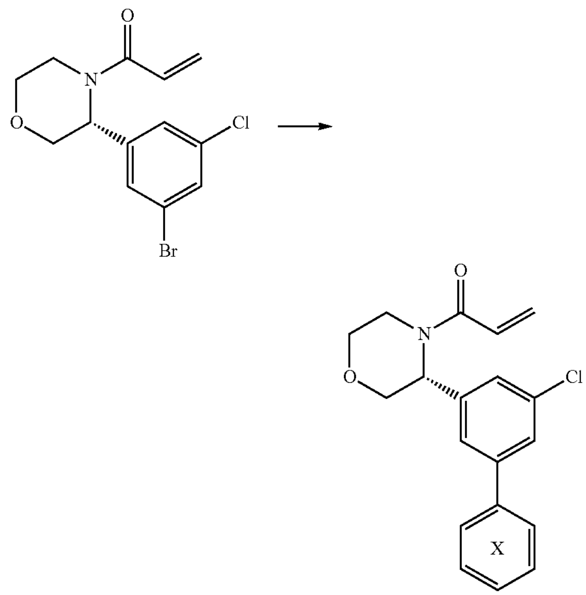

Using the appropriate coupling partner in Procedure C, the title compounds can be obtained. All compounds are single enantiomers of known absolute configuration.

| Cmp. | Name | Coupling Partner in Step 2 | LC-MS m/z [M + 1] |
|---|---|---|---|
| 44 | (R)-3'-(4-acryloylmorpholin-3-yl)-5'-chloro-4-fluoro-[1,1'-biphenyl]-3-carboxamide | 2-fluoro-5-(4,4,5,5-tetramethyl-1,3,2-dioxaborolan-2-yl)benzamide | 389.1 |
| 2 | (R)-N-(3'-(4-acryloylmorpholin-3-yl)-5'-chloro-[1,1'-biphenyl]-3-yl)acetamide | (3-acetamidophenyl)boronic acid | 385.1 |
| 82 | (R)-6-(3-(4-acryloylmorpholin-3-yl)-5-chlorophenyl)isoindolin-1-one | 6-(4,4,5,5-tetramethyl-1,3,2-dioxaborolan-2-yl)isoindolin-1-one | 383.1 |
| 90 | (R)-1-(3-(3-chloro-5-(2-methylpyridin-4-yl)phenyl)morpholino)prop-2-en-1-one | 2-methyl-4-(4,4,5,5-tetramethyl-1,3,2-dioxaborolan-2-yl)pyridine | 343.1 |
| 91 | (R)-1-(3-(3-chloro-5-(2-methoxypyridin-4-yl)phenyl)morpholino)prop-2-en-1-one | 2-methoxy-4-(4,4,5,5-tetramethyl-1,3,2-dioxaborolan-2-yl)pyridine | 359.1 |
| 97 | (R)-1-(3-(3-chloro-5-(1H-pyrrolo[2,3-b]pyridin-4-yl)phenyl)morpholino)prop-2-en-1-one | 4-(4,4,5,5-tetramethyl-1,3,2-dioxaborolan-2-yl)-1H-pyrrolo[2,3-b]pyridine | 368.0 |
| 115 | (R)-1-(3-(3-chloro-5-(1-cyclopropyl-1H-pyrazol-4-yl)phenyl)morpholino)prop-2-en-1-one | 1-cyclopropyl-4-(4,4,5,5-tetramethyl-1,3,2-dioxaborolan-2-yl)-1H-pyrazole | 358.2 |
| 116 | (R)-1-(3-(3-chloro-5-(1-methyl-1H-pyrazol-4-yl)phenyl)morpholino)prop-2-en-1-one | 1-methyl-4-(4,4,5,5-tetramethyl-1,3,2-dioxaborolan-2-yl)-1H-pyrazole | 332.1 |
| 117 | (R)-1-(3-(3-chloro-5-(1H-pyrazol-4-yl)phenyl)morpholino)prop-2-en-1-one | 4-(4,4,5,5-tetramethyl-1,3,2-dioxaborolan-2-yl)-1H-pyrazole | 318.1 |
| 135 | (R)-1-(3-(3-(5-aminopyrimidin-2-yl)-5-chlorophenyl)morpholino)prop-2-en-1-one | (2-aminopyrimidin-5-yl)boronic acid | 345.1 |

Example 5. Procedure D and Synthesis of (R)-1-(3-(3-(4-aminopyrimidin-2-yl)-5-chlorophenyl)morpholino)prop-2-en-1-one (Compound 96)

Procedure D
Procedure D

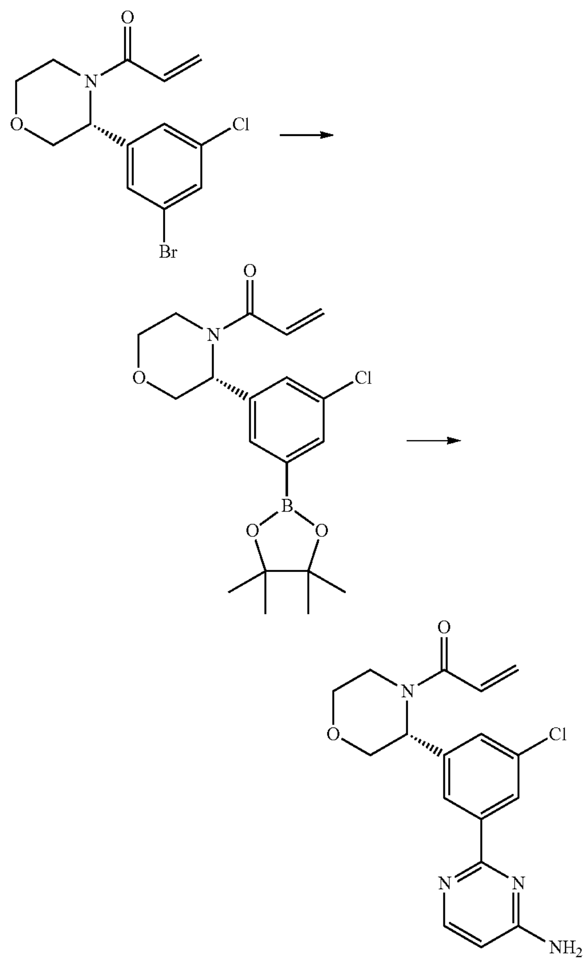

(R)-1-(3-(3-bromo-5-chlorophenyl)morpholino)prop-2-en-1-one was obtained from Procedure C.

To a solution of (R)-1-(3-(3-bromo-5-chlorophenyl)morpholino)prop-2-en-1-one (5.8 g, 17 mmol, 1 equiv) and bis(pinacolato)diboron (6.68 g, 26.31 mmol, 1.5 equiv) in 1,4-dioxane (60 mL, 0.29 M) was added potassium acetate (4.30 g, 43 mmol, 2.5 equiv) and Pd(dppf)$Cl_2$ (0.89 g, 1.22 mmol, 0.07 equiv). The mixture and was stirred at 80° C. under $N_2$ for 16 hours. The solution was filtered and concentrated. The residue was dissolved in EtOAc (10 ml), washed with water (8 mL×2), brine (8 mL×2), dried over $Na_2SO_4$, filtered, and concentrated to afford 5.9 g of crude (R)-1-(3-(3-chloro-5-(4,4,5,5-tetramethyl-1,3,2-dioxaborolan-2-yl)phenyl)morpholino)prop-2-en-1-one as a brown oil. The crude material was used in the next step.

To a solution of (R)-1-(3-(3-chloro-5-(4,4,5,5-tetramethyl-1,3,2-dioxaborolan-2-yl)phenyl)morpholino)prop-2-en-1-one (30 mg, 0.0794 mmol, 1 equiv) and 2-chloropyrimidin-4-amine (10.29 mg, 0.079 mmol, 1 equiv) in 1,4-dioxane (2 mL, 0.03 M) was added Pd(dppf)$Cl_2$ (5.7 mg, 0.0079 mmol, 0.1 equiv) and potassium carbonate (21.9 mg, 0.15 mmol, 2 equiv) at 0° C. The mixture was stirred for 6 hours at 80° C. The reaction mixture was poured into water (5 mL) and extracted with EtOAc (5 mL*3). The combined organic layers were washed with brine (10 mL), dried over $Na_2SO_4$, filtered, and concentrated under reduced pressure. The residue was purified by prep-TLC (EtOAc, Rf=0.45) to afford the title compound (5 mg, 0.014 mmol, 18% yield) as a white solid. LC-MS m/z: 345.1 [M+1].

Stereochemistry: single enantiomer of known absolute configuration.

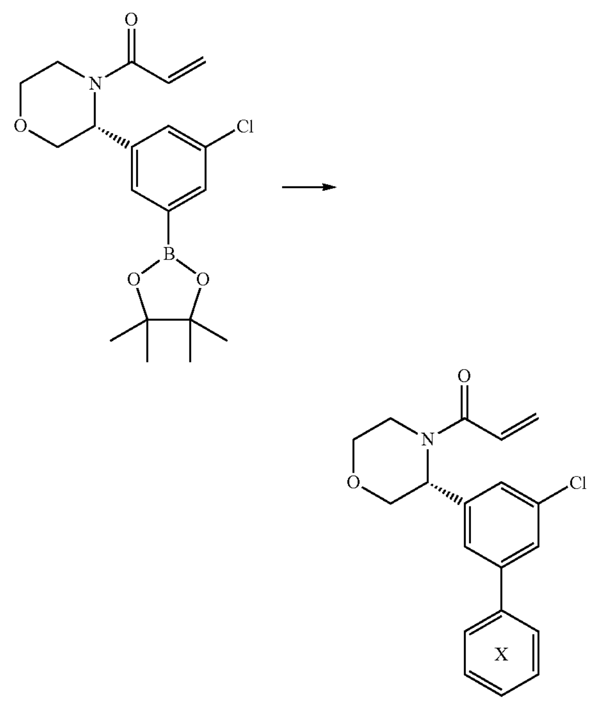

Using the appropriate coupling partner in Procedure D, the title compounds can be obtained. All compounds are single enantiomers of known absolute configuration.

| Cmp | Name | Coupling Partner in Step 2 | LC-MS m/z [M + 1] |
|---|---|---|---|
| 96 | (R)-1-(3-(3-(4-aminopyrimidin-2-yl)-5-chlorophenyl)morpholino)prop-2-en-1-one | 2-chloropyrimidin-4-amine | 345.1 |
| 80 | (R)-1-(3-(3-(6-aminopyrimidin-4-yl)-5-chlorophenyl)morpholino)prop-2-en-1-one | 4-amino-6-chloropyrimidine | 345.1 |
| 86 | (R)-1-(3-(3-chloro-5-(6-methoxypyrimidin-4-yl)phenyl)morpholino)prop-2-en-1-one | 4-chloro-6-methoxypyrimidine | 360.1 |
| 87 | (R)-1-(3-(3-chloro-5-(4-methylpyrimidin-2-yl)phenyl)morpholino)prop-2-en-1-one | 2-chloro-4-methylpyrimidine | 344.1 |

-continued

| Cmp | Name | Coupling Partner in Step 2 | LC-MS m/z [M + 1] |
|---|---|---|---|
| 88 | (R)-1-(3-(3-chloro-5-(4-methoxypyrimidin-2-yl)phenyl)morpholino)prop-2-en-1-one | 2-chloro-4-methoxypyrimidine | 360.1 |
| 92 | (R)-1-(3-(3-chloro-5-(5-methylpyrimidin-2-yl)phenyl)morpholino)prop-2-en-1-one | 2-chloropyrimidin-5-amine | 345.1 |
| 93 | (R)-1-(3-(3-chloro-5-(4,6-dimethylpyrimidin-2-yl)phenyl)morpholino)prop-2-en-1-one | 2-chloro-4,6-dimethylpyrimidine | 358.1 |
| 95 | (R)-1-(3-(3-(4-amino-6-methylpyrimidin-2-yl)-5-chlorophenyl)morpholino)prop-2-en-1-one | 2-chloro-6-methylpyrimidin-4-amine | 359.0 |
| 98 | (R)-1-(3-(3-chloro-5-(6-methylpyridin-2-yl)phenyl)morpholino)prop-2-en-1-one | 2-bromo-6-methylpyridine | 343.1 |
| 100 | (R)-1-(3-(3-chloro-5-(6-methoxypyridin-2-yl)phenyl)morpholino)prop-2-en-1-one | 2-chloro-6-methoxypyridine | 359.2 |
| 101 | (R)-1-(3-(3-chloro-5-(5-methylpyrimidin-2-yl)phenyl)morpholino)prop-2-en-1-one | 2-chloro-5-methylpyrimidine | 344.1 |
| 103 | (R)-1-(3-(3-chloro-5-(5-methoxypyrimidin-2-yl)phenyl)morpholino)prop-2-en-1-one | 2-chloro-5-methoxypyrimidine | 360.1 |
| 104 | (R)-1-(3-(3-chloro-5-(4-methylpyridin-2-yl)phenyl)morpholino)prop-2-en-1-one | 2-chloro-4-methylpyridine | 343.1 |
| 105 | (R)-1-(3-(3-chloro-5-(4-methoxypyridin-2-yl)phenyl)morpholino)prop-2-en-1-one | 2-chloro-4-methoxypyridine | 359.1 |
| 106 | (R)-4-(3-(4-acryloylmorpholin-3-yl)-5-chlorophenyl)pyrimidine-2-carbonitrile | 4-chloropyrimidine-2-carbonitrile | 355.1 |
| 126 | (R)-1-(3-(3-chloro-5-(pyridin-4-yl)phenyl)morpholino)prop-2-en-1-one | 4-chloropyridine | 329.1 |
| 128 | (R)-1-(3-(3-(6-aminopyridazin-3-yl)-5-chlorophenyl)morpholino)prop-2-en-1-one | 6-bromopyridazin-3-amine | 345.1 |
| 132 | (R)-1-(3-(3-(5-aminopyridazin-3-yl)-5-chlorophenyl)morpholino)prop-2-en-1-one | 6-chloropyridazin-4-amine | 345.1 |
| 199 | (R)-1-(3-(3-(4-amino-6-chloro-1,3,5-triazin-2-yl)-5-chlorophenyl)morpholino)prop-2-en-1-one | 4,6-dichloro-1,3,5-triazin-2-amine | 380.0 |
| 218 | (R)-1-(3-(3-(4-amino-6-(methylamino)-1,3,5-triazin-2-yl)-5-chlorophenyl)morpholino)prop-2-en-1-one | 6-chloro-N2-methyl-1,3,5-triazine-2,4-diamine | 375.2 |
| 219 | (R)-1-(3-(3-chloro-5-(4-((2-hydroxyethyl)amino)-1,3,5-triazin-2-yl)phenyl)morpholino)prop-2-en-1-one | 2-((4-chloro-1,3,5-triazin-2-yl)amino)ethan-1-ol | 390.2 |
| 235 | (R)-1-(3-(3-(5-amino-1H-pyrazol-3-yl)-5-chlorophenyl)morpholino)prop-2-en-1-one | 3-bromo-1H-pyrazol-5-amine | 333.2 |
| 250 | (R)-1-(3-(3-(6-aminopyrazin-2-yl)-5-chlorophenyl)morpholino)prop-2-en-1-one | 6-bromopyrazin-2-amine | 345.0 |
| 251 | (R)-1-(3-(3-(5-aminopyrazin-2-yl)-5-chlorophenyl)morpholino)prop-2-en-1-one | 5-bromopyrazin-2-amine | 345.2 |
| 254 | (R)-1-(3-(3-(5-amino-4-methoxypyrimidin-2-yl)-5-chlorophenyl)morpholino)prop-2-en-1-one | 2-chloro-4-methoxypyrimidin-5-amine | 375.2 |
| 255 | (R)-1-(3-(3-(5-amino-6-methoxypyrazin-2-yl)-5-chlorophenyl)morpholino)prop-2-en-1-one | 5-bromo-3-methoxypyrazin-2-amine | 375.2 |
| 258 | (R)-1-(3-(3-chloro-5-(5,6-diaminopyrazin-2-yl)phenyl)morpholino)prop-2-en-1-one | 5-bromopyrazine-2,3-diamine | 360.0 |
| 259 | (R)-1-(3-(3-(6-amino-5-methoxypyrazin-2-yl)-5-chlorophenyl)morpholino)prop-2-en-1-one | 6-chloro-3-methoxypyrazin-2-amine | 375.2 |
| 261 | (R)-1-(3-(3-(4-amino-5-methoxypyrimidin-2-yl)-5-chlorophenyl)morpholino)prop-2-en-1-one | 2-chloro-5-methoxypyrimidin-4-amine | 375.2 |
| 268 | (R)-1-(3-(3-(5-amino-2-chloropyrimidin-4-yl)-5-chlorophenyl)morpholino)prop-2-en-1-one | 2,4-dichloropyrimidin-5-amine | 379.2 |
| 271 | (R)-1-(3-(3-(6-amino-2-chloropyrimidin-4-yl)-5-chlorophenyl)morpholino)prop-2-en-1-one | 2,6-dichloropyrimidin-4-amine | 379.2 |
| 55 | (R)-1-(3-(3-(4-amino-1,3,5-triazin-2-yl)-5-chlorophenyl)morpholino)prop-2-en-1-one | 4-chloro-1,3,5-triazin-2-amine | 346.1 |
| 141 | (R)-1-(3-(3-(6-aminopyridazin-4-yl)-5-chlorophenyl)morpholino)prop-2-en-1-one | 5-bromopyridazin-3-amine | 345.1 |
| 296 | (R)-1-(3-(3-chloro-5-(1H-pyrrolo[3,2-c]pyridin-6-yl)phenyl)morpholino)prop-2-en-1-one | 6-chloro-1H-pyrrolo[3,2-c]pyridine | 368.2 |

Example 6. Synthesis of (R)-1-(3-(3-chloro-5-(4-methyl-1H-pyrazol-1-yl)phenyl)morpholino)prop-2-en-1-one (Compound 118)

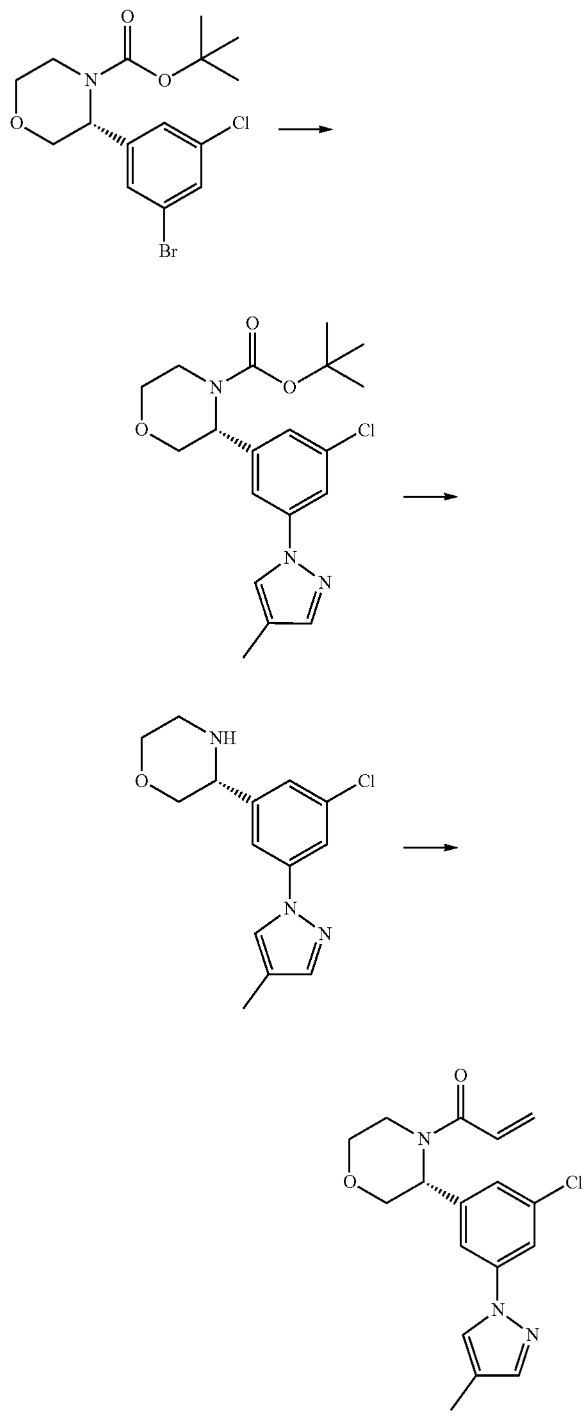

tert-butyl (R)-3-(3-bromo-5-chlorophenyl)morpholine-4-carboxylate was obtained from Step 6 of Procedure B.

To a solution of tert-butyl (R)-3-(3-bromo-5-chlorophenyl)morpholine-4-carboxylate (350 mg, 0.92 mmol, 1 equiv) in DMA (15 mL, 0.062 M) was added 4-methylpyrazole (152 mg, 1.85 mmol, 2 equiv), trans-N—N'-dimethylcyclohexane-1,2-diamine (97%) (26 mg, 0.18 mmol, 0.2 equiv), potassium tert-butoxide (312 mg, 2.78 mmol), and CuI (35 mg, 0.18 mmol). The mixture was stirred at 130° C. for 16 hours. The crude product was purified by prep-HPLC (column: Waters XBridge BEH C18 100*30 mm*10 um; liquid phase: [A-10 mM $NH_4HCO_3$ in $H_2O$; B-ACN] B %: 50%-80%, 10 min]) to afford tert-butyl (R)-3-(3-chloro-5-(4-methyl-1H-pyrazol-1-yl)phenyl)morpholine-4-carboxylate (40 mg, 0.084 mmol, 9% yield) as a white solid.

To a solution of tert-butyl (R)-3-(3-chloro-5-(4-methyl-1H-pyrazol-1-yl)phenyl)morpholine-4-carboxylate (20 mg, 0.053 mmol, 1 equiv) in ethyl acetate (3 mL, 0.017 M) was added HCl in ethyl acetate (4 M, 3 mL). The mixture was stirred at 20° C. for 4 hrs. The solution was concentrated under reduced pressure and the crude product was used directly without further purification.

To a solution (R)-3-(3-chloro-5-(4-methyl-1H-pyrazol-1-yl)phenyl)morpholine (16 mg, 0.057 mmol, 1 equiv) in DCM (3 mL, 0.019 M) was added triethylamine (8.74 mg, 0.086 mmol) and acryloyl chloride (6.25 mg, 0.069 mmol). The mixture was stirred at 20° C. under N2 for 3 hours. The reaction was poured into $H_2O$ (10 mL) and the aqueous layer was extracted with EtOAc (5 mL×3). The combined organic layer was washed with brine (10 mL), dried over $Na_2SO_4$, filtered, and concentrated under vacuum. The residue was purified by prep-TLC (PE:EtOAc=1/1) to afford the title compound (11 mg, 0.032 mmol, 56% yield) as a yellow solid. LC-MS m/z: 332.0 [M+1].

Stereochemistry: single enantiomer of known absolute configuration.

Example 7. Synthesis of (R)-1-(3-(3-chloro-5-(1,3,5-triazin-2-yl)phenyl)morpholino)prop-2-en-1-one (Compound 147)

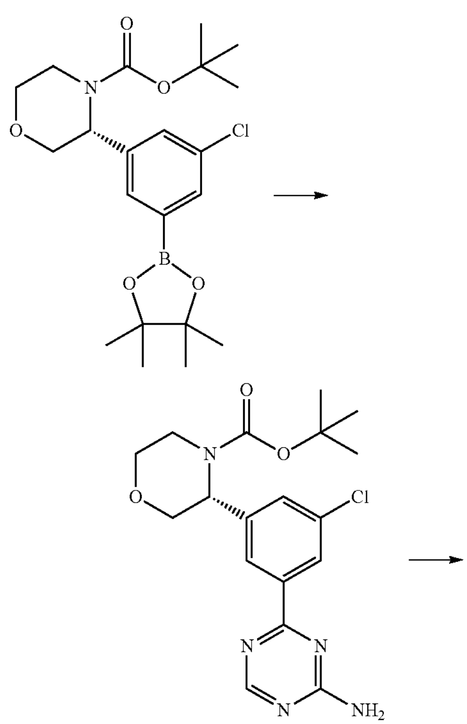

-continued

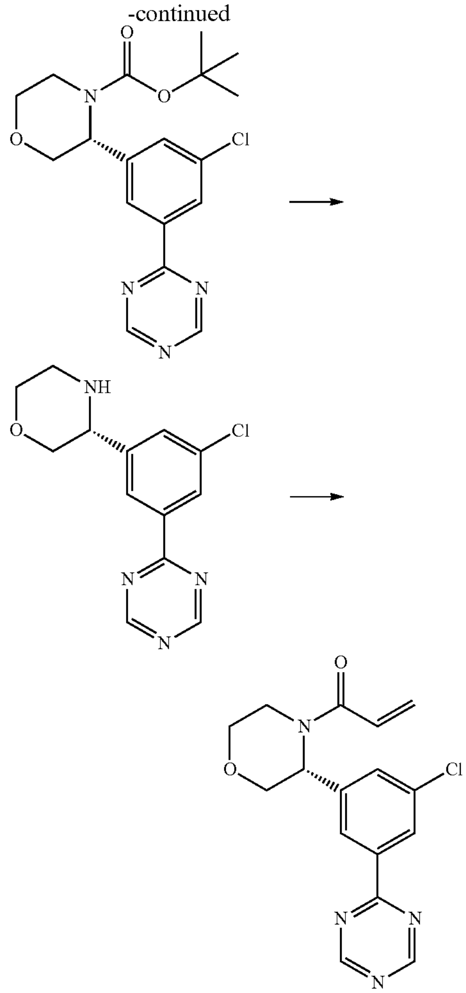

tert-butyl (R)-3-(3-chloro-5-(4,4,5,5-tetramethyl-1,3,2-dioxaborolan-2-yl)phenyl)morpholine-4-carboxylate was obtained from Step 7 of Procedure B.

Pd(dppf)$Cl_2$ (20 mg, 0.1 eq) was added to a solution of tert-butyl (R)-3-(3-chloro-5-(4,4,5,5-tetramethyl-1,3,2-dioxaborolan-2-yl)phenyl)morpholine-4-carboxylate (500 mg, 1.18 mmol, 1 equiv), 4-chloro-1,3,5-triazin-2-amine (231 mg, 1.77 mmol, 1.5 equiv), and potassium carbonate (407 mg, 2.94 mmol, 2.5 equiv) in 1,4-dioxane (2 mL, 0.49 M) and water (0.40 mL, 0.49 M) at 25° C. The reaction was stirred at 80° C. for 3 hours under $N_2$. The mixture was poured into water (4 mL), extracted with ethyl acetate (4 mL*2), washed with brine, dried over $Na_2SO_4$, filtered, and concentrated under vacuum. The residue was purified by prep-TLC ($SiO_2$, PE:ETOAC=1:5) to afford tert-butyl (R)-3-(3-(4-amino-1,3,5-triazin-2-yl)-5-chlorophenyl)morpholine-4-carboxylate (130 mg, 0.33 mmol, 28% yield) as a yellow solid.

To a solution of tert-butyl (R)-3-(3-(4-amino-1,3,5-triazin-2-yl)-5-chlorophenyl)morpholine-4-carboxylate (110 mg, 0.28 mmol, 1 equiv) in DMF (1.5 mL, 0.18 M) was added tert-butyl nitrite (86 mg, 0.84 mmol, 3 equiv) at 0° C. under $N_2$ and stirred at 80° C. for 3 hours. The mixture was poured into water (2 mL), extracted with ethyl acetate (1 mL*3), washed with brine, dried over $Na_2SO_4$, filtered, and concentrated under vacuum. The residue was purified by prep-TLC ($SiO_2$, PE:ETOAC=1:1) to afford tert-butyl (R)-3-(3-chloro-5-(1,3,5-triazin-2-yl)phenyl)morpholine-4-carboxylate (18 mg, 0.052 mmol, 19% yield) as a yellow solid.

HCl in EtOAc (1 mL, 4M) was added to a solution of (R)-3-(3-chloro-5-(1,3,5-triazin-2-yl)phenyl)morpholine-4-carboxylate (20 mg, 0.053 mmol, 1 equiv) in EtOAc (1 mL) at 0° C. The mixture was stirred at 25° C. for 3 hours. The solution was concentrated under vacuo to afford (R)-3-(3-chloro-5-(1,3,5-triazin-2-yl)phenyl)morpholine HCl (10 mg, 0.036 mmol, 68% yield).

Triethylamine (10 mg, 0.11 mmol, 1.5 equiv) was added to a solution (R)-3-(3-chloro-5-(1,3,5-triazin-2-yl)phenyl)morpholine (20 mg, 0.072 mmol, 1 equiv) in DCM (1 mL) at 0° C. A solution of acryloyl chloride (7.8 mg, 0.086 mmol, 1.2 equiv) in DCM (1 mL) was added slowly at 0° C. and then stirred at 25° C. for 1 hour. The reaction mixture was poured into water (3 mL), extracted with DCM (3 mL*3), washed with brine (3 mL*2), dried over $Na_2SO_4$, filtered, and concentrated under reduced pressure. The residue was purified by prep-TLC ($SiO_2$, EtOAc:PE=1:1) to afford the title compound (5.2 mg, 0.015 mmol, 22% yield) as pale yellow solid. LC-MS m/z: 331.1 [M+1].

Stereochemistry: single enantiomer of known absolute configuration.

Example 8. Synthesis of (R)-4-(3-(4-acryloylmorpholin-3-yl)-5-chlorophenyl)-6-amino-1,3,5-triazin-2(1H)-one (Compound 177)

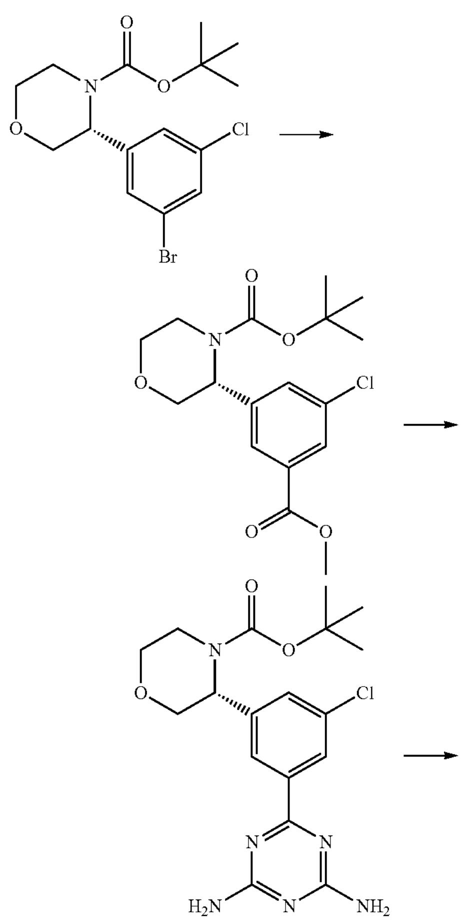

-continued

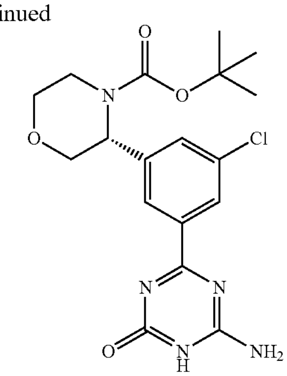

tert-butyl (R)-3-(3-bromo-5-chlorophenyl)morpholine-4-carboxylate was obtained from Procedure B.

To a solution of tert-butyl (R)-3-(3-bromo-5-chlorophenyl)morpholine-4-carboxylate (6.5 g, 17.25 mmol, 1 equiv) in methanol (180 mL, 0.095 M) was added triethylamine (17.46 g, 172 mmol, 10 equiv) and [1,1'Bis(diphenylphosphino)ferrocene]palladium(II) dichloride (1.25 g, 1.72 mmol, 0.1 equiv). The suspension was degassed and purged with CO several times and then stirred for 48 hours at 65° C. under CO (50 psi). The reaction mixture was filtered and concentrated. The material was taken up into water (30 mL), extracted with ethyl acetate (30 mL*2), washed with brine, dried over $Na_2SO_4$, filtered, and concentrated under vacuum. The residue was purified by flash column chromatography (PE:EA=1:0-5:1) to afford tert-butyl (R)-3-(3-chloro-5-(methoxycarbonyl)phenyl)morpholine-4-carboxylate (120 mg, 0.34 mmol, 64% yield) as yellow oil.

To a solution tert-butyl (R)-3-(3-chloro-5-(methoxycarbonyl)phenyl)morpholine-4-carboxylate (520 mg, 1.46 mmol, 1 equiv) in methanol (10 mL, 0.14 M) was added sodium borohydride (0.346 g, 9.15 mmol, 3 equiv), carbamimidoyl urea (596 mg, 5.84 mmol, 4 equiv), and sodium methoxide (631 mg, 11.69 mmol, 8 equiv). The mixture was stirred for 7 hours at 80° C. under $N_2$. The crude was then purified by prep-HPLC (column: Waters Xbridge BEH C18 100*30 mm*10 um; liquid phase: [A-10 mM $NH_4HCO_3$ in $H_2O$; B-ACN] B %: 20%-60%, 8 min]) to give tert-butyl (R)-3-(3-chloro-5-(4,6-diamino-1,3,5-triazin-2-yl)phenyl) morpholine-4-carboxylate (35 mg, 0.085 mmol, 6% yield) as a white solid.

Sodium nitrite (38.15 g, 553 mmol, 50 equiv) in water (40 mL, 0.092 M) was added to a solution of tert-butyl (R)-3-(3-chloro-5-(4,6-diamino-1,3,5-triazin-2-yl)phenyl)morpholine-4-carboxylate (4.5 g, 11.06 mmol, 1 equiv) in acetic acid (80 mL, 0.092 M) at 20° C. The mixture was stirred for 2 days. The reaction mixture was filtered and washed with water (10 mL) to afford tert-butyl (R)-3-(3-(6-amino-4-oxo-4,5-dihydro-1,3,5-triazin-2-yl)-5-chlorophenyl)morpholine-4-carboxylate (3.50 g, 8.58 mmol, 78% yield) as a yellow solid. The crude product was used to the next step without further purification.

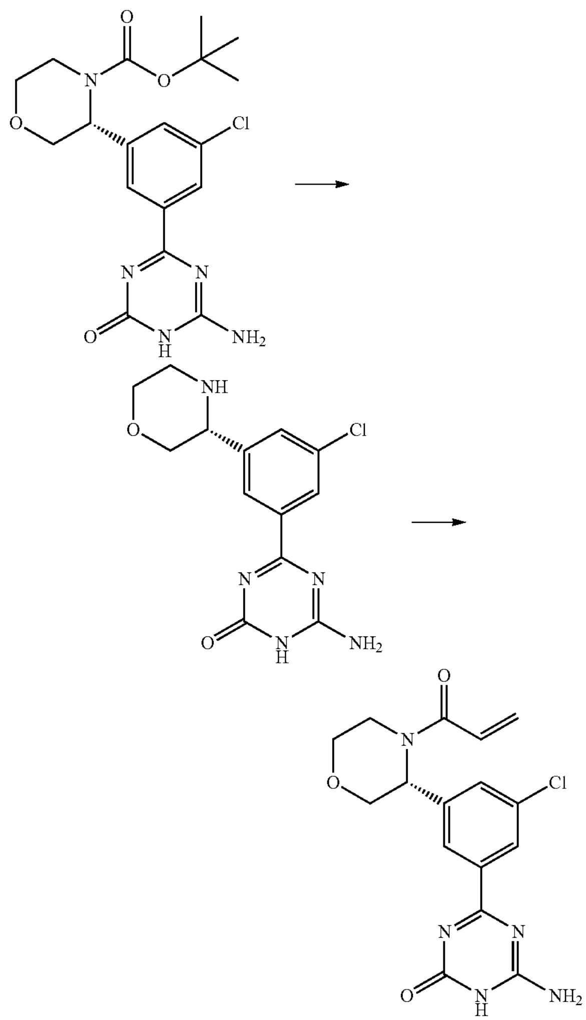

HCl in dioxane (50 mL) was added to a solution of tert-butyl (R)-3-(3-(6-amino-4-oxo-4,5-dihydro-1,3,5-triazin-2-yl)-5-chlorophenyl)morpholine-4-carboxylate (12 g, 23.53 mmol, 1 equiv) in 1,4-dioxane (100 mL, 0.23 M). The mixture was stirred at 15° C. for 6 h and then concentrated to afford crude (R)-6-amino-4-(3-chloro-5-(morpholin-3-yl) phenyl)-1,3,5-triazin-2(1H)-one HCl (8.0 g, 23.2 mmol, 99% yield) as a yellow solid. The crude product was used to the next step without further purification.

Acryloyl chloride (352 mg, 3.89 mmol, 0.5 equiv) was added to a mixture of (R)-6-amino-4-(3-chloro-5-(morpholin-3-yl)phenyl)-1,3,5-triazin-2(1H)-one HCl (2.4 g, 7.79 mmol, 1 equiv) and N,N-diisopropylethylamine (2.01 g, 15.59 mmol, 2 equiv) in DCM (50 mL, 0.15 M) at 0° C. The mixture was stirred at 0° C. for 30 minutes. The reaction mixture was poured into water (100 mL) and extracted with DCM (50 mL*3). The combined organic layer was washed with brine (50 mL), dried over $Na_2SO_4$, filtered, and concentrated. The residue was purified by prep-HPLC (column: Welch Xtimate C18 250*100 mm*10 um; mobile phase: [water ($NH_4HCO_3$)-ACN]; B %: 1%-40%, 20 min) to afford the title compound (600 mg, 1.66 mmol, 21% yield) as a yellow solid. LC-MS m/z: 362.1 [M+1].

Stereochemistry: single enantiomer of known absolute configuration.

Example 9. Synthesis of (R)-4-(3-(4-acryloylmorpholin-3-yl)-5-chlorophenyl)-1,3-dihydro-2H-imidazol-2-one (Compound 184)

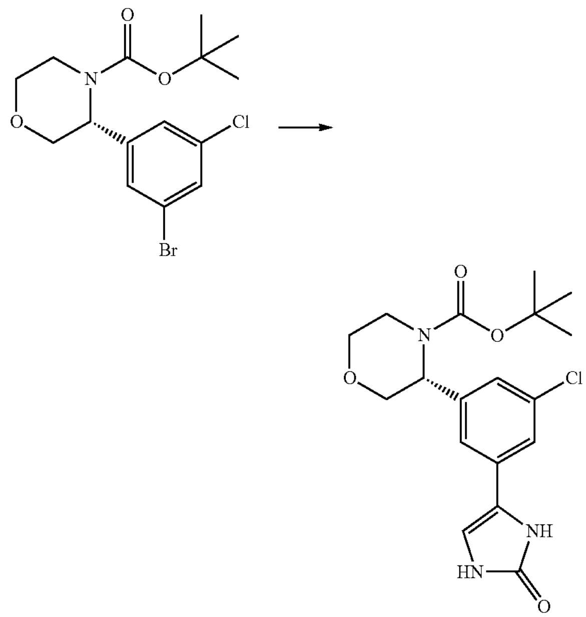

tert-butyl (R)-3-(3-bromo-5-chlorophenyl)morpholine-4-carboxylate was obtained from Procedure B.

A solution of 1,3-dihydroimidazol-2-one (15 mg, 0.17 mmol, 1 equiv), tert-butyl (R)-3-(3-bromo-5-chlorophenyl) morpholine-4-carboxylate (100.8 mg, 0.26 mmol, 1.5 equiv), palladium acetate (4.01 mg, 0.017 mmol, 0.1 equiv), and sodium acetate (43.9 mg, 0.53 mmol, 3 equiv) in DMSO (2 mL, 0.089 M) was stirred at 80° C. for 12 hours. The mixture was poured into water (3 mL), extracted with ethyl acetate (2 mL*2), washed with brine, dried over $Na_2SO_4$, filtered, and concentrated under vacuum. The residue was purified by prep-TLC ($SiO_2$,EtOAc=1) to give tert-butyl (R)-3-(3-chloro-5-(2-oxo-2,3-dihydro-1H-imidazol-4-yl) phenyl)morpholine-4-carboxylate (17 mg, 0.045 mmol, 25% yield) as a yellow oil.

Using tert-butyl (R)-3-(3-chloro-5-(2-oxo-2,3-dihydro-1H-imidazol-4-yl)phenyl)morpholine-4-carboxylate in Step 9 or Procedure B, the title compound was obtained. LC-MS m/z: 334.1 [M+1].

Stereochemistry: single enantiomer of known absolute configuration.

Example 10. Synthesis of (R)-1-(3-(3-(2-amino-1H-imidazol-4-yl)-5-chlorophenyl)morpholino)prop-2-en-1-one (Compound 193)

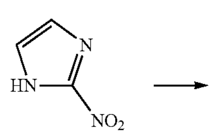

-continued

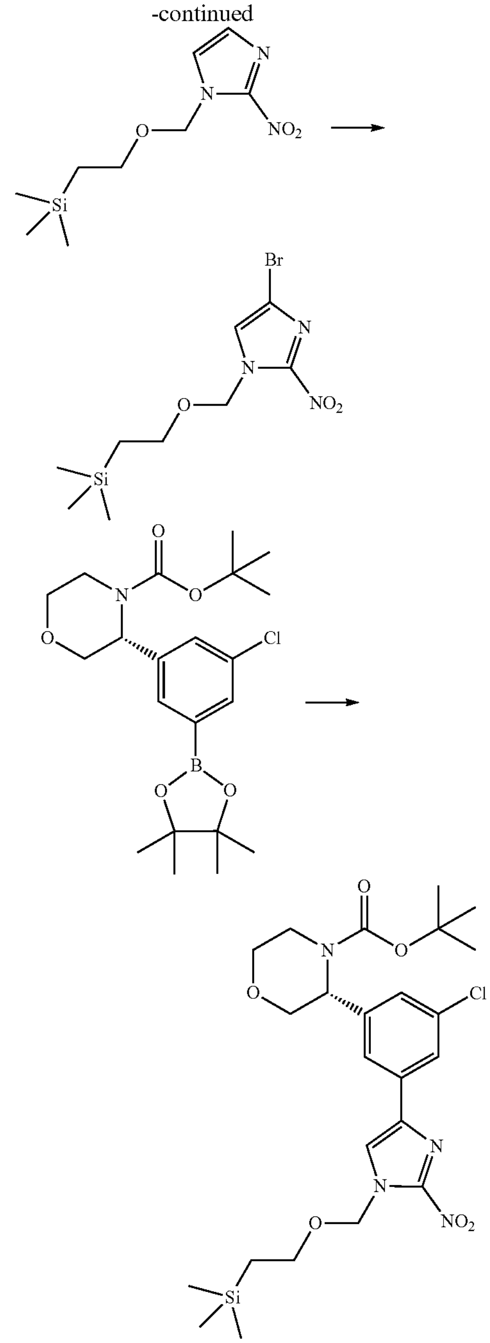

To a solution of 2-nitro-1H-imidazole (1 g, 8.84 mmol, 1 equiv) in THF (20 mL, 0.44 M) was added sodium hydride (459 mg, 11.49 mmol, 1.3 equiv) (60% Purity) under $N_2$ at 0° C. The reaction was stirred at 0° C. for 30 minutes. 2-(trimethylsilyl)ethoxymethyl chloride (1.91 g, 11.49 mmol, 1.3 equiv) was added and the reaction was stirred at 25° C. for 2 hours. The reaction was poured into $H_2O$ (100 mL) and the aqueous layer was extracted with ethyl acetate (20 mL×3). The combined organic layer was washed with brine (50 mL), dried over $Na_2SO_4$, filtered, and concentrated under vacuum. The crude product was purified by column chromatography on silica gel (petroleum ether/ethyl acetate=20:1 to 5:1) to afford trimethyl-[2-[(2-nitroimidazol-1-yl)methoxy]ethyl]silane (1.90 g, 7.81 mmol, 88% yield) as a yellow oil.

To a solution of trimethyl-[2-[(2-nitroimidazol-1-yl)methoxy]ethyl]silane (2.1 g, 8.62 mmol, 1 equiv) in DMF (10 mL, 0.86 M) and $CHCl_3$ (10 mL) was added N-bromosuccinimide (1.68 g, 9.49 mmol, 1.1 equiv). The reaction was stirred at 20° C. for 16 hours. The reaction was poured into $H_2O$ (100 mL) and the aqueous layer was extracted with DCM (20 mL×3). The combined organic layer was washed with brine (20 mL), dried over $Na_2SO_4$, filtered, and concentrated under vacuum. The crude product was purified by column chromatography on silica gel (petroleum ether/ethyl acetate=10:1 to 3:1) to afford 2-[(4-bromo-2-nitro-imidazol-1-yl)methoxy]ethyl-trimethyl-silane (1.50 g, 4.66 mmol, 54% yield) as a yellow oil.

tert-butyl (R)-3-(3-chloro-5-(4,4,5,5-tetramethyl-1,3,2-dioxaborolan-2-yl)phenyl)morpholine-4-carboxylate was obtained from Step 7 of Procedure B.

To a solution of tert-butyl (R)-3-(3-chloro-5-(4,4,5,5-tetramethyl-1,3,2-dioxaborolan-2-yl)phenyl)morpholine-4-carboxylate (580 mg, 1.36 mmol, 1 equiv) in 1,4-dioxane (10 mL, 0.11 M) and water (2.5 mL, 0.11 M) was added 2-[(4-bromo-2-nitro-imidazol-1-yl)methoxy]ethyl-trimethyl-silane (661 mg, 2.05 mmol, 1.5 equiv), potassium phosphate tribasic (581 mg, 2.73 mmol, 2 equiv), and cataCXiumA Pd G2 (91.5 mg, 0.13 mmol, 0.1 equiv) under $N_2$. The reaction was stirred at 80° C. for 16 hours. The reaction was poured into $H_2O$ (20 mL) and the aqueous layer was extracted with ethyl acetate (10 mL×3). The combined organic layer was washed with brine (20 mL), dried over $Na_2SO_4$, filtered, and concentrated under vacuum. The crude product was purified by column chromatography on silica gel (petroleum ether/ethyl acetate=10:1 to 1:1) to afford tert-butyl (R)-3-(3-chloro-5-(2-nitro-1-((2-(trimethylsilyl)ethoxy)methyl)-1H-imidazol-4-yl)phenyl)morpholine-4-carboxylate (470 mg, 0.87 mmol, 64% yield) as a brown oil.

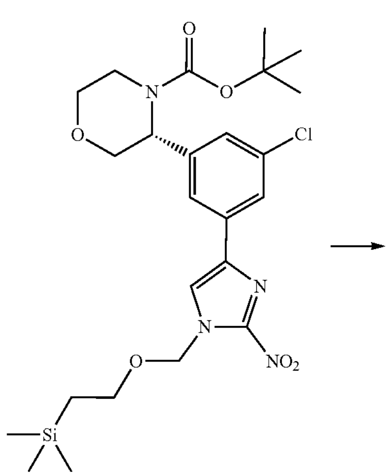

-continued

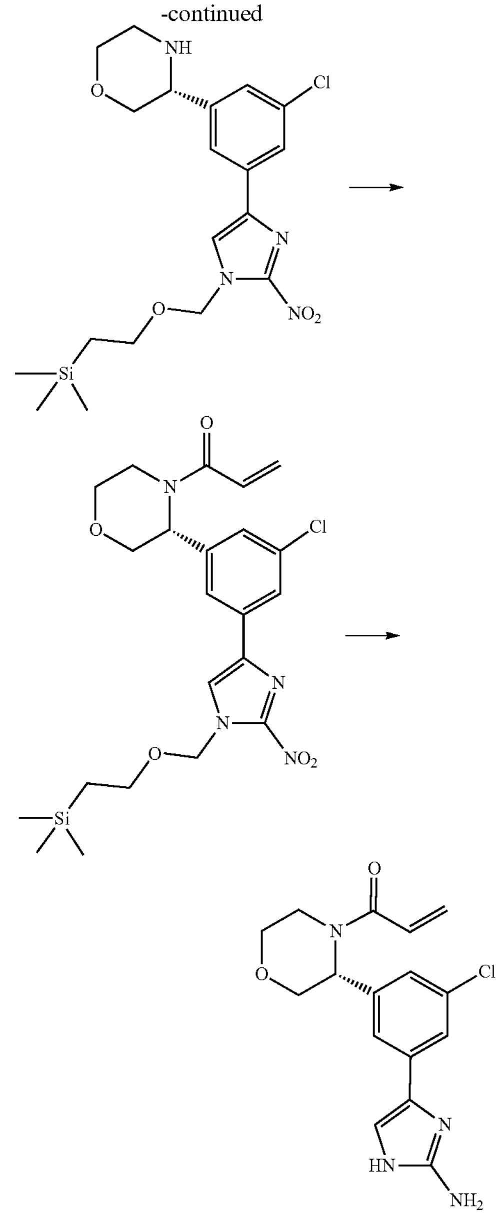

To a solution of tert-butyl (R)-3-(3-chloro-5-(2-nitro-1-((2-(trimethylsilyl)ethoxy)methyl)-1H-imidazol-4-yl)phenyl)morpholine-4-carboxylate (300 mg, 0.55 mmol, 1 equiv) in DCM (10 mL, 0.055 M) was added $ZnBr_2$ (250 mg, 1.11 mmol, 2 equiv). The reaction was stirred at 25° C. for 16 hours. The mixture was filtered and concentrated under reduced pressure to afford 342 mg as a crude brown oil. The product was used for the next step without further purification.

To a solution of (R)-3-(3-chloro-5-(2-nitro-1-((2-(trimethylsilyl)ethoxy)methyl)-1H-imidazol-4-yl)phenyl)morpholine (342 mg, 0.78 mmol, 1 equiv) in DCM (10 mL, 0.078 M) was added acrylic acid (84 mg, 1.17 mmol, 1.5 equiv), N,N-diisopropylethylamine (201 mg, 1.55 mmol, 2 equiv), and 2,4,6-tripropyl-1,3,5,2,4,6-trioxatriphosphorinane-2,4,6-trioxide (991 mg, 1.55 mmol, 2 equiv). The reaction mixture was stirred at 25° C. for 1 hour. The reaction was poured into $H_2O$ (50 mL) and the aqueous layer was extracted with DCM (10 mL×3). The combined organic layer was washed with brine (20 mL), dried over $Na_2SO_4$, filtered, and concentrated under vacuum. The crude product was purified by column chromatography on silica gel (petroleum ether/ethyl acetate=10:1 to 1:1) to afford (R)-1-(3-(3-chloro-5-(2-nitro-1-((2-(trimethylsilyl)ethoxy)methyl)-1H-imidazol-4-yl)phenyl)morpholino)prop-2-en-1-one (177 mg, 0.36 mmol, 46% yield) as yellow oil.

To a solution of (R)-1-(3-(3-chloro-5-(2-nitro-1-((2-(trimethylsilyl)ethoxy)methyl)-1H-imidazol-4-yl)phenyl)morpholino)prop-2-en-1-one (177 mg, 0.35 mmol, 1 equiv) in ethanol (2 mL, 0.14 M) and water (0.6 mL) was added iron powder (60 mg, 1.07 mmol, 3 equiv) and ammonium chloride (19 mg, 0.35 mmol, 1 equiv). The reaction was stirred at 80° C. for 1 hour. The organic layer was filtered and evaporated to dryness to provide a 166 mg of crude product. The crude material was used into the next step without further purification.

To a solution of (R)-1-(3-(3-(2-amino-1-((2-(trimethylsilyl)ethoxy)methyl)-1H-imidazol-4-yl)-5-chlorophenyl)morpholino)prop-2-en-1-one (154 mg, 0.33 mmol, 1 equiv) in DCM (2 mL, 0.11 M) was added trifluoroacetic acid (1 mL, 0.11 M). The reaction was stirred at 25° C. for 1 hour. The mixture was evaporated to dryness and the residue was purified by Pre-HPLC to afford the title compound (55 mg, 0.165 mmol, 49% yield) as a white solid. LC-MS m/z: 333.0 [M+1].

Stereochemistry: single enantiomer of known absolute configuration.

Example 11. Synthesis of (R)-1-(3-(3-(4-amino-1,3,5-triazin-2-yl-6-d)-5-chlorophenyl)morpholino)prop-2-en-1-one (Compound 208)

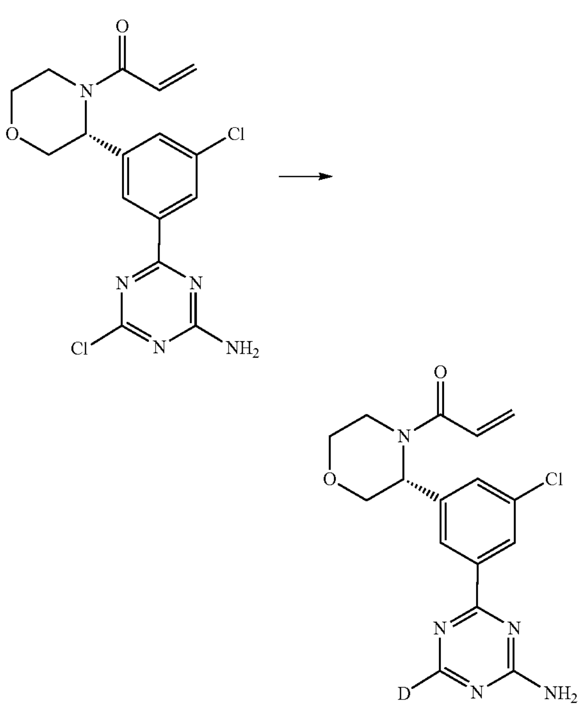

(R)-1-(3-(3-(4-amino-6-chloro-1,3,5-triazin-2-yl)-5-chlorophenyl)morpholino)prop-2-en-1-one was obtained using Procedure D.

To a solution of (R)-1-(3-(3-(4-amino-6-chloro-1,3,5-triazin-2-yl)-5-chlorophenyl)morpholino)prop-2-en-1-one (100 mg, 0.26 mmol, 1 equiv) in $D_2O$ (2 mL) and THF (1 mL, 0.26 M) was added zinc (granular, 200 mg, 3.06 mmol, 11.63 equiv) and acetic acid-D3 (47 mg, 0.78 mmol, 3 equiv) at 25° C. The mixture was stirred at 40° C. for 12 hours under N2. The reaction mixture was filtered, poured into water (15 mL), and extracted with EtOAc (15 mL*3). The combined organic layers were washed with brine (10 mL*2), dried over $Na_2SO_4$, filtered, and concentrated under reduced pressure. The residue was purified by_prep-HPLC (column: Waters Xbridge Prep OBD C18 150*40 mm*10 um; liquid phase: [A-10 mM $NH_4HCO_3$ in $H_2O$; B-ACN]B %: 15%-45%, 8 min]) to afford (R)-1-(3-(3-(4-amino-1,3,5-triazin-2-yl-6-d)-5-chlorophenyl)morpholino)prop-2-en-1-one (10 mg, 0.028 mmol, 11% yield) as a white solid. LC-MS m/z: 347.1 [M+1].

Stereochemistry: single enantiomer of known absolute configuration.

Example 12. Synthesis of (R)-1-(3-(3-chloro-5-(3-hydroxy-1H-1,2,4-triazol-5-yl)phenyl)morpholino)prop-2-en-1-one (Compound 210)

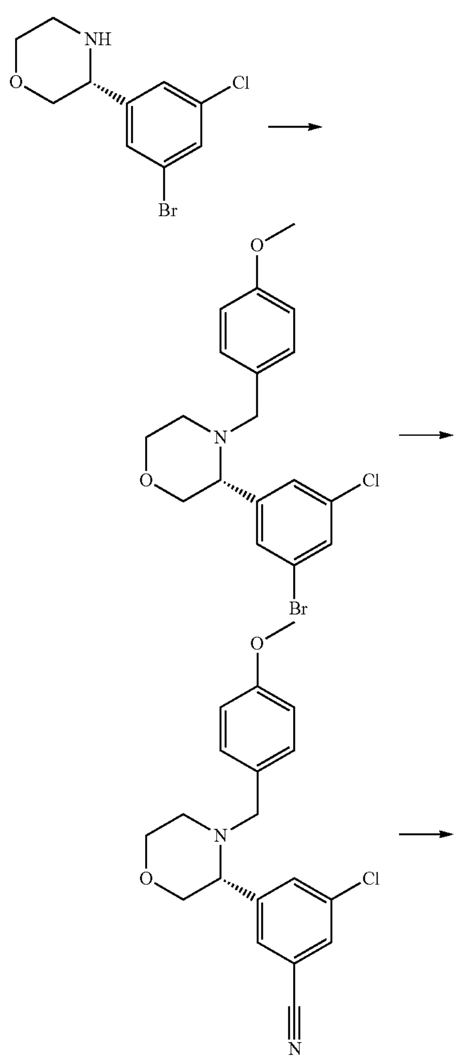

-continued

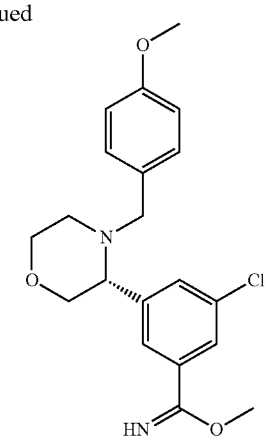

(R)-3-(3-bromo-5-chlorophenyl)morpholine was obtained from Step 5 of Procedure B.

To a solution of (R)-3-(3-bromo-5-chlorophenyl)morpholine (200 mg, 0.72 mmol, 1 equiv) in MeCN (10 mL, 0.072 M) was added potassium carbonate (199.9 mg, 1.44 mmol, 2 equiv) and 4-methoxybenzyl chloride (226.51 mg, 1.44 mmol, 2 equiv). The mixture was stirred for 16 hours at 80° C. The reaction was quenched with water (10 mL) and extracted with EtOAc (20 mL×2). The combined organic layer was washed with brine (10 mL), dried over $Na_2SO_4$, filtered, and concentrated. The crude product was purified by prep-TLC (petroleum ether:EtOAc=3:1) to afford (R)-3-(3-bromo-5-chlorophenyl)-4-(4-methoxybenzyl)morpholine (260 mg, 0.65 mmol, 91% yield) as yellow oil.

Tetrakis(triphenylphosphine) (2.91 g, 2.52 mmol, 0.2 equiv) and zinc cyanide (1.18 g, 10.08 mmol, 0.8 equiv) were added to a solution of (R)-3-(3-bromo-5-chlorophenyl)-4-(4-methoxybenzyl)morpholine (5 g, 12.6 mmol, 1 equiv) in DMF (50 mL, 0.25 M). The mixture was stirred at 120° C. for 16 hours. The reaction mixture was quenched with water (100 mL) and extracted with EtOAc (50 mL*3). The combined organic layer was washed with water (50 mL*2), brine (50 mL), dried over $Na_2SO_4$, filtered, and concentrated. The residue was purified by MPLC (40 g SEPAFLASH® Silica Flash Column, Eluent of 0-15% ethyl acetate/petroleum ether gradient) to afford (R)-3-chloro-5-(4-(4-methoxybenzyl)morpholin-3-yl)benzonitrile (2.50 g, 7.29 mmol, 58% yield) as a colorless oil.

Sodium methoxide (210.1 mg, 1.16 mmol, 0.2equiv) was added to a solution of (R)-3-chloro-5-(4-(4-methoxybenzyl)morpholin-3-yl)benzonitrile (2 g, 5.83 mmol, 1 equiv) in methanol (20 mL, 0.29 M). The resulted mixture was stirred at 50° C. for 5 hours. The reaction mixture was concentrated under reduced pressure. The residue was purified by MPLC (12 g SEPAFLASH® Silica Flash Column, Eluent of 0-20% ethyl acetate/petroleum ether, gradient @ 36 mL/min) to afford (R)-3-chloro-5-(4-(4-methoxybenzyl)morpholin-3-yl)benzimidate (500 mg, 1.33 mmol, 23% yield) as a white solid.

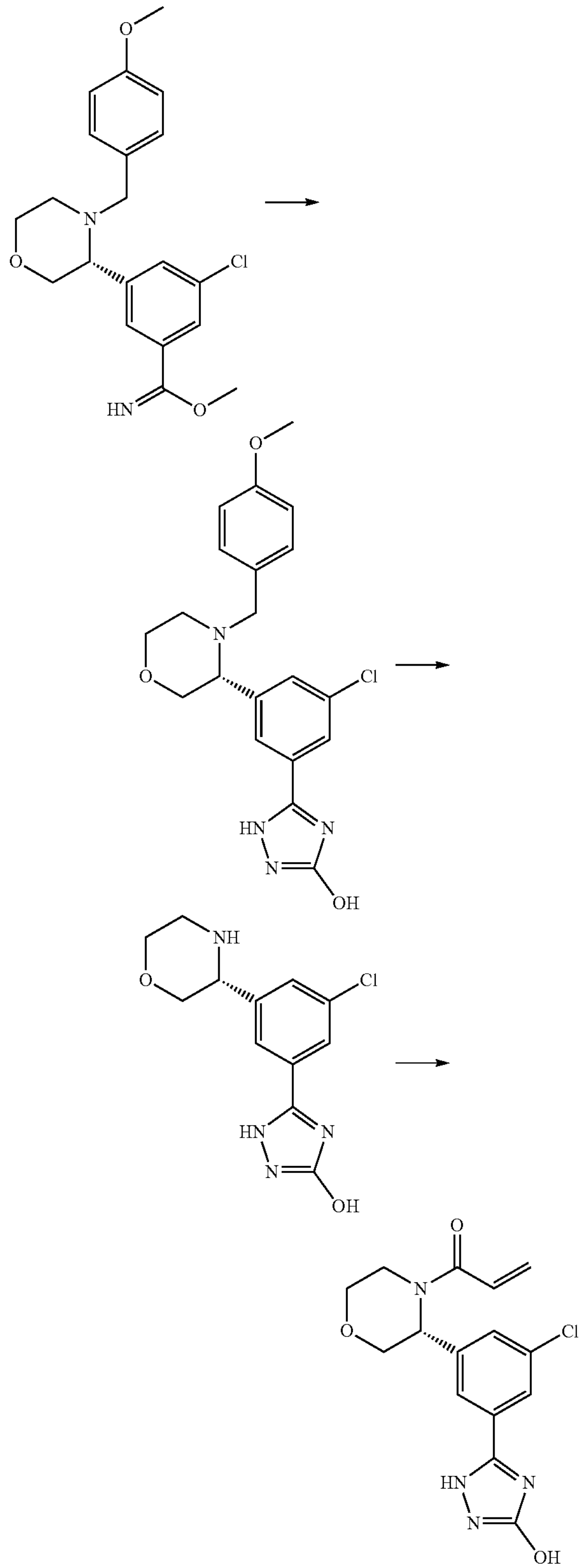

N-methyl morpholine (674 mg, 6.66 mmol, 5 equiv) and aminourea hydrochloride (148 mg, 1.33 mmol, 1 equiv) were added to a solution of methyl (R)-3-chloro-5-(4-(4-methoxybenzyl)morpholin-3-yl)benzimidate (500 mg, 1.33 mmol, 1 equiv) in 1,4-dioxane (10 mL, 0.13 M). The resulted mixture was heated to 120° C. and stirred for 16 hours. The reaction mixture concentrated to give a residue. The residue was purified by MPLC (12 g SEPAFLASH® Silica Flash Column, Eluent of 0-80% Ethyl acetate/Petroleum ether gradient@ 36 mL/min) to afford (R)-5-(3-chloro-5-(4-(4-methoxybenzyl)morpholin-3-yl)phenyl)-1H-1,2,4-triazol-3-ol (300 mg, 0.75 mmol, 56% yield).

The mixture of (R)-5-(3-chloro-5-(4-(4-methoxybenzyl) morpholin-3-yl)phenyl)-1H-1,2,4-triazol-3-ol (280 mg, 0.69 mmol, 1 equiv) in trifluoroacetic acid (3 mL, 0.23 M) and TfOH (3 mL) was stirred at 90° C. for 2 days. The reaction mixture was poured into saturated aqueous $NaHCO_3$ (50 mL) and extracted with EtOAc (10 mL*3). The combined organic layer was washed with brine (10 mL), dried over $Na_2SO_4$, filtered, and concentrated. The residue was purified by prep-HPLC (column: Waters Xbridge BEH C18 100*30 mm*10 um; mobile phase: [water ($NH_4HCO_3$)-ACN]; B %: 1%-30%, 10 min).

Acrylic acid (14.11 mg, 0.19 mmol, 1.1 equiv), N,N-diisopropylethylamine (446 mg, 3.45 mmol), and 2,4,6-tripropyl-1,3,5,2,4,6-trioxatriphosphorinane-2,4,6-trioxide (283 mg, 0.44 mmol, 2.5 equiv) were added to a solution of (R)-5-(3-chloro-5-(morpholin-3-yl)phenyl)-1H-1,2,4-triazol-3-ol (50 mg, 0.17 mmol, 1 equiv) in DCM (1 mL, 0.17 M) at 0° C. The resulted mixture was stirred at 0° C. for 30 minutes. The reaction mixture was purified by prep-TLC (EtOAc:MeOH=10:1) and prep-HPLC (column: Waters Xbridge BEH C18 100*30 mm*10 um; mobile phase: [water ($NH_4HCO_3$)-ACN]; B %: 15%-45%, 8 min.) to afford (R)-1-(3-(3-chloro-5-(3-hydroxy-1H-1,2,4-triazol-5-yl)phenyl)morpholino)prop-2-en-1-one (1.9 mg, 0.0055 mmol, 3% yield) as a white solid. LC-MS m/z: 335.1 [M+1].

Stereochemistry: single enantiomer of known absolute configuration.

Example 13. Synthesis of (R)-1-(3-(3-(4-amino-1H-pyrazol-1-yl)-5-chlorophenyl)morpholino)prop-2-en-1-one (Compound 211)

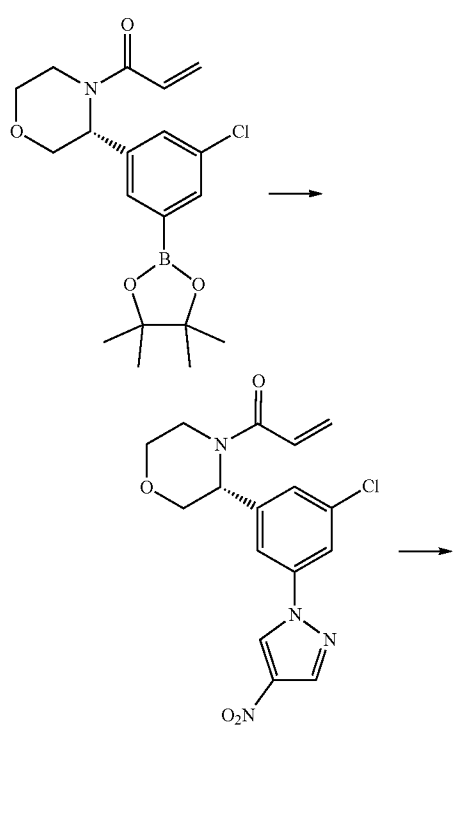

-continued

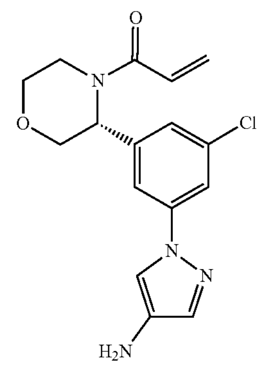

(R)-1-(3-(3-chloro-5-(4,4,5,5-tetramethyl-1,3,2-dioxaborolan-2-yl)phenyl)morpholino)prop-2-en-1-one was obtained from Step 1 of Procedure D.

To a solution of (R)-1-(3-(3-chloro-5-(4,4,5,5-tetramethyl-1,3,2-dioxaborolan-2-yl)phenyl)morpholino)prop-2-en-1-one (300 mg, 0.79 mmol, 1 equiv) in MeCN (8 mL, 0.099 M) was added 4-nitro-1H-pyrazole (233 mg, 2.06 mmol, 2.6 equiv), boric acid (294 mg, 4.76 mmol, 6 equiv), 4A molecular sieves (300 mg), and copper (II) acetate (72 mg, 0.39 mmol, 0.5 equiv) at 25° C. The mixture was stirred at 90° C. for 12 hours. The reaction mixture was filtered and concentrated under reduced pressure. The residue was purified by prep-HPLC (column: Waters Xbridge Prep OBD C18 150*40 mm*10 um; liquid phase: [A-10 mM $NH_4HCO_3$ in $H_2O$; B-ACN]B %: 35%-55%, 8 min]) to afford (R)-1-(3-(3-chloro-5-(4-nitro-1H-pyrazol-1-yl)phenyl)morpholino) prop-2-en-1-one (50 mg, 0.138 mmol, 17% yield) as a yellow solid.

To a solution of (R)-1-(3-(3-chloro-5-(4-nitro-1H-pyrazol-1-yl)phenyl)morpholino)prop-2-en-1-one (50 mg, 0.13 mmol, 1 equiv) in ethanol (3 mL, 0.028 M), water (1.5 mL, 0.028 M) and acetic acid (0.30 mL, 0.028 M) was added zinc (granular, 31.53 mg, 0.48 mmol, 3.5 equiv) at 0° C. The mixture was stirred at 0° C. for 30 minutes. The reaction mixture was poured into water (15 mL) and extracted with EtOAc (15 mL*3). The combined organic layers were washed with brine (10 mL*2), dried over $Na_2SO_4$, filtered, and concentrated under reduced pressure. The residue was purified by prep-HPLC (column: Waters Xbridge BEH C18 100*30 mm*10 um; liquid phase: [A-10 mM $NH_4HCO_3$ in $H_2O$; B-ACN]B %: 20%-40%, 8 min]) to afford (R)-1-(3-(3-(4-amino-1H-pyrazol-1-yl)-5-chlorophenyl)morpholino) prop-2-en-1-one (6.6 mg, 0.019 mmol, 14% yield) as brown solid. LC-MS m/z: 333.1 [M+1].

Stereochemistry: single enantiomer of known absolute configuration.

Example 14. Synthesis of (R)-1-(3-(3-(5-aminoisoxazol-3-yl)-5-chlorophenyl)morpholino)prop-2-en-1-one (Compound 212)

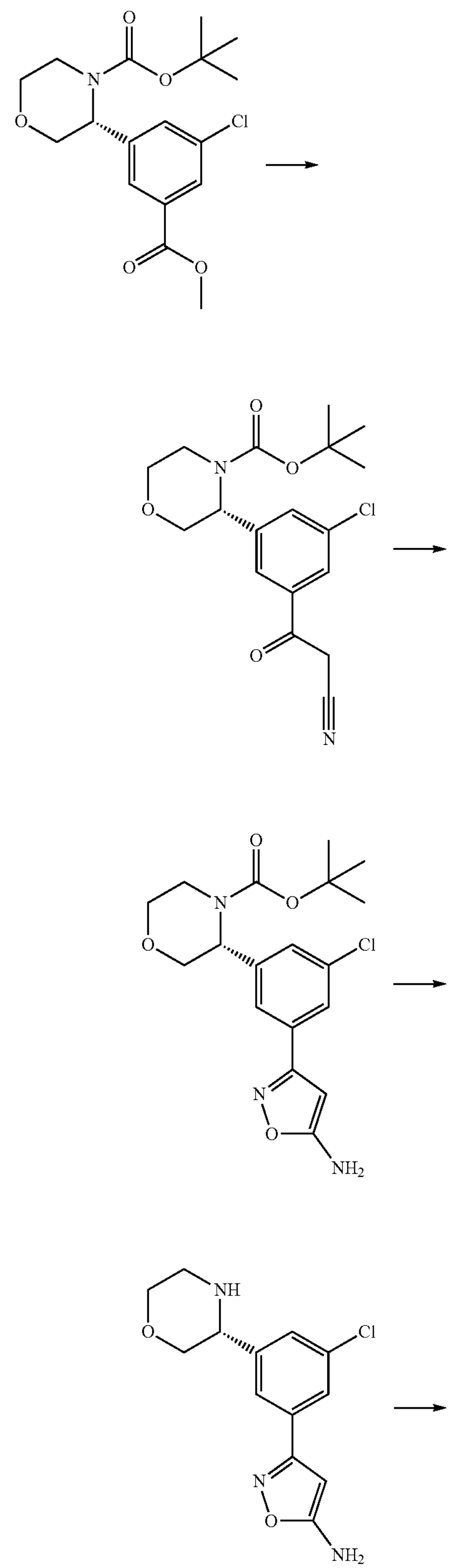

-continued

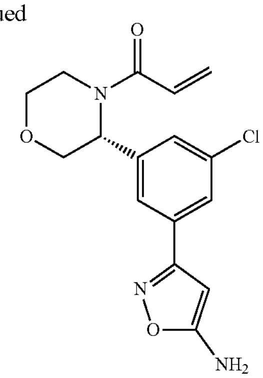

tert-butyl (R)-3-(3-chloro-5-(methoxycarbonyl)phenyl) morpholine-4-carboxylate was obtained from step 1 of the synthesis to Compound 177.

NaH (40 mg, 1.68 mmol, 3 equiv) was added to a solution of acetonitrile (46 mg, 1.12 mmol, 2 equiv) in THF (3 mL, 0.18 M) and stirred for 15 minutes before addition of tert-butyl (R)-3-(3-chloro-5-(methoxycarbonyl)phenyl)morpholine-4-carboxylate (200 mg, 0.56 mmol, 1 equiv) at 25° C. The mixture was stirred at 60° C. for 1 hour under $N_2$. The reaction mixture was poured into saturated aqueous NH4Cl (6 mL) and extracted with EtOAc (6 mL*3). The combined organic layers were washed with brine (5 mL*2), dried over Na2SO4, filtered, and concentrated under reduced pressure. The residue was purified by prep-TLC (SiO2, PE:EtOAc=1:1) to afford tert-butyl (R)-3-(3-chloro-5-(2-cyanoacetyl)phenyl)morpholine-4-carboxylate (100 mg, 0.274 mmol, 49% yield).

To a solution of tert-butyl (R)-3-(3-chloro-5-(2-cyanoacetyl)phenyl)morpholine-4-carboxylate (100 mg, 0.27 mmol, 1 equiv) in methanol (3 mL, 0.091 M) was added hydroxylamine hydrochloride (57 mg, 0.82 mmol, 3 equiv) at 25° C. The mixture was stirred at 25° C. for 16 hours under $N_2$. The reaction mixture was poured into saturated aqueous $NH_4Cl$ (6 mL) and extracted with EtOAc (6 mL*3). The combined organic layers were washed with brine (5 mL*2), dried over $Na_2SO_4$, filtered, and concentrated under reduced pressure. The residue was purified by prep-TLC ($SiO_2$, EtOAc) to afford tert-butyl (R)-3-(3-(5-aminoisoxazol-3-yl)-5-chlorophenyl)morpholine-4-carboxylate (70 mg, 0.184 mmol, 67% yield).

To a solution of tert-butyl (R)-3-(3-(5-aminoisoxazol-3-yl)-5-chlorophenyl)morpholine-4-carboxylate (70 mg, 0.18 mmol, 1 equiv) in DCM (3 mL, 0.061 M) was added THF (1 mL) at 0° C. The mixture was stirred at 25° C. for 1 hour under $N_2$. The reaction mixture was poured into saturated aqueous $NH_4Cl$ (6 mL) and extracted with DCM (6 mL*3). The combined organic layers were washed with brine (5 mL*2), dried over $Na_2SO_4$, filtered, and concentrated under reduced pressure to afford crude (R)-3-(3-chloro-5-(morpholin-3-yl)phenyl)isoxazol-5-amine (51 mg, 0.182 mmol, 99% yield).

To a solution of (R)-3-(3-chloro-5-(morpholin-3-yl)phenyl)isoxazol-5-amine (104 mg, 0.37 mmol, 1 equiv) in DCM (5 mL, 0.078 M) was added DIEA (120 mg, 3 equiv) and acryloyl chloride (16 mg, 0.18 mmol, 0.5 equiv) at 0° C. The mixture was stirred at 25° C. for 1 hour under N2. The reaction mixture was poured into saturated aqueous $NH_4Cl$ (6 mL) and extracted with DCM (6 mL*3). The combined organic layers were washed with brine (5 mL*2), dried over $Na_2SO_4$, filtered, and concentrated under reduced pressure. The residue was purified by Prep-TLC (EtOAc) to afford (R)-1-(3-(3-(5-aminoisoxazol-3-yl)-5-chlorophenyl)morpholino)prop-2-en-1-one (30 mg, 0.089 mmol, 24% yield) as a pale yellow solid. LC-MS m/z: 334.1 [M+1].

Stereochemistry: single enantiomer of known absolute configuration.

Example 15. Synthesis of (R)-1-(3-(3-(3-amino-1H-1,2,4-triazol-1-yl)-5-chlorophenyl)morpholino)prop-2-en-1-one (Compound 215)

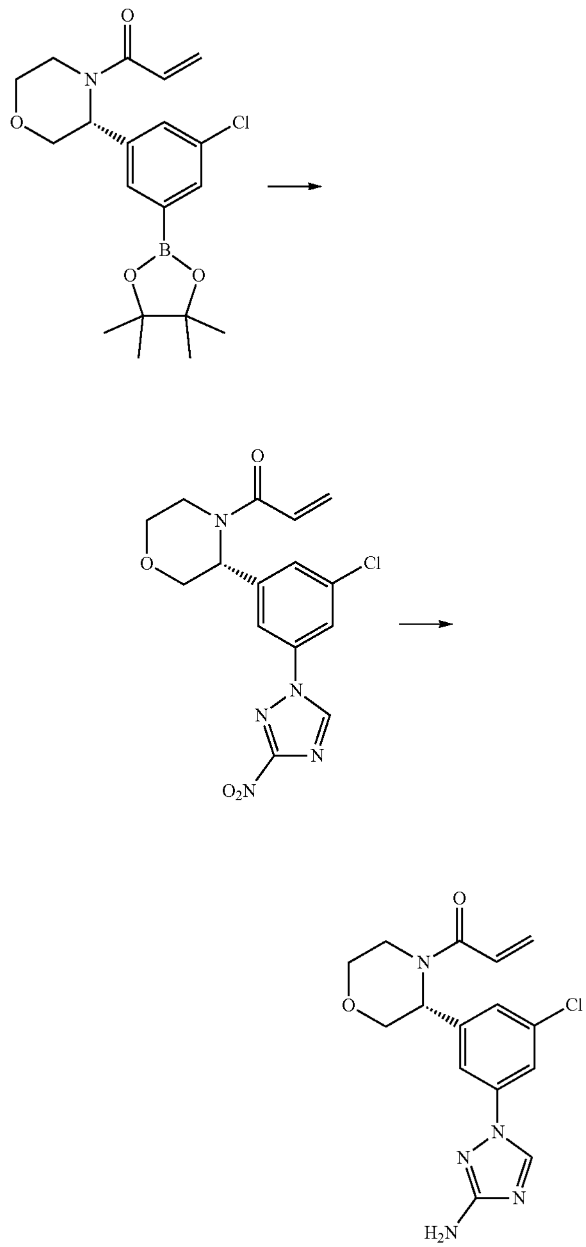

(R)-1-(3-(3-chloro-5-(4,4,5,5-tetramethyl-1,3,2-dioxaborolan-2-yl)phenyl)morpholino)prop-2-en-1-one was obtained from Step 1 of Procedure D.

To a solution of (R)-1-(3-(3-chloro-5-(4,4,5,5-tetramethyl-1,3,2-dioxaborolan-2-yl)phenyl)morpholino)prop-2-en-1-one (400 mg, 1.05 mmol, 1 equiv) in MeCN (8 mL, 0.13 M) was added 3-nitro-1H-1,2,4-triazole (314 mg, 2.75 mmol, 2.6 equiv), boric acid (392 mg, 6.35 mmol, 6 equiv), 4A molecular sieves (400 mg), and copper diacetate (96 mg, 0.52 mmol, 0.5 equiv) at 25° C. The mixture was stirred at 80° C. for 12 hours under $O_2$. The reaction mixture was filtered and concentrated under reduced pressure. The residue was purified by flash silica gel chromatography (ISCO®; 12 g SEPAFLASH® Silica Flash Column, Eluent of 20-60% Ethyl acetate/Petroleum ether gradient @ 60 mL/min) to afford (R)-1-(3-(3-chloro-5-(3-nitro-1H-1,2,4-triazol-1-yl)phenyl)morpholino)prop-2-en-1-one (80 mg, 0.22 mmol, 21% yield) as a yellow oil.

To a solution of (R)-1-(3-(3-chloro-5-(3-nitro-1H-1,2,4-triazol-1-yl)phenyl)morpholino)prop-2-en-1-one (80 mg, 0.22 mmol, 1 equiv) in ethanol (2 mL), water (1 mL) and acetic acid (0.2 mL) was added zinc, granular (50 mg, 0.76 mmol, 3.5 equiv) at 0° C. and stirred for 30 minutes. The reaction mixture was poured into water (15 mL) and extracted with EtOAc (15 mL*3). The combined organic layers were washed with brine (10 mL*2), dried over $Na_2SO_4$, filtered, and concentrated under reduced pressure. The residue was purified by prep-TLC (EA:MeOH=5:1) to afford (R)-1-(3-(3-(3-amino-1H-1,2,4-triazol-1-yl)-5-chlorophenyl)morpholino)prop-2-en-1-one (38 mg, 0.11 mmol, 51% yield) as a white solid. LC-MS m/z: 334.1 [M+1].

Stereochemistry: single enantiomer of known absolute configuration.

Example 16. Synthesis of (R)-2-(3-(4-acryloylmorpholin-3-yl)-5-chlorophenyl)oxazole-5-carboxamide (Compound 220)

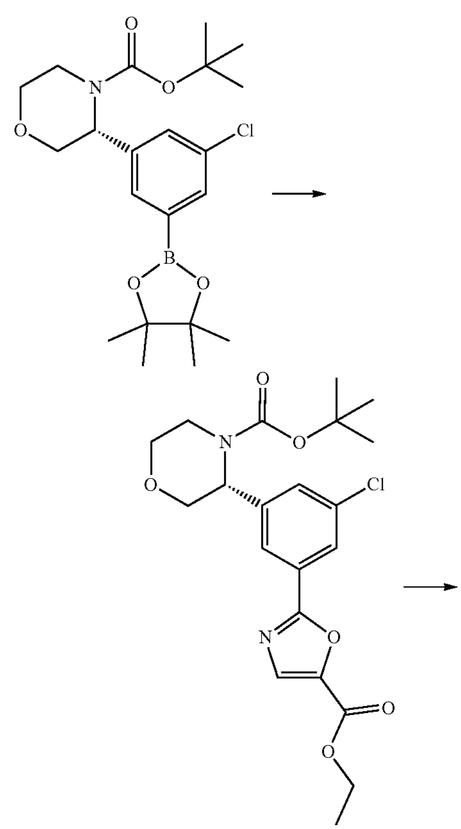

-continued

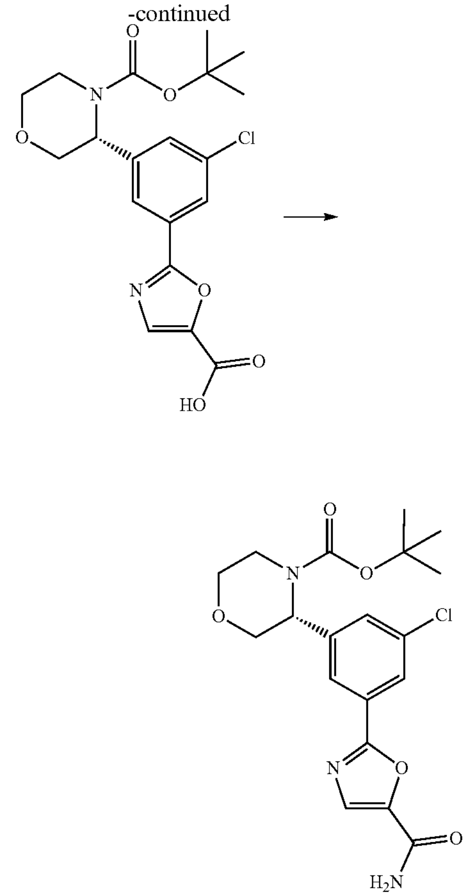

(R)-1-(3-(3-chloro-5-(4,4,5,5-tetramethyl-1,3,2-dioxaborolan-2-yl)phenyl)morpholino)prop-2-en-1-one was obtained from Step 1 of Procedure D.

A solution of (R)-1-(3-(3-chloro-5-(4,4,5,5-tetramethyl-1,3,2-dioxaborolan-2-yl)phenyl)morpholino)prop-2-en-1-one (1200 mg, 2.83 mmol), ethyl 2-bromooxazole-5-carboxylate (560 mg, 2.54 mmol, 0.9 equiv), potassium carbonate (782.8 mg, 5.66 mmol), and Pd(dppf)$Cl_2$ (204 mg, 0.28 mmol, 0.1 equiv) in 1,4-dioxane (12 mL, 0.18 M) and water (3 mL, 0.18 M) was stirred at 80° C. for 12 hours under $N_2$. The reaction mixture was poured into $H_2O$ (10 mL) and extracted with ethyl acetate (10 mL*3). The combined organic layers were washed with brine (20 mL), dried over $Na_2SO_4$, filtered, and concentrated under pressure. The crude residue was purified by flash column chromatography (PE=EA=3:1) to afford tert-butyl (R)-3-(3-chloro-5-(5-(ethoxycarbonyl)oxazol-2-yl)phenyl)morpholine-4-carboxylate (740 mg, 1.69 mmol, 60% yield) as a yellow oil.

tert-butyl (R)-3-(3-chloro-5-(5-(ethoxycarbonyl)oxazol-2-yl)phenyl)morpholine-4-carboxylate (740 mg, 1.69 mmol, 1 equiv) and lithium hydroxide monohydrate (284 mg, 6.77 mmol, 4 equiv) in THF (6 mL, 0.23 M) and water (1.2 mL, 0.23 M) were stirred at 25° C. for 3 hours. The reaction mixture was diluted with $H_2O$ (10 mL) and extracted with MTBA (10 mL*2). 1M aq. HCl was added to adjust the pH to 4~5. The water phase was extracted with ethyl acetate (10 mL*2). The combined organic layers were washed with brine (50 mL), dried over $Na_2SO_4$, filtered, and concentrated to afford (R)-2-(3-(4-(tert-butoxycarbonyl)morpholin-3-yl)-5-chlorophenyl)oxazole-5-carboxylic acid (560 mg, 1.37 mmol, 81% yield) as a yellow oil.

To a solution of (R)-2-(3-(4-(tert-butoxycarbonyl)morpholin-3-yl)-5-chlorophenyl)oxazole-5-carboxylic acid (150 mg, 0.36 mmol, 1 equiv) in THF (2 mL, 0.18 M) was added ammonium bicarbonate (58 mg, 0.73 mmol, 2 equiv), pyridine (58 mg, 0.73 mmol, 2 equiv), and di-tert-butyl dicarbonate (160 mg, 0.73 mmol, 2 equiv) at 25° C. under $N_2$ and stirred for 12 hours. The reaction mixture was diluted with $H_2O$ (5 mL) and extracted with ethyl acetate (5 mL*2). The combined organic layers were washed with brine (10 mL), dried over $Na_2SO_4$, filtered, and concentrated to afford tert-butyl (R)-3-(3-(5-carbamoyloxazol-2-yl)-5-chlorophenyl)morpholine-4-carboxylate (130 mg, 0.319 mmol, 87% yield) as a yellow solid.

tert-butyl (R)-3-(3-(5-carbamoyloxazol-2-yl)-5-chlorophenyl)morpholine-4-carboxylate was used in Step 9 of Procedure B to obtain the title compound. LC-MS m/z: 334.1 [M+1].

Stereochemistry: single enantiomer of known absolute configuration.

Example 17. Synthesis of (R)-1-(3-(3-chloro-5-(4-((3-(dimethylamino)propyl)amino)-1,3,5-triazin-2-yl)phenyl)morpholino)prop-2-en-1-one (Compound 221)

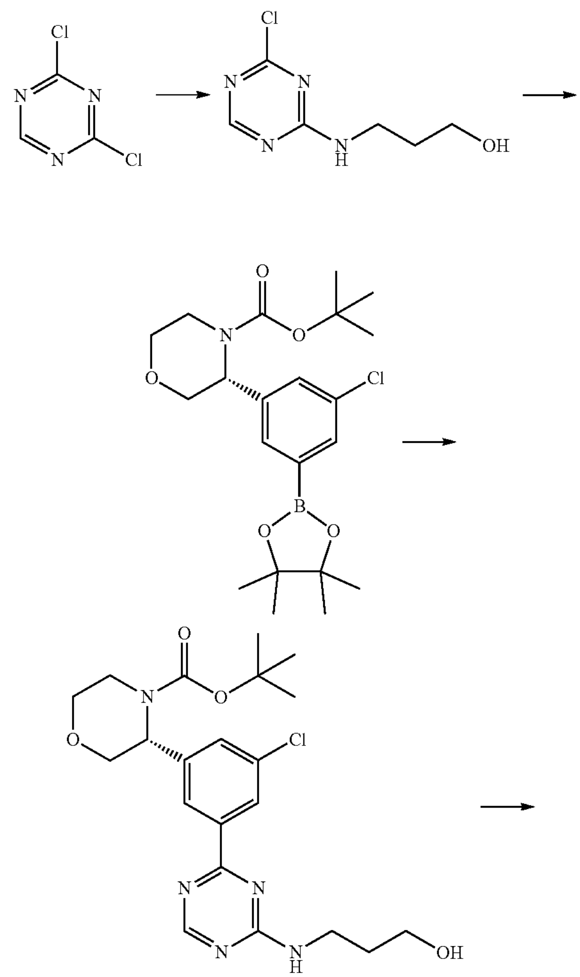

-continued

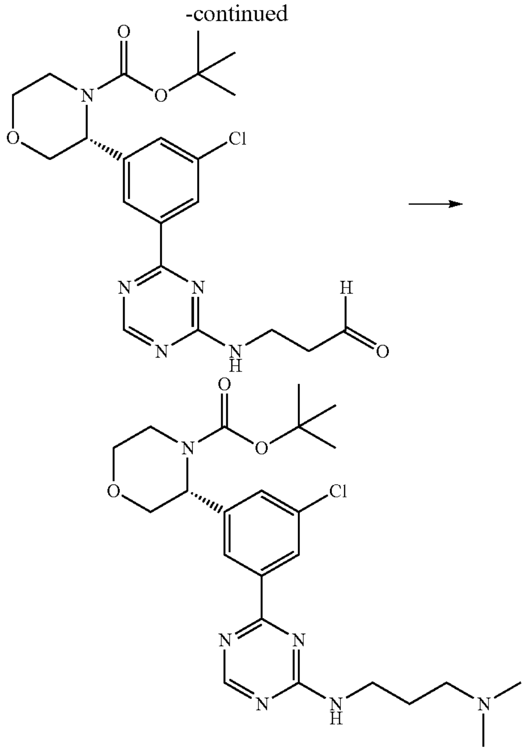

To a solution of 3-amino-1-propanol (601 mg, 8.0 mmol, 1.2 equiv) in 1,4-dioxane (10 mL, 0.66 M) was added DIEA (1.3equiv) and 2,4-dichloro-1,3,5-triazine (1 g, 6.66 mmol) and stirred at 35° C. for 2 hours under $N_2$. The reaction was poured into water (15 mL). The aqueous phase was extracted with EtOAc (10 mL*3). The combined organic phase was washed with brine (10 mL), dried with anhydrous $Na_2SO_4$, filtered, and concentrated under vacuum. The residue was purified by column chromatography (petroleum ether/ethyl acetate=2/1 to 0/1) to afford 3-[(4-chloro-1,3,5-triazin-2-yl) amino]propan-1-ol (820 mg, 4.35 mmol, 65% yield) as a yellow solid.

(R)-1-(3-(3-chloro-5-(4,4,5,5-tetramethyl-1,3,2-dioxaborolan-2-yl)phenyl)morpholino)prop-2-en-1-one was obtained from Step 1 of Procedure D.

To a solution of (R)-1-(3-(3-chloro-5-(4,4,5,5-tetramethyl-1,3,2-dioxaborolan-2-yl)phenyl)morpholino)prop-2-en-1-one (1505.3 mg, 3.55 mmol, 1 equiv) in 1,4-dioxane (10 mL, 0.22 M), $H_2O$ (1.8 mL) was added 3-[(4-chloro-1,3,5-triazin-2-yl)amino]propan-1-ol (670 mg, 3.55 mmol, 1 equiv), $K_2CO_3$ (2 eq, 981 mg), and $Pd(PPh_3)_4$(0.1 eq, 411 mg) under $N_2$ and stirred for 3 hours at 80° C. The reaction was poured into water (15 mL). The aqueous phase was extracted with DCM (10 mL*3). The combined organic phase was dried with anhydrous $Na_2SO_4$, filtered, and concentrated under vacuum to afford tert-butyl (R)-3-(3-chloro-5-(4-((3-hydroxypropyl)amino)-1,3,5-triazin-2-yl) phenyl)morpholine-4-carboxylate (500 mg, 1.11 mmol, 31% yield) as a yellow solid.

To a solution of tert-butyl (R)-3-(3-chloro-5-(4-((3-hydroxypropyl)amino)-1,3,5-triazin-2-yl)phenyl)morpholine-4-carboxylate (200 mg, 0.44 mmol, 1 equiv) in DCM (5 mL, 0.08 M) was added Dess-Martin periodinane (245.1 mg, 0.57 mmol) and stirred at 20° C. for 2 hours under $N_2$. The reaction was poured into water (8 mL). The aqueous phase was extracted with DCM (5 mL*3). The combined organic phase was washed with brine (10 mL*2), dried with anhydrous $Na_2SO_4$, filtered, and concentrated under vacuum. The residue was purified by prep-TLC (EtOAc) to afford tert-butyl (R)-3-(3-chloro-5-(4-((3-oxopropyl)amino)-1,3,5-triazin-2-yl)phenyl)morpholine-4-carboxylate (40 mg, 0.089 mmol, 20% yield) as a yellow solid.

To a solution of tert-butyl (R)-3-(3-chloro-5-(4-((3-oxopropyl)amino)-1,3,5-triazin-2-yl)phenyl)morpholine-4-carboxylate (40 mg, 0.089 mmol, 1 equiv) in DCM (5 mL, 0.018 M) was added dimethylamine hydrochloride (11 mg, 0.13 mmol) and stirred at 20° C. for 12 hours under $N_2$. The reaction was poured into water (8 mL). The aqueous phase was extracted with EtOAc (5 mL*3). The combined organic phase was washed with brine (10 mL*2), dried with anhydrous $Na_2SO_4$, filtered, and concentrated under vacuum to afford tert-butyl (R)-3-(3-chloro-5-(4-((3-(dimethylamino) propyl)amino)-1,3,5-triazin-2-yl)phenyl)morpholine-4-carboxylate (100 mg, 0.084 mmol, 94% yield).

tert-butyl (R)-3-(3-chloro-5-(4-((3-(dimethylamino)propyl)amino)-1,3,5-triazin-2-yl)phenyl)morpholine-4-carboxylate was used in step 9 of Procedure B to afford the title compound. LC-MS m/z: 431.3 [M+1].

Stereochemistry: single enantiomer of known absolute configuration.

Example 18. Synthesis of (R)-5-(3-(4-acryloylmorpholin-3-yl)-5-chlorophenyl)tetrahydropyrimidin-2(1H)-one (Compound 222)

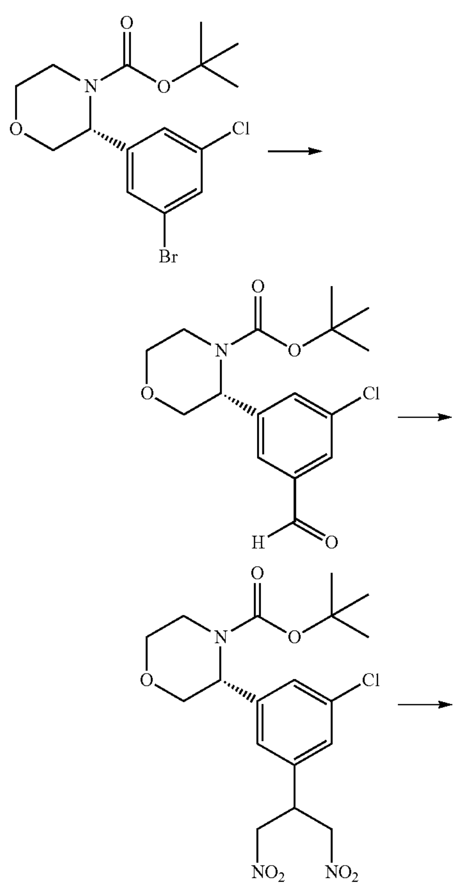

-continued

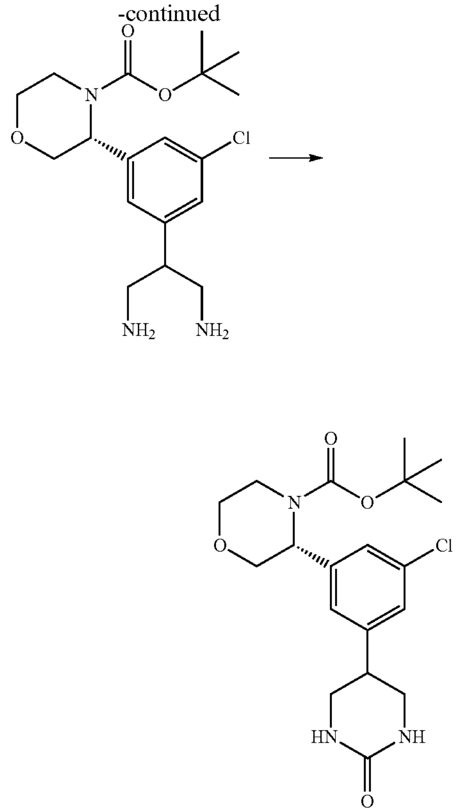

tert-butyl (R)-3-(3-bromo-5-chlorophenyl)morpholine-4-carboxylate was obtained from Step 6 of Procedure B.

To a solution of tert-butyl (R)-3-(3-bromo-5-chlorophenyl)morpholine-4-carboxylate (3 g, 7.96 mmol, 1 equiv) in DMF (30 mL, 0.26 M) was added sodium carbonate (2.53 g, 23.8 mmol, 3 equiv), triethylsilane (2.31 g, 19.91 mmol, 2.5 equiv), and Pd(dppf)$Cl_2$ (404.57 mg, 0.55 mmol, 0.07equiv). The suspension was degassed and purged with CO several times and then stirred for 16 hours at 80° C. under CO (50 psi). The reaction mixture was filtered, and the filtrate was concentrated. The mixture was poured into water (50 mL), extracted with ethyl acetate (30 mL*2), washed with brine, dried over $Na_2SO_4$, filtered, and concentrated under vacuum. The residue was purified by column chromatography ($SiO_2$, petroleum ether/ethyl acetate=1/1 to 5/1) to afford tert-butyl (R)-3-(3-chloro-5-formylphenyl)morpholine-4-carboxylate (2.00 g, 6.14 mmol, 77% yield) as yellow oil.

Nitromethane (937 mg, 15.31 mmol, 50 equiv) was added to a mixture tert-butyl (R)-3-(3-chloro-5-formylphenyl)morpholine-4-carboxylate (100 mg, 0.31 mmol, 1 equiv) and $Al_2O_3$(100 mg). The mixture was stirred at 95° C. for 4 hours. The mixture was filtered and washed with EtOAc (10 mL). After 10% aqueous citric acid solution (10 mL) was added, the mixture was extracted with EtOAc three times and the combined organic layer was dried over $Na_2SO_4$, filtered, and concentrated under vacuum to afford tert-butyl (R)-3-(3-chloro-5-(1,3-dinitropropan-2-yl)phenyl)morpholine-4-carboxylate (100 mg, 0.23 mmol, 76% yield) as a yellow oil.

To a solution of tert-butyl (R)-3-(3-chloro-5-(1,3-dinitropropan-2-yl)phenyl)morpholine-4-carboxylate (600 mg, 1.39 mmol, 1 equiv) and 1,3,5-trichlorobenzene (253 mg, 1.39 mmol, 1 equiv) in THF (1 mL, 1.39 M) was added $PtO_2$ (10 mg) at 25° C. under Ar. The reaction was stirred at 25° C. for 12 hours under $H_2$ (50 PSI). The organic layer was filtered and evaporated to dryness. The crude residue was purified by prep-HPLC (column: Phenomenex Luna C18 75*30 mm*3 um; liquid phase: [A-TFA/$H_2O$=0.075% v/v; B-ACN]B %: 1%-30%, 8 min]) to afford tert-butyl (R)-3-(3-chloro-5-(1,3-diaminopropan-2-yl)phenyl)morpholine-4-carboxylate (100 mg, 0.270 mmol, 20% yield) as a white solid.

To a solution of tert-butyl (R)-3-(3-chloro-5-(1,3-diaminopropan-2-yl)phenyl)morpholine-4-carboxylate (40 mg, 0.11 mmol, 1 equiv) in THF (1 mL, 0.11 M) was slowly added 1,1-carbonyl-diimidazole (17 mg, 0.11 mmol, 1 equiv) in THF (0.5 mL) under N2 at 25° C. and stirred for 16 hours. The solution was concentrated under vacuum and the residue was purified by prep-TLC ($SiO_2$, EA:MeOH=5:1) to afford tert-butyl (R)-3-(3-chloro-5-(2-oxohexahydropyrimidin-5-yl)phenyl)morpholine-4-carboxylate (40 mg, 0.101 mmol, 93% yield) as a yellow oil.

tert-butyl (R)-3-(3-chloro-5-(2-oxohexahydropyrimidin-5-yl)phenyl)morpholine-4-carboxylate was used in Step 9 of Procedure B to afford the title compound. LC-MS m/z: 350.2 [M+1].

Stereochemistry: single enantiomer of known absolute configuration.

Example 19. Synthesis of (R)-2-(3-(4-acryloylmorpholin-3-yl)-5-chlorophenyl)oxazole-4-carboxamide (Compound 224)

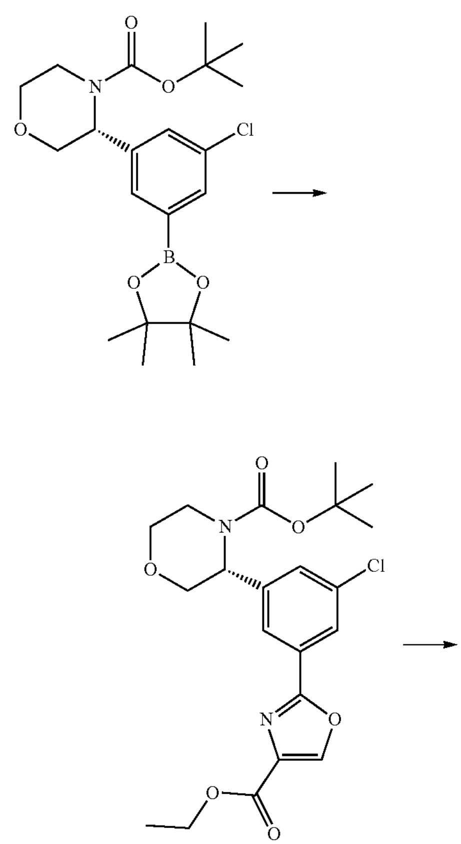

-continued

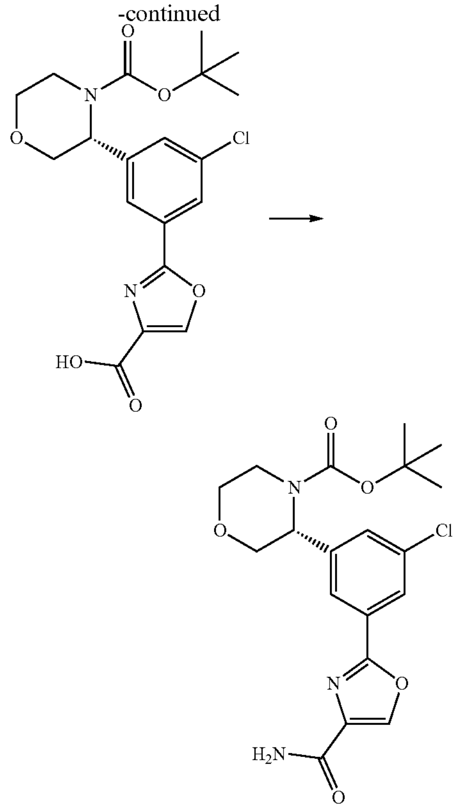

(R)-1-(3-(3-chloro-5-(4,4,5,5-tetramethyl-1,3,2-dioxaborolan-2-yl)phenyl)morpholino)prop-2-en-1-one was obtained from Step 1 of Procedure D.

A solution of (R)-1-(3-(3-chloro-5-(4,4,5,5-tetramethyl-1,3,2-dioxaborolan-2-yl)phenyl)morpholino)prop-2-en-1-one (2.4 g, 5.66 mmol), ethyl 2-bromooxazole-4-carboxylate (1.24 g, 5.66 mmol, 1 equiv), potassium carbonate (1.56 g, 11.32 mmol), and Pd(dppf)$Cl_2$ (0.41 g, 0.56 mmol, 0.1 equiv) in 1,4-dioxane (25 mL, 0.18 M) and water (5 mL, 0.18 M) was stirred at 80° C. for 16 hours under N2. The reaction mixture was poured into $H_2O$ (30 mL) and extracted with ethyl acetate (20 mL*3). The combined organic layers were washed with brine (50 mL), dried over $Na_2SO_4$, filtered, and concentrated under vacuum. The crude residue was purified by column chromatography (PE:EA=0:1-1:1) to afford tert-butyl (R)-3-(3-chloro-5-(4-(ethoxycarbonyl)oxazol-2-yl)phenyl)morpholine-4-carboxylate (2.10 g, 4.81 mmol, 85% yield).

A solution of tert-butyl (R)-3-(3-chloro-5-(4-(ethoxycarbonyl)oxazol-2-yl)phenyl)morpholine-4-carboxylate (0.50 g, 1.14 mmol) and LiOH (0.18 g, 4.43 mmol, 4 equiv) in THF (5 mL, 0.18 M) and water (1.2 mL, 0.18 M) at 25° C. under $N_2$ was stirred for 3 hours. The reaction mixture was diluted with $H_2O$ (10 mL) and extracted with MTBA (10 mL*2). Aqueous HCl (1 M) was added to the water phase to adjust pH to 4-5. The water phase was extracted with ethyl acetate (10 mL*3). The combined organic layers were washed with brine (20 mL), dried over $Na_2SO_4$, filtered, and concentrated under reduced pressure to give the (R)-2-(3-(4-(tert-butoxycarbonyl)morpholin-3-yl)-5-chlorophenyl)oxazole-4-carboxylic acid (0.43 g).

To a solution of (R)-2-(3-(4-(tert-butoxycarbonyl)morpholin-3-yl)-5-chlorophenyl)oxazole-4-carboxylic acid (200 mg, 0.48 mmol, 1 equiv) in THF (2 mL, 0.24 M) was added ammonium bicarbonate (77 mg, 0.97 mmol, 2 equiv), pyridine (77.39 mg, 0.97 mmol, 2 equiv), and di-tert-butyl dicarbonate (213.53 mg, 0.97 mmol, 2 equiv) at 25° C. under $N_2$ and stirred for 12 hours. The reaction mixture was diluted with $H_2O$ (5 mL) and extracted with ethyl acetate (5 mL*2). The combined organic layers were washed with brine (10 mL), dried over $Na_2SO_4$, filtered, and concentrated under reduced pressure to give tert-butyl (R)-3-(3-(4-carbamoyloxazol-2-yl)-5-chlorophenyl)morpholine-4-carboxylate (220 mg).

tert-butyl (R)-3-(3-(4-carbamoyloxazol-2-yl)-5-chlorophenyl)morpholine-4-carboxylate was used in Step 9 of Procedure B to afford the title compound. LC-MS m/z: 362.0 [M+1].

Stereochemistry: single enantiomer of known absolute configuration.

Example 20. Synthesis of (R)-4-(3-(4-acryloylmorpholin-3-yl)-5-chlorophenyl)piperazin-2-one (Compound 228)

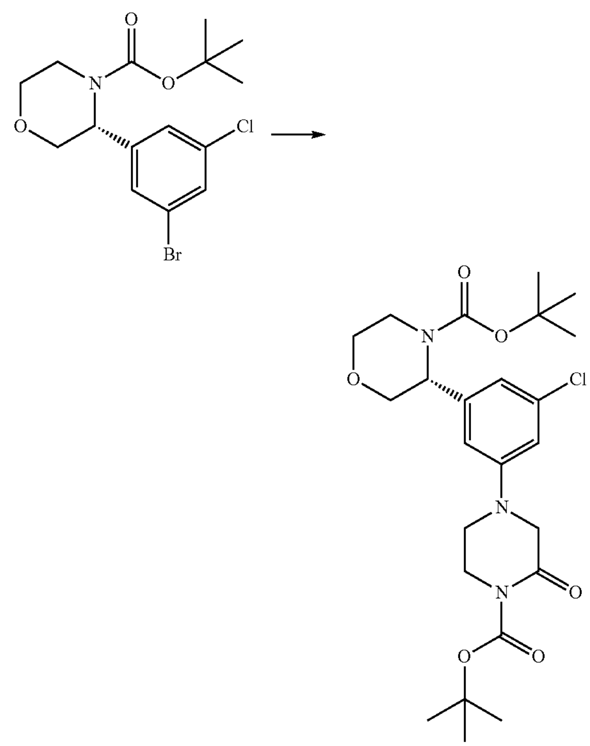

tert-butyl (R)-3-(3-bromo-5-chlorophenyl)morpholine-4-carboxylate was obtained from Step 6 of Procedure B.

A solution of palladium (II) acetate (40.53 mg, 0.18 mmol, 0.10 equiv) and binap (racemic) (224 mg, 0.36 mmol, 0.20 equiv) in 1,4-dioxane (40 mL, 0.045 M) under $N_2$ was stirred at 40° C. for 30 min. tert-butyl (R)-3-(3-bromo-5-chlorophenyl)morpholine-4-carboxylate (680 mg, 1.81 mmol, 1 equiv), 1-boc-2-oxopiperazine (361.47 mg, 1.81 mmol, 1 equiv), and cesium carbonate (882.3 mg, 2.70 mmol, 1.5 equiv) were added and the solution was stirred at 80° C. for 12 hours. The reaction mixture was poured into $H_2O$ (100 mL) and extracted with EtOAc (100 mL*3). The combined organic layers were washed with brine (80 mL), dried over $Na_2SO_4$, filtered, and concentrated under reduced pressure. The residue was purified by flash silica gel chromatography (ISCO®; 40 g SEPAFLASH® Silica Flash Column, Eluent of 0-70% ethyl acetate/petroleum ether gradient @ 80 mL/min) to afford tert-butyl (R)-3-(3-(4-(tert-butoxycarbonyl)-3-oxopiperazin-1-yl)-5-chlorophenyl)morpholine-4-carboxylate (650 mg, 1.31 mmol, 73% yield).

tert-butyl (R)-3-(3-(4-(tert-butoxycarbonyl)-3-oxopiperazin-1-yl)-5-chlorophenyl)morpholine-4-carboxylate was used in Step 9 of Procedure B to afford the title compound. LC-MS m/z: 349.8 [M+1].

Stereochemistry: single enantiomer of known absolute configuration.

Example 21. Synthesis of (R)-1-(3-(3-(4-amino-6-((3-(dimethylamino)propyl)amino)-1,3,5-triazin-2-yl)-5-chlorophenyl)morpholino)prop-2-en-1-one (Compound 229)

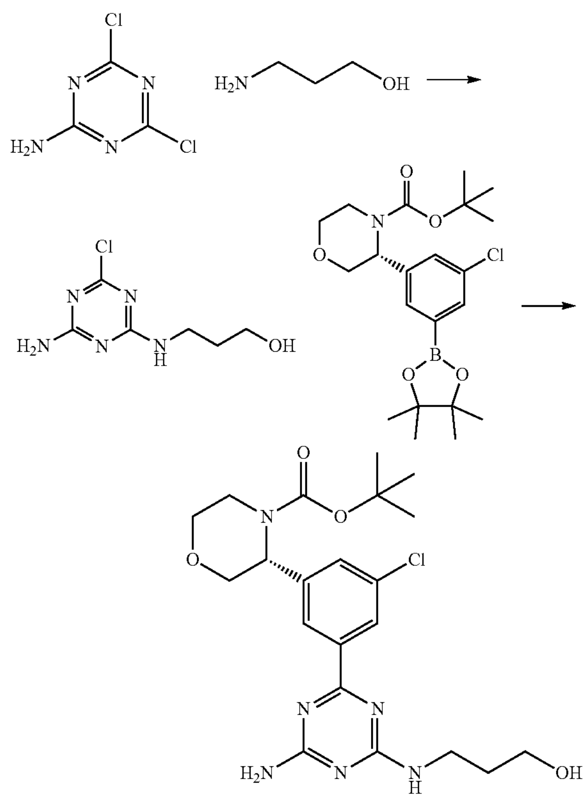

A solution of 4,6-dichloro-1,3,5-triazin-2-amine (1 g, 6.06 mmol, 1 equiv) in 1,4-dioxane (10 mL, 0.61 M), DIEA (1.3 eq, 1.01 g), and 3-amino-1-propanol (546.32 mg, 7.27 mmol) was stirred at 35° C. for 2 hours under $N_2$. The reaction was poured into water (15 mL). The aqueous phase was extracted with EtOAc (10 mL*3). The combined organic phase was washed with brine (10 mL), dried with anhydrous $Na_2SO_4$, filtered, and concentrated under vacuum. The residue was purified by column chromatography (petroleum ether/ethyl acetate=2/1 to 0/1) to afford 3-[(4-amino-6-chloro-1,3,5-triazin-2-yl)amino]propan-1-ol (1.00 g, 4.91 mmol, 81% yield) as yellow solid.

(R)-1-(3-(3-chloro-5-(4,4,5,5-tetramethyl-1,3,2-dioxaborolan-2-yl)phenyl)morpholino)prop-2-en-1-one was obtained from Step 1 of Procedure D.

To a solution of (R)-1-(3-(3-chloro-5-(4,4,5,5-tetramethyl-1,3,2-dioxaborolan-2-yl)phenyl)morpholino)prop-2-en-1-one (228.9 mg, 0.54 mmol, 1.1 equiv) in 1,4-dioxane (2 mL, 0.15 M) and $H_2O$ (1.8 mL) was added 3-[(4-amino-6-chloro-1,3,5-triazin-2-yl)amino]propan-1-ol (100 mg, 0.49 mmol, 1 equiv), $K_2CO_3$ (2 eq, 65 mg), and $Pd(PPh_3)_4$(0.1 eq, 30 mg) and stirred for 12 hours at 80° C. under $N_2$. The reaction was poured into water (8 mL). The aqueous phase was extracted with DCM (10 mL*3). The combined organic phase was dried with anhydrous $Na_2SO_4$, filtered, and concentrated under vacuum. The residue was purified by column chromatography ($SiO_2$, petroleum ether/ethyl acetate=2/1 to 0/1) to afford tert-butyl (R)-3-(3-(4-amino-6-((3-hydroxypropyl)amino)-1,3,5-triazin-2-yl)-5-chlorophenyl)morpholine-4-carboxylate.

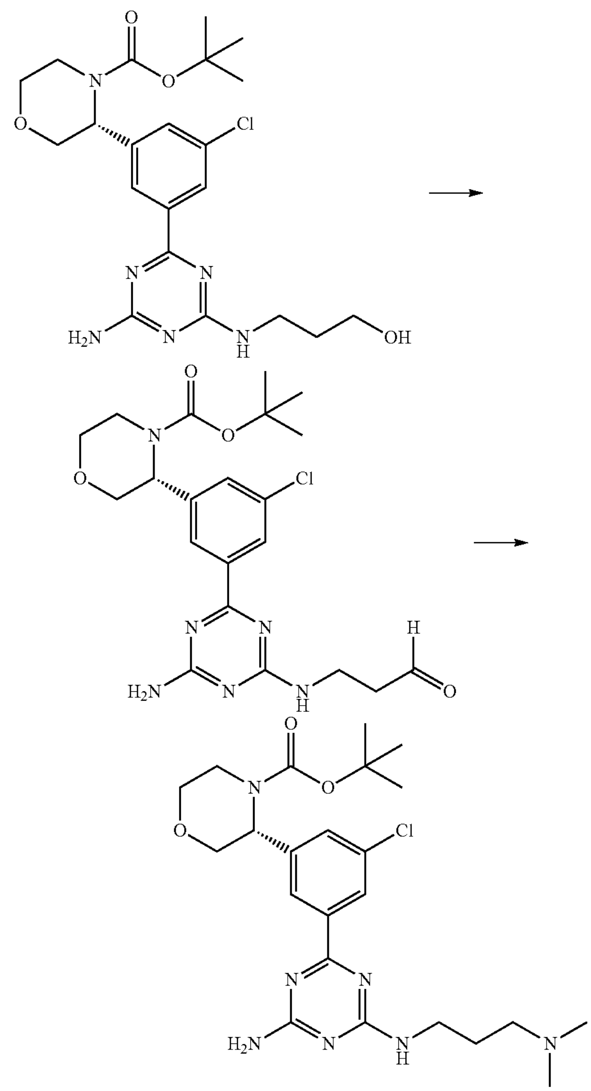

To a solution of tert-butyl (R)-3-(3-(4-amino-6-((3-hydroxypropyl)amino)-1,3,5-triazin-2-yl)-5-chlorophenyl) morpholine-4-carboxylate (500 mg, 1.04 mmol, 1 equiv) in DCM (5 mL, 0.21 M) was added Dess-Martin periodinane (592.95 mg, 1.39 mmol) and stirred at 20° C. for 2 hours under $N_2$. The reaction was poured into water (8 mL). The aqueous phase was extracted with DCM (5 mL*3). The combined organic phase was washed with brine (10 mL*2), dried with anhydrous $Na_2SO_4$, filtered, and concentrated under vacuum to afford tert-butyl (R)-3-(3-(4-amino-6-((3-oxopropyl)amino)-1,3,5-triazin-2-yl)-5-chlorophenyl)morpholine-4-carboxylate (450 mg, 0.680 mmol, 63% yield).

To a solution of tert-butyl (R)-3-(3-(4-amino-6-((3-oxopropyl)amino)-1,3,5-triazin-2-yl)-5-chlorophenyl)morpholine-4-carboxylate (450 mg, 0.91 mmol, 1 equiv) in DCM (5 mL, 0.19 M) was added dimethylamine hydrochloride (119 mg, 1.46 mmol) and sodium triacetoxyborohydride (515 mg, 2.43 mmol) and stirred at 20° C. for 12 hours under $N_2$. The reaction was poured into water (8 mL). The aqueous phase was extracted with DCM (5 mL*3). The combined organic phase was washed with brine (10 mL*2), dried with anhydrous Na2SO4, filtered, and concentrated under vacuum to afford tert-butyl (R)-3-(3-(4-amino-6-((3-(dimethylamino)propyl)amino)-1,3,5-triazin-2-yl)-5-chlorophenyl)morpholine-4-carboxylate (280 mg, 0.39 mmol, 41% yield).

tert-butyl (R)-3-(3-(4-amino-6-((3-(dimethylamino)propyl)amino)-1,3,5-triazin-2-yl)-5-chlorophenyl)morpholine-4-carboxylate was used in Step 9 or Procedure B to afford the title compound. LC-MS m/z: 446.3 [M+1]. Stereochemistry: single enantiomer of known absolute configuration.

Example 22. Synthesis of (R)-1-(3-(3-chloro-5-(2-thioxohexahydropyrimidin-5-yl)phenyl)morpholino)prop-2-en-1-one (Compound 233)

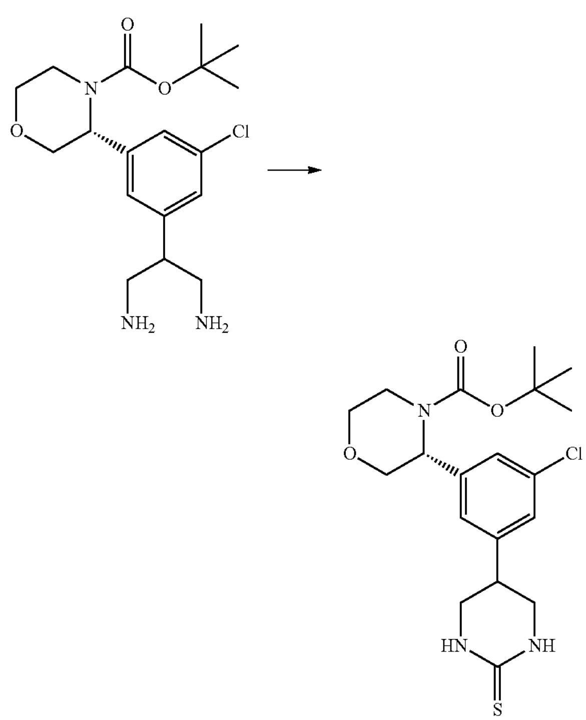

tert-butyl (R)-3-(3-chloro-5-(1,3-diaminopropan-2-yl)phenyl)morpholine-4-carboxylate was obtained from Step 3 of the synthesis for Compound 222.

To a solution of tert-butyl (R)-3-(3-chloro-5-(1,3-diaminopropan-2-yl)phenyl)morpholine-4-carboxylate (320 mg, 0.86 mmol, 1 equiv) in THF (1 mL, 0.86 M) was slowly added di(imidazol-1-yl)methanethione (154 mg, 0.86 mmol, 1 equiv) in THF (0.5 mL) and then stirred for 16 hours. The residue was purified by prep-TLC ($SiO_2$, EA:MeOH=10:1) to give tert-butyl (R)-3-(3-chloro-5-(2-thioxohexahydropyrimidin-5-yl)phenyl)morpholine-4-carboxylate (100 mg, 0.24 mmol, 28% yield).

tert-butyl (R)-3-(3-chloro-5-(2-thioxohexahydropyrimidin-5-yl)phenyl)morpholine-4-carboxylate was used in Step 9 of Procedure B to afford the title compound. LC-MS m/z: 366.2 [M+1].

Stereochemistry: single enantiomer of known absolute configuration.

Example 23. Synthesis of (R)-1-(3-(3-(2-aminooxazol-5-yl)-5-chlorophenyl)morpholino)prop-2-en-1-one (Compound 234)

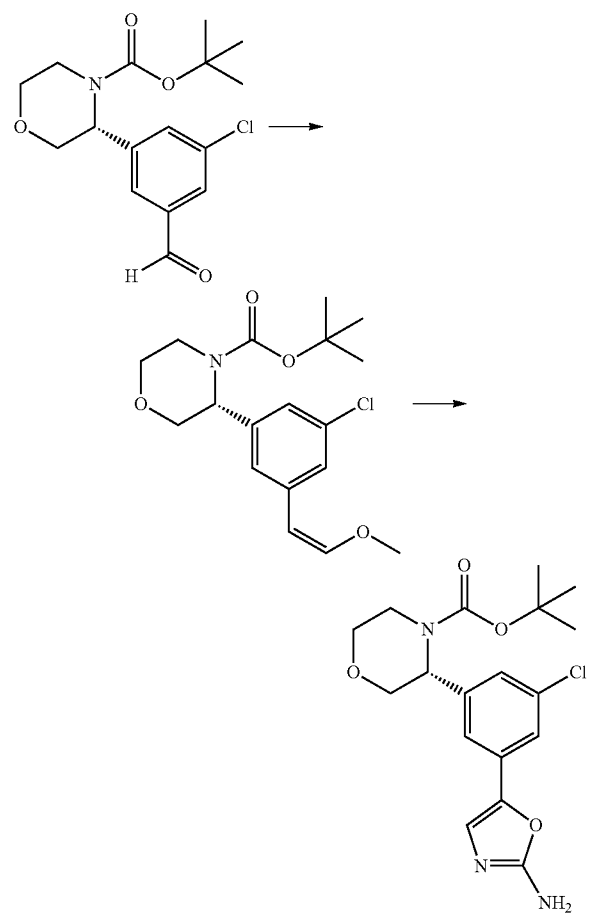

tert-butyl (R)-3-(3-chloro-5-formylphenyl)morpholine-4-carboxylate was obtained from Step 2 of the synthesis of Compound 222.

To a solution of (methoxymethyl)triphenylphosphonium chloride (136.79 mg, 0.39 mmol, 1.3 equiv) in THF (3 mL, 0.10 M) was added sodium bis(trimethylsilyl)amide (1.3 equiv) at 0° C. The mixture was stirred for 1 hour at 0° C. tert-butyl (R)-3-(3-chloro-5-formylphenyl)morpholine-4-carboxylate (100 mg, 0.31 mmol) was then added at 0° C. and the mixture was stirred for 2 hours. The reaction mixture was poured into water (10 mL). The aqueous layer was extracted with ethyl acetate (20 mL*2). The combined organic layers were washed with brine (50 mL), dried over $Na_2SO_4$, and evaporated to dryness. The crude product was purified by prep-TLC (PE:EtOAc=3:1) to afford tert-butyl (R,Z)-3-(3-chloro-5-(2-methoxyvinyl)phenyl)morpholine-4-carboxylate (130 mg) as a colorless oil.

To a solution of tert-butyl (R,Z)-3-(3-chloro-5-(2-methoxyvinyl)phenyl)morpholine-4-carboxylate (130 mg, 0.36 mmol) in 1,4-dioxane (2 mL, 0.09 M) and water (2 mL) was added N-bromosuccinimide (71 mg, 0.40 mmol, 1.1 equiv) at 0° C. and stirred 1 hour. Urea (22. mg, 0.36 mmol, 1 equiv) was added and stirred at 70° C. for 16 hours. The mixture was evaporated to dryness and the crude product was purified by prep-HPLC (column: Phenomenex C18 75*30 mm*3 um; liquid phase: [prep-HPLC (column: Phenomenex C18 75*30 mm*3 um; liquid phase: [A-10 mM $NH_4HCO_3$ in $H_2O$; B-ACN]B %: 25%-70%, 8 min])) to afford tert-butyl (R)-3-(3-(2-aminooxazol-5-yl)-5-chlorophenyl)morpholine-4-carboxylate (15 mg, 0.039 mmol, 11% yield).

tert-butyl (R)-3-(3-(2-aminooxazol-5-yl)-5-chlorophenyl) morpholine-4-carboxylate was used in Step 9 of Procedure B to afford the title compound. LC-MS m/z: 334.0 [M+1].

Stereochemistry: single enantiomer of known absolute configuration.

Example 24. Synthesis of 1-((R)-3-(3-chloro-5-((S)-5-thioxomorpholin-2-yl)phenyl)morpholino)prop-2-en-1-one and 1-((R)-3-(3-chloro-5-((R)-5-thioxomorpholin-2-yl)phenyl)morpholino)prop-2-en-1-one (Compounds 240 and 241)

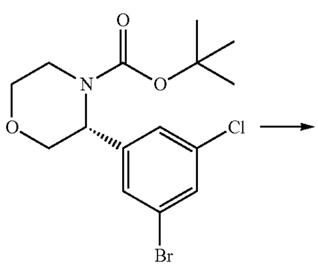

tert-butyl (R)-3-(3-bromo-5-chlorophenyl)morpholine-4-carboxylate was obtained from Step 6 of Procedure B.

To a solution of tert-butyl (R)-3-(3-bromo-5-chlorophenyl)morpholine-4-carboxylate (20 g, 53 mmol, 1 equiv) and potassium vinyltrifluoroborate (8.53 g, 63.71 mmol, 1.2 equiv) in ethanol (200 mL, 0.26 M) was added triethylamine (16.11 g, 159.29 mmol, 3 equiv) and Pd(dppf)$Cl_2$ DCM complex (430.4 mg, 0.53 mmol, 0.01 equiv) under $N_2$ and then stirred for 1 hour at 85° C. The reaction mixture was concentrated under reduced pressure. The crude product was purified by flash silica gel chromatography (Silica Flash Column 12 g, Eluent of 30-70% ethyl acetate/petroleum ether gradient @60 mL/min) to give tert-butyl (R)-3-(3-chloro-5-vinylphenyl)morpholine-4-carboxylate (20.80 g) as a pale yellow oil.

To a solution of tert-butyl (R)-3-(3-chloro-5-vinylphenyl) morpholine-4-carboxylate (5 g, 15.44 mmol, 1 equiv) in DCM (50 mL, 0.31 M) was added 3-chloroperbenzoic acid (6.66 g, 30.88 mmol, 2 equiv) at 0° C. The mixture was stirred for 5 hours at 25° C. An aqueous solution of $Na_2SO_3$ (50 mL) was added to the reaction mixture and then stirred for 30 minutes. The mixture was extracted with DCM (50 mL*3). The combined organic layer was washed with saturated aqueous $NaHCO_3$ (50 mL*2), brine (50 mL), dried over $Na_2SO_4$, filtered, and concentrated. The residue was purified by flash silica gel chromatography (ISCO®; 80 g SEPAFLASH® Silica Flash Column, Eluent of 0-50% ethyl acetate/petroleum ether gradient @ 100 mL/min) to give tert-butyl (3R)-3-(3-chloro-5-(oxiran-2-yl)phenyl)morpholine-4-carboxylate (2.50 g, 7.36 mmol, 48% yield).

tert-butyl (3R)-3-(3-chloro-5-(oxiran-2-yl)phenyl)morpholine-4-carboxylate (2.5 g, 7.35 mmol, 1 equiv) in a large excess of ammonia methanol (26.27 mL, 183 mmol, 25 equiv) was stirred for 12 hours at 70° C. The reaction mixture was concentrated under reduced pressure to give tert-butyl (3R)-3-(3-(2-amino-1-hydroxyethyl)-5-chlorophenyl)morpholine-4-carboxylate (2.30 g, 6.45 mmol, 88% yield) as a yellow solid. Purity of 55% was assigned by $^1$H NMR.

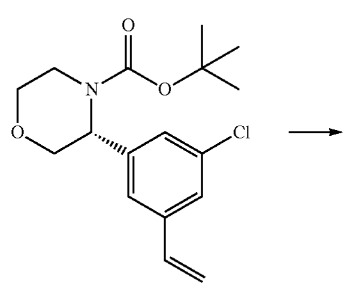

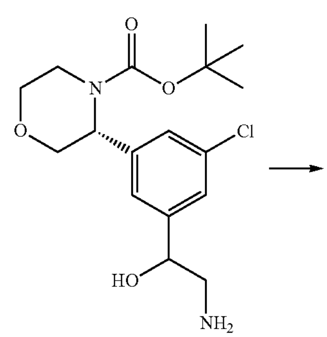

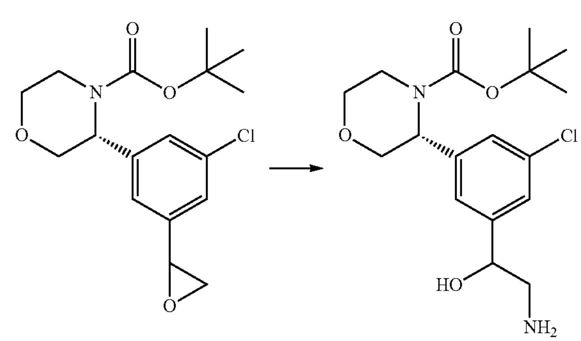

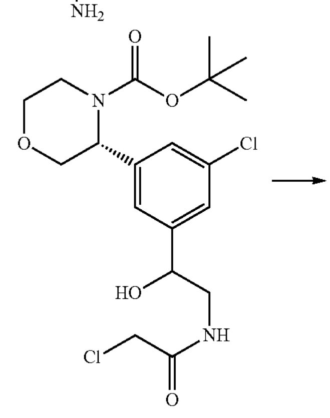

-continued

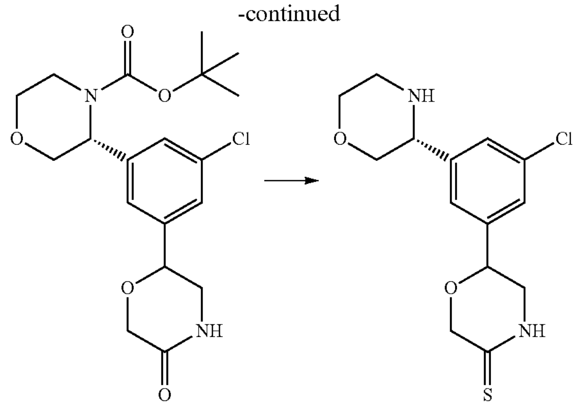

To a solution of tert-butyl (3R)-3-(3-(2-amino-1-hydroxyethyl)-5-chlorophenyl)morpholine-4-carboxylate (2.25 g, 6.30 mmol, 1 equiv) in DCM (20 mL, 0.32 M) was added triethylamine (1091 mg, 10.78 mmol, 1.71 equiv) at 0° C. Chloroacetyl chloride (783 mg, 6.93 mmol, 1.1 equiv) was added slowly at 0° C. and then stirred for 2 hours at 25° C. The mixture was concentrated to afford tert-butyl (3R)-3-(3-chloro-5-(2-(2-chloroacetamido)-1-hydroxyethyl)phenyl)morpholine-4-carboxylate with purity ~40%. The crude residue was not purified.

A solution of tert-butyl (3R)-3-(3-chloro-5-(2-(2-chloroacetamido)-1-hydroxyethyl)phenyl)morpholine-4-carboxylate (2.6 g, 6 mmol, 1 equiv) in THF (30 mL, 0.20 M) was cooled at 0° C. before addition of sodium hydride (480 mg, 12 mmol, 2 equiv). The reaction was stirred for 2 hours at 50° C. The mixture was poured into the saturated aqueous $NH_4Cl$ (30 mL) and extracted with DCM (30 mL*3). The combined organic layer was washed with brine (30 mL), dried over $Na_2SO_4$, filtered, and concentrated. The residue was purified by prep-HPLC to afford tert-butyl (3R)-3-(3-chloro-5-(5-oxomorpholin-2-yl)phenyl)morpholine-4-carboxylate (210 mg, 0.52 mmol, 9% yield).

To a solution of phosphorus pentasulfide (179.22 mg, 0.40 mmol, 1 equiv) in m-Xylene (2 mL, 0.20 M) was added tert-butyl (3R)-3-(3-chloro-5-(5-oxomorpholin-2-yl)phenyl)morpholine-4-carboxylate (160 mg, 0.40 mmol, 1 equiv) at 25° C. The mixture was heated to 135° C. for 16 hours under $N_2$. The reaction mixture was concentrated under reduced pressure and purified by prep-HPLC (instrument: ACSTJ-GX-AP; column: water Xbridge BEH C18 100*30 mm*10 um; conditions: water ($NH_4HCO_3$-ACN)) to afford 6-(3-chloro-5-((R)-morpholin-3-yl)phenyl)morpholine-3-thione (30 mg, 0.096 mmol, 24% yield).

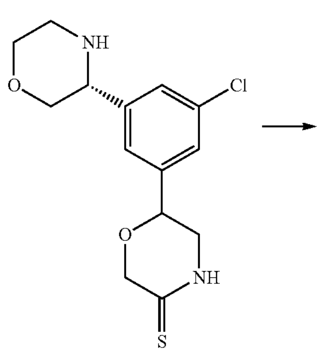

-continued

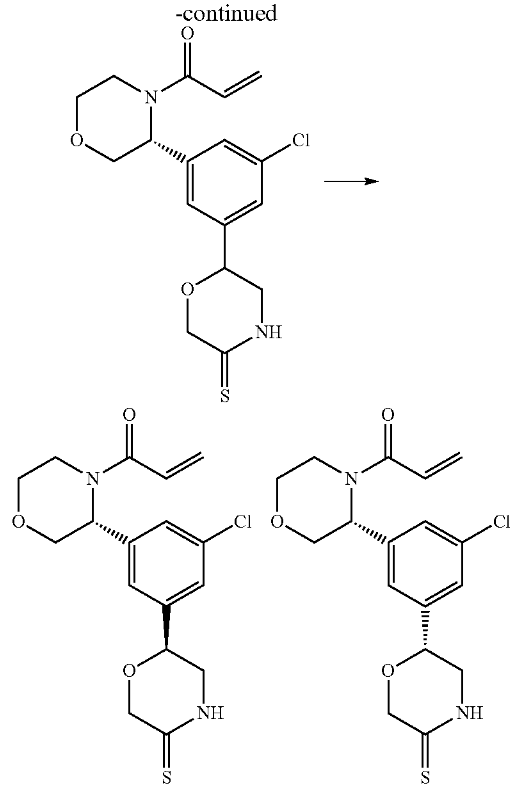

Triethylamine (19.40 mg, 0.19 mmol, 2 equiv) was added to a solution of 6-(3-chloro-5-((R)-morpholin-3-yl)phenyl)morpholine-3-thione (30 mg, 0.095 mmol, 1 equiv) in DCM (1 mL, 0.095 M) under $N_2$ at 0° C. Acryloyl chloride (7.81 mg, 0.086 mmol, 0.9 equiv) was added and the mixture was stirred for 1 hour at 0° C. The mixture was concentrated, and the diastereomers were separated using Prep-HPLC (ACSTJ-GX-AK, column: Waters Xbridge BEH C18 100*30 mm*10 μm, condition: water($NH_4HCO_3$)-ACN) to give 1-((3R)-3-(3-chloro-5-(5-thioxomorpholin-2-yl)phenyl)morpholino)prop-2-en-1-one (20 mg, 0.054 mmol, 56% yield).

Stereochemistry: Single enantiomer of known absolute configuration at the morpholine stereocenter. The stereocenter on the morpholine-3-thione was arbitrarily assigned.

1-((R)-3-(3-chloro-5-((S)-5-thioxomorpholin-2-yl)phenyl)morpholino)prop-2-en-1-one, LC-MS m/z: 367.2 [M+1].

1-((R)-3-(3-chloro-5-((R)-5-thioxomorpholin-2-yl)phenyl)morpholino)prop-2-en-1-one, LC-MS m/z: 367.2 [M+1].

Example 25. Synthesis of (S)-6-(3-((R)-4-acryloylmorpholin-3-yl)-5-chlorophenyl)morpholin-3-one and (R)-6-(3-((R)-4-acryloylmorpholin-3-yl)-5-chlorophenyl)morpholin-3-one (Compounds 231 and 232)

tert-butyl (3R)-3-(3-chloro-5-(5-oxomorpholin-2-yl)phenyl)morpholine-4-carboxylate, from Step 5 of the synthesis of Compounds 240 and 241, was used in Step 9 of Procedure B.

The diastereomeric mixture of 6-(3-((R)-4-acryloylmorpholin-3-yl)-5-chlorophenyl)morpholin-3-one (78 mg, 0.22 mmol, 1 equiv) was separated by chiral SFC.

Chiralpak IH-3,100×4.6 mm I.D., 3 μm; Mobile phase: A: $CO_2$ B: EtOH (0.1% IPAm, v/v); Flow rate: 3.4 mL/min; Column temp.: 35° C.

Stereochemistry: Single enantiomer of known absolute configuration at the morpholine stereocenter. The stereocenter on the morpholine-3-one was arbitrarily assigned.

The compound that eluted first was arbitrarily assigned as (S)-6-(3-((R)-4-acryloylmorpholin-3-yl)-5-chlorophenyl) morpholin-3-one (18.5 mg).

The compound that eluted second was arbitrarily assigned as (R)-6-(3-((R)-4-acryloylmorpholin-3-yl)-5-chlorophenyl)morpholin-3-one (18.7 mg).

Example 26. Synthesis of (R)-1-(3-(3-(5-amino-3,6-dihydropyrazin-1(2H)-yl)-5-chlorophenyl)morpholino)prop-2-en-1-one (Compound 244)

tert-butyl (R)-3-(3-(4-(tert-butoxycarbonyl)-3-oxopiperazin-1-yl)-5-chlorophenyl)morpholine-4-carboxylate was obtained from the synthesis of Compound 228.

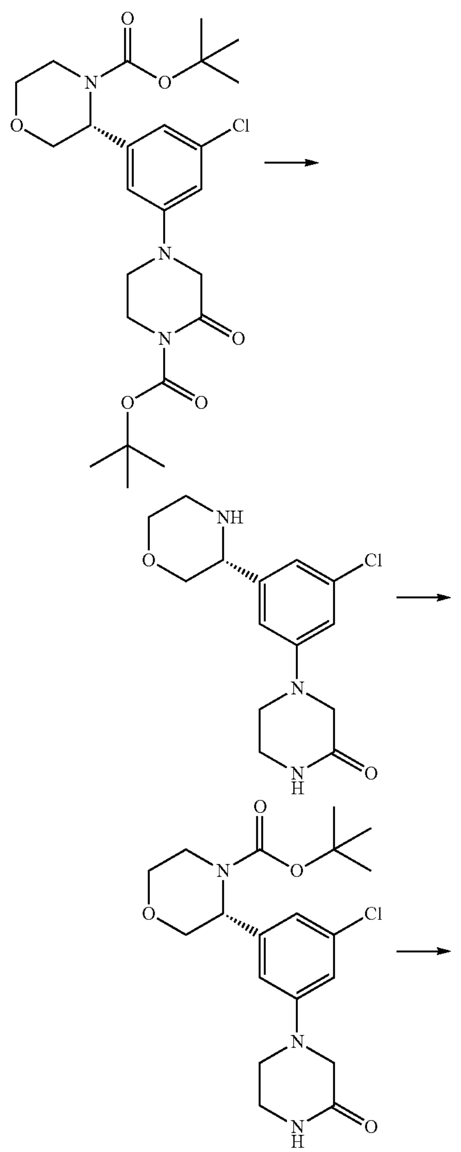

-continued

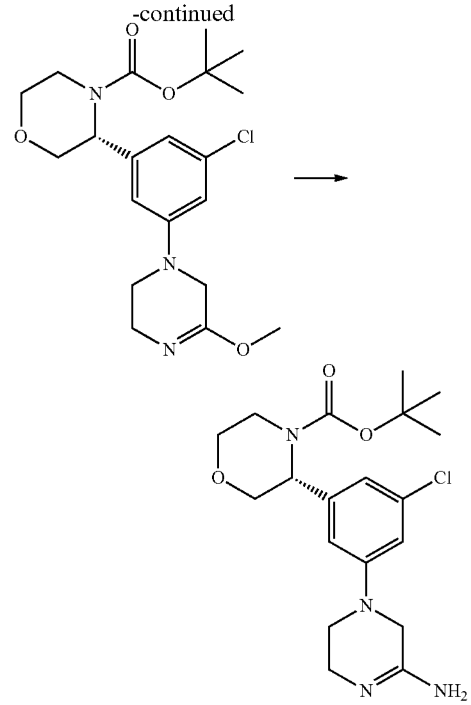

To a solution of tert-butyl (R)-3-(3-(4-(tert-butoxycarbonyl)-3-oxopiperazin-1-yl)-5-chlorophenyl)morpholine-4-carboxylate (840 mg, 1.69 mmol, 1 equiv) in DCM (6 mL, 0.28 M) was added TFA (2 mL) at 25° C. and stirred for 2 hours. The reaction was concentrated under reduced pressure to give a residue (500 mg) and used in the next step without further purification.

To a solution of crude (R)-4-(3-chloro-5-(morpholin-3-yl)phenyl)piperazin-2-one (500 mg, 1.69 mmol, 1 equiv) in DCM (10 mL, 0.17 M) was added triethylamine (342.14 mg, 3.38 mmol, 2 equiv) and di-tert-butyl dicarbonate (368.96 mg, 1.69 mmol, 1 equiv) at 0° C. under $N_2$. The solution was stirred at 25° C. for 12 hours. The reaction mixture was poured into $H_2O$ (15 mL) and extracted with DCM (15 mL*3). The combined organic layers were washed with brine (10 mL), dried over $Na_2SO_4$, filtered, and concentrated under reduced pressure. The residue was purified by flash silica gel chromatography (ISCO®; 12 g SEPAFLASH® Silica Flash Column, Eluent of 50-100% ethyl acetate/petroleum ether gradient @ 60 mL/min) to give tert-butyl (R)-3-(3-chloro-5-(3-oxopiperazin-1-yl)phenyl)morpholine-4-carboxylate (500 mg, 1.26 mmol, 75% yield) as a yellow oil.

To a solution of tert-butyl (R)-3-(3-chloro-5-(3-oxopiperazin-1-yl)phenyl)morpholine-4-carboxylate (500 mg, 1.26 mmol, 1 equiv) in DCM (6 mL, 0.21 M) was added trimethyloxonium tetrafluoroborate (242 mg, 1.64 mmol, 1.3 equiv) at 0° C. under N2. The solution was stirred at 25° C. for 12 hours. The mixture was used into the next step.

To a solution of crude tert-butyl (R)-3-(3-chloro-5-(5-methoxy-3,6-dihydropyrazin-1(2H)-yl)phenyl)morpholine-4-carboxylate (500 mg, 1.22 mmol, 1 equiv) in DCM (6 mL) was added aq. $NH_3$ (6 mL) at −40° C. under $N_2$. The solution was stirred at −40° C. for 2 hours and then returned to 25° C. The reaction mixture was concentrated under reduced pressure. The crude residue was purified by prep-HPLC (column: Phenomenex C18 80*30 mm*3 um; liquid phase: [A-TFA/$H_2O$=0.075% v/v; B-ACN]B %: 20%-50%, 8 min])

to give tert-butyl (R)-3-(3-(5-amino-3,6-dihydropyrazin-1(2H)-yl)-5-chlorophenyl)morpholine-4-carboxylate (125 mg, 0.32 mmol, 26% yield).

tert-butyl (R)-3-(3-(5-amino-3,6-dihydropyrazin-1(2H)-yl)-5-chlorophenyl)morpholine-4-carboxylate was used in Step 9 of Procedure B to afford the title compound. LC-MS m/z: 349.2 [M+1].

Stereochemistry: single enantiomer of known absolute configuration.

Example 27. Synthesis of (R)—N-(2-(3-(4-acryloylmorpholin-3-yl)-5-chlorophenyl)pyrimidin-5-yl) acetamide (Compound 248)

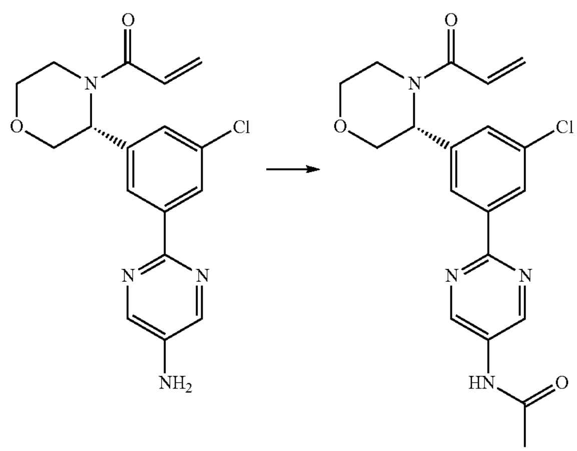 [SMILES: C=CC(=O)N1CCOC[C@H]1c1cc(Cl)cc(-c2ncc(N)cn2)c1 ; C=CC(=O)N1CCOC[C@H]1c1cc(Cl)cc(-c2ncc(NC(C)=O)cn2)c1]

(R)-1-(3-(3-chloro-5-(5-methylpyrimidin-2-yl)phenyl) morpholino)prop-2-en-1-one was obtained from Procedure D.

To a solution of (R)-1-(3-(3-chloro-5-(5-methylpyrimidin-2-yl)phenyl)morpholino)prop-2-en-1-one (250 mg, 0.73 mmol, 1 equiv) in DCM (3 mL, 0.24 M) was added triethylamine (110 mg, 1.08 mmol, 1.5 equiv), acetyl chloride (68.3 mg, 0.87 mmol, 1.2 equiv), and 4-(dimethylamino)pyridine (8.85 mg, 0.072 mmol, 0.1 equiv) at 0° C. The mixture was stirred at 20° C. for 20 hours under $N_2$. The reaction mixture was concentrated, diluted with water (20 mL), and extracted with DCM (15 mL*3). The combined organic layers were washed with brine (10 mL), dried over $Na_2SO_4$, filtered, and concentrated under reduced pressure. The residue was purified by prep-HPLC (column: Phenomenex Luna 80*30 mm*3 um; liquid phase: [A-TFA/$H_2O$=0.075% v/v; B-ACN] B %: 20%-45%, 8 min]) to afford (R)—N-(2-(3-(4-acryloylmorpholin-3-yl)-5-chlorophenyl)pyrimidin-5-yl)acetamide (121 mg, 0.31 mmol, 43% yield) as a white solid. LC-MS m/z: 387.2 [M+1].

Stereochemistry: single enantiomer of known absolute configuration.

Example 28. Synthesis of (R)-1-(3-(3-chloro-5-(4,5-diaminopyrimidin-2-yl)phenyl)morpholino)prop-2-en-1-one (Compound 253)

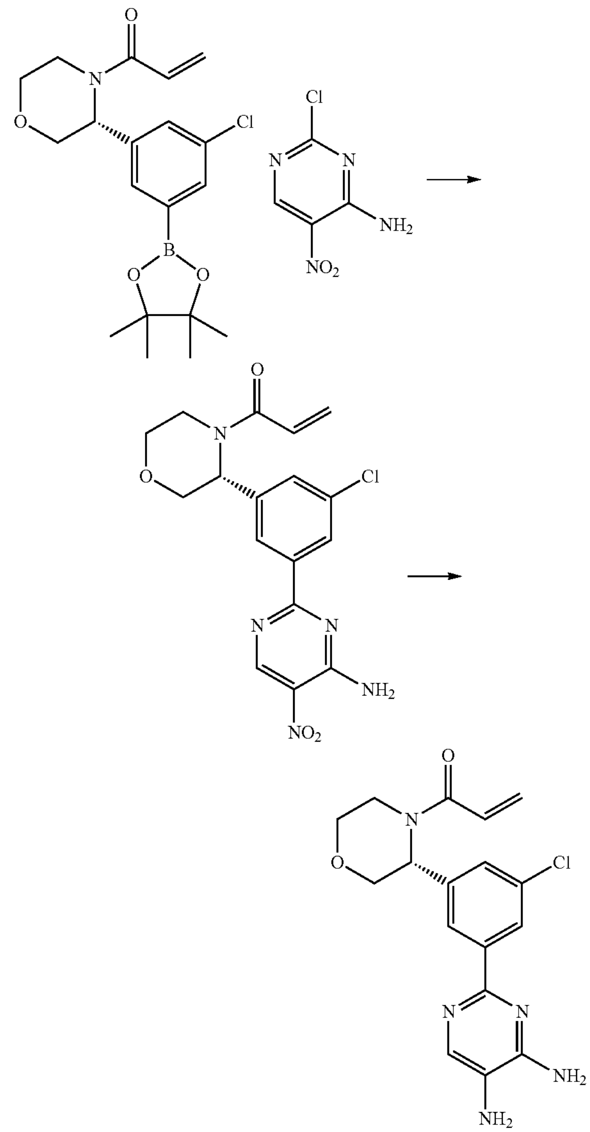

(R)-1-(3-(3-chloro-5-(4,4,5,5-tetramethyl-1,3,2-dioxaborolan-2-yl)phenyl)morpholino)prop-2-en-1-one was obtained from Step 1 of Procedure D.

To a solution of (R)-1-(3-(3-chloro-5-(4,4,5,5-tetramethyl-1,3,2-dioxaborolan-2-yl)phenyl)morpholino)prop-2-en-1-one (300 mg, 0.79 mmol, 1 equiv) in 1,4-dioxane (5 mL, 0.13 M) and water (1 mL, 0.13 M) was added 2-chloro-5-nitro-pyrimidin-4-amine (221.83 mg, 1.27 mmol, 1.6 equiv), potassium carbonate (219.56 mg, 1.58 mmol, 2 equiv), and Pd(dppf)$Cl_2$ (57 mg, 0.079 mmol, 0.1 equiv) at 20° C. The mixture was stirred at 80° C. for 20 hours under $N_2$. The reaction mixture was poured into water (15 mL) and extracted with EtOAc (15 mL*3). The combined organic layers were washed with brine (10 mL*2), dried over $Na_2SO_4$, filtered, and concentrated under reduced pressure. The residue was purified by flash silica gel chromatography (ISCO®; 12 g SEPAFLASH® Silica Flash Column, Eluent of 30-60% ethyl acetate/petroleum ether gradient @ 50 mL/min) to afford (R)-1-(3-(3-(4-amino-5-nitropyrimidin-2-yl)-5-chlorophenyl)morpholino)prop-2-en-1-one (220 mg, 0.56 mmol, 71% yield).

To a solution of (R)-1-(3-(3-(4-amino-5-nitropyrimidin-2-yl)-5-chlorophenyl)morpholino)prop-2-en-1-one (200 mg, 0.51 mmol, 1 equiv) in ethanol (2 mL, 0.12 M), water (1 mL, 0.12 M), and acetic acid (1 mL, 0.12 M) was added zinc, granular (130 mg, 1.98 mmol) at 25° C. The mixture was stirred at 25° C. for 20 hours under $N_2$. The mixture was filtered and the solution was quenched with 1N HCl. The solution pH was adjusted with saturated aqueous $NaHCO_3$ to pH=8-9 and extracted with EtOAc (15 mL*3). The combined organic layers were washed with brine (10 mL*2), dried over $Na_2SO_4$, filtered, and concentrated under reduced pressure to afford (R)-1-(3-(3-chloro-5-(4,5-diaminopyrimidin-2-yl)phenyl)morpholino)prop-2-en-1-one (40.7 mg, 0.11 mmol, 22% yield). LC-MS m/z: 360.2 [M+1].

Stereochemistry: single enantiomer of known absolute configuration.

Example 29. Synthesis of (R)—N-(2-(3-(4-acryloylmorpholin-3-yl)-5-chlorophenyl)pyrimidin-4-yl)acetamide (Compound 256)

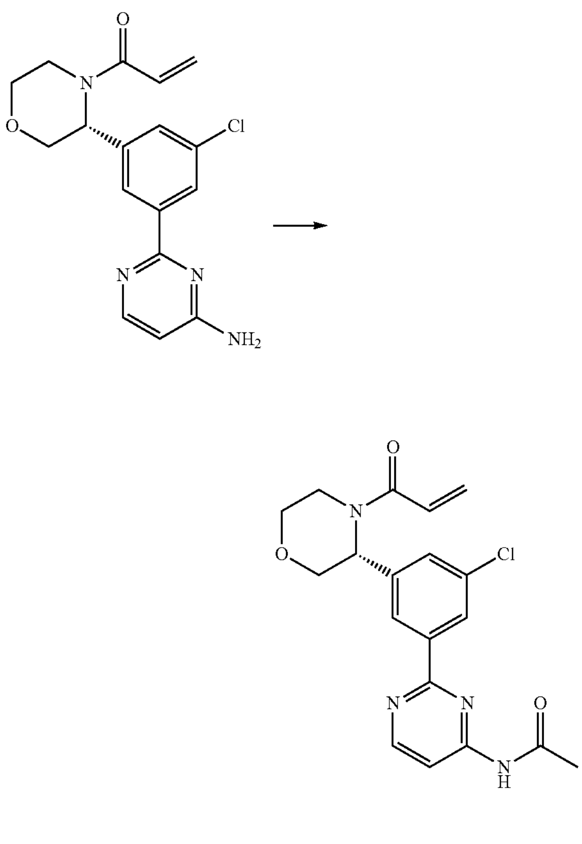 [SMILES: C=CC(=O)N1CCOC[C@H]1c1cc(Cl)cc(-c2nccc(N)n2)c1 ; C=CC(=O)N1CCOC[C@H]1c1cc(Cl)cc(-c2nccc(NC(C)=O)n2)c1]

(R)-1-(3-(3-(4-aminopyrimidin-2-yl)-5-chlorophenyl)morpholino)prop-2-en-1-one was obtained from Procedure D.

To a solution of (R)-1-(3-(3-(4-aminopyrimidin-2-yl)-5-chlorophenyl)morpholino)prop-2-en-1-one (200 mg, 0.58 mmol, 1 equiv) in acetic anhydride (4 mL, 0.14 M) was added 4-(dimethylamino)pyridine (2.12 mg, 0.017 mmol, 0.03 equiv) at 20° C. The mixture was stirred at 80° C. for 4 hours under $N_2$. The mixture was concentrated under reduced pressure and purified by prep-HPLC (column: Waters Xbridge BEH C18 100*30 mm*10 um; liquid phase: [A-10 mM $NH_4HCO_3$ in $H_2O$; B-ACN] B %: 30%-50%, 8 min]) to afford (R)—N-(2-(3-(4-acryloylmorpholin-3-yl)-5-chlorophenyl)pyrimidin-4-yl)acetamide (85 mg, 0.21 mmol, 37% yield) as a white solid. LC-MS m/z: 387.0 [M+1].

Stereochemistry: single enantiomer of known absolute configuration.

Example 30. Synthesis of Compound 263

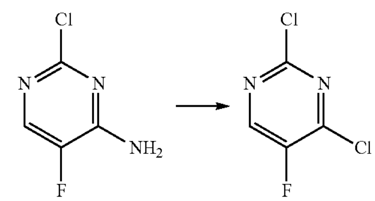 [SMILES: Nc1nc(Cl)ncc1F ; Fc1cnc(Cl)nc1Cl]

To a solution of 2-chloro-5-fluoropyrimidin-4-amine (1 g, 5.98 mmol, 1 equiv) was added aqueous $NH_3$ (40 mL) at 25° C. The mixture was stirred at 35° C. for 3 hours under $N_2$. The reaction mixture was filtered and concentrated under reduced pressure to give a crude 2-chloro-5-fluoro-pyrimidin-4-amine.

2-chloro-5-fluoro-pyrimidin-4-amine was used in Step 2 of Procedure D to afford the title compound. LC-MS m/z: 363.1 [M+1].

Example 31. Synthesis of (R)-1-(3-(3-chloro-5-(1H-1,2,3-triazol-4-yl)phenyl)morpholino)prop-2-en-1-one (Compound 269)

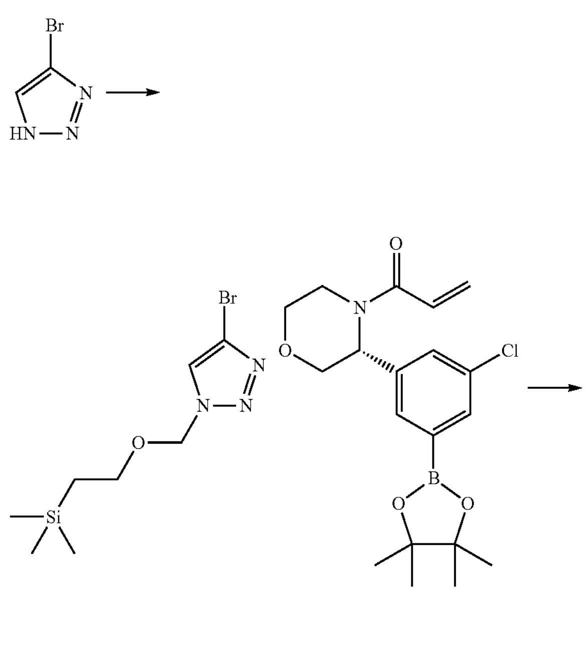

-continued

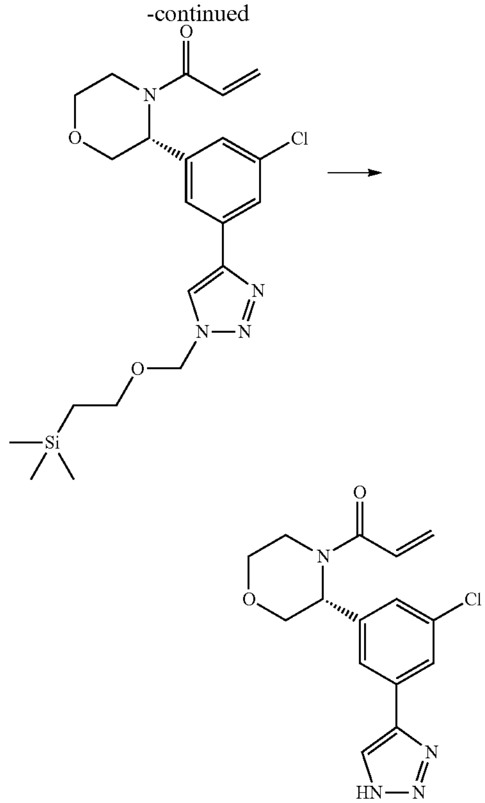

To a solution of 4-bromo-1H-triazole (100 mg, 0.67 mmol, 1 equiv) in DMF (2 mL, 0.33 M) at 0° C. was added cesium carbonate (440.42 mg, 1.37 mmol, 2 equiv) and 2-(trimethylsilyl)ethoxymethyl chloride (169.02 mg, 1.013 mmol, 1.5 equiv). The mixture was stirred at 20° C. for 12 hours. The reaction was poured into $H_2O$ (5 mL) and the aqueous layer was extracted with EtOAc (5 mL×3). The combined organic layer was washed with brine (5 mL), dried over $Na_2SO_4$, and concentrated under vacuum. The residue was purified by prep-TLC (PE:EtOAc=5/1) to afford 2-[(4-bromotriazol-1-yl)methoxy]ethyl-trimethyl-silane (30 mg, 0.108 mmol, 16% yield) as yellow solid.

(R)-1-(3-(3-chloro-5-(4,4,5,5-tetramethyl-1,3,2-dioxaborolan-2-yl)phenyl)morpholino)prop-2-en-1-one was obtained from Step 1 of Procedure D.

To a solution of (R)-1-(3-(3-chloro-5-(4,4,5,5-tetramethyl-1,3,2-dioxaborolan-2-yl)phenyl)morpholino)prop-2-en-1-one (50 mg, 0.13 mmol, 1 equiv) in 1,4-dioxane (2 mL, 0.02 M) and water (0.40 mL, 0.055 M) was added 2-[(4-bromotriazol-1-yl)methoxy]ethyl-trimethyl-silane (36 mg, 0.13 mmol, 1 equiv), potassium carbonate (45 mg, 0.33 mmol, 2.5 equiv), and Pd(dppf)$Cl_2$ (9.5 mg, 0.013 mmol, 0.1 equiv) at 25° C. under $N_2$. The mixture was stirred at 80° C. for 7 hours. The reaction was poured into $H_2O$ (10 mL) and the aqueous layer was extracted with EtOAc (5 mL×3). The combined organic layer was washed with brine (10 mL), dried over $Na_2SO_4$, filtered, and concentrated under vacuum. The residue was purified by prep-TLC (PE: EtOAc=1/1) to afford (R)-1-(3-(3-chloro-5-(1-((2-(trimethylsilyl)ethoxy)methyl)-1H-1,2,3-triazol-4-yl)phenyl)morpholino)prop-2-en-1-one (10 mg, 0.022 mmol, 17% yield).

To a solution of (R)-1-(3-(3-chloro-5-(1-((2-(trimethylsilyl)ethoxy)methyl)-1H-1,2,3-triazol-4-yl)phenyl)morpholino)prop-2-en-1-one (110 mg, 0.24 mmol, 1 equiv) in DCM (2 mL, 0.08 M) was added trifluoroacetic acid (1 mL, 0.08 M) at 20° C. The mixture was stirred at 35° C. for 16 hours under $N_2$ and then concentrated under vacuum. The crude material was purified by prep-HPLC (column: Waters Xbridge BEH C18 100*30 mm*10 um; liquid phase: [A-10 mM $NH_4HCO_3$ in $H_2O$; B-ACN]B %: 10%-40%, 8 min]) to give (R)-1-(3-(3-chloro-5-(1H-1,2,3-triazol-4-yl)phenyl)morpholino)prop-2-en-1-one (47 mg, 0.14 mmol, 59% yield) as a yellow solid. LC-MS m/z: 319.2 [M+1].

Stereochemistry: single enantiomer of known absolute configuration.

Example 32. Synthesis of (R)-1-(3-(3-(5-amino-4-fluoropyrimidin-2-yl)-5-chlorophenyl)morpholino)prop-2-en-1-one (Compound 278)

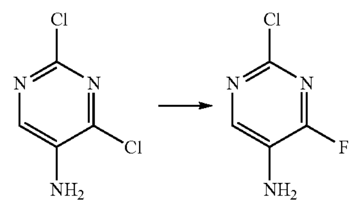 [SMILES: Nc1cnc(Cl)nc1Cl ; Nc1cnc(Cl)nc1F]

To a solution of 2,4-dichloropyrimidin-5-amine (400 mg, 2.43 mmol, 1 equiv) in DMF (3 mL, 0.81 M) was added potassium fluoride (283 mg, 4.87 mmol). The mixture was stirred at 130° C. for 13 hours in the microwave. The reaction was poured into $H_2O$ (10 mL) and the aqueous layer was extracted with EtOAc (5 mL×3). The combined organic layer was washed with brine (10 mL), dried over $Na_2SO_4$, filtered, and concentrated under vacuum to give crude 2-chloro-4-fluoropyrimidin-5-amine (400 mg) as a brown oil. The product was used for the next step without further purification.

Crude 2-chloro-4-fluoropyrimidin-5-amine was used in Procedure D to afford the title compound. LC-MS m/z: 363.1 [M+1].

Stereochemistry: single enantiomer of known absolute configuration.

Example 33. Synthesis of (R)-1-(3-(3-(6-amino-5-fluoropyrazin-2-yl)-5-chlorophenyl)morpholino)prop-2-en-1-one (Compound 279)

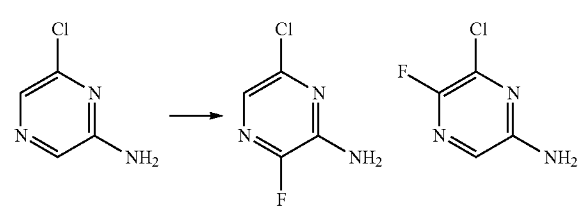 [SMILES: Nc1cncc(Cl)n1 ; Nc1nc(Cl)cnc1F ; Nc1cnc(F)c(Cl)n1]

A solution of 6-chloropyrazin-2-amine (500 mg, 3.85 mmol, 1 equiv), SELECTFLUOR® (1.025 g, 2.89 mmol, 0.75 equiv), and silver carbonate (106.42 mg, 0.38 mmol, 0.1 equiv) in MeCN (8 mL, 0.48 M) was stirred at 85° C. for 24 hours in the microware. The reaction mixture was poured into $H_2O$ (20 mL) and extracted with ethyl acetate (20 mL×3). The organic layer was washed with brine (30 mL) and concentrated. The crude residue was purified by flash column chromatography (pet ether:ethyl acetate=1:0 to 1:1)

to give 6-chloro-3-fluoro-pyrazin-2-amine (200 mg, 1.36 mmol, 35% yield) and 6-chloro-5-fluoro-pyrazin-2-amine (170 mg, 1.15 mmol, 30% yield).

6-chloro-3-fluoro-pyrazin-2-amine was used in Procedure D to afford the title compound. LC-MS m/z: 363.0 [M+1].

Stereochemistry: single enantiomer of known absolute configuration.

Example 34. Synthesis of (R)-1-(3-(3-(6-amino-3-fluoropyrazin-2-yl)-5-chlorophenyl)morpholino) prop-2-en-1-one (Compound 280)

6-chloro-5-fluoro-pyrazin-2-amine from the synthesis of Compound 279 was used in Procedure D to afford the title compound. LC-MS m/z: 363.1 [M+1].

Stereochemistry: single enantiomer of known absolute configuration.

Example 35. Synthesis of (R)-1-(3-(3-(6-amino-2-fluoropyrimidin-4-yl)-5-chlorophenyl)morpholino) prop-2-en-1-one (Compound 283)

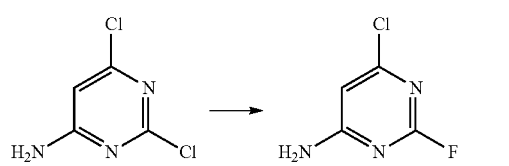 [SMILES: Nc1cc(Cl)nc(Cl)n1 ; Nc1cc(Cl)nc(F)n1]

Potassium fluoride (1.77 g, 30.49 mmol) was added to a solution of 2,6-dichloropyrimidin-4-amine (1 g, 6.09 mmol, 1 equiv) in DMF (10 mL, 0.61 M) at 20° C. The mixture was stirred at 130° C. for 16 hrs. The reaction mixture was poured into water (20 mL) and extracted with EtOAc (30 mL*3). The combined organic layers were washed with brine (30 mL), dried over $Na_2SO_4$, filtered, and concentrated under reduced pressure. The residue was purified by prep-HPLC [column: Phenomenex luna C18 75*30 mm*3 um; mobile phase: [water (0.1% TFA)-ACN]; B %: 1%-30%, 8 min] to afford 6-chloro-2-fluoropyrimidin-4-amine (50 mg, 0.34 mmol, 6% yield) as a white solid. [00410] 6-chloro-2-fluoropyrimidin-4-amine was used in Step 2 of Procedure D to afford the title compound. LC-MS m/z: 363.2 [M+1].

Stereochemistry: single enantiomer of known absolute configuration.

Example 36. Synthesis of (R)-1-(3-(3-(5-amino-6-fluoropyrazin-2-yl)-5-chlorophenyl)morpholino) prop-2-en-1-one (Compound 289)

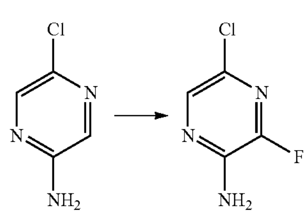 [SMILES: Nc1cnc(Cl)cn1 ; Nc1ncc(Cl)nc1F]

A solution of 5-chloropyrazin-2-amine (500 mg, 3.85 mmol, 1 equiv), SELECTFLUOR® (1.025 g, 2.89 mmol, 0.75 equiv), and silver carbonate (106.42 mg, 0.38 mmol, 0.10 equiv) in MeCN (8 mL, 0.48 M) was stirred at 85° C. for 12 hours in the microwave. The reaction was poured into $H_2O$ (20 mL) and extracted with ethyl acetate (20 mL×3). The organic layer was washed with brine (30 mL) and concentrated. The crude material was purified by flash column chromatography (PE:EA=1:0-1:1) to give 5-chloro-3-fluoro-pyrazin-2-amine (100 mg, 0.67 mmol, 18% yield) as a yellow solid.

5-chloro-3-fluoro-pyrazin-2-amine was used in Procedure D to afford the title compound. LC-MS m/z: 363.1 [M+1].

Stereochemistry: single enantiomer of known absolute configuration.

Example 37. Procedure E and Synthesis of 4-(3-(4-acryloylmorpholin-3-yl)-5-chlorophenyl)pyridin-2 (1H)-one (Compound 11)

Procedure E

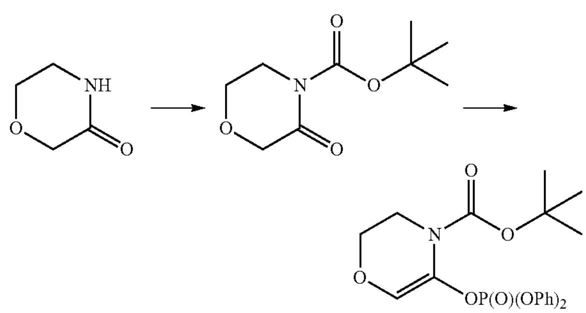

To a solution of morpholin-3-one (10.098 g, 99.88 mmol) in THF (100 mL, 0.99 M) was added triethylamine (15 g) and DMAP (300 mg) at 10° C. Di-tert-butyl dicarbonate (23.97 g, 109.87 mmol) was added in portions and then stirred at 10° C. for 1 hour. The reaction was poured into water (100 mL) and the mixture was extracted with ethyl acetate (100 mL*2). The combined organic layer was washed with brine (100 mL) and concentrated to afford tert-butyl 3-oxomorpholine-4-carboxylate (20 g, 99.39 mmol, 99% yield) as a yellow solid.

To a solution of tert-butyl 3-oxomorpholine-4-carboxylate (5000 mg, 24.84 mmol) in THF (100 mL, 0.24 M) was added LiHMDS (28.4 mL, 1 M) dropwise at −30° C. The reaction was stirred at −30° C. for 30 minutes. Diphenyl phosphorochloridate (7342.5 mg, 27.33 mmol) was added dropwise at −30° C. and then stirred at 10° C. for 1 hour. The reaction was poured into water (100 mL) and extracted with ethyl acetate (30 mL×3). The organic layer was washed with brine (50 mL) and concentrated. The crude product was purified by column chromatography (PE:EA=100:1-10:1) to give tert-butyl 5-((diphenoxyphosphoryl)oxy)-2,3-dihydro-4H-1,4-oxazine-4-carboxylate (4500 mg, 10.38 mmol, 42% yield) as a brown oil.

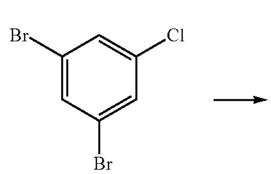

-continued

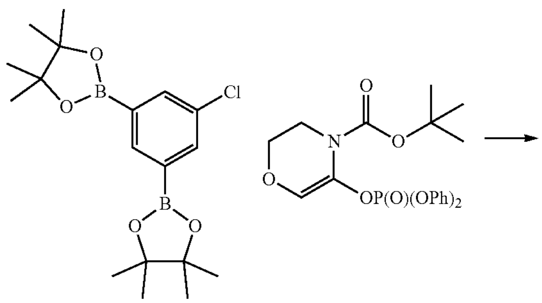

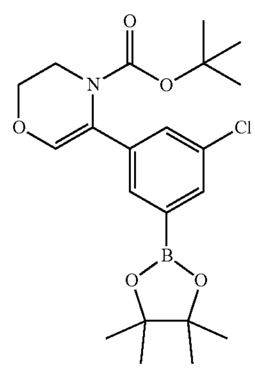

To a solution of 1,3-dibromo-5-chloro-benzene (20 g, 73.97 mmol) in 1,4-dioxane (200 mL, 0.36 M) was added bis(pinacolato)diboron (56 g, 221.9 mmol, 3 eq), KOAc (36 g, 5 eq) and Pd(dppf)$Cl_2$ (2 g). The resulting mixture was stirred at 90° C. for 16 hours under $N_2$. The reaction mixture was quenched with $H_2O$ (100 mL) and extracted with ethyl acetate (100 mL×3). The combined organic layers were washed with 50 mL saturated aqueous brine solution. The organic layer was then separated, dried over $Na_2SO_4$, filtered, and concentrated. The crude residue was purified by flash column chromatography (PE:EtOAc) to afford 2,2'-(5-chloro-1,3-phenylene)bis(4,4,5,5-tetramethyl-1,3,2-dioxaborolane) (16 g, 43.6 mmol, 59% yield) as a white solid.

To a solution of 2,2'-(5-chloro-1,3-phenylene)bis(4,4,5,5-tetramethyl-1,3,2-dioxaborolane) (18 g, 49.38 mmol) in 1,4-dioxane (72 mL, 0.34 M), MeCN (72 mL), and $H_2O$ (36 mL) was added tert-butyl 5-((diphenoxyphosphoryl)oxy)-2,3-dihydro-4H-1,4-oxazine-4-carboxylate (16.49 g, 39.51 mmol), $K_2CO_3$ (2 eq, 13.8 g), and Pd(dppf)$Cl_2$ (1.8 g). The resulting mixture was stirred at 80° C. for 4 hours under $N_2$. The reaction mixture was quenched with $H_2O$ (100 mL) and extracted with EtOAc (100 mL*3). The organic layers were washed 50 mL saturated brine solution, dried over $Na_2SO_4$, filtered, and concentrated. The crude residue was purified by flash column chromatography (PE:EtOAc=10:1 to 1:1) to give tert-butyl 5-(3-chloro-5-(4,4,5,5-tetramethyl-1,3,2-dioxaborolan-2-yl)phenyl)-2,3-dihydro-4H-1,4-oxazine-4-carboxylate (10.0 g, 23.7 mmol, 48% yield) as a yellow oil.

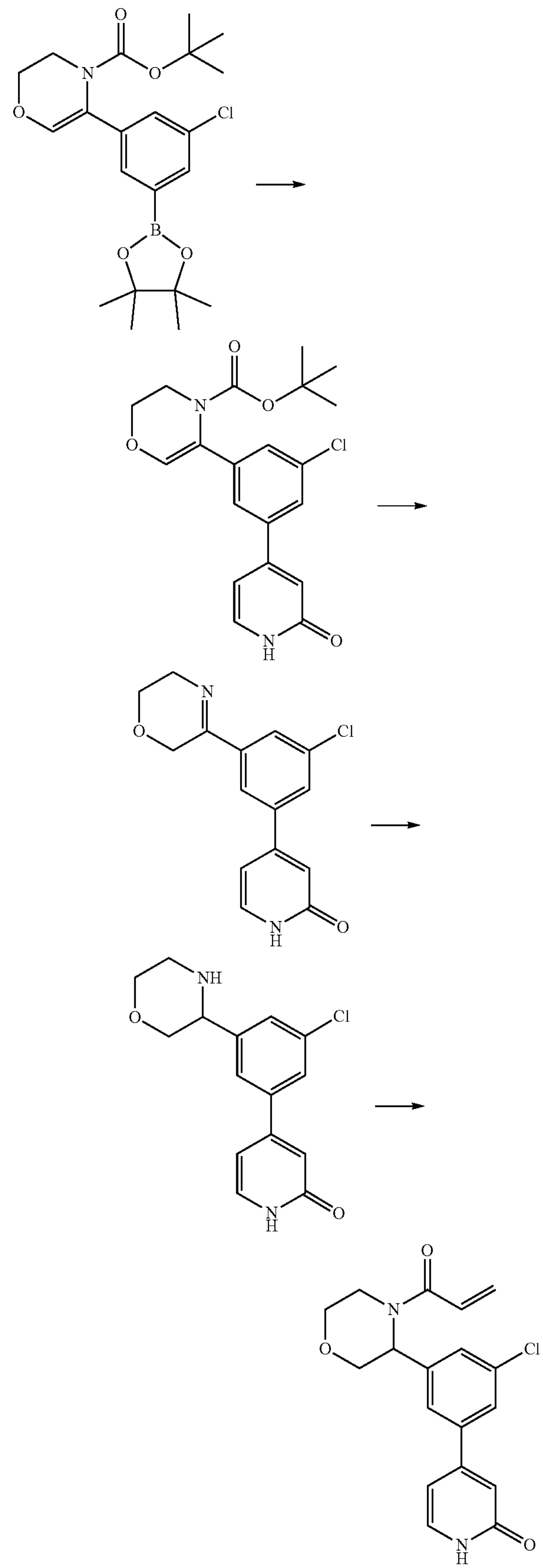

To a solution of tert-butyl 5-(3-chloro-5-(4,4,5,5-tetramethyl-1,3,2-dioxaborolan-2-yl)phenyl)-2,3-dihydro-4H-1,4-oxazine-4-carboxylate (200 mg, 0.47 mmol, 1 equiv) in 1,4-dioxane (1 mL, 0.47 M), MeCN (1 mL), and water (0.5 mL) was added 4-bromo-1-methyl-pyridin-2-one (89.2 mg, 0.47 mmol, 1 equiv), $K_2CO_3$ (131.26 mg) and Pd(dppf)$Cl_2$ (20 mg). The mixture was stirred for 16 hours at 80° C. under $N_2$. The reaction mixture was quenched by $H_2O$ (3 mL) and extracted with EtOAc (3 mL×3). The organic layers were washed 3 mL saturated brine solution. The organic solution was then separated and dried ($Na_2SO_4$) before concentration to dryness. The crude was then purified by column chromatography (PE:EtOAc=0:1) to give tert-butyl 5-(3-chloro-5-(2-oxo-1,2-dihydropyridin-4-yl)phenyl)-2,3-dihydro-4H-1,4-oxazine-4-carboxylate (100 mg, 0.25 mmol, 52% yield) as a yellow oil.

To a solution of tert-butyl 5-(3-chloro-5-(2-oxo-1,2-dihydropyridin-4-yl)phenyl)-2,3-dihydro-4H-1,4-oxazine-4-carboxylate (400 mg, 1.03 mmol, 1 equiv) in DCM (3 mL) was added TFA (1 mL) at 0° C. The reaction was allowed to warm to 25° C. and stirred for 30 minutes. The reaction was concentrated to give crude 4-(3-chloro-5-(5,6-dihydro-2H-1,4-oxazin-3-yl)phenyl)pyridin-2(1H)-one (290 mg) as yellow oil.

To a solution of 4-(3-chloro-5-(5,6-dihydro-2H-1,4-oxazin-3-yl)phenyl)pyridin-2(1H)-one (550 mg, 1.90 mmol, 1 equiv) in methanol (5 mL, 0.38 M) was added $NaBH_4$ (144 mg, 3.80 mmol, 2 equiv) at 0° C. under $N_2$. The reaction mixture was stirred at 25° C. for 30 minutes. The solution was quenched with aqueous HCl to adjust the pH to 5-6 and then concentrated under reduced pressure. The aqueous layers were adjusted to pH=9-10 with saturated aqueous $NaHCO_3$ and then extracted with EtOAc (5 mL*3). The organic layers were washed with brine, dried over $Na_2SO_4$, filtered, and concentrated under reduced pressure. The residue was purified by column chromatography ($Al_2O_3$, dichloromethane/methanol=100/1 to 10/1) to afford 4-(3-chloro-5-morpholin-3-yl-phenyl)-1H-pyridin-2-one (300 mg, 1.03 mmol, 54% yield) as yellow oil.

To a solution of 4-(3-chloro-5-morpholin-3-yl-phenyl)-1H-pyridin-2-one (300 mg, 1.03 mmol, 1 equiv) in DCM (4 mL, 0.25 M) was added triethylamine (156 mg, 1.54 mmol, 1.5 equiv) and acryloyl chloride (112 mg, 1.23 mmol, 1.2 equiv) at 0° C. The mixture was stirred at 25° C. for 1 hour under $N_2$. The reaction mixture was poured into water (12 mL) and extracted with DCM (9 mL*3). The combined organic layers were washed with brine (20 mL), dried over $Na_2SO_4$, filtered, and concentrated under reduced pressure.

The residue was purified by prep-TLC (PE:EtOAc=0:1). Enantiomers were separated by SFC (column: (S,S)-WHELK-O1, 50×4.6 mm ID, 3.5 um) with mobile phase $CO_2$ and EtOH (0.05% IPAm, v/v).

The title compound's absolute stereochemistry was not assigned. LC-MS m/z: 345.1 [M+1].

Stereochemistry: single enantiomer of unknown absolute configuration.

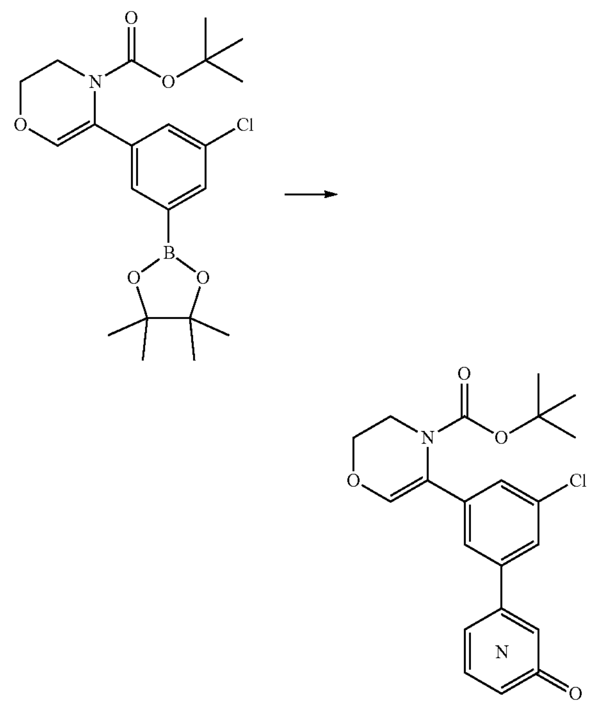

Using the appropriate coupling partner in Procedure E, the title compounds can be obtained. Enantiomers were separated and the absolute stereochemistry was not assigned.

| Cmp | Name | Coupling Partner | LC-MS m/z [M + 1] |
|---|---|---|---|
| 11 | 4-(3-(4-acryloylmorpholin-3-y1)-5-chlorophenyl)pyridin-2(1H)-one | 4-bromo-1-methyl-pyridin-2-one | 345.1 |
| 14 | 1-(3-(3-chloro-5-(pyridazin-4-yl)phenyl)morpholino)prop-2-en-1-one | 4-bromopyridazine | 330.1 |
| 34 | 1-(3-(3-chloro-5-(quinoxalin-6-yl)phenyl)morpholino)prop-2-en-1-one | 6-bromoquinoxaline | 380.1 |
| 35 | 1-(3-(3-chloro-5-(2-methylpyrimidin-4-yl)phenyl)morpholino)prop-2-en-1-one | 4-chloro-2-methylpyrimidine | 344.1 |
| 36 | 3-(3-(4-acryloylmorpholin-3-yl)-5-chlorophenyl)-1-methylpyridin-2(1H)-one | 3-bromo-1-methylpyridin-2(1H)-one | 359.1 |
| 37 | 1-(3-(3-chloro-5-(1,5-naphthyridin-3-yl)phenyl)morpholino)prop-2-en-1-one | 3-bromo-1,5-naphthyridine | 380.1 |
| 38 | 1-(3-(3-chloro-5-(6-methylpyrimidin-4-yl)phenyl)morpholino)prop-2-en-1-one | 4-bromo-6-methylpyrimidine | 344.1 |
| 40 | 1-(3-(3-(2-aminopyrimidin-4-y1)-5-chlorophenyl)morpholino)prop-2-en-1-one | 4-bromopyrimidin-2-amine | 345.1 |
| 42 | 1-(3-(3-chloro-5-(pyrimidin-4-yl)phenyl)morpholino)prop-2-en-1-one | 4-bromopyrimidine | 330.0 |
| 43 | 1-(3-(3-chloro-5-(imidazo[1,2-a]pyridin-7-yl)phenyl)morpholino)prop-2-en-1-one | 7-bromoimidazo[1,2-a]pyridine | 368.1 |
| 49 | 1-(3-(3-chloro-5-(2-methoxypyrimidin-4-yl)phenyl)morpholino)prop-2-en-1-one | 4-bromo-2-methoxypyrimidine | 360.0 |

-continued

| Cmp | Name | Coupling Partner | LC-MS m/z [M + 1] |
|---|---|---|---|
| 53 | 5-(3-(4-acryloylmorpholin-3-yl)-5-chlorophenyl)-2-methylpyridazin-3(2H)-one | 5-iodo-2-methylpyridazin-3(2H)-one | 360.1 |
| 54 | 1-(3-(3-chloro-5-(pyrazin-2-yl)phenyl)morpholino)prop-2-en-1-one | 2-bromopyrazine | 330.1 |
| 57 | 1-(3-(3-chloro-5-(2-methylimidazo[1,2-a]pyridin-7-yl)phenyl)morpholino)prop-2-en-1-one | 7-bromo-2-methylimidazo[1,2-a]pyridine | 382.1 |
| 56 | 1-(3-(3-chloro-5-(6-methoxypyridazin-4-yl)phenyl)morpholino)prop-2-en-1-one | 5-chloro-3-methoxypyridazine | 360.1 |
| 59 | 1-(3-(3-chloro-5-(6-methylpyrazin-2-yl)phenyl)morpholino)prop-2-en-1-one | 2-chloro-6-methylpyrazine | 344.8 |
| 60 | 3'-(4-acryloylmorpholin-3-yl)-5'-chloro-6-fluoro-[1,1'-biphenyl]-3-carboxamide | 3-bromo-4-fluorobenzamide | 389.1 |
| 70 | 3'-(4-acryloylmorpholin-3-yl)-5'-chloro-[1,1'-biphenyl]-4-carboxamide | 4-bromobenzamide | 371.1 |
| 71 | 3'-(4-acryloylmorpholin-3-yl)-5'-chloro-[1,1'-biphenyl]-3-carboxamide | 3-bromobenzamide | 371.0 |
| 72 | 3'-(4-acryloylmorpholin-3-yl)-5'-chloro-5-fluoro-[1,1'-biphenyl]-3-carboxamide | 3-bromo-5-fluorobenzamide | 389.0 |
| 73 | 3'-(4-acryloylmorpholin-3-yl)-5'-chloro-2-fluoro-[1,1'-biphenyl]-3-carboxamide | 3-bromo-2-fluorobenzamide | 389.0 |
| 75 | 4-(3-(4-acryloylmorpholin-3-yl)-5-chlorophenyl)picolinamide | 4-bromopicolinamide | 372.1 |
| 77 | 2-(3-(4-acryloylmorpholin-3-yl)-5-chlorophenyl)pyrimidine-4-carboxamide | 2-chloropyrimidine-4-carboxamide | 373.0 |
| 107 | 6-(3-(4-acryloylmorpholin-3-yl)-5-chlorophenyl)pyrimidine-4-carboxamide | 6-chloropyrimidine-4-carboxamide | 373.1 |

Example 38. Synthesis of 1-(3-(3-chloro-5-(1H-1,24-triazol-3-yl)phenyl)morpholino)prop-2-en-1-one (Compound 41)

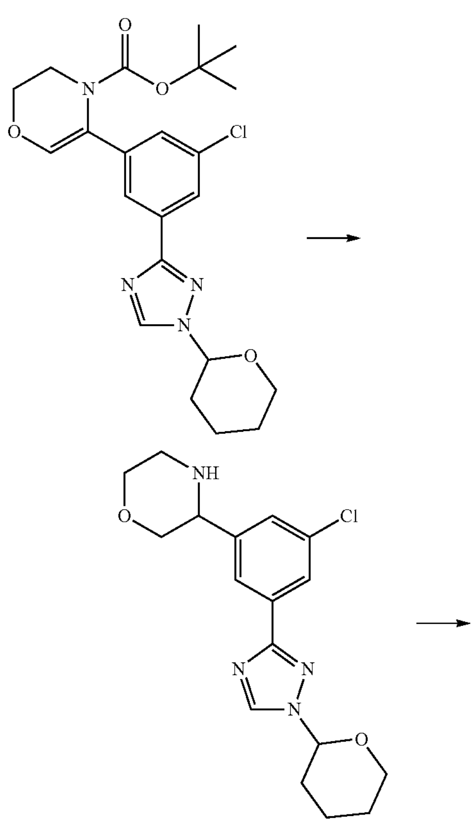

-continued

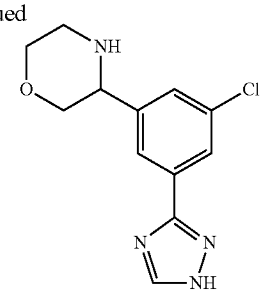

tert-butyl 5-(3-chloro-5-(1-(tetrahydro-2H-pyran-2-yl)-1H-1,2,4-triazol-3-yl)phenyl)-2,3-dihydro-4H-1,4-oxazine-4-carboxylate was obtained from coupling 3-bromo-1-(tetrahydro-2H-pyran-2-yl)-1H-1,2,4-triazole in Procedure E.

To a solution of tert-butyl 5-(3-chloro-5-(1-(tetrahydro-2H-pyran-2-yl)-1H-1,2,4-triazol-3-yl)phenyl)-2,3-dihydro-4H-1,4-oxazine-4-carboxylate (400 mg, 0.89 mmol, 1 equiv) in THF (4 mL, 0.22 M) was added borane dimethylsulfide (430.13 mg, 5.37 mmol, 6 equiv) dropwise at 0° C. under $N_2$. The mixture was stirred for 2 hours at 70° C. Methanol was added dropwise to the reaction mixture at 0° C. until bubble formation dissipated, then the mixture was stirred at 60° C. for 1 hour. The solution was concentrated under reduced pressure to afford 3-(3-chloro-5-(1-(tetrahydro-2H-pyran-2-yl)-1H-1,2,4-triazol-3-yl)phenyl)morpholine (180 mg, 0.52 mmol, 58% yield) as a white solid.

To a solution of crude 3-(3-chloro-5-(1-(tetrahydro-2H-pyran-2-yl)-1H-1,2,4-triazol-3-yl)phenyl)morpholine (180 mg, 0.52 mmol, 1 equiv) and triethylamine (104.43 mg, 1.03 mmol, 2 equiv) in DCM (2 mL, 0.26 M) was added acryloyl chloride (56. mg, 0.62 mmol, 1.2 equiv) dropwise at 0° C. and the mixture was stirred for 2 hours. The mixture was poured into $H_2O$ (5 mL), extracted with DCM (5 mL×3), washed with brine (5 mL×2), dried over $Na_2SO_4$, filtered, and concentrated under reduced pressure. The crude residue was purified by prep-TLC (Ethyl acetate) to afford 3-(3-chloro-5-(1H-1,2,4-triazol-3-yl)phenyl)morpholine (20 mg, 0.063 mmol, 12% yield) as a yellow oil.

3-(3-chloro-5-(1H-1,2,4-triazol-3-yl)phenyl)morpholine was used in Procedure E to obtain the title compound. Enantiomers were separated by SFC. The title compound's absolute stereochemistry was not assigned. LC-MS m/z: 319.1 [M+1].

Stereochemistry: single enantiomer of unknown absolute configuration.

Example 39. Synthesis of (R)-1-(3-(3-chloro-5-(9H-purin-6-yl)phenyl)morpholino)prop-2-en-1-one (Compound 58)

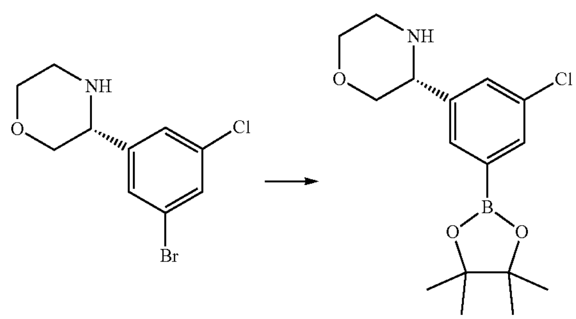 [SMILES: Clc1cc(Br)cc([C@@H]2COCCN2)c1 ; CC1(C)OB(c2cc(Cl)cc([C@@H]3COCCN3)c2)OC1(C)C]

(R)-3-(3-bromo-5-chlorophenyl)morpholine was obtained from Step 5 of Procedure B.

To a solution of bis(pinacolato)diboron (1079.8 mg, 4.25 mmol, 1.2 equiv) (R)-3-(3-bromo-5-chlorophenyl)morpholine (980 mg, 3.54 mmol, 1 equiv) in 1,4-dioxane (10 mL, 0.35 M) was added potassium acetate (1043.3 mg, 10.63 mmol, 3 equiv) and Pd(dppf)$Cl_2$ (257.14 mg, 0.35 mmol, 0.1 equiv) under $N_2$. The resulting mixture was stirred for 12 hours at 90° C. The mixture was concentrated and then used directly in the next step.

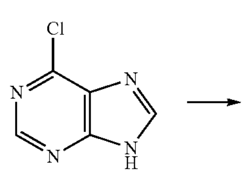

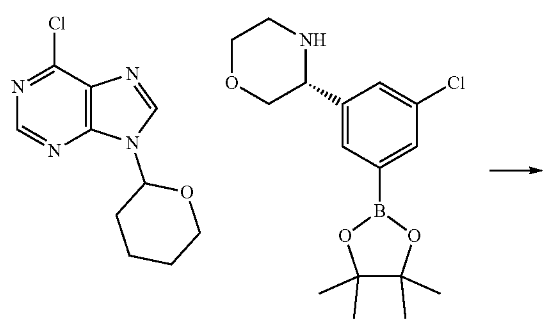

-continued

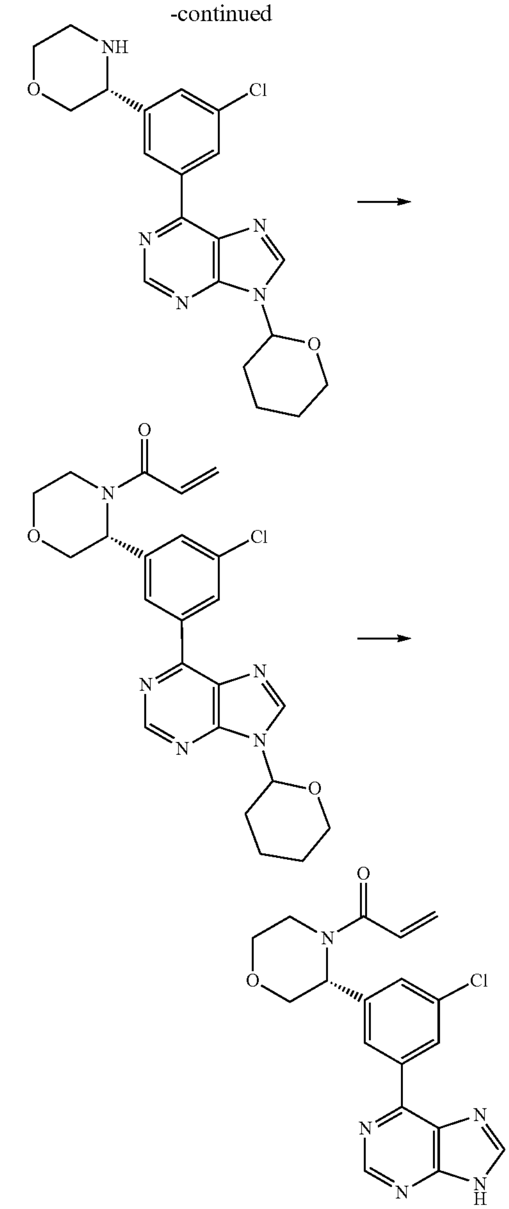

To a solution of 6-chloro-9H-purine (1.64 g, 10.61 mmol, 1 equiv) in ethyl acetate (5 mL, 2.12 M) was added TsOH (0.02 eq, 20 mg) and 3,4-dihydro-2h-pyran (1338.9 mg, 15.92 mmol, 1.5 equiv). The reaction was stirred at 90° C. for 1 hour. The solution was concentrated and then purified by column chromatography (PE:EA=10:1 to 0:1) to afford 6-chloro-9-(tetrahydro-2H-pyran-2-yl)-9H-purine (2.2 g, 9.22 mmol, 87% yield) as a yellow solid.

To a solution of (R)-3-(3-chloro-5-(4,4,5,5-tetramethyl-1,3,2-dioxaborolan-2-yl)phenyl)morpholine (1100 mg, 3.40 mmol) and 6-chloro-9-(tetrahydro-2H-pyran-2-yl)-9H-purine (892.38 mg, 3.74 mmol) in 1,4-dioxane (10 mL), MeCN (10 mL) and water (5 mL) was added potassium carbonate (939.56 mg, 6.80 mmol) and Pd(dppf)$Cl_2$ (246.66 mg, 0.34 mmol) under $N_2$. The resulting mixture was stirred for 12 h at 80° C. The reaction mixture was diluted with water (20 mL) and extracted with EtOAc (15 mL*3). The combined organic layers were washed with brine (9 mL*2), dried over $Na_2SO_4$, filtered, and concentrated under reduced pressure.

The residue was purified by prep-HPLC (column: Welch Xtimate C18 250*70 mm #10 um; liquid phase: [A-10 mM $NH_4HCO_3$ in $H_2O$; B-ACN]B %: 35%-65%, 20 min]) to give (3R)-3-(3-chloro-5-(9-(tetrahydro-2H-pyran-2-yl)-9H-purin-6-yl)phenyl)morpholine (500 mg, 1.25 mmol, 37% yield).

To a solution of (3R)-3-(3-chloro-5-(9-(tetrahydro-2H-pyran-2-yl)-9H-purin-6-yl)phenyl)morpholine (400 mg, 1.0 mmol, 1 equiv) in DCM (6 mL, 0.17 M) was added acrylic acid (86.5 mg, 1.20 mmol), N,N-diisopropylethylamine (193.92 mg, 1.50 mmol, 1.5 equiv), and 2,4,6-tripropyl-1,3,5,2,4,6-trioxatriphosphorinane-2,4,6-trioxide (954.85 mg, 1.50 mmol, 1.5 equiv) at 0° C. The resulting mixture was stirred at 25° C. for 2 hours under $N_2$. The crude was concentrated to afford 1-((3R)-3-(3-chloro-5-(9-(tetrahydro-2H-pyran-2-yl)-9H-purin-6-yl)phenyl)morpholino)prop-2-en-1-one (420 mg, 0.93 mmol, 92% yield) as a brown solid.

A solution of 1-((3R)-3-(3-chloro-5-(9-(tetrahydro-2H-pyran-2-yl)-9H-purin-6-yl)phenyl)morpholino)prop-2-en-1-one (420 mg, 0.93 mmol, 1 equiv) in trifluoroacetic acid (3 mL, 0.15 M) and DCM (3 mL, 0.15 M) at 25° C. was stirred for 1 hour under N2 and then concentrated under vacuum. The crude residue was purified by prep-HPLC (column: Phenomenex Luna 80*30 mm*3 um; liquid phase: [A-TFA/$H_2O$=0.075% v/v; B-ACN] B %: 20%-40%, 8 min]) to afford (R)-1-(3-(3-chloro-5-(9H-purin-6-yl)phenyl)morpholino)prop-2-en-1-one (253 mg, 0.68 mmol, 73% yield). LC-MS m/z: 370.1 [M+1].

Stereochemistry: single enantiomer of known absolute configuration.

Example 40. Synthesis of 1-(3-(3-chloro-5-(imidazo[1,2-a]pyrimidin-7-yl)phenyl)morpholino)prop-2-en-1-one (Compound 63)

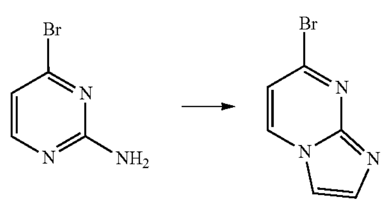 [SMILES: Nc1nccc(Br)n1 ; Brc1ccn2ccnc2n1]

To a solution of 4-bromopyrimidin-2-amine (500 mg, 2.87 mmol, 1 equiv) in water (5 mL, 0.48 M) was added acetic acid (1 mL, 0.48 M) and bromoacetaldehyde diethyl acetal (1506.3 mg, 7.64 mmol, 2.66 equiv). The solution was stirred at 70° C. for 12 hours. The reaction mixture was concentrated to afford 7-bromoimidazo[1,2-a]pyrimidine (100 mg, 0.051 mmol, 18% yield) as a yellow oil.

7-bromoimidazo[1,2-a]pyrimidine was used in Procedure E to obtain the 1-(3-(3-chloro-5-(imidazo[1,2-a]pyrimidin-7-yl)phenyl)morpholino)prop-2-en-1-one. Enantiomers were separated by SFC. Absolute stereochemistry was not assigned. LC-MS m/z: 369.1 [M+1].

Stereochemistry: single enantiomer of unknown absolute configuration.

Example 41. Synthesis of 1-(3-(3-chloro-5-(imidazo[1,5-a]pyrimidin-3-yl)phenyl)morpholino)prop-2-en-1-one (Compound 68)

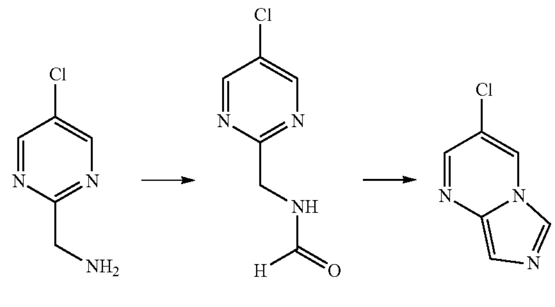 [SMILES: NCc1ncc(Cl)cn1 ; O=CNCc1ncc(Cl)cn1 ; Clc1cnc2cncn2c1]

To a solution of (5-chloropyrimidin-2-yl)methanamine (1 g, 6.96 mmol, 1 equiv) in triethyl orthoformate (10 mL) was added acetic acid (1 mL) at room temperature. The reaction was stirred at 80° C. for 2 hours and then concentrated. The mixture was purified by prep-HPLC (column: Waters Xbridge BEH C18 100*25 mm*5 um; liquid phase: [A-10 mM $NH_4HCO_3$ in $H_2O$; B-ACN]B %: 10%-50%, 10 min]) to afford N-((5-chloropyrimidin-2-yl)methyl)formamide (0.50 g, 2.91 mmol, 42% yield) as a white solid.

A solution of N-((5-chloropyrimidin-2-yl)methyl)formamide (140 mg, 0.82 mmol, 1 equiv) in $POCl_3$ (3 mL) was stirred at 130° C. for 1 hour. The mixture was concentrated, poured into ice-water (15 mL), basified with $Na_2CO_3$ (solid) to pH-9, and extracted with DCM (20 mL×2). The combined organic phase was washed with water (10 mL×2) and brine (10 mL), dried over $Na_2SO_4$, filtered, and concentrated. The crude product was purified by prep-TLC to give 3-chloroimidazo[1,5-a]pyrimidine (67 mg, 0.44 mmol, 53% yield).

3-chloroimidazo[1,5-a]pyrimidine was used in Procedure E to obtain 1-(3-(3-chloro-5-(imidazo[1,5-a]pyrimidin-3-yl)phenyl)morpholino)prop-2-en-1-one. Enantiomers were separated by SFC. The title compound's absolute stereochemistry was not assigned. LC-MS m/z: 369.1 [M+1].

Stereochemistry: single enantiomer of unknown absolute configuration.

Example 42. Synthesis of 7-(3-(4-acryloylmorpholin-3-yl)-5-chlorophenyl)imidazo[1,2-a]pyridine-5-carboxamide (Compound 85)

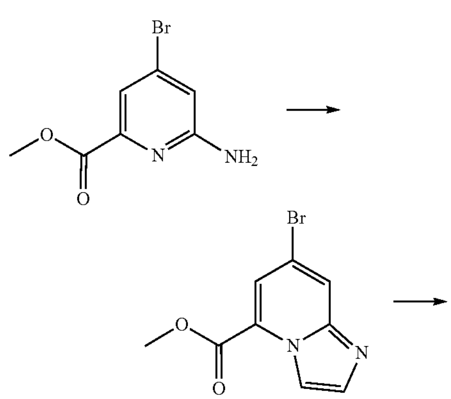

-continued

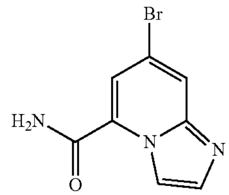

To a solution of methyl 6-amino-4-bromopicolinate (500 mg, 2.16 mmol, 1 equiv) in methanol (10 mL, 0.22 M) was added chloroacetaldehyde (424.69 mg, 2.16 mmol, 1 equiv). The reaction mixture was stirred at 75° C. for 16 hours and then concentrated. The residue was diluted with saturated aqueous $NaHCO_3$ (8 mL), stirred for 30 minutes]s, and then filtered. The filter cake was dried to give methyl 7-bromoimidazo[1,2-a]pyridine-5-carboxylate (500 mg, 1.96 mmol, 91% yield) as a yellow solid.

To a solution of methyl 7-bromoimidazo[1,2-a]pyridine-5-carboxylate (500 mg, 1.96 mmol, 1 equiv) in methanol (5 mL, 0.39 M) was added 7M $NH_3$ in MeOH (5 mL). The reaction mixture was stirred at 20° C. for 16 hours. The reaction was concentrated, and the crude residue was taken up into MTBE, filtered, and dried under reduced pressure to give 7-bromoimidazo[1,2-a]pyridine-5-carboxamide (470 mg, 1.96 mmol, 99% yield) as a yellow solid.

7-bromoimidazo[1,2-a]pyridine-5-carboxamide was used in Procedure E to obtain 7-(3-(4-acryloylmorpholin-3-yl)-5-chlorophenyl)imidazo[1,2-a]pyridine-5-carboxamide. Enantiomers were separated by SFC. The title compound's absolute stereochemistry was not assigned. LC-MS m/z: 411.1 [M+1].

Stereochemistry: single enantiomer of unknown absolute configuration.

Example 43. Synthesis of 4-(3-(4-acryloylmorpholin-3-yl)-5-chlorophenyl)pyrimidine-2-carboxamide (Compound 89)

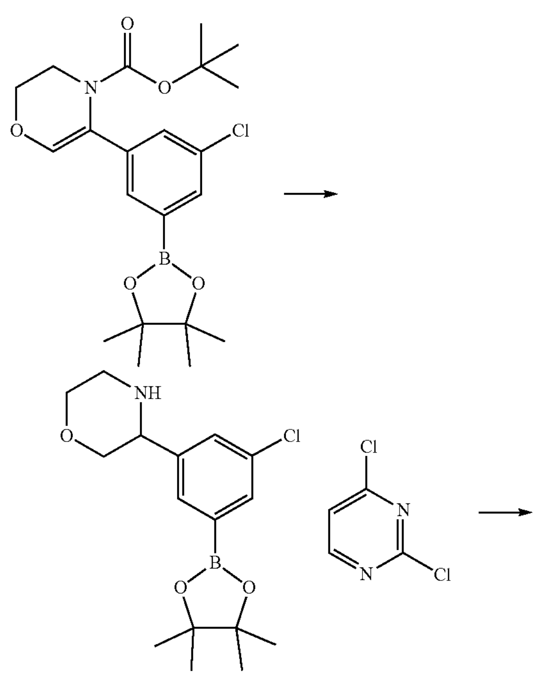

-continued

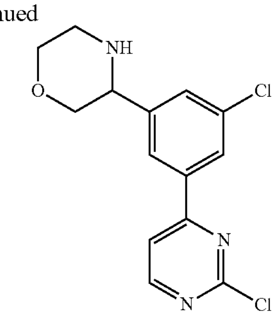

tert-butyl 5-(3-chloro-5-(4,4,5,5-tetramethyl-1,3,2-dioxaborolan-2-yl)phenyl)-2,3-dihydro-4H-1,4-oxazine-4-carboxylate was obtained using Procedure E.

To a solution of tert-butyl 5-(3-chloro-5-(4,4,5,5-tetramethyl-1,3,2-dioxaborolan-2-yl)phenyl)-2,3-dihydro-4H-1,4-oxazine-4-carboxylate (100 mg, 0.24 mmol, 1 equiv) in ethanol (4 mL, 0.059 M) was added $PtO_2$ (10 mg) at 20° C. The mixture was stirred at 20° C. for 3 hours under $H_2$. The solution was filtered and concentrated to afford 3-(3-chloro-5-(4,4,5,5-tetramethyl-1,3,2-dioxaborolan-2-yl)phenyl)morpholine (90 mg, 0.21 mmol, 90% yield) as a brown oil.

To a solution of 3-(3-chloro-5-(4,4,5,5-tetramethyl-1,3,2-dioxaborolan-2-yl)phenyl)morpholine (1 g, 3.09 mmol) in 1,4-dioxane (10 mL) and water (2 mL) was added 2,4-dichloropyrimidine (0.55 g, 3.70 mmol), $K_2CO_3$ (1.3 g, 9.27 mmol), and Pd(dppf)$Cl_2$ (0.1 eq, 0.22 g) at 25° C. The mixture was stirred at 80° C. for 12 hours under $N_2$. The reaction mixture was poured into water (30 mL) and extracted with EtOAc (35 mL*3). The combined organic layers were washed with brine (20 mL*2), dried over $Na_2SO_4$, filtered, and concentrated under reduced pressure. The residue was purified by flash silica gel chromatography (ISCO®; 25 g SEPAFLASH® Silica Flash Column, Eluent of 0-20% MeOH/Ethyl acetate gradient @ 60 mL/min) to afford 3-(3-chloro-5-(2-chloropyrimidin-4-yl)phenyl)morpholine (560 mg, 1.80 mmol, 58% yield).

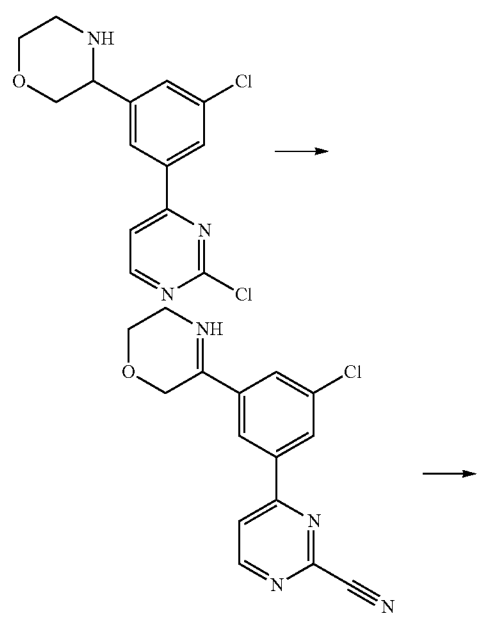

-continued

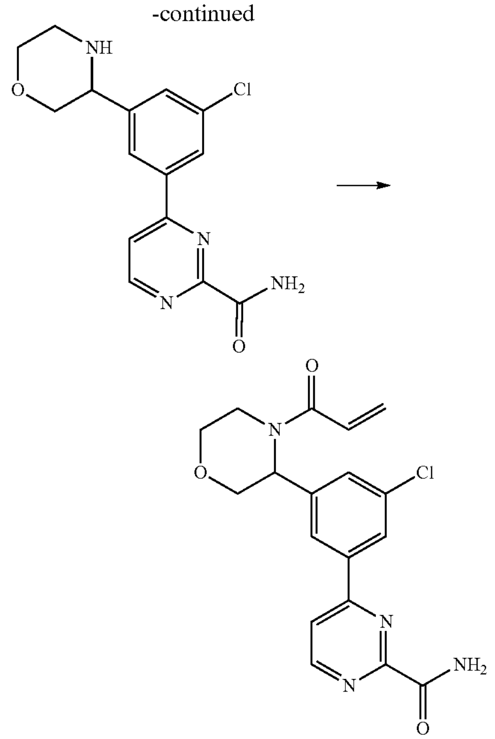

To a solution of 3-[3-chloro-5-(2-chloropyrimidin-4-yl) phenyl]morpholine (560 mg, 1.80 mmol) in DMF (5 mL, 0.36 M) was added zinc cyanide (380 mg, 3.23 mmol) and $Pd(PPh_3)_4$(0.1 eq, 207 mg) at 25° C. The mixture was stirred at 110° C. for 12 hours under $N_2$. The reaction mixture was concentrated under reduced pressure. The residue was purified by flash silica gel chromatography (ISCO®; 12 g SEPAFLASH® Silica Flash Column, Eluent of 0-20% MeOH/Ethyl acetate gradient @ 60 mL/min) to afford 4-(3-chloro-5-morpholin-3-yl-phenyl)pyrimidine-2-carbonitrile (390 mg).

To a solution of 4-(3-chloro-5-morpholin-3-yl-phenyl) pyrimidine-2-carbonitrile (390 mg, 1.29 mmol) in methanol (5 mL, 0.25 M) was added aqueous $H_2O_2$(30%, 410 mg, 3 eq) and NaOH (155.6 mg, 3 eq, 1M, 3.89 mL) at 0° C. The mixture was stirred at 25° C. for 12 hours under $N_2$. The reaction mixture was quenched with aqueous $Na_2SO_3$ (40 mL) and extracted with DCM (30 mL*3). The combined organic layers were washed with brine (20 mL*2), dried over $Na_2SO_4$, filtered, and concentrated under reduced pressure to afford 270 mg of a grey solid.

To a solution of 4-(3-chloro-5-morpholin-3-yl-phenyl) pyrimidine-2-carboxamide (120 mg, 0.37 mmol) in DCM (3 mL, 0.12 M) was added triethylamine (76 mg, 0.75 mmol) and acryloyl chloride (40 mg, 0.45 mmol) at 0° C. The mixture was stirred at 25° C. for 2 hours. The reaction mixture was poured into water (15 mL) and extracted with DCM (15 mL*3). The combined organic layers were washed with brine (10 mL*2), dried over $Na_2SO_4$, filtered, and concentrated under reduced pressure. The residue was purified by prep-HPLC (column: Phenomenex Gemini-NX 80*40 mm*3 um; liquid phase: [A-10 mM $NH_4HCO_3$ in $H_2O$; B-ACN]B %: 10%-40%, 8 min]) to afford 4-(3-(4-acryloylmorpholin-3-yl)-5-chlorophenyl)pyrimidine-2-carboxamide (30 mg, 0.08 mmol, 21% yield).

Enantiomers were separated by SFC. The title compound's absolute stereochemistry was not assigned. LC-MS m/z: 373.1 [M+1]. Stereochemistry: single enantiomer of unknown absolute configuration.

Example 44. Synthesis of 6-(3-(4-acryloylmorpholin-3-yl)-5-chlorophenyl)pyrimidin-4(3H)-one (Compound 94)

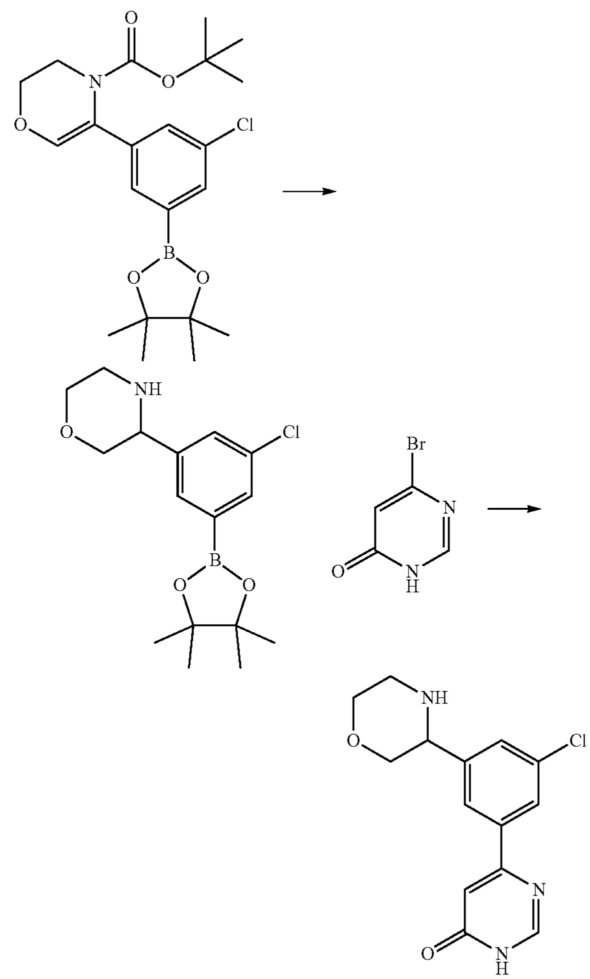

tert-butyl 5-(3-chloro-5-(4,4,5,5-tetramethyl-1,3,2-dioxaborolan-2-yl)phenyl)-2,3-dihydro-4H-1,4-oxazine-4-carboxylate was obtained from Procedure E.

To a solution of tert-butyl 5-(3-chloro-5-(4,4,5,5-tetramethyl-1,3,2-dioxaborolan-2-yl)phenyl)-2,3-dihydro-4H-1,4-oxazine-4-carboxylate (100 mg, 0.24 mmol, 1 equiv) in ethanol (4 mL, 0.059 M) was added $PtO_2$ (10 mg) at 20° C. The mixture was stirred at 20° C. for 3 h under $H_2$. The solution was filtered and concentrated to afford 3-(3-chloro-5-(4,4,5,5-tetramethyl-1,3,2-dioxaborolan-2-yl)phenyl)morpholine (90 mg, 0.21 mmol, 90% yield) as a brown oil.

To a solution of crude 4-bromo-1H-pyrimidin-6-one (216.28 mg, 1.236 mmol, 1 equiv) and 3-(3-chloro-5-(4,4,5,5-tetramethyl-1,3,2-dioxaborolan-2-yl)phenyl)morpholine (500 mg, 1.24 mmol, 1 equiv) in 1,4-dioxane (10 mL, 0.08 M) and water (5 mL, 0.08 M) was added $Na_2CO_3$ (393 mg, 3 eq) and Pd(dppf)Cl2 (18 mg, 0.1 eq). The mixture was stirred at 100° C. for 16 hours. The reaction mixture was filtered and concentrated under reduced pressure. The residue was purified by column chromatography ($SiO_2$, DCM:

MeOH=1/0 to 5/1) to afford 6-(3-chloro-5-(morpholin-3-yl)phenyl)pyrimidin-4(3H)-one (800 mg) as a yellow solid.

Using 6-(3-chloro-5-(morpholin-3-yl)phenyl)pyrimidin-4(3H)-one in Procedure E, the title compound was obtained. LC-MS m/z: 346.1 [M+1].

Stereochemistry: single enantiomer of unknown absolute configuration.

Example 45. Synthesis of 1-(3-(3-chloro-5-(1H-pyrrolo[3,2-c]pyridin-4-yl)phenyl)morpholino)prop-2-en-1-one (Compound 111)

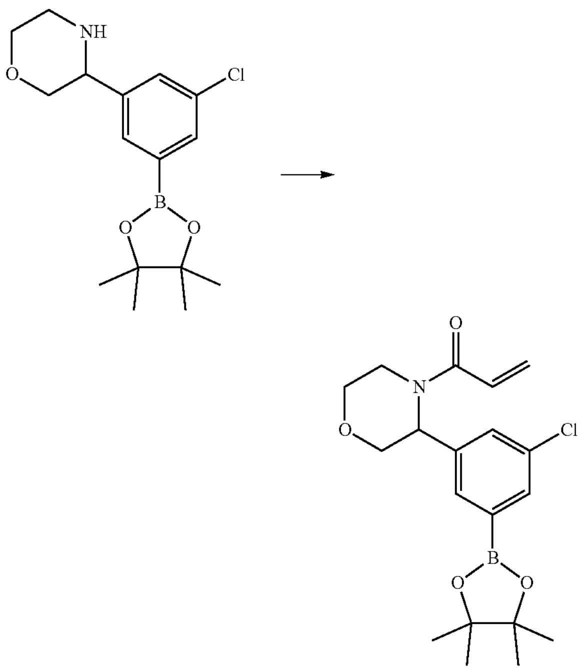

3-(3-chloro-5-(4,4,5,5-tetramethyl-1,3,2-dioxaborolan-2-yl)phenyl)morpholine was obtained from the synthesis of Compound 94.

To a solution 3-(3-chloro-5-(4,4,5,5-tetramethyl-1,3,2-dioxaborolan-2-yl)phenyl)morpholine (1.0 g, 3.09 mmol, 1 equiv) in DCM (10 mL, 0.31 M) was added acryloyl chloride (279.68 mg, 3.09 mmol, 1 equiv) and triethylamine (625.36 mg, 6.18 mmol, 2 equiv) at 25° C. under $N_2$. The reaction was stirred at 25° C. for 2 hours. The reaction was quenched with the water (20 ml) and extracted with DCM (20*2 mL). The organic phase was dried over $Na_2SO_4$, filtered, and concentrated. The crude product was purified by flash column chromatography (EA:PE=0-20%) to afford 1-(3-(3-chloro-5-(4,4,5,5-tetramethyl-1,3,2-dioxaborolan-2-yl)phenyl)morpholino)prop-2-en-1-one (1.2 g, 2.54 mmol, 82% yield) as a white solid which was used the next step without further purification.

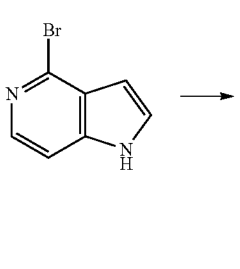

-continued

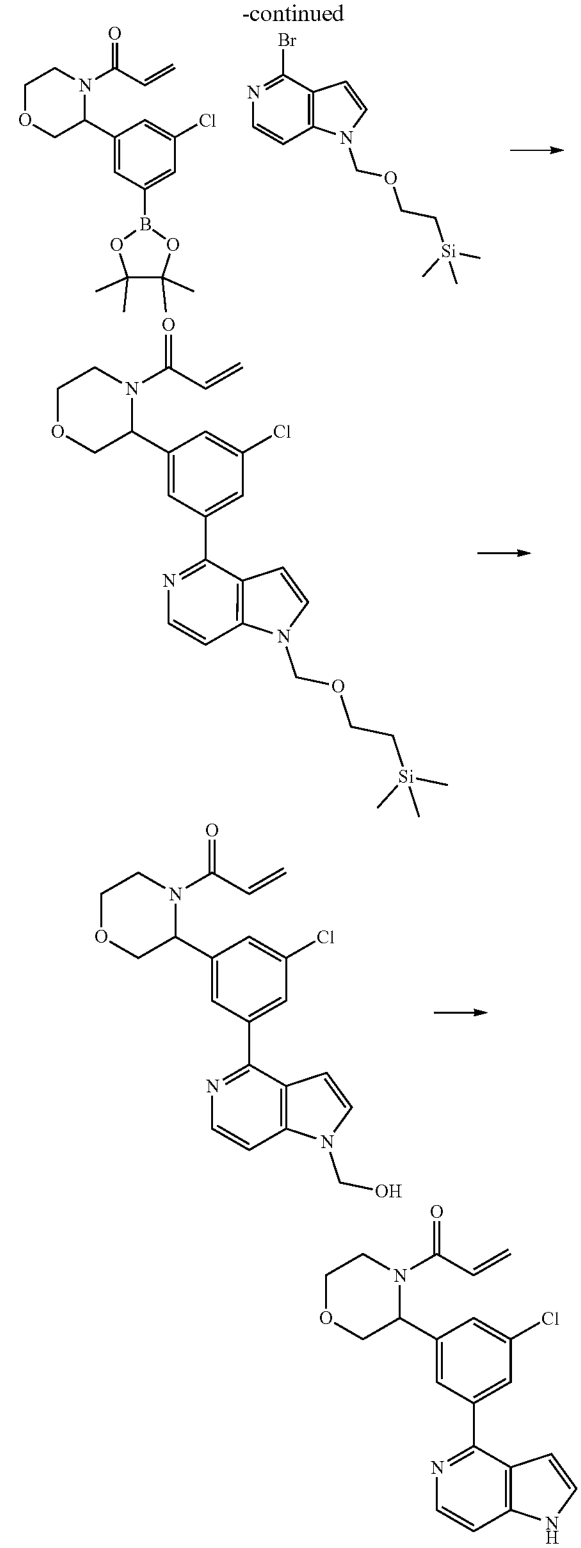

To a solution of 4-bromo-1H-pyrrolo[2,3-b]pyridine (200 mg, 1.02 mmol) in THF (10 mL, 0.10 M) was added sodium hydride (48 mg, 1.22 mmol) at 0° C. and then stirred under a $N_2$ atmosphere for 30 minutes. 2-(trimethylsilyl)ethoxymethyl chloride (203 mg, 1.22 mmol) was added and the mixture was stirred at 25° C. for 2 hours. The mixture was quenched with water (40 mL) and extracted with EtOAc (40 mL). The organic layer was dried over $Na_2SO_4$, filtered, and concentrated. The residue was purified by column chromatography (petroleum ether:ethyl acetate=3:1 to 1:1) to give 2-[(4-bromopyrrolo[2,3-b]pyridin-1-yl)methoxy]ethyl-trimethyl-silane (230 mg, 0.70 mmol, 69% yield).

To a solution of 2-[(4-bromopyrrolo[2,3-b]pyridin-1-yl)methoxy]ethyl-trimethyl-silane (207.98 mg, 0.63 mmol, 1.2 equiv) in 1,4-dioxane (1 mL, 0.44 M) was added 1-(3-(3-chloro-5-(4,4,5,5-tetramethyl-1,3,2-dioxaborolan-2-yl)phenyl)morpholino)prop-2-en-1-one (200 mg, 0.53 mmol, 1 equiv), Pd(dppf)$Cl_2$ (38.42 mg, 0.053 mmol, 0.1 equiv), and potassium carbonate (146.38 mg, 1.059 mmol, 2 equiv) at room temperature under N2. The reaction was stirred at 80° C. for 16 hours. The reaction solution was filtered and then evaporated under reduced pressure. Crude residue was purified by prep-TLC and prep-HPLC to give 1-(3-(3-chloro-5-(1-((2-(trimethylsilyl)ethoxy)methyl)-1H-pyrrolo[3,2-c]pyridin-4-yl)phenyl)morpholino)prop-2-en-1-one (90 mg, 0.181 mmol, 34% yield).

TFA (1.5 mL) was added slowly to a solution of 1-(3-(3-chloro-5-(1-((2-(trimethylsilyl)ethoxy)methyl)-1H-pyrrolo[3,2-c]pyridin-4-yl)phenyl)morpholino)prop-2-en-1-one (90 mg, 0.18 mmol, 1 equiv) in DCM (5 mL) at 0° C. The reaction was stirred at 35° C. for 16 hours. The solution was concentrated to afford crude 1-(3-(3-chloro-5-(1-(hydroxymethyl)-1H-pyrrolo[3,2-c]pyridin-4-yl)phenyl)morpholino)prop-2-en-1-one (95 mg) which was used the next step without further purification.

To a solution of crude 1-(3-(3-chloro-5-(1-(hydroxymethyl)-1H-pyrrolo[3,2-c]pyridin-4-yl)phenyl)morpholino)prop-2-en-1-one (75 mg, 0.19 mmol, 1 equiv) in MeCN (3 mL, 0.06 M) and water (1 mL, 0.06 M) was added $K_2CO_3$ (18 eq, 561 mg). The mixture was stirred at 90° C. for 16 hours. The solution was diluted with water and extracted with ethyl acetate (10 mL*3). The combined organic solutions were dried over $NaSO_4$, filtered, and evaporated under reduced pressure. The crude product was purified by prep-TLC.

Enantiomers were separated by SFC. The title compound's absolute stereochemistry was not assigned. LC-MS m/z: 368.1 [M+1]. Stereochemistry: single enantiomer of unknown absolute configuration.

Example 46. Synthesis of (R)-1-(3-(3-(4-amino-6-methyl-1,3,5-triazin-2-yl)-5-chlorophenyl)morpholino)prop-2-en-1-one (Compound 178)

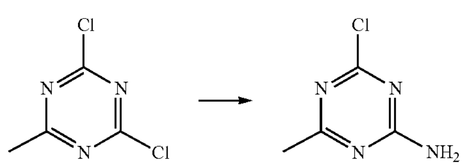

To a solution of 2,4-dichloro-6-methyl-1,3,5-triazine (200 mg, 1.22 mmol, 1 equiv) in toluene (2 mL, 0.61 M) was added $NH_3$ in MeOH (4 M, 1.2 mL). The mixture was stirred at 25° C. for 12 hours. The reaction mixture was concentrated to give the crude product 4-chloro-6-methyl-1,3,5-triazin-2-amine (150 mg 1.04 mmol, 85% yield) as a yellow solid.

4-chloro-6-methyl-1,3,5-triazin-2-amine was used in Procedure D to afford the title compound. LC-MS m/z: 360.1 [M+1]. Stereochemistry: Scalemic mixture of unknown absolute configuration, e.e. =84%.

Example 47. Synthesis of (R)-1-(3-(3-chloro-5-(4,6-diamino-1,3,5-triazin-2-yl)phenyl)morpholino)prop-2-en-1-one (Compound 191)

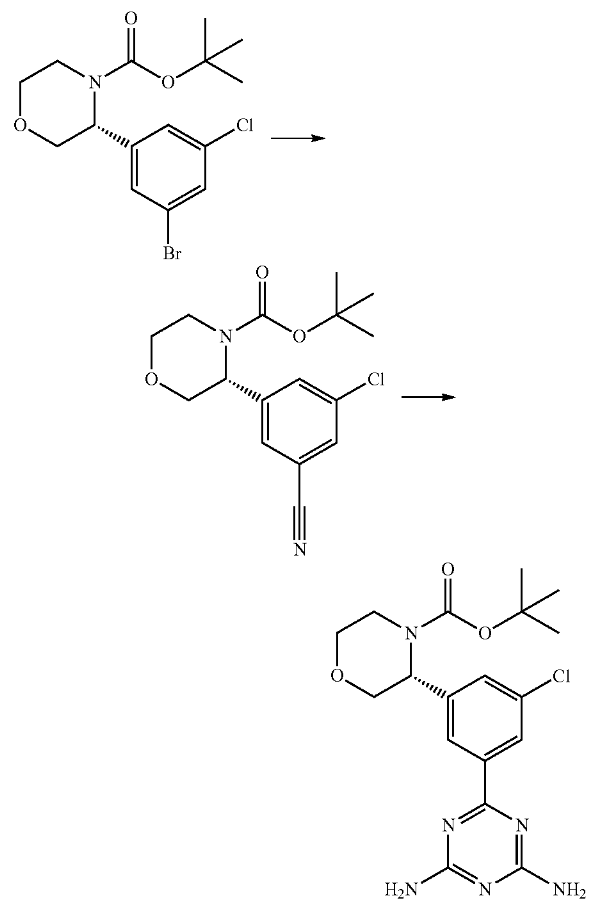

tert-butyl (R)-3-(3-bromo-5-chlorophenyl)morpholine-4-carboxylate was obtained from Procedure B.

Pd$(PPh_3)_4$(2.08 g, 1.81 mmol) and zinc cyanide (847.84 mg, 7.22 mmol, 0.80 equiv) were added to a solution of tert-butyl (R)-3-(3-bromo-5-chlorophenyl)morpholine-4-carboxylate (3.4 g, 9.03 mmol, 1 equiv) in DMF (50 mL, 0.18 M) at 20° C. The mixture was stirred at 120° C. for 16 hours under $N_2$. The reaction mixture was poured into water (50 mL) and extracted with EtOAc (30 mL*2). The combined organic layer was washed with water (20 mL*3), brine (20 mL), dried over $Na_2SO_4$, filtered, and concentrated. The crude residue was purified by MPLC (ISCO®; 40 g SEPA-FLASH® Silica Flash Column, Eluent of 0-15% ethyl acetate/petroleum ether gradient @ 100 mL/min) to afford tert-butyl (R)-3-(3-chloro-5-cyanophenyl)morpholine-4-carboxylate (1.30 g, 4.03 mmol, 45% yield) as a white solid.

2-cyanoguanidine (338.62 mg, 4.03 mmol, 1 equiv) and potassium hydroxide (225.98 mg, 4.03 mmol, 1 equiv) were added to a solution of afford tert-butyl (R)-3-(3-chloro-5-cyanophenyl)morpholine-4-carboxylate (1.3 g, 4.03 mmol, 1 equiv) in DME (20 mL, 0.20 M). The mixture was heated to 125° C. and stirred for 20 minutes. The reaction mixture was concentrated, and the residue was crystallized from MeOH (20 mL). tert-butyl (R)-3-(3-chloro-5-(4,6-diamino-1,3,5-triazin-2-yl)phenyl)morpholine-4-carboxylate (1.30 g, 3.20 mmol, 79% yield) was obtained as pale yellow solid.

tert-butyl (R)-3-(3-chloro-5-(4,6-diamino-1,3,5-triazin-2-yl)phenyl)morpholine-4-carboxylate was used in Procedure B to afford the title compound. LC-MS m/z: 361.1 [M+1].

Stereochemistry: single enantiomer of known absolute configuration.

Example 48. Synthesis both diastereomers of 5-(3-((R)-4-acryloylmorpholin-3-yl)-5-chlorophenyl)-1-methyltetrahydropyrimidin-2(1H)-one (Compounds 216 and 217)

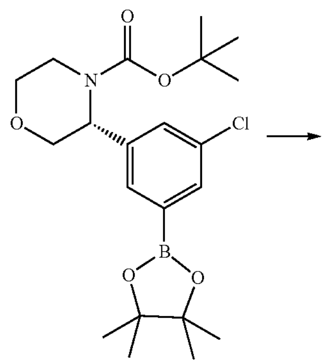

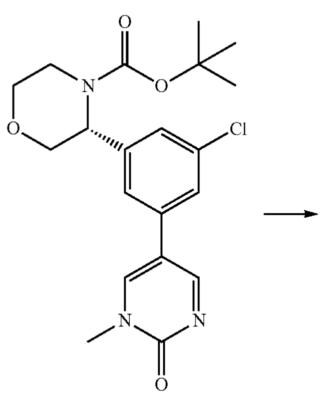

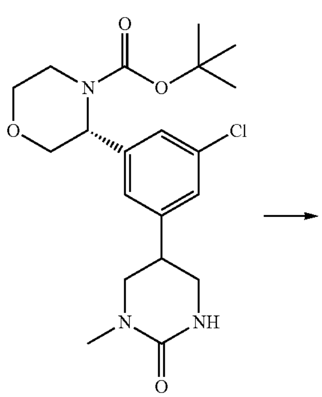

-continued

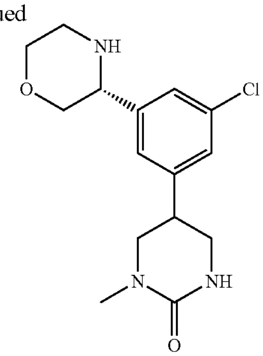

tert-butyl (R)-3-(3-chloro-5-(4,4,5,5-tetramethyl-1,3,2-dioxaborolan-2-yl)phenyl)morpholine-4-carboxylate was obtained from Procedure B.

To a solution of tert-butyl (R)-3-(3-chloro-5-(4,4,5,5-tetramethyl-1,3,2-dioxaborolan-2-yl)phenyl)morpholine-4-carboxylate (500 mg, 1.18 mmol) in 1,4-dioxane (1 mL, 0.98 M) and water (0.20 mL, 0.98 M) was added 5-bromo-1-methyl-pyrimidin-2-one (267.63 mg, 1.41 mmol, 1.2 equiv), Pd(dppf)$Cl_2$ (85.62 mg, 0.12 mmol, 0.10 equiv), and potassium carbonate (407.71 mg, 2.95 mmol, 2.5 equiv). The mixture was stirred at 80° C. for 4 hours under $N_2$. The reaction mixture was poured into water (5 mL) and extracted with EtOAc (5 mL*3). The combined organic layers were washed with brine (5 mL*2), dried over $Na_2SO_4$, filtered, and concentrated under reduced. The residue was purified by column chromatography (SiO2, Ethyl acetate) to afford tert-butyl (R)-3-(3-chloro-5-(1-methyl-2-oxo-1,2-dihydropyrimidin-5-yl)phenyl)morpholine-4-carboxylate (300 mg, 0.74 mmol, 63% yield).

To a solution of tert-butyl (R)-3-(3-chloro-5-(1-methyl-2-oxo-1,2-dihydropyrimidin-5-yl)phenyl)morpholine-4-carboxylate (2.8 g, 6.89 mmol, 1 equiv) in THF (10 mL, 0.69 M) was added platinum dioxide (548.29 mg, 2.41 mmol, 0.35 equiv) and 1,3,5-trichlorobenzene (1.25 g, 6.89 mmol, 1 equiv). The reaction was stirred at 20° C. under $H_2$ (15 psi) for 72 hours. The mixture was filtered and concentrated under vacuum. The crude product was chromatographed on silica gel (PE/EA 20:1-1:1->0:1) to afford tert-butyl (3R)-3-(3-chloro-5-(1-methyl-2-oxohexahydropyrimidin-5-yl)phenyl)morpholine-4-carboxylate.

To a solution of tert-butyl (3R)-3-(3-chloro-5-(1-methyl-2-oxohexahydropyrimidin-5-yl)phenyl)morpholine-4-carboxylate (130 mg, 0.32 mmol, 1 equiv) in 1,4-dioxane (1 mL, 0.25 M) was added HCl in dioxane (4M, 2 mL) at 25° C. The mixture was stirred for 2 hours, filtered, and concentrated under vacuum to afford crude 5-(3-chloro-5-((R)-morpholin-3-yl)phenyl)-1-methyltetrahydropyrimidin-2(1H)-one (100 mg, 0.32 mmol, 83% yield) as a yellow oil.

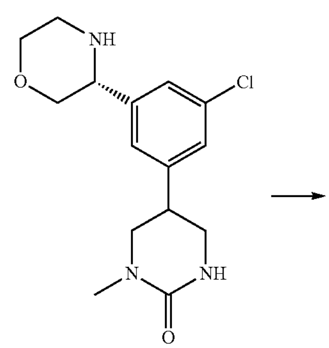

-continued

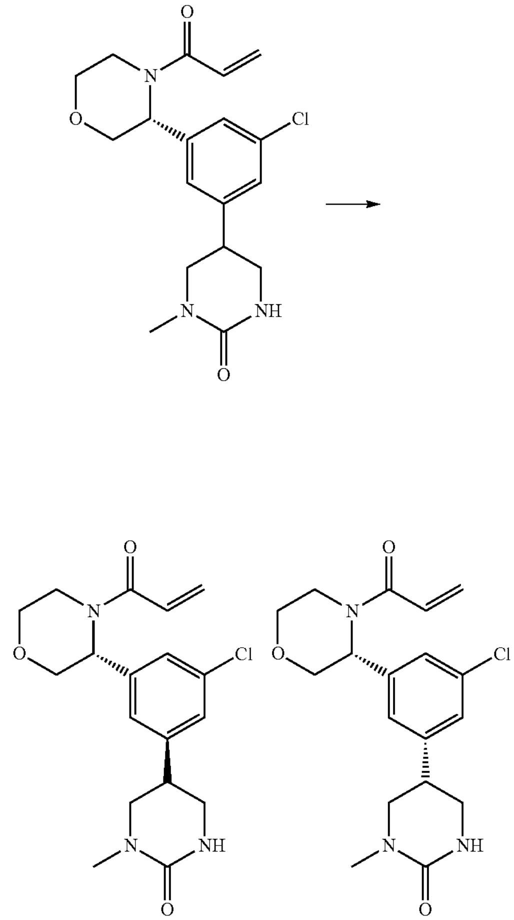

N,N-Diisopropylethylamine (83.43 mg, 0.65 mmol) was added to a solution of 5-(3-chloro-5-((R)-morpholin-3-yl)phenyl)-1-methyltetrahydropyrimidin-2(1H)-one (100 mg, 0.33 mmol) in DCM (5 mL, 0.065 M) at 0° C. Acrylic acid (25.58 mg, 0.35 mmol) was added dropwise at 0° C. before addition a solution of 2,4,6-tripropyl-1,3,5,2,4,6-trioxatriphosphorinane-2,4,6-trioxide (308 mg, 0.48 mmol) in DCM (2 mL, 0.024 M). The mixture was stirred at 25° C. for 30 minutes. The mixture was diluted with water (20 mL), extracted with DCM (10 mL*3), dried over by Na2SO4, filtered, and concentrated under reduced pressure. The residue was purified by prep-TLC ($SiO_2$; PE:EtOAc=1:5) to afford 5-(3-((R)-4-acryloylmorpholin-3-yl)-5-chlorophenyl)-1-methyltetrahydropyrimidin-2(1H)-one (50 mg, 0.14 mmol, 43% yield).

Diastereomers were separated by SFC [Column: Phenomenex-Cellulose-2 (250 mm*30 mm, 10 um) $CO_2$ and EtOH] and the stereochemistry of the 1-methyltetrahydropyrimidin-2(1H)-one was arbitrarily assigned. LC-MS m/z: 364.2 [M+1]. LC-MS m/z: 364.2 [M+1].

Stereochemistry: single diastereomers of known absolute configuration on the morpholine and unknown absolute configuration on the pyrimidine.

Example 49. Synthesis of 1-((R)-3-(3-chloro-5-((R)-1-methyl-2-thioxohexahydropyrimidin-5-yl)phenyl)morpholino)prop-2-en-1-one Diastereomers 1 and 2(Compounds 226 and 227)

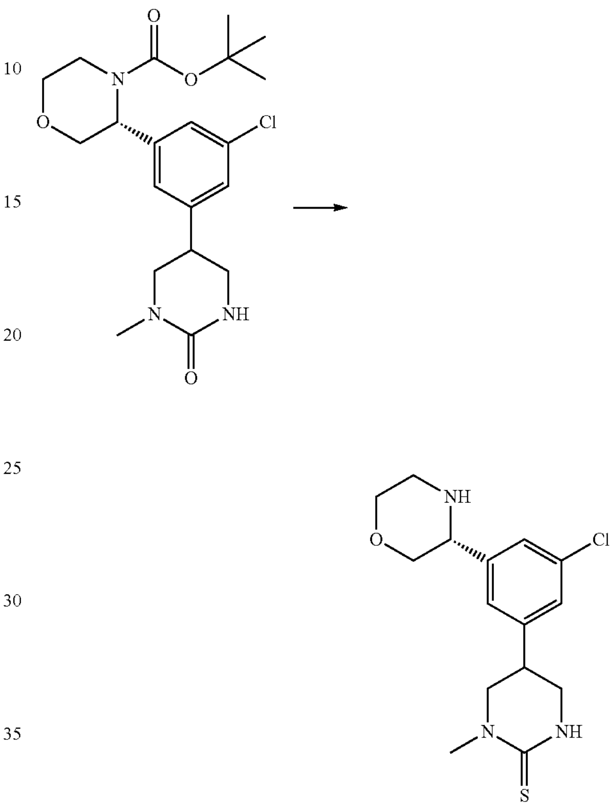

tert-butyl (3R)-3-(3-chloro-5-(1-methyl-2-oxohexahydropyrimidin-5-yl)phenyl)morpholine-4-carboxylate was obtained from the synthesis of Compounds 216 and 217.

To a solution of tert-butyl (3R)-3-(3-chloro-5-(1-methyl-2-oxohexahydropyrimidin-5-yl)phenyl)morpholine-4-carboxylate (2 g, 4.88 mmol, 1 equiv) in m-xylene (40 mL, 0.12 M) was added (dithioxo-λ5-phosphanyl)sulfanyl-dithioxo-λ5-phosphane (2.17 g, 4.87 mmol, 1 equiv) at 25° C. The mixture was heated to 130° C. for 16 hours under $N_2$. The mixture was filtered and concentrated under vacuum. The residue was purified by Prep-HPLC (TFA) to obtain 5-(3-chloro-5-((R)-morpholin-3-yl)phenyl)-1-methyltetrahydropyrimidine-2(1H)-thione (530 mg, 1.63 mmol, 33% yield) as yellow solid.

5-(3-chloro-5-((R)-morpholin-3-yl)phenyl)-1-methyltetrahydropyrimidine-2(1H)-thione was used in the final steps of the route to Compounds 216 and 217 to obtain the title compounds.

Diastereomers were separated by SFC and the stereochemistry of the 1-methyltetrahydropyrimidine-2(1H)-thione was arbitrarily assigned. LC-MS m/z: 380.0 [M+1]. LC-MS m/z: 380.2 [M+1].

Stereochemistry: single stereoisomer of unknown absolute configuration. Morpholine stereocenter is known, 1-methyltetrahydropyrimidine-2(1H)-thione stereochemistry was arbitrarily assigned.

Example 50. Synthesis of 1-(3-((R)-4-acryloylmorpholin-3-yl)-5-chlorophenyl)-3-aminopyrrolidin-2-one (Compound 230)

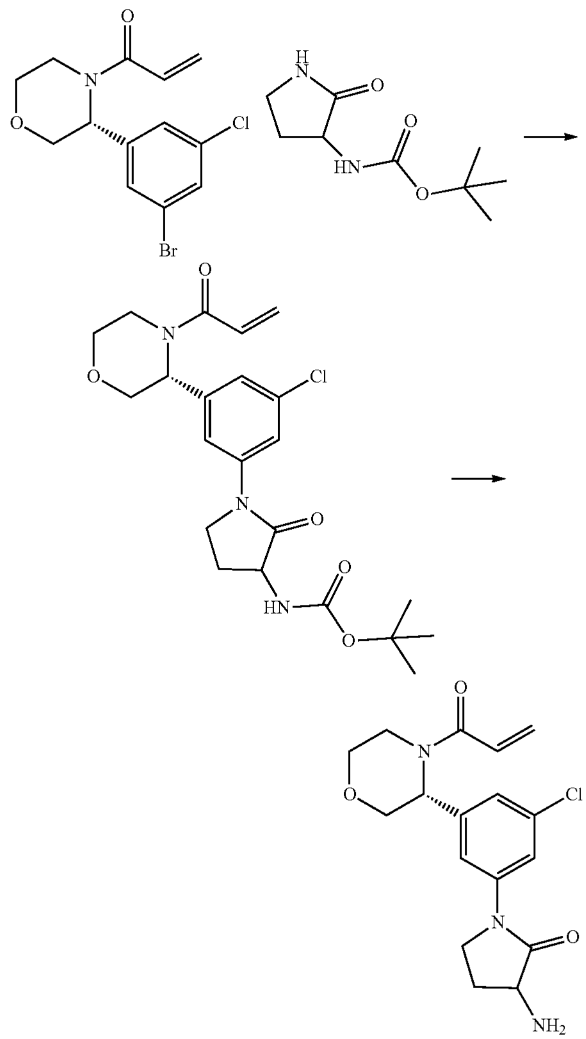

(R)-1-(3-(3-bromo-5-chlorophenyl)morpholino)prop-2-en-1-one was obtained from Procedure C.

A solution of (R)-1-(3-(3-bromo-5-chlorophenyl)morpholino)prop-2-en-1-one (50 mg, 0.15 mmol, 1 equiv) and tert-butyl N-(2-oxopyrrolidin-3-yl)carbamate (60.56 mg, 0.30 mmol, 2 equiv) in 1,4-dioxane (5 mL, 0.03 M) was added tris(dibenzylideneacetone)dipalladium(0) (13.84 mg, 0.015 mmol, 0.10 equiv), 4,5-bis(diphenylphosphino)-9,9-dimethylxanthene (8.75 mg, 0.015 mmol, 0.10 equiv), and cesium carbonate (88.69 mg, 0.27 mmol, 1.8 equiv). The mixture was stirred at 90° C. for 12 hours under $N_2$. The reaction was diluted with water, extracted with EtOAc (20 mL×3), and concentrated under vacuo. The residue was purified by prep-TLC ($SiO_2$, EA:MeOH=10:1) to afford tert-butyl (1-(3-((R)-4-acryloylmorpholin-3-yl)-5-chlorophenyl)-2-oxopyrrolidin-3-yl)carbamate (90 mg) as a yellow oil. The diastereomers were separated by SFC.

To a solution of tert-butyl (1-(3-((R)-4-acryloylmorpholin-3-yl)-5-chlorophenyl)-2-oxopyrrolidin-3-yl)carbamate (35 mg, 0.077 mmol, 1 equiv) in DCM (1.5 mL, 0.04 M) was added trifluoroacetic acid (0.50 mL, 0.038 M) at 0° C. The mixture was stirred at 0° C. for 1 hour under $N_2$. The reaction mixture was concentrated under reduced pressure and then purified by prep-HPLC (column: Phenomenex Luna 80*30 mm*3 um; liquid phase: [A-TFA/$H_2O$=0.075% v/v; B-ACN]B %: 1%-30%, 8 min]) to afford 1-(3-((R)-4-acryloylmorpholin-3-yl)-5-chlorophenyl)-3-aminopyrrolidin-2-one as a white solid. LC-MS m/z: 349.8. [M+1].

Stereochemistry: single enantiomer of known absolute configuration. Morpholine stereocenter is known, 3-aminopyrrolidin-2-one stereochemistry is unknown.

Example 51. Synthesis of 4-(3-((R)-4-acryloylmorpholin-3-yl)-5-chlorophenyl)tetrahydropyrimidin-2(1H)-one (Compound 242)

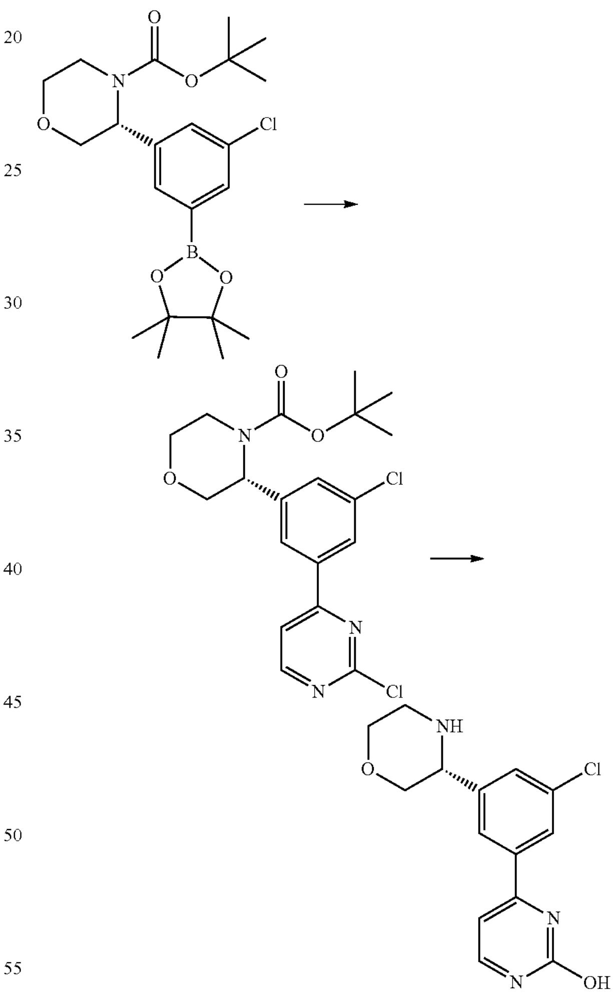

tert-butyl (R)-3-(3-chloro-5-(4,4,5,5-tetramethyl-1,3,2-dioxaborolan-2-yl)phenyl)morpholine-4-carboxylate was obtained from Procedure B.

To a solution of tert-butyl (R)-3-(3-chloro-5-(4,4,5,5-tetramethyl-1,3,2-dioxaborolan-2-yl)phenyl)morpholine-4-carboxylate (1 g, 2.35 mmol, 1 equiv) and 2,4-dichloropyrimidine (703.17 mg, 4.71 mmol, 2 equiv) in 1,4-dioxane (20 mL, 0.098 M) and water (4 mL, 0.098 M) was added potassium carbonate (652.33 mg, 4.71 mmol, 2 equiv) and Pd(dppf)$Cl_2$ (85.62 mg, 0.12 mmol, 0.05 equiv). The mixture was stirred at 80° C. under $N_2$ for 16 hours. The reaction mixture was poured into saturated aqueous $NH_4Cl$ (15 mL) and extracted with EtOAc (10 mL*3). The combined organic layers were washed with brine (5 mL*2), dried over $Na_2SO_4$, filtered, and concentrated under reduced pressure. The residue was purified by Prep-TLC (Petroleum ether: Ethyl acetate=3:1) to give tert-butyl (R)-3-(3-chloro-5-(2-chloropyrimidin-4-yl)phenyl)morpholine-4-carboxylate (192 mg, 0.47 mmol, 20% yield) as a white solid.

tert-butyl (R)-3-(3-chloro-5-(2-chloropyrimidin-4-yl) phenyl)morpholine-4-carboxylate (850 mg, 2.07 mmol, 1 equiv) in 38% aqueous HCl (20 mL) was stirred at 100° C. for 16 hours. The mixture was cooled, and the pH adjusted to 8 with aqueous 1M sodium hydroxide. Most of the water was removed under reduced pressure and the remaining solution was extracted with DCM:iPrOH=3:1 (20 mL×3). The combined organic layer was dried over anhydrous sodium sulfate, filtered, and concentrated under reduced pressure to afford crude (R)-4-(3-chloro-5-(morpholin-3-yl) phenyl)pyrimidin-2-ol (830 mg) as a yellow solid.

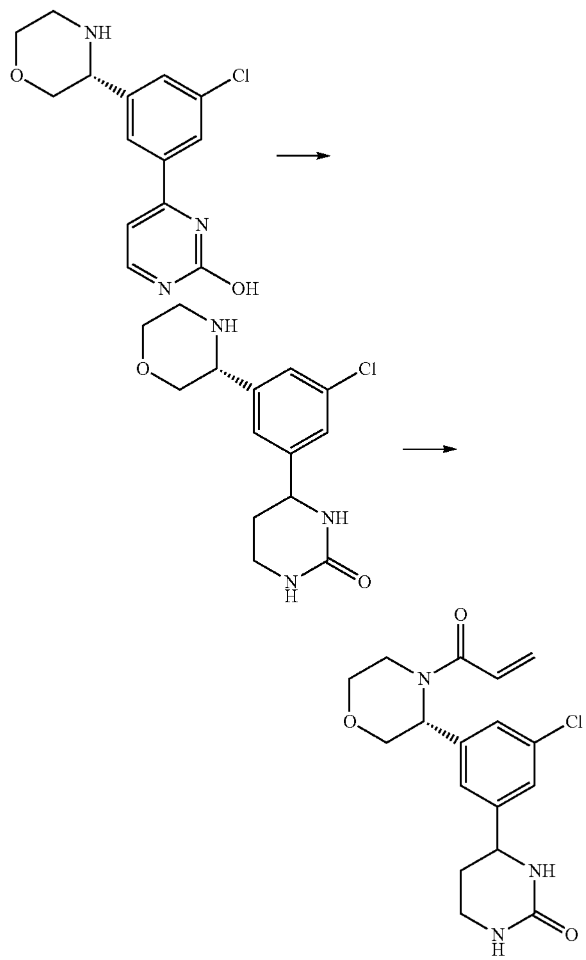

To a solution crude (R)-4-(3-chloro-5-(morpholin-3-yl) phenyl)pyrimidin-2-ol (630 mg, 2.15 mmol, 1 equiv) in THF (5 mL) and EtOH (10 mL) was added $Pt_2O$ (0.2 eq, 98 mg) under $Ar_2$. The suspension was degassed under vacuum and purged with H2 several times. The mixture was stirred under 15 Psi of hydrogen pressure for 16 hours at 25° C. The suspension was filtered through a pad of Celite and the filter cake was washed with EtOH (10 mL×3). The combined filtrates were concentrated to dryness to afford 4-(3-chloro-5-((R)-morpholin-3-yl)phenyl)tetrahydropyrimidin-2(1H)-one (550 mg, 1.49 mmol, 69% yield) as a yellow solid.

To a solution of 4-(3-chloro-5-((R)-morpholin-3-yl)phenyl)tetrahydropyrimidin-2(1H)-one (50 mg, 0.16 mmol), acrylic acid (12.18 mg, 0.16 mmol), and N,N-diisopropylethylamine (43.69 mg, 0.33 mmol) in DCM (2 mL, 0.05 M) was added 2,4,6-tripropyl-1,3,5,2,4,6-trioxatriphosphorinane-2,4,6-trioxide (161.37 mg, 0.25 mmol) at 0° C. under $N_2$. The reaction was stirred for 30 minutes. The reaction mixture was poured into saturated aqueous $NH_4Cl$ (5 mL) and extracted with DCM (5 mL*3). The combined organic layers were washed with brine (3 mL), dried over $Na_2SO_4$, filtered, and concentrated under reduced pressure. The residue was purified by prep-HPLC (neutral conditions) to give desired compound (60 mg) as a white solid. The diastereomers were separated by SFC. LC-MS m/z: 350.2 [M+1].

Stereochemistry: single enantiomer of unknown absolute configuration. Morpholine stereocenter is known, tetrahydropyrimidin-2(1H)-one stereochemistry is unknown.

Example 52. Synthesis of 1-(3-(3-(2-aminooxazol-4-yl)-5-chlorophenyl)morpholino)prop-2-en-1-one (Compound 282)

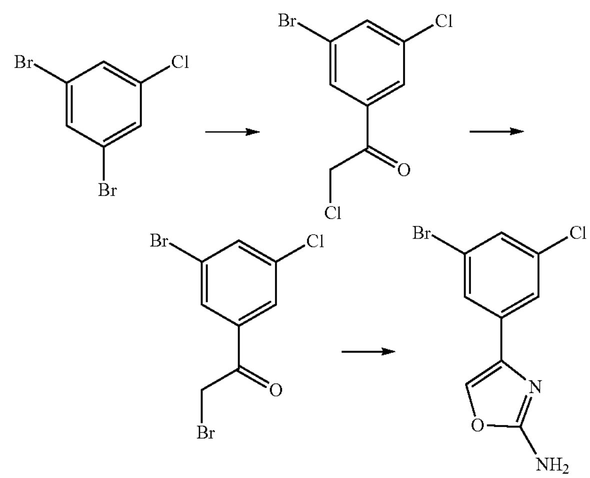

To a solution of 1,3-dibromo-5-chlorobenzene (10 g, 36.98 mmol) in i-$Pr_2O$ (150 mL) at −60° C. was added n-butyllithium solution (10.56 g, 38.83 mmol) under $N_2$ and then stirred for 30 minutes. 2-Chloro-N-methoxy-N-methylacetamide (5.59 g, 40.68 mmol) in i-$Pr_2O$ (20 mL) was added dropwise and the reaction was allowed to warm to 0° C. and stirred for 1 hour. The solution was diluted with saturated aqueous $NH_4Cl$ (300 mL) and extracted with EtOAc (300 mL*3). The combined organic solutions were washed with brine (50 mL), dried over $Na_2SO_4$, filtered, and concentrated under vacuum. The crude product was purified by silica gel column (petroleum ether:ethyl acetate=1:0 to 99:1) to afford 1-(3-bromo-5-chlorophenyl)-2-chloroethan-1-one (3.70 g, 13.8 mmol, 37% yield).

To a solution of 1-(3-bromo-5-chlorophenyl)-2-chloroethan-1-one (1.3 g, 4.85 mmol) in acetone (10 mL, 0.48 M) was added sodium bromide (1.99 g, 19.40 mmol) at 20° C. under $N_2$. The reaction was stirred at 60° C. for 16 hours. The solution was diluted with $H_2O$ (20 mL), extracted with EtOAc (20 mL*3), washed with brine (20 mL*3), dried over $Na_2SO_4$, filtered, and concentrated under vacuum to afford 2-bromo-1-(3-bromo-5-chlorophenyl)ethan-1-one (2.0 g) as a yellow solid.

To a solution of 2-bromo-1-(3-bromo-5-chlorophenyl) ethan-1-one (500 mg, 1.60 mmol, 1 equiv) in MeCN (5 mL, 0.32 M) was added urea (961.3 mg, 16.01 mmol, 10 equiv) at 25° C. The mixture was stirred at 80° C. for 12 hours under $N_2$. The reaction mixture was poured into saturated aqueous NH4Cl (10 mL) and extracted with EtOAc (10 mL*3). The combined organic layers were washed with brine (8 mL*2), dried over $Na_2SO_4$, filtered, and concentrated under reduced pressure. The residue was purified by column chromatography (SiO2, Petroleum ether/Ethyl acetate=3/1 to 1/1) to afford 4-(3-bromo-5-chlorophenyl) oxazol-2-amine (241 mg, 0.88 mmol, 55% yield).

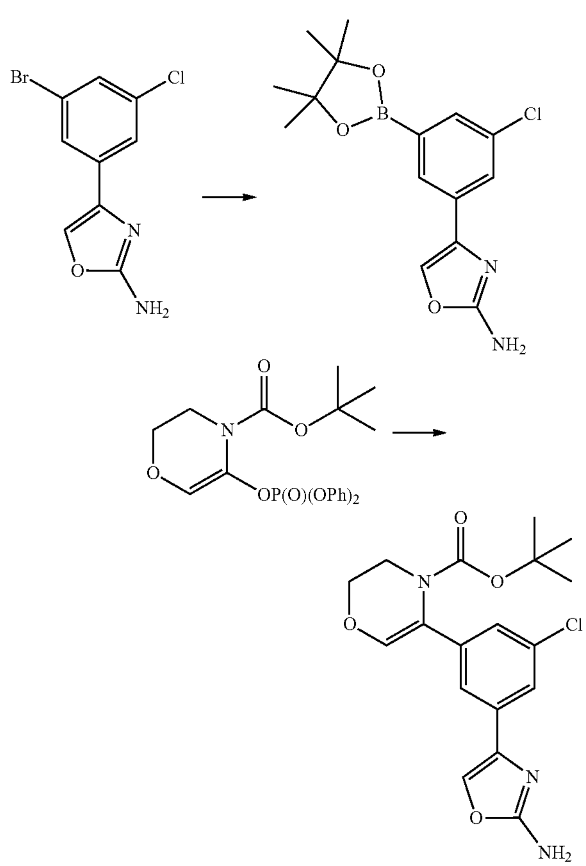

To a solution of a 4-(3-bromo-5-chlorophenyl)oxazol-2-amine (570 mg, 2.08 mmol, 1 equiv) in 1,4-dioxane (5 mL, 0.42 M) was added bis(pinacolato)diboron (582.14 mg, 2.29 mmol, 1.1 equiv), potassium acetate (409.05 mg, 4.16 mmol, 2 equiv), and Pd(dppf)$Cl_2$ (150.81 mg, 0.21 mmol, 0.10 equiv) at 25° C. under N2. The mixture was stirred at 90° C. for 16 hours. The reaction mixture was poured into water (6 mL) and extracted with EtOAc (6 mL*3). The combined organic layers were washed with brine (5 mL*2), dried over $Na_2SO_4$, filtered, and concentrated under reduced pressure to afford 4-(3-chloro-5-(4,4,5,5-tetramethyl-1,3,2-dioxaborolan-2-yl)phenyl)oxazol-2-amine (780 mg) as yellow oil.

To a solution of 4-(3-chloro-5-(4,4,5,5-tetramethyl-1,3,2-dioxaborolan-2-yl)phenyl)oxazol-2-amine (785 mg, 2.44 mmol, 1 equiv) in 1,4-dioxane (5 mL, 0.41 M) and water (1 mL, 0.41 M) was added tert-butyl 5-diphenoxyphosphoryloxy-2,3-dihydro-1,4-oxazine-4-carboxylate (1061.2 mg, 2.44 mmol, 1 equiv), potassium carbonate (676.87 mg, 4.89 mmol, 2 equiv), and Pd(dppf)$Cl_2$ (88.59 mg, 0.12 mmol, 0.05 equiv) at 25° C. The mixture was stirred at 80° C. for 2 h under $N_2$. The reaction mixture was poured into saturated aqueous $NH_4Cl$ (6 mL) and extracted with EtOAc (6 mL*3). The combined organic layers were washed with brine (5 mL*2), dried over $Na_2SO_4$, filtered, and concentrated under reduced pressure. The residue was purified by column chromatography ($SiO_2$, Petroleum ether/Ethyl acetate=3/1 to 1/1) to afford tert-butyl 5-(3-(2-aminooxazol-4-yl)-5-chlorophenyl)-2,3-dihydro-4H-1,4-oxazine-4-carboxylate (300 mg, 0.79 mmol, 32% yield).

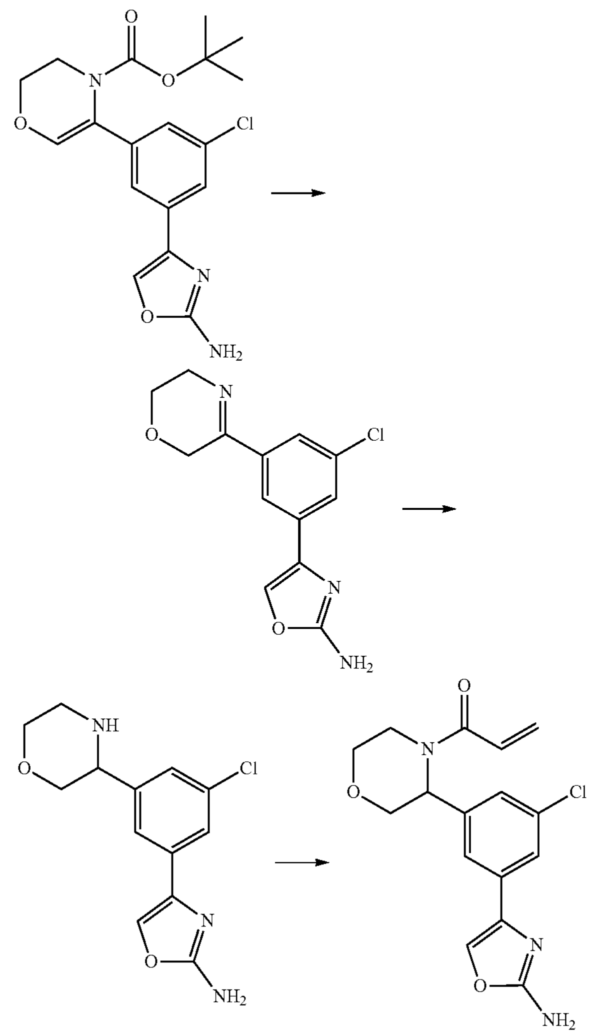

To a solution of tert-butyl 5-(3-(2-aminooxazol-4-yl)-5-chlorophenyl)-2,3-dihydro-4H-1,4-oxazine-4-carboxylate (305 mg, 0.81 mmol, 1 equiv) in DCM (3 mL, 0.20 M) was added trifluoroacetic acid (1 mL, 0.20 M) at 25° C. under $N_2$. The mixture was stirred at 25° C. for 1 hour. The reaction was concentrated under reduced pressure. The mixture was neutralized with 2N NaOH solution at 0° C. and extracted with ethyl acetate. The combined organic layer was washed with water, brine, dried over $Na_2SO_4$, filtered, and concentrated under reduced pressure to afford crude 4-(3-chloro- 5-(5,6-dihydro-2H-1,4-oxazin-3-yl)phenyl)oxazol-2-amine (224 mg, 0.81 mmol, 100% yield). The crude product was used in the next step without further purification.

To a solution of 4-(3-chloro-5-(5,6-dihydro-2H-1,4-oxazin-3-yl)phenyl)oxazol-2-amine (147 mg, 0.53 mmol, 1 equiv) in DCM (2 mL, 0.26 M) was added sodium cyanoborohydride (33.26 mg, 0.59 mmol, 1 equiv) at 0° C. The mixture was stirred at 25° C. for 1 hour under $N_2$. The reaction mixture was poured into saturated aqueous $NH_4Cl$ (5 mL) and extracted with DCM (5 mL*3). The combined organic layers were washed with brine (5 mL*2), dried over $Na_2SO_4$, filtered, and concentrated under reduced pressure. The residue was purified by prep-HPLC (TFA condition) to 4-(3-chloro-5-(morpholin-3-yl)phenyl)oxazol-2-amine (50 mg, 0.18 mmol, 34% yield) as a white solid.

4-(3-chloro-5-(morpholin-3-yl)phenyl)oxazol-2-amine was used Step 8 of Procedure E to obtain the title compound.

Enantiomers were separated by SFC and the absolute stereochemistry was not assigned. LC-MS m/z: 344.2 [M+1].

Stereochemistry: single enantiomer of unknown absolute configuration.

Example 53. Procedure F and Synthesis of 1-(5-chloro-7-phenyl-2H-spiro[benzofuran-3,3'-morpholin]-4'-yl)prop-2-en-1-one (Compound 7)

Procedure F

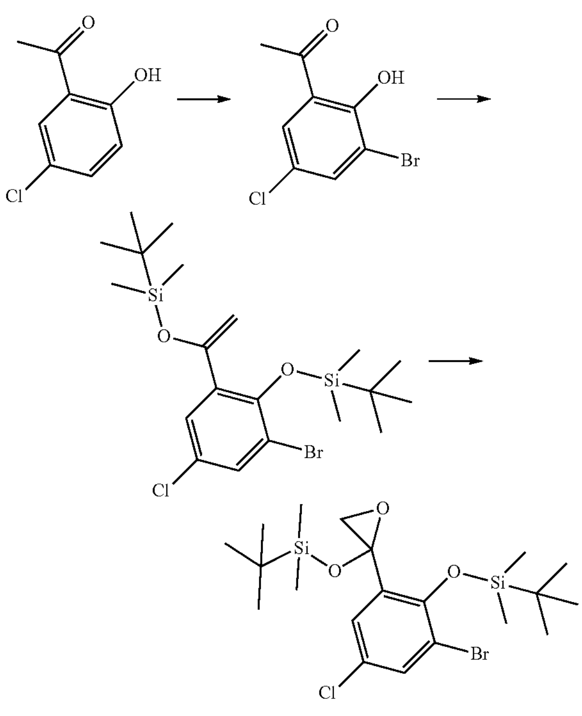

To a solution of 1-(5-chloro-2-hydroxy-phenyl)ethanone (50 g, 293.1 mmol, 1 equiv) in DMF (500 mL, 0.58 M) was added N-bromosuccinimide (54.77 g, 307.76 mmol, 1.05 equiv) at 25° C. The mixture was stirred at 25° C. for 16 hours under $N_2$. The solution was poured into water (600 mL) filtered, washed with aqueous $Na_2SO_3$ (500 mL), dried over $Na_2SO_4$, filtered, and concentrated under reduced pressure to afford 1-(3-bromo-5-chloro-2-hydroxy-phenyl)ethanone (65.0 g, 261 mmol, 89% yield) as brown solid.

To a solution of 1-(3-bromo-5-chloro-2-hydroxy-phenyl) ethanone (5000 mg, 20.04 mmol, 1 equiv) in DCM (50 mL, 0.40 M) was added triethylamine (6083 mg, 60.12 mmol, 3 equiv) and tert-butyldimethylsilyl trifluoromethanesulfonate (10595 mg, 40.08 mmol, 2 equiv) at 0° C. The mixture was stirred at 25° C. for 12 hours under $N_2$. The reaction mixture was poured into water (60 mL) and extracted with DCM (50 mL*3). The combined organic layers were washed with brine (50 mL*2), dried over $Na_2SO_4$, filtered, and concentrated under reduced pressure. The residue was purified by flash silica gel chromatography (ISCO®; 80 g SEPA-FLASH® Silica Flash Column, Eluent of 0-10% Ethyl acetate/Petroleum ether gradient @ 80 mL/min) to afford ((1-(3-bromo-2-((tert-butyldimethylsilyl)oxy)-5-chlorophenyl)vinyl)oxy)(tert-butyl)dimethylsilane (7.25 g, 14.7 mmol, 73% yield) as a colorless oil.

To a solution of ((1-(3-bromo-2-((tert-butyldimethylsilyl) oxy)-5-chlorophenyl)vinyl)oxy)(tert-butyl)dimethylsilane (7.25 g, 15.17 mmol) in DCM (80 mL, 0.19 M) was added sodium bicarbonate (3185 mg, 37.91 mmol, 2.5 equiv) and 3-chloroperbenzoic acid (4926 mg, 24.26 mmol) at 0° C. The mixture was stirred at 25° C. for 4 hours under $N_2$. The reaction mixture was quenched with aqueous $Na_2SO_3$ (100 mL) and extracted with DCM (60 mL*3). The combined organic layers were washed with brine (50 mL*2), dried over $Na_2SO_4$, filtered, and concentrated under reduced pressure. The residue was purified by flash silica gel chromatography (ISCO®; 80 g SEPAFLASH® Silica Flash Column, Eluent of 0-10% Ethyl acetate/Petroleum ether gradient @ 80 mL/min) to afford ((2-(3-bromo-2-((tert-butyldimethylsilyl)oxy)-5-chlorophenyl)oxiran-2-yl)oxy) (tert-butyl)dimethylsilane (5.00 g, 10.1 mmol, 67% yield) as a yellow oil.

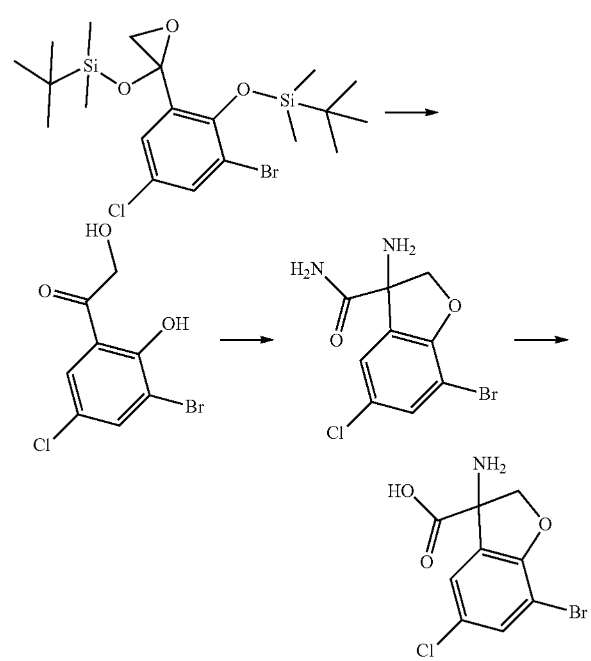

To a solution of ((2-(3-bromo-2-((tert-butyldimethylsilyl) oxy)-5-chlorophenyl)oxiran-2-yl)oxy)(tert-butyl)dimethylsilane (20 g, 40.48 mmol) in THF (200 mL, 0.18 M) and water (20 mL, 0.18 M) was added p-toluenesulfonic acid monohydrate (1.54 g, 8.09 mmol) at 25° C. The mixture was stirred at 70° C. for 12 hours under $N_2$. The reaction mixture was poured into water (650 mL) and extracted with EtOAc (750 mL*3). The combined organic layers were washed with brine (300 mL*2), dried over $Na_2SO_4$, filtered, and concentrated under reduced pressure to give a crude 1-(3-bromo-5-chloro-2-hydroxyphenyl)-2-hydroxyethan-1-one (10.00 g, 37.7 mmol, 93% yield) as a yellow solid.

To a solution 1-(3-bromo-5-chloro-2-hydroxyphenyl)-2-hydroxyethan-1-one (6.72 g, 25 mmol, 1 equiv) in ethanol (50 mL, 0.25 M) and water (50 mL, 0.25 M) was added diammonium carbonate (12647 mg, 131 mmol, 5.2 equiv) and trimethylsilyl cyanide (98%) (3264 mg, 32 mmol, 1.3 equiv) at 0° C. The mixture was stirred at 55° C. for 12 hours under $N_2$. The reaction mixture was filtered, and the filter cake was dried under reduced pressure to afford 3-amino-7-bromo-5-chloro-2,3-dihydrobenzofuran-3-carboxamide (5.14 g, 17.6 mmol, 70% yield) as a yellow solid.

To a solution of 3-amino-7-bromo-5-chloro-2,3-dihydrobenzofuran-3-carboxamide (5.14 g, 17.63 mmol, 1 equiv) in ethanol (30 mL, 0.58 M) was added potassium hydroxide (2967 mg, 52 mmol, 3 equiv) (dissolved in 30 mL of water) at 0° C. The mixture was stirred at 55° C. for 12 hours under $N_2$. The muddy mixture turned clear. The reaction mixture pH was adjusted to 4 with HCl in EtOAc. The filter cake was collected by filtration and dried under reduced pressure to afford 3-amino-7-bromo-5-chloro-2,3-dihydrobenzofuran-3-carboxylic acid (4.26 g, 14.6 mmol, 82% yield) as a white solid.

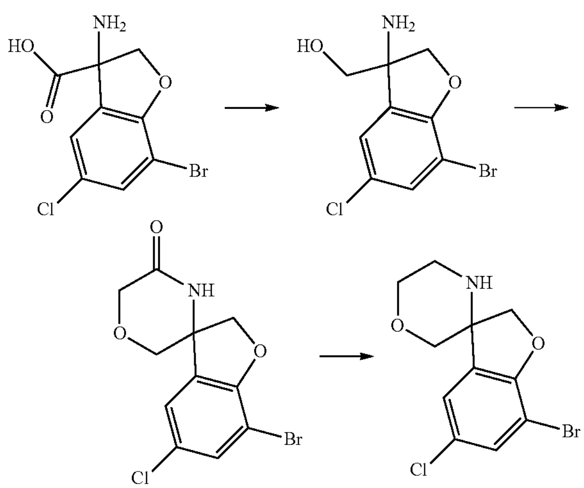

To a solution of 3-amino-7-bromo-5-chloro-2,3-dihydrobenzofuran-3-carboxylic acid (4.26 g, 14.56 mmol, 1 equiv) in THF (40 mL, 0.36 M) was added borane THF (72.8 mL, 72.8 mmol, 5 equiv) at 0° C. The mixture was stirred at 70° C. for 2 hours under $N_2$ and then quenched with MeOH (100 mL). The solution was stirred at 70° C. for 1 hour and then concentrated under reduced pressure to afford (3-amino-7-bromo-5-chloro-2,3-dihydrobenzofuran-3-yl) methanol (4.60 g, 13.2 mmol, 90% yield) as a white solid.

To a solution of (3-amino-7-bromo-5-chloro-2,3-dihydrobenzofuran-3-yl)methanol (1000 mg, 3.59 mmol, 1 equiv) in THF (10 mL, 0.3 M) was added NaH (287 mg, 7.18 mmol, 2 equiv) at 0° C. The mixture was stirred at 0° C. for 30 min under N2. Ethyl chloroacetate (659 mg, 5.38 mmol, 1.5 equiv) was then added slowly at 0° C. The mixture was stirred at 25° C. for 12 hours under $N_2$ and then poured into water (30 mL) and extracted with EtOAc (30 mL*3). The combined organic layers were washed with brine (20 mL*2), dried over $Na_2SO_4$, filtered, and concentrated under reduced pressure. The residue was purified by flash silica gel chromatography (ISCO®; 12 g SEPAFLASH® Silica Flash Column, Eluent of 10-30% Ethyl acetate/Petroleum ether gradient @ 60 mL/min) to afford 7-bromo-5-chloro-2H-spiro[benzofuran-3,3'-morpholin]-5'-one (413 mg, 1.30 mmol, 36% yield) as a yellow solid.

To a solution of 7-bromo-5-chloro-2H-spiro[benzofuran-3,3'-morpholin]-5'-one (413 mg, 1.29 mmol, 1 equiv) in THF (10 mL, 0.13 M) was added borane THF (6.5 mL, 6.48 mmol, 5 equiv) at 0° C. The mixture was stirred at 70° C. for 2 hours under $N_2$. The mixture was quenched by MeOH (30 mL) at 0° C. and then stirred at 70° C. for 12 hours under $N_2$. The mixture was concentrated under reduced pressure to afford 7-bromo-5-chloro-2H-spiro[benzofuran-3,3'-morpholine] (470 mg, 1.23 mmol, 95% yield) as a yellow oil.

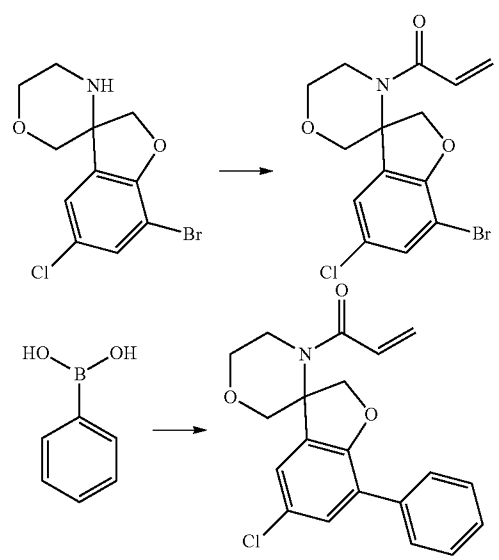

To a solution of 7-bromo-5-chloro-2H-spiro[benzofuran-3,3'-morpholine] (470 mg, 1.54 mmol, 1 equiv) in DCM (5 mL, 0.31 M) was added triethylamine (0.43 mL, 3.08 mmol, 2 equiv) and acryloyl chloride (139.67 mg, 1.54 mmol, 1 equiv) at 0° C. The mixture was stirred at 0° C. for 1 hour under $N_2$. The reaction mixture was poured into water (15 mL) and extracted with DCM (15 mL*3). The combined organic layers were washed with brine (10 mL*2), dried over $Na_2SO_4$, filtered, and concentrated under reduced pressure. The residue was purified by flash silica gel chromatography (ISCO®; 4 g SEPAFLASH® Silica Flash Column, Eluent of 20-40% Ethyl acetate/Petroleum ether gradient @ 36 mL/min) to afford 1-(7-bromo-5-chloro-2H-spiro[benzofuran-3,3'-morpholin]-4'-yl)prop-2-en-1-one (346 mg, 0.97 mmol, 62% yield) as a yellow solid.

To a solution of phenylboronic acid (3.43 mg, 0.028 mmol) and 1-(7-bromo-5-chloro-2H-spiro[benzofuran-3,3'-morpholin]-4'-yl)prop-2-en-1-one (15 mg, 0.042 mmol) in MeCN (3 mL), 1,4-dioxane (3 mL), and water (1 mL) was added $K_2CO_3$ (23 mg) and $Pd(dppf)Cl_2$ (20 mg). The resulting mixture was stirred at 80° C. for 1 hour. The reaction was quenched with brine (20 mL) and then extracted with EtOAc (20 mL*2). The organic layers were combined, dried over $Na_2SO_4$, filtered, and concentrated under reduced pressure. The crude product was purified by prep-TLC to afford racemic 1-(5-chloro-7-phenyl-2H-spiro[benzofuran-3,3'- morpholin]-4'-yl)prop-2-en-1-one (8.7 mg, 83% yield) as a yellow solid. LC-MS m/z: 356.1 [M+1].

Stereochemistry: racemic.

Example 54. Synthesis of 1-(7-(4-amino-1,3,5-triazin-2-yl)-5-chloro-2H-spiro[benzofuran-3,3'-morpholin]-4'-yl)prop-2-en-1-one (Compound 151)

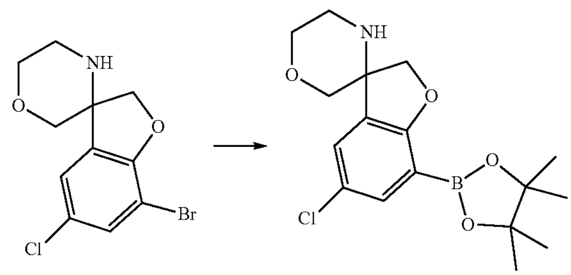 [SMILES: Clc1cc(Br)c2c(c1)C1(COCCN1)CO2 ; CC1(C)OB(c2cc(Cl)cc3c2OCC32COCCN2)OC1(C)C]

7-bromo-5-chloro-spiro[2H-benzofuran-3,3'-morpholine] was obtained from Procedure F.

To a solution of 7-bromo-5-chloro-spiro[2H-benzofuran-3,3'-morpholine] (300 mg, 0.98 mmol, 1 equiv) in CPME (3 mL) was added potassium acetate (290 mg, 2.95 mmol, 3 equiv), bis(pinacolato)diboron (250.13 mg, 0.985 mmol, 1 equiv), and CPy3 Pd G2 (0.1 eq, 58.16 mg) at 25° C. in a glove box. The mixture was stirred at 80° C. for 12 hours under $N_2$. The solution was used directly in the next step.

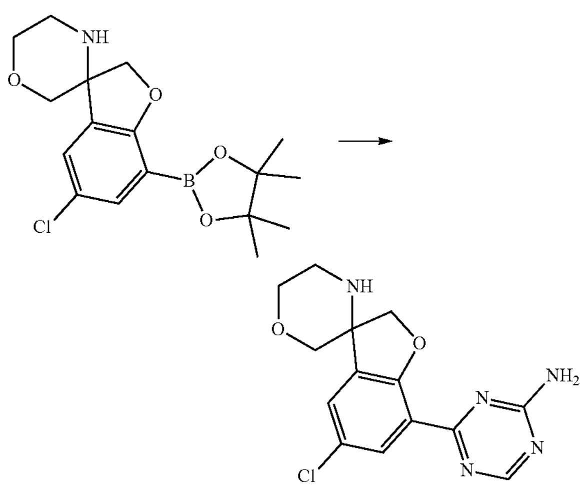

To a solution of 5-chloro-7-(4,4,5,5-tetramethyl-1,3,2-dioxaborolan-2-yl)spiro[2H-benzofuran-3,3'-morpholine] (300 mg, 0.85 mmol, 1 equiv) in CPME (3 mL) and water (0.6 mL) was added potassium carbonate (353 mg, 2.55 mmol), 4-chloro-1,3,5-triazin-2-amine (111 mg, 0.85 mmol), and Pd(dppf)$Cl_2$ (0.1 eq, 62.41 mg) at 25° C. The mixture was stirred at 80° C. for 12 hours under $N_2$. The reaction mixture was poured into water (15 mL) and extracted with EtOAc (15 mL*3). The combined organic layers were washed with brine (10 mL*2), dried over $Na_2SO_4$, filtered, and concentrated under reduced pressure. The residue was purified by flash silica gel chromatography (ISCO®; 4 g SEPAFLASH® Silica Flash Column, Eluent of 0-20% MeOH/EtOAc @ 36 mL/min) to afford 4-(5-chloro-2H-spiro[benzofuran-3,3'-morpholin]-7-yl)-1,3,5-triazin-2-amine (110 mg, 0.344 mmol, 40% yield) as a yellow oil.

The title compound was obtained using 4-(5-chloro-2H-spiro[benzofuran-3,3'-morpholin]-7-yl)-1,3,5-triazin-2-amine in Procedure F. LC-MS m/z: 374.1 [M+1].

Enantiomers were separated by chiral SFC (column: Chiralpak AS-3, 50×4.6 mm ID, 3 um) with mobile phase $CO_2$ and 0.1% IPAm in MeOH. The title compound's absolute stereochemistry was not assigned. Stereochemistry: single enantiomer of unknown absolute configuration.

Example 55. Synthesis of 5-(4'-acryloyl-5-chloro-2H-spiro[benzofuran-3,3'-morpholin]-7-yl)-2-fluorobenzamide (Compound 143)

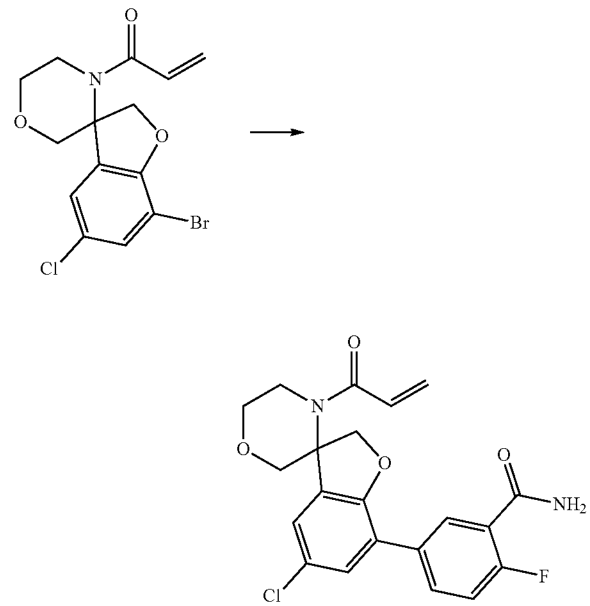

1-(7-bromo-5-chloro-spiro[2H-benzofuran-3,3'-morpholine]-4'-yl)prop-2-en-1-one was obtained from Procedure F.

To a solution of 1-(7-bromo-5-chloro-spiro[2H-benzofuran-3,3'-morpholine]-4'-yl)prop-2-en-1-one (100 mg, 0.27 mmol) in 1,4-Dioxane (3 mL) and water (0.6 mL) was added 2-fluoro-5-(4,4,5,5-tetramethyl-1,3,2-dioxaborolan-2-yl) benzamide (96 mg, 0.36 mmol, 1.3 equiv), potassium carbonate (115 mg, 0.83 mmol, 3 equiv), and Pd(dppf)$Cl_2$ (0.1 eq, 20 mg) at 25° C. The mixture was stirred at 80° C. for 12 hours under $N_2$. The reaction mixture was poured into water (20 mL) and extracted with EtOAc (20 mL*3). The combined organic layers were washed with brine (15 mL*2), dried over $Na_2SO_4$, filtered, and concentrated under reduced pressure. The residue was purified by prep-TLC (ethyl acetate) to give 100 mg of crude product as a yellow oil. The product was further purified by prep-HPLC to 5-(4'-acryloyl-5-chloro-2H-spiro[benzofuran-3,3'-morpholin]-7-yl)-2-fluorobenzamide.

Enantiomers were separated by chiral SFC (column: Chiralpak AD-3, 50×4.6 mm ID, 3 um) with mobile phase CO2 and 0.1% IPAm in MeOH. The title compound's absolute stereochemistry was not assigned. LC-MS m/z: 417.1 [M+1].

Stereochemistry: single enantiomer of unknown absolute configuration.

Example 56. Synthesis of 1-(7-(2-aminopyrimidin-4-yl)-5-chloro-2H-spiro[benzofuran-3,3'-morpholin]-4'-yl)prop-2-en-1-one (Compound 158)

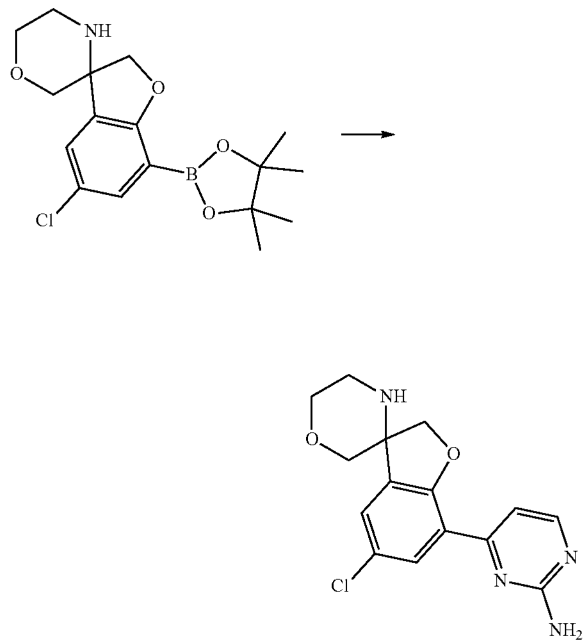 [SMILES: CC1(C)OB(c2cc(Cl)cc3c2OCC32COCCN2)OC1(C)C ; Nc1nccc(-c2cc(Cl)cc3c2OCC32COCCN2)n1]

5-chloro-7-(4,4,5,5-tetramethyl-1,3,2-dioxaborolan-2-yl) spiro[2H-benzofuran-3,3'-morpholine] was obtained from the synthesis of Compound 151.

To a solution of 5-chloro-7-(4,4,5,5-tetramethyl-1,3,2-dioxaborolan-2-yl)spiro[2H-benzofuran-3,3'-morpholine] (400 mg, 1.13 mmol, 1 equiv) in 1,4-dioxane (5 mL, 0.19 M) and water (1 mL, 0.19 M) was added potassium carbonate (471 mg, 3.41 mmol, 3 equiv), 4-chloropyrimidin-2-amine (147 mg, 1.13 mmol, 1 equiv), and Pd(dppf)$Cl_2$ (0.1 eq, 83.19 mg) at 25° C. The mixture was stirred at 80° C. for 12 hours under $N_2$. The reaction mixture was poured into water (15 mL) and extracted with EtOAc (15 mL*3). The combined organic layers were washed with brine (10 mL*2), dried over $Na_2SO_4$, filtered, and concentrated under reduced pressure. The residue was purified by flash silica gel chromatography (ISCO®; 4 g SEPAFLASH® Silica Flash Column, Eluent of 0-20% MeOH/EtOAc @ 60 mL/min) to afford 4-(5-chlorospiro[2H-benzofuran-3,3'-morpholine]-7-yl)pyrimidin-2-amine (115 mg, 0.361 mmol, 32% yield) as a yellow oil.

The title compound was obtained using 4-(5-chlorospiro [2H-benzofuran-3,3'-morpholine]-7-yl)pyrimidin-2-amine in Procedure F.

Enantiomers were separated by chiral SFC (column: Chiralpak AD-3, 50×4.6 mm ID, 3 um) with mobile phase $CO_2$ and 0.1% IPAm in EtOH. The title compound's absolute stereochemistry was not assigned. LC-MS m/z: 373.0 [M+1].

Stereochemistry: single enantiomer of unknown absolute configuration.

Example 57. Synthesis of 7-(2-aminopyrimidin-4-yl)-5-chloro-2H-dispiro[benzofuran-3,5'-morpholine-2',1"-cyclopropan]-3'-one (Compound 192)

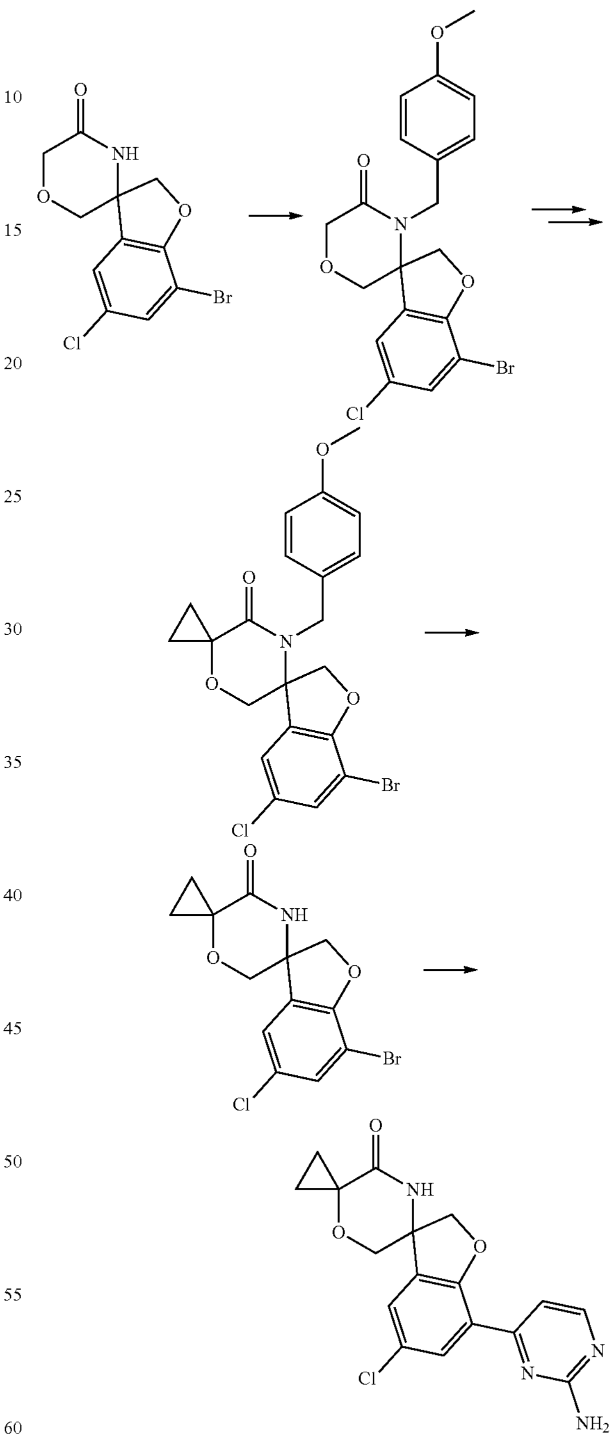

Installation of the cyclopropane was achieved on 7-bromo-5-chloro-2H-spiro[benzofuran-3,3'-morpholin]-5'-one from Procedure F. The product was taken forward to obtain 7-(2-aminopyrimidin-4-yl)-5-chloro-2H-dispiro[benzofuran-3,5'-morpholine-2',1"-cyclopropan]-3'-one.

Enantiomers were separated by SFC. The title compound's absolute stereochemistry was not assigned. LC-MS m/z: 399.1 [M+1].

Stereochemistry: single enantiomer of unknown absolute configuration.

Example 58. Procedure G and Synthesis of 1-(3-(3-(4-amino-1,3,5-triazin-2-yl)-5-chlorophenyl)-3-methylmorpholino)prop-2-en-1-one (Compound 112)

Procedure G

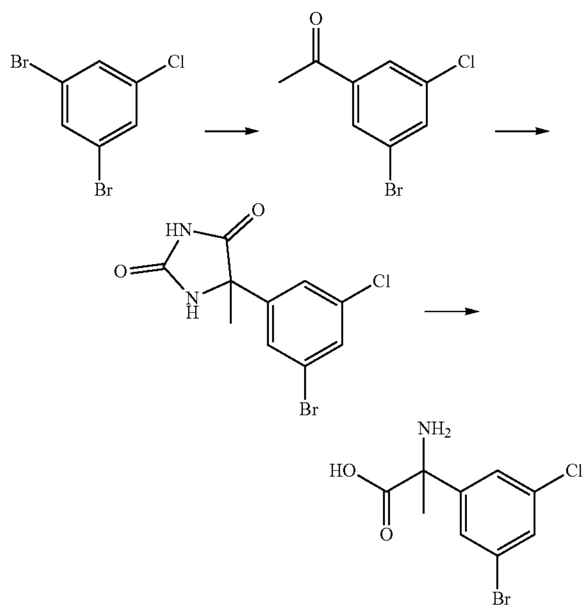

1,3-dibromo-5-chloro-benzene (30 g, 110.97 mmol) was dissolved in anhydrous i-$Pr_2O$ (300 mL) in a dried flask under nitrogen. The reaction mixture was cooled to −78° C. A 2.5 M solution of n-BuLi in hexanes (44.40 mL, 110.97 mmol) was added dropwise to the above solution and the reaction mixture was stirred at −78° C. for 30 min. N-Methoxy-N-methylacetamide (13.73 g, 133.16 mmol, 1.2 equiv) was added slowly at −78° C. The reaction mixture was warmed slowly to room temperature and stirred for 30 minutes. The reaction mixture was poured into 120 mL of saturated aqueous $NH_4Cl$ and the mixture was stirred for 15 minutes. The organic phase was separated, dried over anhydrous $Na_2SO_4$, filtered, and concentrated. The residue was purified by column chromatography ($SiO_2$, Petroleum ether/Ethyl acetate=10/1) to afford 1-(3-bromo-5-chlorophenyl)ethan-1-one (21 g, 89.9 mmol, 81% yield) as a yellow oil.

A solution of 1-(3-bromo-5-chloro-phenyl)ethanone (21 g, 89.94 mmol, 1 equiv), $(NH_4)_2CO_3$ (45 g, 5.2 eq), and TMSCN (12 g, 1.31 eq) in ethanol (250 mL, 0.18 M) and water (250 mL, 0.18 M) was stirred at 55° C. for 12 hours. The reaction mixture was cooled to room temperature and filtered. The solid was collected, washed with water, and dried under vacuo to afford 5-(3-bromo-5-chlorophenyl)-5-methylimidazolidine-2,4-dione (24.5 g, 80.7 mmol, 90% yield) as a white solid.

To a solution of 5-(3-bromo-5-chlorophenyl)-5-methylimidazolidine-2,4-dione (24.5 g, 80.71 mmol, 1 equiv) in water (250 mL, 0.32 M) was added NaOH (12.9 g, 322.8 mmol, 4 equiv) at 25° C. The resulting mixture was stirred at 135° C. for 10 hours under $N_2$. The reaction mixture was cooled to 0° C. and 2N aqueous HCl was added until pH-6. The solid was collected by filtration, washed with water, and dried under vacuo to afford 2-amino-2-(3-bromo-5-chlorophenyl)propanoic acid (20 g, 71.8 mmol, 89% yield) as a white solid.

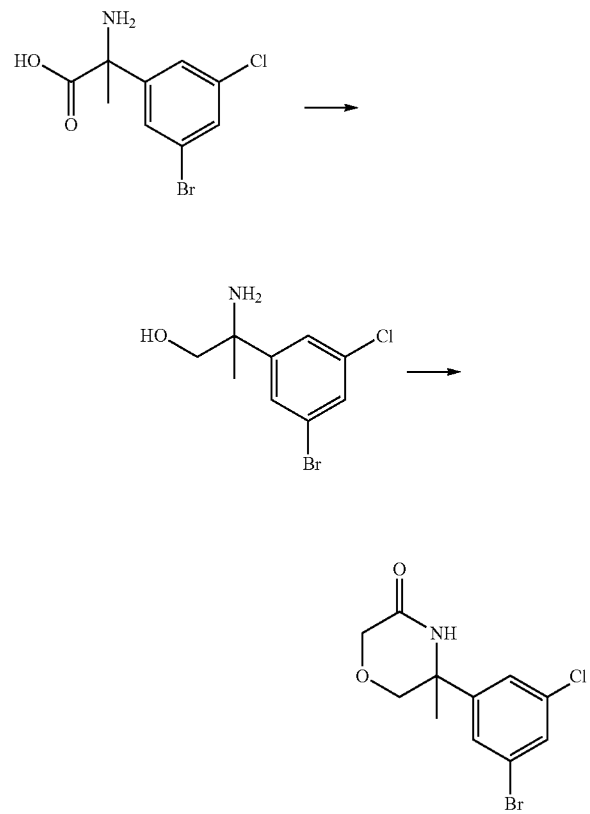

To a solution of 2-amino-2-(3-bromo-5-chloro-phenyl)propanoic acid (15 g, 53.85 mmol, 1 equiv) in THF (150 mL, 0.36 M) was added a borane tetrahydrofuran complex solution (235.88 g, 269.27 mmol, 5 equiv) at 0° C. The mixture was stirred at 25° C. for 2 hours under $N_2$. The reaction mixture was quenched with MeOH (200 mL) and aqueous HCl (5 mL), stirred for 1 hour, and then concentrated under reduced pressure. The mixture was neutralized with 2N NaOH solution at 0° C. and extracted with ethyl acetate. The combined organic layer was washed with water, brine, dried over anhydrous $Na_2SO_4$, and concentrated under reduced pressure to afford 2-amino-2-(3-bromo-5-chlorophenyl)propan-1-ol (13.8 g, 52.1 mmol, 97% yield).

To a solution of 2-amino-2-(3-bromo-5-chloro-phenyl)propan-1-ol (2 g, 7.56 mmol, 1 equiv) in toluene (30 mL, 0.25 M) was added NaH (10.65 g, 2 eq) at 0° C. The reaction was stirred for 30 mins before ethyl chloroacetate (1.11 g, 9.07 mmol, 1.2 equiv) was added dropwise. The reaction was allowed to warm to 25° C. and stirred for 30 minutes. The mixture was then heated to 130° C. for 16 hours. The reaction was quenched with saturated aqueous $NH_4Cl$ (30 mL) and extracted with ethyl acetate (30 mL*3). The organic layers were washed 100 mL saturated brine solution, dried over $Na_2SO_4$, filtered, and concentrated. The crude material was purified by flash column chromatography (PE:EA=1:0-1:1) to afford 5-(3-bromo-5-chlorophenyl)-5-methylmorpholin-3-one (1.4 g, 4.59 mmol, 61% yield) as a white solid.

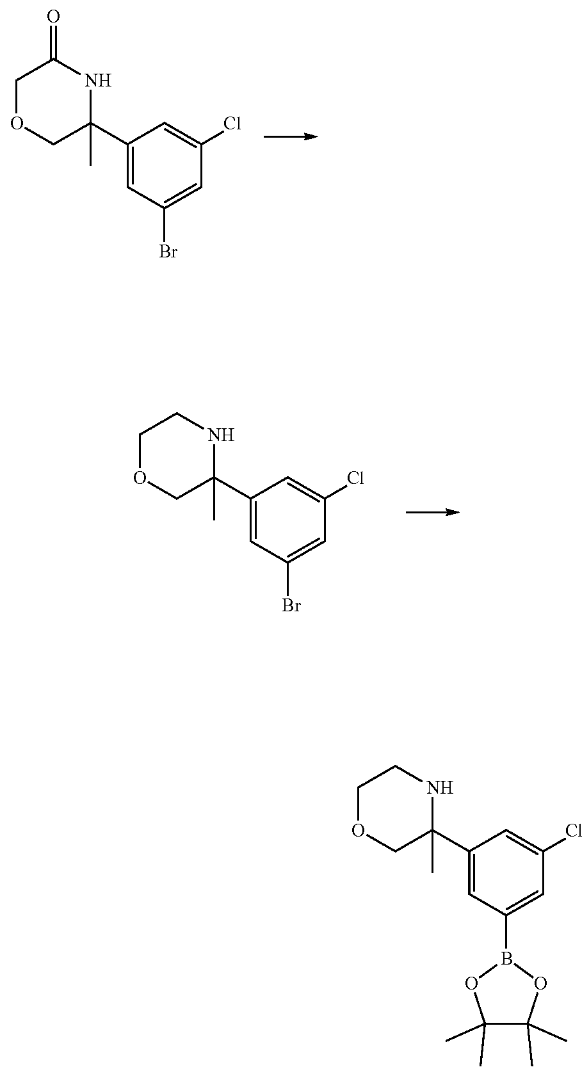

To a solution of 5-(3-bromo-5-chlorophenyl)-5-methylmorpholin-3-one (0.50 g, 1.64 mmol, 1 equiv) in THF (5 mL, 0.32 M) was added a borane tetrahydrofuran complex solution (8.628 g, 9.85 mmol, 6 equiv) at 0° C. The mixture was stirred at 25° C. for 2 hours under $N_2$. The reaction mixture was quenched with MeOH (15 mL) and HCl (1 mL) and then stirred for 1 hour before concentration under reduced pressure. The mixture was neutralized with 2N NaOH solution at 0° C., extracted with ethyl acetate, washed with water and brine, dried over anhydrous $Na_2SO_4$, and concentrated under reduced pressure. The crude product was purified was by flash silica gel column (EA:PE=0-60%) to afford 3-(3-bromo-5-chlorophenyl)-3-methylmorpholine (240 mg, 0.83 mmol, 50% yield) as a yellow oil.

To a solution of 3-(3-bromo-5-chlorophenyl)-3-methylmorpholine (240 mg, 0.82 mmol, 1 equiv) and bis(pinacolato)diboron (251.69 mg, 0.99 mmol, 1.2 equiv) in 1,4-dioxane (2 mL, 0.41 M) was added potassium acetate (243.17 mg, 2.47 mmol, 3 equiv) and Pd(dppf)$Cl_2$ (59.9 mg, 0.082 mmol, 0.1 equiv) under $N_2$. The resulting mixture was stirred for 12 hours at 90° C. under $N_2$. The mixture was concentrated and used directly for the next step without purification.

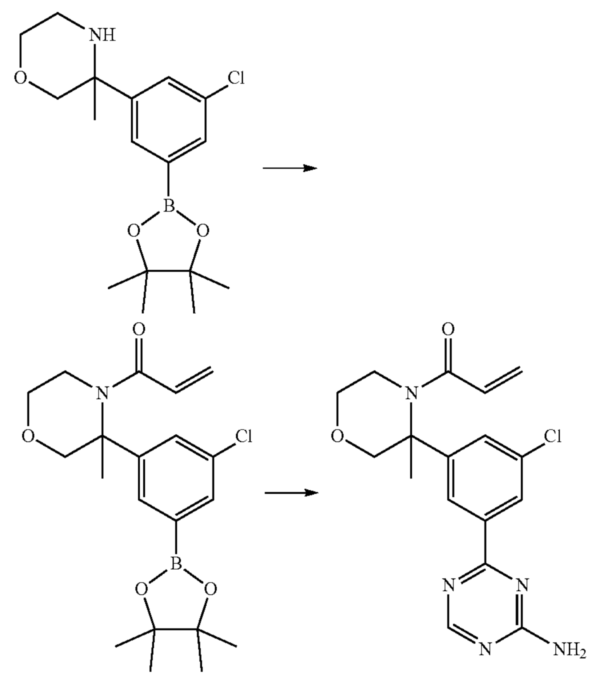

To a solution of crude 3-[3-chloro-5-(4,4,5,5-tetramethyl-1,3,2-dioxaborolan-2-yl)phenyl]-3-methyl-morpholine (500 mg, 1.48 mmol, 1 equiv) and triethylamine (449 mg, 4.44 mmol, 3 equiv) in DCM (6 mL, 0.25 M) was added acryloyl chloride (160 mg, 1.77 mmol, 1.2 equiv) dropwise at 0° C. under $N_2$. The reaction mixture was quenched with water (1 mL) and extracted with DCM (2 mL*3). The organic layers were washed with saturated brine solution, dried over $Na_2SO_4$, filtered, and concentrated.

The crude was purified by flash column chromatography (PE:EA=1:0-1:1) to give 1-(3-(3-chloro-5-(4,4,5,5-tetramethyl-1,3,2-dioxaborolan-2-yl)phenyl)-3-methylmorpholino)prop-2-en-1-one (110 mg 0.281 mmol, 19% yield) as a yellow oil.

To a solution of 1-(3-(3-chloro-5-(4,4,5,5-tetramethyl-1,3,2-dioxaborolan-2-yl)phenyl)-3-methylmorpholino)prop-2-en-1-one (300 mg, 0.76 mmol, 1 equiv) and 4-chloro-1,3,5-triazin-2-amine (109.98 mg, 0.84 mmol, 1.1 equiv)) in 1,4-dioxane (5 mL, 0.14 M) and water (0.5 mL, 0.14 M) was added Pd(dppf)$Cl_2$ (55.42 mg, 0.076 mmol) and potassium carbonate (211.71 mg, 1.53 mmol) under $N_2$. The resulting mixture was stirred for 12 hours at 80° C. under $N_2$. The reaction mixture was quenched with water (2 mL) and extracted with EtOAc (3 mL*3). The combined organic layers were washed with brine (3 mL*2), dried over $Na_2SO_4$, filtered, and concentrated under reduced pressure. The residue was purified by column chromatography (PE:EA=1:0-0:1) to afford 1-(3-(3-(4-amino-1,3,5-triazin-2-yl)-5-chlorophenyl)-3-methylmorpholino)prop-2-en-1-one (150 mg, 0.42 mmol, 54% yield) as a yellow solid.

Enantiomers of 1-(3-(3-(4-amino-1,3,5-triazin-2-yl)-5-chlorophenyl)-3-methylmorpholino)prop-2-en-1-one were separated by SFC. Absolute stereochemistry was not assigned. LC-MS m/z: 360.1 [M+1].

Stereochemistry: single enantiomer of unknown absolute configuration.

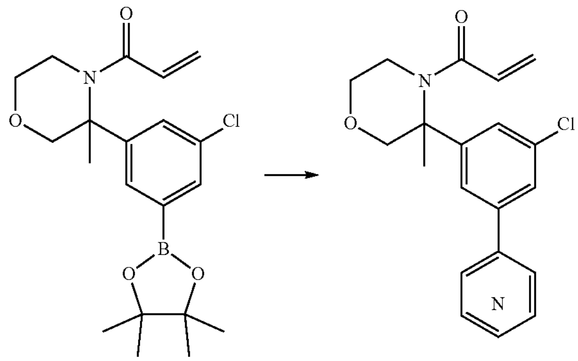

Using the appropriate coupling partner Procedure G, the title compounds can be obtained.

| Cmp | Name | Coupling Partner Step 9 | LC-MS m/z [M + 1] |
|---|---|---|---|
| 112 | 1-(3-(3-(4-amino-1,3,5-triazin-2-yl)-5-chlorophenyl)-3-methylmorpholino)prop-2-en-1-one | 4-chloro-1,3,5-triazin-2-amine | 360.1 |
| 113 | 1-(3-(3-(2-aminopyrimidin-4-yl)-5-chlorophenyl)-3-methylmorpholino)prop-2-en-1-one | 4-bromopyrimidin-2-amine | 359.2 |
| 114 | 3'-(4-acryloyl-3-methylmorpholin-3-yl)-5'-chloro-4-fluoro-[1,1'-biphenyl]-3-carboxamide | 5-bromo-2-fluorobenzamide | 403.1 |

Example 59. Procedure H and Synthesis of 1-((3R,5R)-3-(2-(2-aminopyrimidin-4-yl)-6-chloropyridin-4-yl)-5-methylmorpholino)prop-2-en-1-one (Compound 144)

Procedure H

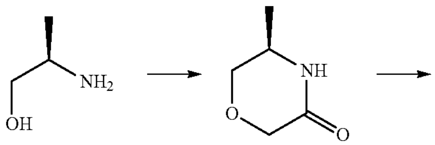

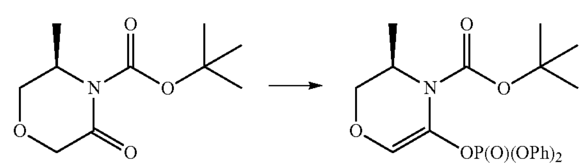

To a solution of D-alaninol (25 g, 332 mmol) in toluene (500 mL, 0.66 M) was added NaH (19.17 g, 2 eq) at 0° C. and stirred for 30 minutes. Ethyl chloroacetate (48.94 g, 399.41 mmol, 1.2 equiv) was added dropwise and then allowed to warm to 25° C. and stir for 30 minutes. The reaction mixture was heated to 130° C. for 16 hours. The solution was quenched with saturated aqueous $NH_4Cl$ (1000 mL) and extracted with ethyl acetate (1000 mL*3). The organic layers were washed with saturated brine solution, dried over $Na_2SO_4$, filtered, and concentrated to afford to (R)-5-methylmorpholin-3-one.

To a solution of (R)-5-methylmorpholin-3-one (25 g, 217.15 mmol, 1 equiv) in DCM (300 mL, 0.72 M) was added di-tert-butyl dicarbonate (56.87 g, 260.58 mmol, 1.2 equiv), triethylamine (43.94 g, 434.29 mmol, 2 equiv), and 4-(dimethylamino)pyridine (5.30 g, 43.49 mmol, 0.2 equiv) at 25° C. and then stirred for 16 hours. The reaction mixture was quenched with water (300 ml) and extracted with DCM (300*3 mL). The organic phase was dried over $Na_2SO_4$, filtered, and then concentrated. The crude product was purified was by flash column chromatography (petroleum ether & ethyl acetate) to afford tert-butyl (R)-3-methyl-5-oxomorpholine-4-carboxylate.

To a solution of tert-butyl (R)-3-methyl-5-oxomorpholine-4-carboxylate (5 g, 23.23 mmol) in THF (50 mL, 0.46 M) was added lithium bis(trimethylsilyl)amide (4275 mg, 25.55 mmol) dropwise at −30° C. The reaction was stirred for 30 minutes before dropwise addition of diphenyl phosphorochloridate (6863 mg, 25.55 mmol) at −30° C. The reaction was allowed to warm to room temperature and stirred for 1 hour. The reaction was poured into water (50 mL) and extracted with ethyl acetate (50 mL×3). The organic layer was washed with brine (50 mL) and concentrated. The crude product was purified by column chromatography (PE:EA=5:1 to 2:1) to afford tert-butyl (R)-5-((diphenoxyphosphoryl)oxy)-3-methyl-2,3-dihydro-4H-1,4-oxazine-4-carboxylate (9300 mg, 20.8 mmol, 89% yield) as a yellow oil.

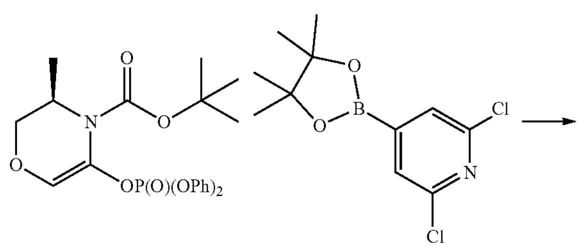

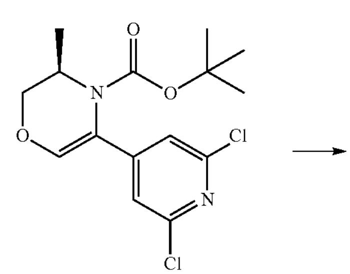

-continued

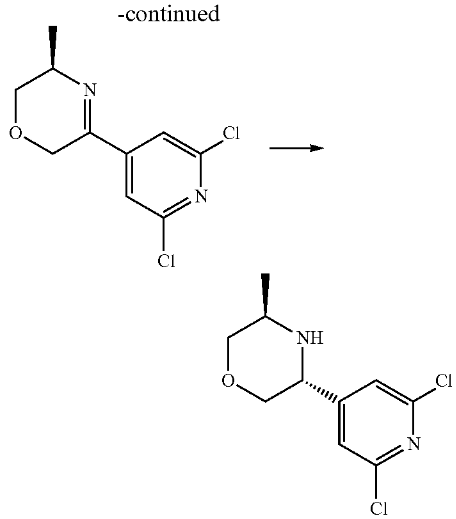

A solution of tert-butyl (R)-5-((diphenoxyphosphoryl)oxy)-3-methyl-2,3-dihydro-4H-1,4-oxazine-4-carboxylate (6.3 g, 14.08 mmol), 2,6-dichloro-4-(4,4,5,5-tetramethyl-1,3,2-dioxaborolan-2-yl)pyridine (4.24 g, 15.49 mmol, 1.1 equiv), $K_2CO_3$ (5.86 g, 111.75 mmol, 2.0 eq), and Pd(dppf)$Cl_2$ (1.55 g, 0.1 eq) in MeCN (20 mL, 0.28 M), 1,4-dioxane (20 mL, 0.28 M), and water (10 mL, 0.28 M) was stirred at 80° C. for 12 hours under $N_2$. The reaction was quenched with $H_2O$ (200 mL) and extracted with EtOAc (200 ml×3). The organic layer was concentrated and then purified by column chromatography (PE/EA=10/1 to PE/EA=5/1) to afford tert-butyl (R)-5-(2,6-dichloropyridin-4-yl)-3-methyl-2,3-dihydro-4H-1,4-oxazine-4-carboxylate (3.6 g, 10.42 mmol, 74% yield) as a white solid.

A solution of tert-butyl (R)-5-(2,6-dichloropyridin-4-yl)-3-methyl-2,3-dihydro-4H-1,4-oxazine-4-carboxylate (26 g, 75.31 mmol) in 4M HCl in EtOAC (60 mL) was stirred 25° C. for 1 hour. The reaction mixture was concentrated under reduced pressure to (R)-5-(2,6-dichloropyridin-4-yl)-3-methyl-3,6-dihydro-2H-1,4-oxazine HCl (21 g, 70.6 mmol, 94% yield) as a yellow solid.

Zn (2.32 g, 2 eq, 24.4 mmol) was added to a solution of (R)-5-(2,6-dichloropyridin-4-yl)-3-methyl-3,6-dihydro-2H-1,4-oxazine HCl (4000 mg, 14.21 mmol) in acetic acid (40 mL) and then stirred 25° C. for 20 minutes. The reaction was quenched with 1N HCl (50 mL), extracted with DCM (50 ml*3), washed with brine (50 mL), dried over $Na_2SO_4$, filtered, and concentrated. The residue was purified by flash silica gel chromatography (ISCO®; 12 g SEPAFLASH® Silica Flash Column, Eluent of 0-30% Ethyl acetate/Petroleum ether gradient @ 80 mL/min) to afford (3R,5R)-3-(2,6-dichloropyridin-4-yl)-5-methylmorpholine (3000 mg, 12.1 mmol, 86% yield) as a yellow oil.

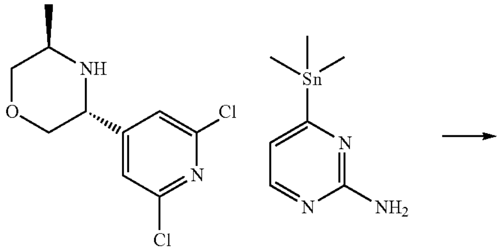

-continued

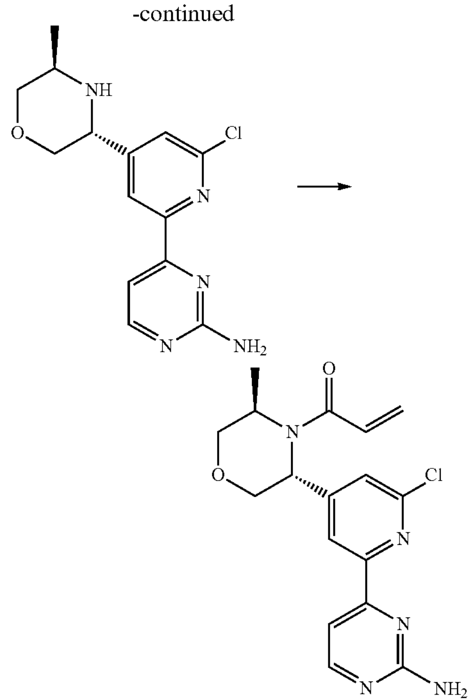

A solution of (3R,5R)-3-(2,6-dichloropyridin-4-yl)-5-methylmorpholine (200 mg, 0.81 mmol), 4-trimethylstannylpyrimidin-2-amine (187.86 mg, 0.73 mmol, 0.9 equiv), LiCl (3.43 mg, 0.081 mmol, 0.10 equiv), and $Pd(PPh_3)_4$ (93.52 mg, 0.081 mmol, 0.1 equiv) in 1,4-dioxane (5 mL, 0.16 M) was stirred at 90° C. for 12 hours under $N_2$. The reaction was quenched with $H_2O$ (5 mL) and extracted with EtOAc (2 ml×3). The organic layer was concentrated and purified by Prep-TLC (PE/EtOAc=0/1) to afford 4-(6-chloro-4-((3R,5R)-5-methylmorpholin-3-yl)pyridin-2-yl)pyrimidin-2-amine (80 mg, 0.26 mmol, 32% yield) as a yellow oil.

A solution of 4-(6-chloro-4-((3R,5R)-5-methylmorpholin-3-yl)pyridin-2-yl)pyrimidin-2-amine (80 mg, 0.26 mmol, 1 equiv), acryloyl chloride (23.68 mg, 0.26 mmol, 1 equiv), and triethylamine (0.5 mL) in DCM (2 mL, 0.13 M) was stirred at 25° C. for 2 hours. The reaction was quenched with H2O (5 mL) and extracted with DCM (5 mL×3). The organic layer was concentrated and purified by prep TLC (EtOAc/MeOH=10/1) to afford 1-((3R,5R)-3-(2-(2-aminopyrimidin-4-yl)-6-chloropyridin-4-yl)-5-methylmorpholino)prop-2-en-1-one (7.2 mg, 0.02 mmol, 8% yield) as a white solid. LC-MS m/z: 360.1 [M+1].

Stereochemistry: single enantiomer of known absolute configuration.

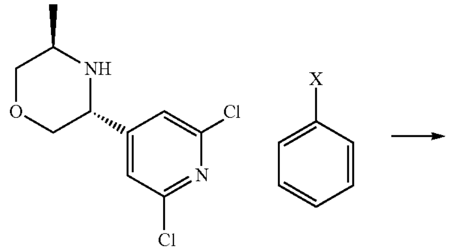

-continued

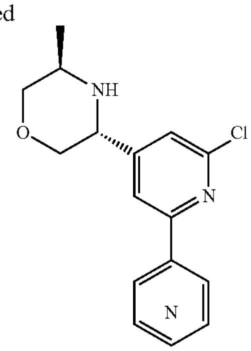

Using the appropriate coupling partner Procedure H, the title compounds can be obtained.

| Cmp | Name | Coupling Partner | LC-MS m/z [M+1] |
|---|---|---|---|
| 144 | 1-((3R,5R)-3-(2-(2-aminopyrimidin-4-yl)-6-chloropyridin-4-yl)-5-methylmorpholino)prop-2-en-1-one | 4-(trimethylstannyl)pyrimidin-2-amine | 360.1 |
| 142 | 1-((3R,5R)-3-(2-chloro-6-(2-methylpyrimidin-4-yl)pyridin-4-yl)-5-methylmorpholino)prop-2-en-1-one | 2-methyl-4-(trimethylstannyl)pyrimidine | 359.1 |
| 145 | 4-((3R,5R)-4-acryloyl-5-methylmorpholin-3-yl)-6-chloro-[2,4'-bipyridine]-2'-carboxamide | 4-(4,4,5,5-tetramethyl-1,3,2-dioxaborolan-2-yl)picolinamide | 387.0 |

Example 60. Procedure I and Synthesis of 1-((3R,5R)-3-(2-chloro-6-(imidazo[1,2-a]pyridin-7-yl)pyridin-4-yl)-5-methylmorpholino)prop-2-en-1-one (Compound 138)

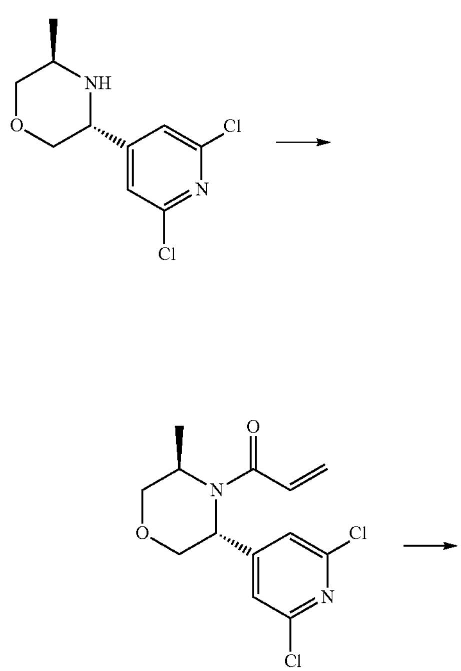

-continued

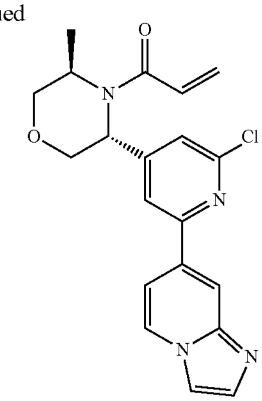

(3R,5R)-3-(2,6-dichloropyridin-4-yl)-5-methylmorpholine was obtained from Procedure H.

To a solution of (3R,5R)-3-(2,6-dichloropyridin-4-yl)-5-methylmorpholine (470 mg, 1.90 mmol) and acryloyl chloride (189.36 mg, 2.09 mmol) in DCM (5 mL, 0.38 M) was added DIEA (0.8 mL) at 25° C. and then allowed to stir for 2 hours. The mixture was diluted with $H_2O$ (15 mL) and extracted with DCM (15 mL*3). The combined organic solutions were washed with brine (20 mL), dried over $Na_2SO_4$, filtered, and concentrated under vacuo. The residue was purified by flash silica gel chromatography (ISCO®; 12 g SEPAFLASH® Silica Flash Column, Eluent of 0-30% Ethyl acetate/Petroleum ether gradient @ 80 mL/min) to afford 1-((3R,5R)-3-(2,6-dichloropyridin-4-yl)-5-methylmorpholino)prop-2-en-1-one (440 mg, 1.46 mmol, 77% yield).

To a solution of 1-((3R,5R)-3-(2,6-dichloropyridin-4-yl)-5-methylmorpholino)prop-2-en-1-one (100 mg, 0.33 mmol, 1 equiv) and imidazo[1,2-a]pyridin-7-ylboronic acid pinacol ester (64.84 mg, 0.26 mmol, 0.8 equiv) in 1,4-dioxane (3 mL, 0.09 M) and water (0.60 mL, 0.09 M) was added AcOK (65.17 mg, 0.66 mmol, 2 eq) and Pd(dppf)$Cl_2$ (24.29 mg, 0.033 mmol, 0.1 eq). The mixture was stirred for 12 hours at 80° C. under $N_2$. The reaction mixture was quenched with water (10 mL) and extracted with EtOAc (20 mL×2). The combined organic layer was washed with brine (10 mL), dried over $Na_2SO_4$, filtered, and concentrated. The crude product was purified by Prep-HPLC (column: Waters Xbridge BEH C18 100*25 mm*5 um; liquid phase: [A-10 mM $NH_4HCO_3$ in $H_2O$; B-ACN]B %: 30%-60%, 10 min]) to afford 1-((3R,5R)-3-(2-chloro-6-(imidazo[1,2-a]pyridin-7-yl)pyridin-4-yl)-5-methylmorpholino)prop-2-en-1-one (10 mg, 0.027 mmol, 8% yield) as a yellow solid. LC-MS m/z: 383.0 [M+1].

Stereochemistry: single enantiomer of known absolute configuration.

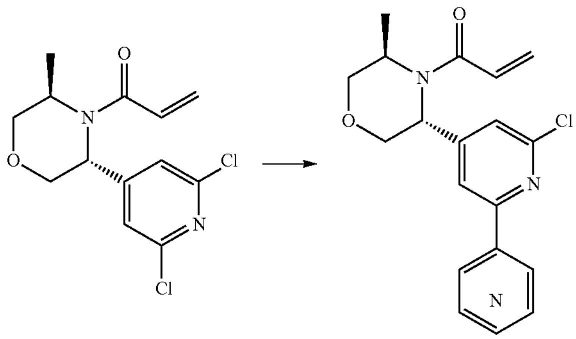

Using the appropriate coupling partner in Procedure I, the title compounds can be obtained.

| Cmp | Name | Coupling Partner Step 9 | LC-MS m/z [M + 1] |
|---|---|---|---|
| 138 | 1-((3R,5R)-3-(2-chloro-6-(imidazo[1,2-a]pyridin-7-yl)pyridin-4-yl)-5-methylmorpholino)prop-2-en-1-one | imidazo[1,2-a]pyridin-7-ylboronic acid pinacol ester | 383.0 |
| 139 | 5-(4-((3R,5R)-4-acryloyl-5-methylmorpholin-3-yl)-6-chloropyridin-2-yl)-2-fluorobenzamide | (3-carbamoyl-4-fluorophenyl)boronic acid | 404.0 |

Example 61. Synthesis of 1-(5-(3-(4-amino-1,3,5-triazin-2-yl)-5-chlorophenyl)-1,4-oxazepan-4-yl)prop-2-en-1-one (Compound 152)

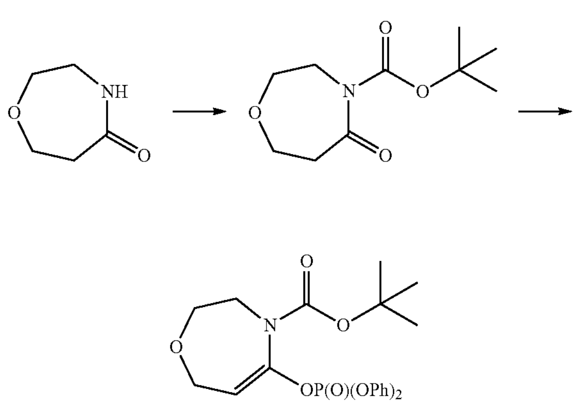

-continued

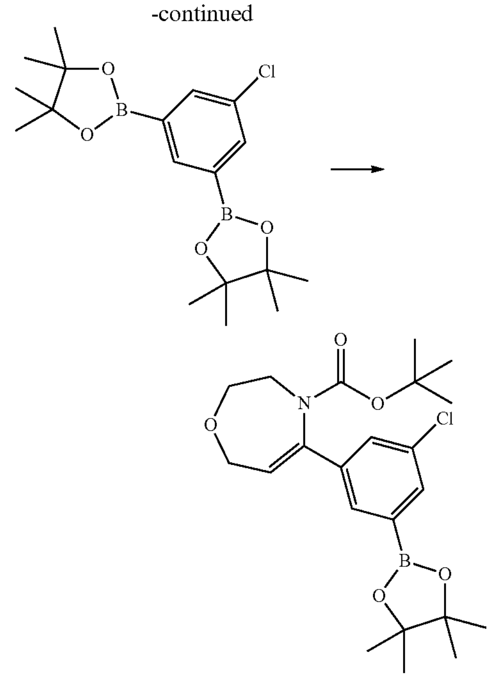

To a solution of 1,4-oxazepan-5-one (3000 mg, 26.05 mmol) and di-tert-butyl dicarbonate (7393.2 mg, 33.87 mmol) in DCM (60 mL, 0.43 M) was added DMAP (3.42 g, 1 eq) and triethylamine (3.94 g, 2 eq) at 0° C. The mixture was stirred at 25° C. for 12 hours. The reaction was diluted with $H_2O$ (150 mL) and extracted with EtOAc (150 mL*3). The combined organic solutions were washed with brine (200 mL), dried over $Na_2SO_4$, filtered, and concentrated in vacuo. The residue was purified by flash silica gel chromatography (ISCO®; 12 g SEPAFLASH® Silica Flash Column, Eluent of 0-30% Ethyl acetate/Petroleum ether gradient @ 80 mL/min) to give tert-butyl 5-oxo-1,4-oxazepane-4-carboxylate (3000 mg, 13.9 mmol 53% yield).

To a solution of tert-butyl 5-oxo-1,4-oxazepane-4-carboxylate (2500 mg, 11.61 mmol) in THF (30 mL, 0.38 M) was added LiHMDS (13.7 mL, 1.1 equiv) dropwise at −30° C. The reaction was stirred at −30° C. for 30 minutes before dropwise addition of diphenyl phosphorochloridate (3432 mg, 12.77 mmol, 1.1 equiv). The reaction was warmed to 25° C. and then stirred for 1 hour under $N_2$. The reaction was poured into water (10 mL) and extracted with ethyl acetate (10 mL×3). The organic layer was washed with brine (10 mL) and concentrated under reduced pressure. The crude product was purified by column chromatography (PE: EA=5:1 to 2:1) to give tert-butyl 5-diphenoxyphosphoryloxy-3,7-dihydro-2H-1,4-oxazepine-4-carboxylate (2100 mg, 4.69 mmol, 40% yield).

2,2'-(5-chloro-1,3-phenylene)bis(4,4,5,5-tetramethyl-1,3,2-dioxaborolane) was obtained from Procedure A.

To a solution of tert-butyl 5-diphenoxyphosphoryloxy-3,7-dihydro-2H-1,4-oxazepine-4-carboxylate (4.3 g, 9.61 mmol) and 2,2'-(5-chloro-1,3-phenylene)bis(4,4,5,5-tetramethyl-1,3,2-dioxaborolane) (4203 mg, 11.53 mmol) in 1,4-dioxane (40 mL, 0.2 M) and water (8 mL, 0.2 M) was added $K_2CO_3$ (3 eq, 3.978 g) and $Pd(dppf)Cl_2$ (0.1 eq, 600 mg) at 25° C. The mixture was stirred at 80° C. for 12 hours under $N_2$. The mixture was diluted with $H_2O$ (50 mL) and extracted with EtOAc (50 mL*3). The combined organic solutions were washed with brine (50 mL), dried over $Na_2SO_4$, filtered, and concentrated in vacuo. The residue was purified by flash silica gel chromatography (ISCO®; 12 g SEPAFLASH® Silica Flash Column, Eluent of 0-30% Ethyl acetate/Petroleum ether gradient @ 80 mL/min) to give tert-butyl 5-(3-chloro-5-(4,4,5,5-tetramethyl-1,3,2-dioxaborolan-2-yl)phenyl)-2,3-dihydro-1,4-oxazepine-4(7H)-carboxylate (1500 mg, 3.44 mmol, 36%).

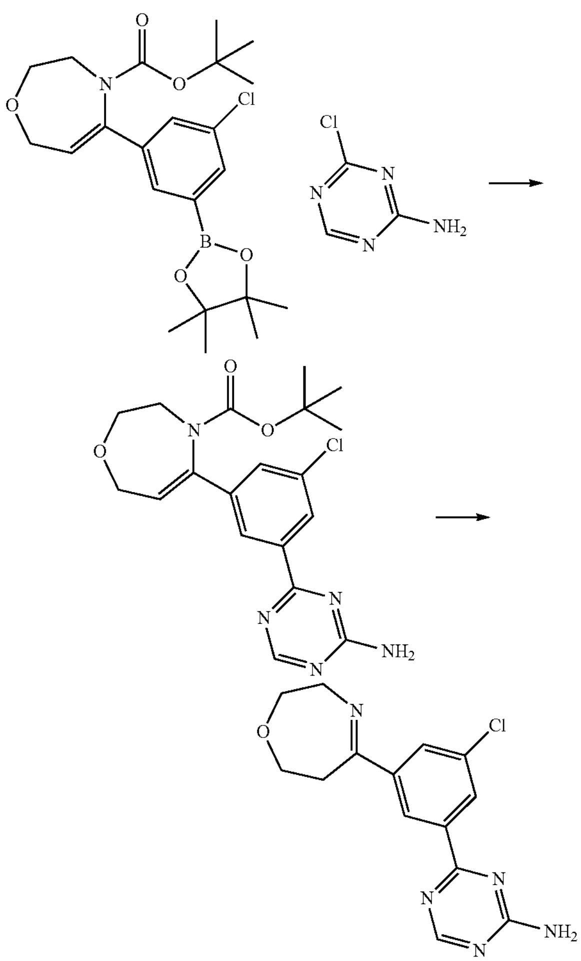

To a solution of tert-butyl 5-(3-chloro-5-(4,4,5,5-tetramethyl-1,3,2-dioxaborolan-2-yl)phenyl)-2,3-dihydro-1,4-oxazepine-4(7H)-carboxylate (200 mg, 0.45 mmol, 1 equiv) and 4-chloro-1,3,5-triazin-2-amine (71 mg, 0.55 mmol, 1.2 equiv) in 1,4-dioxane (2.5 mL, 0.15 M) and water (0.5 mL, 0.15 M) was added $K_2CO_3$ (3 eq, 182 mg) and $Pd(dppf)Cl_2$ (0.1 eq, 32 mg) at 25° C. The mixture was stirred at 80° C. for 12 hours under $N_2$. The mixture was diluted with $H_2O$ (15 mL) and extracted with EtOAc (15 mL*3). The combined extracts were washed with brine (15 mL), dried over $Na_2SO_4$, filtered, and concentrated in vacuo. The crude product was purified by prep-TLC (PE:EtOAc=1:1) to give tert-butyl 5-(3-(4-amino-1,3,5-triazin-2-yl)-5-chlorophenyl)-2,3-dihydro-1,4-oxazepine-4(7H)-carboxylate (50 mg, 0.123 mmol, 27% yield) as a white solid.

A solution of tert-butyl 5-(3-(4-amino-1,3,5-triazin-2-yl)-5-chlorophenyl)-2,3-dihydro-1,4-oxazepine-4(7H)-carboxylate (80 mg, 0.19 mmol, 1 equiv) in 4M HCl in ethyl acetate (10 mL) was stirred at room temperature for 2 hours. The reaction mixture was concentrated under reduced pressure to give 4-(3-chloro-5-(2,3,6,7-tetrahydro-1,4-oxazepin-5-yl)phenyl)-1,3,5-triazin-2-amine (60 mg).

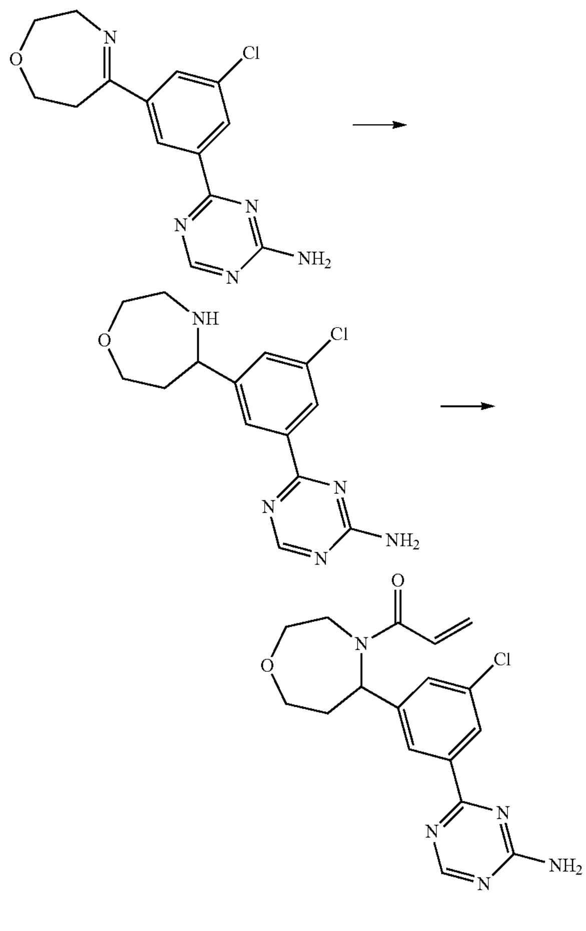

To a solution of 4-(3-chloro-5-(2,3,6,7-tetrahydro-1,4-oxazepin-5-yl)phenyl)-1,3,5-triazin-2-amine (60 mg, 0.19 mmol, 1 equiv) in methanol (1 mL, 0.19 M) was added $NaBH_4$ (24.6 mg, 2 eq, 0.39 mmol) at 0° C. The mixture was stirred at room temperature for 2 hours under $N_2$. The mixture was diluted with $NH_4Cl$ (3 mL) and extracted with EtOAc (5 mL*3). The extract was washed with brine (5 mL), dried over $Na_2SO_4$, filtered, and concentrated in vacuo. The crude product was purified by prep-TLC (DCM: MeOH=10:1) to give 4-(3-chloro-5-(1,4-oxazepan-5-yl)phenyl)-1,3,5-triazin-2-amine (20 mg, 0.065 mmol, 33% yield).

To a solution of 4-(3-chloro-5-(1,4-oxazepan-5-yl)phenyl)-1,3,5-triazin-2-amine (20 mg, 0.065 mmol, 1 equiv) in DCM (1 mL, 0.065 M) and Et3N (0.1 mL) was added acryloyl chloride (5.92 mg, 0.06 mmol, 1 equiv) at 0° C. The mixture was stirred at 25° C. for 2 hours under $N_2$. The mixture was diluted with $H_2O$ (13 mL) and extracted with EtOAc (15 mL*3). The combined organic solution was washed with brine (15 mL), dried over $Na_2SO_4$, filtered, and concentrated in vacuo. The crude product was purified by prep-TLC (EtOAc:PE=1:0) to give 1-(5-(3-(4-amino-1,3,5-triazin-2-yl)-5-chlorophenyl)-1,4-oxazepan-4-yl)prop-2-en-1-one (13 mg, 0.036 mmol, 55% yield) as a white solid. LC-MS m/z: 360.1 [M+1].

Stereochemistry: racemic.

Example 62. Synthesis of 1-(3-(3-(4-amino-1,3,5-triazin-2-yl)-5-chlorophenyl)-1,4-oxazepan-4-yl) prop-2-en-1-one (Compound 162)

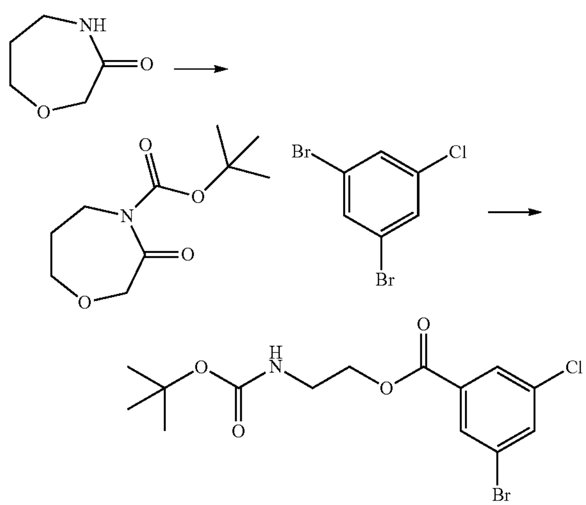

To a solution of 1,4-oxazepan-3-one (9 g, 78.17 mmol, 1 equiv) in DCM (100 mL, 0.78 M) was added di-tert-butyl dicarbonate (22.17 g, 101.62 mmol, 1.3 equiv), DMAP (2.33 g, 0.2 eq), and triethylamine (15.82 g, 156.35 mmol, 2 equiv). The mixture was stirred at 25° C. for 12 hours and then concentrated under reduced pressure. The product was purified by column chromatography (petroleum ether:EtOAc=3:1) to give the product tert-butyl 3-oxo-1,4-oxazepane-4-carboxylate (2500 mg, 11.6 mmol, 15% yield) as a yellow oil.

To a solution of 1,3-dibromo-5-chloro-benzene (1.256 g, 4.64 mmol, 1 equiv) in i-$Pr_2O$ (10 mL) at −78° C. was added n-BuLi (1.86 ml, 1 eq). The mixture was stirred at −78° C. for 1 hour under $N_2$. A solution of tert-butyl 3-oxo-1,4-oxazepane-4-carboxylate (1000 mg, 4.64 mmol, 1 equiv) in i-$Pr_2O$ (10 mL) was added slowly at −78° C. The mixture was stirred at −78° C. for 1 hour. The mixture was diluted with $H_2O$ (50 mL) and extracted with EtOAc (50 mL*3). The extract was washed with brine (50 mL), dried over Na2SO4, and concentrated in vacuo. The crude product was purified by column chromatography (petroleum ether:ethyl acetate=3:1) to give tert-butyl N-[2-[3-(3-bromo-5-chloro-phenyl)-3-oxo-propoxy]ethyl]carbamate (600 mg, 1.48 mmol, 32% yield).

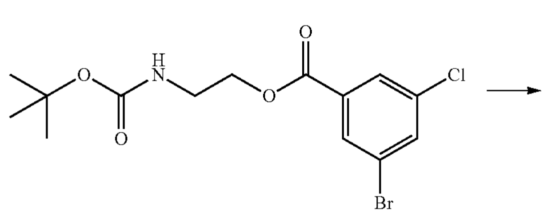

-continued

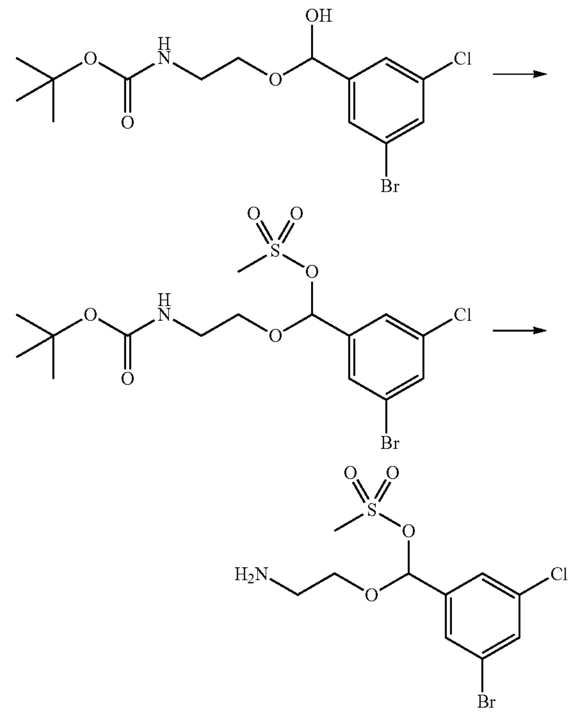

To a solution of tert-butyl N-[2-[3-(3-bromo-5-chloro-phenyl)-3-oxo-propoxy]ethyl]carbamate (600 mg, 1.47 mmol, 1 equiv) in methanol (6 mL, 0.25 M) was added $NaBH_4$ (279 mg, 7.35 mmol, 5 equiv) at 0° C. under $N_2$. The reaction was stirred at room temperature for 1.5 hours. The mixture was diluted with $H_2O$ (15 mL) and extracted with DCM (15 mL*3). The extract was washed with brine (20 mL), dried over $Na_2SO_4$, filtered, and concentrated in vacuo. The residue was purified by flash silica gel chromatography (ISCO®; 12 g SEPAFLASH® Silica Flash Column, Eluent of 0-30% Ethyl acetate/Petroleum ether gradient @ 80 mL/min) to give tert-butyl N-[2-[3-(3-bromo-5-chloro-phenyl)-3-hydroxy-propoxy]ethyl]carbamate (540 mg, 1.32 mmol, 90% yield) as a yellow oil.

To a solution of tert-butyl N-[3-[2-(3-bromo-5-chloro-phenyl)-2-hydroxyethoxy]propyl]carbamate (540 mg, 1.32 mmol) in DCM (6 mL, 0.22 M) was added $Ms_2O$ (343 mg, 1.97 mmol, 1.5 equiv), DMAP (80 mg, 0.5 eq), and triethylamine (399 mg, 3.95 mmol, 3 equiv). The mixture was stirred at 25° C. for 12 hours. The solution was concentrated under reduced pressure. The product was purified by column chromatography (petroleum ether:EtOAc=3:1) to give [1-(3-bromo-5-chloro-phenyl)-2-[3-(tert-butoxycarbonylamino)propoxy]ethyl] methanesulfonate (400 mg, 0.82 mmol, 62% yield).

4M HCl in EtOAc (5 mL) was added to [1-(3-bromo-5-chloro-phenyl)-2-[3-(tert-butoxycarbonylamino)propoxy] ethyl] methanesulfonate (400 mg, 0.82 mmol, 1 equiv) and then stirred at 25° C. for 1 hour. The reaction mixture was poured into water (15 mL) and extracted with DCM (15 mL*3). The combined organic layers were washed with brine (10 mL*2), dried over $Na_2SO_4$, filtered, and concentrated under reduced pressure to afford [2-(3-amino-propoxy)-1-(3-bromo-5-chloro-phenyl)ethyl]methanesulfonate (400 mg) as a yellow solid.

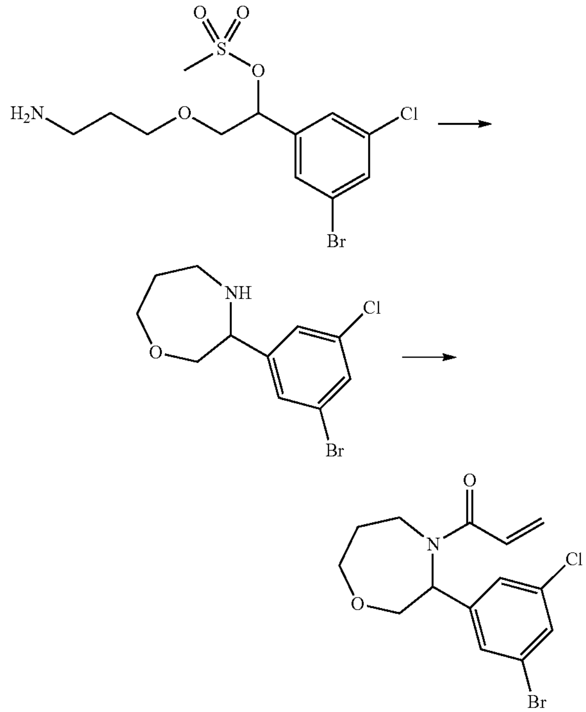

$Cs_2CO_3$ (450 mg, 3 equiv) was added to a solution of [2-(3-aminopropoxy)-1-(3-bromo-5-chloro-phenyl)ethyl] methanesulfonate (400 mg, 1.03 mmol, 1 equiv) in MeCN (5 mL, 0.21 M) at room temperature. The mixture was heated to 80° C. for 16 hours under $N_2$. The reaction mixture was poured into water (15 mL), extracted with DCM (15 mL*3), washed with brine (10 mL*2), dried over $Na_2SO_4$, filtered, and concentrated under reduced pressure. The crude material was purified by prep-TLC (petroleum ether:ethyl acetate) to afford 3-(3-bromo-5-chloro-phenyl)-1,4-oxazepane (40 mg, 0.14 mmol, 13% yield) as a white oil.

To a solution of 3-(3-bromo-5-chloro-phenyl)-1,4-oxazepane (40 mg, 0.14 mmol, 1 equiv) in DCM (3 mL, 0.045 M) was added acryloyl chloride (12 mg, 0.13 mmol, 1 equiv) at 0° C. The mixture was stirred at 25° C. for 2 hours under $N_2$. The mixture was diluted with $H_2O$ (13 mL) and extracted with DCM (15 mL*3). The extract was washed with brine (15 mL), dried over Na2SO4, and concentrated in vacuo. The crude product was purified by prep-TLC (EtOAc:PE=1:5) to give 1-[3-(3-bromo-5-chloro-phenyl)-1,4-oxazepan-4-yl]prop-2-en-1-one (40 mg, 0.12 mmol, 84% yield) as a white solid.

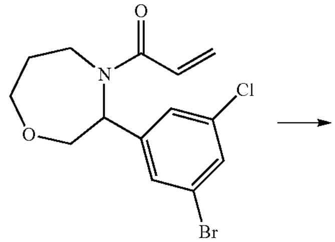

-continued

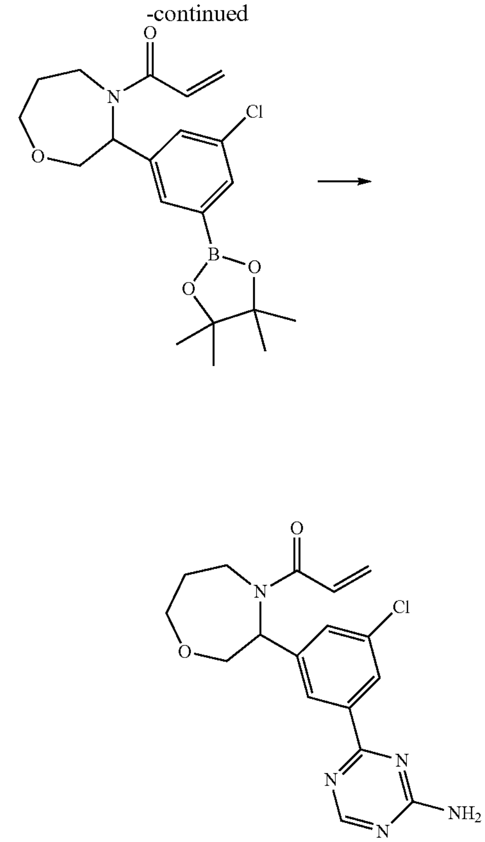

To a solution of 1-[3-(3-bromo-5-chloro-phenyl)-1,4-oxazepan-4-yl]prop-2-en-1-one (40 mg, 0.12 mmol, 1 equiv) and $Pin_2B_2$(44 mg, 2 eq) in 1,4-dioxane (3 mL, 0.04 M) was added KOAc (24.5 mg) and Pd(dppf)$Cl_2$ (10.4 mg, 0.1 eq). The reaction mixture was stirred at 90° C. for 16 h under $N_2$. Water (20 mL) was added to the reaction mixture and then extracted with ethyl acetate (15 mL*3). The combined organic layers were washed with brine (20 mL), dried over $Na_2SO_4$, filtered, and concentrated under reduced pressure to afford crude 1-[3-[3-chloro-5-(4,4,5,5-tetramethyl-1,3,2-dioxaborolan-2-yl)phenyl]-1,4-oxazepan-4-yl]prop-2-en-1-one (45 mg, 0.12 mmol, 99% yield) as a dark oil.

To a solution of 1-[3-[3-chloro-5-(4,4,5,5-tetramethyl-1,3,2-dioxaborolan-2-yl)phenyl]-1,4-oxazepan-4-yl]prop-2-en-1-one (45 mg, 0.11 mmol) and 4-chloro-1,3,5-triazin-2-amine (17 mg, 0.13 mmol, 1.2 equiv) in 1,4-dioxane (3 mL, 0.03 M) and water (0.60 mL, 0.032 M) was added $K_2CO_3$ (47.5 mg, 3 eq) and Pd(dppf)$Cl_2$ (10.4 mg, 0.1 eq). The reaction mixture was stirred at 80° C. for 16 hours under $N_2$. The mixture was diluted with $H_2O$ (15 mL) and extracted with EtOAc (15 mL*3). The extract was washed with brine (20 mL), dried over $Na_2SO_4$, filtered, and concentrated in vacuo. The residue was purified by prep-HPLC to give 1-(3-(3-(4-amino-1,3,5-triazin-2-yl)-5-chlorophenyl)-1,4-oxazepan-4-yl)prop-2-en-1-one (19 mg, 0.051 mmol, 44% yield) as a pale yellow solid. LC-MS m/z: 360.0 [M+1].

Stereochemistry: racemic.

Example 63. Procedure J and Synthesis of 1-((3R, 5R)-3-(2-chloro-6-(imidazo[1,2-a]pyridin-7-yl)pyridin-4-yl)-5-(hydroxymethyl)morpholino)prop-2-en-1-one (Compound 157)

Procedure J

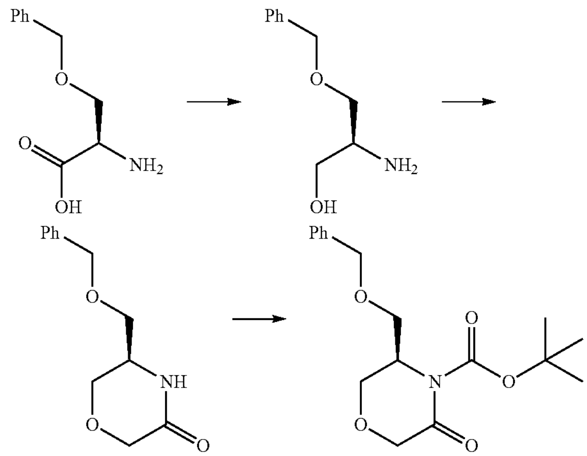

LiAlH$_4$ (17.11 g, 1.5 eq) was added to a solution of O-benzyl-D-serine (60 g, 307.35 mmol, 1 equiv) in THF (1 L, 0.3 M) under N2. The mixture was stirred 70° C. for 16 hours. The reaction mixture was diluted carefully water (18 mL), 15% aq. NaOH 15 (18 mL), and then water (36 mL). The mixture was stirred for 3 hours and then extracted with EtOAc (200 mL*3). The combined organic layers were washed with brine (300 mL), dried over $Na_2SO_4$, filtered, and concentrated under reduced pressure. The residue was purified by column chromatography ($SiO_2$, DCM: MeOH=100/1 to 5/1) to afford (S)-2-amino-3-(benzyloxy)propan-1-ol (20.0 g, 110 mmol, 36% yield) as a yellow oil.

NaH (60 wt %) (8.828 g, 2 eq) was added to a solution of (S)-2-amino-3-(benzyloxy)propan-1-ol (20 g, 110.36 mmol) in toluene (300 mL, 0.37 M) at 0° C. under $N_2$ and stirred for 30 minutes. Ethyl chloroacetate (20.286 g, 165.54 mmol, 1.5 equiv) was added dropwise and stirred at 0° C. for 30 minutes. The mixture was heated to 130° C. for 16 hours. The reaction mixture was poured into water (80 mL) and extracted with EtOAc (40 mL*3). The combined organic layers were washed with brine (80 mL), dried over $Na_2SO_4$, filtered, and concentrated under reduced pressure to afford crude (R)-5-((benzyloxy)methyl)morpholin-3-one (23.00 g, 104 mmol, 94% yield) as a brown oil.

To a solution of (R)-5-((benzyloxy)methyl)morpholin-3-one (23 g, 103.95 mmol, 1 equiv) in DCM (250 mL, 0.42 M) was added di-tert-butyl dicarbonate (27.226 g, 124.75 mmol, 1.2 equiv), triethylamine (28.89 mL, 2 eq) and DMAP (2.54 g, 0.2 eq). The mixture was stirred 25° C. for 16 hours. The reaction mixture was poured into water (100 mL) and extracted with DCM (40 mL*3). The combined organic layers were washed with brine (50 mL), dried over $Na_2SO_4$, filtered, and concentrated under reduced pressure. The residue was purified by column chromatography ($SiO_2$, Petroleum ether/Ethyl acetate=1/0 to 0/1) to afford tert-butyl (R)-3-((benzyloxy)methyl)-5-oxomorpholine-4-carboxylate (8.10 g, 25.2 mmol, 24% yield) as a yellow oil.

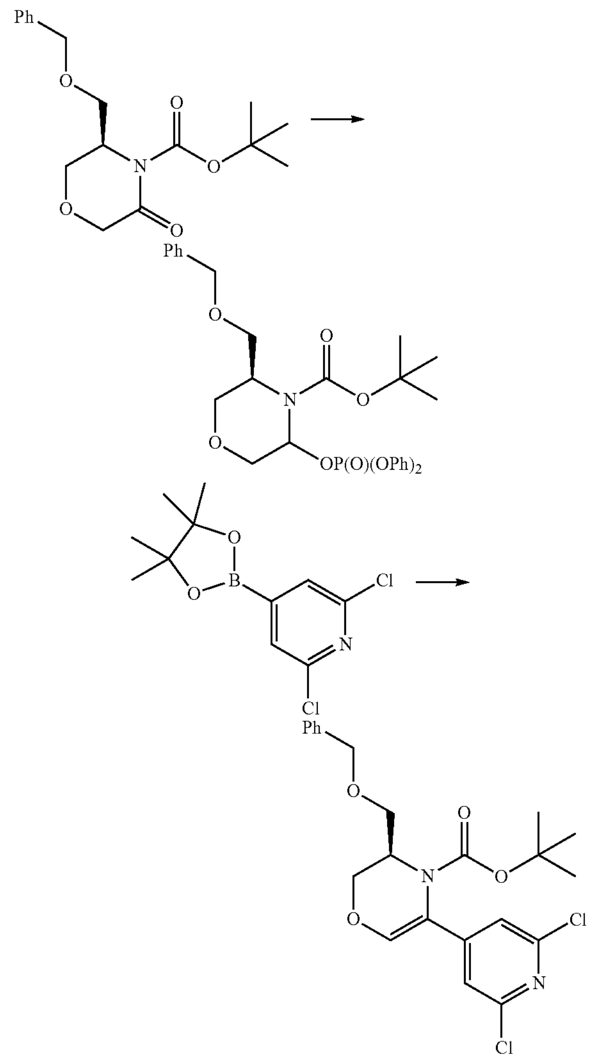

To a solution of tert-butyl (R)-3-((benzyloxy)methyl)-5-oxomorpholine-4-carboxylate (8.1 g, 25.20 mmol, 1 equiv) in THF (100 mL, 0.2520 M) was added lithium bis(trimethylsilyl)amide (4.639 g, 27.72 mL, 1 M, 1.1 eq) dropwise at −30° C. under $N_2$. The reaction was stirred at −30° C. for 1 hour. Diphenyl phosphorochloridate (7.447 g, 27.75 mmol, 1.1 equiv) in THF (50 mL) was added dropwise at −30° C. and then stirred at 25° C. for 1 hour. The reaction was poured into water (80 mL) and extracted with ethyl acetate (30 mL×3). The organic layer was washed with brine (100 mL) and concentrated. The crude product was purified by column chromatography (PE:EA=5:1 to 2:1) to give tert-butyl (R)-3-((benzyloxy)methyl)-5-((diphenoxyphosphoryl)oxy)-2,3-dihydro-4H-1,4-oxazine-4-carboxylate (13.00 g, 23.5 mmol, 93% yield) as a yellow oil.

A solution of tert-butyl (R)-3-((benzyloxy)methyl)-5-((diphenoxyphosphoryl)oxy)-2,3-dihydro-4H-1,4-oxazine-4-carboxylate (13 g, 23.48 mmol), 2,6-dichloro-4-(4,4,5,5-tetramethyl-1,3,2-dioxaborolan-2-yl)pyridine (7.077 g, 25.83 mmol, 1.1 equiv), potassium carbonate (6491 mg, 46.97 mmol), and Pd(dppf)$Cl_2$ (852.11 mg, 1.17 mmol, 0.05 equiv) in MeCN (50 mL, 0.18 M), 1,4-dioxane (50 mL, 0.18 M) and water (25 mL, 0.18 M) was stirred at 80° C. for 16 hours under $N_2$. The reaction was diluted with $H_2O$ (40 ml)

and extracted with EtOAc (20 ml×3). The organic layer was concentrated and purified by column chromatography (PE/EA=10/1 to PE/EA=1/1) to give tert-butyl (R)-3-((benzyloxy)methyl)-5-(2,6-dichloropyridin-4-yl)-2,3-dihydro-4H-1,4-oxazine-4-carboxylate (7.5 g, 16.6 mmol 71% yield).

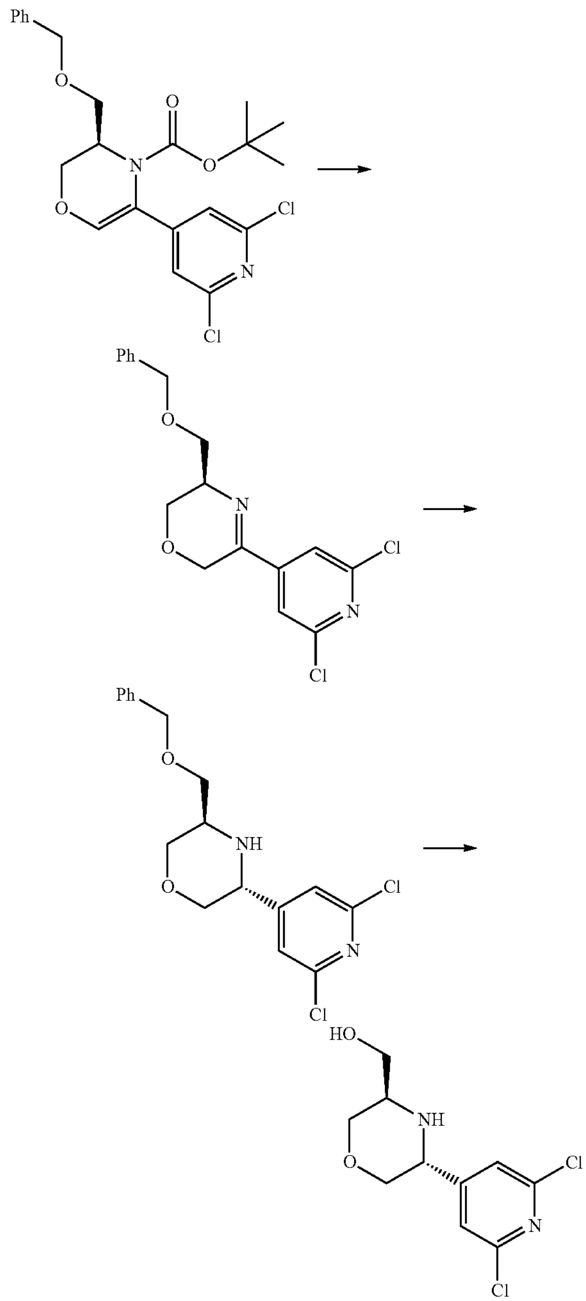

To a solution of tert-butyl (R)-3-((benzyloxy)methyl)-5-(2,6-dichloropyridin-4-yl)-2,3-dihydro-4H-1,4-oxazine-4-carboxylate (7.5 g, 16.62 mmol, 1 equiv) in ethyl acetate (30 mL, 0.55 M) was added HCl in EtOAc (40 mL). The mixture was stirred 25° C. for 1 hour. The reaction mixture was concentrated under reduced pressure to afford (R)-3-((benzyloxy)methyl)-5-(2,6-dichloropyridin-4-yl)-3,6-dihydro-2H-1,4-oxazine (6.00 g) as a yellow oil.

To a solution of (R)-3-((benzyloxy)methyl)-5-(2,6-dichloropyridin-4-yl)-3,6-dihydro-2H-1,4-oxazine (6 g, 17.08 mmol, 1 equiv) in acetic acid (30 mL) was added Zn (2.23 g, 2 eq, 34.16 mmol). The mixture was stirred at 25° C. for 30 minutes. The reaction was quenched with 1N HCl (25 mL) and then adjusted with saturated aqueous $NaHCO_3$ until pH=8-9. The resulting solution was extracted with DCM (40 mL*3), washed with brine (45 mL), dried over $Na_2SO_4$, filtered, and concentrated in vacuo. The residue was purified by prep-TLC ($SiO_2$, PE:EtOAc=3:1) to afford (3R,5R)-3-((benzyloxy)methyl)-5-(2,6-dichloropyridin-4-yl)morpholine (1700 mg, 4.81 mmol, 28% yield) as a yellow oil, and 2.2 of the cis diastereomer.

To a solution of (3R,5R)-3-((benzyloxy)methyl)-5-(2,6-dichloropyridin-4-yl)morpholine (1700 mg, 4.81 mmol, 1 equiv) in DCM (25 mL, 0.19 M) was added $BCl_3$ (1 M, 9.624 mL, 2 eq) at 0° C. The mixture was stirred 25° C. for 30 minutes. The reaction mixture was poured into MeOH (20 mL), stirred for 30 minutes, and then concentrated. The resulting mixture was taken up into DCM (20 mL) and triethylamine (5 mL) was added dropwise until pH=8-9. The solution was diluted with water (20 mL) and then extracted with DCM (20 mL×3). The combined organic layers were washed with brine (20 mL×2), dried over $Na_2SO_4$, filtered, and concentrated under reduced pressure. The residue was purified by column chromatography ($SiO_2$, Petroleum ether/Ethyl acetate=1/0 to 0/1) to afford ((3R,5R)-5-(2,6-dichloropyridin-4-yl)morpholin-3-yl)methanol (1000 mg, 3.80 mmol, 79% yield) as a yellow oil.

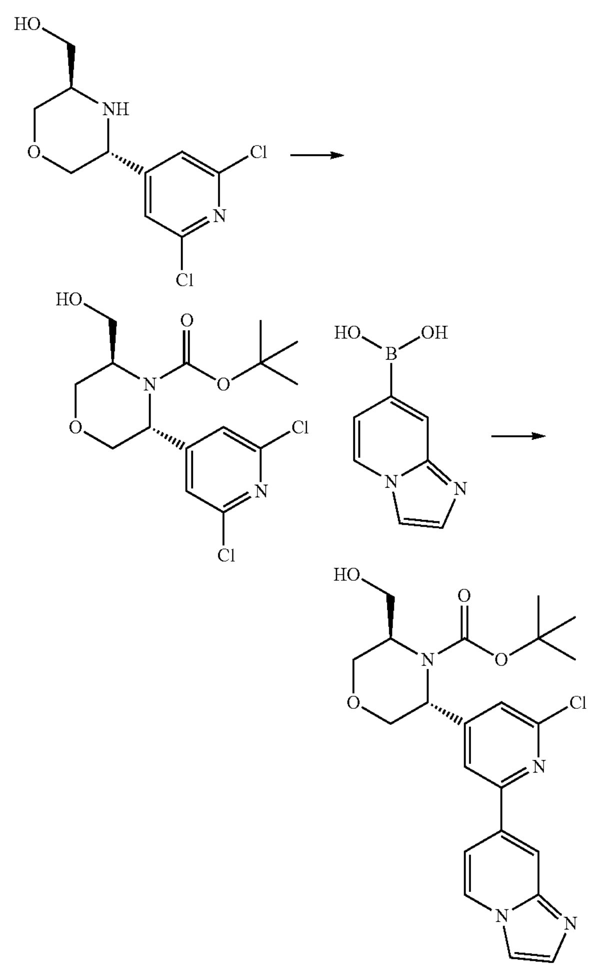

To a solution of ((3R,5R)-5-(2,6-dichloropyridin-4-yl)morpholin-3-yl)methanol (0.8 g, 3.04 mmol, 1 equiv) in DCM (10 mL, 0.30 M) was added di-tert-butyl dicarbonate (0.663 g, 3.04 mmol, 1 equiv), triethylamine (0.847 mL, 6.08 mmol, 2 equiv), and 4-(dimethylamino)pyridine (74.29 mg, 0.60 mmol, 0.2 equiv). The mixture was stirred 25° C. for 5 hours. The reaction mixture was quenched by H2O (20 mL) and extracted with DCM (20 mL×3). The organic phases were dried over $Na_2SO_4$, filtered, and concentrated. The residue was purified by column chromatography (PE/EA=0/1 to 1/1) to give tert-butyl (3R,5R)-3-(2,6-dichloropyridin-4-yl)-5-(hydroxymethyl)morpholine-4-carboxylate (800 mg, 2.20 mmol, 72% yield).

A solution of tert-butyl (3R,5R)-3-(2,6-dichloropyridin-4-yl)-5-(hydroxymethyl)morpholine-4-carboxylate (200 mg, 0.55 mmol), imidazo[1,2-a]pyridin-7-ylboronic acid (80 mg, 0.49 mmol, 0.9 equiv), KOAc (107 mg, 2.0 eq), and Pd(dppf)$Cl_2$ (39 mg, 0.055 mmol, 0.1 equiv) in 1,4-dioxane (5 mL, 0.09 M) and water (1 mL, 0.09 M) was stirred at 90° C. for 12 hours under N2. The reaction mixture was poured into water (15 mL) and extracted with EtOAc (15 mL×3). The combined organic layers were washed with brine (10 mL×2), dried over $Na_2SO_4$, filtered, and concentrated under reduced pressure. The residue was purified by prep-TLC ($SiO_2$, DCM:MeOH=10:1) to afford tert-butyl (3R,5R)-3-(2-chloro-6-(imidazo[1,2-a]pyridin-7-yl)pyridin-4-yl)-5-(hydroxymethyl)morpholine-4-carboxylate (80 mg, 0.180 mmol, 33% yield).

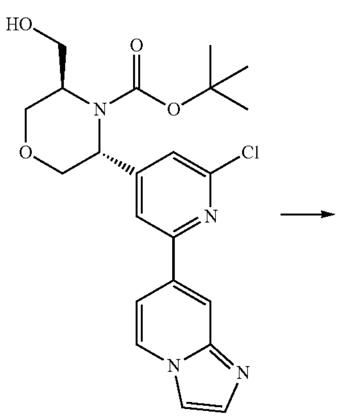

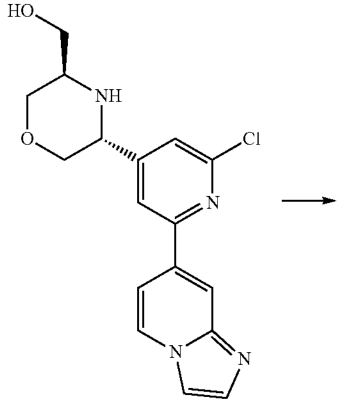

-continued

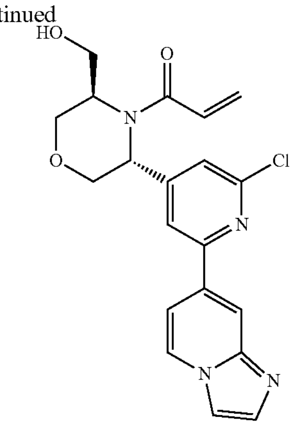

To a solution of tert-butyl (3R,5R)-3-(2-chloro-6-(imidazo[1,2-a]pyridin-7-yl)pyridin-4-yl)-5-(hydroxymethyl)morpholine-4-carboxylate (60 mg, 0.13 mmol) in dioxane (2 mL) at 0° C. was added HCl in dioxane (2 mL, 4M) under $N_2$. The mixture was stirred at room temperature for 30 minutes. The reaction mixture was concentrated under reduced pressure to afford ((3R,5R)-5-(2-chloro-6-(imidazo[1,2-a]pyridin-7-yl)pyridin-4-yl)morpholin-3-yl)methanol HCl (50 mg, 0.131 mmol, 97% yield).

To a solution of ((3R,5R)-5-(2-chloro-6-(imidazo[1,2-a]pyridin-7-yl)pyridin-4-yl)morpholin-3-yl)methanol HCl (110 mg, 0.28 mmol) in THF (2 mL, 0.14 M) was added acrylic acid (20 mg, 0.28 mmol, 1 equiv), triethylamine (0.12 mL, 0.86 mmol, 3 equiv), and bis(2-oxo-3-oxazolidinyl)phosphinic chloride (95 mg, 0.37 mmol, 1.3 equiv) at 0° C. The mixture was stirred at room temperature for 2 hours. The reaction was diluted with $H_2O$ (5 mL) and extracted with DCM (5 mL×3). The organic layer was concentrated and purified by prep TLC (DCM/MeOH=10/1) to give 1-((3R,5R)-3-(2-chloro-6-(imidazo[1,2-a]pyridin-7-yl)pyridin-4-yl)-5-(hydroxymethyl)morpholino)prop-2-en-1-one (9.9 mg, 0.025 mmol, 9% yield). LC-MS m/z: 399.1 [M+1].

Stereochemistry: Single enantiomer of known absolute configuration.

Example 64. Procedure K and Synthesis of 1-(6-(3-(4-amino-1,3,5-triazin-2-yl)-5-chlorophenyl)-6-methyl-4-oxa-7-azaspiro[2.5]octan-7-yl)prop-2-en-1-one (Compound 160)

Procedure K

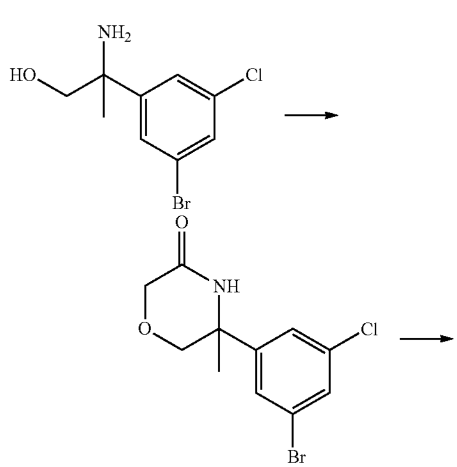

-continued

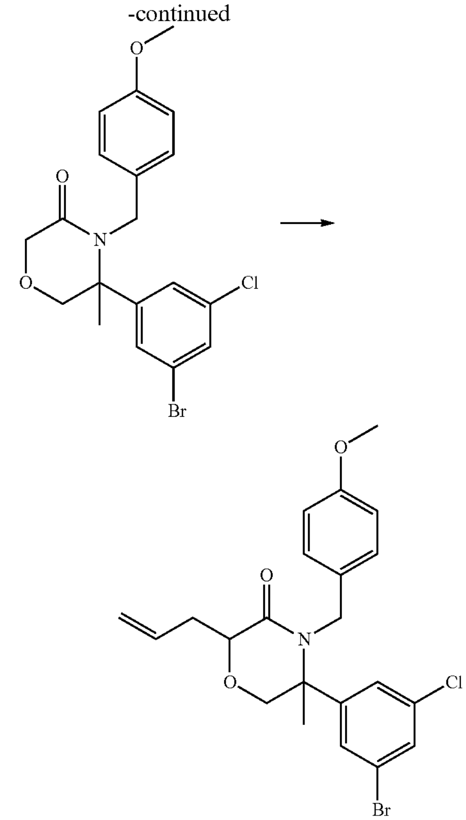

2-amino-2-(3-bromo-5-chlorophenyl)propan-1-ol was obtained from Procedure G.

To a solution of 2-amino-2-(3-bromo-5-chlorophenyl) propan-1-ol (6 g, 22.68 mmol, 1 equiv) in toluene (50 mL, 0.45 M) was added NaH (1.814 g, 60 wt %, 2 eq) at 0° C. and stirred for 30 minutes. Ethyl chloroacetate (3.335 g, 27.21 mmol, 1.2 equiv) was added dropwise and stirred at 25° C. for 30 minutes, and then heated to 130° C. for 16 hours. The reaction mixture was quenched with saturated aqueous $NH_4Cl$ (100 mL) and extracted with EtOAc (50 mL*3). The organic layers were washed 30 mL saturated brine solution. The organic solution was then separated, dried over $Na_2SO_4$, filtered, and concentrated under reduced pressure. The crude material was purified by flash column chromatography (PE:EA=5:1-0:1) to give 5-(3-bromo-5-chlorophenyl)-5-methylmorpholin-3-one (3 g, 9.85 mmol, 43% yield) as a white solid.

To a solution of 5-(3-bromo-5-chloro-phenyl)-5-methyl-morpholin-3-one (3000 mg, 9.85 mmol, 1 equiv) in DMF (30 mL, 0.32 M) was added sodium hydride (472.8 mg, 11.82 mmol, 1.2 equiv) at 0° C. The reaction was stirred for 20 minutes at 0° C. under $N_2$ before dropwise addition of 4-chloroanisole (1685 mg, 11.82 mmol, 1.2 equiv). The reaction was stirred for 3 hours at 25° C. The reaction mixture was poured into saturated aqueous $NH_4Cl$ (150 mL) and extracted with EtOAc (40 mL*3). The combined organic layers were washed with brine (20 mL*3), water (10 mL*3), dried over $Na_2SO_4$, filtered, and concentrated under reduced pressure. The residue was purified by column chromatography ($SiO_2$, Petroleum ether/Ethyl acetate=10/1 to 3/1) to give 5-(3-bromo-5-chloro-phenyl)-4-(4-methoxy-phenyl)-5-methyl-morpholin-3-one (4000 mg, 9.42 mmol, 96% yield) as a white solid.

To a solution of 5-(3-bromo-5-chloro-phenyl)-4-[(4-methoxyphenyl)methyl]-5-methyl-morpholin-3-one (4 g, 9.41 mmol, 1 equiv) in THF (40 mL, 0.23 M) was added LDA (1.5 eq, 7 mL, 2 M) at −78° C. under $N_2$ and stirred for 30 minutes. 3-Bromoprop-1-ene (1253.3 mg, 10.36 mmol) was added and the mixture was stirred for 1 hour at −78° C. The reaction mixture was poured into saturated aqueous $NH_4Cl$ (50 mL) and extracted with EtOAc (50 mL*3). The combined organic layers were washed with brine (30 mL), dried over $Na_2SO_4$, filtered, and concentrated under reduced pressure. The residue was purified by column chromatography ($SiO_2$, Petroleum ether/Ethyl acetate=10/1 to 3/1) to give 2-allyl-5-(3-bromo-5-chloro-phenyl)-4-[(4-methoxyphenyl)methyl]-5-methyl-morpholin-3-one (2.50 g, 5.38 mmol, 57% yield) and 2,2-diallyl-5-(3-bromo-5-chloro-phenyl)-4-[(4-methoxyphenyl)methyl]-5-methyl-morpholin-3-one (0.60 g, 1.19 mmol, 13% yield).

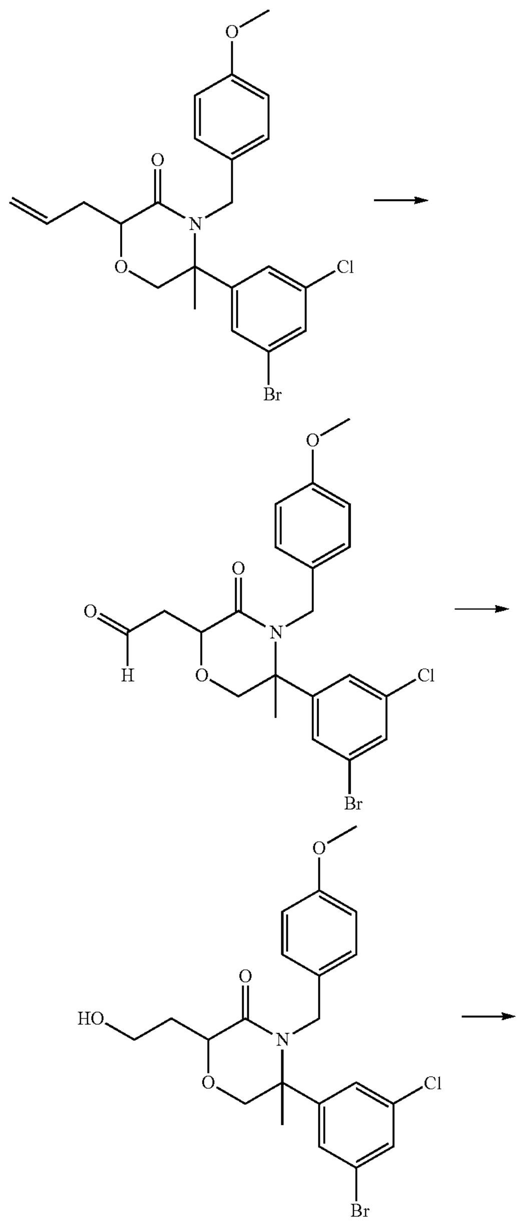

-continued

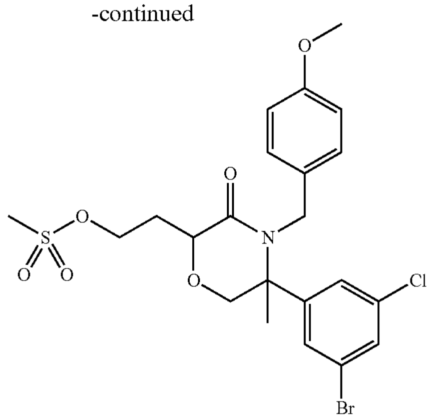

A stream of ozone was bubbled through a solution of 2-allyl-5-(3-bromo-5-chloro-phenyl)-4-[(4-methoxyphenyl)methyl]-5-methyl-morpholin-3-one (2.15 g, 4.6258 mmol, 1 equiv) in $CH_2Cl_2$ (22 mL) at −78° C. for 15 minutes until the distinctive blue color of ozone was clearly observed. The reaction mixture was purged with $O_2$ for 30 minutes and then quenched with triethylamine (2 mL). The resulting mixture was used directly in the next step.

To a solution of 2-[5-(3-bromo-5-chloro-phenyl)-4-[(4-methoxyphenyl)methyl]-5-methyl-3-oxo-morpholin-2-yl]acetaldehyde (2.15 g, 4.60 mmol, 1 equiv) in MeOH (10 mL) was added $NaBH_4$ (5 eq, 874 mg) at 0° C. under $N_2$ and then stirred for 1 hour. The reaction mixture was poured into saturated aqueous $NH_4Cl$ (50 mL) and extracted with DCM (20 mL*3). The combined organic layers were washed with brine (10 mL), dried over $Na_2SO_4$, filtered, and concentrated under reduced pressure. The residue was purified by column chromatography ($SiO_2$, Petroleum ether/Ethyl acetate=10/1 to 1/1) to give 5-(3-bromo-5-chloro-phenyl)-2-(2-hydroxyethyl)-4-[(4-methoxyphenyl)methyl]-5-methyl-morpholin-3-one (1000 mg, 2.13 mmol, 46% yield) as a yellow oil.

To a solution of 5-(3-bromo-5-chloro-phenyl)-2-(2-hydroxyethyl)-4-[(4-methoxyphenyl)methyl]-5-methyl-morpholin-3-one (1 g, 2.13 mmol) and triethylamine (647 mg, 6.39 mmol) in DCM (10 mL, 0.21 M) was added methanesulfonyl chloride (450 mg, 3.92 mmol) at 0° C. under $N_2$. The mixture was stirred for 15 minutes at 0° C. The reaction mixture was poured into saturated aqueous $NH_4Cl$ (10 mL) and extracted with DCM (10 mL*3). The combined organic layers were washed with brine (5 mL), dried over $Na_2SO_4$, filtered, and concentrated under reduced pressure to give 2-[5-(3-bromo-5-chloro-phenyl)-4-[(4-methoxyphenyl)methyl]-5-methyl-3-oxo-morpholin-2-yl]ethyl methanesulfonate (950 mg, 1.74 mmol, 81% yield) as a yellow oil.

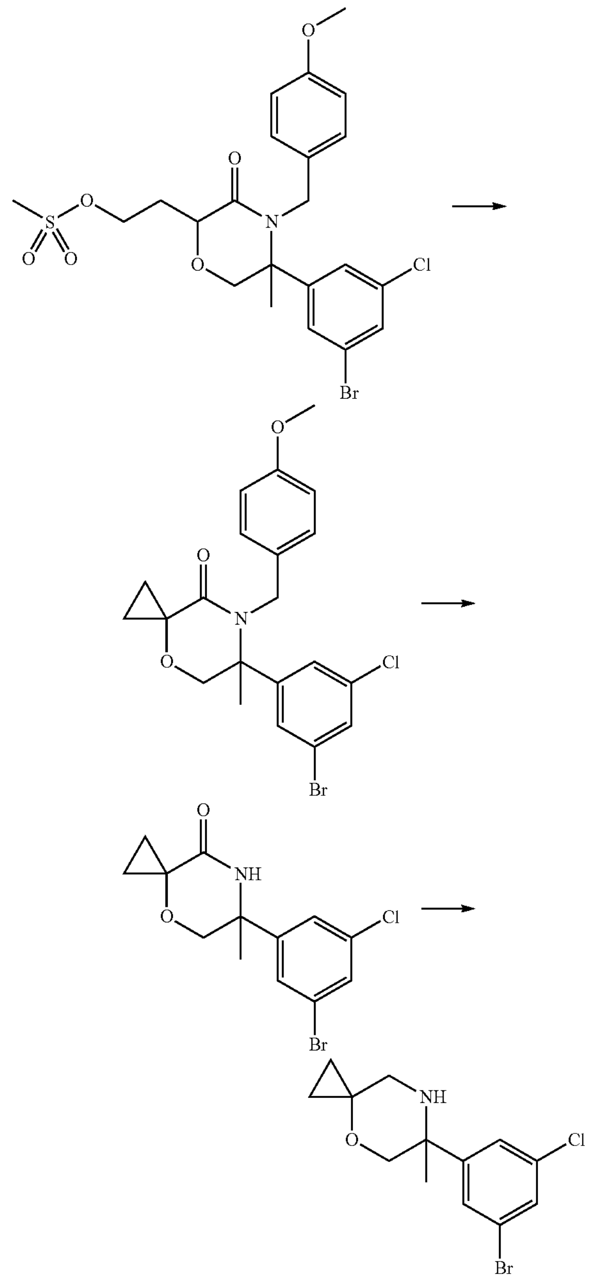

To a solution of 2-[5-(3-bromo-5-chloro-phenyl)-4-[(4-methoxyphenyl)methyl]-5-methyl-3-oxo-morpholin-2-yl]ethyl methanesulfonate (950 mg, 1.73 mmol) in THF (10 mL, 0.17 M) was added LDA (3 eq, 2.6 mL, 2M) at 0° C. under $N_2$ and then stirred for 1 hour. The reaction mixture was poured into saturated aqueous $NH_4Cl$ (15 mL) and extracted with EtOAc (15 mL*3). The combined organic layers were washed with brine (10 mL*2), dried over $Na_2SO_4$, filtered, and concentrated under reduced pressure. The residue was purified by column chromatography ($SiO_2$, PE:EtOAc=3:1; Petroleum ether/Ethyl acetate=10/1 to 3/1) to give 6-(3-bromo-5-chloro-phenyl)-7-[(4-methoxyphenyl)methyl]-6-methyl-4-oxa-7-azaspiro[2.5]octan-8-one (277 mg, 0.61 mmol, 35% yield) as a yellow oil.

To a solution of 6-(3-bromo-5-chloro-phenyl)-7-[(4-methoxyphenyl)methyl]-6-methyl-4-oxa-7-azaspiro[2.5]octan-8-one (277 mg, 0.61 mmol, 1 equiv) in MeCN (3 mL) and water (3 mL) was added CAN (3 eq, 1 g). The resulting mixture was stirred for 2 hours at 50° C. The reaction was treated with saturated aqueous $Na_2CO_3$ and extracted with DCM (5 mL*3). The combined organic layers were washed with brine (3 mL), dried over $Na_2SO_4$, filtered, and concentrated under reduced pressure. The residue was purified by column chromatography ($SiO_2$, Petroleum ether/Ethyl acetate=10/1 to 1/1) to give 6-(3-bromo-5-chloro-phenyl)-6-methyl-4-oxa-7-azaspiro[2.5]octan-8-one (138 mg, 0.41 mmol, 68% yield) as a yellow oil.

To a solution of 6-(3-bromo-5-chloro-phenyl)-6-methyl-4-oxa-7-azaspiro[2.5]octan-8-one (138 mg, 0.41 mmol) in THF (3 mL) was added BH3-$Me_2S$ (5 equiv) dropwise under N2 at 0° C. The mixture was stirred for 2 hours at 40° C. MeOH (2 mL) was added dropwise at 0° C. and then stirred for 30 minutes at 60° C. The mixture was concentrated under reduced pressure to give the crude 6-(3-bromo-5-chlorophenyl)-6-methyl-4-oxa-7-azaspiro[2.5]octane (150 mg) as a yellow solid.

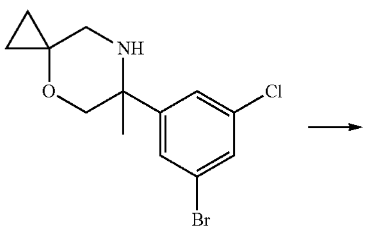

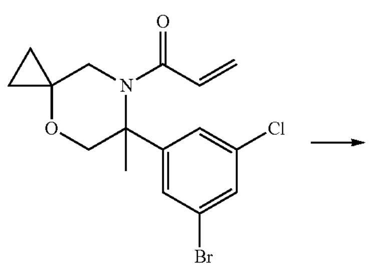

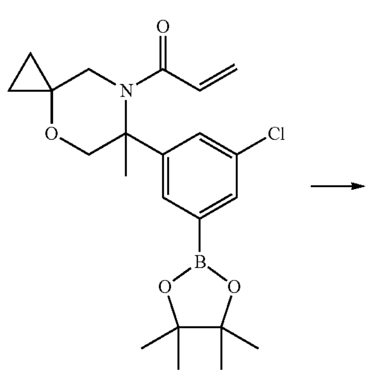

-continued

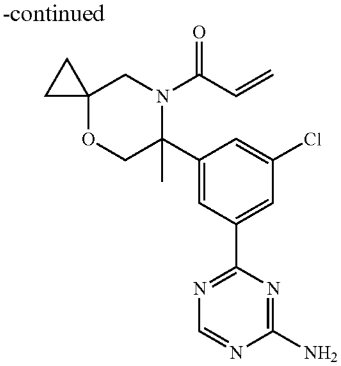

To a solution of 6-(3-bromo-5-chlorophenyl)-6-methyl-4-oxa-7-azaspiro[2.5]octane (150 mg, 0.47 mmol) and triethylamine (95 mg, 0.94 mmol) in DCM (2 mL, 0.23 M) was added acryloyl chloride (42.87 mg, 0.47 mmol) dropwise at 0° C. under N2. The reaction mixture was poured into saturated aqueous $NH_4Cl$ (5 mL) and extracted with EtOAc (5 mL*3). The combined organic layers were washed with brine (3 mL), dried over $Na_2SO_4$, filtered, and concentrated under reduced pressure. The residue was purified by column chromatography ($SiO_2$, Petroleum ether/Ethyl acetate=10/1 to 3/1) to give 1-(6-(3-bromo-5-chlorophenyl)-6-methyl-4-oxa-7-azaspiro[2.5]octan-7-yl)prop-2-en-1-one (100 mg, 0.270 mmol, 57% yield) as a yellow oil.

To a mixture of 1-(6-(3-bromo-5-chlorophenyl)-6-methyl-4-oxa-7-azaspiro[2.5]octan-7-yl)prop-2-en-1-one (100 mg, 0.27 mmol), potassium acetate (52 mg, 0.54 mmol), and bis(pinacolato)diboron (82 mg, 0.32 mmol) in 1,4-dioxane (2 mL, 0.13 M) was added Pd(dppf)$Cl_2$ (20 mg). The reaction was stirred for 16 hours at 90° C. under $N_2$. The reaction mixture was filtered, and the filtrate was poured into water (5 mL) and extracted with EtOAc (5 mL*3). The combined organic layers were washed with brine (3 mL*2), dried over $Na_2SO_4$, filtered, and concentrated under reduced pressure to give a crude 1-(6-(3-chloro-5-(4,4,5,5-tetramethyl-1,3,2-dioxaborolan-2-yl)phenyl)-6-methyl-4-oxa-7-azaspiro[2.5]octan-7-yl)prop-2-en-1-one (90 mg, 0.22 mmol, 80% yield) as a yellow oil.

To a mixture of 1-(6-(3-chloro-5-(4,4,5,5-tetramethyl-1,3,2-dioxaborolan-2-yl)phenyl)-6-methyl-4-oxa-7-azaspiro[2.5]octan-7-yl)prop-2-en-1-one (110 mg, 0.26 mmol), 4-chloro-1,3,5-triazin-2-amine (34 mg, 0.26 mmol), and potassium carbonate (36 mg, 0.26 mmol) in 1,4-dioxane (2 mL, 0.11 M) and water (0.40 mL, 0.11 M) was added Pd(dppf)$Cl_2$ (22 mg) at 25° C. under $N_2$. The mixture was stirred at 85° C. for 4 hours under $N_2$. The reaction mixture was poured into water (5 mL) and extracted with EtOAc (5 mL*3). The combined organic layers were washed with brine (3 mL*2), dried over $Na_2SO_4$, filtered, and concentrated under reduced pressure. The residue was purified by prep-TLC ($SiO_2$, EtOAc) to give 1-(6-(3-(4-amino-1,3,5-triazin-2-yl)-5-chlorophenyl)-6-methyl-4-oxa-7-azaspiro[2.5]octan-7-yl)prop-2-en-1-one (30 mg, 0.078 mmol, 30% yield) as a yellow oil.

Enantiomers of were separated by SFC. Absolute stereochemistry was not assigned. LC-MS m/z: 386.1 [M+1]. Stereochemistry: Single enantiomer of unknown absolute configuration.

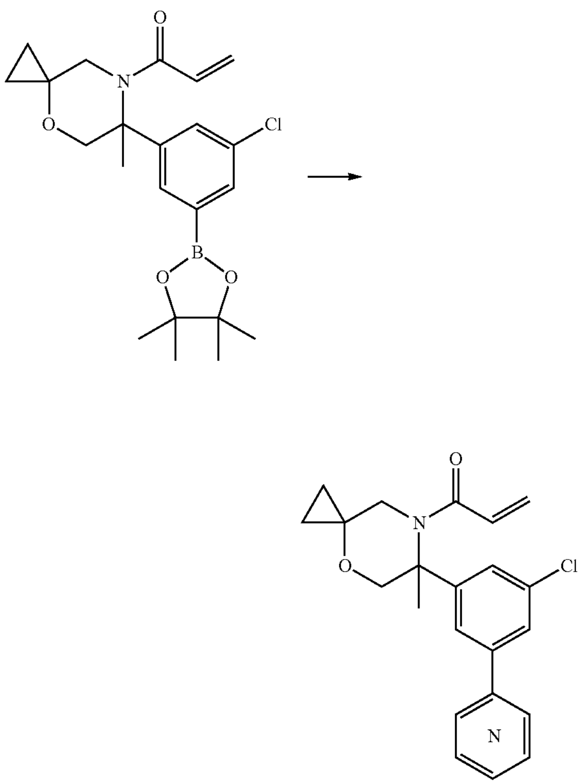

Using the appropriate coupling partner in Procedure K, the title compounds can be obtained.

| Cmp | Name | Coupling Partner Step 12 | LC-MS m/z [M + 1] |
|---|---|---|---|
| 160 | 1-(6-(3-(4-amino-1,3,5-triazin-2-yl)-5-chlorophenyl)-6-methyl-4-oxa-7-azaspiro[2.5]octan-7-yl)prop-2-en-1-one | 4-chloro-1,3,5-triazin-2-amine | 386.1 |
| 161 | 1-(6-(3-(2-aminopyrimidin-4-yl)-5-chlorophenyl)-6-methyl-4-oxa-7-azaspiro[2.5]octan-7-yl)prop-2-en-1-one | 4-bromopyrimidin-2-amine | 385.1 |
| 165 | 1-(6-(3-chloro-5-(5-fluoropyrimidin-2-yl)phenyl)-6-methyl-4-oxa-7-azaspiro[2.5]octan-7-yl)prop-2-en-1-one | 2-bromo-5-fluoropyrimidine | 388.1 |
| 167 | 1-(6-(3-(6-aminopyrimidin-4-yl)-5-chlorophenyl)-6-methyl-4-oxa-7-azaspiro[2.5]octan-7-yl)prop-2-en-1-one | 4-chloropyrimidin-2-amine | 385.2 |

Example 65. Procedure L and Synthesis of 1-(8-(3-(2-aminopyrimidin-4-yl)-5-chlorophenyl)-8-methyl-6-oxa-9-azaspiro[4.5]decan-9-yl)prop-2-en-1-one (Compound 163)

Procedure L

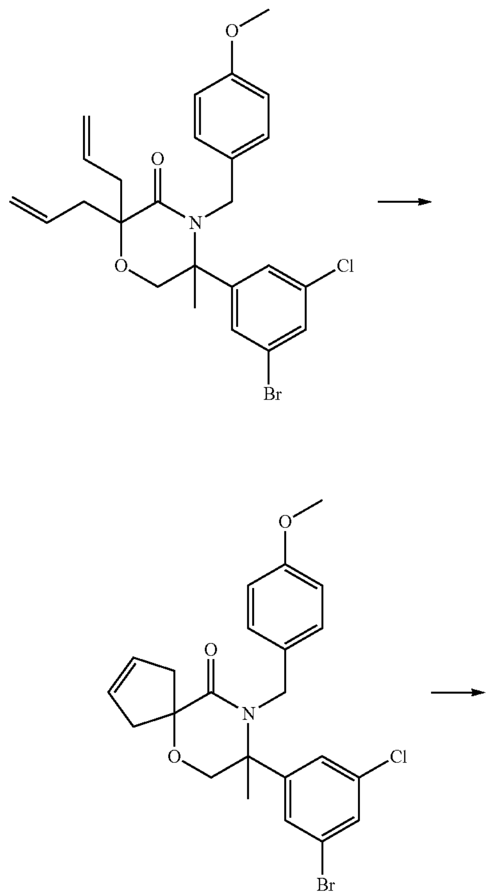

-continued

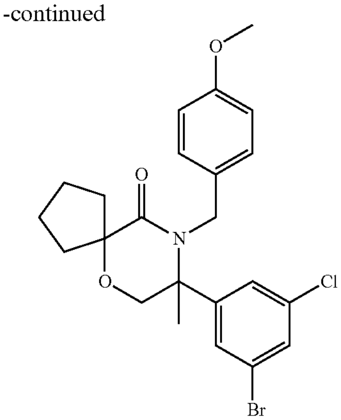

2,2-diallyl-5-(3-bromo-5-chlorophenyl)-4-(4-methoxybenzyl)-5-methylmorpholin-3-one was obtained from Procedure K.

To a solution of 2,2-diallyl-5-(3-bromo-5-chlorophenyl)-4-(4-methoxybenzyl)-5-methylmorpholin-3-one (6.6 g, 12.33 mmol) in DCM (100 mL, 0.12 M) was added Grubbs II Catalyst (525 mg, 0.62 mmol, 0.05 equiv) at room temperature under $N_2$ and then stirred for 4 hours. The reaction mixture was quenched with water (80 mL) and extracted with DCM (60 mL*3). The combined organic phases were dried over $Na_2SO_4$ and then concentrated under produce pressure. The residue was purified by flash silica gel column chromatography to give 8-(3-bromo-5-chloro-phenyl)-9-[(4-methoxyphenyl)methyl]-8-methyl-6-oxa-9-azaspiro[4.5]dec-2-en-10-one; ethane (5.60 g, 11.0 mmol, 90% yield) as a white solid.

To a solution of 8-(3-bromo-5-chloro-phenyl)-9-[(4-methoxyphenyl)methyl]-8-methyl-6-oxa-9-azaspiro[4.5]decan-10-one (20 mg, 0.042 mmol, 1 equiv) in ethyl acetate (2 mL, 0.02 M) was added $PtO_2$ (0.05 eq, 300 mg) at room temperature under $H_2$ (15 psi). The reaction was stirred at room temperature for 5 hours. The reaction was filtered and then concentrated under reduced pressure to afford 8-(3-bromo-5-chloro-phenyl)-9-[(4-methoxyphenyl)methyl]-8-methyl-6-oxa-9-azaspiro[4.5]decan-10-one (5.30 g, 11.1 mmol, 94% yield) as a white solid.

1-(8-(3-(2-aminopyrimidin-4-yl)-5-chlorophenyl)-8-methyl-6-oxa-9-azaspiro[4.5]decan-9-yl)prop-2-en-1-one was obtained using 8-(3-bromo-5-chloro-phenyl)-9-[(4-methoxyphenyl)methyl]-8-methyl-6-oxa-9-azaspiro[4.5]decan-10-one in Procedure K. LC-MS m/z: 413.2 [M+1].

Stereochemistry: Single enantiomer of unknown absolute configuration.

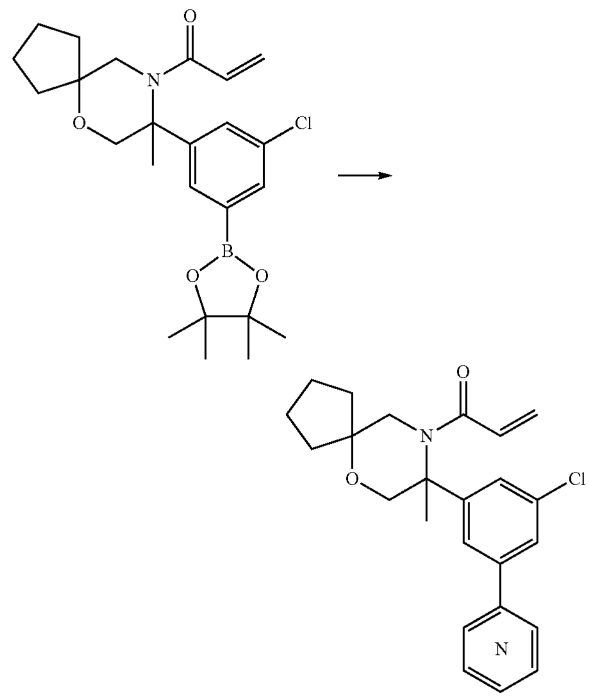

Using the appropriate coupling partner in Procedure L, the title compounds can be obtained.

| Cmp | Name | Coupling Partner | LC-MS m/z [M + 1] |
|---|---|---|---|
| 163 | 1-(8-(3-(2-aminopyrimidin-4-yl)-5-chlorophenyl)-8-methyl-6-oxa-9-azaspiro[4.5]decan-9-yl)prop-2-en-1-one | 4-bromopyrimidin-2-amine | 413.2 |
| 164 | 1-(8-(3-(4-amino-1,3,5-triazin-2-yl)-5-chlorophenyl)-8-methyl-6-oxa-9-azaspiro[4.5]decan-9-yl)prop-2-en-1-one | 4-chloro-1,3,5-triazin-2-amine | 414.2 |
| 166 | 1-(8-(3-chloro-5-(5-fluoropyrimidin-2-yl)phenyl)-8-methyl-6-oxa-9-azaspiro[4.5]decan-9-yl)prop-2-en-1-one | 2-bromo-5-fluoropyrimidine | 416.1 |
| 170 | 1-(8-(3-(6-aminopyrimidin-4-y1)-5-chlorophenyl)-8-methyl-6-oxa-9-azaspiro[4.5]decan-9-yl)prop-2-en-1-one | 6-chloropyrimidin-4-amine | 413.2 |
| 171 | 1-(8-(3-(4-aminopyrimidin-2-yl)-5-chlorophenyl)-8-methyl-6-oxa-9-azaspiro[4.5]decan-9-yl)prop-2-en-1-one | 2-chloropyrimidin-4-amine | 413.2 |

Example 66. Procedure M and Synthesis of (3S,5R)-4-acryloyl-5-(2-(6-aminopyrimidin-4-yl)-6-chloropyridin-4-yl)morpholine-3-carboxamide (Compound 172)

Procedure M

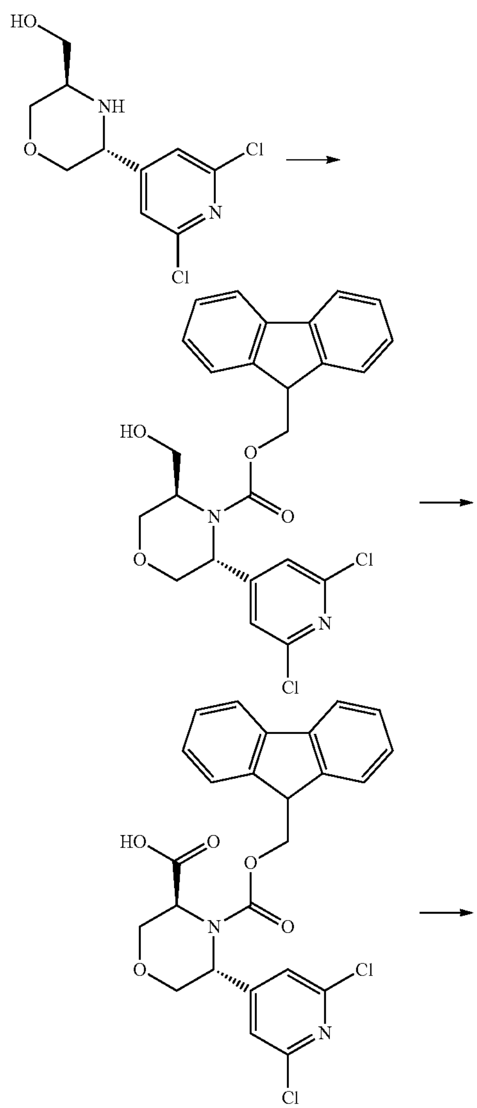

((3R,5R)-5-(2,6-dichloropyridin-4-yl)morpholin-3-yl)methanol was obtained from Procedure J.

To a solution of ((3R,5R)-5-(2,6-dichloropyridin-4-yl)morpholin-3-yl)methanol (1.5 g, 5.70 mmol, 1 equiv) in THF (20 mL, 0.28 M) and saturated aqueous $NaHCO_3$ (15 mL) was added 9H-Fluoren-9-ylmethyl chloroformate (1.769 g, 6.84 mmol, 1.2 equiv) in THF (10 mL) dropwise. The resulting mixture was stirred at room temperature for 3.5 hours. The reaction mixture was poured into $H_2O$ (10 mL) and extracted with EtOAc (20 mL*3). The combined organic layers were washed with brine (10 mL), dried over $Na_2SO_4$, filtered, and concentrated under reduced pressure. The residue was purified by column chromatography ($SiO_2$, Petroleum ether/Ethyl acetate=1/0 to 0/1) to afford (9H-fluoren-9-yl)methyl (3R,5R)-3-(2,6-dichloropyridin-4-yl)-5-(hydroxymethyl)morpholine-4-carboxylate (2400 mg, 4.94 mmol, 86% yield) as a yellow oil.

To a solution of (9H-fluoren-9-yl)methyl (3R,5R)-3-(2,6-dichloropyridin-4-yl)-5-(hydroxymethyl)morpholine-4-carboxylate (1.8 g, 3.70 mmol, 1 equiv) in MeCN (7 mL, 0.17 M), ethyl acetate (7 mL, 0.17 M), and water (7 mL, 0.17 M) was added $NaIO_4$ (2 eq, 1.58 g) and $RuCl_3$ (0.01 eq, 8 mg) at 0° C. The resulting mixture was stirred at 25° C. for 2 hours. The reaction mixture was poured into $H_2O$ (20 mL) and extracted with EtOAc (20 mL*3). The combined organic layers were washed with brine (20 mL), dried over $Na_2SO_4$, filtered, and concentrated under reduced pressure to afford (3S,5R)-4-(((9H-fluoren-9-yl)methoxy)carbonyl)-5-(2,6-dichloropyridin-4-yl)morpholine-3-carboxylic acid (1.75 g, 3.50 mmol, 95% yield).

To a solution of (3S,5R)-4-(((9H-fluoren-9-yl)methoxy)carbonyl)-5-(2,6-dichloropyridin-4-yl)morpholine-3-carboxylic acid (600 mg, 1.20 mmol, 1 equiv) in 1,4-dioxane (10 mL, 0.12 M) was added di-tert-butyl dicarbonate (524 mg, 2.40 mmol, 2 equiv), pyridine (190.09 mg, 2.40 mmol, 2 equiv), and $NH_4HCO_3$ (189 mg, 2 eq) at 25° C. The mixture was stirred 25° C. for 3 hours. The reaction mixture was poured into water (10 mL) and extracted with EtOAc (20 mL*3). The combined organic layers were washed with brine (10 mL), dried over $Na_2SO_4$, filtered, and concentrated under reduced. The residue was purified by column chromatography ($SiO_2$, Petroleum ether/Ethyl acetate=1/0 to 0/1) to give (9H-fluoren-9-yl)methyl (3S,5R)-3-carbamoyl-5-(2,6-dichloropyridin-4-yl)morpholine-4-carboxylate (350 mg, 0.70 mmol 58% yield) as a white solid.

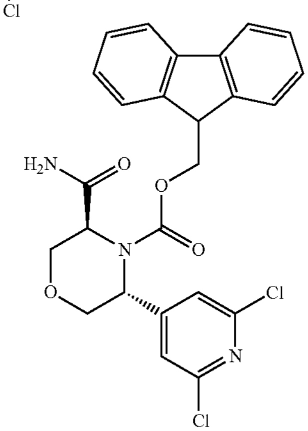

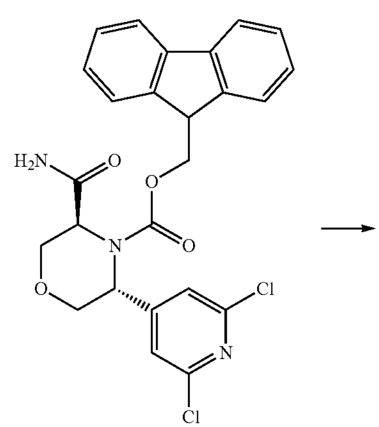

-continued

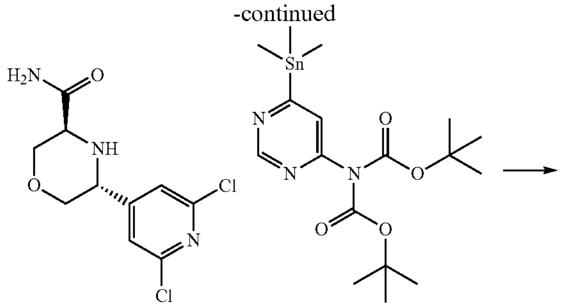

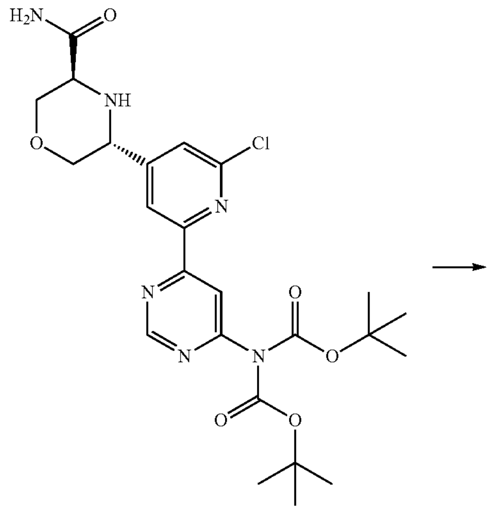

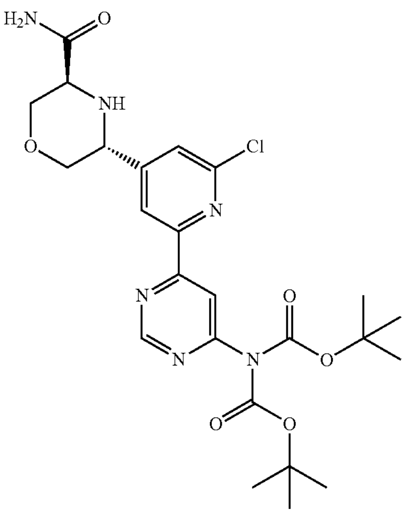

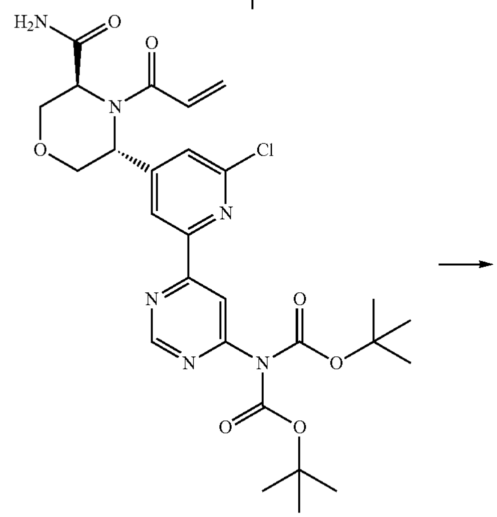

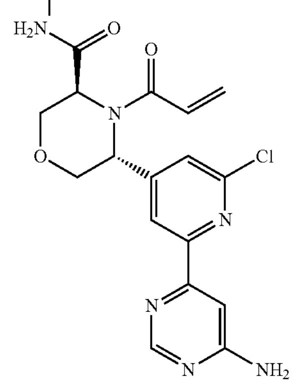

To a solution of (9H-fluoren-9-yl)methyl (3S,5R)-3-carbamoyl-5-(2,6-dichloropyridin-4-yl)morpholine-4-carboxylate (280 mg, 0.56 mmol, 1 equiv) in MeCN (3 mL, 0.18 M) was added diethylamine (821.86 mg, 11.23 mmol, 20 equiv) and the resulting mixture was stirred at 25° C. for 1 hour. The mixture was concentrated, and the residue was purified by prep-TLC ($SiO_2$, PE:EtOAc=1:2) to afford (3S,5R)-5-(2,6-dichloropyridin-4-yl)morpholine-3-carboxamide (120 mg, 0.43 mmol, 77% yield) as a white solid.

To a solution of (3S,5R)-5-(2,6-dichloropyridin-4-yl)morpholine-3-carboxamide (110 mg, 0.39 mmol, 1 equiv) in 1,4-dioxane (1 mL, 0.39 M) was added tert-butyl (tert-butoxycarbonyl)(6-(trimethylstannyl)pyrimidin-4-yl)carbamate (164.26 mg, 0.35 mmol, 0.9 equiv) and $Pd(dppf)Cl_2$ (0.1 eq, 8.8 mg). The resulting mixture was stirred at 100° C. for 16 hours. The reaction mixture was poured into H2O (5 mL) and extracted with EtOAc (5 mL*3). The combined organic layers were washed with brine (10 mL), dried over $Na_2SO_4$, filtered, and concentrated under reduced pressure. The residue was purified by prep-HPLC to afford tert-butyl (tert-butoxycarbonyl)(6-(4-((3R,5S)-5-carbamoylmorpholin-3-yl)-6-chloropyridin-2-yl)pyrimidin-4-yl)carbamate (15 mg, 0.028 mmol, 7% yield) as a white solid.

To a solution of tert-butyl (tert-butoxycarbonyl)(6-(4-((3R,5S)-5-carbamoylmorpholin-3-yl)-6-chloropyridin-2-yl)pyrimidin-4-yl)carbamate (20 mg, 0.037 mmol, 1 equiv) in DCM (1 mL, 0.03 M) was added acryloyl chloride (3.38 mg, 0.037 mmol, 1 equiv) and N,N-diisopropylethylamine (4.8 mg, 0.037 mmol, 1 equiv). The resulting mixture was stirred at 25° C. for 1 hour. The reaction mixture was poured into $H_2O$ (5 mL) and extracted with EtOAc (5 mL*3). The combined organic layers were washed with brine (10 mL), dried over $Na_2SO_4$, filtered, and concentrated under reduced pressure. The residue was purified by prep-TLC ($SiO_2$, EtOAc:MeOH=10:1) to afford tert-butyl (6-(4-((3R,5S)-4-acryloyl-5-carbamoylmorpholin-3-yl)-6-chloropyridin-2-yl)

pyrimidin-4-yl)(tert-butoxycarbonyl)carbamate (15 mg, 0.025 mmol, 68% yield) as a white solid.

To a solution of tert-butyl (6-(4-((3R,5S)-4-acryloyl-5-carbamoylmorpholin-3-yl)-6-chloropyridin-2-yl)pyrimidin-4-yl)(tert-butoxycarbonyl)carbamate (10 mg, 0.017 mmol, 1 equiv) in DCM (1 mL, 0.017 M) was added TFA (0.3 mL). The resulting mixture was stirred at 25° C. for 1 hour. The reaction liquid was concentrated to afford (3S,5R)-4-acryloyl-5-(2-(6-aminopyrimidin-4-yl)-6-chloropyridin-4-yl) morpholine-3-carboxamide (7.9 mg) as a yellow oil. LC-MS m/z: 389.1 [M+1].

Stereochemistry: Single enantiomer of known absolute configuration.

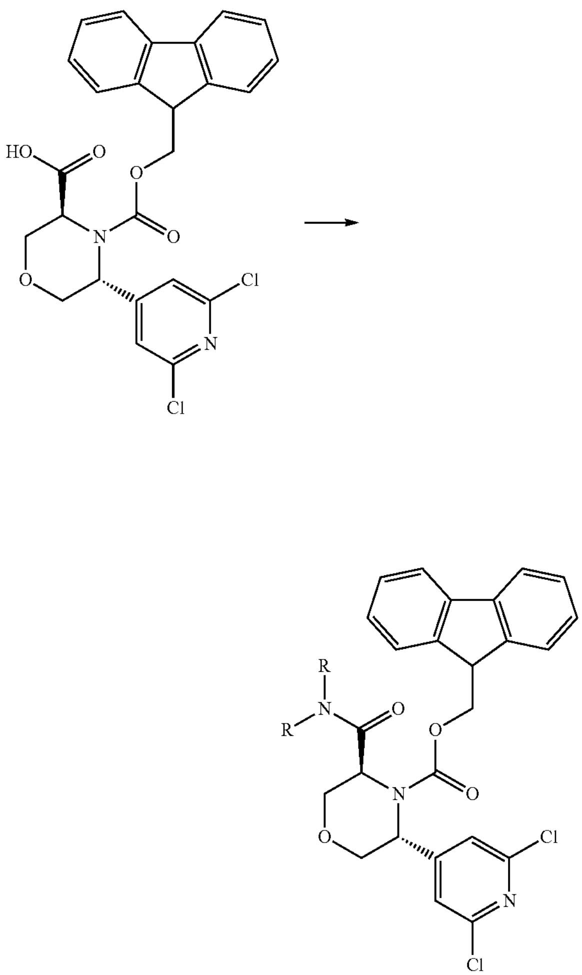

-continued

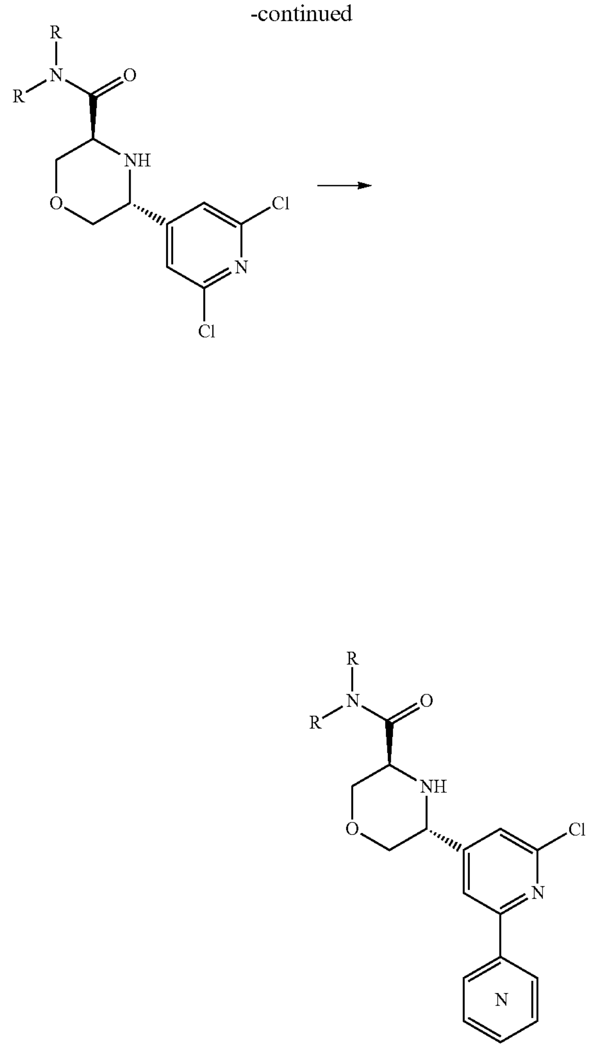

Using the appropriate coupling partners in both steps of Procedure M, the title compounds can be obtained.

| Cmp | Name | LC-MS m/z [M + 1] |
|---|---|---|
| 172 | (3S,5R)-4-acryloy1-5-(2-(6-aminopyrimidin-4-yl)-6-chloropyridin-4-yl)morpholine-3-carboxamide | 389.1 |
| 181 | (3S,5R)-4-acryloy1-5-(2-(3-carbamoyl-4-fluorophenyl)-6-chloropyridin-4-yl)morpholine-3-carboxamide | 433.1 |
| 169 | (3S,5R)-4-acryloyl-5-(2-(6-aminopyrimidin-4-yl)-6-chloropyridin-4-yl)-N,N-dimethylmorpholine-3-carboxamide | 417.0 |
| 173 | (3S,5R)-4-acryloyl-5-(2-(6-aminopyrimidin-4-yl)-6-chloropyridin-4-yl)-N-methylmorpholine-3-carboxamide | 403.1 |

Example 67. Synthesis of 3-(4-acryloylmorpholin-3-yl)-5-(pyrimidin-2-yl)benzonitrile (Compound 8)

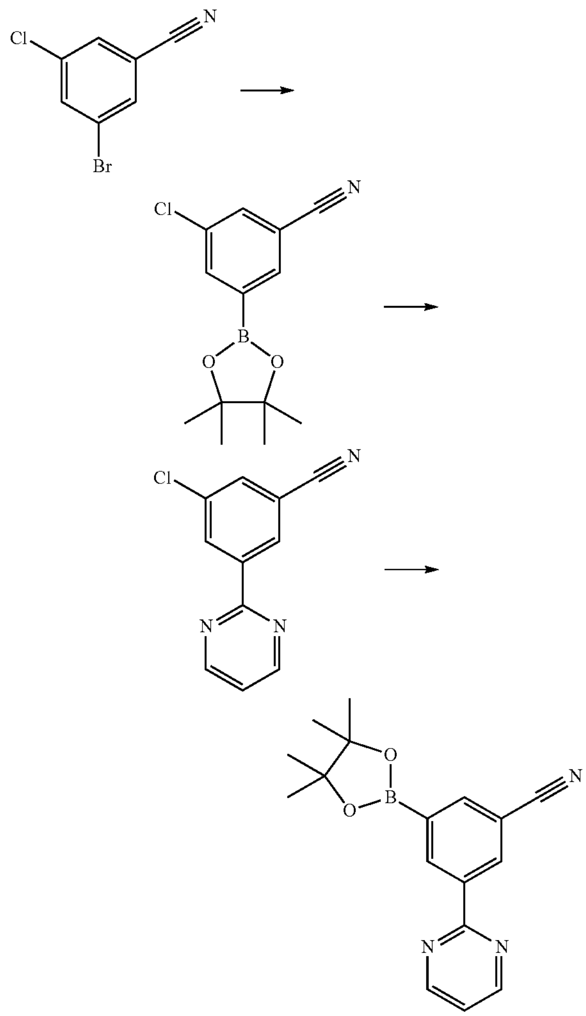

A solution of 3-bromo-5-chloro-benzonitrile (3770 mg, 17.41 mmol, 1 equiv) and bis(pinacolato)diboron (5749 mg, 22.64 mmol, 1.3 equiv) in 1,4-dioxane (40 mL, 0.43 M) was added $PdCl_2$(dppf) (1.27 g, 0.1 eq) and KOAc (4.29 g, 2.5 eq) under $N_2$. The mixture was stirred at 90° C. for 12 hours. The solution was poured into water (40 mL) and extracted with ethyl acetate (40 mL*3). The combined organic phase was washed with brine (20 mL*2), dried over $Na_2SO_4$, filtered, and concentrated under vacuum. The crude product was purified by silica gel chromatography (petroleum ether: ethyl acetate=30:1) to afford 3-chloro-5-(4,4,5,5-tetramethyl-1,3,2-dioxaborolan-2-yl)benzonitrile (4500 mg, 17.07 mmol, 98% yield) as a yellow solid.

To a solution of 3-chloro-5-(4,4,5,5-tetramethyl-1,3,2-dioxaborolan-2-yl)benzonitrile (2000 mg, 7.58 mmol, 1 equiv) and 2-bromopyrimidine (1085 mg, 6.83 mmol, 0.9 equiv) in 1,4-dioxane (15 mL), MeCN (15 mL), and water (7.5 mL) was added $PdCl_2$(dppf) (277 mg, 0.05 eq) and $K_2CO_3$ (2622 mg, 2.5 eq) under $N_2$. The mixture was stirred at 90° C. for 5 hours. The mixture was cooled to 25° C. and concentrated under reduced pressure. The residue was poured into ice-water (w/w=1/1) (20 mL) and extracted with ethyl acetate (20 mL*3). The combined organic phase was washed with brine (20 mL*2), dried over $Na_2SO_4$, filtered, and concentrated under vacuum. The residue was purified by silica gel chromatography (Petroleum ether/Ethyl acetate=15:1) to afford 3-chloro-5-pyrimidin-2-yl-benzonitrile (950 mg, 4.40 mmol, 58% yield) as a yellow solid.

A solution of 3-chloro-5-pyrimidin-2-yl-benzonitrile (720 mg, 3.33 mmol, 1 equiv) and bis(pinacolato)diboron (1017.5 mg, 4 mmol, 1.2 equiv) in toluene (7 mL, 0.47 M) was added x-Phos PdG2 (131 mg, 0.05 eq) and KOAc (983 mg, 3.0 eq) under $N_2$. The mixture was stirred at 110° C. for 12 hours. The solution was poured into water (10 mL) and extracted with ethyl acetate (10 mL*3). The combined organic phase was washed with brine (10 mL*2), dried over $Na_2SO_4$, filtered, and concentrated under vacuum. The crude product was purified by silica gel chromatography (petroleum ether: ethyl acetate=15:1) to give 3-pyrimidin-2-yl-5-(4,4,5,5-tetramethyl-1,3,2-dioxaborolan-2-yl)benzonitrile (1000 mg, 3.26 mmol, 97% yield) as a yellow solid.

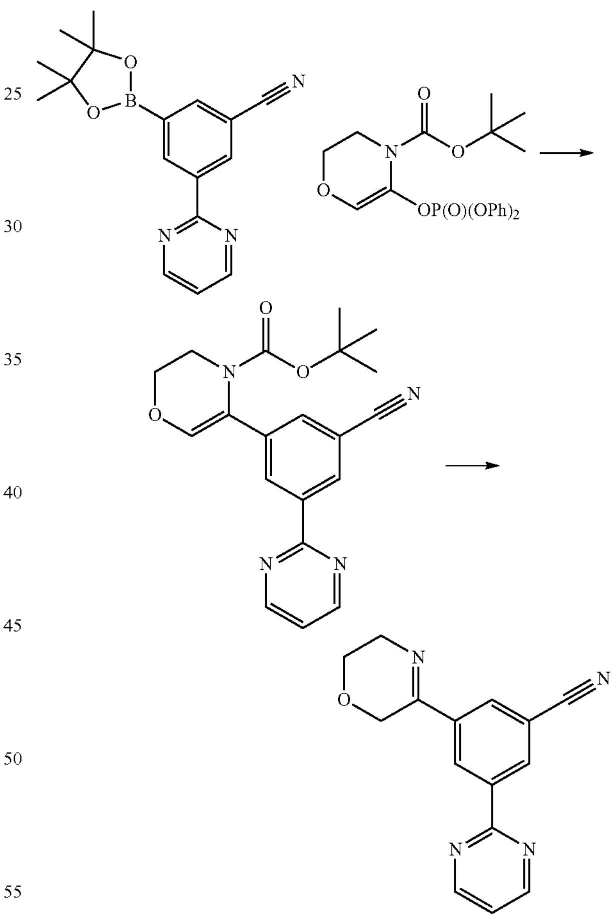

A solution of 3-pyrimidin-2-yl-5-(4,4,5,5-tetramethyl-1,3,2-dioxaborolan-2-yl)benzonitrile (1000 mg, 3.25 mmol, 1 equiv) and tert-butyl 5-((diphenoxyphosphoryl)oxy)-2,3-dihydro-4H-1,4-oxazine-4-carboxylate (1630 mg, 3.90 mmol, 1.2 equiv) in 1,4-dioxane (10 mL), MeCN (10 mL), and water (5 mL) was added $PdCl_2$(dppf) (100 mg, 0.05 eq) and $K_2CO_3$ (900 mg, 2.0 eq) under $N_2$. The mixture was stirred at 80° C. for 5 hours. The solution was poured into water (20 mL) and extracted with ethyl acetate (20 mL*3). The combined organic phase was washed with brine (20 mL*2), dried over $Na_2SO_4$, filtered, and concentrated under vacuum. The crude product was purified by silica gel chromatography (petroleum ether:ethyl acetate=15:1) to give tert-butyl 5-(3-cyano-5-pyrimidin-2-yl-phenyl)-2,3-dihydro-1,4-oxazine-4-carboxylate (800 mg, 2.19 mmol, 67% yield) as a yellow solid.

To a solution of tert-butyl 5-(3-cyano-5-pyrimidin-2-yl-phenyl)-2,3-dihydro-1,4-oxazine-4-carboxylate (300 mg, 0.82 mmol) in DCM (0.5 mL) was added TFA (2.5 mL) and stirred 25° C. for 30 minutes. The reaction was concentrated to give 3-(3,6-dihydro-2H-1,4-oxazin-5-yl)-5-pyrimidin-2-yl-benzonitrile (200 mg, 0.75 mmol) as yellow oil.

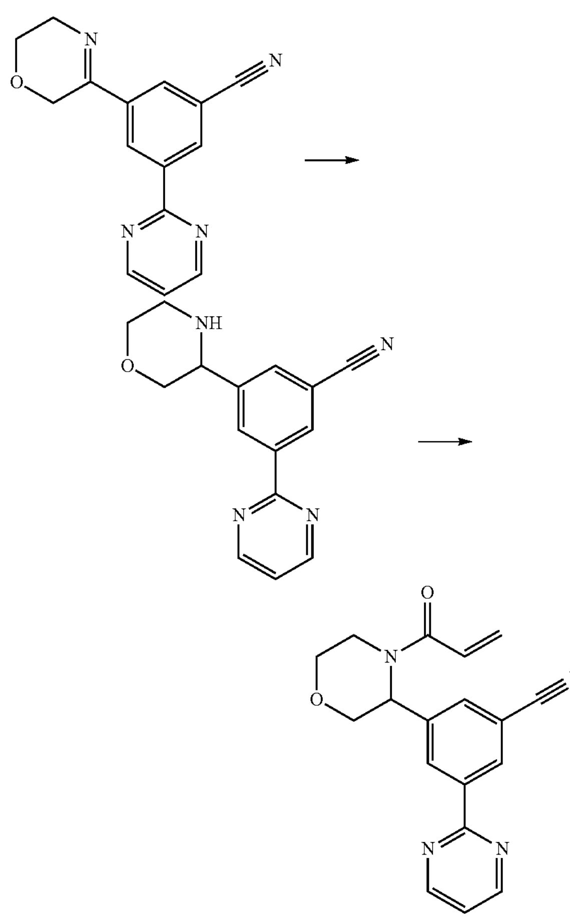

To a solution of 3-(3,6-dihydro-2H-1,4-oxazin-5-yl)-5-pyrimidin-2-yl-benzonitrile (200 mg, 0.75 mmol) in methanol (3 mL) was added $NaBH_4$ (45 mg) and stirred 25° C. for 10 minutes. The reaction was concentrated and purified by prep-HPLC to afford 3-morpholin-3-yl-5-pyrimidin-2-yl-benzonitrile (150 mg, 0.56 mmol) as a yellow oil.

To a solution of 3-morpholin-3-yl-5-pyrimidin-2-yl-benzonitrile (60 mg, 0.22 mmol) in DCM (2 mL, 0.1 M) was added triethylamine (44 mg, 2.5 eq) and acryloyl chloride (24.47 mg, 0.27 mmol, 1.2 equiv) at 25° C. The reaction was stirred for 30 minutes. The solution was concentrated and purified by prep-TLC (EtOAc) to afford 3-(4-acryloylmorpholin-3-yl)-5-(pyrimidin-2-yl)benzonitrile (6.8 mg, 0.021 mmol, 9.4% yield).

Enantiomers were separated by SFC. The title compound's absolute stereochemistry was not assigned. LC-MS m/z: 321.1 [M+1].

Stereochemistry: single enantiomer of unknown absolute configuration.

Example 68. Synthesis of 3'-(4-acryloylmorpholin-3-yl)-5'-cyano-4-fluoro-[1,1'-biphenyl]-3-carboxamide (Compound 67)

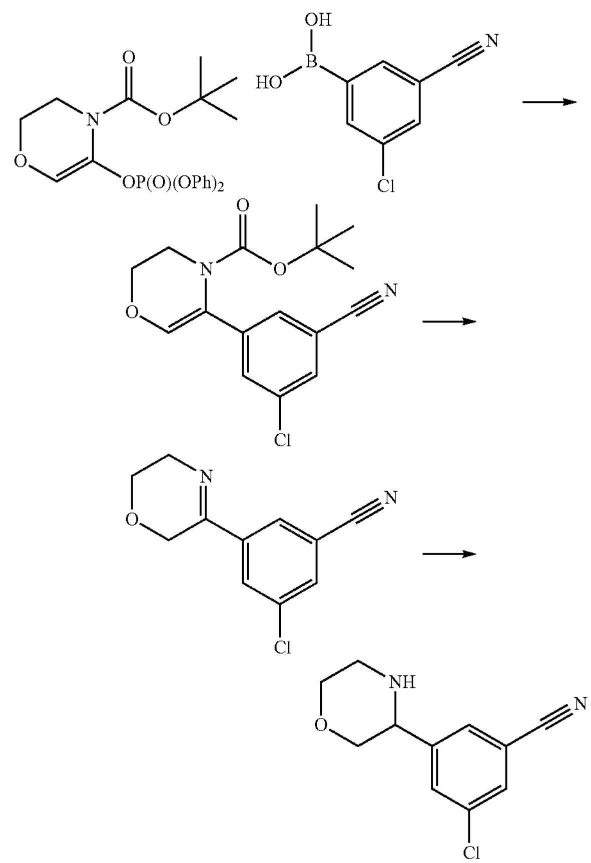

To a solution of 3-chloro-5-cyanophenylboronic acid (2 g, 11.027 mmol, 1 equiv) in 1,4-dioxane (30 mL) and water (6 mL) was added tert-butyl 5-((diphenoxyphosphoryl)oxy)-2,3-dihydro-4H-1,4-oxazine-4-carboxylate (5.73 g, 13.23 mmol, 1.2 equiv), potassium carbonate (3.048 g, 22.053 mmol, 2 equiv), and $Pd(dppf)Cl_2$ (800 mg, 1.10 mmol, 0.1 equiv). The reaction was stirred at 80° C. for 2 hours under $N_2$. The reaction mixture was quenched with $H_2O$ (10 mL) and extracted with ethyl acetate (10 mL×2). The organic layers were washed with a brine solution, dried over $Na_2SO_4$, filtered, and concentrated. The crude material was purified by column chromatography (PE:EA=10:1 to EA) to give tert-butyl 5-(3-chloro-5-cyano-phenyl)-2,3-dihydro-1,4-oxazine-4-carboxylate (3 g, 9.35 mmol, 85% yield) as a yellow solid.

HCl in ethyl acetate (5 mL) was added to tert-butyl 5-(3-chloro-5-cyano-phenyl)-2,3-dihydro-1,4-oxazine-4-carboxylate (200 mg, 0.62 mmol, 1 equiv) and stirred at 25° C. for 2 hours. The reaction mixture was concentrated directly to afford 3-chloro-5-(3,6-dihydro-2H-1,4-oxazin-5-yl)benzonitrile hydrochloride (210 mg) as a yellow solid.

To a solution of 3-chloro-5-(3,6-dihydro-2H-1,4-oxazin-5-yl)benzonitrile hydrochloride (210 mg, 0.81 mmol, 1 equiv) in methanol (5 mL, 0.16 M) was added $NaBH_4$ (100 mg, 4 eq) at 0° C. The reaction was stirred at 25° C. for 1 hour. The mixture was quenched with 1M aqueous HCl and then extracted with ethyl acetate (10 mL×2). The organic layers were washed with brine, dried over $Na_2SO_4$, filtered, and concentrated to afford crude 3-chloro-5-morpholin-3-yl-benzonitrile (60 mg) as a yellow solid.

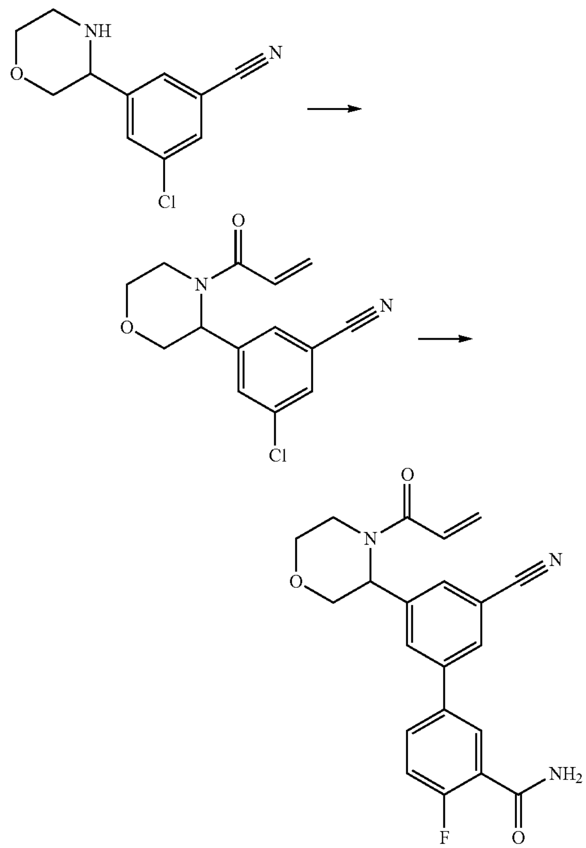 [SMILES: N#Cc1cc(Cl)cc(C2COCCN2)c1 ; C=CC(=O)N1CCOCC1c1cc(Cl)cc(C#N)c1 ; C=CC(=O)N1CCOCC1c1cc(C#N)cc(-c2ccc(F)c(C(N)=O)c2)c1]

To a solution of 3-chloro-5-morpholin-3-yl-benzonitrile (60 mg, 0.26 mmol, 1 equiv) in DCM (3 mL, 0.08 M) was added acryloyl chloride (36 mg, 0.40 mmol, 1.5 equiv) and triethylamine (54 mg, 0.53 mmol, 2 equiv). The solution was stirred at 25° C. for 2 hours. The reaction mixture was quenched with $H_2O$ (10 mL) and extracted with DCM (10 mL×2). The organic layers were washed with a brine solution, dried over $Na_2SO_4$, filtered, and concentrated to afford crude 3-chloro-5-(4-prop-2-enoylmorpholin-3-yl)benzonitrile (100 mg) as a yellow solid.

To a solution of 3-chloro-5-(4-prop-2-enoylmorpholin-3-yl)benzonitrile (50 mg, 0.18 mmol, 1 equiv) in 1,4-dioxane (5 mL) and water (1 mL) was added 2-fluoro-5-(4,4,5,5-tetramethyl-1,3,2-dioxaborolan-2-yl)benzamide (71.84 mg, 0.27 mmol, 1.5 equiv), potassium carbonate (49.94 mg, 0.36 mmol, 2 equiv), and [2-(2-aminophenyl)phenyl]-chloro-palladium; dicyclohexyl-[3-(2,4,6-triisopropylphenyl)phenyl] phosphane (14.21 mg, 0.018 mmol, 0.1 equiv). The reaction was heated to 80° C. for 12 hours under $N_2$. The mixture was concentrated directly to provide 3'-(4-acryloylmorpholin-3-yl)-5'-cyano-4-fluoro-[1,1'-biphenyl]-3-carboxamide as a yellow oil.

Enantiomers were separated by SFC. The title compound's absolute stereochemistry was not assigned. LC-MS m/z: 380.1 [M+1].

Stereochemistry: single enantiomer of unknown absolute configuration.

Example 69. Procedure N and Synthesis of 4-(3-((3R,5R)-4-acryloyl-5-methylmorpholin-3-yl)-5-chlorophenyl)picolinamide (Compound 134)

Procedure N

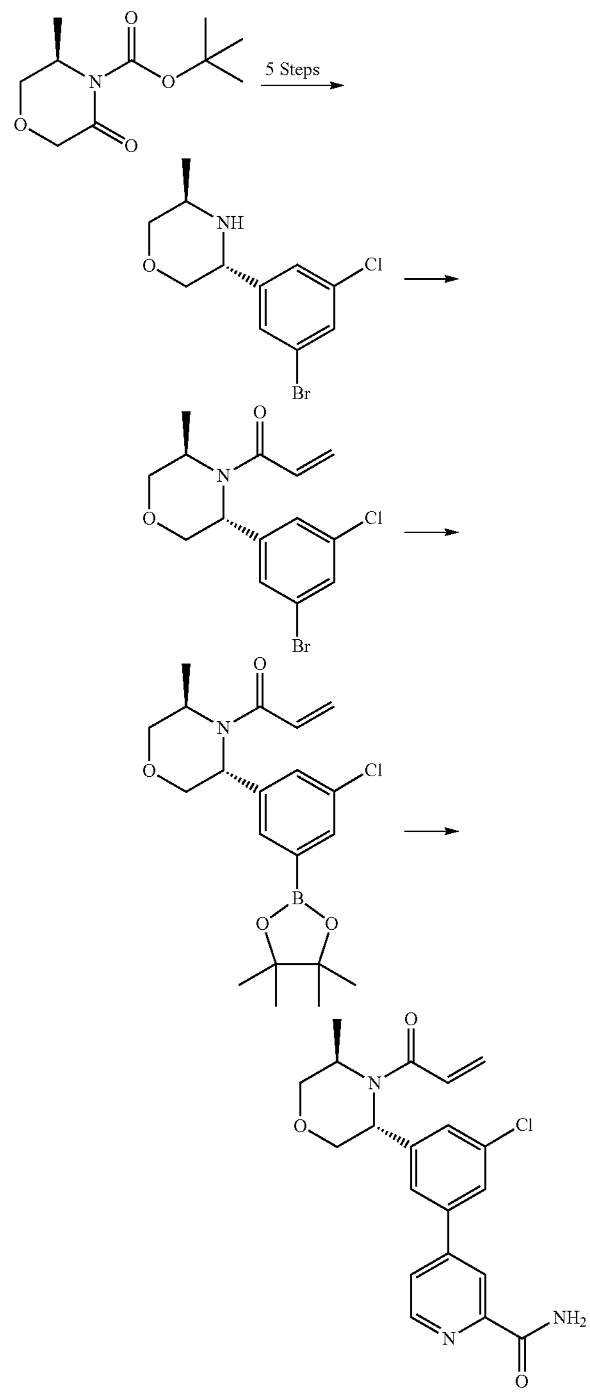

tert-butyl (R)-3-methyl-5-oxomorpholine-4-carboxylate, obtained from Procedure H, was taken through the first 5 steps of Procedure B to afford (3R,5R)-3-(3-bromo-5-chlorophenyl)-5-methylmorpholine.

To a solution of (3R,5R)-3-(3-bromo-5-chlorophenyl)-5-methylmorpholine (2500 mg, 8.60 mmol) and acryloyl chloride (856.57 mg, 9.46 mmol) in DCM (30 mL, 0.28 M) was added DIEA (0.5 mL) at room temperature and allowed to stir for 90 minutes. The mixture was diluted with $H_2O$ (15 mL) and extracted with DCM (15 mL*3). The combined organic extracts were washed with brine (20 mL), dried over $Na_2SO_4$, filtered, and concentrated in vacuo. The residue was purified by flash silica gel chromatography (ISCO®; 12 g SEPAFLASH® Silica Flash Column, Eluent of 0-30% Ethyl acetate/Petroleum ether gradient @ 80 mL/min) to afford 1-((3R,5R)-3-(3-bromo-5-chlorophenyl)-5-methylmorpholino)prop-2-en-1-one (2.50 g, 7.25 mmol, 84% yield) as a yellow oil.

To a solution of 1-((3R,5R)-3-(3-bromo-5-chlorophenyl)-5-methylmorpholino)prop-2-en-1-one (2500 mg, 7.25 mmol) and bis(pinacolato)diboron (2763.2 mg, 10.88 mmol) in 1,4-dioxane (30 mL, 0.24 M) was added KOAc (14.51 mmol, 1.53 g) and Pd(dppf)$Cl_2$ (650 mg, 0.1 eq). The reaction mixture was stirred at 90° C. for 16 hours under N2. Water (20 mL) was added to the reaction mixture and extracted with ethyl acetate (15 mL*3). The combined organic layers were washed with brine (20 mL), dried over $Na_2SO_4$, filtered, and concentrated under reduced pressure to give the crude 1-((3R,5R)-3-(3-chloro-5-(4,4,5,5-tetramethyl-1,3,2-dioxaborolan-2-yl)phenyl)-5-methylmorpholino)prop-2-en-1-one (2.7 g, 6.89 mmol, 95% yield) as a dark oil.

To a solution of 1-((3R,5R)-3-(3-chloro-5-(4,4,5,5-tetramethyl-1,3,2-dioxaborolan-2-yl)phenyl)-5-methylmorpholino)prop-2-en-1-one (100 mg, 0.25 mmol, 1 equiv) and 4-bromopyridine-2-carboxamide (66 mg, 0.33 mmol, 1.3 equiv) in 1,4-dioxane (4 mL) and $H_2O$ (0.8 mL) was added $K_2C_3$ (70 mg, 0.51 mmol, 2 equiv) and Pd(dppf)$Cl_2$ (18 mg, 0.025 mmol, 0.1 equiv) under $N_2$. The mixture was stirred at 80° C. for 15 hours. The reaction was quenched with water (10 mL) and extracted with EtOAc (20 mL×2). The combined organic layer was washed with brine (10 mL), dried over $Na_2SO_4$, filtered, and concentrated under reduced pressure. The crude product was purified by Prep-HPLC (column: Waters Xbridge BEH C18 100*30 mm*10 um; liquid phase: [A-10 mM $NH_4HCO_3$ in $H_2O$; B-ACN]B %: 20%-50%, 8 min]) to afford 4-(3-((3R,5R)-4-acryloyl-5-methylmorpholin-3-yl)-5-chlorophenyl)picolinamide (34 mg, 0.085 mmol, 34% yield) as a pale yellow solid. LC-MS mz: 386.1 [M+1].

Stereochemistry: single enantiomer of known absolute configuration.

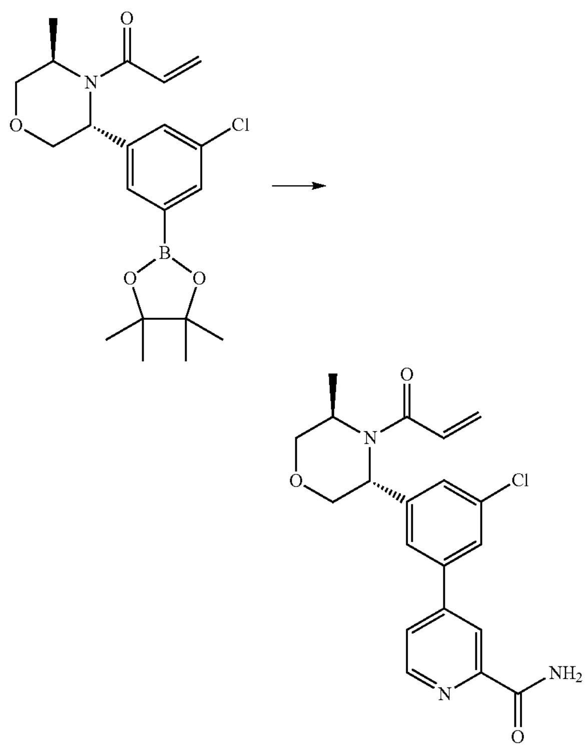 [SMILES: C=CC(=O)N1[C@H](C)COC[C@H]1c1cc(Cl)cc(B2OC(C)(C)C(C)(C)O2)c1 ; C=CC(=O)N1[C@H](C)COC[C@H]1c1cc(Cl)cc(-c2ccnc(C(N)=O)c2)c1]

Using the appropriate coupling partner in Procedure N, the title compounds can be obtained.

| Cmp | Name | Coupling Partner | LC-MS m/z [M + 1] |
|---|---|---|---|
| 134 | 4-(3-((3R,5R)-4-acryloyl-5-methylmorpholin-3-yl)-5-chlorophenyl)picolinamide | 4-bromopyridine-2-carboxamide | 386.1 |
| 18 | 1-(4-(3-((3R,5R)-4-acryloyl-5-methylmorpholin-3-yl)-5-chlorophenyl)pyridin-2-yl)pyrrolidin-2-one | 1-(4-bromopyridin-2-yl)pyrrolidin-2-one | 426.1 |
| 20 | 1-((3R,5R)-3-(3-chloro-5-(pyrimidin-2-yl)phenyl)-5-methylmorpholino)prop-2-en-1-one | 2-bromopyrimidine | 344.0 |
| 24 | 4-(3-((3R,5R)-4-acryloyl-5-methylmorpholin-3-yl)-5-chlorophenyl)-1-methylpyridin-2(1H)-one | 4-bromo-1-methylpyridin-2(1H)-one | 373.1 |
| 102 | 1-((3R,5R)-3-(3-(4-amino-1,3,5-triazin-2-yl)-5-chlorophenyl)-5-methylmorpholino)prop-2-en-1-one | 4-chloro-1,3,5-triazin-2-amine | 360.0 |
| 108 | 3'-((3R,5R)-4-acryloyl-5-methylmorpholin-3-y1)-5'-chloro-4-fluoro-[1,1'-biphenyl]-3-carboxamide | 5-bromo-2-fluorobenzamide | 403.1 |
| 109 | 1-((3R,5R)-3-(3-chloro-5-(2-methylpyrimidin-4-yl)phenyl)-5-methylmorpholino)prop-2-en-1-one | 4-chloro-2-methylpyrimidine | 358.1 |
| 110 | 1-((3R,5R)-3-(3-(2-aminopyrimidin-4-yl)-5-chlorophenyl)-5-methylmorpholino)prop-2-en-1-one | 4-chloropyrimidin-2-amine | 359.0 |
| 130 | 1-((3R,5R)-3-(3-(5-aminopyrimidin-2-yl)-5-chlorophenyl)-5-methylmorpholino)prop-2-en-1-one | 2-chloropyrimidin-5-amine | 359.0 |
| 131 | 1-((3R,5R)-3-(3-(6-aminopyrimidin-4-yl)-5-chlorophenyl)-5-methylmorpholino)prop-2-en-1-one | 6-chloropyrimidin-4-amine | 359.1 |

-continued

| Cmp | Name | Coupling Partner | LC-MS m/z [M + 1] |
|---|---|---|---|
| 137 | 1-((3R,5R)-3-(3-chloro-5-(9H-purin-6-yl)phenyl)-5-methylmorpholino)prop-2-en-1-one | 6-chloro-9-(tetrahydro-2H-pyran-2-yl)-9H-purine | 384.0 |

Example 70. Procedure O and Synthesis of 1-(3-(2-(4-amino-1,3,5-triazin-2-yl)-6-chloropyridin-4-yl)morpholino)prop-2-en-1-one (Compound 146)

Procedure O

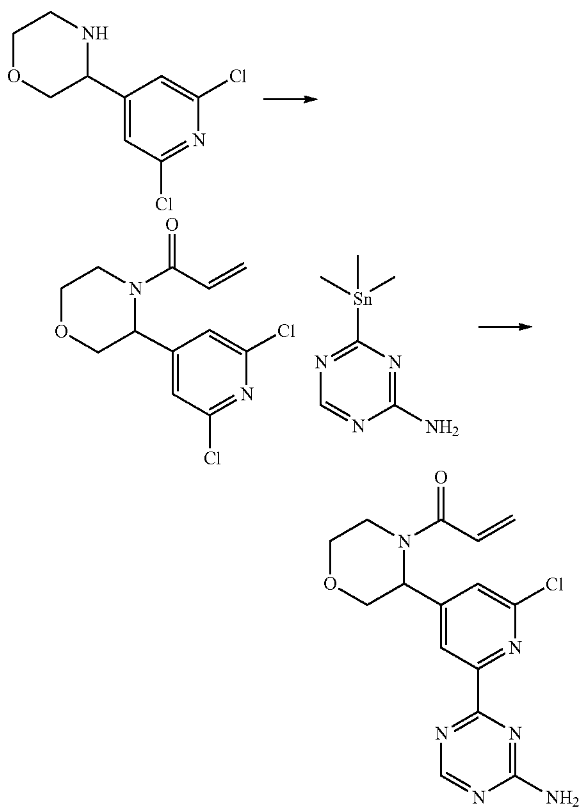

3-(2,6-dichloropyridin-4-yl)morpholine was prepared in a similar fashion to Procedure H starting with 2-aminoethan-1-ol.

To a solution of 3-(2,6-dichloropyridin-4-yl)morpholine (2 g, 8.58 mmol, 1 equiv) in DCM (15 mL, 0.57 M) was added triethylamine (1.302 g, 12.87 mmol, 1.5 equiv) and acryloyl chloride (0.931 g, 10.29 mmol, 1.2 equiv) at 0° C. under $N_2$. The mixture was stirred at 25° C. for 1 hour. The reaction mixture was poured into water (100 mL), extracted with DCM (100 mL×3), washed with brine (100 mL), dried over $Na_2SO_4$, filtered, and concentrated under reduced pressure. The crude residue was purified by column chromatography ($SiO_2$, Petroleum ether/Ethyl acetate=100/1 to 1/1) to give 1-(3-(2,6-dichloropyridin-4-yl)morpholino)prop-2-en-1-one (1.1 g, 3.83 mmol, 45% yield) as a white solid.

To a solution of 4-(trimethylstannyl)-1,3,5-triazin-2-amine (140 mg, 0.54 mmol, 1 equiv) and 1-(3-(2,6-dichloropyridin-4-yl)morpholino)prop-2-en-1-one (232.91 mg, 0.81 mmol, 1.5 equiv) in toluene (5 mL) was added lithium chloride (22.92 mg, 0.54 mmol) under $N_2$. The solution was stirred for 8 hours at 90° C. The reaction mixture was filtered and then concentrated. The residue was purified by prep-HPLC (column: Waters Xbridge C18 150×50 mm×10 um; liquid phase: [A-10 mM $NH_4HCO_3$ in $H_2O$; B-ACN]B %: 20%-40%, 10 min]) to give 1-(3-(2-(4-amino-1,3,5-triazin-2-yl)-6-chloropyridin-4-yl)morpholino)prop-2-en-1-one (15 mg, 0.043 mmol, 8% yield) as a white solid.

Enantiomers were separated by SFC. The title compound's absolute stereochemistry was not assigned. LC-MS m/z: 347.1 [M+1].

Stereochemistry: single enantiomer of unknown absolute configuration.

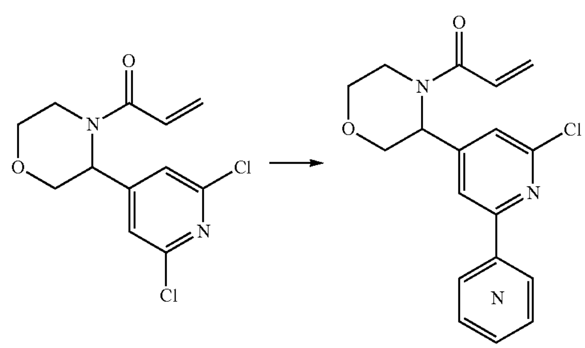

Using the appropriate coupling partner in Procedure 0, the title compounds can be obtained.

| Cmp | Name | Coupling Partner | LC-MS m/z [M + 1] |
|---|---|---|---|
| 146 | 1-(3-(2-(4-amino-1,3,5-triazin-2-yl)-6-chloropyridin-4-yl)morpholino)prop-2-en-1-one | 4-(trimethylstannyl)-1,3,5-triazin-2-amine | 347.1 |
| 119 | 1-(3-(2-(6-aminopyrimidin-4-yl)-6-chloropyridin-4-yl)morpholino)prop-2-en-1-one | tert-butyl (tert-butoxycarbonyl)(6-(trimethylstannyl)pyrimidin-4-yl)carbamate | 346.1 |
| 127 | 1-(3-(2-(6-aminopyrimidin-4-yl)-6-chloropyridin-4-yl)morpholino)prop-2-en-1-one | 4-methyl-6-(trimethylstannyl)pyrimidine | 345.0 |

-continued

| Cmp | Name | Coupling Partner | LC-MS m/z [M + 1] |
|---|---|---|---|
| 125 | 6-(4-(4-acryloylmorpholin-3-yl)-6-chloropyridin-2-yl)pyrimidine-4-carboxamide | 6-(trimethylstannyl)pyrimidine-4-carbonitrile (additional step for hydrolysis to amide) | 374.1 |
| 65 | 5-(4-(4-acryloylmorpholin-3-yl)-6-chloropyridin-2-y1)-2-fluorobenzamide | 2-fluoro-5-(4,4,5,5-tetramethyl-1,3,2-dioxaborolan-2-yl)benzamide | 390.0 |
| 25 | 4-(4-acryloylmorpholin-3-yl)-6-chloro-1'-methyl-[2,4'-bipyridin]-2'(1'H)-one | 1-methyl-4-(4,4,5,5-tetramethyl-1,3,2-dioxaborolan-2-yl)pyridin-2(1H)-one | 360.0 |
| 129 | 6-(4-(4-acryloylmorpholin-3-yl)-6-chloropyridin-2-yl)pyrimidine-4-carbonitrile | 6-(trimethylstannyl)pyrimidine-4-carbonitrile | 356.1 |
| 33 | 4-(4-acryloylmorpholin-3-yl)-6-chloro-[2,4'-bipyridin]-2'(1'H)-one | (2-oxo-1,2-dihydropyridin-4-yl)boronic acid | 346.0 |
| 121 | 1-(3-(2-chloro-6-(2-methylpyrimidin-4-yl)pyridin-4-yl)morpholino)prop-2-en-1-one | 2-methyl-4-(trimethylstannyl)pyrimidine | 345.0 |
| 64 | 1-(3-(2-chloro-6-(imidazo[1,2-a]pyridin-7-yl)pyridin-4-yl)morpholino)prop-2-en-1-one | imidazo[1,2-a]pyridin-7-ylboronic acid | 369.1 |
| 30 | 1-(3-(2-chloro-6-(pyridazin-4-yl)pyridin-4-yl)morpholino)prop-2-en-1-one | 4-(4,4,5,5-tetramethyl-1,3,2-dioxaborolan-2-yl)pyridazine | 331.0 |
| 23 | 1-(3-(2-chloro-6-(2-methyl-2H-tetrazol-5-yl)pyridin-4-yl)morpholino)prop-2-en-1-one | 2-methyl-5-(4,4,5,5-tetramethyl-1,3,2-dioxaborolan-2-y1)-2H-tetrazole (generated in situ) | 335.0 |

Example 71. Procedure P and Synthesis of (R)-1-(5-(3-chloro-5-(5,6-diaminopyrazin-2-yl)phenyl)-2,2-dimethylmorpholino)prop-2-en-1-one (Compound 286)

Procedure P

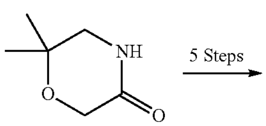

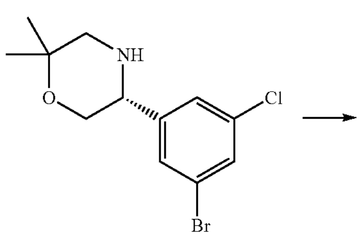

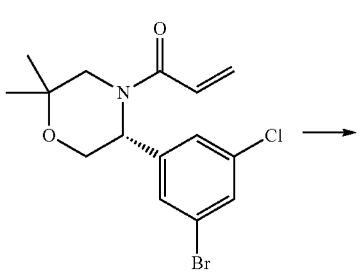

-continued

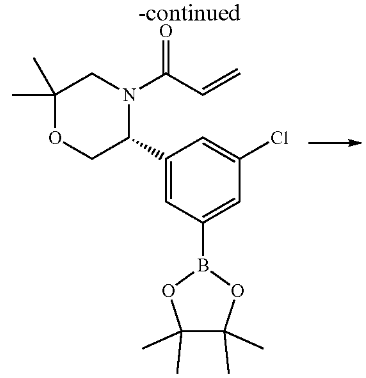

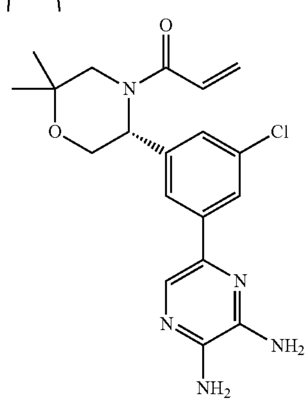

(R)-5-(3-bromo-5-chlorophenyl)-2,2-dimethylmorpholine was obtained from 6,6-dimethylmorpholin-3-one according to Procedure B.

To a solution of (R)-5-(3-bromo-5-chlorophenyl)-2,2-dimethylmorpholine (10 g, 32.82 mmol, 1 equiv) and triethylamine (6.643 g, 65.65 mmol, 2 equiv) in DCM (100 mL, 0.32 M) at 0° C. was added acryloyl chloride (3.268 g, 36.11 mmol, 1.1 equiv). The reaction was stirred at room temperature for 30 minutes. The mixture was poured into ice water (100 mL), extracted with DCM (50 mL*2), washed with brine, dried over $Na_2SO_4$, filtered, and concentrated. The crude product was chromatographed on silica gel (EA/PE 0→50%) to afford (R)-1-(5-(3-bromo-5-chlorophenyl)-2,2-dimethylmorpholino)prop-2-en-1-one (10.30 g, 28.7 mmol, 88% yield) as a yellow solid.

To a solution of afford (R)-1-(5-(3-bromo-5-chlorophenyl)-2,2-dimethylmorpholino)prop-2-en-1-one (10.3 g, 28.71 mmol, 1 equiv) and bis(pinacolato)diboron (8.021 g, 31.59 mmol, 1.1 equiv) in 1,4-dioxane (100 mL, 0.28 M) was added potassium acetate (5.636 g, 57.46 mmol, 2 equiv) and Pd(dppf)$Cl_2$ (2.084 g, 2.87 mmol, 0.1 equiv). The mixture and was stirred at 90° C. under $N_2$ for 4 hours. The reaction was poured into $H_2O$ (100 mL) and the aqueous layer was extracted with ethyl acetate (50 mL×3). The combined organic layer was washed with brine (100 mL), dried over $Na_2SO_4$, filtered, and concentrated under vacuum. The crude product was chromatographed on silica gel (EA/PE 0-1:1) to give the (R)-1-(5-(3-chloro-5-(4,4,5,5-tetramethyl-1,3,2-dioxaborolan-2-yl)phenyl)-2,2-dimethylmorpholino)prop-2-en-1-one (9.00 g, 22.2 mmol, 77% yield) as a brown oil.

To a solution of (R)-1-(5-(3-chloro-5-(4,4,5,5-tetramethyl-1,3,2-dioxaborolan-2-yl)phenyl)-2,2-dimethylmorpholino)prop-2-en-1-one (50 mg, 0.123 mmol, 1 equiv) and 5-bromopyrazine-2,3-diamine (23 mg, 0.12 mmol, 1 equiv) in 1,4-dioxane (2 mL, 0.05 M) and water (0.50 mL, 0.05 M) was added potassium phosphate tribasic (78 mg, 0.36 mmol, 3 equiv) and [1,1'-Bis(di-tert-butylphosphino)ferrocene]dichloropalladium(II) (7.9 mg, 0.012 mmol, 0.1 equiv) under $N_2$. The reaction was stirred at 90° C. for 16 hours. The mixture was poured into water (20 mL), extracted with ethyl acetate (10 mL*2), washed with brine, dried over $Na_2SO_4$, filtered, and concentrated under vacuum. The crude product was purified by prep-HPLC ($NH_4HCO_3$) to obtain (R)-1-(5-(3-chloro-5-(5,6-diaminopyrazin-2-yl)phenyl)-2,2-dimethylmorpholino)prop-2-en-1-one (13 mg, 0.033 mmol, 27% yield) as a yellow solid. LC-MS m/z: 388.1 [M+1].

Stereochemistry: single enantiomer of known absolute configuration.

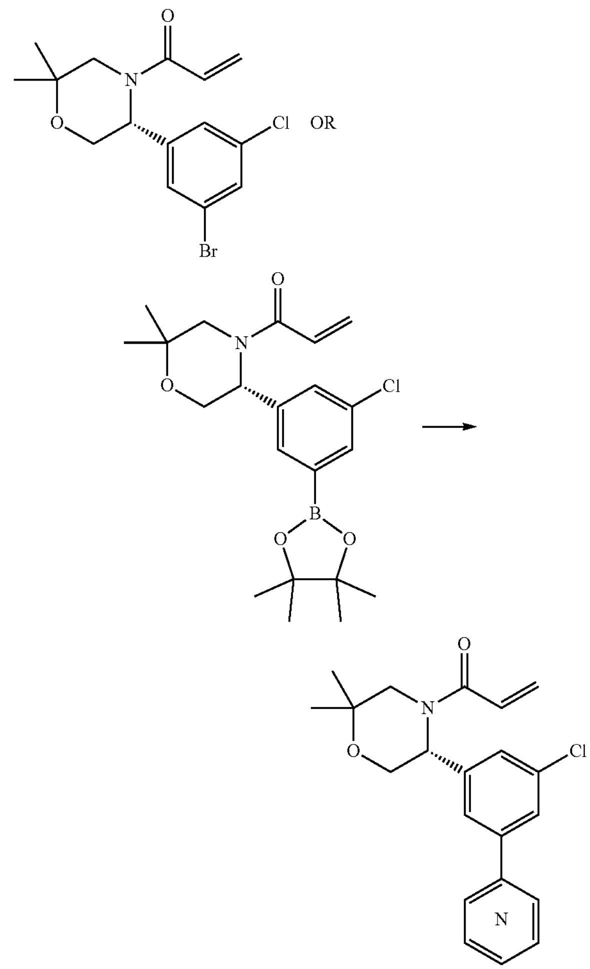

Using the appropriate coupling partner in Procedure P, the title compounds can be obtained.

| Cmp | Name | Coupling Partner | LC-MS m/z [M + 1] |
|---|---|---|---|
| 286 | (R)-1-(5-(3-chloro-5-(5,6-diaminopyrazin-2-yl)phenyl)-2,2-dimethylmorpholino)prop-2-en-1-one | 5-bromopyrazine-2,3-diamine (B) | 388.1 |
| 287 | (R)-1-(5-(3-chloro-5-(4,5-diaminopyrimidin-2-yl)phenyl)-2,2-dimethylmorpholino)prop-2-en-1-one | 2-chloropyrimidine-4,5-diamine (B) | 388.1 |
| 155 | (R)-1-(5-(3-(4-aminopyrimidin-2-y1)-5-chlorophenyl)-2,2-dimethylmorpholino)prop-2-en-1-one | 2-chloropyrimidin-4-amine (B) | 373.1 |
| 149 | (R)-1-(5-(3-(6-aminopyrimidin-4-y1)-5-chlorophenyl)-2,2-dimethylmorpholino)prop-2-en-1-one | 6-chloropyrimidin-4-amine (B) | 373.1 |
| 148 | (R)-1-(5-(3-(2-aminopyrimidin-4-y1)-5-chlorophenyl)-2,2-dimethylmorpholino)prop-2-en-1-one | 4-chloropyrimidin-2-amine (B) | 373.1 |
| 133 | (R)-4-(3-(4-acryloyl-6,6-dimethylmorpholin-3-yl)-5-chlorophenyl)picolinamide | 4-bromopicolinamide (B) | 400.1 |
| 66 | (R)-1-(5-(3-(4-amino-1,3,5-triazin-2-yl)-5-chlorophenyl)-2,2-dimethylmorpholino)prop-2-en-1-one | 4-chloro-1,3,5-triazin-2-amine (B) | 374.1 |
| 61 | (R)-3'-(4-acryloyl-6,6-dimethylmorpholin-3-y1)-5'-chloro-4-fluoro-[1,1'-biphenyl]-3-carboxamide | 5-bromo-2-fluorobenzamide (B) | 417.1 |
| 48 | (R)-1-(5-(3-chloro-5-(2-methylpyrimidin-4-yl)phenyl)-2,2-dimethylmorpholino)prop-2-en-1-one | 4-chloro-2-methylpyrimidine | 372.0 |
| 47 | (R)-1-(5-(3-chloro-5-(quinoxalin-6-yl)phenyl)-2,2-dimethylmorpholino)prop-2-en-1-one | 6-bromoquinoxaline | 408.1 |

-continued

| Cmp | Name | Coupling Partner | LC-MS m/z [M + 1] |
|---|---|---|---|
| 46 | (R)-1-(5-(3-chloro-5-(6-methylpyrimidin-4-yl)phenyl)-2,2-dimethylmorpholino)prop-2-en-1-one | 4-bromo-6-methylpyrimidine | 372.1 |
| 45 | (R)-1-(5-(3-chloro-5-(5-fluoropyrimidin-2-yl)phenyl)-2,2-dimethylmorpholino)prop-2-en-1-one | 2-bromo-5-fluoropyrimidine | 376.1 |

Example 72. Synthesis of (R)-1-(5-(3-(5-aminopyrimidin-2-yl)-5-chlorophenyl)-2,2-dimethylmorpholino)prop-2-en-1-one (Compound 156)

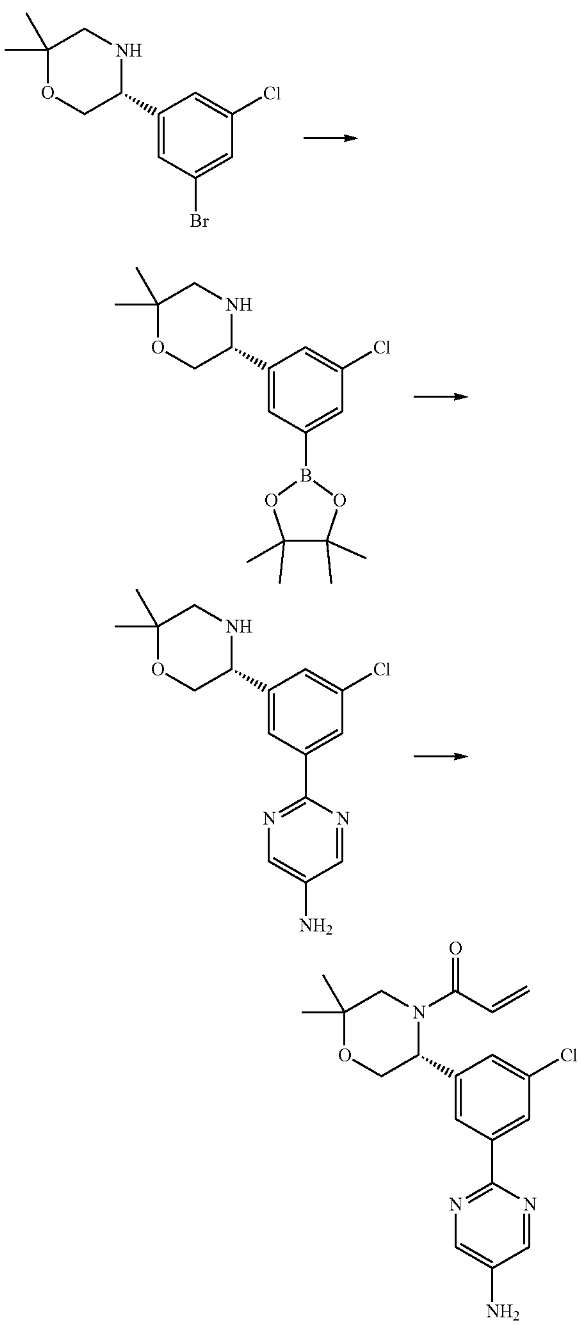

(R)-5-(3-bromo-5-chlorophenyl)-2,2-dimethylmorpholine was obtained from 6,6-dimethylmorpholin-3-one according to Procedure B.

To a solution of (R)-5-(3-bromo-5-chlorophenyl)-2,2-dimethylmorpholine (1 g, 3.28 mmol, 1 equiv) and bis(pinacolato)diboron (1 g, 3.94 mmol, 1.2 equiv) in 2-MeTHF (10 mL) was added potassium acetate (0.64 g, 6.56 mmol, 2 equiv) and Pd(dppf)$Cl_2$ (0.119 g, 0.16 mmol, 0.05 equiv). The mixture was stirred at 80° C. under $N_2$ for 16 hours. The reaction was diluted with $H_2O$ (20 mL) and extracted with ethyl acetate (10 mL*3). The combined organic phase was washed with brine, dried over anhydrous $Na_2SO_4$, filtered, and concentrated to afford crude (R)-5-(3-chloro-5-(4,4,5,5-tetramethyl-1,3,2-dioxaborolan-2-yl)phenyl)-2,2-dimethylmorpholine (1.15 g, 3.27 mmol, 99% yield) as a brown oil.

To a solution of (R)-5-(3-chloro-5-(4,4,5,5-tetramethyl-1,3,2-dioxaborolan-2-yl)phenyl)-2,2-dimethylmorpholine (500 mg, 1.42 mmol, 1 equiv) and 5-amino-2-chloropyrimidine (221 mg, 1.70 mmol, 1.2 equiv) in 1,4-dioxane (8 mL, 0.14 M) and water (2 mL, 0.14 M) was added potassium carbonate (393 mg, 2.84 mmol, 2 equiv) and Pd(dppf)$Cl_2$ (51.5 mg, 0.07 mmol, 0.05 equiv). The solution was stirred at 100° C. under $N_2$ for 18 hours. The mixture was filtered, concentrated, taken up into $H_2O$ (30 mL), and extracted with EtOAc (10 mL*3). The solution was dried over $Na_2SO_4$, filtered, and concentrated under reduced pressure. The residue was purified by prep-TLC (PE:EA=0:1) to afford (R)-2-(3-chloro-5-(6,6-dimethylmorpholin-3-yl)phenyl)pyrimidin-5-amine (160 mg, 0.50 mmol, 35% yield) as a white solid.

Acryloyl chloride (45 mg, 0.50 mmol, 1 equiv) in MeCN (1 mL, 0.17 M) was added dropwise to a solution of (R)-2-(3-chloro-5-(6,6-dimethylmorpholin-3-yl)phenyl)pyrimidin-5-amine (160 mg, 0.50 mmol) and triethylamine (101 mg, 1 mmol, 2 equiv) in MeCN (2 mL, 0.16 M) at −15° C. and then stirred for 30 minutes. The mixture was concentrated under vacuum. The residue was purified by prep-HPLC (column: Waters Xbridge Prep OBD C18 150*40 mm*10 um; liquid phase: [A-10 mM $NH_4HCO_3$ in $H_2O$; B-ACN]) to afford (R)-1-(5-(3-(5-aminopyrimidin-2-yl)-5-chlorophenyl)-2,2-dimethylmorpholino)prop-2-en-1-one (40 mg, 0.107 mmol, 21% yield) as a white solid. LC-MS m/z: 373.2 [M+1].

Stereochemistry: single enantiomer of known absolute configuration.

Example 73. Procedure 0 and Synthesis of 5-(4-(4-acryloyl-6,6-dimethylmorpholin-3-yl)-6-chloropyridin-2-yl)-2-fluorobenzamide (Compound 69)

Procedure Q

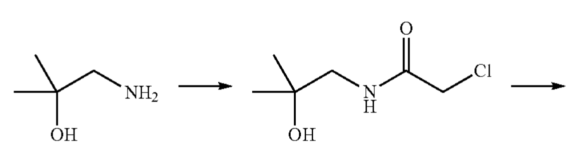

-continued

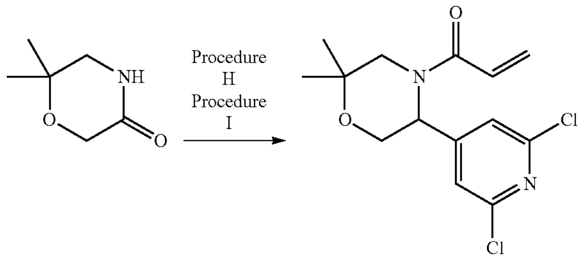

To a solution of 1-amino-2-methyl-propan-2-ol (50 g, 560.92 mmol, 1 equiv) in DCM (1000 mL, 0.56 M) was added 2M aqueous NaOH (50 mL) and chloroacetyl chloride (63.350 g, 560.92 mmol, 1 equiv) at 0° C. under $N_2$ and stirred for 2 hours. The reaction mixture was quenched with the water (200 mL) and extracted with DCM/isopropanol (3/1) (300*2 mL). The organic phase was dried over $Na_2SO_4$, filtered, and concentrated to afford 2-chloro-N-(2-hydroxy-2-methylpropyl)acetamide (62 g, 374.3 mmol, 67% yield) as a colorless oil.

To a solution of 2-chloro-N-(2-hydroxy-2-methylpropyl) acetamide (62 g, 374.35 mmol, 1 equiv) in isopropanol (500 mL) was added potassium tert-butoxide (84.012 g, 748.7 mmol, 2 equiv) at 25° C. under $N_2$ and then stirred for 2 hours. The reaction mixture was quenched with water (200 mL) and extracted with DCM/isopropanol (3/1) (200*2 mL). The organic phase was dried over $Na_2SO_4$, filtered, and concentrated. The crude product was purified was by flash silica gel chromatography (EA:PE=0-60%) to give 6,6-dimethylmorpholin-3-one (8.5 g, 65.81 mmol, 18% yield) as a yellow oil.

1-(5-(2,6-dichloropyridin-4-yl)-2,2-dimethylmorpholino) prop-2-en-1-one was obtained by using 6,6-dimethylmorpholin-3-one in Procedures H and I.

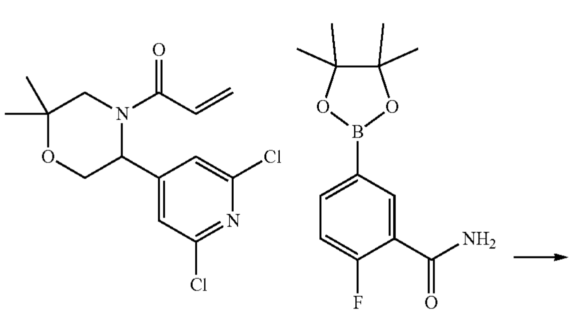

-continued

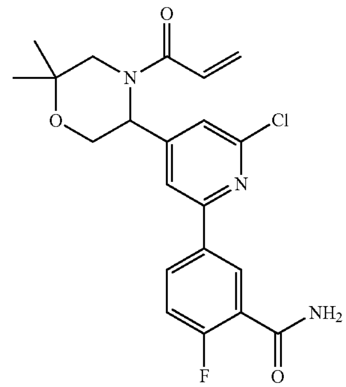

To a solution of 1-(5-(2,6-dichloropyridin-4-yl)-2,2-dimethylmorpholino)prop-2-en-1-one (0.30 g, 0.95 mmol, 1 equiv) in 1,4-dioxane (2.4 mL, 0.15 M), MeCN (2.4 mL, 0.15 M) and water (1.2 mL, 0.15 M) was added 2-fluoro-5-(4,4,5,5-tetramethyl-1,3,2-dioxaborolan-2-yl)benzamide (252.31 mg, 0.95 mmol, 1 equiv), Pd(dppf)$Cl_2$ (69 mg, 0.0952 mmol, 0.10 equiv), and potassium carbonate (263.09 mg, 1.90 mmol, 2 equiv) at room temperature under $N_2$. The reaction was stirred at 80° C. for 16 hours. The reaction solution was filtered and then evaporated under reduced pressure. The crude product was purified by prep-TLC to give 5-(4-(4-acryloyl-6,6-dimethylmorpholin-3-yl)-6-chloropyridin-2-yl)-2-fluorobenzamide (140 mg, 0.33 mmol, 35% yield) as a colorless oil.

Enantiomers were separated by SFC [Column: REGIS(s, s) WHELK-O1 (250 mm*30 mm, 10 um), CO2 and EtOH). The title compound's absolute stereochemistry was not assigned. LC-MS m/z: 487.1 [M+1].

Stereochemistry: single enantiomer of unknown absolute configuration.

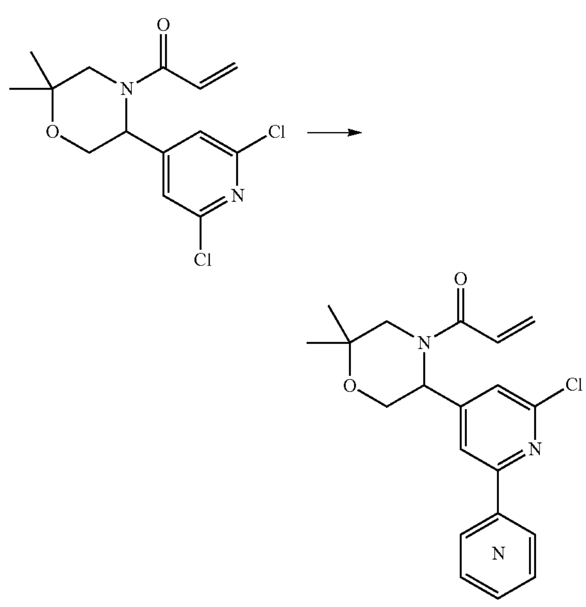

Using the appropriate coupling partner in Procedure Q, the title compounds can be obtained.

| Cmp | Name | Coupling Partner | LC-MS m/z [M + 1] |
|---|---|---|---|
| 69 | 5-(4-(4-acryloyl-6,6-dimethylmorpholin-3-yl)-6-chloropyridin-2-yl)-2-fluorobenzamide | 2-fluoro-5-(4,4,5,5-tetramethyl-1,3,2-dioxaborolan-2-yl)benzamide | 487.1 |
| 150 | 1-(5-(2-(6-aminopyrimidin-4-yl)-6-chloropyridin-4-yl)-2,2-dimethylmorpholino)prop-2-en-1-one | 6-(trimethylstannyl)pyrimidin-4-amine | 374.1 |
| 99 | 1-(5-(2-(2-aminopyrimidin-4-yl)-6-chloropyridin-4-y1)-2,2-dimethylmorpholino)prop-2-en-1-one | 4-(trimethylstannyl)pyrimidin-2-amine | 374.1 |
| 78 | 1-(5-(2-chloro-6-(imidazo[1,2-a]pyridin-7-yl)pyridin-4-yl)-2,2-dimethylmorpholino)prop-2-en-1-one | 7-(4,4,5,5-tetramethyl-1,3,2-dioxaborolan-2-yl)imidazo[1,2-a]pyridine | 397.1 |
| 120 | 1-(5-(2-chloro-6-(2-methylpyrimidin-4-yl)pyridin-4-yl)-2,2-dimethylmorpholino)prop-2-en-1-one | 2-methyl-4-(trimethylstannyl)pyrimidine | 373.0 |

Example 74. Procedure R and Synthesis of 3'-(7-acryloyl-4-oxa-7-azaspiro[2.5]octan-6-yl)-5'-chloro-4-fluoro-[1,1'-biphenyl]-3-carboxamide (Compound 76)

Procedure R

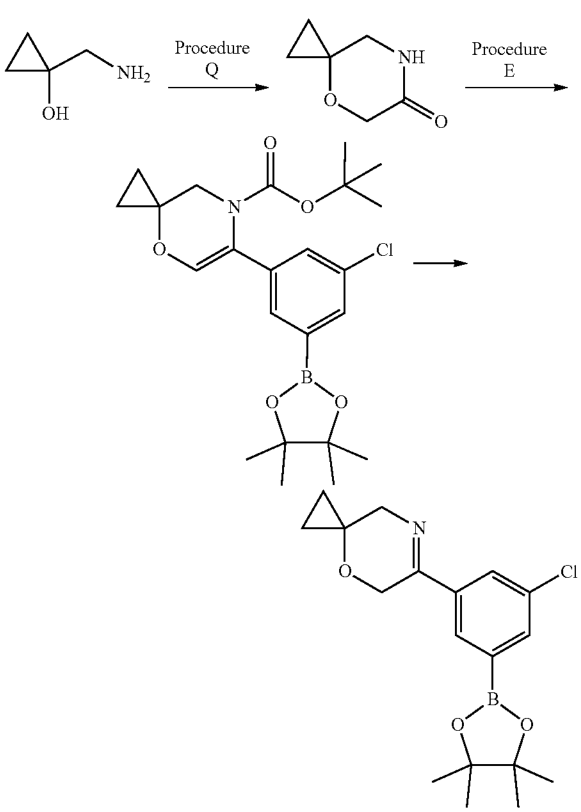

tert-butyl 6-(3-chloro-5-(4,4,5,5-tetramethyl-1,3,2-dioxaborolan-2-yl)phenyl)-4-oxa-7-azaspiro[2.5]oct-5-ene-7-carboxylate was obtained using Procedures Q and E with 1-(aminomethyl)cyclopropan-1-ol.

To a solution of tert-butyl 6-(3-chloro-5-(4,4,5,5-tetramethyl-1,3,2-dioxaborolan-2-yl)phenyl)-4-oxa-7-azaspiro [2.5]oct-5-ene-7-carboxylate (1.5 g, 3.35 mmol, 1 equiv) in ethyl acetate (10 mL, 0.33 M) was added HCl in EtOAc (10 mL). The mixture was stirred at 20° C. for 5 hours and then concentrated to give 6-(3-chloro-5-(4,4,5,5-tetramethyl-1,3,2-dioxaborolan-2-yl)phenyl)-4-oxa-7-azaspiro[2.5]oct-6-ene (800 mg, 2.30 mmol, 69% yield) as a yellow solid.

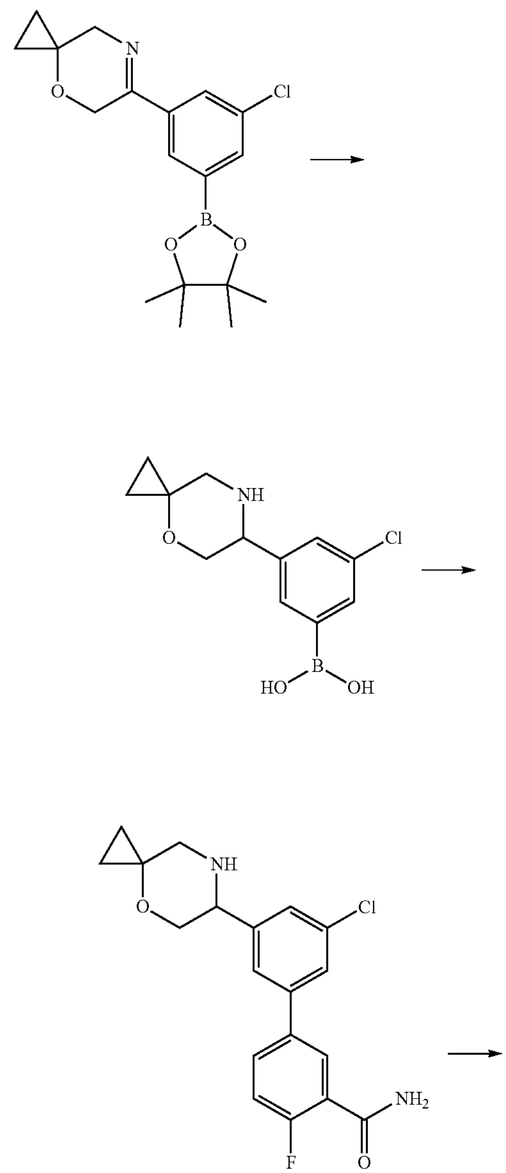

-continued

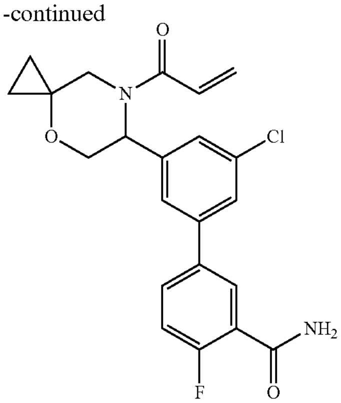

To a solution of 6-(3-chloro-5-(4,4,5,5-tetramethyl-1,3,2-dioxaborolan-2-yl)phenyl)-4-oxa-7-azaspiro[2.5]oct-6-ene (900 mg, 3.89 mmol) in methanol (10 mL, 0.34 M) was added sodium cyanoborohydride (852 mg, 13.55 mmol) under $N_2$ and stirred at 20° C. for 1.5 hours. The solution was diluted with $H_2O$ (20 mL), extracted with EtOAc (20 mL*3), washed with brine (5 mL), dried over $Na_2SO_4$, filtered, and concentrated under vacuum to afford crude (3-chloro-5-(4-oxa-7-azaspiro[2.5]octan-6-yl)phenyl)boronic acid (850 mg, 2.99 mmol, 88% yield).

To a solution of (3-chloro-5-(4-oxa-7-azaspiro[2.5]octan-6-yl)phenyl)boronic acid (780 mg, 2.92 mmol, 1 equiv) in 1,4-dioxane (2 mL, 1.21 M) was added 5-bromo-2-fluorobenzamide (635.67 mg, 2.91 mmol, 1 equiv). The mixture was stirred at 80° C. under $N_2$ atmosphere for 16 hrs. The mixture was quenched by water and extracted with EtOAc. The organic solution was dried over $Na_2SO_4$, filtered, and concentrated to give 3'-chloro-4-fluoro-5'-(4-oxa-7-azaspiro[2.5]octan-6-yl)-[1,1'-biphenyl]-3-carboxamide (700 mg, 1.94 mmol, 67% yield).

To a solution of 3'-chloro-4-fluoro-5'-(4-oxa-7-azaspiro[2.5]octan-6-yl)-[1,1'-biphenyl]-3-carboxamide (200 mg, 0.55 mmol, 1 equiv) in DCM (3 mL, 0.18 M) was added acryloyl chloride (50.17 mg, 0.55 mmol, 1 equiv). The mixture was stirred at 20° C. under $N_2$ atmosphere for 2 hours. The mixture was quenched by water and extracted with EtOAc. The organic was dried over $Na_2SO_4$, filtered, and concentrated. The residue was purified by prep-HPLC (column: Nano-micro Kromasil C18 100*30 mm 5 um; mobile phase: [water (0.1% TFA)-ACN]; B %: 40%-60%, 2 min) to give the racemic product and then separated by SFC to give 3'-(7-acryloyl-4-oxa-7-azaspiro[2.5]octan-6-yl)-5'-chloro-4-fluoro-[1,1'-biphenyl]-3-carboxamide (33.6 mg, 0.081 mmol, 15% yield) as a yellow solid.

Enantiomers were separated by SFC [Column: REGIS(s, s) WHELK-O1 (250 mm*30 mm, 10 um) CO2 and EtOH]. LC-MS m/z: 415.0 [M+1].

Stereochemistry: single enantiomer of unknown absolute configuration.

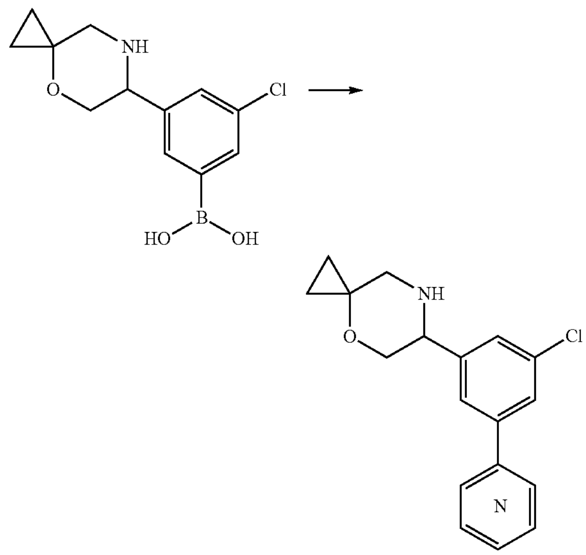

Using the appropriate coupling partner in Procedure Q, the title compounds can be obtained.

| Cmp | Name | Coupling Partner | LC-MS m/z [M + 1] |
|---|---|---|---|
| 76 | 3'-(7-acryloyl-4-oxa-7-azaspiro[2.5]octan-6-yl)-5'-chloro-4-fluoro-[1,1'-biphenyl]-3-carboxamide | 5-bromo-2-fluoro-benzamide | 415.0 |
| 153 | 1-(6-(3-(4-amino-1,3,5-triazin-2-yl)-5-chlorophenyl)-4-oxa-7-azaspiro[2.5]octan-7-yl)prop-2-en-1-one | 4-chloro-1,3,5-triazin-2-amine | 372.0 |
| 84 | 1-(6-(3-(2-aminopyrimidin-4-yl)-5-chlorophenyl)-4-oxa-7-azaspiro[2.5]octan-7-yl)prop-2-en-1-one | 4-bromopyrimidin-2-amine | 371.0 |
| 122 | 4-(3-(7-acryloyl-4-oxa-7-azaspiro[2.5]octan-6-yl)-5-chlorophenyl)picolinamide | 4-bromopicolinamide | 398.0 |
| 83 | 1-(6-(3-chloro-5-(2-methylpyrimidin-4-yl)phenyl)-4-oxa-7-azaspiro[2.5]octan-7-yl)prop-2-en-1-one | 4-chloro-2-methylpyrimidine | 370.0 |
| 140 | 1-(6-(3-(6-aminopyrimidin-4-yl)-5-chlorophenyl)-4-oxa-7-azaspiro[2.5]octan-7-yl)prop-2-en-1-one | 6-bromopyrimidin-4-amine | 371.0 |

Example 75. Synthesis of Compounds 174 and 175

Enantiomer 1: 1-(6-(2-(6-aminopyrimidin-4-yl)-6-chloropyridin-4-yl)-4-oxa-7-azaspiro[2.5]octan-7-yl)prop-2-en-1-one Enantiomer 2: 1-(6-(2-(6-aminopyrimidin-4-yl)-6-chloropyridin-4-yl)-4-oxa-7-azaspiro[2.5]octan-7-yl)prop-2-en-1-one

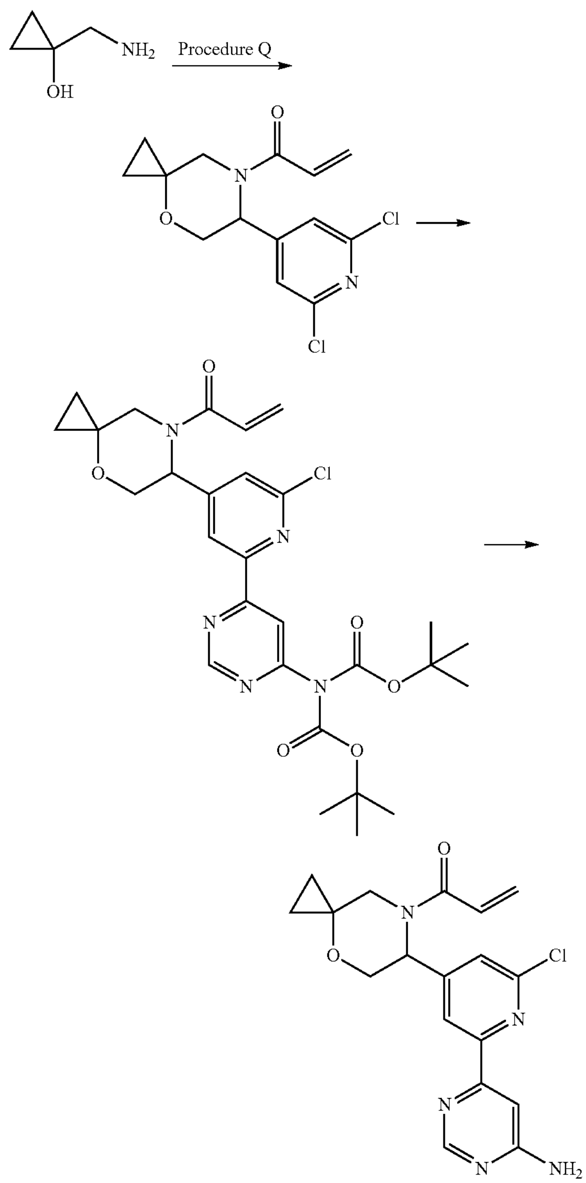

1-(6-(2,6-dichloropyridin-4-yl)-4-oxa-7-azaspiro[2.5]octan-7-yl)prop-2-en-1-one was obtained according to Procedure Q using 1-(aminomethyl)cyclopropan-1-ol.

To a solution of 1-(6-(2,6-dichloropyridin-4-yl)-4-oxa-7-azaspiro[2.5]octan-7-yl)prop-2-en-1-one (200 mg, 0.63 mmol, 1 equiv) in 1,4-dioxane (5 mL, 0.12 M) was added tert-butyl N-tert-butoxycarbonyl-N-(6-trimethylstannylpyrimidin-4-yl)carbamate (292 mg, 0.63 mmol, 1 equiv) and $Pd(PPh_3)_4$(73 mg, 0.063 mmol, 0.10 equiv) at 25° C. The resulting mixture was stirred at 100° C. for 16 hours. The reaction mixture was poured into water (15 mL) and extracted with EtOAc (15 mL*3). The combined organic layers were washed with brine (10 mL*2), dried over $Na_2SO_4$, filtered, and concentrated under reduced pressure. The residue was purified by flash silica gel chromatography (ISCO®; 12 g SEPAFLASH® Silica Flash Column, Eluent of 10-50% Ethyl acetate/Petroleum ether gradient @ 60 mL/min) to afford tert-butyl (6-(4-(7-acryloyl-4-oxa-7-azaspiro[2.5]octan-6-yl)-6-chloropyridin-2-yl)pyrimidin-4-yl)(tert-butoxycarbonyl)carbamate (125 mg, 0.22 mmol, 34% yield) as a yellow oil.

To a solution of tert-butyl (6-(4-(7-acryloyl-4-oxa-7-azaspiro[2.5]octan-6-yl)-6-chloropyridin-2-yl)pyrimidin-4-yl)(tert-butoxycarbonyl)carbamate (125 mg, 0.22 mmol, 1 equiv) in DCM (3 mL, 0.054 M) was added TFA (1 mL, 0.054 M) at 25° C. and allowed to stir for 16 hours. The reaction mixture was concentrated under reduced pressure. The residue was purified by prep-HPLC (column: Phenomenex C18 80*40 mm*3 um; liquid phase: [A-10 mM $NH_4HCO_3$ in $H_2O$; B-ACN]B %: 15%-35%, 8 min]) to afford 1-(6-(2-(6-aminopyrimidin-4-yl)-6-chloropyridin-4-yl)-4-oxa-7-azaspiro[2.5]octan-7-yl)prop-2-en-1-one (50 mg, 0.134 mmol, 62% yield) as a white solid.

Enantiomers were separated by SFC to afford Compound 174 (10.2 mg) and Compound 175 (13 mg). The title compound's absolute stereochemistry was not assigned. LC-MS m/z: 372.1 [M+1] and LC-MS m/z: 372.1 [M+1].

Stereochemistry: single enantiomer of unknown absolute configuration.

Example 76. Synthesis of 1-(6-(2-chloro-6-(imidazo[1,2-a]pyridin-7-yl)pyridin-4-yl)-4-oxa-7-azaspiro[2.5]octan-7-yl)prop-2-en-1-one (Compound 190)

The title compound was obtained in a similar fashion as Compound 174 using 7-(4,4,5,5-tetramethyl-1,3,2-dioxaborolan-2-yl)imidazo[1,2-a]pyridine.

Enantiomers were separated by SFC. The title compound's absolute stereochemistry was not assigned. LC-MS m/z: 395.1 [M+1].

Stereochemistry: single enantiomer of unknown absolute configuration.

Example 77. Synthesis of 3'-((3R,6R)-4-acryloyl-6-methylmorpholin-3-yl)-5'-chloro-4-fluoro-[1,1'-biphenyl]-3-carboxamide (Compound 179)

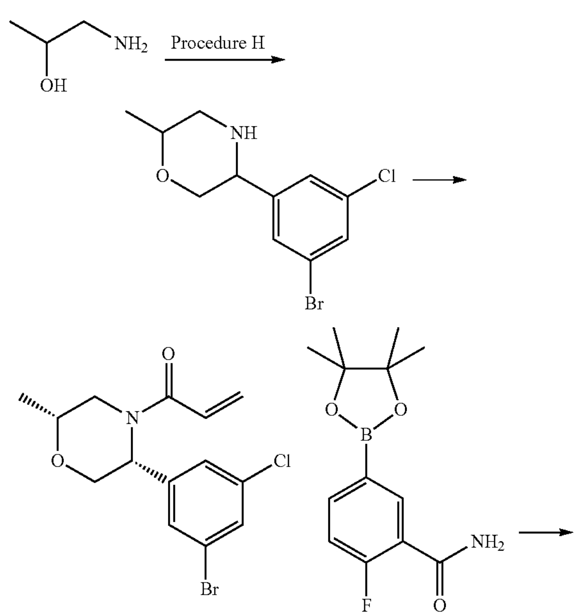

-continued

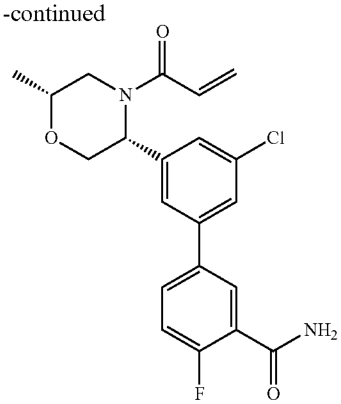

5-(3-bromo-5-chlorophenyl)-2-methylmorpholine can be obtained in a similar fashion to Procedure H and Procedure I using 1-aminopropan-2-ol.

To a solution of 5-(3-bromo-5-chlorophenyl)-2-methylmorpholin (250 mg, 0.86 mmol, 1 equiv) in DCM (5 mL, 0.17 M) was added N,N-diisopropylethylamine (0.224 mL, 1.29 mmol, 1.5 equiv) and acryloyl chloride (116 mg, 1.29 mmol, 1.5 equiv) at 0° C. The mixture was stirred for 30 minutes at 25° C. The reaction mixture was quenched with water (10 mL) and extracted with EtOAc (20 mL×2). The combined organic layer was washed with brine (10 mL), dried over $Na_2SO_4$, filtered, and concentrated. The crude product was purified by prep-TLC (petroleum ether: EtOAc=2:1). The mixture was separated by SFC to afford 100 mg of this unassigned cis enantiomer.

The title compound was obtained using Procedure P and 2-fluoro-5-(4,4,5,5-tetramethyl-1,3,2-dioxaborolan-2-yl) benzamide. LC-MS m/z: 403.1 [M+1].

Stereochemistry: single enantiomer of unknown absolute configuration.

Example 78. Synthesis of 3'-((3R,6S)-4-acryloyl-6-methylmorpholin-3-yl)-5'-chloro-4-fluoro-[1,1'-biphenyl]-3-carboxamide (Compound 182)

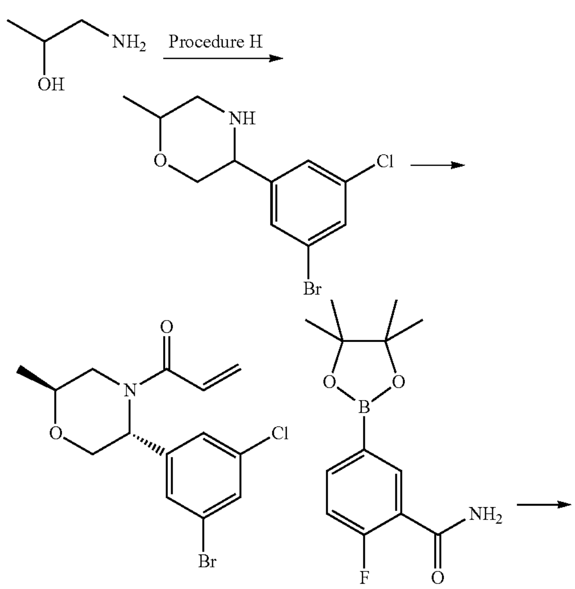

-continued

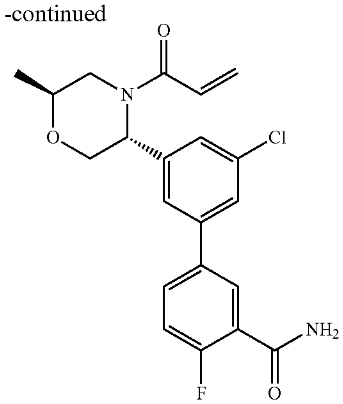

5-(3-bromo-5-chlorophenyl)-2-methylmorpholine can be obtained in a similar fashion to Procedure H and Procedure I using 1-aminopropan-2-ol.

To a solution of 5-(3-bromo-5-chlorophenyl)-2-methylmorpholin (250 mg, 0.86 mmol, 1 equiv) in DCM (5 mL, 0.17 M) was added N,N-diisopropylethylamine (0.224 mL, 1.29 mmol, 1.5 equiv) and acryloyl chloride (116 mg, 1.29 mmol, 1.5 equiv) at 0° C. The mixture was stirred for 30 minutes at 25° C. The reaction mixture was quenched with water (10 mL) and extracted with EtOAc (20 mL×2). The combined organic layer was washed with brine (10 mL) and dried over $Na_2SO_4$, filtered, and concentrated. The crude product was purified by prep-TLC (petroleum ether: EtOAc=2:1). The mixture was separated by SFC to afford 25 mg of this single unassigned trans enantiomer.

3'-((3R,6S)-4-acryloyl-6-methylmorpholin-3-yl)-5'-chloro-4-fluoro-[1,1'-biphenyl]-3-carboxamide was obtained using Procedure P and 2-fluoro-5-(4,4,5,5-tetramethyl-1,3,2-dioxaborolan-2-yl)benzamide. LC-MS m/z: 403.1 [M+1].

Stereochemistry: single enantiomer of unknown absolute configuration.

Example 79. Synthesis of 5-(4-((3R,5S)-4-acryloyl-5-(difluoromethyl)morpholin-3-yl)-6-chloropyridin-2-yl)-2-fluorobenzamide (Compound 180)

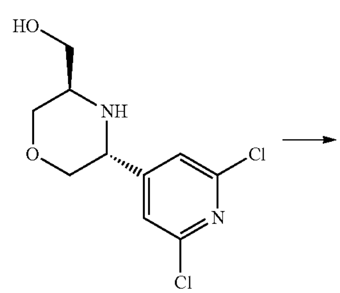

-continued

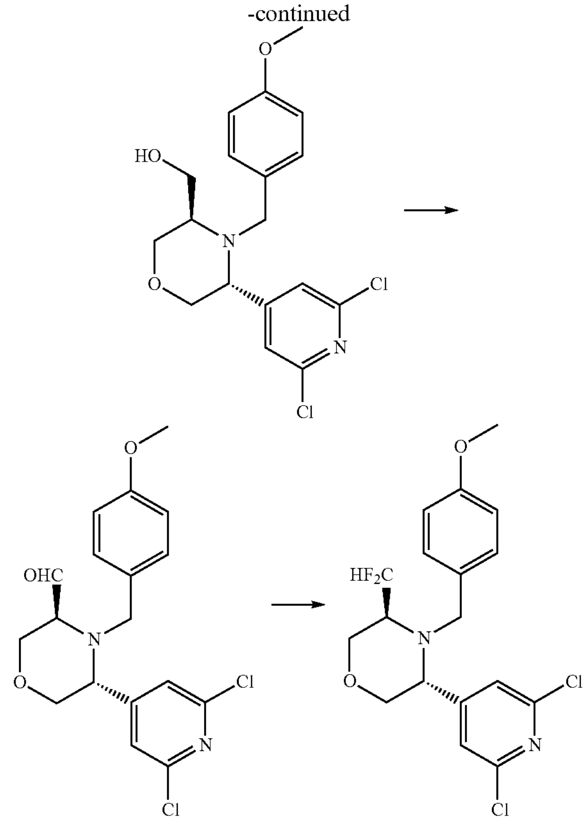

((3R,5R)-5-(2,6-dichloropyridin-4-yl)morpholin-3-yl) methanol was obtained from Procedure J.

To a solution of ((3R,5R)-5-(2,6-dichloropyridin-4-yl) morpholin-3-yl)methanol (100 mg, 0.38 mmol, 1 equiv) in DMF (1 mL, 0.38 M) was added 4-methoxybenzyl chloride (59.52 mg, 0.38 mmol, 1 equiv) and NaI (40 mg, 1 equiv) and then stirred at 80° C. for 12 hours. The reaction was quenched by $H_2O$ (5 mL) and extracted with EtOAc (5 mL×3). The organic phases were dried with $Na_2SO_4$, filtered, and concentrated. The residue was purified by prep TLC (PE/EA=2/1) to afford ((3R,5R)-5-(2,6-dichloropyridin-4-yl)-4-(4-methoxybenzyl)morpholin-3-yl)methanol (56 mg, 0.15 mmol, 38% yield).

To a solution of ((3R,5R)-5-(2,6-dichloropyridin-4-yl)-4-(4-methoxybenzyl)morpholin-3-yl)methanol (1 g, 2.61 mmol, 1 equiv) in DCM (10 mL, 0.26 M) was added DMP (2 eq, 2.2 g) at 0° C. The resulting mixture was stirred at 25° C. for 3 hours. The reaction mixture was quenched with $Na_2S_2O_3$ (4 g) and poured into saturated aqueous $NaHCO_3$ (20 mL). The resulting mixture was stirred at 25° C. for 30 minutes and then extracted with DCM (20 mL*3). The combined organic layers were washed with brine (20 mL), dried over $Na_2SO_4$, filtered, and concentrated under reduced pressure to afford (3S,5R)-5-(2,6-dichloropyridin-4-yl)-4-(4-methoxybenzyl)morpholine-3-carbaldehyde (990 mg, 2.60 mmol, 99% yield).

To a solution of (3S,5R)-5-(2,6-dichloropyridin-4-yl)-4-(4-methoxybenzyl)morpholine-3-carbaldehyde (1 g, 2.62 mmol, 1 equiv) in DCM (10 mL, 0.26 M) was added DAST (2 eq, 844 mg) at 0° C. The resulting mixture was stirred at 25° C. for 30 minutes. The reaction mixture was poured into $H_2O$ (5 mL) and extracted with EtOAc (10 mL*3). The combined organic layers were washed with brine (10 mL), dried over $Na_2SO_4$, filtered, and concentrated under reduced pressure. The residue was purified by column chromatography (SiO2, Petroleum ether/Ethyl acetate=1/0 to 0/1) to afford (3R,5S)-3-(2,6-dichloropyridin-4-yl)-5-(difluoromethyl)-4-(4-methoxybenzyl)morpholine (400 mg, 0.99 mmol, 38% yield) as a white solid.

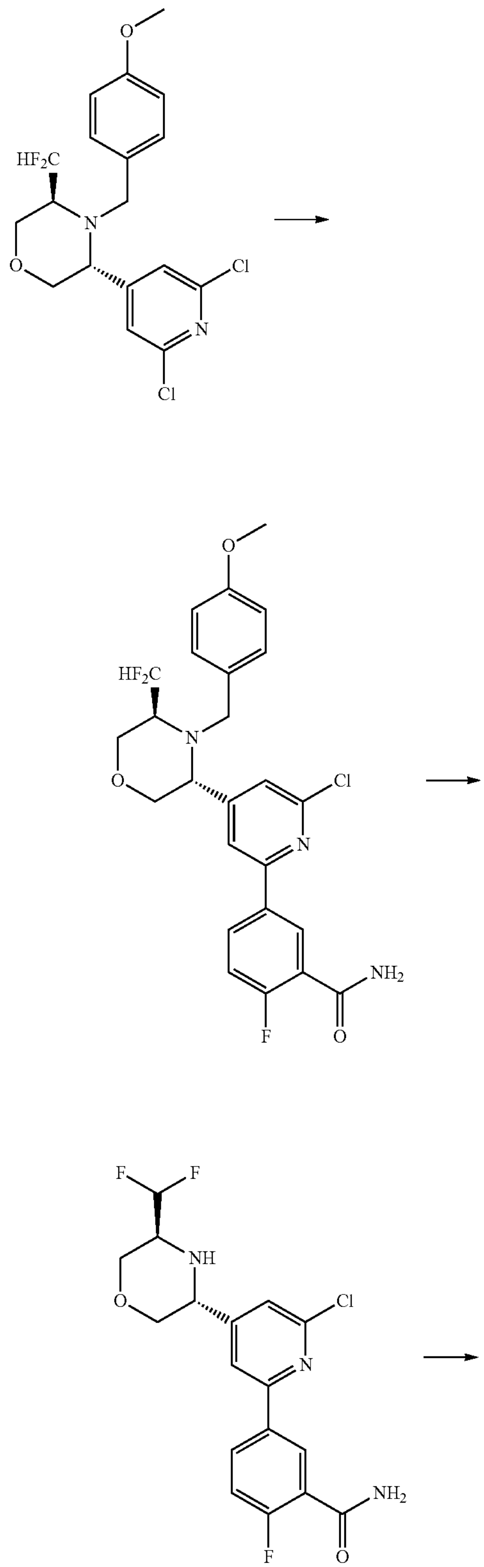

-continued

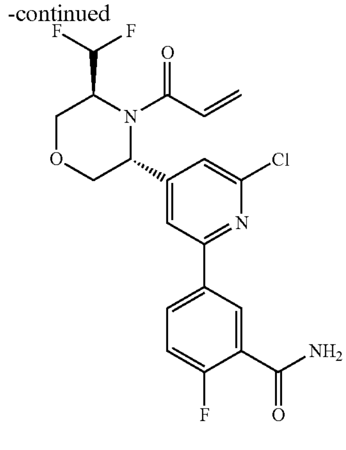

To a solution of (3R,5S)-3-(2,6-dichloropyridin-4-yl)-5-(difluoromethyl)-4-(4-methoxybenzyl)morpholine (120 mg, 0.29 mmol, 1 equiv) in 1,4-dioxane (2 mL, 0.12 M) and water (0.4 mL, 0.12 M) was added 2-fluoro-5-(4,4,5,5-tetramethyl-1,3,2-dioxaborolan-2-yl)benzamide (78 mg, 0.29 mmol, 1 equiv), $K_2CO_3$ (90 mg, 2 eq), and Pd(dppf)$Cl_2$ (0.1 eq, 30 mg). The resulting mixture was stirred at 80° C. for 16 hours under $N_2$. The reaction mixture was filtered, and the filtrate was concentrated under vacuum. The residue was purified by prep-TLC ($SiO_2$, PE:EtOAc=1:1,) to afford 5-(6-chloro-4-((3R,5S)-5-(difluoromethyl)-4-(4-methoxybenzyl)morpholin-3-yl)pyridin-2-yl)-2-fluorobenzamide (70 mg, 0.14 mmol, 47% yield) as a white solid.

Trifluoroacetic acid (2.5 mL, 0.06 M) was added to 5-(6-chloro-4-((3R,5S)-5-(difluoromethyl)-4-(4-methoxybenzyl)morpholin-3-yl)pyridin-2-yl)-2-fluorobenzamide (80 mg, 0.15 mmol, 1 equiv) and the resulting mixture was stirred at 80° C. for 12 hours. The reaction mixture was poured into saturated aqueous $NaHCO_3$ (5 mL) and extracted with DCM (10 mL*3). The combined organic layers were washed with brine (10 mL), dried over $Na_2SO_4$, filtered, and concentrated under reduced pressure. The residue was purified by prep-TLC ($SiO_2$, PE:EtOAc=1:2) to afford 5-(6-chloro-4-((3R,5S)-5-(difluoromethyl)morpholin-3-yl)pyridin-2-yl)-2-fluorobenzamide (40 mg, 0.104 mmol, 66% yield).

To a solution 5-(6-chloro-4-((3R,5S)-5-(difluoromethyl) morpholin-3-yl)pyridin-2-yl)-2-fluorobenzamide (35 mg, 0.09 mmol, 1 equiv) in DCM (1 mL, 0.09 M) was added acryloyl chloride (16 mg, 0.18 mmol, 2 equiv) and N,N-diisopropylethylamine (11 mg, 0.09 mmol, 1 equiv) and the resulting mixture was stirred at 25° C. for 30 minutes. The reaction mixture was poured into $H_2O$ (1 mL) and extracted with DCM (3 mL*3). The combined organic layers were washed with brine (5 mL), dried over $Na_2SO_4$, filtered, and concentrated under reduced pressure. The residue was purified by prep-TLC ($SiO_2$, PE:EtOAc=1:2) to afford 5-(4-((3R,5S)-4-acryloyl-5-(difluoromethyl)morpholin-3-yl)-6-chloropyridin-2-yl)-2-fluorobenzamide (27 mg, 0.058 mmol, 64% yield) as a white solid. LC-MS Vz: 440.0 [M+1].

Stereochemistry: single enantiomer ofknown absolute configuration

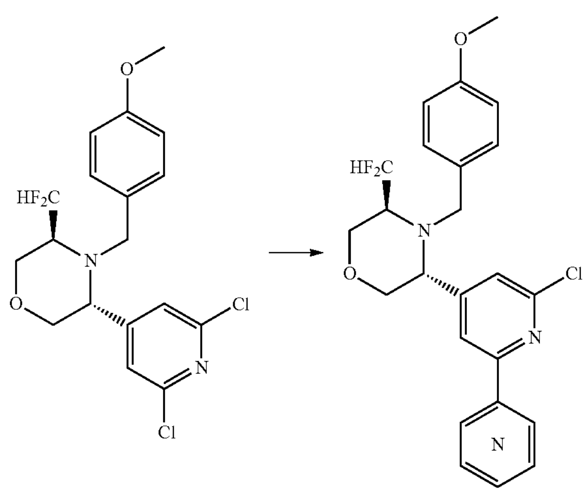

Using the appropriate coupling partner in Procedure T, the title compounds can be obtained.

| Cmp | Name | Coupling Partner | LC-MS m/z [M + 1] |
|---|---|---|---|
| 180 | 5-(4-((3R,5S)-4-acryloyl-5-(difluoromethyl)morpholin-3-yl)-6-chloropyridin-2-yl)-2-fluorobenzamide | 2-fluoro-5-(4,4,5,5-tetramethyl-1,3,2-dioxaborolan-2-yl)benzamide | 440.0 |
| 202 | 1-((3R,5S)-3-(2-(6-aminopyrimidin-4-yl)-6-chloropyridin-4-yl)-5-(difluoromethyl)morpholino)prop-2-en-1-one | tert-butyl (tert-butoxycarbonyl)(6-(trimethylstannyl)pyrimidin-4-yl)carbamate | 396.0 |
| 223 | 6-(4-((3R,5S)-4-acryloyl-5-(difluoromethyl)morpholin-3-y1)-6-chloropyridin-2-yl)pyrimidine-4-carboxamide | 6-(trimethylstannyl)pyrimidine-4-carboxamide | 424.2 |
| 201 | 1-((3R,5S)-3-(2-chloro-6-(6-methylpyrimidin-4-yl)pyridin-4-y1)-5-(difluoromethyl)morpholino)prop-2-en-1-one | 4-methyl-6-(trimethylstannyl)pyrimidine | 395.1 |
| 203 | 1-((3R,5S)-3-(2-chloro-6-(2-methylpyrimidin-4-yl)pyridin-4-yl)-5-(difluoromethyl)morpholino)prop-2-en-1-one | 2-methyl-4-(trimethylstannyl)pyrimidine | 396.1 |
| 194 | 1-((3R,5S)-3-(2-chloro-6-(imidazo[1,2-a]pyridin-7-yl)pyridin-4-yl)-5-(difluoromethyl)morpholino)prop-2-en-1-one | 7-(4,4,5,5-tetramethyl-1,3,2-dioxaborolan-2-yl)imidazo[1,2-a]pyridine | 419.0 |

Example 80. Synthesis of 1-((3R,6R)-3-(2-(6-aminopyrimidin-4-yl)-6-chloropyridin-4-yl)-6-fluoro-1,4-oxazepan-4-yl)prop-2-en-1-one (Compound 198)

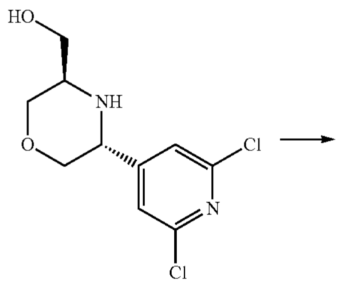

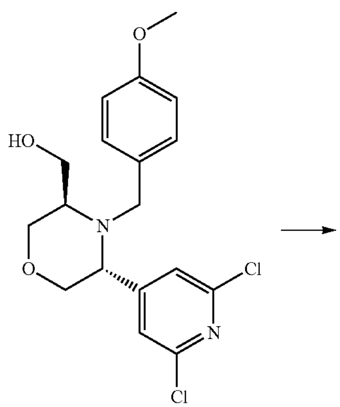

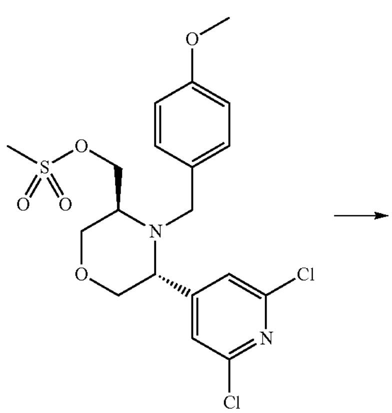

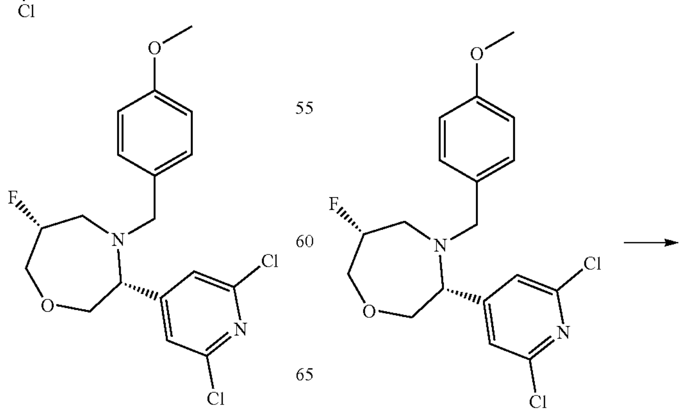

((3R,5R)-5-(2,6-dichloropyridin-4-yl)morpholin-3-yl)methanol was obtained from Procedure J.

To a solution of ((3R,5R)-5-(2,6-dichloropyridin-4-yl)morpholin-3-yl)methanol (100 mg, 0.38 mmol, 1 equiv) in DMF (1 mL, 0.38 M) was added 4-methoxybenzyl chloride (59.52 mg, 0.38 mmol, 1 equiv) and NaI (40 mg, 1 eq). The reaction was stirred at 80° C. for 12 hours. The reaction was quenched by $H_2O$ (5 mL) and extracted with EtOAc (5 mL×3). The organic phases were dried with $Na_2SO_4$, filtered, and concentrated. The residue was purified by prep TLC (PE/EA=2/1) to give ((3R,5R)-5-(2,6-dichloropyridin-4-yl)-4-(4-methoxybenzyl)morpholin-3-yl)methanol (56 mg, 0.146 mmol, 38% yield).

To a solution of ((3R,5R)-5-(2,6-dichloropyridin-4-yl)-4-(4-methoxybenzyl)morpholin-3-yl)methanol (450 mg, 1.05 mmol, 1 equiv) in DCM (5 mL, 0.21 M) was added 4-(dimethylamino)pyridine (6.4 mg, 0.052 mmol, 0.05 equiv) and triethylamine (0.44 mL, 3.16 mmol, 3 equiv) at 0° C. A solution of methylsulfonyl methanesulfonate (275 mg, 1.58 mmol, 1.5 equiv) in DCM (1 mL) was added at 0° C. under $N_2$ and then stirred at room temperature for 1 hour. The reaction mixture was poured into $H_2O$ (10 mL) and extracted with DCM (10 mL×3). The combined organic layers were washed with brine (10 mL×2), dried over $Na_2SO_4$, filtered, and concentrated under reduced pressure. The crude product was purified by flash silica gel column chromatography to give ((3S,5R)-5-(2,6-dichloropyridin-4-yl)-4-(4-methoxybenzyl)morpholin-3-yl)methyl methanesulfonate (437 mg, 0.87 mmol, 82% yield).

To a solution of ((3S,5R)-5-(2,6-dichloropyridin-4-yl)-4-(4-methoxybenzyl)morpholin-3-yl)methyl methanesulfonate (437 mg, 0.94 mmol, 1 equiv) in t-BuOH (5 mL) was added cesium fluoride (1448 mg, 9.472 mmol, 10 equiv) at room temperature. The reaction was stirred at 90° C. for 8 hours. The reaction was poured into saturated aqueous $NaHCO_3$ (5 mL) and the aqueous layer was extracted with ethyl acetate (10 mL×3). The combined organic layer was washed with brine (10 mL), dried over $Na_2SO_4$, filtered, and concentrated. The crude product was purified by column chromatography (PE:EA=3:1) to obtain 400 mg of an inseparable mixture of (3R,6R)-3-(2,6-dichloropyridin-4-yl)-6-fluoro-4-(4-methoxybenzyl)-1,4-oxazepane and (3R,5S)-3-(2,6-dichloropyridin-4-yl)-5-(fluoromethyl)-4-(4-methoxybenzyl)morpholine.

-continued

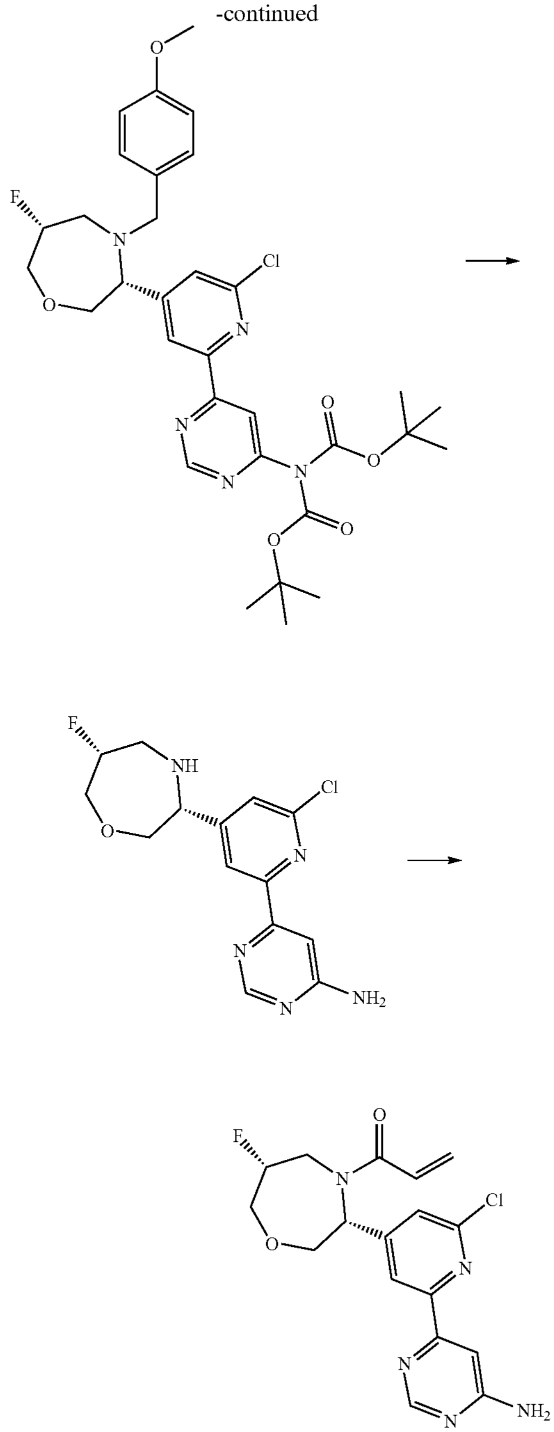

To a solution of a 700 mg of mixture of (3R,6R)-3-(2,6-dichloropyridin-4-yl)-6-fluoro-4-(4-methoxybenzyl)-1,4-oxazepane and (3R,5S)-3-(2,6-dichloropyridin-4-yl)-5-(fluoromethyl)-4-(4-methoxybenzyl)morpholine) in 1,4-dioxane (10 mL, 0.091 M) was added tert-butyl N-tert-butoxycarbonyl-N-(6-trimethylstannylpyrimidin-4-yl) carbamate (417 mg, 0.91 mmol, 1 equiv), $Pd(PPh_3)_4$(105 mg, 0.09 mmol, 0.1 equiv), and lithium chloride (3.8 mg, 0.09 mmol, 0.1 equiv). The reaction mixture was stirred at 110° C. for 3 hours. The reaction was poured into water (10 mL) and the aqueous layer was extracted with ethyl acetate (10 mL×3). The combined organic layer was washed with brine (20 mL), dried over $Na_2SO_4$, filtered, and concentrated. The crude product was purified by prep-TLC (Petroleum ether:Ethyl acetate=1:1) to obtain 300 mg of a mixture of tert-butyl (tert-butoxycarbonyl)(6-(6-chloro-4-((3R,6R)-6-fluoro-4-(4-methoxybenzyl)-1,4-oxazepan-3-yl)pyridin-2-yl)pyrimidin-4-yl)carbamate and tert-butyl (tert-butoxycarbonyl)(6-(6-chloro-4-((3R,5S)-5-(fluoromethyl)-4-(4-methoxybenzyl)morpholin-3-yl)pyridin-2-yl)pyrimidin-4-yl)carbamate. [00727] 300 mg of a mixture of tert-butyl (tert-butoxycarbonyl)(6-(6-chloro-4-((3R,6R)-6-fluoro-4-(4-methoxybenzyl)-1,4-oxazepan-3-yl)pyridin-2-yl)pyrimidin-4-yl)carbamate and tert-butyl (tert-butoxycarbonyl)(6-(6-chloro-4-((3R,5S)-5-(fluoromethyl)-4-(4-methoxybenzyl)morpholin-3-yl)pyridin-2-yl)pyrimidin-4-yl)carbamate was taken up into TFA (3 mL) and then stirred at 60° C. for 3 hours. The reaction was concentrated under vacuum. The crude product was adjusted pH to 9 with saturated aqueous $NaHCO_3$ and extracted with ethyl acetate (10 mL*3). The combined organic phases were concentrated under reduced pressure. The crude residue was purified by prep-TLC afford 6-(6-chloro-4-((3R,6R)-6-fluoro-1,4-oxazepan-3-yl)pyridin-2-yl)pyrimidin-4-amine (50 mg, 0.15 mmol).

To a solution of afford 6-(6-chloro-4-((3R,6R)-6-fluoro-1,4-oxazepan-3-yl)pyridin-2-yl)pyrimidin-4-amine (50 mg, 0.15 mmol) in DCM (3 mL, 0.03 M) was added acryloyl chloride (11 mg, 0.12 mmol) and triethylamine (39 mg, 0.38 mmol). The reaction mixture was stirred at room temperature for 2 hours. The reaction was poured into water (10 mL) and the aqueous layer was extracted with ethyl acetate (10 mL×3). The combined organic layer was washed with brine (50 mL), dried over $Na_2SO_4$, filtered, and concentrated. The crude product was purified by prep-TLC (EA:MeOH=20:1) to obtain 1-((3R,6R)-3-(2-(6-aminopyrimidin-4-yl)-6-chloropyridin-4-yl)-6-fluoro-1,4-oxazepan-4-yl)prop-2-en-1-one (16 mg, 0.042 mmol, 27% yield) as a white solid. LC-MS m/z: 378.1 [M+1].

Stereochemistry: single enantiomer of known absolute configuration.

Example 81. Synthesis of 2-((3R,5R)-4-acryloyl-5-(3-(6-aminopyrimidin-4-yl)-5-chlorophenyl)morpholin-3-yl)acetonitrile (Compound 204)

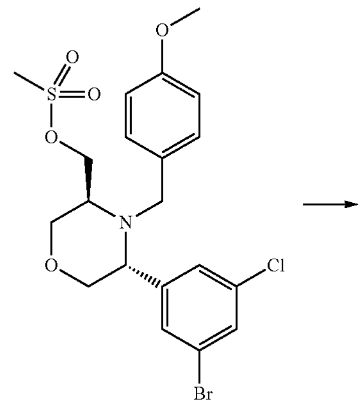

-continued

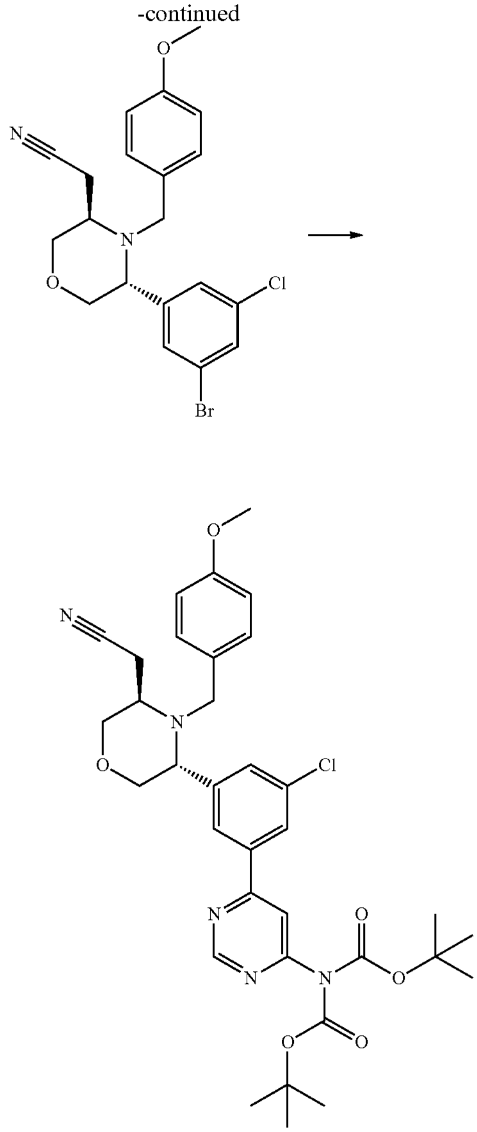

((3S,5R)-5-(3-bromo-5-chlorophenyl)-4-(4-methoxybenzyl)morpholin-3-yl)methyl methanesulfonate was obtained in a similar fashion to the synthesis of Compound 198.

NaCN (210 mg, 4.28 mmol, 2.16 equiv) was added to a solution of ((3S,5R)-5-(3-bromo-5-chlorophenyl)-4-(4-methoxybenzyl)morpholin-3-yl)methyl methanesulfonate (1000 mg, 1.98 mmol, 1 equiv) in DMF (10 mL, 0.19 M) at room temperature. The mixture was stirred at 80° C. for 16 hours under $N_2$. The reaction was quenched by addition of $H_2O$ (20 mL) and extracted with ethyl acetate (20 mL*3). The combined organic phase was washed by brine (20 mL*3), dried over sodium sulfate, filtered, and concentrated under reduced pressure. The residue was purified by column chromatography ($SiO_2$, Petroleum ether/Ethyl acetate=1/0 to 1/1) to afford 2-((3R,5R)-5-(3-bromo-5-chlorophenyl)-4-(4-methoxybenzyl)morpholin-3-yl)acetonitrile (660 mg, 1.51 mmol, 76% yield).

To a solution of 2-((3R,5R)-5-(3-bromo-5-chlorophenyl)-4-(4-methoxybenzyl)morpholin-3-yl)acetonitrile (7500 mg, 17.21 mmol, 1 equiv) in 1,4-dioxane (8 mL, 2.15 M) was added tert-butyl N-tert-butoxycarbonyl-N-(6-trimethylstannylpyrimidin-4-yl)carbamate (7885 mg, 17.212 mmol, 1 equiv), $Pd(PPh_3)_4$(1989 mg, 1.72 mmol, 0.1 equiv), and lithium chloride (72 mg, 1.72 mmol, 0.1 equiv). The reaction mixture was stirred at 110° C. for 16 hours under $N_2$. The reaction was poured into aqueous KF (15 mL) and the aqueous layer was extracted with ethyl acetate (15 mL×3). The combined organic layer was washed with brine (15 mL), dried over $Na_2SO_4$, filtered, and concentrated. The crude product was purified by column chromatography ($SiO_2$, Petroleum ether/Ethyl acetate=1/0 to 0/1) to obtain tert-butyl (tert-butoxycarbonyl)(6-(3-chloro-5-((3R,5R)-5-(cyanomethyl)-4-(4-methoxybenzyl)morpholin-3-yl)phenyl)pyrimidin-4-yl)carbamate (400 mg, 0.62 mmol, 4% yield) as a white solid.

The title compound was obtained from tert-butyl (tert-butoxycarbonyl)(6-(3-chloro-5-((3R,5R)-5-(cyanomethyl)-4-(4-methoxybenzyl)morpholin-3-yl)phenyl)pyrimidin-4-yl)carbamate in a similar manner to the synthesis of Compound 198. LC-MS m/z: 394.1 [M+1].

Stereochemistry: single enantiomer of known absolute configuration.

Example 82. Procedure U and Synthesis of 1-((3R,5S)-3-(3-(2-aminopyrimidin-4-yl)-5-chlorophenyl)-5-(difluoromethyl)morpholino)prop-2-en-1-one (Compound 290)

Procedure U

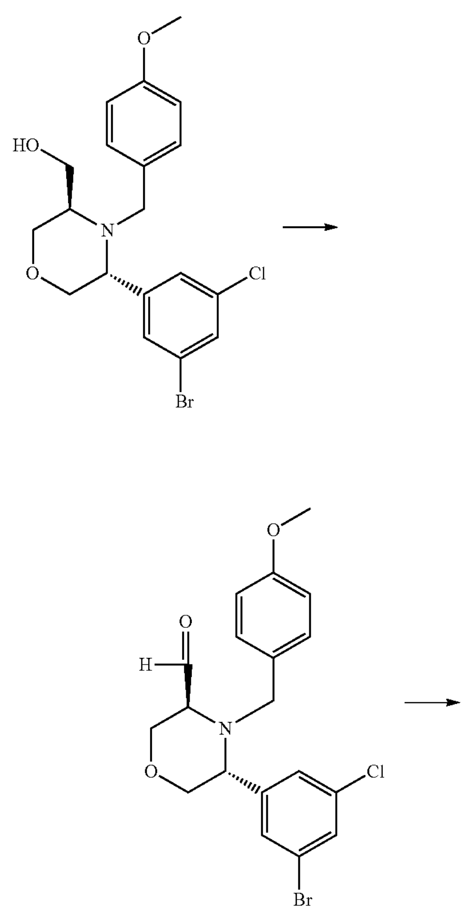

-continued

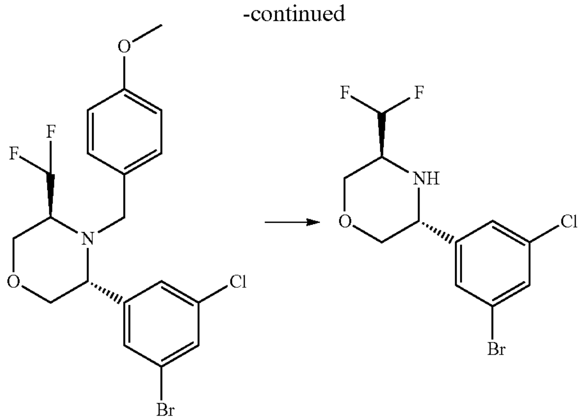

((3R,5R)-5-(3-bromo-5-chlorophenyl)-4-(4-methoxybenzyl)morpholin-3-yl)methanol was obtained in a similar fashion to the synthesis of Compound 198.

To a solution of ((3R,5R)-5-(3-bromo-5-chlorophenyl)-4-(4-methoxybenzyl)morpholin-3-yl)methanol (3.151 g, 7.38 mmol, 1 equiv) in DCM (30 mL, 0.24 M) was added Dess-Martin periodinane (4.698 g, 11.07 mmol, 1.5 equiv) at 0° C. The mixture was stirred at room temperature for 2 hours. The mixture was quenched with 10% aqueous $Na_2S_2O_3$ (40 mL) and stirred for 30 minutes. Saturated aqueous $NaHCO_3$ (20 mL) was added and stirred for 30 minutes. The solution was extracted with DCM (30 mL×3), washed with brine (30 mL), dried over $Na_2SO_4$, filtered, and concentrated to afford crude (3S,5R)-5-(3-bromo-5-chlorophenyl)-4-(4-methoxybenzyl)morpholine-3-carbaldehyde (3.61 g).

To a solution of (3S,5R)-5-(3-bromo-5-chlorophenyl)-4-(4-methoxybenzyl)morpholine-3-carbaldehyde (3.606 g, 8.49 mmol, 1 equiv) in DCM (30 mL, 0.283M) at 0° C. was added diethylaminosulfur trifluoride (3.041 g, 16.98 mmol, 2 equiv). The mixture was stirred at 0° C. for 2 hours. The reaction was poured into saturated aqueous $NaHCO_3$ (30 mL) and then extracted by DCM (3×30 mL). The residue was purified by column chromatography ($SiO_2$, Petroleum ether/Ethyl acetate=100/0 to 93/7) to afford (3R,5S)-3-(3-bromo-5-chlorophenyl)-5-(difluoromethyl)-4-(4-methoxybenzyl)morpholine (1.57 g, 3.52 mmol, 41% yield).

A mixture of (3R,5S)-3-(3-bromo-5-chlorophenyl)-5-(difluoromethyl)-4-(4-methoxybenzyl)morpholine (1.571 g, 3.51 mmol, 1 equiv) in trifluoroacetic acid (16 mL, 0.22 M) was stirred at 60° C. for 2 hours. The reaction mixture was filtered and concentrated afford (3R,5S)-3-(3-bromo-5-chlorophenyl)-5-(difluoromethyl)morpholine (1.92 g) as a brown solid.

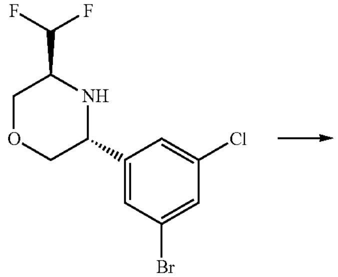

-continued

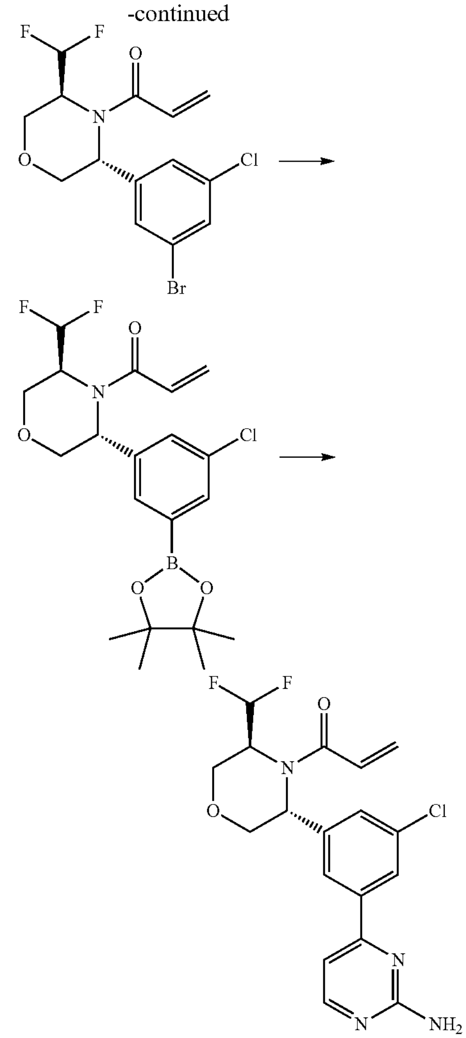

To a solution of (3R,5S)-3-(3-bromo-5-chlorophenyl)-5-(difluoromethyl)morpholine (300 mg, 0.91 mmol, 1 equiv) in DCM (3 mL, 0.3 M) was added N,N-diisopropylethylamine (237.46 mg, 1.83 mmol, 2 equiv) and acryloyl chloride (108.09 mg, 1.19 mmol, 1.3 equiv). The mixture was stirred at 0° C. for 1 hour. The solution was quenched with brine (10 mL) and extracted with DCM (10 mL*3). The organic phases were dried over $Na_2SO_4$, filtered, and concentrated. The residue was purified by prep-TLC ($SiO_2$, PE:EA=5:1) to afford 1-((3R,5S)-3-(3-bromo-5-chlorophenyl)-5-(difluoromethyl)morpholino)prop-2-en-1-one (177 mg, 0.46 mmol, 51% yield).

To a solution of 1-((3R,5S)-3-(3-bromo-5-chlorophenyl)-5-(difluoromethyl)morpholino)prop-2-en-1-one (176.7 mg, 0.46 mmol, 1 equiv) in 1,4-dioxane (2 mL, 0.23 M) was added bis(pinacolato)diboron (176.84 mg, 0.69 mmol, 1.5 equiv), potassium acetate (115.08 mg, 1.1606 mmol, 2.5 equiv), and $Pd(dppf)Cl_2$ (33 mg, 0.046 mmol, 0.10 equiv) at room temperature under $N_2$. The reaction was stirred at 80° C. for 48 hours. The solution was quenched with water (20 mL) and extracted with ethyl acetate (20 mL*3). The organic phases were dried over $Na_2SO_4$, filtered, and concentrated to afford 200 mg of a brown oil.

To a solution of 1-((3R,5S)-3-(3-chloro-5-(4,4,5,5-tetramethyl-1,3,2-dioxaborolan-2-yl)phenyl)-5-(difluoromethyl)morpholino)prop-2-en-1-one (199 mg, 0.46 mmol) in 1,4- dioxane (2 mL, 0.19 M) was added potassium carbonate (160.77 mg, 1.16 mmol, 2.5 equiv) in water (0.40 mL, 0.2 M), 2-amino-4-bromopyrimidine (105.25 mg, 0.60 mmol, 1.3 equiv), and $Pd(dppf)Cl_2$ (33.671 mg, 0.045 mmol, 0.1 equiv) at 25° C. The mixture was stirred at 80° C. under $N_2$ for 16 hours. The reaction mixture was poured into water (10 mL) and extracted with EtOAc (10 mL*3). The combined organic layers were washed with brine (10 mL*2), dried over $Na_2SO_4$, filtered, and concentrated. The residue was purified by prep-TLC (EA:MeOH=10:1) to afford 1-((3R,5S)-3-(3-(2-aminopyrimidin-4-yl)-5-chlorophenyl)-5-(difluoromethyl)morpholino)prop-2-en-1-one (38.6 mg, 0.097 mmol, 21% yield). LC-MS m/z: 395.2 [M+1].

Stereochemistry: single enantiomer of known absolute configuration.

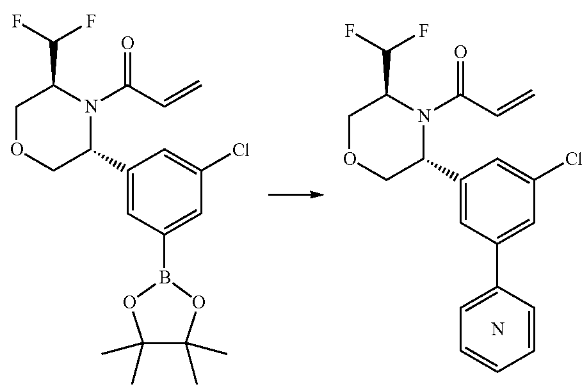

Using the appropriate coupling partner in Procedure U, the title compounds can be obtained.

| Cmp | Name | Coupling Partner | LC-MS m/z [M + 1] |
|---|---|---|---|
| 290 | 1-((3R,5S)-3-(3-(2-aminopyrimidin-4-yl)-5-chlorophenyl)-5-(difluoromethyl)morpholino)prop-2-en-1-one | 2-amino-4-bromopyrimidine | 395.2 |
| 291 | 1-((3R,5S)-3-(3-(5-aminopyrimidin-2-yl)-5-chlorophenyl)-5-(difluoromethyl)morpholino)prop-2-en-1-one | 2-bromopyrimidin-5-amine | 395.1 |

Example 83. Synthesis of 1-(5-(3-(4-amino-1,3,5-triazin-2-yl)-5-chlorophenyl)-2-oxa-6-azaspiro[3.3]heptan-6-yl)prop-2-en-1-one (Compound 159)

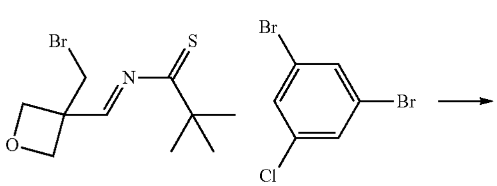

-continued

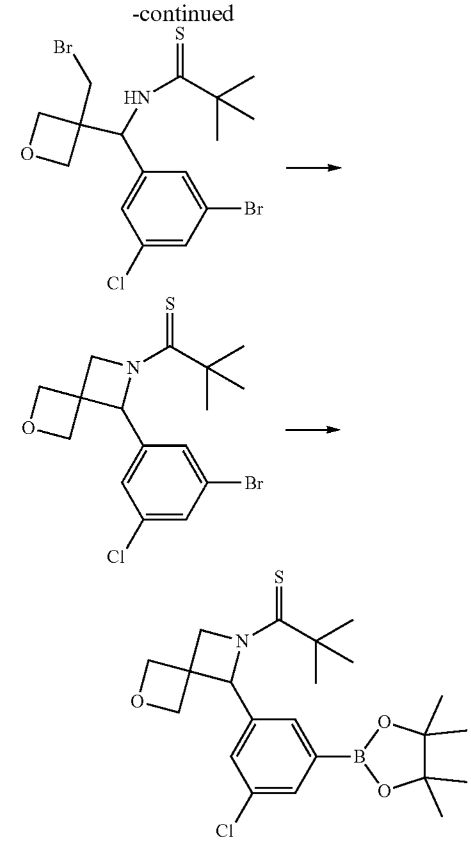

To a solution of 1,3-dibromo-5-chloro-benzene (195 mg, 0.72 mmol, 1 equiv) in i-$Pr_2O$ (5 mL) was added n-Butyllithium solution (0.259 mL, 0.64 mmol, 0.9 equiv) dropwise at −70° C. under $N_2$. The reaction mixture was stirred for 30 minutes before (NE)-N-[[3-(bromomethyl)oxetan-3-yl]methylene]-2-methyl-propane-2-sulfinamide (203.55 mg, 0.7213 mmol, 1 equiv) in 1 mL of i-$Pr_2O$ was added and then stirred at −70° C. and stirred for 1 hour. The reaction was poured into $H_2O$ (10 mL) and the aqueous layer was extracted with ethyl acetate (5 mL×3). The combined organic layer was washed with brine (20 mL), dried over $Na_2SO_4$, filtered, and concentrated. The crude product was purified by prep-TLC (Petroleum ether:Ethyl acetate=1:1) to obtain N-[(3-bromo-5-chloro-phenyl)-[3-(bromomethyl)oxetan-3-yl]methyl]-2-methyl-propane-2-sulfinamide (35 mg, 0.073 mmol, 10% yield) as colorless oil.

To a solution of N-[(3-bromo-5-chloro-phenyl)-[3-(bromomethyl)oxetan-3-yl]methyl]-2-methyl-propane-2-sulfinamide (796 mg, 1.68 mmol, 1 equiv) in THF (4 mL, 0.42 M) was added potassium tert-butoxide (264 mg, 2.35 mmol, 1.4 equiv) at 0° C. and then stirred for 1 hour. The reaction was poured into $H_2O$ (20 mL) and the aqueous layer was extracted with ethyl acetate (10 mL×3). The combined organic layer was washed with brine (20 mL), dried over $Na_2SO_4$, filtered, and concentrated under vacuum to afford 510 mg of crude product.

To a solution of 7-(3-bromo-5-chloro-phenyl)-6-tert-butylsulfinyl-2-oxa-6-azaspiro[3.3]heptane (255 mg, 0.64 mmol, 1 equiv)) and bis(pinacolato)diboron (197 mg, 0.77 mmol, 1.2 equiv) in 1,4-dioxane (5 mL, 0.13 M) was added potassium acetate (191 mg, 1.94 mmol, 3 equiv) and Pd(dppf)$Cl_2$ (47 mg, 0.064 mmol, 0.1 equiv) under $N_2$. The resulting mixture was stirred for 2 hours at 90° C. under $N_2$. The reaction was poured into $H_2O$ (20 mL) and the aqueous layer was extracted with ethyl acetate (10 mL×3). The combined organic layer was washed with brine (20 mL), dried over $Na_2SO_4$, filtered, and concentrated under vacuum to afford 285 mg which was taken forward without purification.

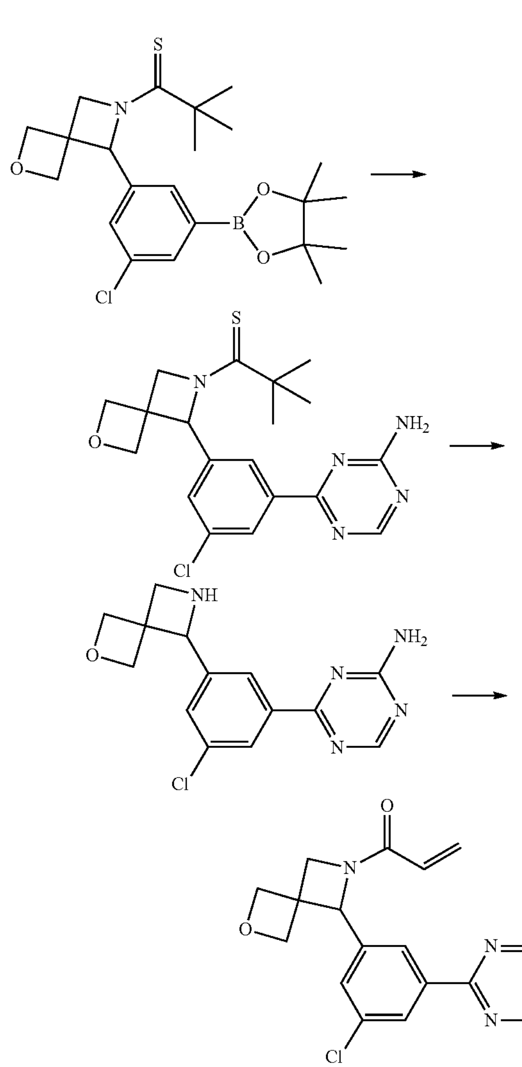

To a solution of 6-tert-butylsulfinyl-7-[3-chloro-5-(4,4,5,5-tetramethyl-1,3,2-dioxaborolan-2-yl)phenyl]-2-oxa-6-azaspiro[3.3]heptane (285 mg, 0.64 mmol, 1 equiv) and 4-chloro-1,3,5-triazin-2-amine (101 mg, 0.77 mmol, 1.2 equiv) in 1,4-dioxane (10 mL, 0.05 M) and water (2 mL, 0.05 M) was added potassium carbonate (268 mg, 1.94 mmol, 3 equiv) and Pd(dppf)$Cl_2$ (47 mg, 0.064 mmol, 0.10 equiv) under $N_2$. The resulting mixture was stirred for 2 hours at 90° C. The reaction was poured into $H_2O$ (50 mL) and the aqueous layer was extracted with ethyl acetate (10 mL×3). The combined organic layer was washed with brine (50 mL), dried over $Na_2SO_4$, filtered, and concentrated. The crude product was purified by prep-TLC (Ethyl acetate) to obtain 4-[3-(6-tert-butylsulfinyl-2-oxa-6-azaspiro[3.3]heptan-7-yl)-5-chloro-phenyl]-1,3,5-triazin-2-amine (255 mg, 0.625 mmol, 97% yield) as a brown solid.

A solution of 4-[3-(6-tert-butylsulfinyl-2-oxa-6-azaspiro[3.3]heptan-7-yl)-5-chloro-phenyl]-1,3,5-triazin-2-amine (250 mg, 0.61 mmol, 1 equiv) in trifluoroacetic acid (3 mL, 0.20 M) was stirred at 25° C. for 16 hours. The mixture was evaporated to dryness and the residue was used for the next step without further purification.

To a solution of 4-[3-chloro-5-(2-oxa-6-azaspiro[3.3]heptan-7-yl)phenyl]-1,3,5-triazin-2-amine (186 mg, 0.61 mmol, 1 equiv) in DCM (5 mL, 0.12 M) was added triethylamine (123 mg, 1.22 mmol, 2 equiv) and acryloyl chloride (16 mg, 0.18 mmol, 0.3 equiv). The reaction was stirred for 2 hours at room temperature. The crude product was purified by pre-HPLC (column: Waters Xbridge Prep OBD C18 150*40 mm*10 um; liquid phase: [A-10 mM $NH_4HCO_3$ in $H_2O$; B-ACN]B %: 10%-40%, 8 min]) to obtain 1-(5-(3-(4-amino-1,3,5-triazin-2-yl)-5-chlorophenyl)-2-oxa-6-azaspiro[3.3]heptan-6-yl)prop-2-en-1-one (18 mg, 0.051 mmol, 8% yield) as a white solid. The title compound's absolute stereochemistry was not assigned. Stereochemistry: single enantiomer of unknown absolute configuration.

Enantiomers were separated by SFC. Absolute stereochemistry was not assigned. LC-MS m/z: 358.0 [M+1].

Stereochemistry: single enantiomer of unknown absolute configuration.

Example 84. Synthesis of 1-(5-(3-(2-aminopyrimidin-4-yl)-5-chlorophenyl)-2-oxa-6-azaspiro[3.3]heptan-6-yl)prop-2-en-1-one (Compound 168)

The title compound was obtained in a similar fashion as compound 159 using 4-bromopyrimidin-2-amine. LC-MS m/z: 357.0 [M+1]. The title compound's absolute stereochemistry was not assigned. Stereochemistry: single enantiomer of unknown absolute configuration.

Stereochemistry: single enantiomer of unknown absolute configuration.

Example 85. Synthesis of (R)-1-(3-(3-(4-amino-1,3,5-triazin-2-yl)-5-chlorophenyl)morpholino)-2-cyclopropylideneethan-1-one (Compound 293)

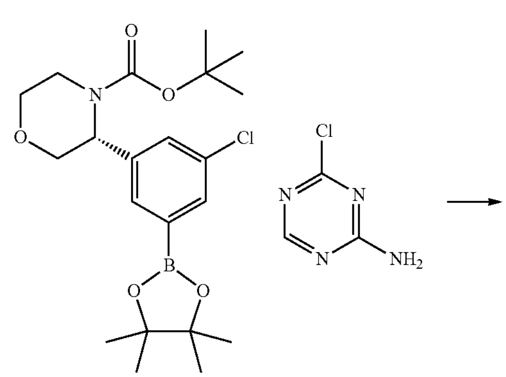

-continued

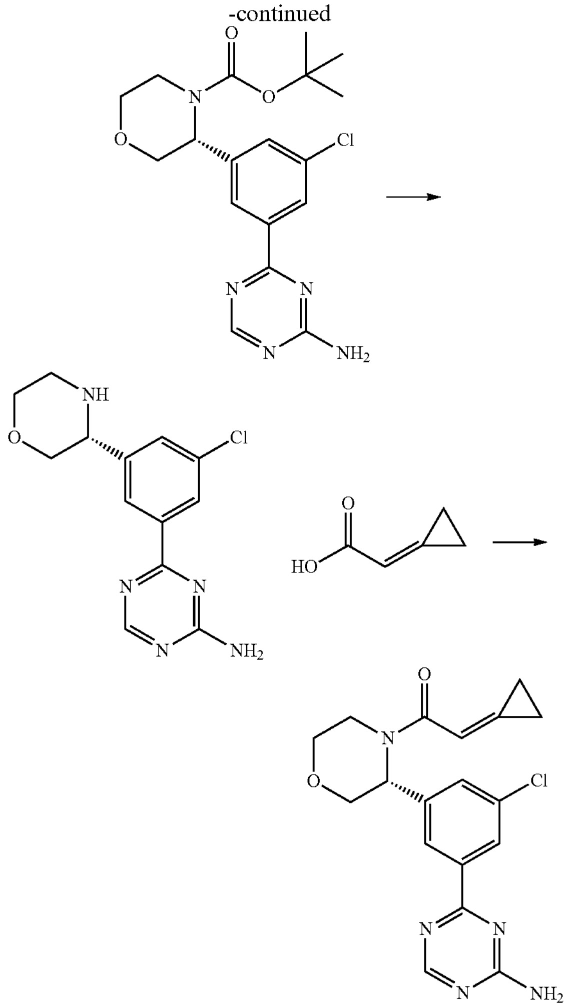

tert-butyl (R)-3-(3-chloro-5-(4,4,5,5-tetramethyl-1,3,2-dioxaborolan-2-yl)phenyl)morpholine-4-carboxylate was obtained from Procedure B.

To a solution of tert-butyl (R)-3-(3-chloro-5-(4,4,5,5-tetramethyl-1,3,2-dioxaborolan-2-yl)phenyl)morpholine-4-carboxylate (1.77 g, 4.17 mmol, 1 equiv) in 1,4-dioxane (20 mL, 0.18 M) and water (3 mL, 0.18 M) was added 4-chloro-1,3,5-triazin-2-amine (0.817 g, 6.26 mmol, 1.5 equiv), potassium carbonate (1.154 g, 8.35 mmol, 2 equiv), and Pd(dppf)$Cl_2$ (0.302 g, 0.42 mmol, 0.1 equiv) at 25° C. The mixture was stirred at 85° C. for 12 hours under $N_2$. The mixture was poured into water (10 mL), extracted with ethyl acetate (10 mL*3), washed with brine, dried over $Na_2SO_4$, filtered, and concentrated. The residue was purified by column chromatography ($SiO_2$, Petroleum ether/Ethyl acetate=10/1 to 3/1) to give tert-butyl (R)-3-(3-(4-amino-1,3,5-triazin-2-yl)-5-chlorophenyl)morpholine-4-carboxylate as a yellow solid.

A solution of tert-butyl (R)-3-(3-(4-amino-1,3,5-triazin-2-yl)-5-chlorophenyl)morpholine-4-carboxylate (90 mg, 0.23 mmol, 1 equiv) in 4M HCl in dioxane (2 mL) was stirred at 25° C. for 30 minutes. The mixture was concentrated to afford (R)-4-(3-chloro-5-(morpholin-3-yl)phenyl)-1,3,5-triazin-2-amine (67 mg, 0.23 mmol, 100% yield) as white solid.

To a solution of 2-cyclopropylideneacetic acid (33 mg, 0.34 mmol, 1.5 equiv) in DCM (5 mL, 0.04 M) was added HATU (130 mg, 0.34 mmol, 1.5 equiv) and triethylamine (69 mg, 0.68 mmol, 3 equiv) at 0° C. under $N_2$. The mixture was stirred for 5 minutes before addition of (R)-4-(3-chloro-5-(morpholin-3-yl)phenyl)-1,3,5-triazin-2-amine (67 mg, 0.23 mmol, 1 equiv). The reaction mixture was stirred for 16 hours. The mixture was poured into water (10 mL), extracted with ethyl acetate (5 mL*2), washed with brine, dried over $Na_2SO_4$, filtered and concentrated. The residue was purified by Prep-HPLC($NH_4HCO_3$) to obtain (R)-1-(3-(3-(4-amino-1,3,5-triazin-2-yl)-5-chlorophenyl)morpholino)-2-cyclopropylideneethan-1-one (8.9 mg, 0.024 mmol, 10% yield) as a white solid. LC-MS m/z: 372.1 [M+1].

Stereochemistry: single enantiomer of known absolute configuration.

Example 86. Synthesis of (R)-1-(3-(3-(4-amino-1,3,5-triazin-2-yl)-5-chlorophenyl)morpholino)-2-chloroprop-2-en-1-one (Compound 294)

The title compound was obtained according to the synthesis of Compound 293 using 2-chloroacryloyl chloride. LC-MS m/z: 380.2 [M+1].

Stereochemistry: single enantiomer of known absolute configuration.

Example 87. Synthesis of (R)-1-(3-(3-(4-amino-1,3,5-triazin-2-yl)-5-chlorophenyl)morpholino)-2-(trifluoromethyl)prop-2-en-1-one (Compound 295)

The title compound was obtained according to the synthesis of Compound 293 using 2-(trifluoromethyl)acryloyl chloride. LC-MS m/z: 414.1 [M+1].

Stereochemistry: single enantiomer of known absolute configuration.

Example 88. Synthesis of ((R)-1-(3-(3-(4-amino-1,3,5-triazin-2-yl)-5-chlorophenyl)morpholino)-2-fluoroprop-2-en-1-one (Compound 297)

The title compound was obtained according to the synthesis of Compound 293 using 2-fluoroacrylic acid. LC-MS m/z: 364.1 [M+1].

Stereochemistry: single enantiomer of known absolute configuration.

Example 89. Procedure W and Synthesis of Compounds 205 and 206

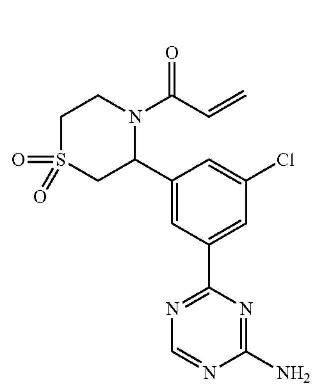 [SMILES: C=CC(=O)N1CCS(=O)(=O)CC1c1cc(Cl)cc(-c2ncnc(N)n2)c1]

Ent 1: 1-(3-(3-(4-amino-1,3,5-triazin-2-yl)-5-chlorophenyl)-1,1-dioxidothiomorpholino)prop-2-en-1-one Ent 2: 1-(3-(3-(4-amino-1,3,5-triazin-2-yl)-5-chlorophenyl)-1,1-dioxidothiomorpholino)prop-2-en-1-one Procedure W

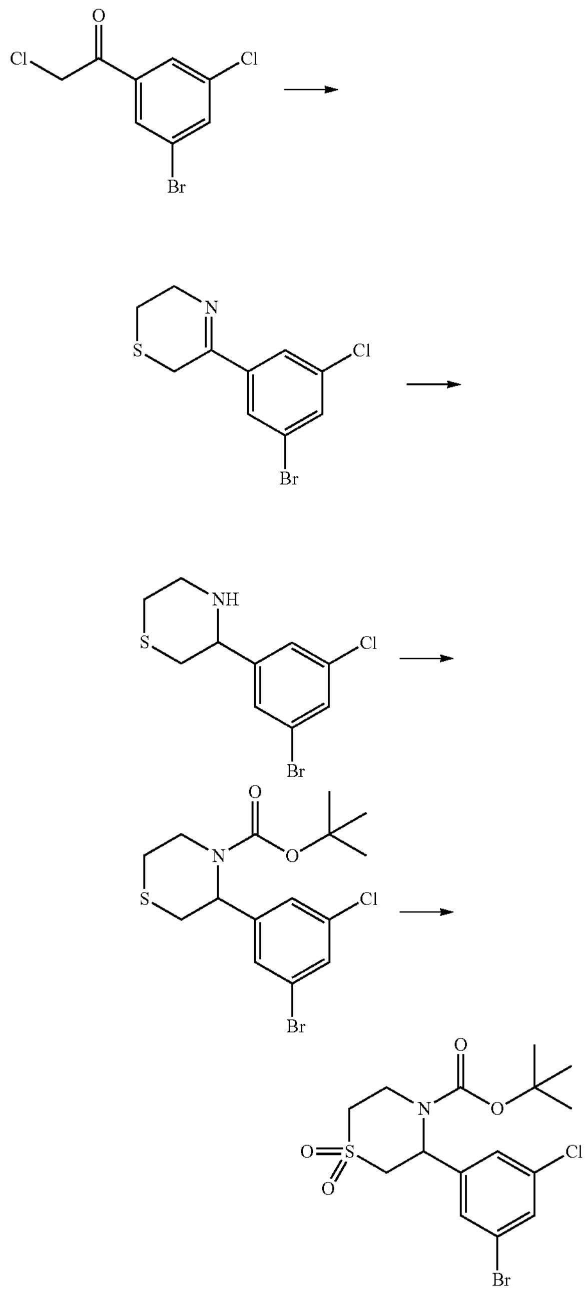

1-(3-bromo-5-chlorophenyl)-2-chloroethan-1-one was obtained from the synthesis of Compound 282.

To a solution of 1-(3-bromo-5-chlorophenyl)-2-chloroethan-1-one (19.7 g, 73.52 mmol) in 1,4-dioxane (200 mL, 0.14 M) was added a solution of 2-aminoethanethiol (28.363 g, 367.63 mmol) in 1,4-dioxane (300 mL, 0.14 M) at 0° C. The reaction was treated with molecular sieves (50 g) at 10° C. and then stirred at 25° C. for 16 hours. The solution was filtered and concentrated under reduced pressure to afford crude 5-(3-bromo-5-chlorophenyl)-3,6-dihydro-2H-1,4-thiazine (28.8 g).

To a solution of 5-(3-bromo-5-chlorophenyl)-3,6-dihydro-2H-1,4-thiazine (21.4 g, 73.63 mmol, 1 equiv) in methanol (220 mL, 0.33 M) was added sodium borohydride (27.99 g, 739.89 mmol, 10 equiv) in portions at 0° C. under $N_2$. The mixture was stirred for 2 hours at 25° C. The reaction mixture was poured into saturated aqueous $NH_4Cl$ (600 mL) and extracted with EtOAc (100 mL*3). The combined organic layers were washed with brine (40 mL*2), dried over $Na_2SO_4$, filtered, and concentrated under reduced pressure to give a crude 3-(3-bromo-5-chlorophenyl)thiomorpholine (17.5 g).

To a solution of crude 3-(3-bromo-5-chlorophenyl)thiomorpholine (15.5 g, 52.97 mmol, 1 equiv) in DCM (160 mL, 0.31 M) was added pyridine (8.379 g, 105.94 mmol, 2 equiv), DMAP (1 eq, 542 mg), and di-tert-butyl dicarbonate (17.341 g, 79.45 mmol, 1.5 equiv). The mixture was stirred for 42 hours at room temperature. The reaction mixture was poured into saturated aqueous $NH_4Cl$ (100 mL) and extracted with DCM (100 mL*3). The combined organic layers were washed with brine (50 mL*2), dried over $Na_2SO_4$, filtered, and concentrated under reduced pressure. The residue was purified by column chromatography ($SiO_2$, Petroleum ether/Ethyl acetate=25/1) to afford tert-butyl 3-(3-bromo-5-chlorophenyl)thiomorpholine-4-carboxylate (8.5 g, 21.64 mmol, 41% yield) as a yellow oil.

To a solution tert-butyl 3-(3-bromo-5-chlorophenyl)thiomorpholine-4-carboxylate (8.5 g, 21.64 mmol, 1 equiv) in DCM (90 mL, 0.24 M) was added 3-chloroperbenzoic acid (18.675 g, 86.57 mmol, 4 equiv) at 0° C., and then stirred at room temperature for 16 hours. The mixture was quenched with aqueous $Na_2SO_3$ (60 mL) and the mixture was stirred at room temperature for 30 minutes. The solution was extracted with DCM (50 mL*2), washed with brine (20 mL*2), dried over $Na_2SO_4$, filtered, and concentrated under vacuum. The residue was purified by column chromatography ($SiO_2$, Petroleum ether/Ethyl acetate=4/1) to afford tert-butyl 3-(3-bromo-5-chlorophenyl)thiomorpholine-4-carboxylate 1,1-dioxide (6.50 g, 15.3 mmol, 71% yield) as a white solid.

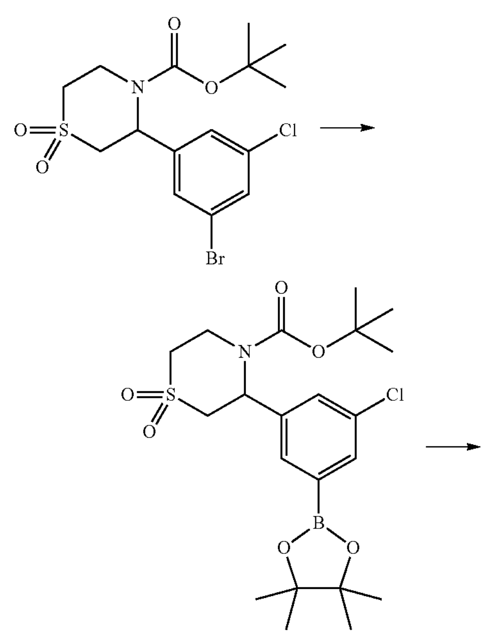

-continued

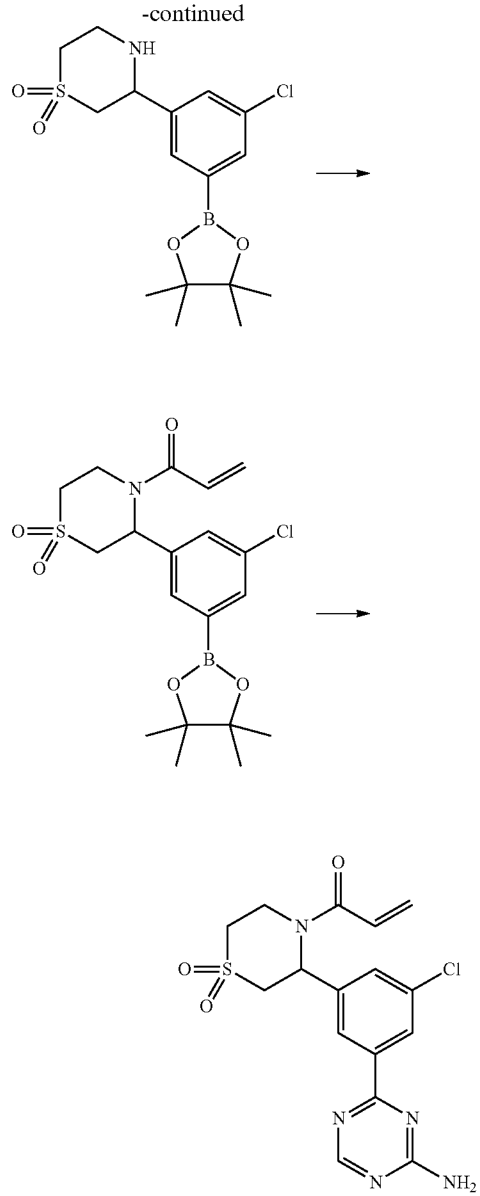

To a solution of tert-butyl 3-(3-bromo-5-chlorophenyl) thiomorpholine-4-carboxylate 1,1-dioxide (1 g, 2.35 mmol, 1 equiv) in 1,4-dioxane (10 mL, 0.23 M) was added bis (pinacolato)diboron (0.717 g, 2.82 mmol, 1.2 equiv), $Pd(dppf)Cl_2$ (0.171 g, 0.23 mmol, 0.1 equiv), and potassium acetate (0.577 g, 5.88 mmol, 2.5 equiv) at 25° C. The mixture was stirred at 90° C. for 12 hours under $N_2$. The reaction mixture was poured into water (15 mL) and extracted with EtOAc (15 mL*3). The combined organic layers were washed with brine (10 mL*2), dried over $Na_2SO_4$, filtered, and concentrated under reduced pressure. The residue was purified by flash silica gel chromatography (Eluent of 12% Ethyl acetate in Petroleum ether gradient @ 80 mL/min) to afford tert-butyl 3-(3-chloro-5-(4,4,5,5-tetramethyl-1,3,2-dioxaborolan-2-yl)phenyl)thiomorpholine-4-carboxylate 1,1-dioxide (860 mg, 1.82 mmol, 77% yield) as a yellow oil.

To a solution of tert-butyl 3-(3-chloro-5-(4,4,5,5-tetramethyl-1,3,2-dioxaborolan-2-yl)phenyl)thiomorpholine-4-carboxylate 1,1-dioxide (860 mg, 1.82 mmol, 1 equiv) in 1,4-dioxane (10 mL, 0.18 M) was added 4M HCl in dioxane (5 mL) at 25° C. The mixture was stirred at 25° C. for 2 hours under N2. The mixture was concentrated under reduced pressure to afford 3-(3-chloro-5-(4,4,5,5-tetramethyl-1,3,2-dioxaborolan-2-yl)phenyl)thiomorpholine 1,1-dioxide (660 mg, 1.78 mmol, 97% yield) as a yellow solid.

To a solution of crude 3-(3-chloro-5-(4,4,5,5-tetramethyl-1,3,2-dioxaborolan-2-yl)phenyl)thiomorpholine 1,1-dioxide (677 mg, 1.82 mmol, 1 equiv) in DCM (6 mL, 0.3 M) was added triethylamine (0.507 mL, 3.64 mmol, 2 equiv) and acryloyl chloride (0.162 mL, 2.00 mmol, 1.1 equiv) at 0° C. The mixture was stirred at 25° C. for 5 hours under N2. The reaction mixture was poured into water (15 mL) and extracted with DCM (15 mL*3). The combined organic layers were washed with brine (10 mL*2), dried over $Na_2SO_4$, filtered, and concentrated under reduced pressure. The residue was purified by flash silica gel chromatography (25% Ethyl acetate 75% Petroleum ether gradient @ 80 mL/min) to afford 1-(3-(3-chloro-5-(4,4,5,5-tetramethyl-1,3,2-dioxaborolan-2-yl)phenyl)-1,1-dioxidothiomorpholino) prop-2-en-1-one (500 mg, 1.17 mmol, 65% yield) as a yellow oil.

To a solution of 1-(3-(3-chloro-5-(4,4,5,5-tetramethyl-1,3,2-dioxaborolan-2-yl)phenyl)-1,1-dioxidothiomorpholino) prop-2-en-1-one (335 mg, 0.78 mmol, 1 equiv) in 1,4-dioxane (5 mL, 0.13 M) and water (1 mL, 0.13 M) was added 4-chloro-1,3,5-triazin-2-amine (123 mg, 0.944 mmol, 1.2 equiv), $Pd(dppf)Cl_2$ (56.9 mg, 0.078 mmol, 0.01 equiv), and $K_2CO_3$ (271.9 mg, 1.96 mmol, 2.5 equiv) at 25° C. The mixture was stirred at 80° C. for 5 hours under $N_2$. The reaction mixture was poured into water (10 mL) and extracted with EtOAc (15 mL*3). The combined organic layers were washed with brine (10 mL*2), dried over $Na_2SO_4$, filtered, and concentrated under reduced pressure. The residue was purified by prep-TLC (SiO2, EA:MeOH=10:1) to afford 1-(3-(3-(4-amino-1,3,5-triazin-2-yl)-5-chlorophenyl)-1,1-dioxidothiomorpholino)prop-2-en-1-one (290 mg, 0.736 mmol, 94% yield) as a yellow oil.

Enantiomers were separated and the absolute stereochemistry was not assigned.

Enantiomer 1: 1-(3-(3-(4-amino-1,3,5-triazin-2-yl)-5-chlorophenyl)-1,1-dioxidothiomorpholino)prop-2-en-1-one or Compound 205. LC-MS m/z: 394.1 [M+1].

Enantiomer 2: 1-(3-(3-(4-amino-1,3,5-triazin-2-yl)-5-chlorophenyl)-1,1-dioxidothiomorpholino)prop-2-en-1-one or Compound 206. LC-MS m/z: 394.1 [M+1].

Stereochemistry: single enantiomer of unknown absolute configuration.

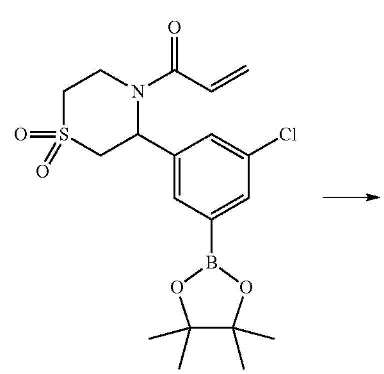

-continued

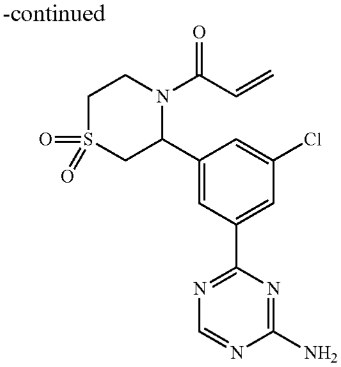

Using the appropriate coupling partner in Procedure W, the title compounds can be obtained. All compounds are single enantiomers of unknown absolute configuration.

| Cmp. | Name | Coupling Partner | LC-MS m/z [M + 1] |
|---|---|---|---|
| 205 | Ent 1: 1-(3-(3-(4-amino-1,3,5-triazin-2-yl)-5-chlorophenyl)-1,1-dioxidothiomorpholino)prop-2-en-1-one | 4-chloro-1,3,5-triazin-2-amine | 394.1 |
| 206 | Ent 2: 1-(3-(3-(4-amino-1,3,5-triazin-2-yl)-5-chlorophenyl)-1,1-dioxidothiomorpholino)prop-2-en-1-one | 4-chloro-1,3,5-triazin-2-amine | 394.1 |
| 209 | 1-(3-(3-(4-aminopyrimidin-2-yl)-5-chlorophenyl)-1,1-dioxidothiomorpholino)prop-2-en-1-one | 2-chloropyrimidin-4-amine | 393.1 |
| 207 | 1-(3-(3-(5-aminopyrimidin-2-yl)-5-chlorophenyl)-1,1-dioxidothiomorpholino)prop-2-en-1-one | 2-chloropyrimidin-5-amine | 393.1 |
| 51 | Ent 1: 1-(3-(3-chloro-5-(2-methylpyrimidin-4-yl)phenyl)-1,1-dioxidothiomorpholino)prop-2-en-1-one | 4-bromo-2-methylpyrimidine | 393.0 |
| 50 | Ent 2: 1-(3-(3-chloro-5-(2-methylpyrimidin-4-yl)phenyl)-1,1-dioxidothiomorpholino)prop-2-en-1-one | 4-bromo-2-methylpyrimidine | 393.0 |
| 52 | 1-(3-(3-chloro-5-(6-methylpyrimidin-4-yl)phenyl)-1,1-dioxidothiomorpholino)prop-2-en-1-one | 4-bromo-6-methylpyrimidine | 392.0 |
| 31 | 1-(3-(3-chloro-5-(pyrimidin-2-yl)phenyl)-1,1-dioxidothiomorpholino)prop-2-en-1-one | 2-bromopyrimidine | 378.0 |
| 39 | 4-(3-(4-acryloyl-1,1-dioxidothiomorpholin-3-yl)-5-chlorophenyl)pyridin-2(1H)-one | 4-bromopyridin-2(1H)-one | 393.1 |
| 29 | 4-(3-(4-acryloyl-1,1-dioxidothiomorpholin-3-yl)-5-chlorophenyl)-1-methylpyridin-2(1H)-one, racemic | 4-bromo-1-methylpyridin-2(1H)-one | 407.2 |
| 32 | 1-(3-(3-chloro-5-(2-methyl-2H-tetrazol-5-yl)phenyl)-1,1-dioxidothiomorpholino)prop-2-en-1-one | 5-iodo-2-methyl-2H-tetrazole | 382.0 |
| 28 | 1-(3-(3-chloro-5-(tetrahydro-2H-pyran-4-yl)phenyl)-1,1-dioxidothiomorpholino)prop-2-en-1-one, racemic, additional reduction step | 2-(3,6-dihydro-2H-pyran-4-yl)-4,4,5,5-tetramethyl-1,3,2-dioxaborolane | 384.0 |

Example 90. Synthesis of 1-(5-(3-(4-aminopyrimidin-2-yl)-5-chlorophenyl)-2,2-dimethyl-1,1-dioxidothiomorpholino)prop-2-en-1-one (Compound 246)

The title compound can be prepared in a similar fashion to Procedure W using 2-methyl-2-(methylthio)propan-1-amine. LC-MS m/z: 421.2 [M+1].

Stereochemistry: single enantiomer of unknown absolute configuration.

Example 91. Synthesis of 1-(6-(3-(4-aminopyrimidin-2-yl)-5-chlorophenyl)-4,4-dioxido-4-thia-7-azaspiro[2.5]octan-7-yl)prop-2-en-1-one (Compound 249)

The title compound can be prepared in a similar fashion to Procedure W using (1-(methylthio)cyclopropyl)methanamine. LC-MS m/z: 421.2 [M+1].

Stereochemistry: single enantiomer of unknown absolute configuration.

Example 92. Procedure X and Synthesis of (R)-1-(4-acetyl-2-(3-(5-aminopyrimidin-2-yl)-5-chlorophenyl)piperazin-1-yl)prop-2-en-1-one (Compound 188)

Procedure X

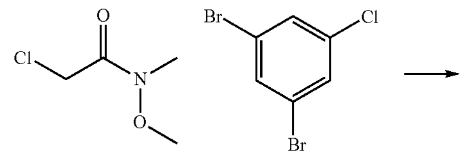

-continued

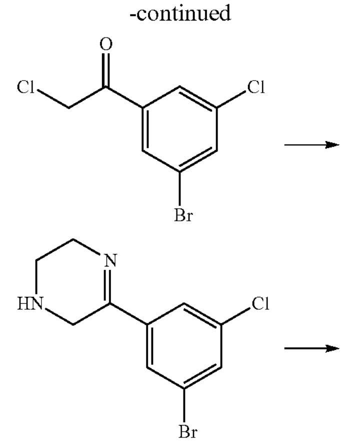

-continued

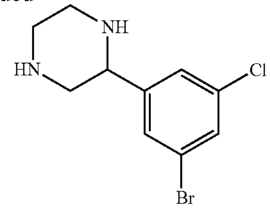

To a solution of 1,3-dibromo-5-chloro-benzene (50 g, 184.95 mmol) in i-$Pr_2O$ (500 mL) at −78° C. was added n-BuLi (75 mL, 1 eq) dropwise. The resulting yellow mixture was stirred at −78° C. for 30 minutes. 2-chloro-N-methoxy-N-methyl-acetamide (27985 mg, 203.44 mmol) was added to the reaction mixture drop-wise and then stirred at −78° C. for 1 hour. The reaction mixture was quenched with saturated aqueous $NH_4Cl$ (100 mL) at −40° C. and then poured into water (400 mL). The solution was extracted with EtOAc (200 mL*2). The organic layers were washed with brine (300 mL), dried over $Na_2SO_4$, filtered, and concentrated. The crude product was purified by column chromatography (PE:EtOAc=10:1) to afford 1-(3-bromo-5-chloro-phenyl)-2-chloro-ethanone (30 g, 60% yield) as a white solid.

To a solution of 1-(3-bromo-5-chloro-phenyl)-2-chloro-ethanone (5000 mg, 18.6 mmol) in 1,4-dioxane (75 mL, 0.20 M) was added a solution of ethylene diamine (5607 mg, 93.30 mmol) in 1,4-dioxane (15 mL, 0.21 M) at 0° C. Molecular sieves (5 g) were added at 15° C. and the reaction was stirred at 15° C. for 20 hours. The reaction was filtered, and the organic layer was concentrated to afford crude 5-(3-bromo-5-chloro-phenyl)-1,2,3,6-tetrahydropyrazine (6 g).

To a solution of 5-(3-bromo-5-chloro-phenyl)-1,2,3,6-tetrahydropyrazine (30 g, 109.67 mmol) in methanol (300 mL, 0.36 M) at 0° C. was added $NaBH_4$ (10 g) portion wise. The reaction mixture was stirred at 0° C. for 2 hours. The reaction mixture was quenched with 1M aqueous HCl (200 mL), adjusted to pH 5~6, and then concentrated. The crude product was purified by column chromatography (DCM:MeOH=10:1) to afford 2-(3-bromo-5-chlorophenyl)piperazine (10 g, 33% yield) as a white solid.

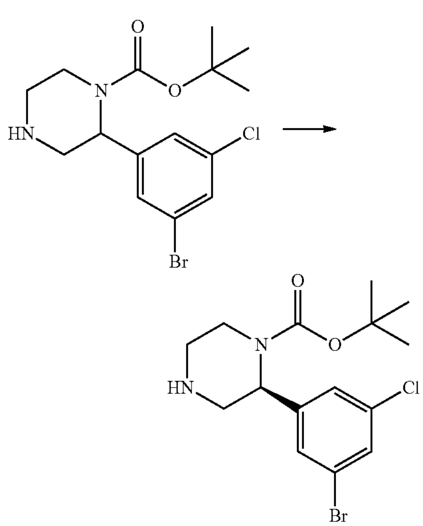

-continued

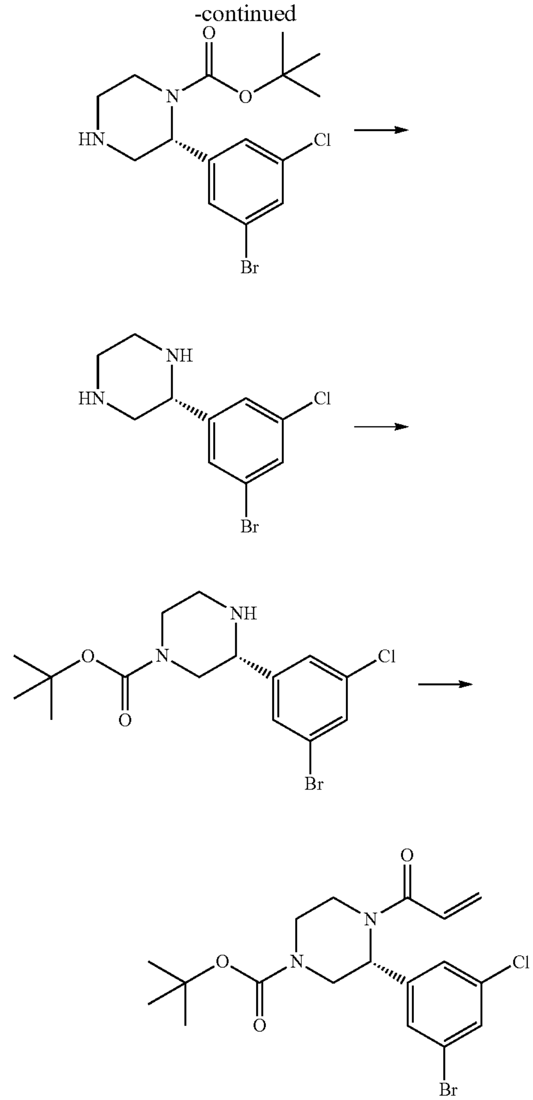

To a solution of 2-(3-bromo-5-chlorophenyl)piperazine (10 g, 36.3 mmol) in DCM (150 mL, 0.24 M) was added 9H-fluoren-9-ylmethyl carbonochloridate (4.693 g, 18.14 mmol). The reaction mixture was stirred at 15° C. for 2 hours. The reaction was filtered, and the organic layer was concentrated to afford 10 g of crude product.

To a solution of 9H-fluoren-9-ylmethyl 3-(3-bromo-5-chloro-phenyl)piperazine-1-carboxylate (20 g, 40.17 mmol) in DCM (200 mL, 0.2 M) was added 4-(dimethylamino)pyridine (2.45 g, 20 mmol) and di-tert-butyl dicarbonate (13.15 g, 60.2 mmol) portion-wise at 0° C. and stirred for 1 hour. The reaction was filtered, and the organic layer was concentrated to give 30 g of crude product.

To a mixture of 01-tert-butyl 04-(9H-fluoren-9-ylmethyl) 2-(3-bromo-5-chloro-phenyl)piperazine-1,4-dicarboxylate (15 g, 25.1 mmol) in DCM (100 mL, 0.25 M) was added piperidine (12.82 g, 150 mmol) at 20° C. and stirred for 16 hours. The mixture was cooled to 20° C. and concentrated under reduced pressure. The residue was poured into water (10 mL) and extracted with ethyl acetate (10 mL*2). The combined organic phase was washed with brine (10 mL*2), dried with anhydrous $Na_2SO_4$, filtered, and concentrated to afford tert-butyl 2-(3-bromo-5-chloro-phenyl)piperazine-1-carboxylate (5 g, 53% yield) as a white solid.

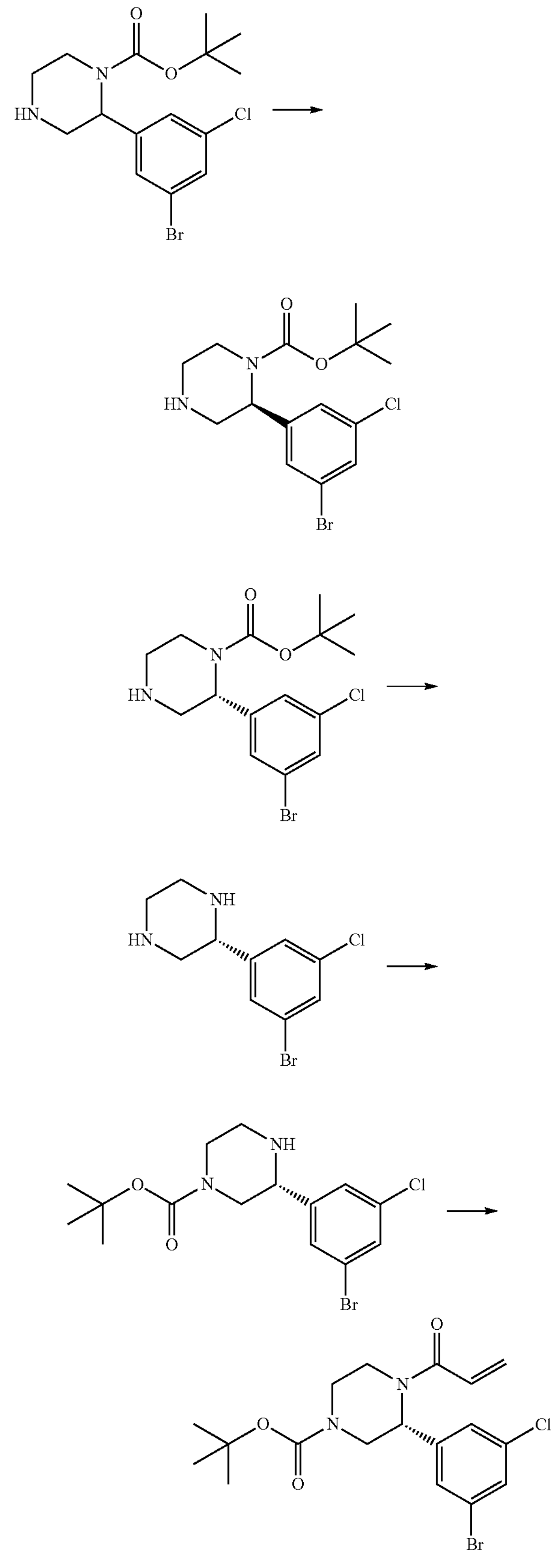

Enantiomers were separated by SFC to afford tert-butyl (S)-2-(3-bromo-5-chlorophenyl)piperazine-1-carboxylate and tert-butyl (R)-2-(3-bromo-5-chlorophenyl)piperazine-1-carboxylate. Absolute stereochemistry was established by crystallography.

To a solution of tert-butyl (R)-2-(3-bromo-5-chlorophenyl)piperazine-1-carboxylate (2500 mg, 6.65 mmol, 1 equiv) in ethyl acetate (20 mL, 0.33 M) was added HCl in EtOAc (30 mL) at 0° C. and stirred for 1 hour. The reaction solution was concentrated in vacuo.

To a solution of (R)-2-(3-bromo-5-chlorophenyl)piperazine dihydrochloride (7800 mg, 22.38 mmol, 1 equiv) in DCM (80 mL, 0.28 M) was added triethylamine (6794 mg, 67.14 mmol, 3 equiv) and di-tert-butyl dicarbonate (4396 mg, 20.14 mmol, 0.9 equiv) at 0° C. The mixture was stirred at 0° C. for 1 hour under $N_2$. The reaction mixture was poured into saturated aqueous $NH_4Cl$ (100 mL) and extracted with EtOAc (80 mL*3). The combined organic layers were washed with brine (40 mL), dried over $Na_2SO_4$, filtered, and concentrated under reduced pressure. The residue was purified by column chromatography ($SiO_2$, Petroleum ether/Ethyl acetate=1/1 to 0/1) to afford tert-butyl (R)-3-(3-bromo-5-chlorophenyl)piperazine-1-carboxylate (7.7 g, 20.49 mmol, 92% yield) as a yellow oil.

To a solution of tert-butyl (R)-3-(3-bromo-5-chlorophenyl)piperazine-1-carboxylate (6 g, 15.97 mmol, 1 equiv) in DCM (60 mL, 0.26 M) was added triethylamine (4.45 mL, 31.91 mmol, 2 equiv) and acryloyl chloride (1.734 g, 19.16 mmol, 1.2 equiv) at 0° C. under $N_2$ and stirred for 40 minutes. The solution was quenched with water (150 mL) and extracted with DCM (150 mL*3). The organic phases were dried over $Na_2SO_4$, filtered, and concentrated. The crude product was purified by column chromatography on silica gel (petroleum ether/ethyl acetate=100:0 to 1:1) to afford tert-butyl (R)-4-acryloyl-3-(3-bromo-5-chlorophenyl)piperazine-1-carboxylate (6.666 g, 15.51 mmol, 97% yield).

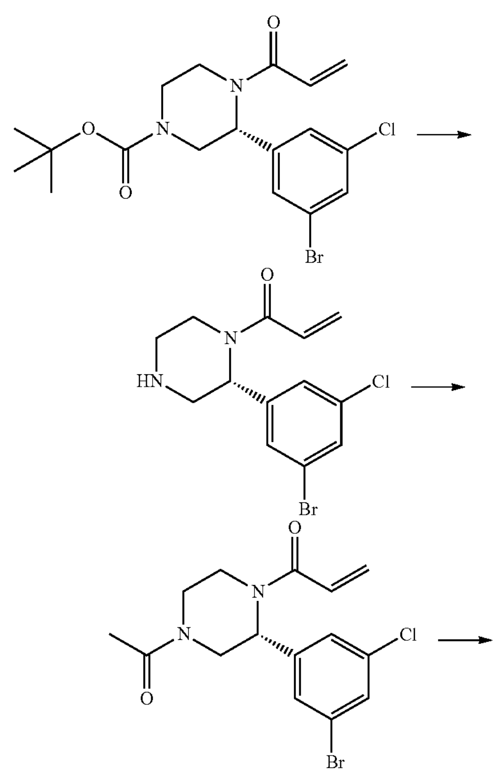

-continued

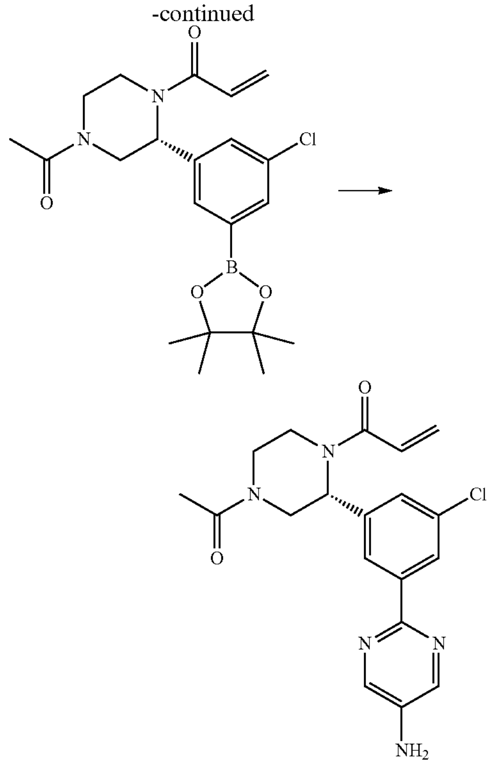

To a solution of tert-butyl (R)-4-acryloyl-3-(3-bromo-5-chlorophenyl)piperazine-1-carboxylate (4.26 g, 9.91 mmol, 1 equiv) in DCM (20 mL) was added TFA (20 mL). The reaction was stirred at room temperature for 1.5 hours. The mixture was concentrated under reduced pressure to afford (R)-1-(2-(3-bromo-5-chlorophenyl)piperazin-1-yl)prop-2-en-1-one.

To a solution of (R)-1-(2-(3-bromo-5-chlorophenyl)piperazin-1-yl)prop-2-en-1-one (4 g, 12.13 mmol, 1 equiv) in DCM (50 mL, 0.24 M) was added triethylamine (1.841 g, 18.20 mmol, 1.5 equiv) and acetyl chloride (1.238 g, 15.77 mmol, 1.3 equiv) at 0° C. under $N_2$ and stirred for 40 minutes. The solution was quenched with water (150 mL) and extracted with DCM (150 mL*3). The organic phases were dried over $Na_2SO_4$, filtered, and concentrated. The crude product was purified by column chromatography on silica gel (Petroleum ether/Ethyl acetate=100:0 to 0:100) to afford (R)-1-(4-acetyl-2-(3-bromo-5-chlorophenyl)piperazin-1-yl)prop-2-en-1-one (3.239 g, 8.71 mmol, 72% yield).

To a solution of (R)-1-(4-acetyl-2-(3-bromo-5-chlorophenyl)piperazin-1-yl)prop-2-en-1-one (3.239 g, 8.71 mmol, 1 equiv) in 1,4-dioxane (35 mL, 0.25 M) was added bis(pinacolato)diboron (2.656 g, 10.46 mmol, 1.2 equiv), potassium acetate (2.160 g, 21.79 mmol, 2.5 equiv), and $Pd(dppf)Cl_2$ (0.6308 g, 0.8717 mmol, 0.1 equiv). The reaction was heated to 80° C. for 17 hours. The solution was quenched with water (150 mL) and extracted with DCM (150 mL*3). The organic phases were dried over Na2SO4, filtered, and concentrated. The crude product was purified by column chromatography on silica gel (Petroleum ether/Ethyl acetate=100:0 to 0:100) to afford (R)-1-(4-acetyl-2-(3-chloro-5-(4,4,5,5-tetramethyl-1,3,2-dioxaborolan-2-yl)phenyl)piperazin-1-yl)prop-2-en-1-one (2.285 g, 5.45 mmol, 63% yield).

To a solution of (R)-1-(4-acetyl-2-(3-chloro-5-(4,4,5,5-tetramethyl-1,3,2-dioxaborolan-2-yl)phenyl)piperazin-1-yl)prop-2-en-1-one (50 mg, 0.11 mmol, 1 equiv) in 1,4-dioxane (2 mL, 0.2 M) and water (0.5 mL) was added the 2-bromopyrimidin-5-amine (24 mg, 0.14 mmol, 1.2 equiv), potassium carbonate (33 mg, 0.24 mmol), and $Pd(dppf)Cl_2$ (8.6 mg, 0.01 mmol, 0.1 equiv). The reaction was heated to 80° C. for 12 hours under $N_2$. The reaction mixture was quenched with $H_2O$ (5 mL) and extracted with ethyl acetate (5 mL×2). The organic layers were washed with 10 mL saturated brine solution. The organic layer was then separated, dried over $Na_2SO_4$, filtered, and concentrated. The crude residue was purified by column chromatography (PE:EA=10:1 to 0:1) to give (R)-1-(4-acetyl-2-(3-(5-aminopyrimidin-2-yl)-5-chlorophenyl)piperazin-1-yl)prop-2-en-1-one (8.0 mg, 0.02 mmol, 17% yield) as white solid. LC-MS m/z: 386.1 [M+1].

Stereochemistry: single enantiomer of known absolute configuration.

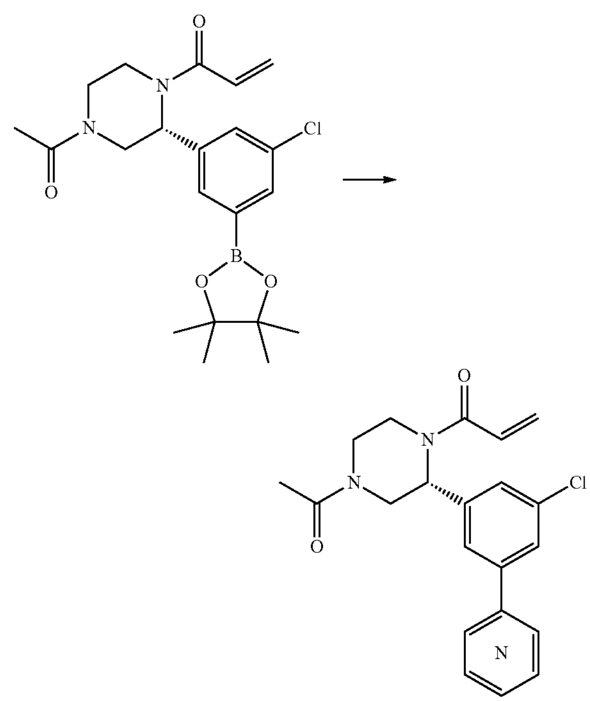

Using the appropriate coupling partner in Procedure X, the title compounds can be obtained. All compounds are single enantiomers of known absolute configuration.

| Cmp | Name | Coupling Partner in Step 2 | LC-MS m/z [M + 1] |
|---|---|---|---|
| 188 | (R)-1-(4-acetyl-2-(3-(5-aminopyrimidin-2-yl)-5-chlorophenyl)piperazin-1-yl)prop-2-en-1-one | 2-bromopyrimidin-5-amine | 386.1 |
| 17 | (R)-1-(4-acetyl-2-(3-chloro-5-(pyrimidin-2-yl)phenyl)piperazin-1-yl)prop-2-en-1-one | 2-bromopyrimidine | 371.1 |

-continued

| Cmp | Name | Coupling Partner in Step 2 | LC-MS m/z [M + 1] |
|---|---|---|---|
| 22 | (R)-1-(4-acetyl-2-(3-chloro-5-(2-methyl-2H-tetrazol-5-yl)phenyl)piperazin-1-yl)prop-2-en-1-one | 5-iodo-2-methyl-2H-tetrazole | 375.1 |
| 26 | (R)-1-(4-acetyl-2-(3-chloro-5-(tetrahydro-2H-pyran-4-yl)phenyl)piperazin-1-yl)prop-2-en-1-one | 3,6-dihydro-2H-pyran-4-yltrifluoromethanesulfonate (additional reduction step) | 377.2 |
| 74 | (R)-1-(4-acetyl-2-(3-(4-amino-1,3,5-triazin-2-yl)-5-chlorophenyl)piperazin-1-yl)prop-2-en-1-one | 4-chloro-1,3,5-triazin-2-amine | 387.0 |
| 79 | (R)-3'-(4-acetyl-1-acryloylpiperazin-2-yl)-5'-chloro-4-fluoro-[1,1'-biphenyl]-3-carboxamide | 5-bromo-2-fluorobenzamide | 430.1 |
| 81 | (R)-1-(4-acetyl-2-(3-(2-aminopyrimidin-4-yl)-5-chlorophenyl)piperazin-1-yl)prop-2-en-1-one | 4-bromopyrimidin-2-amine | 386.1 |
| 183 | (R)-1-(4-acetyl-2-(3-(4-aminopyrimidin-2-yl)-5-chlorophenyl)piperazin-1-yl)prop-2-en-1-one | 2-bromopyrimidin-4-amine | 386.1 |
| 187 | (R)-1-(4-acetyl-2-(3-(6-aminopyrimidin-4-yl)-5-chlorophenyl)piperazin-1-yl)prop-2-en-1-one | 6-bromopyrimidin-4-amine | 386.1 |

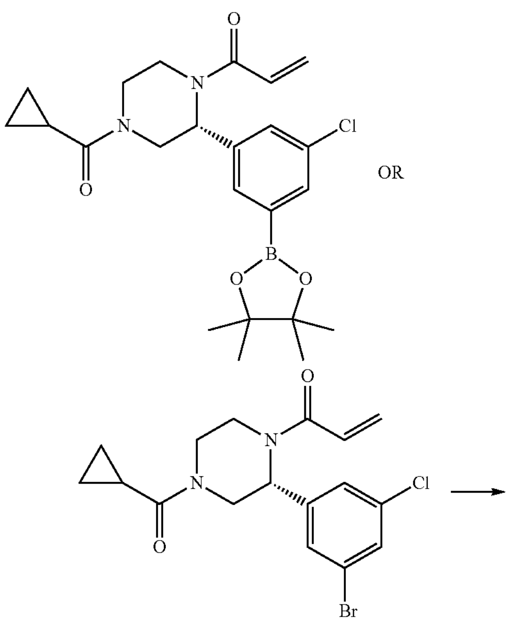

OR

-continued

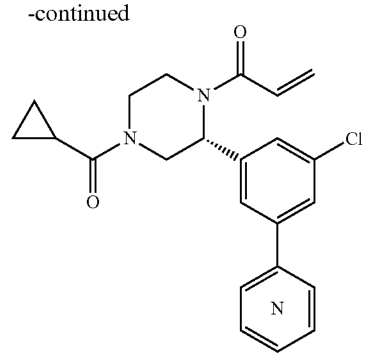

(R)-1-(2-(3-chloro-5-(4,4,5,5-tetramethyl-1,3,2-dioxaborolan-2-yl)phenyl)-4-(cyclopropanecarbonyl)piperazin-1-yl)prop-2-en-1-one was obtained from Procedure X using cyclopropanecarbonyl chloride. Using the appropriate coupling partner similar to Procedure X, the title compounds can be obtained. All compounds are single enantiomers of known absolute configuration.

| Cmp | Name | Coupling Partner | LC-MS m/z [M + 1] |
|---|---|---|---|
| 195 | (R)-3'-(1-acryloyl-4-(cyclopropanecarbonyl)piperazin-2-yl)-5'-chloro-4-fluoro-[1,1'-biphenyl]-3-carboxamide | 2-fluoro-5-(4,4,5,5-tetramethyl-1,3,2-dioxaborolan-2-yl)benzamide | 456.1 |
| 196 | (R)-1-(2-(3-(4-aminopyrimidin-2-yl)-5-chlorophenyl)-4-(cyclopropanecarbonyl)piperazin-1-yl)prop-2-en-1-one | 2-chloropyrimidin-4-amine | 412.1 |
| 197 | (R)-1-(2-(3-(6-aminopyrimidin-4-yl)-5-chlorophenyl)-4-(cyclopropanecarbonyl)piperazin-1-yl)prop-2-en-1-one | 6-bromopyrimidin-4-amine | 412.2 |
| 200 | (R)-1-(2-(3-(5-aminopyrimidin-2-yl)-5-chlorophenyl)-4-(cyclopropanecarbonyl)piperazin-1-yl)prop-2-en-1-one | 2-bromopyrimidin-5-amine | 412.1 |
| 185 | (R)-1-(2-(3-(2-aminopyrimidin-4-yl)-5-chlorophenyl)-4-(cyclopropanecarbonyl)piperazin-1-yl)prop-2-en-1-one | 4-bromopyrimidin-2-amine | 412.2 |

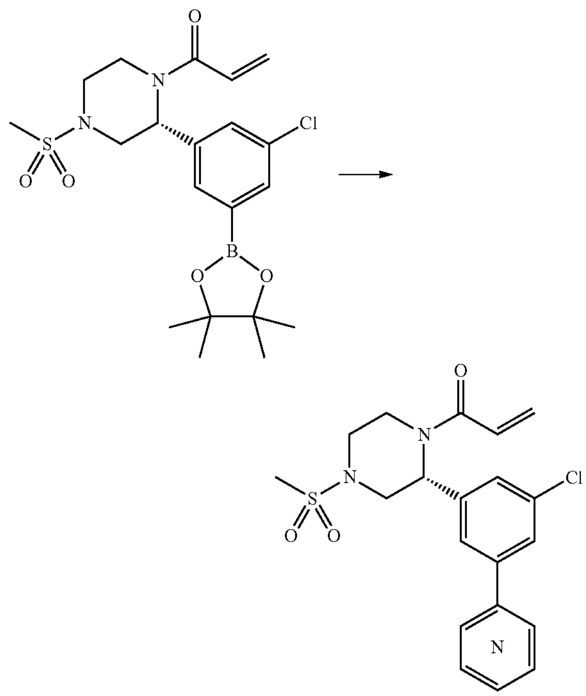

(R)-1-(2-(3-chloro-5-(4,4,5,5-tetramethyl-1,3,2-dioxaborolan-2-yl)phenyl)-4-(methylsulfonyl)piperazin-1-yl)prop-2-en-1-one was obtained from Procedure X using sulfonyl chloride. Using the appropriate coupling partner similar to Procedure X, the title compounds can be obtained. All compounds are single enantiomers of known absolute configuration.

| Cmp. | Name | Coupling Partner | LC-MS m/z [M + 1] |
|---|---|---|---|
| 6 | N-(4-(3-(1-acryloyl-4-(methylsulfonyl)piperazin-2-yl)-5-chlorophenyl)pyridin-2-yl)acetamide | N-(3-bromophenyl)acetamide | 463.1 |
| 15 | (R)-4-(3-(1-acryloyl-4-(methylsulfonyl)piperazin-2-yl)-5-chlorophenyl)pyridin-2(1H)-one | 4-bromopyridin-2(1H)-one | 422.1 |
| 16 | (R)-1-(4-(3-(1-acryloyl-4-(methylsulfonyl)piperazin-2-yl)-5-chlorophenyl)pyridin-2-yl)pyrrolidin-2-one | 1-(4-bromopyridin-2-yl)pyrrolidin-2-one | 489.1 |
| 21 | (R)-1-(2-(3-chloro-5-(2-methyl-2H-tetrazol-5-yl)phenyl)-4-(methylsulfonyl)piperazin-1-yl)prop-2-en-1-one | 5-iodo-2-methyl-2H-tetrazole | 411.1 |
| 123 | (R)-1-(2-(3-(4-amino-1,3,5-triazin-2-yl)-5-chlorophenyl)-4-(methylsulfonyl)piperazin-1-yl)prop-2-en-1-one | 4-chloro-1,3,5-triazin-2-amine | 423.1 |
| 124 | (R)-1-(2-(3-(2-aminopyrimidin-4-yl)-5-chlorophenyl)-4-(methylsulfonyl)piperazin-1-yl)prop-2-en-1-one | 4-bromopyrimidin-2-amine | 422.1 |

Example 93. Synthesis of (R)-3-(4-acryloyl-3-(3-(2-aminopyrimidin-4-yl)-5-chlorophenyl)piperazin-1-yl)-3-oxopropanenitrile (Compound 186)

The title compound was obtained in a similar fashion to Compound 81 using 2-cyanoacetyl chloride. LC-MS m/z: 411.1 [M+1].

Stereochemistry: single enantiomer of known absolute configuration.

Example 94. Synthesis of (R)—N-(4-(3-(1-acryloyl-4-(2-cyanoacetyl)piperazin-2-yl)-5-chlorophenyl)pyrimidin-2-yl)-2-cyanoacetamide (Compound 189)

The title compound was obtained in a similar fashion to Compound 81 using excess 2-cyanoacetyl chloride. LC-MS m/z: 478.0 [M+1].

Stereochemistry: single enantiomer of known absolute configuration.

Example 95. Synthesis of 1-((2S,5R)-4-acetyl-2-(3-(5-aminopyrimidin-2-yl)-5-chlorophenyl)-5-methylpiperazin-1-yl)prop-2-en-1-one (Compound 236)

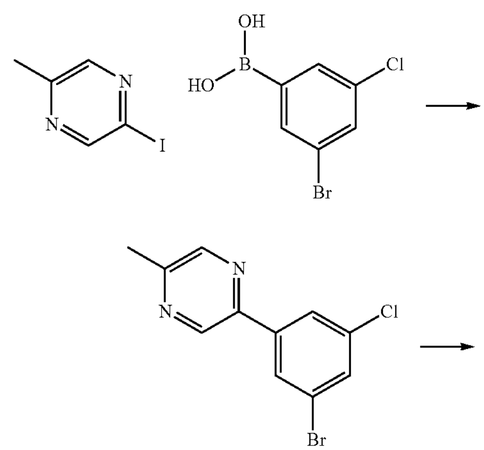

-continued

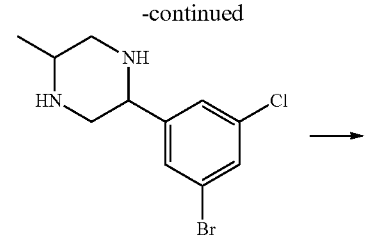

-continued

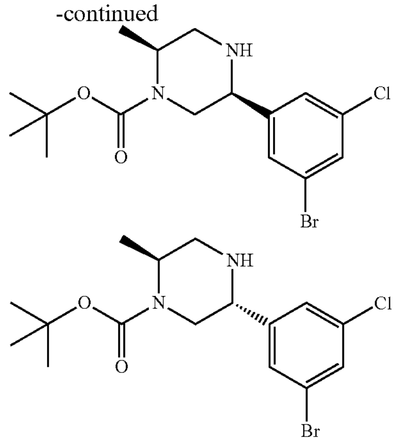

To a solution of 3-bromo-5-chlorophenylboronic acid (4.3 g, 18.27 mmol, 1 equiv) in 1,4-dioxane (80 mL, 0.09 M), MeCN (80 mL, 0.09 M), and water (40 mL, 0.09 M) was added 2-iodo-5-methyl-pyrazine (4021 mg, 18.27 mmol, 1 equiv), potassium carbonate (6315 mg, 45.69 mmol, 2.5 equiv), and Pd(dppf) (1326 mg, 1.82 mmol, 0.1 equiv) at 25° C. The mixture was stirred at 65° C. for 3 hours under $N_2$. The reaction mixture was poured into water (150 mL) and extracted with EtOAc (150 mL*3). The combined organic layers were washed with brine (100 mL*2), dried over $Na_2SO_4$, filtered, and. The residue was purified by flash silica gel chromatography (ISCO®; 80 g SEPAFLASH® Silica Flash Column, Eluent of 0-30% Ethyl acetate/Petroleum ether gradient @ 100 mL/min) to afford 2-(3-bromo-5-chloro-phenyl)-5-methyl-pyrazine (4.36 g, 15.4 mmol, 84% yield) as a yellow solid.

To a solution of 2-(3-bromo-5-chloro-phenyl)-5-methyl-pyrazine (4.1 g, 14.46 mmol, 1 equiv), pinacolborane (9.252 g, 72.29 mmol, 5 equiv), and N-phenylaniline (9.787 g, 57.8 mmol, 4 equiv) in toluene (100 mL, 0.14 M) was added tris(2,3,4,5,6-pentafluorophenyl)borane (740.3 mg, 1.44 mmol, 0.1 equiv) at room temperature. The reaction mixture was stirred for 12 hours at 110° C. under $N_2$. The reaction mixture was concentrated under reduced pressure. The residue was purified by flash silica gel chromatography (ISCO®; 80 g SEPAFLASH® Silica Flash Column, Eluent of 100-70% Ethyl acetate/MeOH gradient @ 120 mL/min) to afford 2-(3-bromo-5-chloro-phenyl)-5-methyl-piperazine (4.50 g, 12.4 mmol, 86% yield).

To a solution of 2-(3-bromo-5-chloro-phenyl)-5-methyl-piperazine (1000 mg, 3.45 mmol, 1 equiv) in DCM (15 mL, 0.23 M) was added triethylamine (349 mg, 3.45 mmol, 1 equiv) and di-tert-butyl dicarbonate (678 mg, 3.10 mmol, 0.9 equiv) at 0° C. The reaction mixture was stirred for 12 hours at room temperature. The reaction mixture was poured into water (20 mL) and extracted with DCM (20 mL*3). The combined organic layers were washed with brine (10 mL*2), dried over $Na_2SO_4$, filtered, and concentrated. The residue was purified by flash silica gel chromatography (ISCO®; 12 g SEPAFLASH® Silica Flash Column, Eluent of 0-40% Ethyl acetate/Petroleum ether gradient @ 60 mL/min) to afford tert-butyl rac-(2S,5R)-5-(3-bromo-5-chloro-phenyl)-2-methyl-piperazine-1-carboxylate (400 mg, 1.03 mmol, 30% yield) and tert-butyl rac-(2S,5S)-5-(3-bromo-5-chloro-phenyl)-2-methyl-piperazine-1-carboxylate (390 mg, 1.00 mmol, 29% yield).

The title compound was obtained using tert-butyl rac-(2S,5S)-5-(3-bromo-5-chloro-phenyl)-2-methyl-piperazine-1-carboxylate in Procedure X. Enantiomers were separated by SFC. LC-MS m/z: 400.1 [M+1].

Stereochemistry: single enantiomer of unknown absolute configuration.

Example 96. Synthesis of 1-((2S,5S)-4-acetyl-2-(3-(5-aminopyrimidin-2-yl)-5-chlorophenyl)-5-methylpiperazin-1-yl)prop-2-en-1-one (Compound 237)

The title compound was obtained using tert-butyl rac-(2S,5R)-5-(3-bromo-5-chloro-phenyl)-2-methyl-piperazine-1-carboxylate from the synthesis of Compound 236 in Procedure X.

Enantiomers were separated by SFC. LC-MS m/z: 400.1 [M+1].

Stereochemistry: single enantiomer of unknown absolute configuration.

Example 97. Synthesis of 1-((2S,5R)-2-(3-(5-aminopyrimidin-2-yl)-5-chlorophenyl)-4-(cyclopropanecarbonyl)-5-methylpiperazin-1-yl)prop-2-en-1-one (Compound 243)

The title compound was obtained in a similar fashion to Compound 236 using cyclopropanecarbonyl chloride. LC-MS m/z: 426.3 [M+1].

Stereochemistry: single enantiomer of unknown absolute configuration.

Example 98. Synthesis of 1-((2R,5R)-2-(3-(5-aminopyrimidin-2-yl)-5-chlorophenyl)-4-(cyclopropanecarbonyl)-5-methylpiperazin-1-yl)prop-2-en-1-one (Compound 245)

The title compound was obtained in a similar fashion to Compound 237 using cyclopropanecarbonyl chloride. LC-MS m/z: 426.3 [M+1].

Stereochemistry: single enantiomer of unknown absolute configuration.

Example 99. Synthesis of 1-(6-(3-(5-aminopyrimidin-2-yl)-5-chlorophenyl)-4-(cyclopropanecarbonyl)-4,7-diazaspiro[2.5]octan-7-yl)prop-2-en-1-one (Compound 260)

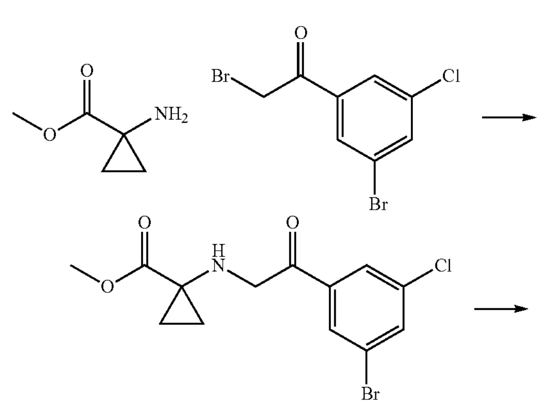

-continued

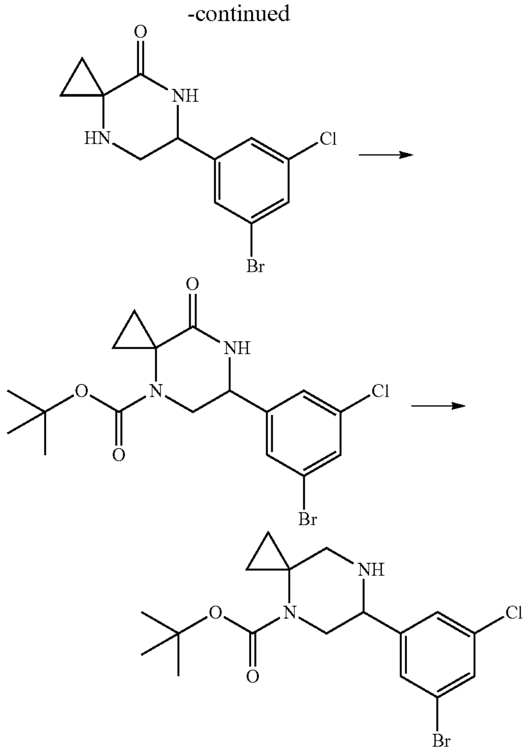

To a solution of 2-bromo-1-(3-bromo-5-chloro-phenyl) ethanone (10.853 g, 34.74 mmol) in DMF (120 mL, 0.29 M) was slowly added $NaHCO_3$ (7.297 g, 86.85 mmol) at 0° C. under $N_2$ and stirred for 30 minutes. Methyl 1-aminocyclopropanecarboxylate (4 g, 34.74 mmol) was added and the mixture was stirred at 20° C. for 2 hours. The solution was diluted with saturated aqueous $NH_4Cl$ (800 mL), extracted with EtOAc (150 mL*3), washed with brine (500 mL), dried over $Na_2SO_4$, filtered, and concentrated. The crude product was used directly for the next step without purification.

To a solution of methyl methyl 1-[[2-(3-bromo-5-chloro-phenyl)-2-oxo-ethyl]amino]cyclopropanecarboxylate (5 g, 14.42 mmol) in methanol (100 mL, 0.14 M) was added ammonium acetate (11.119 g, 144.26 mmol) at 20° C. under $N_2$ and stirred for 2 hours. Sodium cyanoborohydride (1.813 g, 28.85 mmol) was added at 0° C. The reaction was heated to 50° C. for 16 hours. The solution was diluted with $H_2O$ (500 mL), extracted with DCM (300 mL*3), washed with brine (1000 mL), dried over $Na_2SO_4$, filtered, and concentrated. The crude product was diluted with MTBE (50 ml) and stirred at 20° C. for 30 minutes. The suspension was filtered, and the filtrate was concentrated to afford 6-(3-bromo-5-chloro-phenyl)-4,7-diazaspiro[2.5]octan-8-one (160 mg, 0.50 mmol, 43% yield) as a yellow solid.

To a solution of 6-(3-bromo-5-chloro-phenyl)-4,7-diazaspiro[2.5]octan-8-one (2.4 g, 7.60 mmol) in 1,4-dioxane (30 mL) was added triethylamine (1.539 g, 15.20 mmol) and di-tert-butyl dicarbonate (2.157 g, 9.88 mmol) at room temperature under $N_2$ and then stirred at 80° C. for 4 hours. The reaction was diluted with water (50 mL) and extracted with ethyl acetate (35 ml*3). The combined organic layers were washed with brine (100 mL), dried over $Na_2SO_4$, filtered, and concentrated. The crude product was purified by silica gel chromatography (PE:EtOAc=100:0 to PE:EtOAc=80:20) to give tert-butyl 6-(3-bromo-5-chloro-phenyl)-8-oxo-4,7-diazaspiro[2.5]octane-4-carboxylate (3.05 g, 7.34 mmol, 96% yield) as a yellow solid.

To a solution of tert-butyl 6-(3-bromo-5-chloro-phenyl)-8-oxo-4,7-diazaspiro[2.5]octane-4-carboxylate (3.05 g, 7.35 mmol) in THF (40 mL, 0.18 M) was slowly added borane dimethylsulfide (1.763 g, 22.01 mmol) dropwise at 0° C. under $N_2$ and then stirred at room temperature for 16 hours. MeOH (30 mL) was added dropwise at 0° C. and then stirred at 70° C. for 4 hours. The solution was concentrated to afford crude tert-butyl 6-(3-bromo-5-chlorophenyl)-4,7-diazaspiro[2.5]octane-4-carboxylate (3.2 g) that was used directly without purification.

The title compound was obtained using tert-butyl 6-(3-bromo-5-chlorophenyl)-4,7-diazaspiro[2.5]octane-4-carboxylate in Procedure X. Enantiomers were separated by SFC. LC-MS m/z: 412.0 [M+1].

Stereochemistry: single enantiomer of unknown absolute configuration.

Example 100. Synthesis of 1-(4-acetyl-6-(3-(5-aminopyrimidin-2-yl)-5-chlorophenyl)-4,7-diazaspiro[2.5]octan-7-yl)prop-2-en-1-one (Compound 267)

The title compound was obtained in a similar fashion to Compound 260. LC-MS m/z: 438.0 [M+1].

Stereochemistry: single enantiomer of unknown absolute configuration.

Example 101. Synthesis of 1-(2-(3-(5-aminopyrimidin-2-yl)-5-chlorophenyl)-5,5-difluoropiperidin-1-yl)prop-2-en-1-one (Compound 238)

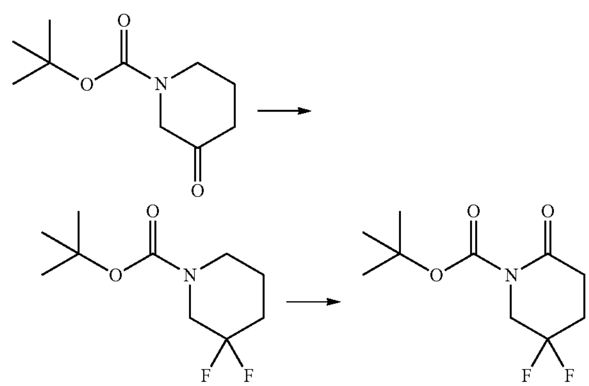

To a solution of tert-butyl 3-oxopiperidine-1-carboxylate (5 g, 25.09 mmol, 1 equiv) in DCM (100 mL, 0.25 M) at −70° C. was added diethylaminosulfur trifluoride (8.988 g, 50.18 mmol, 2 equiv). The mixture was stirred at −70° C. for 19 hours. The reaction was poured into saturated aqueous $NaHCO_3$ (200 mL) and then extracted by DCM (3×100 mL). The residue was purified by column chromatography ($SiO_2$, Petroleum ether/Ethyl acetate=100/0 to 5/95) to afford tert-butyl 3,3-difluoropiperidine-1-carboxylate (3.36 g, 15.2 mmol, 61% yield) as a yellow oil.

Sodium periodate (5.367 g, 24.86 mmol, 5 equiv) was dissolved in water (40 mL, 0.045 M) before addition of $RuCl_3$ (0.355 g, 1.69 mmol, 0.34 equiv). The resulting solution was taken up in ethyl acetate (70 mL, 0.04 M). tert-Butyl 3,3-difluoropiperidine-1-carboxylate (1.1 g, 4.97 mmol, 1 equiv) was added and then stirred at room temperature for 21 hours. The reaction solution was diluted with ethyl acetate, washed with water and brine, dried over magnesium sulfate, filtered, and concentrated. The residue was purified by column chromatography ($SiO_2$, Petroleum ether/Ethyl acetate=100/1 to 90/10) to give tert-butyl 5,5-difluoro-2-oxo-piperidine-1-carboxylate (858 mg, 3.65 mmol, 74% yield) as a yellow oil.

The title compound was obtained by Procedure B using tert-butyl 5,5-difluoro-2-oxo-piperidine-1-carboxylate. Enantiomers were separated by SFC. LC-MS m/z: 379.2 [M+1].

Stereochemistry: single enantiomer of unknown absolute configuration.

Example 102. Synthesis of 1-(2-(3-(5-aminopyrimidin-2-yl)-5-chlorophenyl)piperidin-1-yl)prop-2-en-1-one (Compound 239)

The title compound was obtained with Procedure B using tert-butyl 2-oxopiperidine-1-carboxylate. Enantiomers were separated by SFC. LC-MS m/z: 343.2 [M+1].

Stereochemistry: single enantiomer of unknown absolute configuration.

Example 103. Synthesis of 1-(2-(3-(5-aminopyrimidin-2-yl)-5-chlorophenyl)-4,4-difluoropiperidin-1-yl)prop-2-en-1-one (Compound 247)

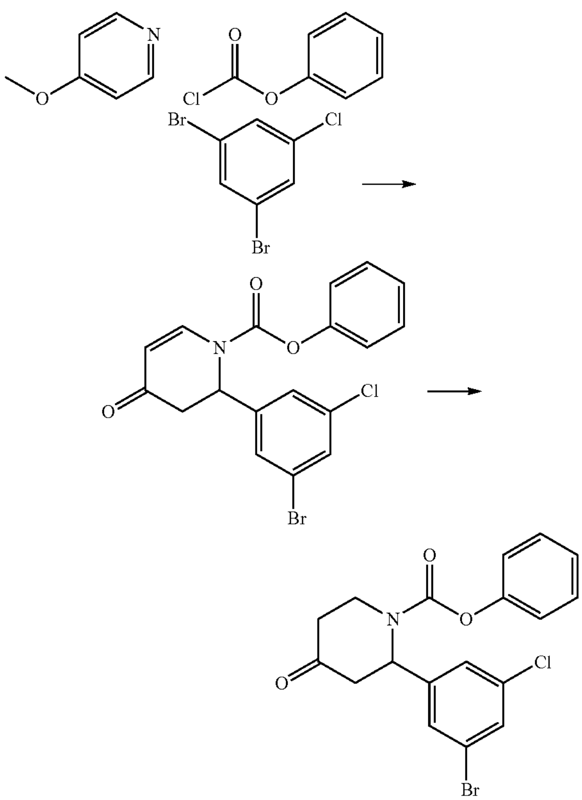

To a solution of 1,3-dibromo-5-chloro-benzene (1 g, 3.69 mmol, 1 equiv) in THF (15 mL, 0.25 M) was added lithium isopropylmagnesiumchloride LiCl (3.129 mL, 4.06 mmol, 1.1 equiv) at −23° C. and stirred at that temperature for 30 minutes under $N_2$. 4-methoxypyridine (403.66 mg, 3.69 mmol, 1 equiv) and phenyl chloroformate (579.14 mg, 3.69 mmol, 1 equiv) were added at −23° C. and then stirred for 20 minutes. The reaction mixture was poured into 10% aqueous HCl (15 mL) and the mixture was stirred at room temperature for 10 minutes. The solution was extracted with EtOAc (15 mL*3), washed with brine (10 mL*2), dried over $Na_2SO_4$, filtered, and concentrated. The residue was purified by flash silica gel chromatography (ISCO®; 20 g SEPAFLASH® Silica Flash Column, Eluent of 21% Ethyl acetate/Petroleum ether gradient @ 78 mL/min) to afford phenyl 2-(3-bromo-5-chloro-phenyl)-4-oxo-2,3-dihydropyridine-1-carboxylate (955 mg, 2.35 mmol, 64% yield) as a white solid.

To a solution of phenyl 2-(3-bromo-5-chloro-phenyl)-4-oxo-2,3-dihydropyridine-1-carboxylate (30.625 g, 75.30 mmol, 1 equiv) in acetic acid (306 mL, 0.25 M) was added granular zinc (51 g, 780.13 mmol, 10 equiv) at 25° C. The mixture was stirred at 25° C. for 17 hours under $N_2$. The reaction solution was filtered and then adjusted by $NaHCO_3$ to pH=8-9. The filtrate was adjusted with saturated aqueous $NaHCO_3$ to pH=8-9 and then extracted with EtOAc (500 mL*3). The combined organic layers were washed with brine (300 mL*2), dried over $Na_2SO_4$, filtered, and concentrated. The residue was purified by flash silica gel chromatography (ISCO®; 220 g SEPAFLASH® Silica Flash Column, Eluent of 20-30% Ethyl acetate/Petroleum ether gradient @ 150 mL/min) to afford phenyl 2-(3-bromo-5-chloro-phenyl)-4-oxo-piperidine-1-carboxylate (20.70 g, 50.7 mmol, 67% yield) as a yellow oil.

The title compound was obtained in a similar fashion to Compound 238 using phenyl 2-(3-bromo-5-chloro-phenyl)-4-oxo-piperidine-1-carboxylate. LC-MS m/z: 379.3 [M+1]. Stereochemistry: single enantiomer of unknown absolute configuration.

Using the appropriate coupling partner in synthesis of Compound 247, the title compounds can be obtained. All compounds are single enantiomers of unknown absolute configuration.

| Cmp | Name | LC-MS m/z [M + 1] |
|---|---|---|
| 247 | 1-(2-(3-(5-aminopyrimidin-2-yl)-5-chlorophenyl)-4,4-difluoropiperidin-1-yl)prop-2-en-1-one | 379.3 |
| 281 | 1-(2-(3-chloro-5-(2-methylpyrimidin-4-yl)phenyl)-4,4-difluoropiperidin-1-yl)prop-2-en-1-on | 378.2 |
| 284 | 1-(2-(3-(2-aminopyrimidin-4-yl)-5-chlorophenyl)-4,4-difluoropiperidin-1-yl)prop-2-en-1-one | 379.2 |
| 285 | 1-(2-(3-chloro-5-(6-methylpyrimidin-4-yl)phenyl)-4,4-difluoropiperidin-1-yl)prop-2-en-1-one | 378.2 |

Example 104. Synthesis of 1-((2R,5R)-2-(3-(5-aminopyrimidin-2-yl)-5-chlorophenyl)-5-hydroxy-5-methylpiperidin-1-yl)prop-2-en-1-one & 1-((2R,5S)-2-(3-(5-aminopyrimidin-2-yl)-5-chlorophenyl)-5-hydroxy-5-methylpiperidin-1-yl)prop-2-en-1-one (Compounds 257 and 273)

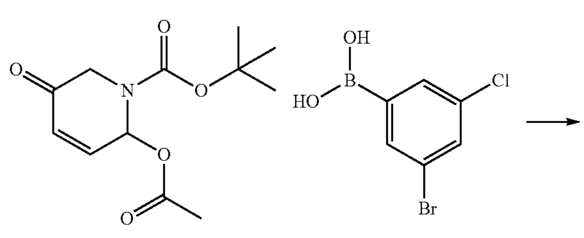

-continued

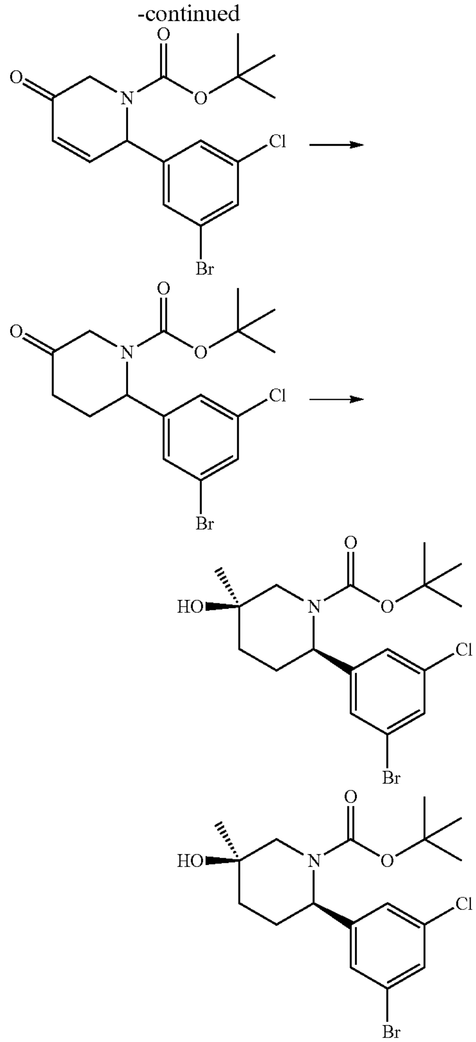

To a solution of tert-butyl 2-acetoxy-5-oxo-2,6-dihydropyridine-1-carboxylate (3.8 g, 14.88 mmol, 1 equiv) in toluene (30 mL, 0.49 M) was added 3-bromo-5-chlorophenylboronic acid (7004.6 mg, 29.77 mmol, 2 equiv), potassium carbonate (4114.8 mg, 29.77 mmol, 2 equiv), and palladium (II) acetate (334.21 mg, 1.48 mmol, 0.1 equiv) at 25° C. under $N_2$. The mixture was stirred at 25° C. for 30 minutes. The reaction mixture was poured into water (150 mL) and extracted with EtOAc (150 mL*3). The combined organic layers were washed with brine (100 mL*2), dried over $Na_2SO_4$, filtered, and concentrated. The residue was purified by flash silica gel chromatography (ISCO®; 40 g SEPAFLASH® Silica Flash Column, Eluent of 20-30% Ethyl acetate/Petroleum ether gradient @ 80 m/min) to afford tert-butyl 2-(3-bromo-5-chloro-phenyl)-5-oxo-2,6-dihydropyridine-1-carboxylate (1.70 g, 4.40 mmol, 30% yield).

To a solution of tert-butyl 2-(3-bromo-5-chloro-phenyl)-5-oxo-2,6-dihydropyridine-1-carboxylate (1.5 g, 3.87 mmol, 1 equiv) in THF (15 mL, 0.13 M) and tert-butanol (15 mL, 0.13 M) was added tris(triphenylphosphine)rhodium(I) chloride (358.92 mg, 0.38 mmol, 0.1 equiv) at 25° C. The mixture was stirred at 35° C. for 12 hours under $H_2$. The reaction mixture was poured into water (15 mL) and extracted with EtOAc (25 mL*3). The combined organic layers were washed with brine (20 mL*2), dried over $Na_2SO_4$, filtered, and concentrated. The residue was purified by flash silica gel chromatography (ISCO®; 25 g SEPAFLASH® Silica Flash Column, Eluent of 20-40% Ethyl acetate/Petroleum ether gradient @ 80 mL/min) to afford tert-butyl 2-(3-bromo-5-chloro-phenyl)-5-oxo-piperidine-1-carboxylate (1.30 g, 3.34 mmol, 86% yield).

To a solution of methylmagnesium bromide (0.247 mL, 0.74 mmol, 1.5 equiv) in i-$Pr_2O$ (3 mL) was added tert-butyl 2-(3-bromo-5-chloro-phenyl)-5-oxo-piperidine-1-carboxylate (200 mg, 0.49 mmol, 1 equiv) at 0° C. The mixture was stirred at this temperature under $N_2$ for 2 hours. The solution was diluted with saturated aqueous $NH_4Cl$ (15 mL) and extracted with EtOAc (2×10 mL). The combined organic extracts were washed with brine (15 mL), dried over $Na_2SO_4$, filtered, and concentrated. The residue was purified by prep-TLC ($SiO_2$, PE:EtOAc=3:1) to afford 1 tert-butyl rac-(2R,5R)-2-(3-bromo-5-chloro-phenyl)-5-hydroxy-5-methyl-piperidine-1-carboxylate and tert-butyl rac-(2S,5R)-2-(3-bromo-5-chloro-phenyl)-5-hydroxy-5-methyl-piperidine-1-carboxylate.

1-((2R,5R)-2-(3-(5-aminopyrimidin-2-yl)-5-chlorophenyl)-5-hydroxy-5-methylpiperidin-1-yl)prop-2-en-1-one was obtained using Procedure B and tert-butyl rac-(2S,5R)-2-(3-bromo-5-chloro-phenyl)-5-hydroxy-5-methyl-piperidine-1-carboxylate. Enantiomers were separated by SFC. LC-MS m/z: 373.2 [M+1].

1-((2R,5S)-2-(3-(5-aminopyrimidin-2-yl)-5-chlorophenyl)-5-hydroxy-5-methylpiperidin-1-yl)prop-2-en-1-one was obtained using Procedure B and 1 tert-butyl rac-(2R,5R)-2-(3-bromo-5-chloro-phenyl)-5-hydroxy-5-methyl-piperidine-1-carboxylate. Enantiomers were separated by SFC. LC-MS m/z: 373.2 [M+1].

Stereochemistry: single enantiomer of unknown absolute configuration.

Example 105. Synthesis of 1-((2R,4R)-2-(3-(5-aminopyrimidin-2-yl)-5-chlorophenyl)-4-hydroxy-4-methylpiperidin-1-yl)prop-2-en-1-one & 1-((2S,4S)-2-(3-(5-aminopyrimidin-2-yl)-5-chlorophenyl)-4-hydroxy-4-methylpiperidin-1-yl)prop-2-en-1-one (Compounds 264 and 265)

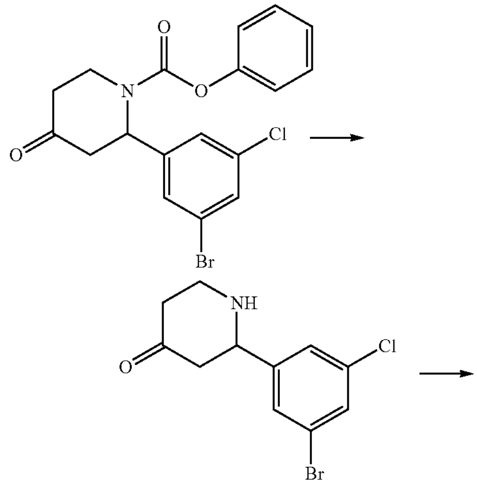

-continued

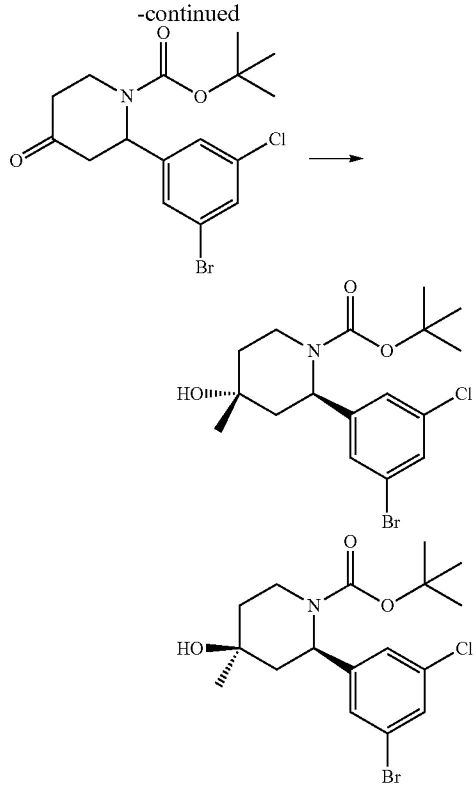

Phenyl 2-(3-bromo-5-chloro-phenyl)-4-oxo-piperidine-1-carboxylate was obtained from the synthesis of Compound 247.

To a solution of phenyl 2-(3-bromo-5-chloro-phenyl)-4-oxo-piperidine-1-carboxylate (8 g, 19.57 mmol, 1 equiv) in MeCN (80 mL, 0.12 M) and water (80 mL, 0.12 M) was added lithium hydroxide monohydrate (7.392 g, 176.18 mmol, 9 equiv) at 25° C. The mixture was stirred at 50° C. for 8 hours under $N_2$. The reaction mixture was poured into water (100 mL) and extracted with EtOAc (100 mL*3). The combined organic layers were washed with brine (50 mL*2), dried over $Na_2SO_4$, filtered, and concentrated. The crude material was obtained as yellow oil and used into the next step without further purification.

To a solution of 2-(3-bromo-5-chloro-phenyl)piperidin-4-one (10.64 g, 36.87 mmol, 1 equiv) in DCM (100 mL, 0.4 M) was added triethylamine (3.731 g, 36.87 mmol, 1 equiv) and di-tert-butyl dicarbonate (8.047 g, 36.87 mmol, 1 equiv) at 25° C. The mixture was stirred at room temperature for 16 hours. The mixture was poured into water (40 mL) and extracted with DCM (40 mL*3). The combined organic layers were dried over $Na_2SO_4$, filtered, and concentrated. The crude product was purified by column chromatography on silica gel (petroleum ether/ethyl acetate=100:0 to 40:60) to give tert-butyl 2-(3-bromo-5-chloro-phenyl)-4-oxo-piperidine-1-carboxylate (5.87 g, 15.1 mmol, 41% yield).

To a solution of tert-butyl 2-(3-bromo-5-chloro-phenyl)-4-oxo-piperidine-1-carboxylate (1 g, 2.57 mmol) in THF (10 mL, 0.25 M) under $N_2$ was added methylmagnesium bromide (5.145 mL, 15.436 mmol, 6 equiv) at 0° C. and then stirred for 1 hour. The reaction was quenched with saturated aqueous $NH_4Cl$ (40 mL) and extracted with ethyl acetate (30 mL). The organic solution was washed with water, a brine solution, dried over sodium sulfate, filtered, and concentrated. The residue was purified by column chromatography ($SiO_2$, Petroleum ether/Ethyl acetate=100/0 to 14/86) to afford racemic tert-butyl (2R,4R)-2-(3-bromo-5-chlorophenyl)-4-hydroxy-4-methylpiperidine-1-carboxylate and racemic tert-butyl (2R,4S)-2-(3-bromo-5-chlorophenyl)-4-hydroxy-4-methylpiperidine-1-carboxylate.

The title compounds were obtained using Procedure B starting with tert-butyl (2R,4R)-2-(3-bromo-5-chlorophenyl)-4-hydroxy-4-methylpiperidine-1-carboxylate. Enantiomers were separated by SFC. LC-MS m/z: 373.2 [M+1] and LC-MS m/z: 373.2 [M+1].

Stereochemistry: single enantiomer of unknown absolute configuration.

Example 106. Synthesis of 1-((2R,4S)-2-(3-(5-aminopyrimidin-2-yl)-5-chlorophenyl)-4-hydroxy-4-methylpiperidin-1-yl)prop-2-en-1-one (Compound 266)

The title compounds was obtained using Procedure B starting with racemic tert-butyl (2R,4S)-2-(3-bromo-5-chlorophenyl)-4-hydroxy-4-methylpiperidine-1-carboxylate from the synthesis of Compounds 264 and 265. Enantiomers were separated by SFC. LC-MS m/z: 373.2 [M+1].

Stereochemistry: single enantiomer of unknown absolute configuration.

Example 107. Nrf2 TMT Measurement

In vitro $TE_{50}$ values for KEAP1_C151 were obtained by treating 500 μg of cell lysate generated from MDA-MB-468 breast cancer cells with DMSO or compound for 1 hour at room temperature followed by the addition of 200 μM IA-DTB (in DMSO) for one hour at room temperature. Samples were then precipitated by the addition of 8× ice cold acetonitrile and incubated at −80° C. for two hours. Protein was then pelleted by centrifugation (4,200 RPM, 45 min, 4° C.). The pelleted material was resuspended in 9M Urea, 50 mM ammonium bicarbonate and proteins were reduced and alkylated by the addition of DTT and iodoacetamide (10 and 30 mM, respectively). Following reduction and alkylation, samples were exchanged into 2M urea (Zeba spin desalting plates, Thermo Fisher) and digested with Trypsin. IA-DTB labeled peptides were isolated with streptavidin agarose resin. Enriched peptides were eluted by the addition of 50% acetonitrile (ACN) 0.1% Formic Acid (FA) and dried in a SpeedVac vacuum concentrator.

Dried peptides were resuspended in 0.2 M EPPS pH 8.5 and treated with 6.5 μL of 11-plex tandem mass tag (TMT) (8.3 μg/μL in dry ACN) for 2 hours at room temperature. Reactions were quenched by the addition of 6.5 μL of 5% Hydroxylamine. Samples were then combined and desalted on a Biotage Evolute express ABN plate (600-0010-PX01).

Targeted TMT. Targeted TMT measurements were collected using an Orbitrap LumosTribrid Mass Spectrometer (Thermo Scientific) coupled to an UltiMate 3000 Series Rapid Separation LC system and autosampler (Thermo Scientific Dionex). Peptides were eluted onto a custom C18 capillary analytical column (75-gm inner diameter fused silica, packed with Acclaim PepMap C18 resin (Thermo Scientific)) using an Acclaim PepMap 100 (Thermo 164535) loading column, and separated at a flow rate of 1.0 μl min-1. Data were acquired using a specific MS3-based TMT method targeting the peptide containing KEAP1 $C_{151}$ (C(+324.2)VLHVMNGAVMYQIDSVVR, +3 charge state) where MS2 peptide fragmentation is triggered upon detection of the peptide precursor ion. Subsequent MS3 analysis was then performed using pre-selected peptide fragment ions that were isolated for fragmentation using synchronous precursor selection. RAW files were converted to MZXML format and searched with the SEQUEST algorithm using the MassPike software package. TMT quantitation was performed with a filter requiring at least ten summed signal-to-noise for control channels. Quantified signals were used for dose response curve-fitting and $IC_{50}$ calculation using R's drc package.

Example 108. Nrf2 Antagonism Assay

NRF2 binds to a promoter region, antioxidant response element (ARE), to initiate expression of multiple genes. ARE luciferase reporter assays are used to test whether a ligand can activate or repress the expression of target genes using luciferase as a reporter gene.

KYSE-70 is an esophageal squamous cell carcinoma cell line with a Nrf2 mutation at amino acid position W24C. This mutation lowers the affinity between the E3 ligase that includes KEAP1 and Nrf2, resulting in a state in which the synthesis rate of new Nrf2 is faster than the E3's degradation rate of Nrf2, resulting in a "Nrf2 high" state. In KYSE-70 cells, genes are inserted directly after the ARE that trigger the expression of luciferase. Without a NRF2 antagonist in this modified KYSE70 cell line which has an inherently "NRF2 high state", luciferase is expressed, and a signal is observed.

Nrf2 antagonists bind at C151 of KEAP1 and stabilize the E3 which results in an increased degradation rate of Nrf2. Increased degradation of Nrf2 results in less expression of luciferase, and therefore a less intense signal.

An $IC_{50}$ is generated from the dose-response curve and an Imax. A positive Imax corresponds to Nrf2 antagonism. Imax>90% correlates with in vivo tumor grown inhibition. Compounds with Imax>50% were included in this description.

Representative data for exemplary compounds disclosed herein is presented in Table 2.

TABLE 2

Data for representative compounds of the disclosure.

| No. | KEAP1_C151 $TE_{50}$ (μM) | KYSE70 Cellular ARE Luciferase $I_{max}$ (%) |
|---|---|---|
| 1 | 0.41 | 56 |
| 2 | 0.0107 | 52 |
| 5 | 0.13 | 70 |
| 6 | 0.0026 | 58 |
| 7 | 5.26 | 55 |
| 8 | 0.055 | 53 |
| 9 | 0.0605 | 76 |
| 10 | 0.0228 | 79 |
| 11 | 0.067 | 79 |
| 12 | 0.0039 | 68 |
| 13 | 0.05 | 72 |
| 14 | 0.1442 | 55 |
| 15 | 0.022 | 57 |
| 16 | 0.0022 | 62 |
| 17 | 0.0963 | 65 |
| 18 | 0.01 | 69 |
| 19 | 0.033 | 84 |
| 20 | | 67 |
| 21 | | 54 |
| 22 | | 64 |
| 23 | | 55 |
| 24 | | 73 |
| 25 | 0.0584 | 86 |
| 26 | 0.088 | 56 |
| 28 | 0.15 | 50 |
| 29 | 0.33 | 62 |
| 30 | | 72 |
| 31 | 0.036 | 66 |
| 32 | 0.063 | 52 |
| 33 | 0.12 | 82 |
| 34 | 0.018 | 83 |
| 35 | 0.0178 | 89 |
| 36 | 0.11 | 69 |
| 37 | 0.022 | 85 |
| 38 | 0.027 | 89 |
| 39 | 0.049 | 66 |
| 40 | 0.04 | 93 |
| 41 | 0.2 | 68 |
| 42 | 0.037 | 79 |
| 43 | 0.025 | 87 |
| 44 | 0.0157 | 93 |
| 45 | 0.089 | 83 |
| 46 | 0.14 | 84 |
| 47 | 0.02 | 74 |
| 48 | 0.066 | 85 |
| 49 | 0.042 | 91 |
| 50 | 0.5735 | 86 |
| 51 | 0.237 | 89 |
| 52 | 0.1739 | 80 |
| 53 | 0.066 | 55 |
| 54 | 0.049 | 70 |
| 55 | 0.022 | 93 |
| 56 | | 74 |
| 57 | 100 | 84 |
| 58 | 0.0305 | 95 |
| 59 | | 81 |
| 60 | 0.058 | 70 |
| 61 | 0.0513 | 89 |
| 62 | 0.22 | 55 |
| 63 | 0.0033 | 63 |
| 64 | 0.001 | 75 |
| 65 | 0.024 | 88 |
| 66 | 0.023 | 93 |
| 67 | 0.019 | 73 |
| 68 | 0.09 | 72 |
| 69 | 0.0884 | 82 |
| 70 | 0.054 | 81 |
| 71 | 0.03 | 78 |
| 72 | 0.027 | 80 |
| 73 | 0.056 | 74 |
| 74 | 0.022 | 89 |
| 75 | 0.016 | 92 |
| 76 | 0.024 | 90 |
| 77 | 0.086 | 82 |
| 78 | 0.018 | 78 |
| 79 | 0.018 | 85 |
| 80 | 0.29 | 94 |
| 81 | 0.012 | 85 |
| 82 | <0.01 | 77 |
| 83 | 0.089 | 86 |
| 84 | 0.047 | 93 |
| 85 | 0.036 | 89 |
| 86 | 0.0073 | 83 |
| 87 | 0.01 | 81 |
| 88 | 0.014 | 85 |
| 89 | 0.036 | 73 |
| 90 | 0.12 | 81 |
| 91 | 0.011 | 82 |
| 92 | 0.023 | 94 |
| 93 | 0.04 | 91 |
| 94 | 0.016 | 87 |

TABLE 2-continued

Data for representative compounds of the disclosure.

| No. | KEAP1_C151 $TE_{50}$ (μM) | KYSE70 Cellular ARE Luciferase $I_{max}$ (%) |
|---|---|---|
| 95 | 0.025 | 94 |
| 96 | 0.02 | 94 |
| 97 | 0.023 | 86 |
| 98 | 0.026 | 76 |
| 99 | | 82 |
| 100 | 0.14 | 78 |
| 101 | 0.024 | 87 |
| 102 | 0.0432 | 92 |
| 103 | 0.017 | 85 |
| 104 | 0.045 | 91 |
| 105 | 0.036 | 92 |
| 106 | 0.037 | 67 |
| 107 | 0.018 | 92 |
| 108 | | 70 |
| 109 | | 91 |
| 110 | | 93 |
| 111 | | 90 |
| 112 | | 95 |
| 113 | | 94 |
| 114 | | 87 |
| 115 | | 74 |
| 116 | | 84 |
| 117 | | 84 |
| 118 | | 63 |
| 119 | | 96 |
| 120 | 0.11 | 77 |
| 121 | 0.026 | 82 |
| 122 | 0.011 | 88 |
| 123 | 0.013 | 73 |
| 124 | 0.018 | 72 |
| 125 | <0.0064 | 91 |
| 126 | 0.05 | 72 |
| 127 | 0.039 | 92 |
| 128 | 0.12 | 70 |
| 129 | 0.079 | 84 |
| 130 | 0.094 | 89 |
| 131 | 0.3 | 91 |
| 132 | <0.0064 | 78 |
| 133 | 0.072 | 85 |
| 134 | 0.063 | 85 |
| 135 | 0.01 | 83 |
| 136 | 0.052 | 81 |
| 137 | 0.025 | 92 |
| 138 | 0.041 | 75 |
| 139 | 0.074 | 90 |
| 140 | | 72 |
| 141 | | 89 |
| 142 | | 81 |
| 143 | 0.77 | 56 |
| 144 | 0.083 | 86 |
| 145 | 0.011 | 90 |
| 146 | 181.9 | 71 |
| 147 | 0.18 | 74 |
| 148 | 0.051 | 93 |
| 149 | 0.015 | 95 |
| 150 | 0.031 | 97 |
| 151 | | 81 |
| 152 | | 78 |
| 153 | | 94 |
| 155 | 0.067 | 94 |
| 156 | 0.105 | 94 |
| 157 | 0.012 | 81 |
| 158 | 2.72 | 71 |
| 159 | 0.32 | 63 |
| 160 | | 91 |
| 161 | 0.87 | 83 |
| 162 | 0.6 | 80 |
| 163 | 0.61 | 72 |
| 164 | 0.44 | 85 |

TABLE 2-continued

Data for representative compounds of the disclosure.

| No. | KEAP1_C151 $TE_{50}$ (μM) | KYSE70 Cellular ARE Luciferase $I_{max}$ (%) |
|---|---|---|
| 165 | 0.33 | 53 |
| 166 | 0.53 | 50 |
| 167 | 2.89 | 87 |
| 168 | 0.12 | 74 |
| 169 | 0.07 | 82 |
| 170 | 1.67 | 81 |
| 171 | 0.35 | 72 |
| 172 | 0.02 | 71 |
| 173 | <0.0064 | 86 |
| 174 | 0.076 | 51 |
| 175 | 0.032 | 92 |
| 177 | 0.15 | 87 |
| 178 | 0.03 | 93 |
| 179 | 0.19 | 92 |
| 180 | 0.0073 | 90 |
| 181 | | 66 |
| 182 | 0.016 | 89 |
| 183 | 0.027 | 87 |
| 184 | | 72 |
| 185 | | 94 |
| 186 | | 83 |
| 187 | 0.12 | 71 |
| 188 | 0.018 | 86 |
| 189 | | 79 |
| 190 | 0.0066 | 75 |
| 191 | 0.012 | 93 |
| 192 | 6.71 | 64 |
| 193 | 0.097 | 91 |
| 194 | | 84 |
| 195 | | 90 |
| 196 | | 90 |
| 197 | | 87 |
| 198 | | 93 |
| 199 | | 92 |
| 200 | | 91 |
| 201 | | 93 |
| 202 | | 94 |
| 203 | 0.011 | 87 |
| 204 | 0.011 | 86 |
| 205 | 0.034 | 92 |
| 206 | 0.52 | 55 |
| 207 | 0.045 | 90 |
| 208 | 0.033 | 94 |
| 209 | 0.082 | 93 |
| 210 | 0.38 | 55 |
| 211 | 0.085 | 57 |
| 212 | 0.069 | 90 |
| 213 | 0.47 | 75 |
| 214 | 0.1 | 93 |
| 215 | 0.35 | 65 |
| 216 | 0.14 | 86 |
| 217 | 0.03 | 78 |
| 218 | 0.016 | 92 |
| 219 | | 81 |
| 220 | 0.049 | 73 |
| 221 | 0.28 | 78 |
| 222 | 0.33 | 85 |
| 223 | 0.0035 | 94 |
| 224 | 0.17 | 90 |
| 226 | 0.2 | 85 |
| 227 | 0.095 | 90 |
| 228 | 0.13 | 79 |
| 229 | 0.56 | 92 |
| 230 | 0.82 | 51 |
| 231 | 0.32 | 55 |
| 232 | 0.14 | 84 |
| 233 | 0.66 | 83 |
| 234 | 0.22 | 89 |

TABLE 2-continued

Data for representative compounds of the disclosure.

| No. | KEAP1_C151 $TE_{50}$ (μM) | KYSE70 Cellular ARE Luciferase $I_{max}$ (%) |
|---|---|---|
| 235 | 0.11 | 86 |
| 236 | 0.025 | 87 |
| 237 | 0.14 | 50 |
| 238 | 0.034 | 82 |
| 239 | 0.22 | 83 |
| 240 | 0.15 | 61 |
| 241 | 0.17 | 87 |
| 242 | 0.25 | 59 |
| 243 | 0.022 | 88 |
| 244 | 0.15 | 81 |
| 245 | 0.09 | 53 |
| 246 | 0.043 | 90 |
| 247 | 0.016 | 91 |
| 248 | 0.01 | 89 |
| 249 | 0.0053 | 89 |
| 250 | 0.036 | 92 |
| 251 | 0.017 | 93 |
| 253 | 0.05 | 93 |
| 254 | 0.086 | 92 |
| 255 | 0.05 | 93 |
| 256 | 0.086 | 63 |
| 257 | 0.077 | 83 |
| 258 | 0.016 | 93 |
| 259 | 0.14 | 93 |
| 260 | 0.02 | 88 |
| 261 | 0.019 | 95 |
| 263 | 0.019 | 93 |
| 264 | 0.16 | 86 |
| 265 | 11.16 | 51 |
| 266 | 0.32 | 90 |
| 267 | 0.01 | 94 |
| 268 | 0.49 | 53 |
| 269 | 0.95 | 72 |
| 271 | 0.059 | 93 |
| 273 | 1.36 | 88 |
| 278 | 0.0061 | 87 |
| 279 | 0.045 | 92 |
| 280 | 0.032 | 90 |
| 281 | 0.061 | 84 |
| 282 | 0.051 | 78 |
| 283 | 0.018 | 94 |
| 284 | 0.083 | 94 |
| 285 | 0.022 | 83 |
| 286 | 0.032 | 96 |
| 287 | 0.11 | 96 |
| 289 | <0.0064 | 95 |
| 290 | 0.015 | 93 |
| 291 | <0.0064 | 93 |
| 293 | 0.031 | 54 |
| 294 | 1.38 | 91 |
| 295 | 0.20 | 88 |
| 296 | 0.036 | 96 |
| 297 | — | 58 |
| 298 | 0.032 | 94 |

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A compound of Formula (V), or a pharmaceutically acceptable salt thereof:

Formula (V)

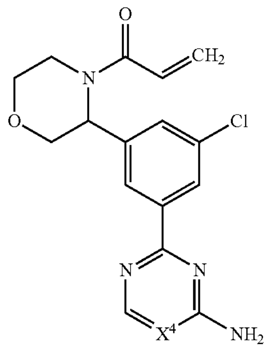

wherein $X^4$ is N or $CR^3$; and $R^3$ is H or D.

2. The compound of claim 1, or a pharmaceutically acceptable salt thereof, wherein the compound is of Formula (Va):

Formula (Va)

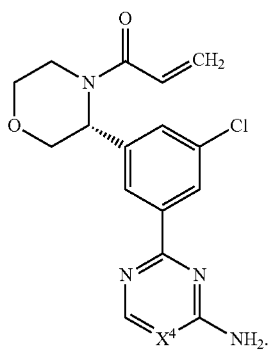

3. The compound of claim 1, or a pharmaceutically acceptable salt thereof, wherein $X^4$ is $CR^3$.

4. The compound of claim 1, or a pharmaceutically acceptable salt thereof, wherein $R^3$ is H.

5. The compound of claim 1, or a pharmaceutically acceptable salt thereof, wherein $X^4$ is N.

6. A compound that is (R)-1-(3-(3-(4-aminopyrimidin-2-yl)-5-chlorophenyl) morpholino) prop-2-en-1-one of formula:

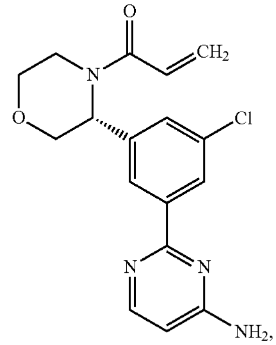 [SMILES: C=CC(=O)N1CCOC[C@H]1c1cc(Cl)cc(-c2nccc(N)n2)c1]

or a pharmaceutically acceptable salt thereof.

7. A compound that is (R)-1-(3-(3-(4-amino-1,3,5-triazin-2-yl)-5-chlorophenyl) morpholino) prop-2-en-1-one of formula:

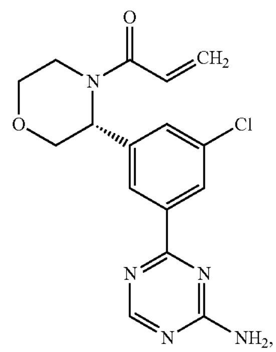 [SMILES: C=CC(=O)N1CCOC[C@H]1c1cc(Cl)cc(-c2ncnc(N)n2)c1]

or a pharmaceutically acceptable salt thereof.

8. A pharmaceutical composition comprising a compound of claim 1, or a pharmaceutically acceptable salt thereof; and a pharmaceutically acceptable excipient or carrier.

9. A pharmaceutical composition comprising a compound of claim 3, or a pharmaceutically acceptable salt thereof, and a pharmaceutically acceptable excipient or carrier.

10. A pharmaceutical composition comprising a compound of claim 6, or a pharmaceutically acceptable salt thereof; and a pharmaceutically acceptable excipient or carrier.

* * * * *